US011634396B2

(12) United States Patent
Medina et al.

(10) Patent No.: US 11,634,396 B2
(45) Date of Patent: Apr. 25, 2023

(54) OPIOID RECEPTOR MODULATORS

(71) Applicant: Epiodyne, Inc., San Francisco, CA (US)

(72) Inventors: Julio Cesar Medina, South San Francisco, CA (US); Alok Nerurkar, San Diego, CA (US); Corinne Sadlowski, London (GB); Frederick Seidl, San Mateo, CA (US); Heng Cheng, Fremont, CA (US); Jason Duquette, Millbrae, CA (US); John Lee, Pacifica, CA (US); Martin Holan, Stamford, CT (US); Pingyu Ding, Foster City, CA (US); Xiaodong Wang, South San Francisco, CA (US); Tien Widjaja, Lafayette, CO (US); Thomas Nguyen, Newbury Park, CA (US); Ulhas Bhatt, Fremont, CA (US); Yihong Li, South San Francisco, CA (US); Zhi-liang Wei, Foster City, CA (US)

(73) Assignee: EPIODYNE, INC., San Francisco, CA (US)

( * ) Notice: Subject to any disclaimer, the term of this patent is extended or adjusted under 35 U.S.C. 154(b) by 0 days.

(21) Appl. No.: 17/714,030

(22) Filed: Apr. 5, 2022

(65) Prior Publication Data
US 2022/0356157 A1 Nov. 10, 2022

Related U.S. Application Data

(60) Provisional application No. 63/318,486, filed on Mar. 10, 2022, provisional application No. 63/171,008, filed on Apr. 5, 2021.

(51) Int. Cl.
| | | |
|---|---|---|
| C07D 277/30 | (2006.01) | |
| C07D 239/26 | (2006.01) | |
| C07D 213/56 | (2006.01) | |
| C07C 233/65 | (2006.01) | |
| C07D 263/58 | (2006.01) | |
| C07D 333/24 | (2006.01) | |
| C07D 401/12 | (2006.01) | |
| C07D 295/155 | (2006.01) | |
| C07D 413/12 | (2006.01) | |
| C07D 307/54 | (2006.01) | |

(52) U.S. Cl.
CPC .......... *C07D 277/30* (2013.01); *C07C 233/65* (2013.01); *C07D 213/56* (2013.01); *C07D 239/26* (2013.01); *C07D 263/58* (2013.01); *C07D 295/155* (2013.01); *C07D 307/54* (2013.01); *C07D 333/24* (2013.01); *C07D 401/12* (2013.01); *C07D 413/12* (2013.01)

(58) Field of Classification Search
None
See application file for complete search history.

(56) References Cited

U.S. PATENT DOCUMENTS

| | | |
|---|---|---|
| 6,593,348 B2 | 7/2003 | Carroll et al. |
| 7,807,704 B2 | 10/2010 | Thomas et al. |
| 10,702,498 B2 | 7/2020 | Shoichet et al. |
| 10,780,078 B2 | 9/2020 | Shoichet et al. |
| 2005/0277674 A1 | 12/2005 | Hinze et al. |
| 2007/0135402 A1 | 6/2007 | Habashita et al. |
| 2007/0265301 A1 | 11/2007 | Edwards et al. |
| 2014/0288077 A1 | 9/2014 | Fujii et al. |
| 2016/0095854 A1 | 4/2016 | Carroll et al. |
| 2020/0109126 A1 | 4/2020 | Shoichet et al. |
| 2021/0052548 A1 | 2/2021 | Shoichet et al. |
| 2021/0147343 A1 | 5/2021 | Medina et al. |
| 2021/0163402 A1 | 6/2021 | Medina et al. |

FOREIGN PATENT DOCUMENTS

| | | | |
|---|---|---|---|
| CN | 101823987 B | 6/2014 | |
| EP | 0147211 B1 | 9/1990 | |
| WO | WO-9310089 A1 | 5/1993 | |
| WO | WO-9731940 A1 | 9/1997 | |
| WO | WO-9817636 A1 | 4/1998 | |
| WO | WO-2005009315 A1 | 2/2005 | |
| WO | WO-2005120494 A1 | 12/2005 | |
| WO | WO-2008093960 A1 | 8/2008 | |
| WO | WO-2010013037 A1 | 2/2010 | |
| WO | WO-2011054844 A1 | 5/2011 | |
| WO | WO-2013033310 A1 | 3/2013 | |
| WO | WO-2013068467 A1 | 5/2013 | |
| WO | WO-2017007695 A1 | 1/2017 | |
| WO | WO-2017035366 A1 | 3/2017 | |
| WO | WO-2018129393 A1 | 7/2018 | |
| WO | WO-2019036678 A1 | 2/2019 | |
| WO | WO 2019/195634 | * 10/2019 | ........... C07C 233/62 |
| WO | WO-2019195634 A1 | 10/2019 | |

OTHER PUBLICATIONS

CAS RN 1328450-73-2 (entered into STN on Sep. 5, 2011) (Year: 2011).*
PCT/US2022/023546 International Search Report and Written Opinion dated Aug. 1, 2022.
Anderson. The process of structure-based drug design. Chem Biol 10:787-797 (2003).
Andrews et al. Stabilised G protein-coupled receptors in structure-based drug design: a case study with adenosine A2A receptor. MedChemComm. 4(1):52-67 (2013).
Balter et al. Thermal sensitivity as a measure of spontaneous morphine withdrawal in mice. J Pharmacol Toxicol Methods 67:162-168 (2013).
Berge et al. Pharmaceutical Salts. Journal of Pharmaceutical Sciences 66(1):1-19 (Jan. 1977).

(Continued)

*Primary Examiner* — Craig D Ricci
(74) *Attorney, Agent, or Firm* — Wilson Sonsini Goodrich & Rosati

(57) ABSTRACT

Provided herein are opioid receptor modulators and pharmaceutical compositions comprising said compounds.

16 Claims, No Drawings

(56) References Cited

OTHER PUBLICATIONS

Bissantz C et al. Protein-based virtual screening of chemical databases. II. Are homology models of G-Protein Coupled Receptors suitable targets? Proteins 50(1):5-25 (2003).
Bohn et al. Enhanced morphine analgesia in mice lacking beta-arrestin 2. Science 286(5449):2495-2498 (1999).
Calvey et al. Chapter 3: Drug Action. Principles and Practice of Pharmacology for Anaesthetists (pp. 43-67) (2009).
Carlsson et al. Structure-based discovery of A2A adenosine receptor ligands. J Med Chem 53(9):3748-3755 (2010).
Carlsson et al. Ligand discovery from a dopamine D3 receptor homology model and crystal structure. Nat Chem Biol. 7(11):769-778 (2011).
Clougherty et al. Chronic social stress and susceptibility to concentrated ambient fine particles in rats. Environ Health Perspect. 18(6):769-75 (2010).
De Graaf et al. Crystal structure-based virtual screening for fragment-like ligands of the human histamine H(1) receptor. J Med Chem 54(23):8195-8206 (2011).
Deekonda et al. Design synthesis and structure-activity relationship of 5-substituted (tetrahydronaphthalen-2y1)methyl with N-phenyl-N-(piperidin-2-yl)propionamide derivatives as opioid ligands. Bioorg Med Chem 24(2):85-91 (Jan. 15, 2016, e-published Nov. 23, 2015).
Dewire et al. A G protein-biased ligand at the μ-opioid receptor is potently analgesic with reduced gastrointestinal and respiratory dysfunction compared with morphine. J Pharmacol Exp Ther 344(3):708-717 (2013).
Emerich et al. Central analgesic actions of loperamide following transient permeation of the blood brain barrier with Cereport (RMP-7). Brain Research 801(1-2):259-266 (1998).
Gaulton et al. ChEMBL: a large-scale bioactivity database for drug discovery. Nucleic Acids Res 40(D1):D1100-D1107 (2012).
Gomes et al. Identification of a μ-δ opioid receptor heteromer-biased agonist with antinociceptive activity. PNAS USA 110(29):12072-12077 (2013).
Gould et al. Salt Selection for Basic Drugs. Int J. Pharm. 33:201-217 (1986).
Granier et al. Structure of the δ-opioid receptor bound to naltrindole. Nature 485(7398):400-404 (2012).
Hermann et al. Metal impurities cause false positives in high-throughput screening campaigns. ACS Med Chem Lett 4(2):197-200 (2012).
Irwin et al. Automated docking screens: a feasibility study. J Med Chem 52(18):5712-5720 (2009).
Irwin et al. ZINC: a free tool to discover chemistry for biology. J Chem Inf Model 52(7):1757-1768 (2012).
Irwin et al. ZINC—a free database of commercially available compounds for virtual screening J Chem Inf Model 45(1):177-182 (2004).
Kalani et al. The predicted 3D structure of the human D2 dopamine receptor and the binding site and binding affinities for agonists and antagonists. PNAS USA 101(11):3815-3820 (2004).
Katritch et al. Structure-based discovery of novel chemotypes for adenosine A(2A) receptor antagonists. J Med Chem 53(4):1799-1809 (2010).
Kieffer. Drug discovery: Designing the ideal opioid. Nature 537(7619):170-171 (2016).
Kolb et al. Structure-based discovery of beta2-adrenergic receptor ligands. PNAS USA 106(16):6843-6848 (2009).
Kolb et al. The golden age of GPCR structural biology: any impact on drug design? Angew Chem Int Ed Engl. 50(49):11573-11575 (2011).
Kruse et al. Muscarinic receptors as model targets and antitargets for structure-based ligand discovery. Mol Pharmacol 84(4):528-540 (2013).
Laferriere et al. Ontogeny of respiratory sensitivity and tolerance to the mu-opioid agonist fentanyl in rat. Brain Res Dev Brain Res 156(2):210-217 (2005).

Langmead et al. Identification of novel adenosine A(2A) receptor antagonists by virtual screening. J Med Chem 55(5):1904-1909 (2012).
Link et al. G-Protein-Coupled Receptors: Sustained Signaling via Intracellular Megaplexes and Pathway-Specific Drugs. Angewandte Chemie, International Edition 55(52):15962-15964 (2016).
Lorber et al. Hierarchical docking of databases of multiple ligand conformations. Curr Top med Chem 5(8):739-749 (2005).
Manglik et al. Crystal structure of the μ-opioid receptor bound to a morphinan antagonist. Nature, 485(7398):321-326 (2012).
Manglik et al. Structure-based discovery of opioid analgesics with reduced side effects. Nature 537(7619):185-190 (2016).
Muchmore et al. Application of belief theory to similarity data fusion for use in analog searching and lead hopping. J Chem Inf Model 48(5):941-948 (2008).
Mysinger et al. Rapid context-dependent ligand desolvation in molecular docking. J Chem Inf Model 50(9):1561-1573 (2010).
Mysinger et al. Structure-based ligand discovery for the protein-protein interface of chemokine receptor CXCR4. PNAS USA 109(14):5517-5522 (2012).
Negri et al. Discovery of a novel selective kappa-opioid receptor agonist using crystal structure-based virtual screening. J Chem Inf Model 53(3):521-526 (2013).
Noel et al. Synthesis and SAR of tetrahydroisoquinolines as Rev-erbα agonists. Bioorg Med Chem Lett 22(11):3739-3742 (2012).
Oprea. Virtual Screening in Lead Discovery: A Viewpoint. Molecules 7(1):51-62 (2002).
Page et al. New scaffolds in the development of Mu opioid-receptor ligands. Bioorg Med Chem Lett 13(9):1585-1589 (2003).
PCT/US2016/040553 International Search Report and Written Opinion dated Dec. 12, 2016.
PCT/US2018/012683 International Search Report and Written Opinion dated May 2, 2018.
PCT/US2018/046983 International Search Report and Written Opinion dated Oct. 31, 2018.
PCT/US2019/025910 International Search Report and Written Opinion dated Jul. 15, 2019.
Philippe et al. Mu opioid receptor expression is increased in inflammatory bowel diseases: implications for homeostatic intestinal inflammation. Gut 55(6):815-823 (2006).
Powers et al. Structure-based discovery of a novel, noncovalent inhibitor of AmpC beta-lactamase. Structure 10(7):1013-1023.
PubChem CID 18589025, date created: Dec. 4, 2007, date accessed: Nov. 8, 2016.
PubChem CID 63120296, date created: Oct. 22, 2012, date accessed Nov. 8, 2016.
Sherrill et al. An Improved Synthesis and Resolution of 3-Amino-1,3-dihydro-5-phenyl-2H-1,4-benzodiazepin-2-ones. J. Org. Chem. 60:730-734 (1995).
Shi et al. Unpredictable stereochemical preferences for mu opioid receptor activity in an exhaustively stereo diversified library of 1,4-enediols. Organic Letters 5(5):633-636 (2003).
Spetea et al. The p opioid receptor and ligands acting at the p opioid receptor, as therapeutics and potential therapeutics. Curr Pharm Des 19(42):7415-7434 (2013).
Thiel. Structure-aided drug design's next generation. Nat Biotechnol 22(5):513-319 (2004).
Thompson et al. Structure-based discovery of a novel, noncovalent inhibitor of AmpC beta-lactamase. Nature 485(7398):395-399 (2012).
Tondi et al. Structure-based optimization of a non-beta-lactam lead results in inhibitors that do not up-regulate beta-lactamase expression in cell culture. J Am Chem Soc 127(13):4632-4639 (2005).
Totah et al. Detection of aminium ion intermediates: N-cyclopropyl versus N-carboxymethyl groups as reporters. J Am Chem Soc 123(41):10107-8 (2001).
U.S. Appl. No. 15/743,079 Office Action dated Jul. 16, 2019.
U.S. Appl. No. 15/743,079 Office Action dated Nov. 27, 2019.
U.S. Appl. No. 16/104,803 Office Action dated Sep. 19, 2019.
U.S. Appl. No. 16/475,208 Office Action dated Nov. 10, 2020.
U.S. Appl. No. 16/921,843 Office Action dated Jan. 13, 2022.
U.S. Appl. No. 16/926,536 Office Action dated Aug. 6, 2021.
U.S. Appl. No. 17/045,152 Office Action dated Apr. 1, 2022.

(56) References Cited

OTHER PUBLICATIONS

Weiss et al. Conformation guides molecular efficacy in docking screens of activated β-2 adrenergic G protein coupled receptor. ACS Chemical Biol 8(5):1018-1026 (2013).
Wu et al. Structure of the human κ-opioid receptor in complex with JDTic. Nature 485(7398):327-332 (2012).
U.S. Appl. No. 16/921,843, Inventors Schoichet Brian K. et al, filed Jul. 6, 2020.
U.S. Appl. No. 16/926,536, Inventors Medina Julio Cesar et al, filed Jul. 10, 2020.
U.S. Appl. No. 17/045,152, Inventors Medina Julio Cesar et al, filed Oct. 2, 2020.

\* cited by examiner

OPIOID RECEPTOR MODULATORS

CROSS-REFERENCE

This application claims priority to U.S. Provisional Application Nos. 63/171,008 filed on Apr. 5, 2021 and 63/318,486 filed on Mar. 10, 2022, each of which is incorporated herein by reference in its entirety.

STATEMENT AS TO FEDERALLY SPONSORED RESEARCH

This invention was made with government support under DA047723, and DA049598 awarded by the National Institutes of Health. The government has certain rights in the invention.

BACKGROUND

Opioid receptors are a group of inhibitory G protein-coupled receptors with opioids as ligands, which have long been used to treat pain. Opioids generally act on these receptors as agonists, antagonists, or partial agonists. There are three classical opioid receptors, originally named mu (after morphine, its most commonly recognized exogenous ligand), delta (after vas deferens, the tissue within which it was first isolated) and kappa (after the first ligand to act at this receptor, ketocyclazocine). These opioid receptors are distributed widely within the central nervous system and, to a lesser extent, throughout the periphery. Opioids, whether naturally occurring or synthetic, exhibit any number of problematic side effects, such as constipation, addiction and respiratory depression, and efforts to eliminate such attributes have been meet with only limited successes. Accordingly, there remains a need in the art for agents that can modulate opioid receptors in a manner that limit the side effects normally associated with such agents.

BRIEF SUMMARY OF THE INVENTION

This disclosure provides, for example, opioid receptor modulators, processes for their preparation, their use as medicinal agents for the treatment of neuropsychiatric disorders, depression, obsessive compulsive disorder, alcohol addiction, gambling addiction, pain, opioid overdose, opioid use disorders and addiction and pharmaceutical compositions that include the disclosed compounds as at least one active ingredient. The disclosure also provides for the use of compounds described herein as medicaments and/or in the manufacture of medicaments for the treatment of neuropsychiatric disorders, depression, obsessive compulsive disorder, alcohol addiction, gambling addiction, pain, opioid overdose, opioid use disorders and addiction.

In one aspect is a compound of Formula (I):

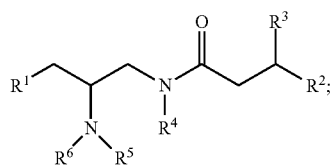

Formula (I)

wherein:
$R^1$ is selected from $C_{6-10}$aryl and $C_{1-9}$heteroaryl, wherein $C_{6-10}$aryl and $C_{1-9}$heteroaryl are optionally substituted with one, two, three, four, or five $R^1$;
$R^2$ is selected from $C_{6-10}$aryl and $C_{1-9}$heteroaryl, wherein $C_{6-10}$aryl and $C_{1-9}$heteroaryl are optionally substituted with one, two, three, four, or five $R^8$;
$R^3$ is $-X-R^{3a}$, $C_2-C_8$alkyl, $C_2-C_8$haloalkyl, or $C_1-C_8$alkenyl;
X is a bond or $C_{1-6}$alkylene;
$R^{3a}$ is $C_{3-8}$cycloalkyl optionally substituted with one, two, three, four, or five $R^9$;
$R^4$ is hydrogen, $C_1-C_6$alkyl, or $C_1-C_6$haloalkyl;
$R^1$ and $R^6$ are each independently selected from hydrogen, $C_1-C_6$alkyl, and $C_1-C_6$haloalkyl; or $R^5$ and $R^6$ are combined to form an azetidinyl, pyrrolidinyl, piperidinyl, or piperazinyl ring;
each $R^7$ is independently selected from halogen, $-CN$, $C_{1-6}$alkyl, $C_{1-6}$haloalkyl, $C_{2-6}$ alkenyl, $C_{2-6}$alkynyl, $C_{3-6}$cycloalkyl, $C_{2-9}$heterocycloalkyl, $C_{6-10}$aryl, $C_{1-9}$heteroaryl, $-OR^{10}$, $-SR^{10}$, $-C(O)OR^{10}$, $-OC(O)N(R^{10})(R^{11})$, $-N(R^{12})C(O)N(R^{10})(R^{11})$, $-N(R^{12})C(O)R^{13}$, $-N(R^{12})C(O)OR^{13}$, $-N(R^{12})S(O)_2R^{13}$, $-C(O)R^{13}$, $-OC(O)R^{10}$, $-C(O)N(R^{10})(R^{11})$, $-C(O)C(O)N(R^{10})(R^{11})$, $-S(O)R^{13}$, $-S(O)_2R^{13}$, and $-S(O)_2N(R^{10})(R^{11})$, wherein $C_{1-6}$alkyl, $C_{2-6}$ alkenyl, $C_{2-6}$alkynyl, $C_{3-6}$cycloalkyl, $C_{2-9}$heterocycloalkyl, $C_{6-10}$aryl, and $C_{2-9}$heteroaryl are optionally substituted with one, two, or three groups selected from halogen, $-CN$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, $-OR^{14}$, $-SR^{14}$, $-C(O)OR^{14}$, $-OC(O)N(R^{14})(R^{15})$, $-N(R^{16})C(O)N(R^{14})(R^{15})$, $-N(R^{16})C(O)R^{17}$, $-N(R^{16})C(O)OR^{17}$, $-N(R^{16})S(O)_2R^{17}$, $-C(O)R^{17}$, $-OC(O)R^{17}$, $-C(O)N(R^{14})(R^{15})$, $-C(O)C(O)N(R^{14})(R^{15})$, $-S(O)R^{17}$, $-S(O)_2R^{17}$, and $-S(O)_2N(R^{14})(R^{15})$; or two $R^7$ are combined to form a heterocycloalkyl ring optionally substituted with oxo; or $R^7$ and $R^6$ are combined to form a heterocycloalkyl ring;
each $R^8$ and each $R^9$ are each independently selected from halogen, $-CN$, $C_{1-6}$alkyl, $C_{1-6}$ haloalkyl, $C_{2-6}$alkenyl, $C_{2-6}$alkynyl, $C_{3-6}$cycloalkyl, $C_{2-9}$heterocycloalkyl, $C_{6-10}$aryl, $C_1$, heteroaryl, $-OR^{10}$, $-SR^{10}$, $-C(O)OR^{10}$, $-OC(O)N(R^{10})(R^{11})$, $-N(R^{12})C(O)N(R^{10})(R^{11})$, $-N(R^{12})C(O)R^{11}$, $-N(R^{12})C(O)OR^{13}$, $-N(R^{12})S(O)_2R^{13}$, $-C(O)R^{13}$, $-OC(O)R^{13}$, $-C(O)N(R^{10})(R^{11})$, $-C(O)C(O)N(R^{10})(R^{11})$, $-S(O)R^{13}$, $-S(O)_2R^{13}$, and $-S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-6}$heterocycloalkyl, $C_{6-10}$aryl, and $C_{1-9}$heteroaryl are optionally substituted with one, two, or three groups selected from halogen, $-CN$, $C_{1-6}$alkyl, $C_{1-6}$haloalkyl, $C_{2-6}$alkenyl, $C_{2-6}$alkynyl, $C_{3-6}$cycloalkyl, $C_2$, heterocycloalkyl, $C_{6-10}$aryl, $C_{1-6}$heteroaryl, $-OR^{14}$, $-SR^{14}$, $-C(O)OR^{14}$, $-OC(O)N(R^{14})(R^{15})$, $-N(R^{16})C(O)N(R^{14})(R^{15})$, $-N(R^{16})C(O)R^{17}$, $-N(R^{16})C(O)OR^{17}$, $-N(R^{16})S(O)_2R^{17}$, $-C(O)R^7$, $-OC(O)R^{17}$, $-C(O)N(R^{14})(R^{15})$, $-C(O)C(O)N(R^{14})(R^{15})$, $-S(O)R^7$, $-S(O)_2R^{17}$, and $-S(O)_2N(R^{14})(R^{15})$;
each $R^{10}$ is independently selected from hydrogen, $C_{1-6}$alkyl, $C_{1-6}$ haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$ alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$ heteroaryl are optionally substituted with one, two, or three groups selected from halogen, $C_{1-6}$alkyl, $C_{1-6}$haloalkyl, $C_{1-6}$alkoxy, $C_{1-6}$cycloalkyl, $C_{2-9}$heterocycloalkyl, $C_{6-10}$-aryl, and $C_{1-9}$heteroaryl;
each $R^{10}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-4}$cycloalkyl, $C_{2-9}$ heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-4}$heterocycloalkyl, $C_{6-10}$aryl, and $C_{1-9}$heteroaryl are optionally substituted with one, two, or three groups selected from halogen, $C_{1-6}$alkyl, $C_{1-6}$haloalkyl, $C_{1-6}$alkoxy, $C_{3-6}$ cycloalkyl, $C_{2-9}$heterocycloalkyl, $C_{6-10}$aryl, and $C_{1-9}$heteroaryl;

each $R^{14}$ is independently selected from hydrogen, $C_{1-6}$alkyl, $C_{1-6}$ haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$ alkyl, $C_{2-6}$alkenyl, $C_{2-6}$alkynyl, $C_{3-6}$cycloalkyl, $C_{2-6}$heterocycloalkyl, $C_{6-10}$aryl, and $C_{1-9}$ heteroaryl are optionally substituted with one, two, or three groups selected from halogen, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{15}$ is independently selected from hydrogen, $C_{1-6}$alkyl, and $C_{1-6}$haloalkyl;

each $R^{16}$ is independently selected from hydrogen, $C_{1-6}$alkyl, and $C_{1-6}$haloalkyl; and each $R^{17}$ is independently selected $C_{1-6}$alkyl, $C_{2-6}$alkenyl, $C_{2-6}$alkynyl, $C_{3-6}$cycloalkyl, $C_{2-9}$ heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-4}$heterocycloalkyl, $C_{6-10}$aryl, and $C_{1-9}$heteroaryl are optionally substituted with one, two, or three groups selected from halogen, $C_{1-6}$alkyl, $C_{1-6}$haloalkyl, $C_{1-6}$alkoxy, $C_{3-6}$ cycloalkyl, $C_{2-9}$heterocycloalkyl, $C_{6-10}$aryl, and $C_{1-9}$heteroaryl;

or a pharmaceutically acceptable salt or solvate thereof.

In one embodiment is a compound of Formula (I), or a pharmaceutically acceptable salt thereof, having the structure of Formula (Ia):

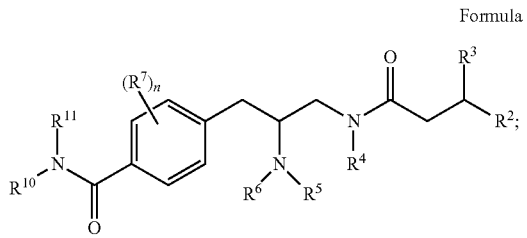

Formula (Ia)

wherein n is 0, 1, 2, 3, or 4.

In another embodiment is a compound of Formula (I), or a pharmaceutically acceptable salt thereof, having the structure of Formula (Ib):

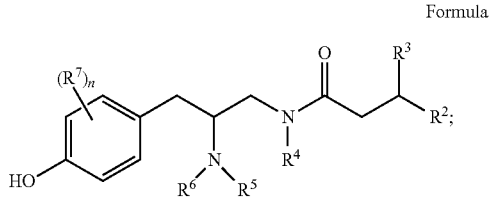

Formula (Ib)

wherein n is 0, 1, 2, 3, or 4.

In another embodiment is a compound of Formula (I), or a pharmaceutically acceptable salt thereof, having the structure of Formula (Ic);

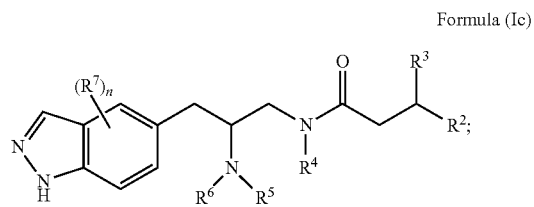

Formula (Ic)

wherein n is 0, 1, 2, 3, or 4.

In another embodiment is a compound of Formula (I), or a pharmaceutically acceptable salt thereof, having the structure of Formula (Id):

Formula (Id)

wherein n is 0, 1, 2, or 3.

In another embodiment is a compound of Formula (I) or a pharmaceutically acceptable salt thereof, having the structure of Formula (Ie):

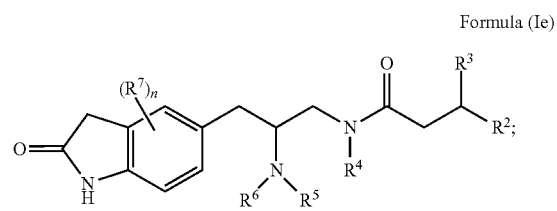

Formula (Ie)

wherein n is 0, 1, 2, or 3.

In another embodiment is a compound of Formula (I), or a pharmaceutically acceptable salt thereof, having the structure of Formula (If):

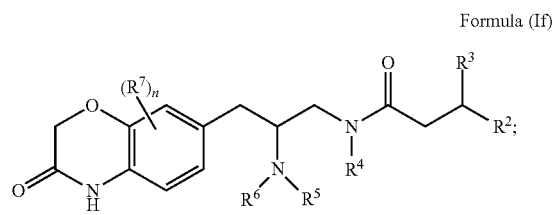

Formula (If)

wherein n is 0, 1, 2, or 3.

In another embodiment is a compound of Formula (I), or a pharmaceutically acceptable salt thereof, having the structure of Formula (Ig):

Formula (Ig)

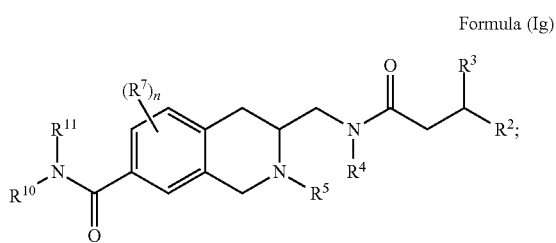

wherein n is 0, 1, 2, or 3.

In another embodiment is a compound of Formula (I), or a pharmaceutically acceptable salt thereof, having the structure of Formula (Ih):

Formula (Ih)

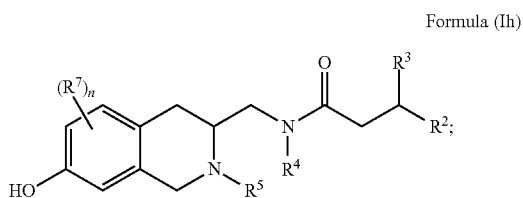

wherein n is 0, 1, 2, or 3.

In another embodiment is a compound of Formula (I), (Ia), (Ib), (Ic), (Id), (Ie), (If), (Ig), or (Ih), or a pharmaceutically acceptable salt or solvate thereof, wherein $R^0$ is independently selected from hydrogen and $C_{1-6}$alkyl. In another embodiment is a compound of Formula (I), (Ia), (Ib), (Ic), (Id), (Ie), (If), (Ig), or (Ih), or a pharmaceutically acceptable salt thereof, wherein $R^{11}$ is hydrogen. In another embodiment is a compound of Formula (I), (Ia), (Ib), (Ic), (Id), (Ie), (If), (Ig), or (Ih), or a pharmaceutically acceptable salt or solvate thereof, wherein n is 2. In another embodiment is a compound of Formula (I), (Ia), (Ib), (Ic), (Id), (Ie), (If), (Ig), or (Ih), or a pharmaceutically acceptable salt or solvate thereof, wherein n is 1. In another embodiment is a compound of Formula (I), (Ia), (Ib), (Ic), (Id), (Ie), (If), (Ig), or (Ih), or a pharmaceutically acceptable salt or solvate thereof, wherein n is 0. In another embodiment is a compound of Formula (I), (Ia), (Ib), (Ic), (Id), (Ie), (If), (Ig), or (Ih), or a pharmaceutically acceptable salt or solvate thereof, wherein each $R^7$ is independently selected from halogen, $C_{1-6}$alkyl, $C_{1-6}$haloalkyl, $-OR^{10}$, and $-C(O)N(R^{10})(R^{11})$. In another embodiment is a compound of Formula (I), (Ia), (Ib), (Ic), (Id), (Ie), (If), (Ig), or (Ih), or a pharmaceutically acceptable salt or solvate thereof, wherein each $R^{10}$ is independently selected from hydrogen and $C_{1-6}$alkyl. In another embodiment is a compound of Formula (I), (Ia), (Ib), (Ic), (Id), (Ie), (If), (Ig), or (Ih), or a pharmaceutically acceptable salt or solvate thereof, wherein each $R^7$ is independently selected from halogen and $C_{1-6}$alkyl. In another embodiment is a compound of Formula (I), (Ia), (Ib), (Ic), (Id), (Ie), (If), (Ig), or (Ih), or a pharmaceutically acceptable salt or solvate thereof, wherein $R^3$ is $-X-R^{3a}$. In another embodiment is a compound of Formula (I), (Ia), (Ib), (Ic), (Id), (Ie), (If), (Ig), or (Ih), or a pharmaceutically acceptable salt or solvate thereof, wherein X is a bond. In another embodiment is a compound of Formula (I), (Ia), (Ib), (Ic), (Id), (Ie), (If), (Ig), or (Ih), or a pharmaceutically acceptable salt or solvate thereof, wherein X is $C_{1-6}$alkylene. In another embodiment is a compound of Formula (I), (Ia), (Ib), (Ic), (Id), (Ie), (If), (Ig), or (Ih), or a pharmaceutically acceptable salt or solvate thereof, wherein X is $-CH_2-$. In another embodiment is a compound of Formula (I), (Ia), (Ib), (Ic), (Id), (Ie), (If), (Ig), or (Ih), or a pharmaceutically acceptable salt or solvate thereof, wherein $R^3$ is $C_{3-8}$cycloalkyl optionally substituted with one, two, or three $R^9$. In another embodiment is a compound of Formula (I), (Ia), (Ib), (Ic), (Id), (Ie), (If), (Ig), or (Ih), or a pharmaceutically acceptable salt or solvate thereof, wherein $R^{3a}$ is $C_{3-8}$cycloalkyl substituted with one, two, or three $R^9$. In another embodiment is a compound of Formula (I), (Ia), (Ib), (Ic), (Id), (Ie), (If), (Ig), or (i), or a pharmaceutically acceptable salt or solvate thereof, wherein $R^3$ is $C_{3-8}$cyclopropyl substituted with one, two, or three $R^9$. In another embodiment is a compound of Formula (I), (Ia), (Ib), (Ic), (Id), (Ie), (If), (Ig), or (Ih), or a pharmaceutically acceptable salt or solvate thereof, wherein each $R^9$ is independently selected from halogen, $-CN$, $C_{1-6}$alkyl, and $C_{1-6}$ haloalkyl. In another embodiment is a compound of Formula (I), (Ia), (Ib), (Ic), (Id), (Ie), (If), (Ig), or (Ih), or a pharmaceutically acceptable salt or solvate thereof, wherein $R^{3a}$ is cyclopropyl substituted with one $R^9$. In another embodiment is a compound of Formula (I), (Ia), (Ib), (Ic), (Id), (Ie), (If), (Ig), or (Ih), or a pharmaceutically acceptable salt or solvate thereof, wherein $R^{3a}$ is cyclopropyl substituted with $C_{1-6}$haloalkyl. In another embodiment is a compound of Formula (I), (Ia), (Ib), (Ic), (Id), (Ie), (If), (Ig), or (Ih), or a pharmaceutically acceptable salt or solvate thereof, wherein $R^{3a}$ is cyclopropyl substituted with $-CF_3$. In another embodiment is a compound of Formula (I), (Ia), (Ib), (Ic), (Id), (Ie), (If), (Ig), or (Ih), or a pharmaceutically acceptable salt or solvate thereof, wherein $R^{3a}$ is unsubstituted $C_{3-8}$cycloalkyl. In another embodiment is a compound of Formula (I), (Ia), (Ib), (Ic), (Id), (Ie), (If), (Ig), or (Ih), or a pharmaceutically acceptable salt or solvate thereof, wherein $R^{3a}$ is unsubstituted cyclopropyl. In another embodiment is a compound of Formula (I), (Ia), (Ib), (Ic), (Id), (Ie), (If), (Ig), or (Ih), or a pharmaceutically acceptable salt or solvate thereof, wherein $R^3$ is $C_2$-$C_8$alkyl. In another embodiment is a compound of Formula (I), (Ia), (Ib), (Ic), (Id), (Ie), (If), (Ig), or (Ih), or a pharmaceutically acceptable salt or solvate thereof, wherein $R^3$ is $-CH(CH_3)_2$, $-C(CH_3)_3$, $-CH_2CH(CH_3)_2$, or $-CH_2CH_2CH_2CH_3$. In another embodiment is a compound of Formula (I), (Ia), (Ib), (Ic), (Id), (Ie), (If), (Ig), or (i), or a pharmaceutically acceptable salt or solvate thereof, wherein $R^3$ is $C_2$-$C_8$alkenyl. In another embodiment is a compound of Formula (I), (Ia), (Ib), (Ic), (Id), (Ie), (If), (Ig), or (Ih), or a pharmaceutically acceptable salt or solvate thereof, wherein $R^3$ is $-CH_2CH_2CH=CH$. In another embodiment is a compound of Formula (I), (Ia), (Ib), (Ic), (Id), (Ie), (If), (Ig), or (Ih), or a pharmaceutically acceptable salt or solvate thereof, wherein $R^3$ is $C_2$-$C_8$haloalkyl. In another embodiment is a compound of Formula (I), (Ia), (Ib), (Ic), (Id), (Ie), (If), (Ig), or (Ih), or a pharmaceutically acceptable salt or solvate thereof, wherein $R^2$ is $C_{6-10}$aryl optionally substituted with one, two, three, four, or five $R^8$. In another embodiment is a compound of Formula (I), (Ia), (Ib), (Ic), (Id), (Ie), (If), (Ig), or (Ih), or a pharmaceutically acceptable salt or solvate thereof, wherein $R^2$ is phenyl optionally substituted with one, two, three, four, or five $R^8$. In another embodiment is a compound of Formula (I), (Ia), (Ib), (Ic), (Id), (Ie), (If), (Ig), or (Ih), or a pharmaceutically acceptable salt or solvate thereof, wherein $R^2$ is phenyl substituted with one, two, or three $R^8$. In another embodiment is a compound of Formula (I), (Ia), (Ib), (Ic), (Id), (Ie), (If), (Ig), or (Ih), or a pharmaceutically acceptable salt or solvate thereof, wherein $R^2$ is $C_{1-9}$heteroaryl optionally substituted with one, two, three, four, or five $R^8$. In another embodiment is a compound of Formula (I), (Ia), (Ib), (Ic), (Id), (Ie), (If), (Ig), or (Ih), or a pharmaceutically acceptable salt or solvate thereof, wherein $R^2$ is $C_{1-4}$heteroaryl substituted with one, two, or three $R^8$. In another embodiment is a compound of Formula (I), (Ia), (Ib), (Ic), (Id), (Ie), (If), (Ig), or (Ih), or a pharmaceutically acceptable salt or solvate thereof, wherein $R^2$ is pyridinyl, pyrimidinyl, or thiazolyl, wherein pyridinyl, pyrimidinyl, and thiazolyl are substituted with one, two, or three $R^a$. In another embodiment is a compound of Formula (I), (Ia), (Ib), (Ic), (Id), (Ie), (If), (Ig), or (Ih), or a pharmaceutically acceptable salt or solvate thereof, wherein each $R^8$ is independently selected from halogen, $C_{1-6}$alkyl, $C_{1-6}$haloalkyl, and —$OR^{10}$. In another embodiment is a compound of Formula (I), (Ia), (Ib), (Ic), (Id), (Ie), (If), (Ig), or (Ih), or a pharmaceutically acceptable salt or solvate thereof, wherein each $R^{10}$ is $C_{1-6}$alkyl. In another embodiment is a compound of Formula (I), (Ia), (Ib), (Ic), (Id), (Ie), (If), (Ig), or (Ih), or a pharmaceutically acceptable salt or solvate thereof, wherein $R^2$ is unsubstituted phenyl. In another embodiment is a compound of Formula (I), (Ia), (Ib), (Ic), (Id), (Ie), (If), (Ig), or (Ih), or a pharmaceutically acceptable salt or solvate thereof, wherein $R^2$ is unsubstituted $C_{1-9}$heteroaryl. In another embodiment is a compound of Formula (I), (Ia), (Ib), (Ic), (Id), (Ie), (If), (Ig), or (Ih), or a pharmaceutically acceptable salt or solvate thereof, wherein $R^2$ is unsubstituted pyridinyl, unsubstituted pyrimidinyl, or unsubstituted thiazolyl. In another embodiment is a compound of Formula (I), (Ia), (Ib), (Ic), (Id), (Ie), (If), (Ig), or (Ih), or a pharmaceutically acceptable salt or solvate thereof, wherein $R^5$ and $R^6$ are each independently selected from hydrogen, $C_1$-$C_6$alkyl, and $C_1$-$C_6$haloalkyl. In another embodiment is a compound of Formula (I), (Ia), (Ib), (Ic), (Id), (Ie), (If), (Ig), or (Ih), or a pharmaceutically acceptable salt or solvate thereof, wherein $R^5$ is selected from hydrogen and $C_1$-$C_6$alkyl. In another embodiment is a compound of Formula (I), (Ia), (Ib), (Ic), (Id), (Ie), (If), (Ig), or (Ih), or a pharmaceutically acceptable salt or solvate thereof, wherein $R^6$ is selected from hydrogen and $C_1$-$C_6$alkyl. In another embodiment is a compound of Formula (I), (Ia), (Ib), (Ic), (Id), (Ie), (If), (Ig), or (Ih), or a pharmaceutically acceptable salt or solvate thereof, wherein $R^5$ and $R^6$ are $C_1$-$C_6$alkyl. In another embodiment is a compound of Formula (I), (Ia), (Ib), (Ic), (Id), (Ie), (If), (Ig), or (Ih), or a pharmaceutically acceptable salt or solvate thereof, wherein $R^5$ and $R^6$ are combined to form an azetidinyl, pyrrolidinyl, piperidinyl, or piperazinyl ring. In another embodiment is a compound of Formula (I), (Ia), (Ib), (Ic), (Id), (Ie), (If), (Ig), or (Ih), or a pharmaceutically acceptable salt or solvate thereof, wherein $R^4$ is hydrogen.

In another embodiment is a pharmaceutical composition comprising a compound of Formula (I) described herein, or a pharmaceutically acceptable salt thereof, and at least one pharmaceutically acceptable excipient.

In another embodiment is a method of treating a disease or condition selected from neuropsychiatric disorders, depression, obsessive compulsive disorder, alcohol addiction, gambling addiction, pain, opioid overdose, opioid use disorders and addiction in a subject in need thereof comprising administering to the subject a therapeutically effective amount of a compound of Formula (I) described herein, or a pharmaceutically acceptable salt thereof.

DETAILED DESCRIPTION OF THE INVENTION

The compounds disclosed herein modulate one, two or three of the mu opioid receptor (MOR), the kappa opioid receptor (KOR) and/or the delta opioid receptor (DOR). As used herein, a "modulator" of MOR and/or KOR and/or DOR a compound which, when administered to a subject, provides the desired modulation of the target receptor. For example, the compound may function as a full or partial antagonist or agonist of the receptor, either by interacting directly or indirectly with the target receptor.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ . . . $C_1$-$C_x$ $C_1$-$C_x$ refers to the number of carbon atoms that make up the moiety to which it designates (excluding optional substituents).

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Alkyl" or "alkylene" refers to a straight or branched hydrocarbon chain radical consisting solely of carbon and hydrogen atoms, containing no unsaturation, having from one to eighteen carbon atoms (e.g., $C_1$-$C_{18}$ alkyl). In certain embodiments, an alkyl comprises three to eighteen carbon atoms (e.g., $C_3$-$C_{18}$ alkyl). In certain embodiments, an alkyl comprises one to fifteen carbon atoms (e.g., $C_1$-$C_{15}$ alkyl). In certain embodiments, an alkyl comprises one to twelve carbon atoms (e.g., $C_1$-$C_{12}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_2$-$C_5$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (isobutyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)$OR^a$, —C(O)$N(R^a)_2$, —$N(R^a)$C(O)$OR^f$, —OC(O)—$NR^aR^f$, —$N(R^a)$C(O)$R^f$, —$N(R^a)$S(O)$R^f$ (where t is 1 or 2), —S(O)$_t OR^a$ (where t is 1 or 2), —S(O)$R^f$ (where t is 1 or 2) and —S(O)$_t N(R^a)$, (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to eighteen carbon atoms. In certain embodiments, an alkenyl comprises three to eighteen carbon atoms. In certain embodiments, an alkenyl comprises three to twelve carbon atoms. In certain embodiments, an alkenyl comprises six to twelve carbon atoms. In certain embodiments, an alkenyl comprises six to ten carbon atoms. In certain embodiments, an alkenyl comprises eight to ten carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)$OR^a$, —C(O)$N(R^a)_2$, —$N(R^a)$C(O)$OR^f$, —OC(O)—$NR^aR^f$, —$N(R^a)$C(O)$R^f$, —$N(R^a)$S(O)$R^f$ (where t is 1 or 2), —S(O)$_t OR^a$ (where t is 1 or 2), —S(O)$R^f$ (where t is 1 or 2) and —S(O)$_t N(R^a)$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to eighteen carbon atoms. In certain embodiments, an alkynyl comprises three to eighteen carbon atoms. In certain embodiments, an alkynyl comprises three to twelve carbon atoms. In certain embodiments, an alkynyl comprises six to twelve carbon atoms. In certain embodiments, an alkynyl comprises six to ten carbon atoms. In certain embodiments, an alkynyl comprises eight to ten carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)$OR^a$, —C(O)$N(R^a)$?, —$N(R^a)$C(O)$OR^f$, —OC(O)—$NR^aR^f$, —$N(R^a)$C(O)$R^f$, —$N(R^a)$S(O)$R^f$ (where t is 1 or 2), —S(O)$_t OR^a$ (where t is 1 or 2), —S(O)$R^f$ (where t is 1 or 2) and —S(O)$_t N(R^a)$, (where t is 1 or 2) where each $R^8$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system is accordance with the Hackel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$_t R^a$ (where t is 1 or 2), —$R^b$—S(O)$_t OR^a$ (where t is 1 or 2), —$R^b$—S(O)$_t OR^a$ (where t is 1 or 2), and —$R^b$—S(O)$_t N(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O— aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or poly cyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond.

Cycloalkyls are saturated, (i.e., containing single C—C bonds only) or partially unsaturated (i. e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_6$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless stated otherwise specifically in the specification, the term "cycloalkyl" is meant to include cycloalkyl radicals that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2), and —$R^b$—S(O)$_t$N($R^a$)$_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Haloalkoxy" refers to an alkoxy radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic, or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidornyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2), and —$R^b$—S(O)$_t$N($R^a$)$_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^x$ is a straight or branched alkylene or alkenylene chain.

"Heteroaryl" refers to a radical derived from a 3- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above which are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2), and —$R^b$—S(O)$_t$N($R^a$)$_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the contemplated by this disclosure. When the compounds described herein contain alkene double bonds, and unless specified otherwise, it is intended that this disclosure includes both F and Z geometric isomers (e.g., cis or trans.) Likewise, all possible isomers, as well as their racemic and optically pure forms, and all tautomeric forms are also intended to be included. The term "geometric isomer" refers to F or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

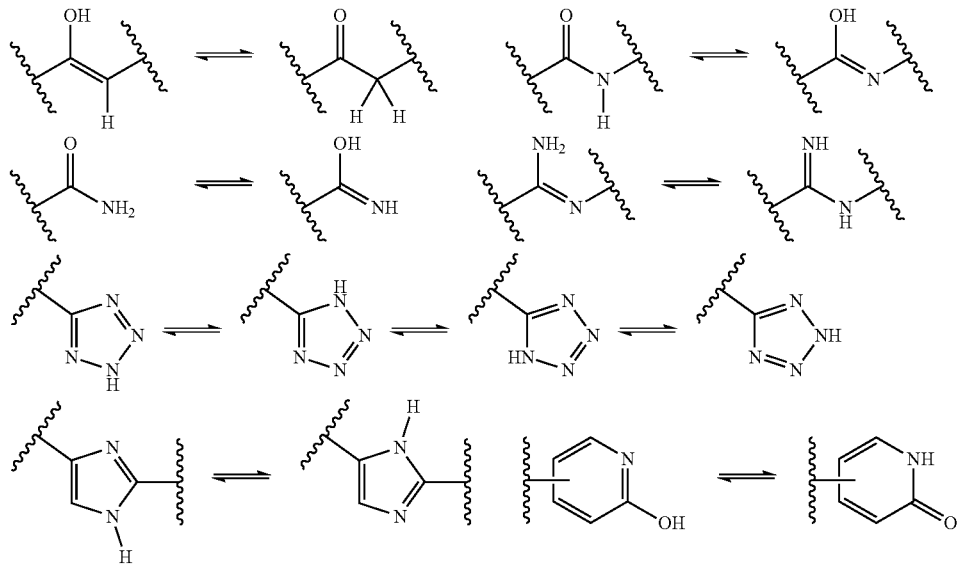

nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are "Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobuty rates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, poly amine resins, and the like. See Berge et al., supra.

The term "subject" or "patient" encompasses mammals. Examples of mammals include, but are not limited to, any member of the Mammalian class; humans, non-human primates such as chimpanzees, and other apes and monkey species: farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

The compounds of Formula (I), (Ia), (Ib), (Ic), (Id), (Ie), (If), (Ig), or (Ih), described herein are opioid receptor modulators. In some embodiments, the compounds of Formula (I), (Ia), (Ib), (Ic), (Id), (Ie), (If), (Ig), or (Ih), described herein are mu opioid receptor antagonists. In some embodiments, the compounds of Formula (I) described herein are delta opioid receptor antagonists. In some embodiments, the compounds of Formula (I), (Ia), (Ib), (Ic), (Id), (Ie), (If), (Ig), or (Ih), described herein are kappa opioid receptor antagonists. In some embodiments, the compounds of Formula (I), (Ia), (Ib), (Ic), (Id), (Ie), (If), (Ig), or (Ih), described herein are selective opioid receptor antagonists. In some embodiments, the compounds of Formula (I), (Ia), (Ib), (Ic), (Id), (Ie), (If), (Ig), or (Ih), described herein, and compositions comprising these compounds, are useful for the treatment of one or more conditions selected from neuropsychiatric disorders, depression, obsessive compulsive disorder, alcohol addiction, gambling addiction, pain, opioid overdose, opioid use disorders and addiction.

In some embodiments is a compound of Formula (I):

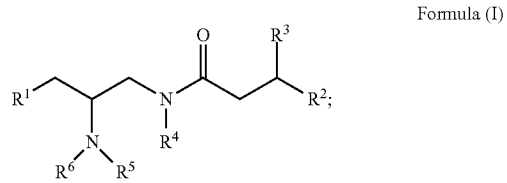

Formula (I)

wherein:

$R^1$ is selected from $C_{6-10}$aryl and $C_{1-9}$heteroaryl, wherein $C_{6-10}$aryl and $C_{1-9}$heteroaryl are optionally substituted with one, two, three, four, or five $R^7$;

$R^2$ is selected from $C_{6-10}$aryl and $C_{1-9}$heteroaryl, wherein $C_{6-10}$aryl and $C_{1-9}$heteroaryl are optionally substituted with one, two, three, four, or five $R^8$;

$R^3$ is —X—$R^{3a}$, $C_2$-$C_8$alkyl, $C_2$-$C_8$haloalkyl, or $C_1$-$C_8$alkenyl;

X is a bond or $C_{1-6}$alkylene;

$R^{3a}$ is $C_{3-8}$cycloalkyl optionally substituted with one, two, three, four, or five $R^9$;

$R^4$ is hydrogen, $C_1$-$C_6$alkyl, or $C_1$-$C_6$haloalkyl:

$R^5$ and $R^6$ are each independently selected from hydrogen, $C_1$-$C_6$alkyl, and $C_1$-$C_6$haloalkyl; or $R^5$ and $R^6$ are combined to form an azetidinyl, pyrrolidinyl, piperidinyl, or piperazinyl ring:

each $R^7$ is independently selected from halogen, —CN, $C_{1-6}$alkyl, $C_{1-6}$haloalkyl, $C_{2-6}$ alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$C(O)OR^{10}$, —$OC(O)N(R^{10})(R^{11})$, —$N(R^{12})C(O)N(R^{10})(R^{11})$, —$N(R^{12})C(O)R^{13}$, —$N(R^{12})C(O)OR^{13}$, —$N(R^{12})S(O)_2R^{13}$, —$C(O)R^{13}$, —$OC(O)R^{13}$, —$C(O)N(R^{10})(R^{11})$, —$C(O)C(O)N(R^{10})(R^{11})$, —$S(O)R^{13}$, —$S(O)_2R^3$, and —$S(O)_2N(R^{10})(R^1)$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, $C_{6-10}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$ heteroaryl, —OR$^{14}$, —SR$^{14}$, —C(O)OR$^{14}$, —OC(O)N(R$^{14}$)(R$^{15}$), —N(R$^{16}$)C(O)N(R$^{14}$)(R$^{15}$), —N(R$^{16}$)C(O)R$^{17}$, —N(R$^{16}$)C(O)OR$^{17}$, —N(R$^{16}$)S(O)$_2$R$^{17}$, —C(O)R$^{17}$, —OC(O)R$^{17}$, —C(O)N(R$^{14}$)(R$^{15}$), —C(O)C(O)N(R$^{14}$)(R$^{15}$), —S(O)R$^{17}$, —S(O)$_2$R$^{17}$, and —S(O)$_2$N(R$^{14}$)(R$^{15}$); or two R$^7$ are combined to form a heterocycloalkyl ring optionally substituted with oxo; or R$^7$ and R$^6$ are combined to form a heterocycloalkyl ring;

each R$^8$ and each R$^9$ are each independently selected from halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —C(O)OR$^{10}$, —OC(O)N(R$^{10}$)(R$^{11}$), —N(R$^{12}$)C(O)N(R$^{10}$)(R$^{11}$), —N(R$^{12}$)C(O)R$^{13}$, —N(R$^{12}$)C(O)OR$^{13}$, —N(R$^{12}$)S(O)$_2$R$^{13}$, —C(O)R$^{13}$, —OC(O)R$^{13}$, —C(O)N(R$^{10}$)(R$^{11}$), —C(O)C(O)N(R$^{10}$)(R$^{11}$), —S(O)R$^{13}$, —S(O)$_2$R$^3$, and —S(O)$_2$N(R$^{10}$)(R$^{11}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, $C_{1-6}$alkyl, $C_{1-4}$haloalkyl, $C_{2-6}$alkenyl, $C_{2-6}$alkynyl, $C_{3-6}$cycloalkyl, $C_{2-9}$ heterocycloalkyl, $C_{6-10}$aryl, $C_{1-9}$heteroaryl, —OR$^{14}$, —SR$^{14}$, —C(O)OR$^{14}$, —OC(O)N(R$^{14}$)(R$^{15}$), —N(R$^{16}$)C(O)N(R$^{14}$)(R$^{15}$), —N(R$^{16}$)C(O)R$^{17}$, —N(R$^{16}$)C(O)OR$^{17}$, —N(R$^{16}$)S(O)$_2$R$^{17}$—, —C(O)R$^{17}$, —OC(O)R$^{17}$, —C(O)N(R$^{14}$)(R$^{15}$), —C(O)C(O)N(R$^{14}$)(R$^{15}$), —S(O)R$^{17}$, —S(O)$_2$R$^{17}$, and —S(O)$_2$N(R$^{14}$)(R$^{13}$);

each R$^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$ alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$ heteroaryl are optionally substituted with one, two, or three groups selected from halogen, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$ heteroaryl;

each R$^{15}$ is independently selected from hydrogen, $C_{1-6}$alkyl, and $C_{1-6}$haloalkyl;

each R$^{12}$ is independently selected from hydrogen, $C_{1-6}$alkyl, and $C_{1-6}$haloalkyl;

each R$^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl. $C_{3-6}$cycloalkyl, $C_{2-9}$heterocycloalkyl, $C_{6-10}$aryl, and $C_{1-4}$heteroaryl are optionally substituted with one, two, or three groups selected from halogen, $C_{1-6}$alkyl, $C_{1-6}$ haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each R$^{14}$ is independently selected from hydrogen, $C_{1-6}$alkyl, $C_{1-6}$ haloalkyl, $C_{2-6}$alkenyl, $C_{2-4}$alkynyl, $C_{1-6}$cycloalkyl, $C_{2-9}$heterocycloalkyl, $C_{6-10}$ aryl, and $C_{1-9}$heteroaryl, wherein $C_{1-6}$alkyl, $C_{2-4}$alkenyl, $C_{2-6}$alkynyl, $C_{3-6}$cycloalkyl, $C_{2-6}$heterocycloalkyl, $C_{6-10}$aryl, and $C_{1-9}$ heteroaryl are optionally substituted with one, two, or three groups selected from halogen, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$ heteroaryl;

each R$^{15}$ is independently selected from hydrogen, $C_{1-6}$alkyl, and $C_{1-6}$haloalkyl;

each R$^{16}$ is independently selected from hydrogen, $C_{1-6}$alkyl, and $C_{1-6}$haloalkyl; and each R$^{17}$ is independently selected $C_{1-6}$alkyl, $C_{2-6}$alkenyl, $C_{2-6}$alkynyl, $C_{1-6}$cycloalkyl, $C_{2-9}$ heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$ aryl, and $C_{1-9}$heteroaryl; or a pharmaceutically acceptable salt or solvate thereof.

In some embodiments is a compound of Formula (I), or a pharmaceutically acceptable salt or solvate thereof, wherein R$^1$ is $C_{6-10}$aryl optionally substituted with one, two, three, four, or five R$^7$. In some embodiments is a compound of Formula (I), or a pharmaceutically acceptable salt or solvate thereof, wherein R$^1$ is phenyl optionally substituted with one, two, three, four, or five R$^7$. In some embodiments is a compound of Formula (I), or a pharmaceutically acceptable salt or solvate thereof, wherein R$^1$ is phenyl substituted with one, two, three, four, or five R$^7$. In some embodiments is a compound of Formula (I), or a pharmaceutically acceptable salt or solvate thereof, wherein R$^1$ is phenyl substituted with one, two, or three R$^7$. In some embodiments is a compound of Formula (I), or a pharmaceutically acceptable salt or solvate thereof, wherein R$^1$ is $C_{1-9}$heteroaryl optionally substituted with one, two, three, four, or five R$^7$. In some embodiments is a compound of Formula (I), or a pharmaceutically acceptable salt or solvate thereof, wherein R$^1$ is $C_{1-9}$heteroaryl substituted with one, two, three, four, or five R$^7$. In some embodiments is a compound of Formula (I), or a pharmaceutically acceptable salt or solvate thereof, wherein R$^1$ is $C_{1-9}$heteroaryl substituted with one, two, or three R$^7$. In some embodiments is a compound of Formula (I), or a pharmaceutically acceptable salt or solvate thereof, wherein R$^1$ is unsubstituted $C_{1-9}$ heteroaryl.

In some embodiments is a compound of Formula (I), or a pharmaceutically acceptable salt thereof, having the structure of Formula (Ia):

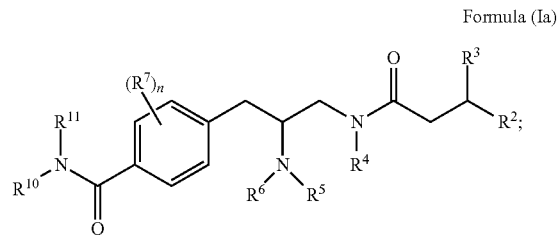

Formula (Ia)

wherein n is 0, 1, 2, 3, or 4.

In some embodiments is a compound of Formula (Ia), or a pharmaceutically acceptable salt or solvate thereof, wherein R$^{10}$ is independently selected from hydrogen and $C_{1-6}$alkyl. In some embodiments is a compound of Formula (Ia), or a pharmaceutically acceptable salt or solvate thereof, wherein R$^{10}$ is hydrogen. In some embodiments is a compound of Formula (Ia), or a pharmaceutically acceptable salt or solvate thereof, wherein R$^{10}$ is $C_{1-6}$alkyl. In some embodiments is a compound of Formula (Ia), or a pharmaceutically acceptable salt or solvate thereof, wherein R$^{10}$ is hydrogen and R$^{11}$ is hydrogen. In some embodiments is a compound of Formula (Ia), or a pharmaceutically acceptable salt or solvate thereof, wherein at least one R$^7$ substituent is present ortho to —C(O)N(R$^{10}$)(R$^{11}$), R$^{10}$ is hydrogen, R$^{11}$ is hydrogen, and the at least one ortho R$^7$ substituent is fluoro. In some embodiments is a compound of Formula (Ia), or a pharmaceutically acceptable salt or solvate thereof, wherein R$^{10}$ is $C_{1-6}$alkyl and R$^{11}$ is hydrogen.

In another embodiment is a compound of Formula (I), or a pharmaceutically acceptable salt thereof, having the structure of Formula (Ib):

Formula (Ib)

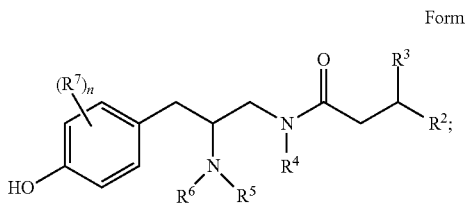

wherein n is 0, 1, 2, 3, or 4.

In another embodiment is a compound of Formula (I), or a pharmaceutically acceptable salt thereof, having the structure of Formula (Ic):

Formula (Ic)

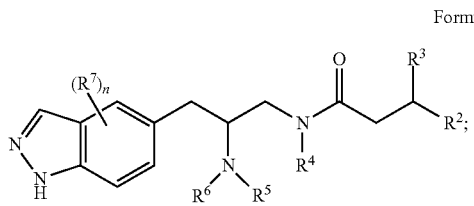

wherein n is 0, 1, 2, 3, or 4.

In another embodiment is a compound of Formula (I), or a pharmaceutically acceptable salt thereof, having the structure of Formula (Id):

Formula (Id)

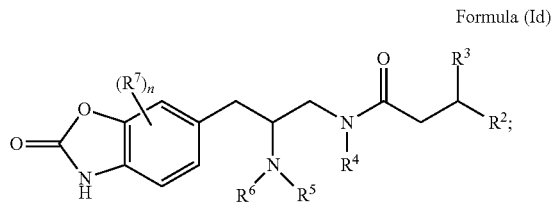

wherein n is 0, 1, 2, or 3.

In another embodiment is a compound of Formula (I), or a pharmaceutically acceptable salt thereof, having the structure of Formula (Ie):

Formula (Ie)

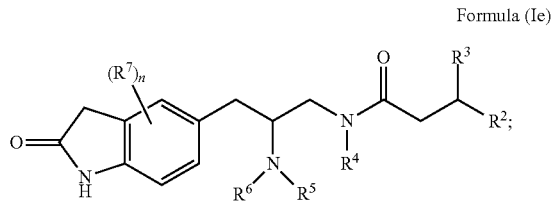

wherein n is 0, 1, 2, or 3.

In another embodiment is a compound of Formula (I), or a pharmaceutically acceptable salt thereof, having the structure of Formula (If):

Formula (If)

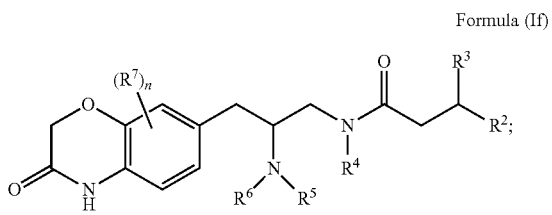

wherein n is 0, 1, 2, or 3.

In another embodiment is a compound of Formula (I) or a pharmaceutically acceptable salt thereof, having the structure of Formula (Ig):

Formula (Ig)

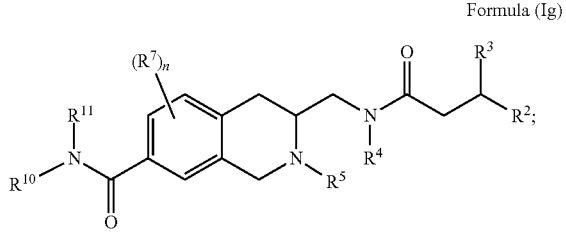

wherein n is 0, 1, 2, or 3.

In some embodiments is a compound of Formula (Ig), or a pharmaceutically acceptable salt or solvate thereof, wherein $R^{10}$ is independently selected from hydrogen and $C_{1-6}$alkyl. In some embodiments is a compound of Formula (Ig), or a pharmaceutically acceptable salt or solvate thereof, wherein $R^{10}$ is hydrogen. In some embodiments is a compound of Formula (Ig), or a pharmaceutically acceptable salt or solvate thereof, wherein $R^{10}$ is $C_{1-6}$alkyl. In some embodiments is a compound of Formula (Ig), or a pharmaceutically acceptable salt or solvate thereof, wherein $R^{10}$ is hydrogen and $R^{11}$ is hydrogen. In some embodiments is a compound of Formula (Ig), or a pharmaceutically acceptable salt or solvate thereof, wherein at least one $R^7$ substituent is present ortho to —C(O)N($R^{10}$)($R^{11}$), $R^{10}$ is hydrogen, $R^{11}$ is hydrogen, and the at least one ortho $R^7$ substituent is fluoro. In some embodiments is a compound of Formula (Ig), or a pharmaceutically acceptable salt or solvate thereof, wherein $R^{10}$ is $C_{1-6}$alkyl and $R^{11}$ is hydrogen.

In another embodiment is a compound of Formula (I), or a pharmaceutically acceptable salt thereof, having the structure of Formula (Ih).

Formula (Ih)

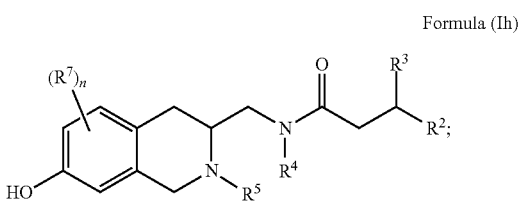

wherein n is 0, 1, 2, or 3.

In another embodiment is a compound of Formula (I), (Ia), (Ib), (Ic), (Id), (Ie), (If), (Ig), or (Ih), or a pharmaceutically acceptable salt or solvate thereof, wherein $R^{10}$ is independently selected from hydrogen and $C_{1-6}$alkyl. In another embodiment is a compound of Formula (I), (Ia), (Ib), (Ic), (Id), (Ie), (If), (Ig), or (Ih), or a pharmaceutically acceptable salt or solvate thereof, wherein $R^{10}$ is hydrogen. In another embodiment is a compound of Formula (I), (Ia), (Ib), (Ic), (Id), (Ie), (If), (Ig), or (Ih), or a pharmaceutically acceptable salt or solvate thereof, wherein $R^{10}$ is $C_{1-6}$alkyl. In another embodiment is a compound of Formula (I), (Ia), (Ib), (Ic), (Id), (Ie), (If), (Ig), or (Ih), or a pharmaceutically acceptable salt or solvate thereof, wherein $R^{11}$ is hydrogen. In another embodiment is a compound of Formula (I), (Ia), (Ib), (Ic), (Id), (Ie), (If), (Ig), or (Ih), or a pharmaceutically acceptable salt or solvate thereof, wherein n is 3. In another embodiment is a compound of Formula (I), (Ia), (Ib), (Ic), (Id), (Ie), (If), (Ig), or (Ih), or a pharmaceutically acceptable salt or solvate thereof, wherein n is 2. In another embodiment is a compound of Formula (I), (Ia), (Ib), (Ic), (Id), (Ie), (If), (Ig), or (Ih), or a pharmaceutically acceptable salt or solvate thereof, wherein n is 1. In another embodiment is a compound of Formula (I), (Ia), (Ib), (Ic), (Id), (Ie), (If), (Ig), or (Ih), or a pharmaceutically acceptable salt or solvate thereof, wherein n is 0. In another embodiment is a compound of Formula (I), (Ia), (Ib), (Ic), (Id), (Ie), (If), (Ig), or (Ih), or a pharmaceutically acceptable salt or solvate thereof, wherein n is 1 and $R^7$ is selected from halogen, $C_{1-6}$alkyl, $C_{1-6}$haloalkyl, —$OR^{10}$, and —$C(O)N(R^{10})(R^{11})$. In another embodiment is a compound of Formula (I), (Ia), (Ib), (Ic), (Id), (Ie), (If), (Ig), or (Ih), or a pharmaceutically acceptable salt or solvate thereof, wherein is 1, $R^7$ is selected from halogen, $C_{1-6}$alkyl, $C_{1-6}$haloalkyl, —$OR^{10}$, and —$C(O)N(R^{10})(R^{11})$, and each $R^{10}$ and each $R^{11}$ is independently selected from hydrogen and $C_{1-6}$alkyl. In another embodiment is a compound of Formula (I), (Ia), (Ib), (Ic), (Id), (Ie), (If), (Ig), or (Ih), or a pharmaceutically acceptable salt or solvate thereof, wherein n is 1 and $R^7$ is selected from halogen and $C_{1-6}$alkyl. In another embodiment is a compound of Formula (I), (Ia), (Ib), (Ic), (Id), (Ie), (If), (Ig), or (Ih), or a pharmaceutically acceptable salt or solvate thereof, wherein n is 1 and $R^7$ is halogen. In another embodiment is a compound of Formula (I), (Ia), (Ib), (Ic), (Id), (Ie), (If), (Ig), or (h), or a pharmaceutically acceptable salt or solvate thereof, wherein n is 1 and $R^7$ is $C_{1-6}$alkyl. In another embodiment is a compound of Formula (I), (Ia), (Ib), (Ic), (Id), (Ie), (If), (Ig), or (Th), or a pharmaceutically acceptable salt or solvate thereof, wherein n is 2 and each $R^7$ is independently selected from halogen, $C_{1-6}$alkyl, $C_{1-6}$haloalkyl, —$OR^{10}$, and —$C(O)N(R^{10})(R^{11})$. In another embodiment is a compound of Formula (I), (Ia), (Ib), (Ic), (Id), (Ie), (If), (Ig), or (Ih), or a pharmaceutically acceptable salt or solvate thereof, wherein n is 2, each $R^7$ is independently selected from halogen, $C_{1-6}$alkyl, $C_{1-6}$haloalkyl, —$OR^{10}$, and —$C(O)N(R^{10})(R^1)$, and each $R^{10}$ and each $R^{11}$ is independently selected from hydrogen and $C_{1-6}$alkyl. In another embodiment is a compound of Formula (I), (Ia), (Ib), (Ic), (Id), (Ie), (If), (Ig), or (Ih), or a pharmaceutically acceptable salt or solvate thereof, wherein n is 2 and each $R^7$ is independently selected from halogen and $C_{1-6}$alkyl. In another embodiment is a compound of Formula (I), (Ia), (Ib), (Ic), (Id), (Ie), (If), (Ig), or (Ih), or a pharmaceutically acceptable salt or solvate thereof, wherein n is 2 and each $R^7$ is halogen. In another embodiment is a compound of Formula (I), (Ia), (Ib), (Ic), (Id), (Ie), (If), (Ig), or (Ih), or a pharmaceutically acceptable salt or solvate thereof, wherein n is 2 and each $R^7$ is $C_{1-6}$alkyl. In another embodiment is a compound of Formula (I), (Ia), (Ib), (Ic), (Id), (Ie), (If), (Ig), or (Ih), or a pharmaceutically acceptable salt or solvate thereof, wherein n is 3 and each $R^7$ is independently selected from halogen, $C_{1-6}$alkyl, $C_{1-6}$haloalkyl, —$OR^{10}$, and —$C(O)N(R^{10})(R^{11})$. In another embodiment is a compound of Formula (I), (Ia), (Ib), (Ic), (Id), (Ie), (If), (Ig), or (Ih), or a pharmaceutically acceptable salt or solvate thereof, wherein n is 3, each $R^7$ is independently selected from halogen, $C_{1-6}$alkyl, $C_{1-4}$haloalkyl, —$OR^{10}$, and —$C(O)N(R^{10})(R^{11})$, and each $R^{10}$ and each $R^{11}$ is independently selected from hydrogen and $C_{1-6}$alkyl. In another embodiment is a compound of Formula (I), (Ia), (Ib), (Ic), (Id), (Ie), (If), (Ig), or (Ih), or a pharmaceutically acceptable salt or solvate thereof, wherein n is 3 and each $R^7$ is independently selected from halogen and $C_{1-6}$alkyl. In another embodiment is a compound of Formula (I), (Ia), (Ib), (Ic), (Id), (Ie), (If), (Ig), or (Ih), or a pharmaceutically acceptable salt or solvate thereof, wherein n is 3 and each $R^7$ is halogen. In another embodiment is a compound of Formula (I), (Ia), (Ib), (Ic), (Id), (Ie), (If), (Ig), or (Ih), or a pharmaceutically acceptable salt or solvate thereof, wherein n is 3 and each $R^7$ is $C_{1-6}$alkyl.

In another embodiment is a compound of Formula (I), (Ia), (Ib), (Ic), (Id), (Ie), (If), (Ig), or (Ih), or a pharmaceutically acceptable salt or solvate thereof, wherein $R^3$ is —X—$R^{3a}$. In another embodiment is a compound of Formula (I), (Ia), (Ib), (Ic), (Id), (Ie), (If), (Ig), or (Ih), or a pharmaceutically acceptable salt or solvate thereof, wherein X is a bond. In another embodiment is a compound of Formula (I), (Ia), (Ib), (Ic), (Id), (Ie), (If), (Ig), or (Ih), or a pharmaceutically acceptable salt or solvate thereof, wherein X is $C_{1-6}$alkylene. In another embodiment is a compound of Formula (I), (Ia), (Ib), (Ic), (Id), (Ie), (If), (Ig), or (Ih), or a pharmaceutically acceptable salt or solvate thereof, wherein X is —$CH_2$—. In another embodiment is a compound of Formula (I), (Ia), (Ib), (Ic), (Id), (Ie), (If), (Ig), or (Ih), or a pharmaceutically acceptable salt or solvate thereof, wherein $R^3$ is $C_{3-8}$cycloalkyl optionally substituted with one, two, or three $R^9$. In another embodiment is a compound of Formula (I), (Ia), (Ib), (Ic), (Id), (Ie), (If), (Ig), or (Ih), or a pharmaceutically acceptable salt or solvate thereof, wherein $R^3$ is $C_{3-8}$cycloalkyl substituted with one, two, or three $R^9$. In another embodiment is a compound of Formula (I), (Ia), (Ib), (Ic), (Id), (Ie), (If), (Ig), or (Ih), or a pharmaceutically acceptable salt or solvate thereof, wherein $R^{3a}$ is $C_{3-8}$cyclopropyl substituted with one, two, or three $R^9$. In another embodiment is a compound of Formula (I), (Ia), (Ib), (Ic), (Id), (Ie), (If), (Ig), or (Ih), or a pharmaceutically acceptable salt or solvate thereof, wherein each $R^9$ is independently selected from halogen, —CN, $C_{1-6}$alkyl, and $C_{1-6}$haloalkyl. In another embodiment is a compound of Formula (I), (Ia), (Ib), (Ic), (Id), (Ie), (If), (Ig), or (Ih), or a pharmaceutically acceptable salt or solvate thereof, wherein $R^{3a}$ is cyclopropyl substituted with one $R^9$. In another embodiment is a compound of Formula (I), (Ia), (Ib), (Ic), (Id), (Ie), (If), (Ig), or (Ih), or a pharmaceutically acceptable salt or solvate thereof, wherein $R^{3a}$ is cyclopropyl substituted with $C_{1-6}$haloalkyl. In another embodiment is a compound of Formula (I), (Ia), (Ib), (Ic), (Id), (Ie), (If), (Ig), or (Ih), or a pharmaceutically acceptable salt or solvate thereof, wherein $R^3$ is cyclopropyl substituted with —$CF_3$. In another embodiment is a compound of Formula (I), (Ia), (Ib), (Ic), (Id), (Ie), (If), (Ig), or (Ih), or a pharmaceutically acceptable salt or solvate thereof, wherein $R^3$ is unsubstituted $C_{3-8}$cycloalkyl. In another embodiment is a compound of Formula (I), (Ia), (Ib), (Ic), (Id), (Ie), (If), (Ig), or (Ih), or a pharmaceutically acceptable salt or solvate thereof, wherein $R^{3a}$ is unsubstituted cyclopropyl.

In some embodiments of a compound of Formula (I), (Ia), (Ib), (Ic), (Id), (Ie), (If), (Ig), or (Ih), or a pharmaceutically acceptable salt or solvate thereof, wherein $R^3$ is cyclopropyl substituted with —$CF_3$, one or more pharmacokinetic properties are enhanced compared to an embodiment wherein Rh is unsubstituted cyclopropyl. In some embodiments wherein $R^3$ is cyclopropyl substituted with —$CF_3$, CNS exposure (i.e., brain:plasma ratio) is enhanced compared to an embodiment wherein $R^3$ is unsubstituted cyclopropyl. In some embodiments, the enhanced pharmacokinetic property is increased permeability (e.g., cell permeability, tissue permeability, blood-brain barrier permeability, CNS permeability, etc.). In some embodiments, the enhanced pharmacokinetic property is increased lipophilicity or log P. In some embodiments, the enhanced pharmacokinetic property is increased bioavailability (e.g., oral bioavailability). In some embodiments, the enhanced pharmacokinetic property is increased metabolic stability. In some embodiments, the enhanced pharmacokinetic property is decreased efflux. In some embodiments, the enhanced pharmacokinetic property is decreased clearance. In some embodiments, the enhanced pharmacokinetic property is decreased non-specific binding (e.g., plasma protein binding). In some embodiments, the enhanced pharmacokinetic property is decreased off-target binding (e.g., cytochrome P450 enzymes or other metabolizing enzymes).

In some embodiments of a compound of Formula (I), (Ia), (Ib), (Ic), (Id), (Ie), (If), (Ig), or (Ih), or a pharmaceutically acceptable salt or solvate thereof, wherein $R^{3a}$ is cyclopropyl substituted with —$CF_3$, one or more pharmacological properties are enhanced compared to an embodiment wherein $R^{3a}$ is unsubstituted cyclopropyl. In some embodiments, the enhanced pharmacological property is increased mu opioid receptor binding. In some embodiments, the enhanced pharmacological property is decreased mu opioid receptor binding. In some embodiments, the enhanced pharmacological property is increased delta opioid receptor binding. In some embodiments, the enhanced pharmacological property is decreased delta opioid receptor binding. In some embodiments, the enhanced pharmacological property is increased kappa opioid receptor binding. In some embodiments, the enhanced pharmacological property is decreased kappa opioid receptor binding. In some embodiments, the enhanced pharmacological property is increased selectivity for mu over delta and/or kappa opioid receptors. In some embodiments, the enhanced pharmacological property is a modulated efficacy at the mu opioid receptor (e.g., increased or decreased activation (e.g., beta-arrestin activation, G-protein activation)). In some embodiments, the enhanced pharmacological property is increased mu opioid receptor efficacy. In some embodiments, the enhanced pharmacological property is decreased mu opioid receptor efficacy (e.g., G-protein activation).

In another embodiment is a compound of Formula (I), (Ia), (Ib), (Ic), (Id), (Ie), (If), (Ig), or (Ih), or a pharmaceutically acceptable salt or solvate thereof, wherein $R^3$ is $C_2$-$C_8$alkyl. In another embodiment is a compound of Formula (I), (Ia), (Ib), (Ic), (id), (Ie), (If), (Ig), or (Ih), or a pharmaceutically acceptable salt or solvate thereof, wherein $R^3$ is —$CH_2CH_3$, —$CH(CH_3)_2$, —$C(CH_3)_3$, —$CH_2CH(CH_3)_2$, or —$CH_2CH_2CH_2CH_3$. In another embodiment is a compound of Formula (I), (Ia), (Ib), (Ic), (Id), (Ie), (If), (Ig), or (Ih), or a pharmaceutically acceptable salt or solvate thereof, wherein $R^3$ is —$CH(CH_3)_2$, —$C(CH_3)_3$, —$CH_2CH(CH_3)_2$, or —$CH_2CH_2CH_2CH_3$. In another embodiment is a compound of Formula (I), (Ia), (Ib), (Ic), (Id), (Ie), (If), (Ig), or (Ih), or a pharmaceutically acceptable salt or solvate thereof, wherein $R^3$ is —$CH_2CH_3$. In another embodiment is a compound of Formula (I), (Ia), (Ib), (Ic), (Id), (Ie), (If), (Ig), or (Ih), or a pharmaceutically acceptable salt or solvate thereof, wherein $R^3$ is —$CH(CH_3)_2$. In another embodiment is a compound of Formula (I), (Ia), (Ib), (Ic), (Id), (Ie), (If), (Ig), or (Ih), or a pharmaceutically acceptable salt or solvate thereof, wherein $R^3$ is —$C(CH_3)_3$. In another embodiment is a compound of Formula (I), (Ia), (Ib), (Ic), (Id), (Ie), (If), (Ig), or (Ih), or a pharmaceutically acceptable salt or solvate thereof, wherein $R^3$ is —$CH_2CH(CH_3)_2$. In another embodiment is a compound of Formula (I), (Ia), (Ib), (Ic), (Id), (Ie), (If), (Ig), or (Ih), or a pharmaceutically acceptable salt or solvate thereof, wherein $R^3$ is —$CH_2CH_2CH_2CH_3$. In another embodiment is a compound of Formula (I), (Ia), (Ib), (Ic), (Id), (Ie), (If), (Ig), or (Ih), or a pharmaceutically acceptable salt or solvate thereof, wherein $R^3$ is —$CH_2CH_2CH_3$.

In another embodiment is a compound of Formula (I), (Ia), (Ib), (Ic), (Id), (Ie), (If), (Ig), or (Ih), or a pharmaceutically acceptable salt or solvate thereof, wherein $R^3$ is $C_2$-$C_8$alkenyl. In another embodiment is a compound of Formula (I), (Ia), (Ib), (Ic), (Id), (Ie), (If), (Ig), or (Ih), or a pharmaceutically acceptable salt or solvate thereof, wherein $R^3$ is —$CH_2CH_2CH$=$CH$.

In another embodiment is a compound of Formula (I), (Ia), (Ib), (Ic), (Id), (Ie), (If), (Ig), or (Ih), or a pharmaceutically acceptable salt or solvate thereof, wherein $R^3$ is $C_2$-$C_8$haloalkyl.

In another embodiment is a compound of Formula (I), (Ia), (Ib), (Ic), (Id), (Ie), (If), (Ig), or (Ih), or a pharmaceutically acceptable salt or solvate thereof, wherein $R^2$ is $C_{6-10}$aryl optionally substituted with one, two, three, four, or five $R^8$. In another embodiment is a compound of Formula (I), (Ia), (Ib), (Ic), (Id), (Ie), (If), (Ig), or (Ih), or a pharmaceutically acceptable salt or solvate thereof, wherein $R^2$ is phenyl optionally substituted with one, two, three, four, or five $R^8$. In another embodiment is a compound of Formula (I), (Ia), (Ib), (Ic), (Id), (Ie), (If), (Ig), or (Ih), or a pharmaceutically acceptable salt or solvate thereof, wherein $R^2$ is phenyl substituted with one, two, or three $R^8$. In another embodiment is a compound of Formula (I), (Ia), (Ib), (Ic), (Id), (Ie), (If), (Ig), or (Ih), or a pharmaceutically acceptable salt or solvate thereof, wherein $R^2$ is $C_{1-9}$heteroaryl optionally substituted with one, two, three, four, or five $R^8$. In another embodiment is a compound of Formula (I), (Ia), (Ib), (Ic), (Id), (Ie), (If), (Ig), or (Ih), or a pharmaceutically acceptable salt or solvate thereof, wherein $R^2$ is $C_{1-9}$heteroaryl substituted with one, two, or three $R^8$. In another embodiment is a compound of Formula (I), (Ia), (Ib), (Ic), (Id), (Ie), (If), (Ig), or (Ih), or a pharmaceutically acceptable salt or solvate thereof, wherein $R^2$ is pyridinyl, pyridinyl, or thiazolyl, wherein pyridinyl, pyridinyl, and thiazolyl are substituted with one, two, or three $R^8$. In another embodiment is a compound of Formula (I), (Ia), (Ib), (Ic), (Id), (Ie), (If), (Ig), or (Ih), or a pharmaceutically acceptable salt or solvate thereof, wherein each $R^{11}$ is independently selected from halogen, $C_{1-6}$alkyl, $C_{1-6}$haloalkyl, and —$OR^{10}$. In another embodiment is a compound of Formula (I), (Ia), (Ib), (Ic), (Id), (Ie), (If), (Ig), or (Ih), or a pharmaceutically acceptable salt or solvate thereof, wherein each $R^{10}$ is $C_{1-6}$alkyl. In another embodiment is a compound of Formula (I), (Ia), (Ib), (Ic), (Id), (Ie), (If), (Ig), or (Ih), or a pharmaceutically acceptable salt or solvate thereof, wherein $R^2$ is unsubstituted phenyl. In another embodiment is a compound of Formula (I), (Ia), (Ib), (Ic), (Id), (Ie), (If), (Ig), or (Ih), or a pharmaceutically acceptable salt or solvate thereof, wherein $R^2$ is unsubstituted $C_{1-9}$heteroaryl. In another embodiment is a compound of Formula (I), (Ia), (Ib), (Ic), (Id), (Ie), (If), (Ig), or (Ih), or a pharmaceutically acceptable salt or solvate thereof, wherein $R^2$ is unsubstituted pyridinyl, unsubstituted pyrmidinyl, or unsubstituted thiazolyl.

In another embodiment is a compound of Formula (I), (Ia), (Ib), (Ic), (Id), (Ie), (If), (Ig), or (Ih), or a pharmaceutically acceptable salt or solvate thereof, wherein $R^5$ and $R^6$ are each independently selected from hydrogen, $C_1$-$C_6$alkyl, and $C_1$-$C_6$haloalkyl. In another embodiment is a compound of Formula (I), (Ia), (Ib), (Ic), (Id), (Ie), (If), (Ig), or (Ih), or a pharmaceutically acceptable salt or solvate thereof, wherein $R^5$ is selected from hydrogen and $C_1$-$C_6$alkyl. In another embodiment is a compound of Formula (I), (Ia), (Ib), (Ic), (Id), (Ie), (If), (Ig), or (Ih), or a pharmaceutically acceptable salt or solvate thereof, wherein $R^6$ is selected from hydrogen and $C_1$-$C_6$alkyl. In another embodiment is a compound of Formula (I), (Ia), (Ib), (Ic), (Id), (Ie), (If), (Ig), or (Ih), or a pharmaceutically acceptable salt or solvate thereof, wherein $R^5$ and $R^6$ are each hydrogen. In another embodiment is a compound of Formula (I), (Ia), (Ib), (Ic), (Id), (Ie), (If), (Ig), or (Ih), or a pharmaceutically acceptable salt or solvate thereof, wherein $R^5$ and $R^6$ are each $C_1$-$C_6$alkyl. In another embodiment is a compound of Formula (I), (Ia), (Ib), (Ic), (Id), (Ie), (If), (Ig), or (Ih), or a pharmaceutically acceptable salt or solvate thereof, wherein $R^5$ and $R^6$ are $C_1$-$C_6$alkyl. In another embodiment is a compound of Formula (I), (Ia), (Ib), (Ic), (Id), (Ie), (If), (Ig), or (Ih), or a pharmaceutically acceptable salt or solvate thereof, wherein $R^5$ and $R^6$ are combined to form an azetidinyl, pyrrolidinyl, piperidinyl, or piperazinyl ring. In another embodiment is a compound of Formula (I), (Ia), (Ib), (Ic), (Id), (Ie), (If), (Ig), or (Ih), or a pharmaceutically acceptable salt or solvate thereof, wherein $R^5$ and $R^6$ are combined to form an azetidinyl ring. In another embodiment is a compound of Formula (I), (Ia), (Ib), (Ic), (Id), (Ie), (If), (Ig), or (Ih), or a pharmaceutically acceptable salt or solvate thereof, wherein $R^5$ and $R^6$ are combined to form a pyrrolidinyl ring. In another embodiment is a compound of Formula (I), (Ia), (Ib), (Ic), (Id), (Ie), (If), (Ig), or (Ih), or a pharmaceutically acceptable salt or solvate thereof, wherein $R^5$ and $R^6$ are combined to form a piperidinyl ring. In another embodiment is a compound of Formula (I), (Ia), (Ib), (Ic), (Id), (Ie), (If), (Ig), or (Ih), or a pharmaceutically acceptable salt or solvate thereof, wherein $R^5$ and $R^6$ are combined to form a piperazinyl ring.

In another embodiment is a compound of Formula (I), (Ia), (Ib), (Ic), (Id), (Ie), (If), (Ig), or (Ih), or a pharmaceutically acceptable salt or solvate thereof, wherein $R^4$ is hydrogen.

Further embodiments provided herein include combinations of one or more of the particular embodiments set forth above.

In some embodiments is a compound selected from:

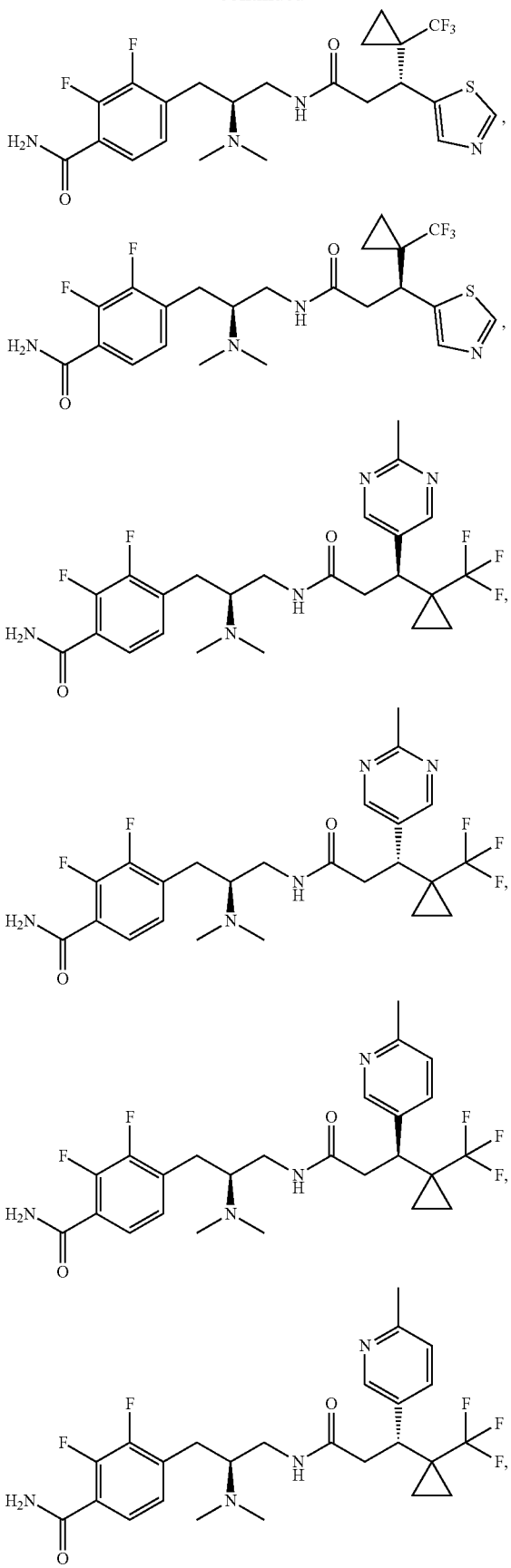

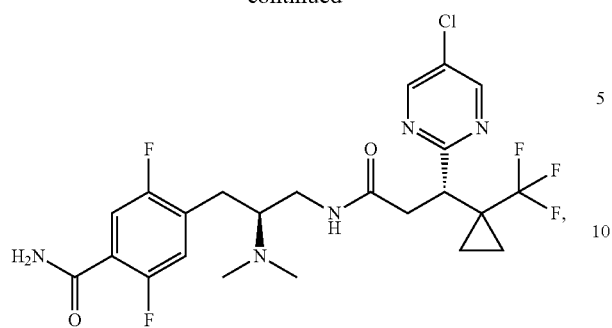
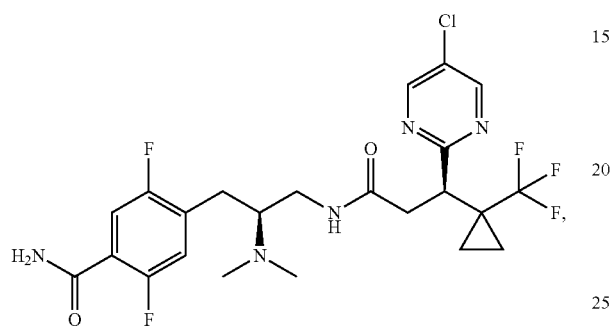
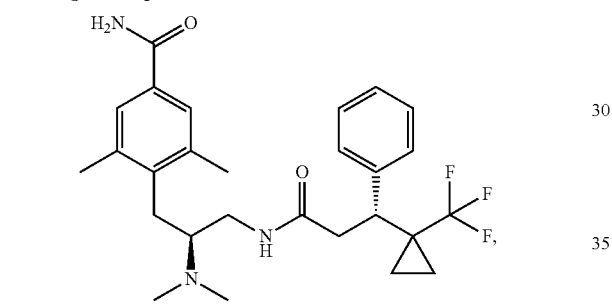
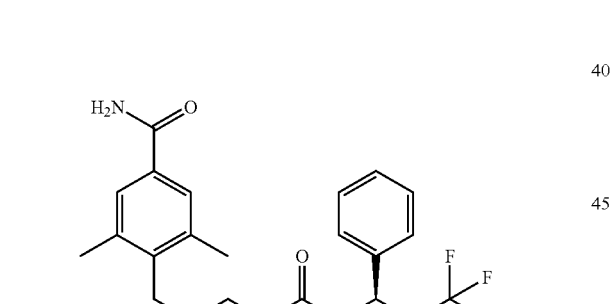
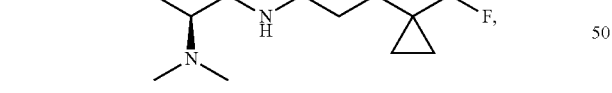
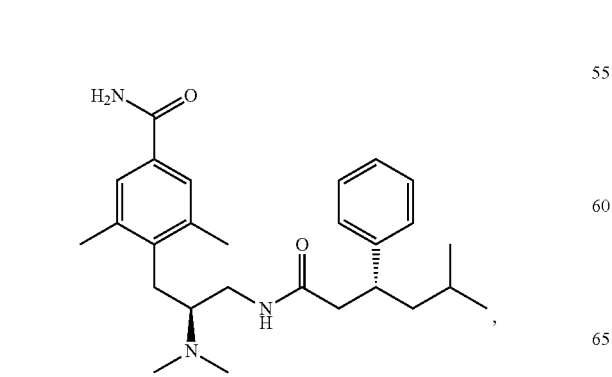
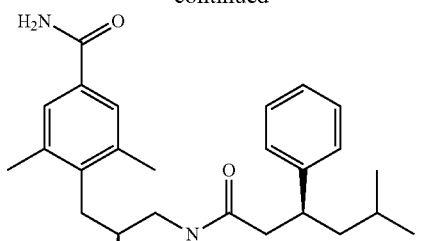
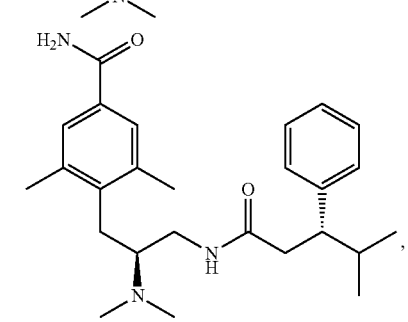
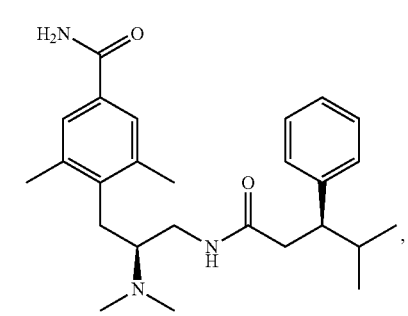
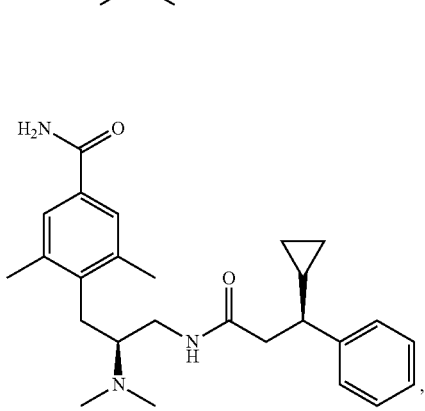
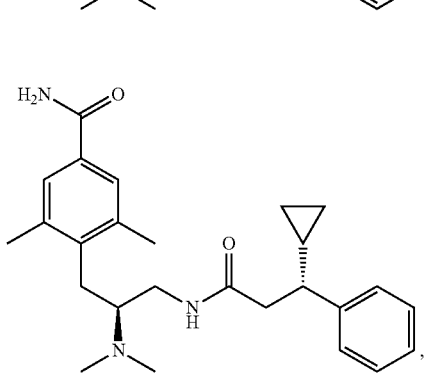

-continued
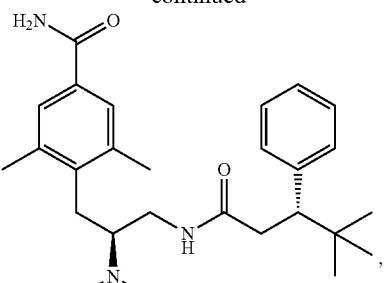
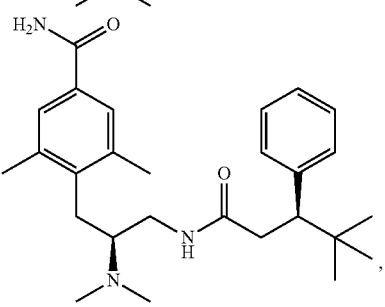
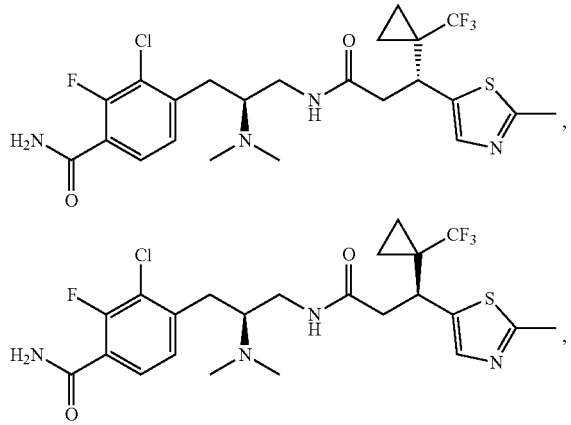
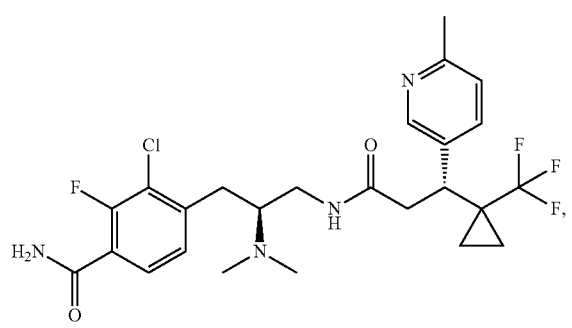
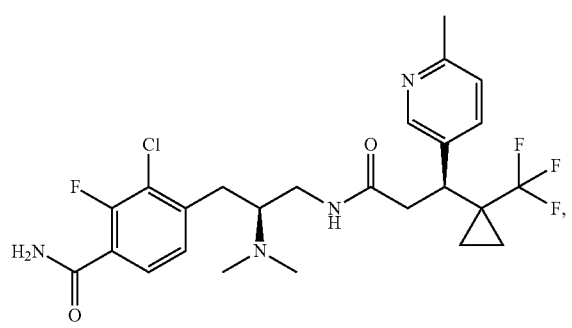
-continued
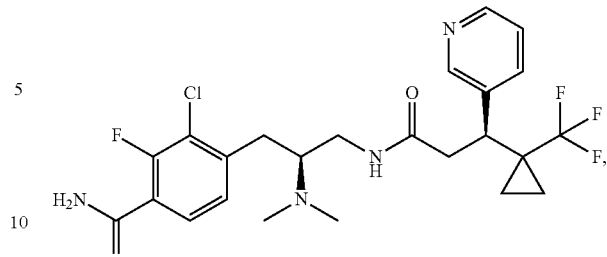
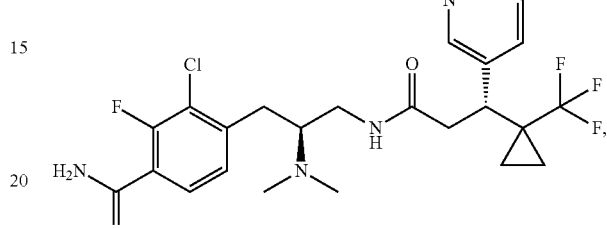
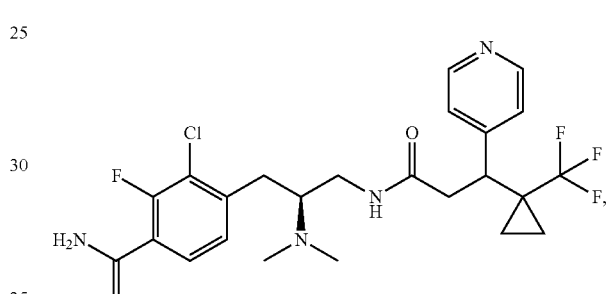
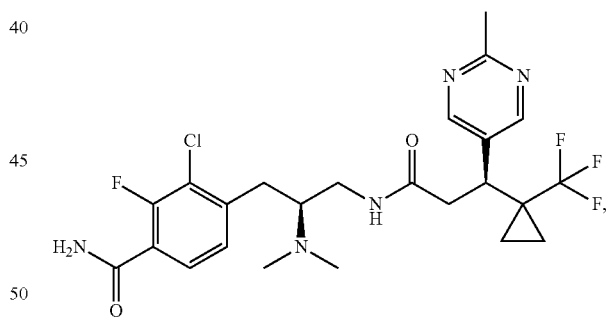
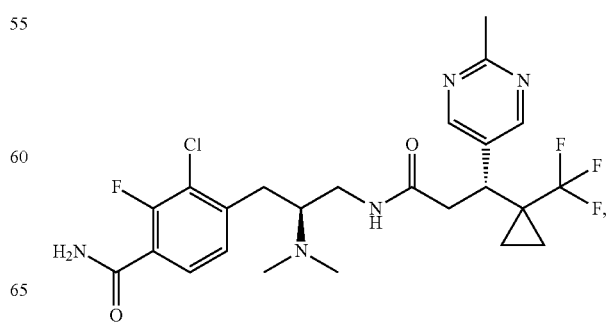

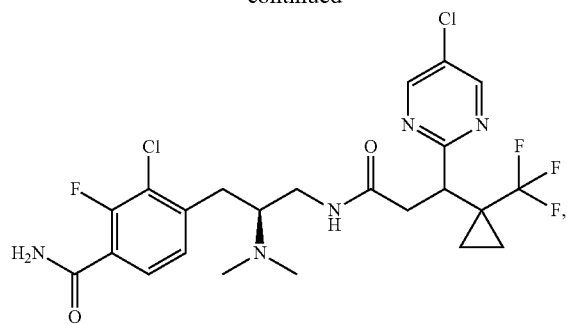
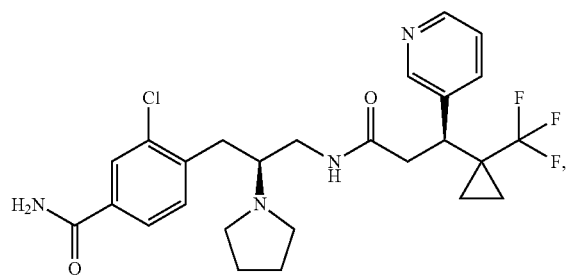
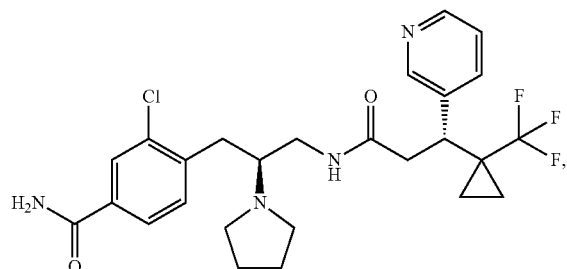
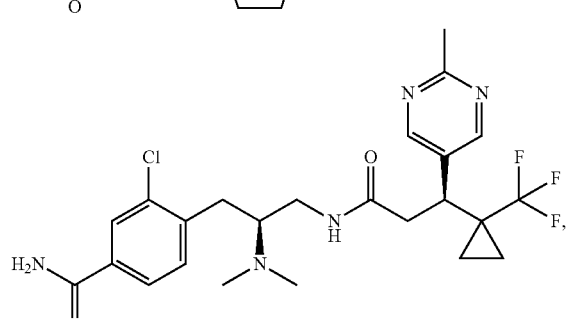

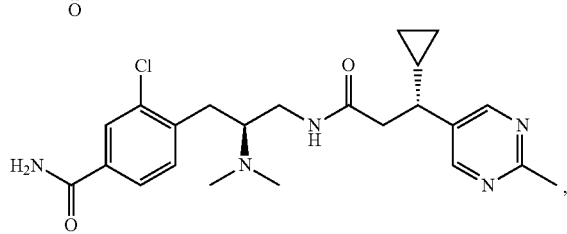
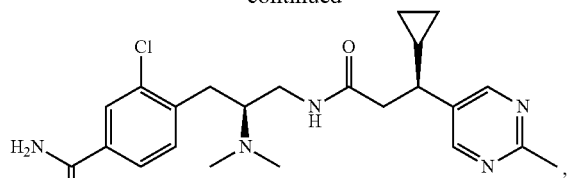
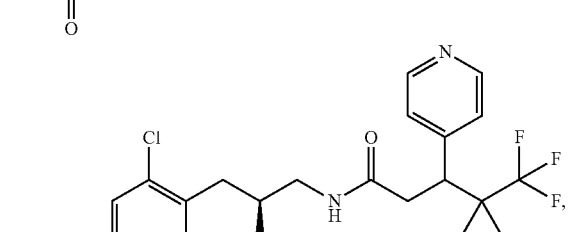
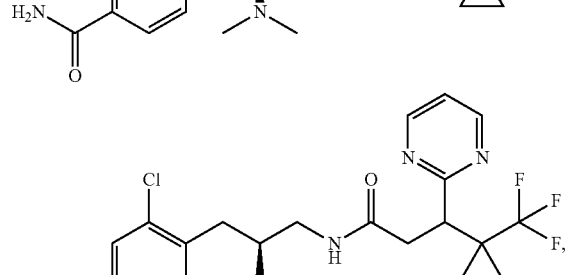
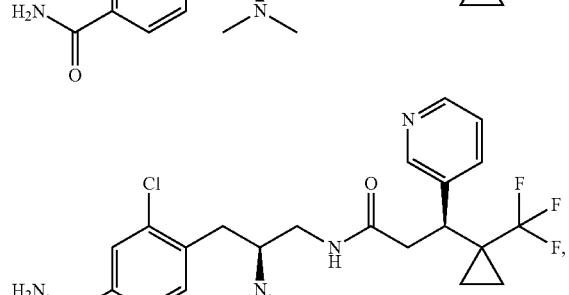
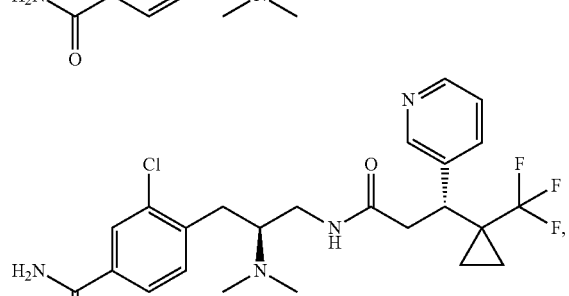
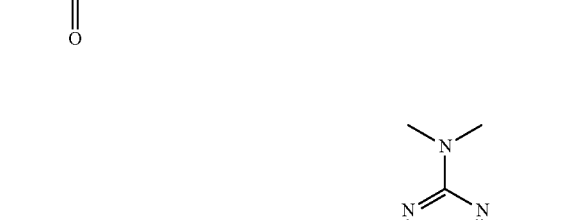
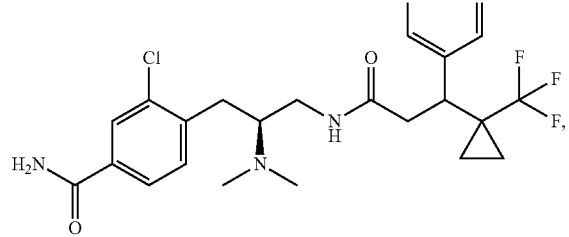

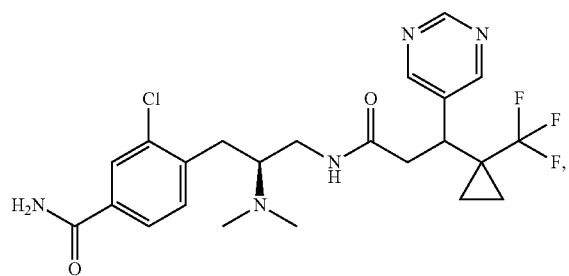
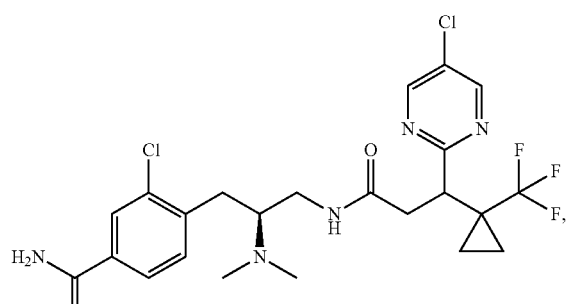
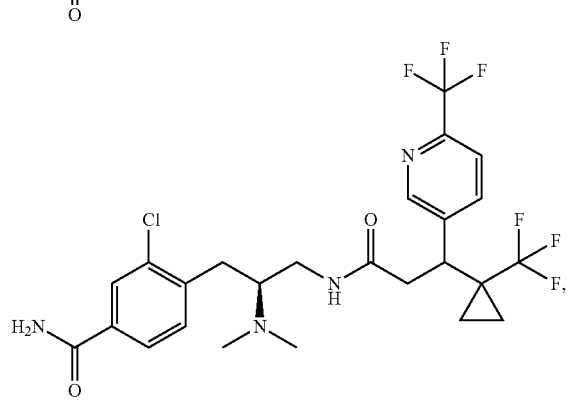
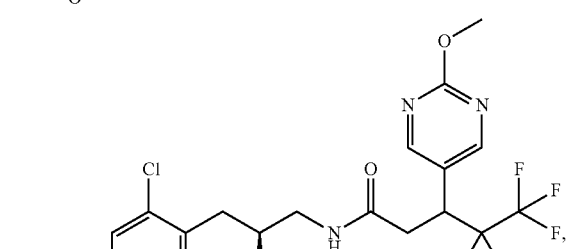
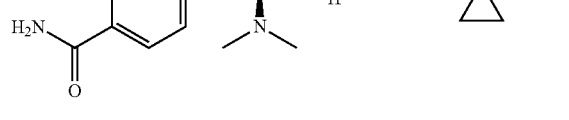
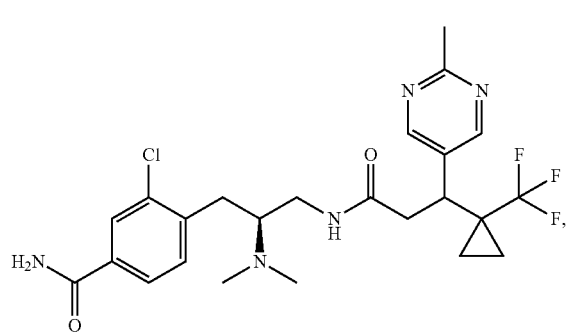
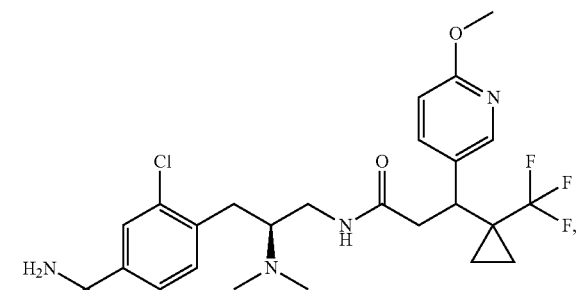
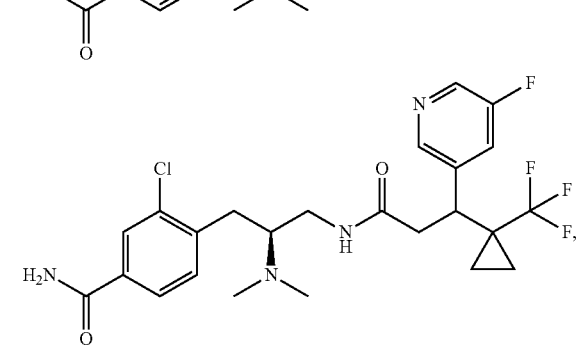
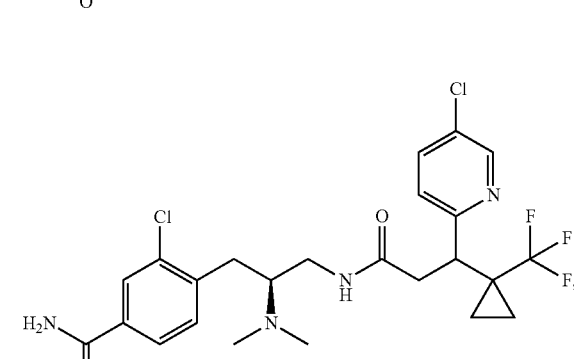
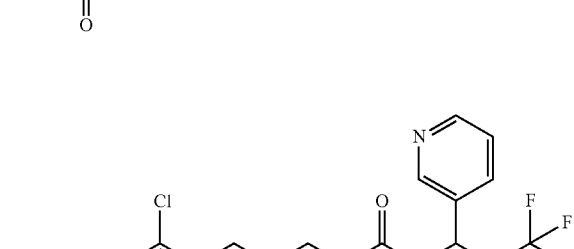
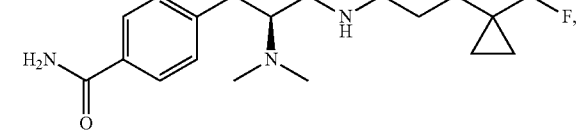
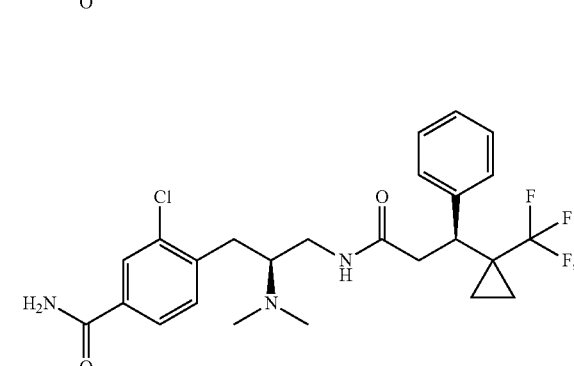

-continued
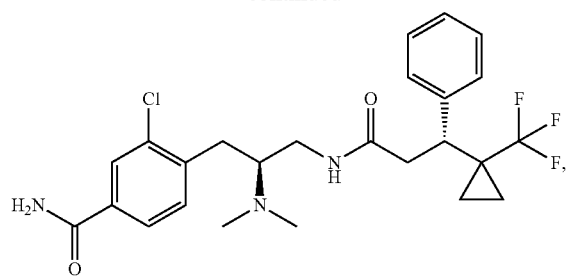
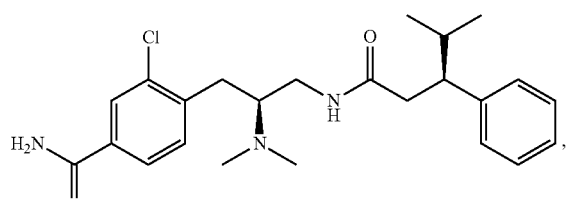
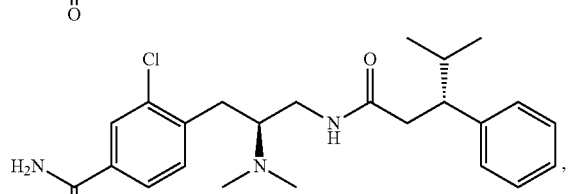
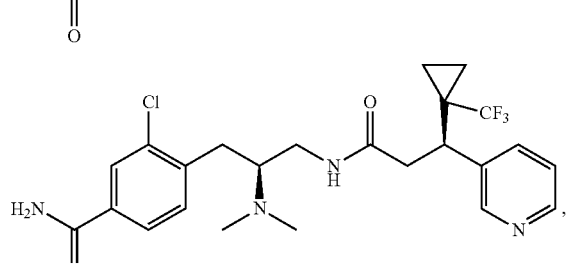
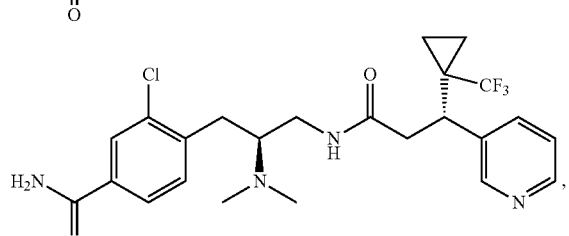
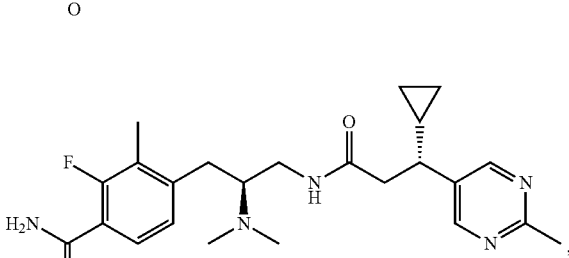
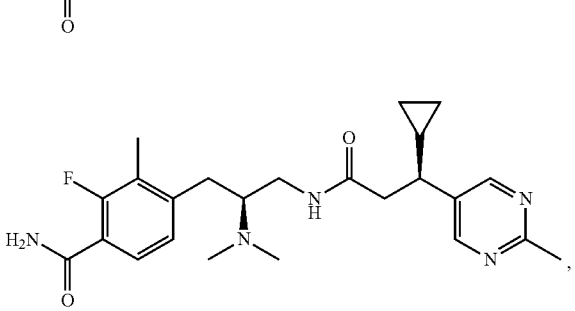
-continued
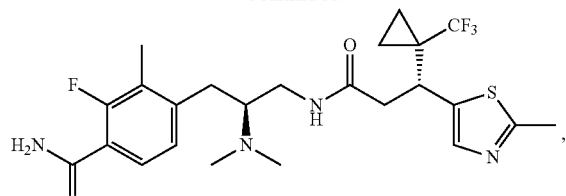
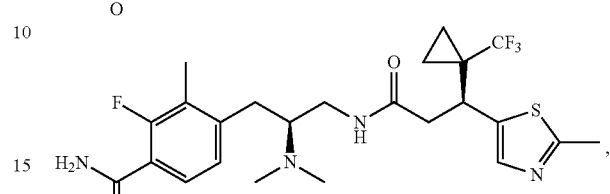
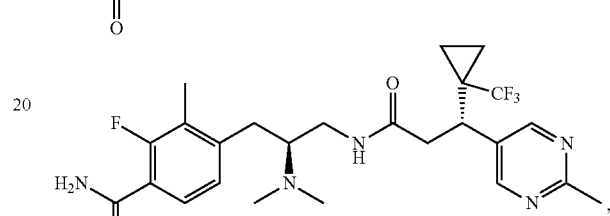
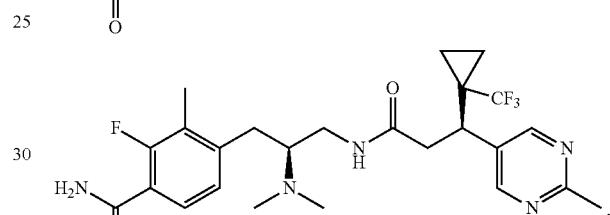
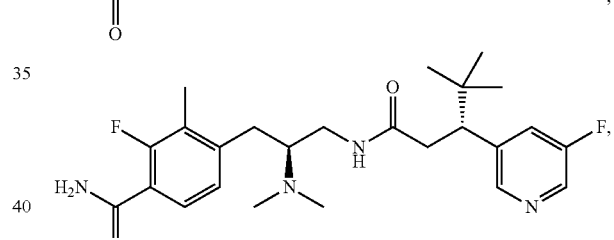

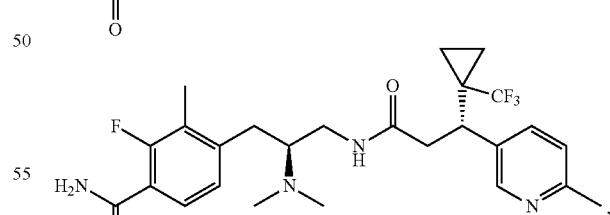
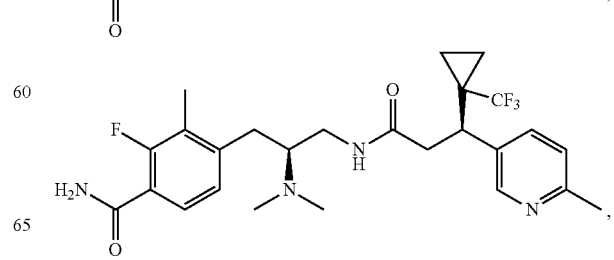

37
-continued
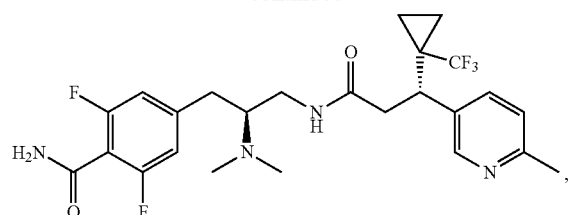
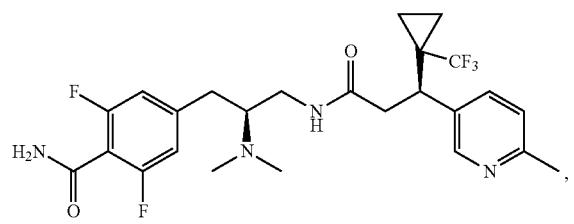
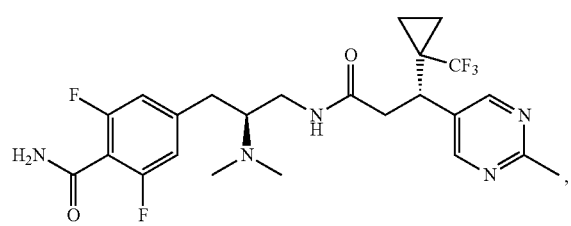
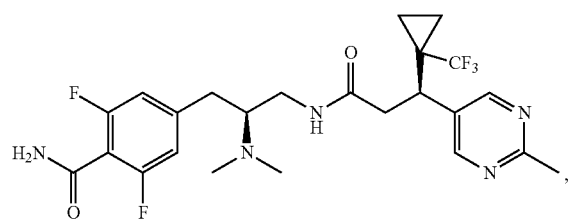
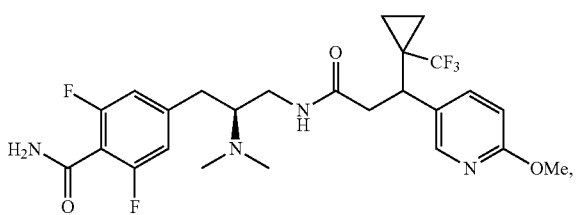
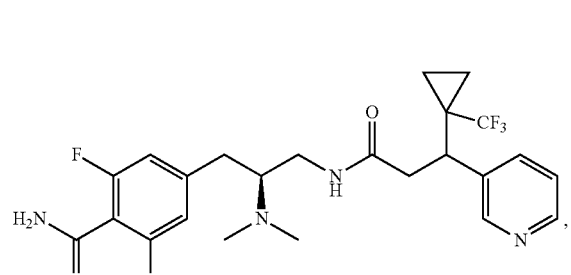
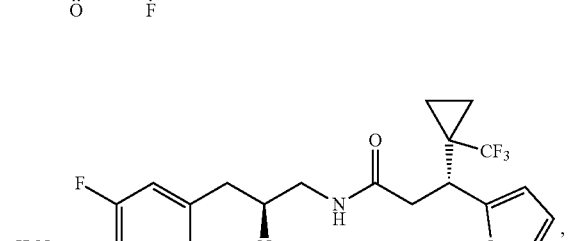
38
-continued
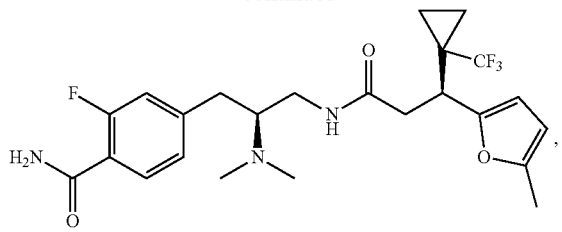
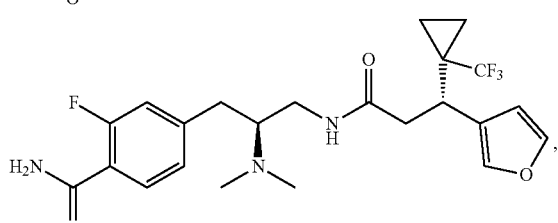
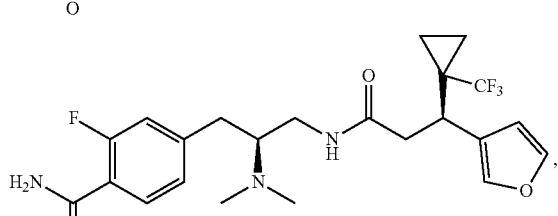
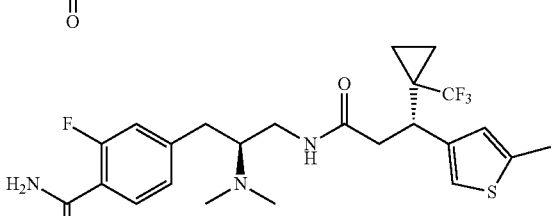
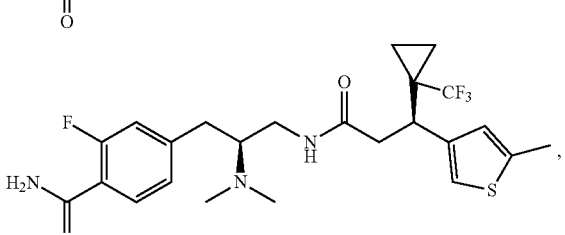
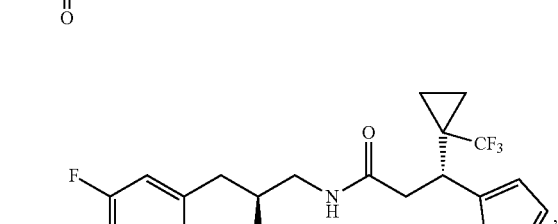
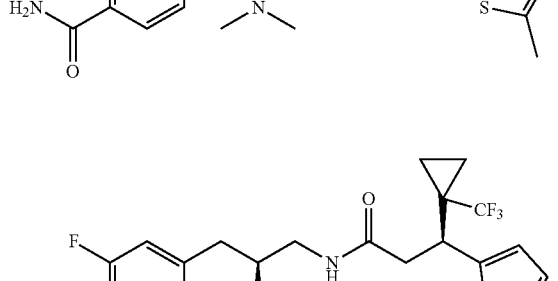

-continued
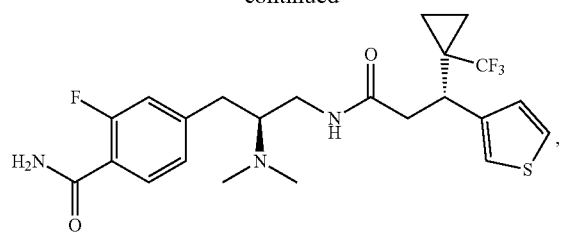
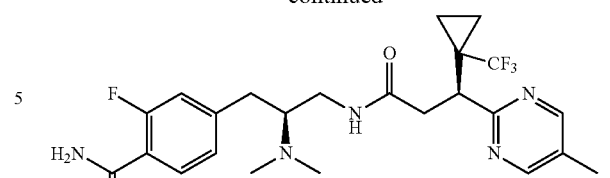
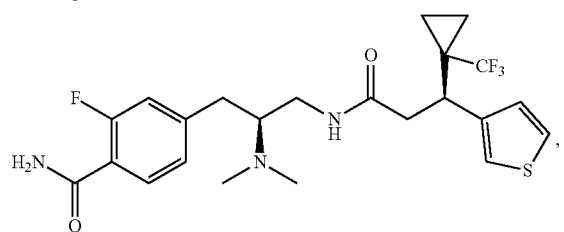
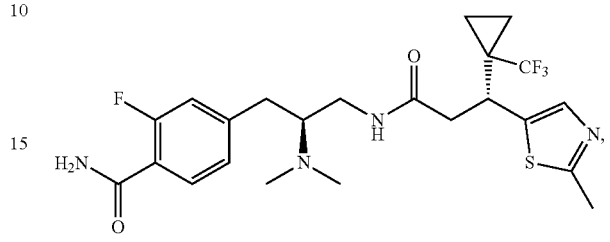
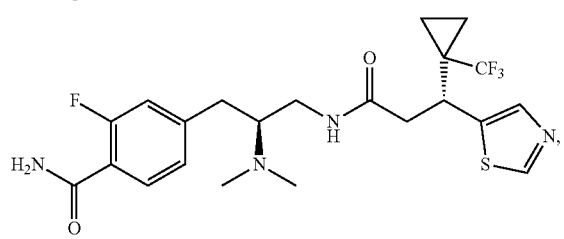
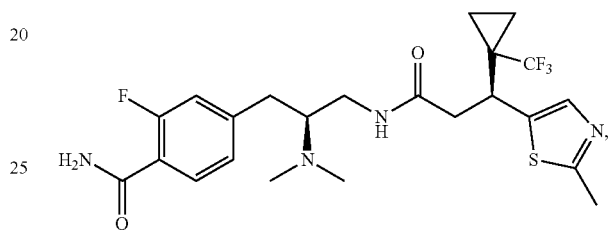
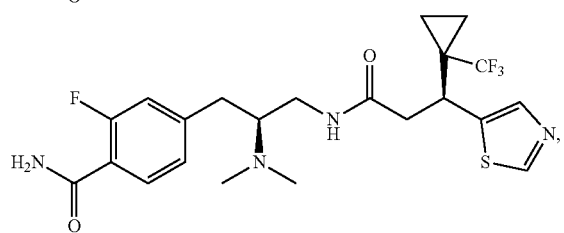
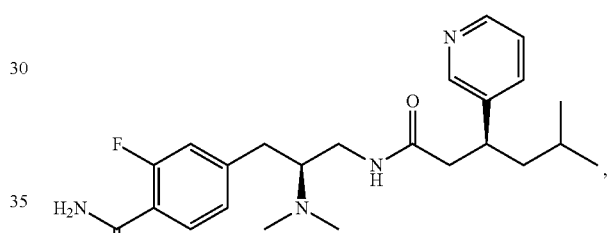
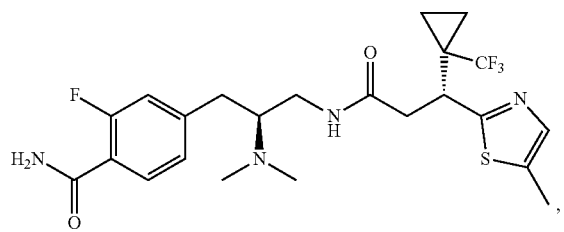
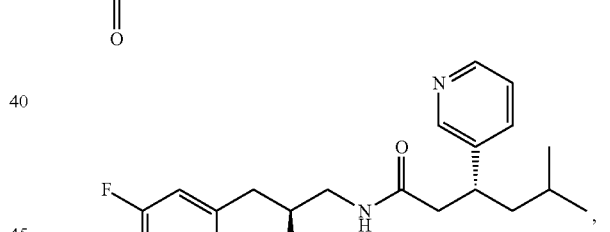
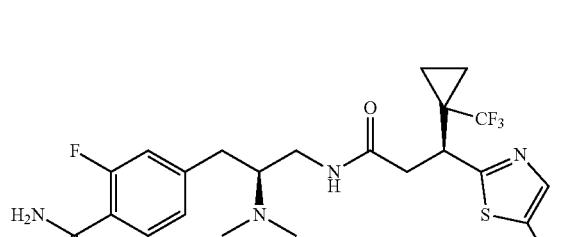
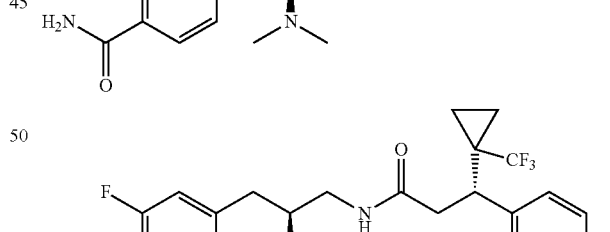
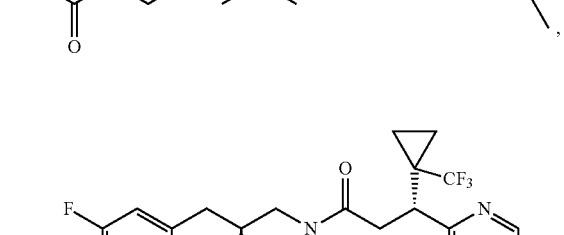
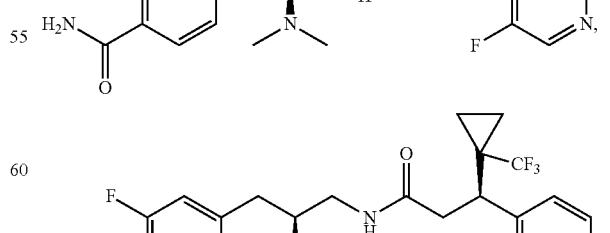

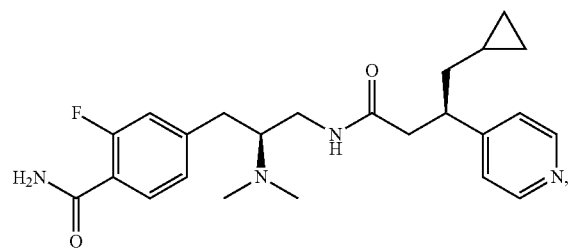
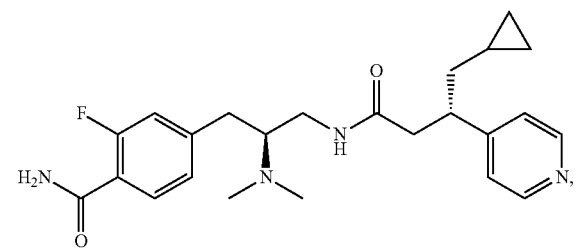
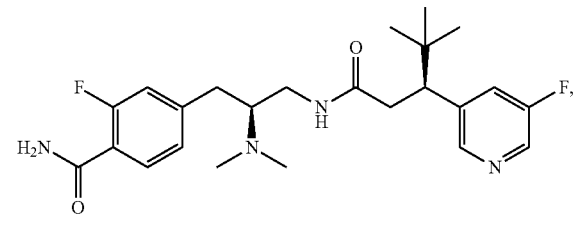
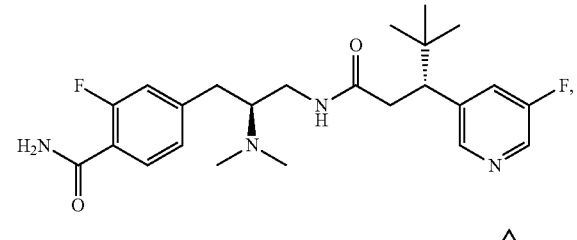
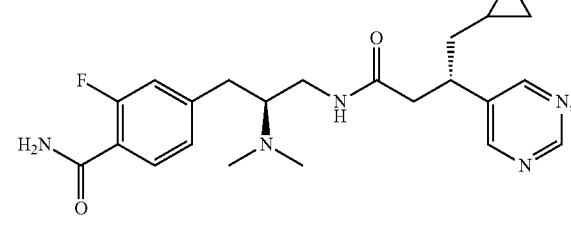
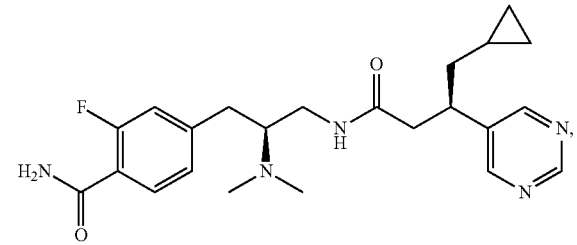
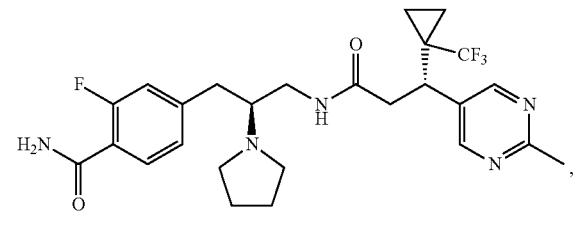
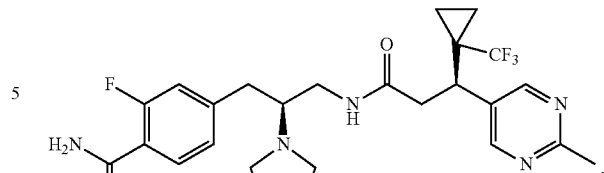

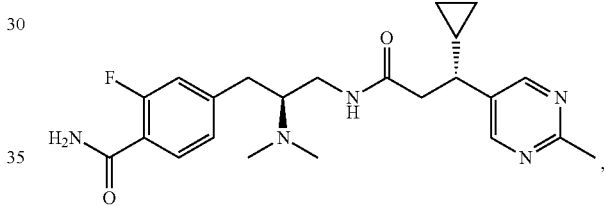
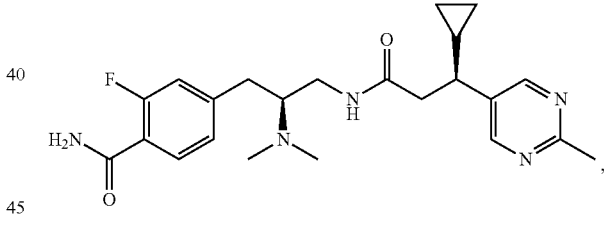
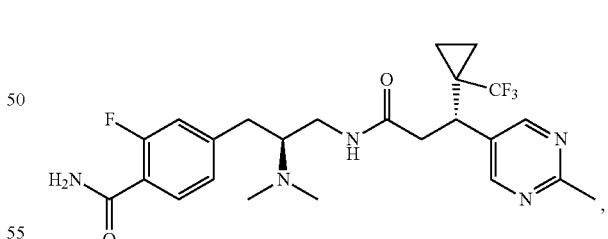
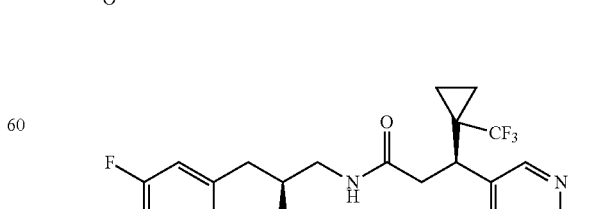
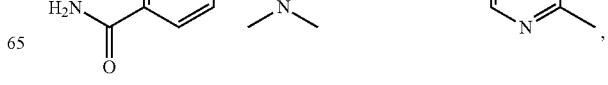

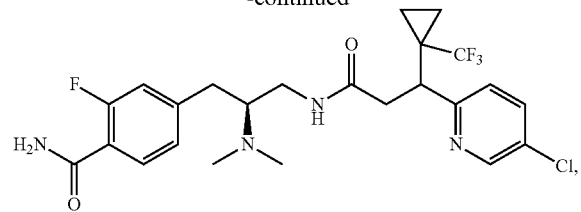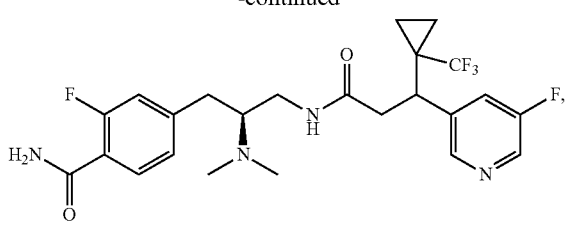

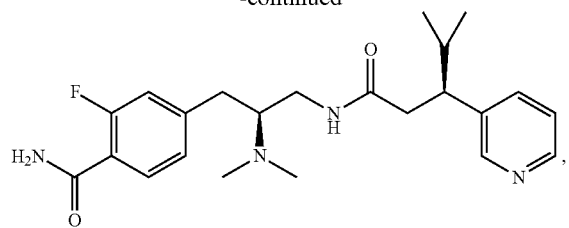
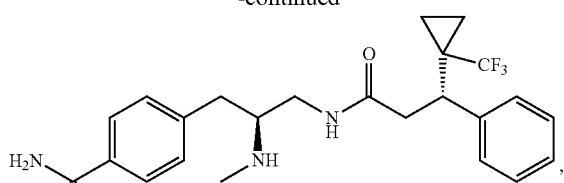
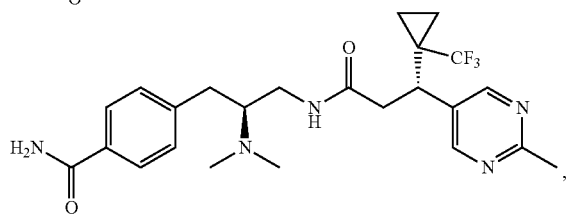
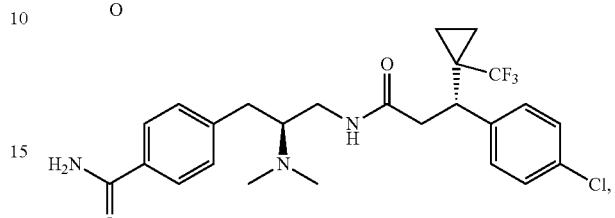
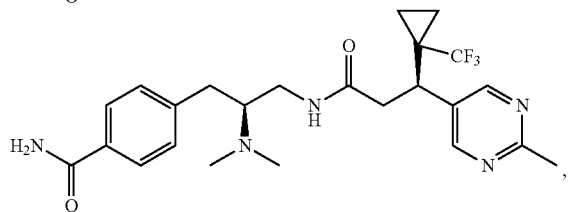
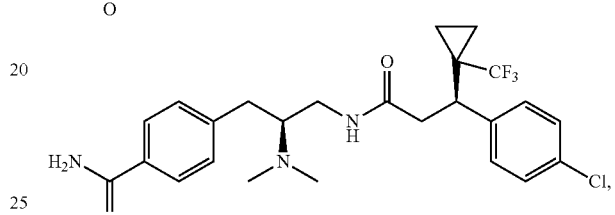
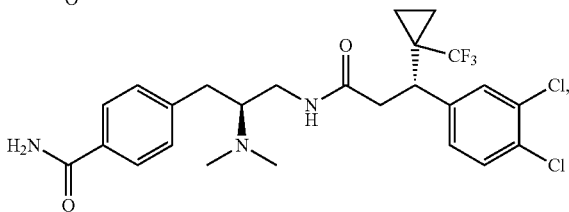
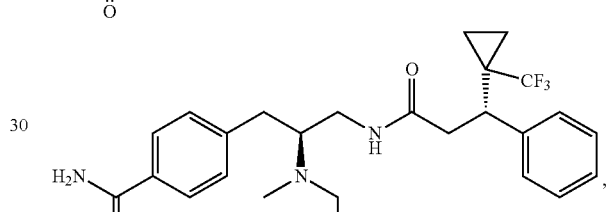
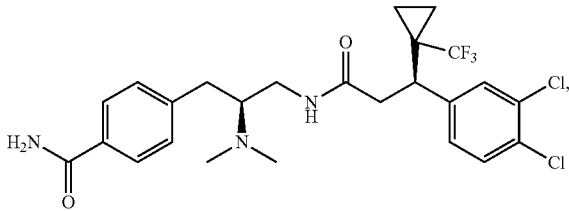
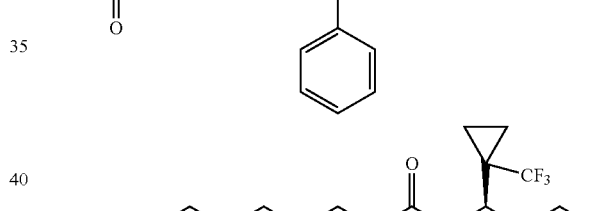
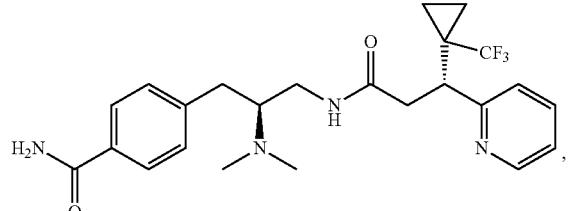
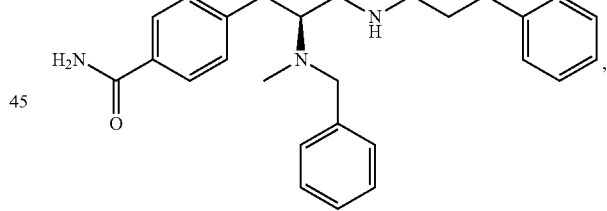
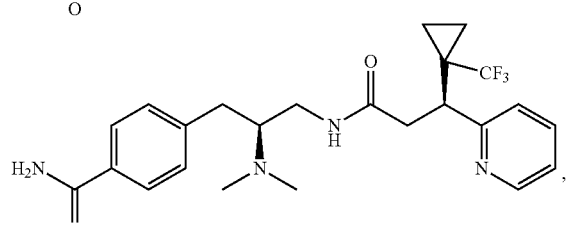
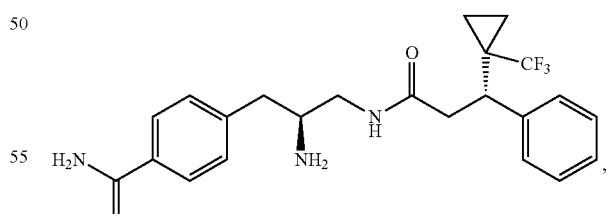
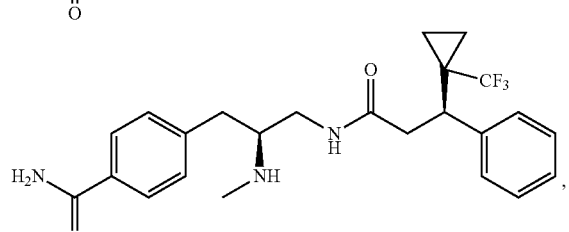
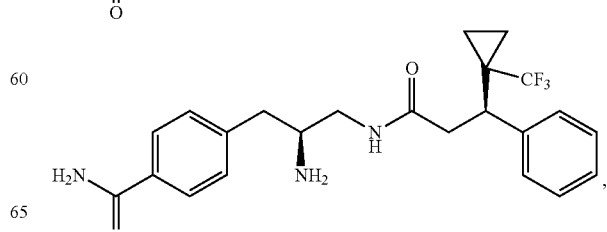

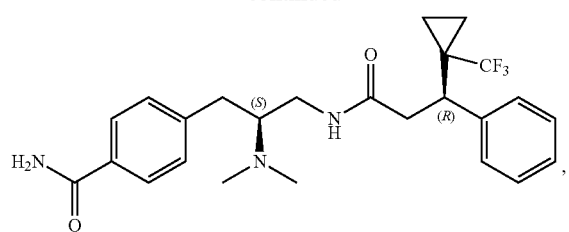
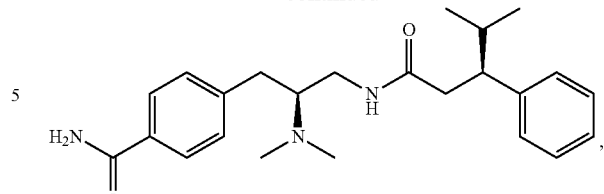
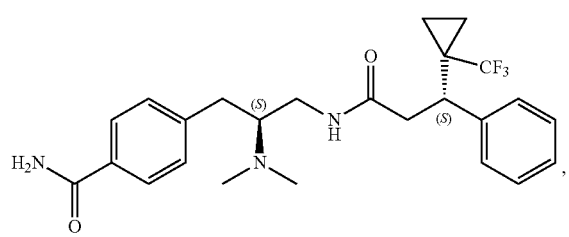
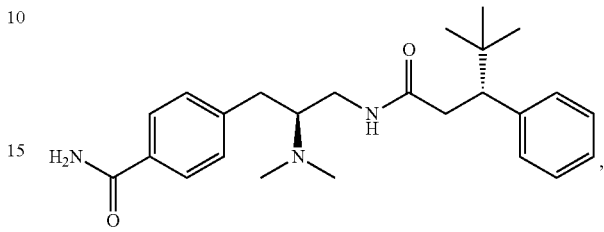
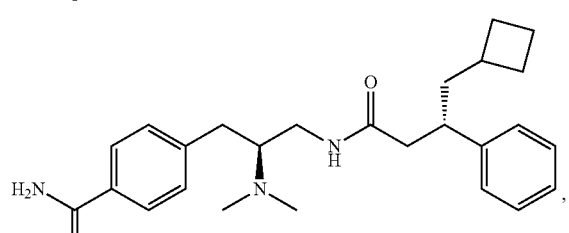
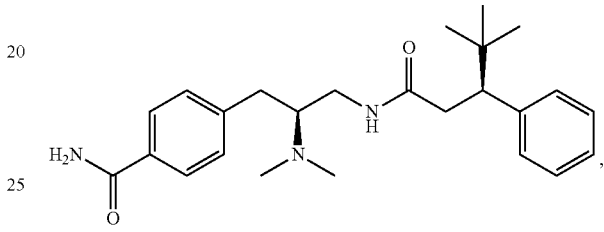
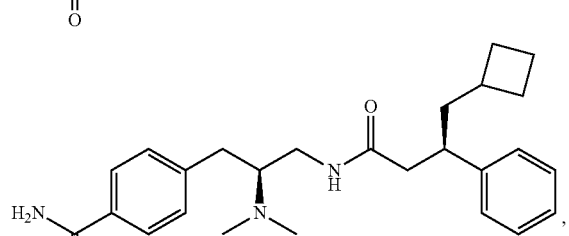
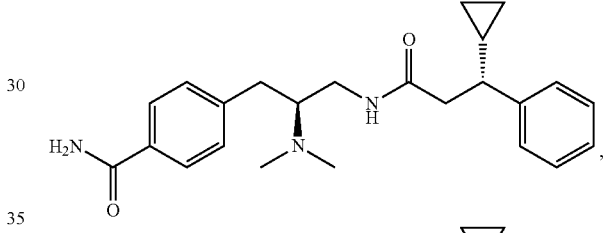
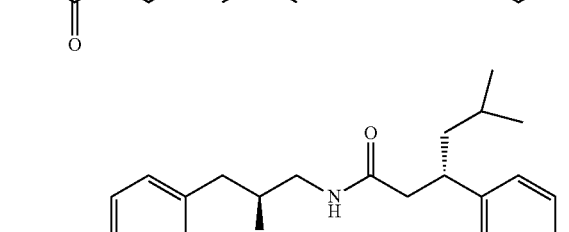
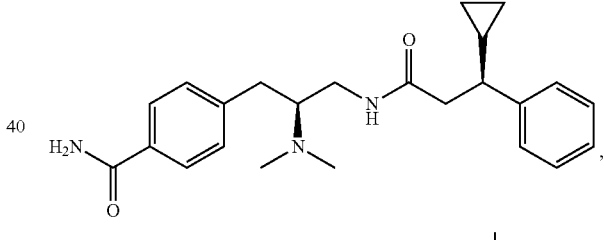
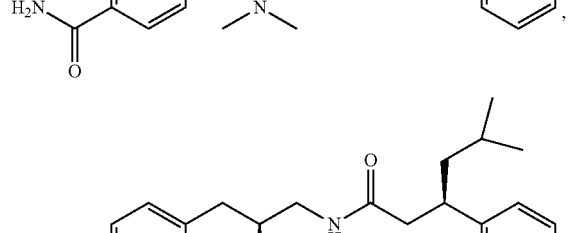
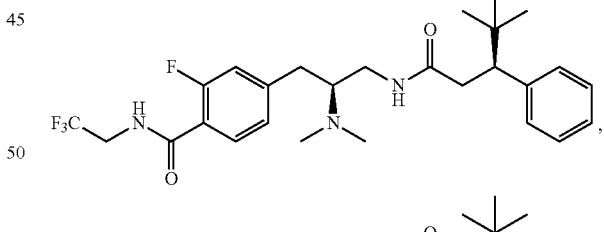
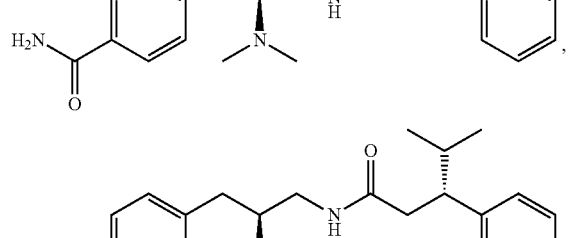
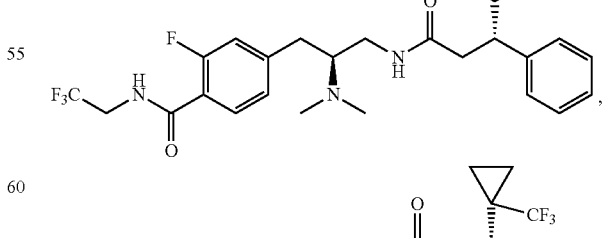
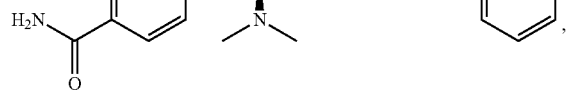
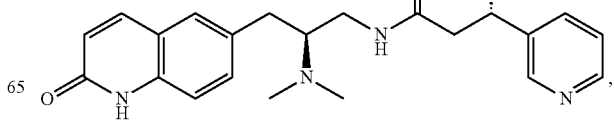

-continued
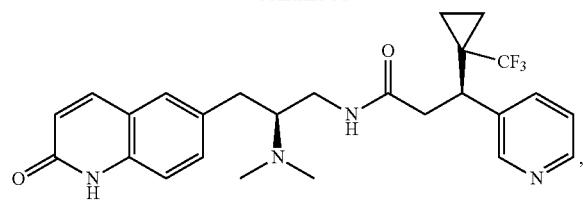
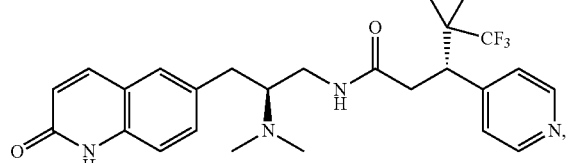
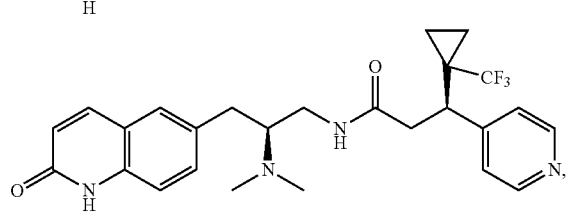
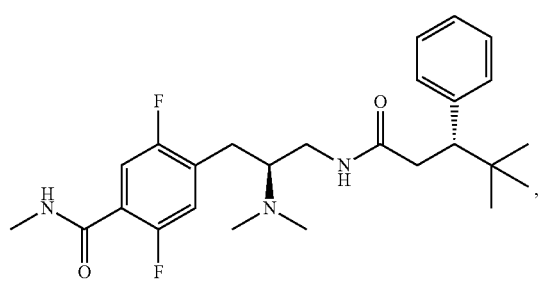
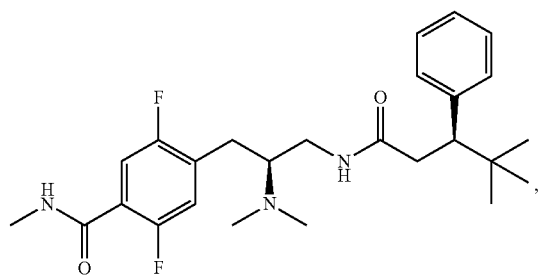
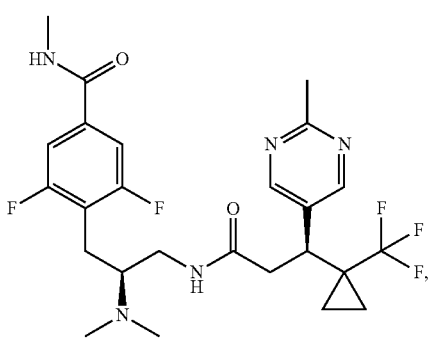
-continued
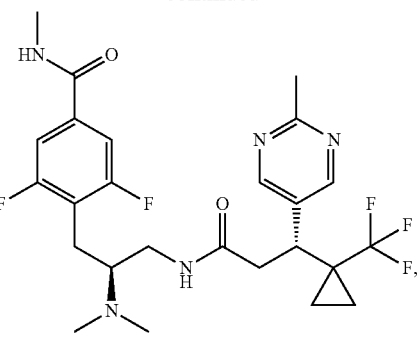
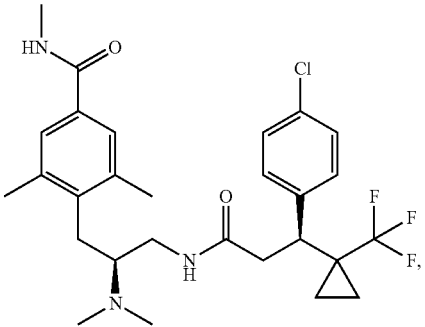
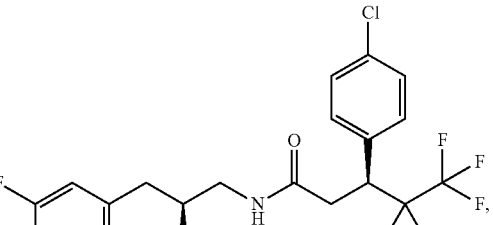
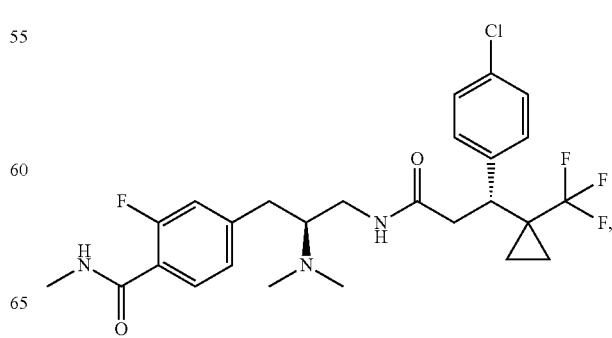

51
-continued
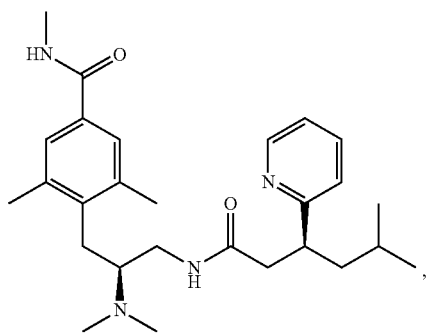
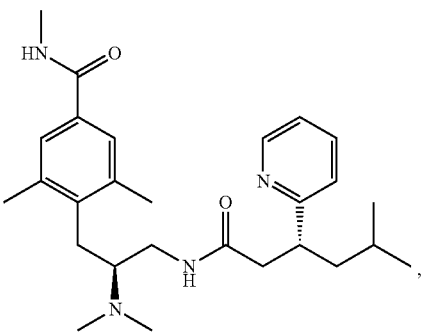
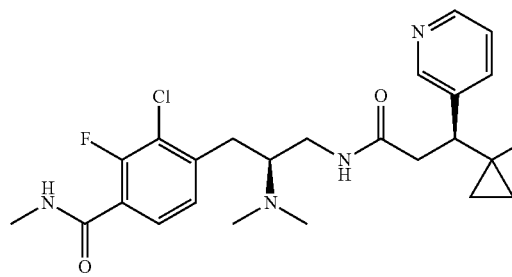
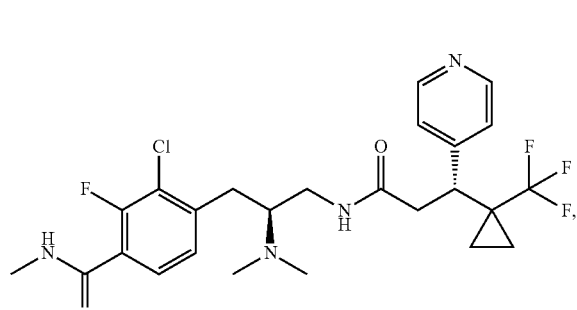
52
-continued
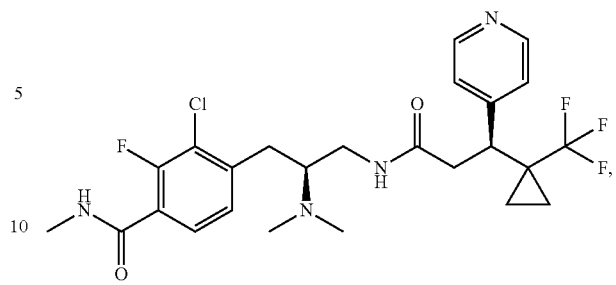
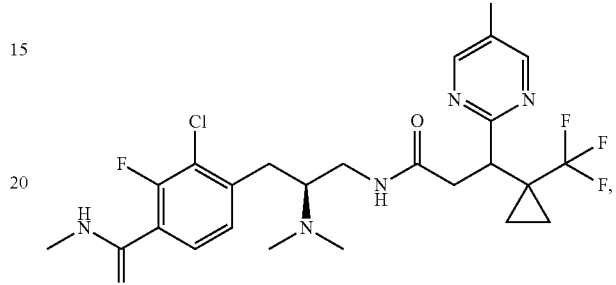
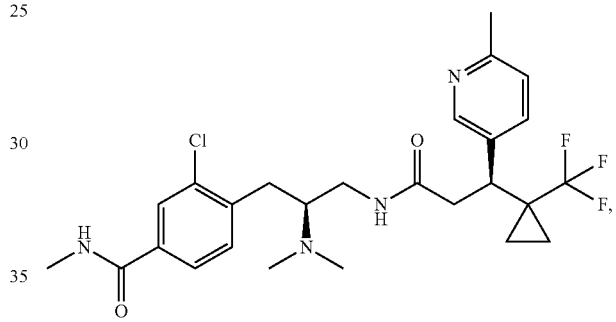
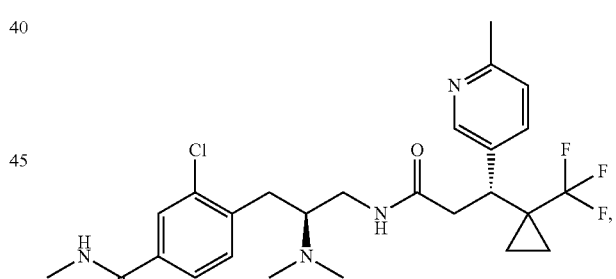
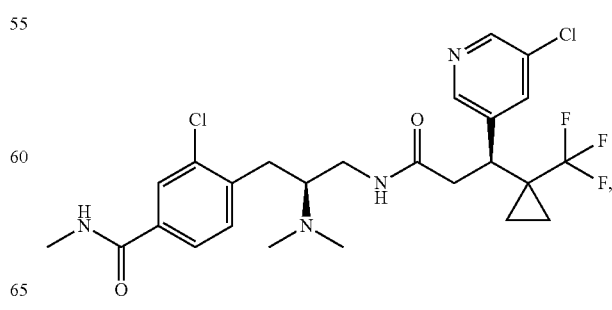

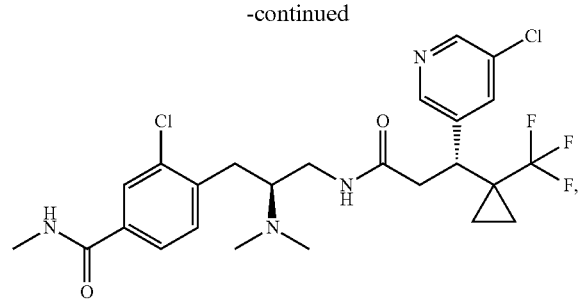
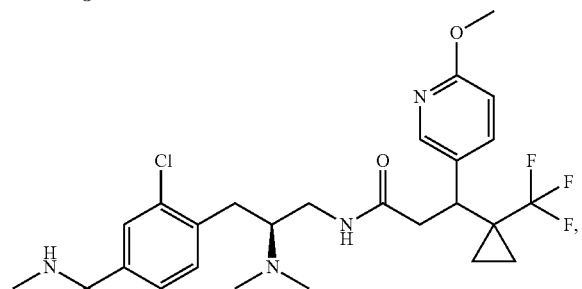
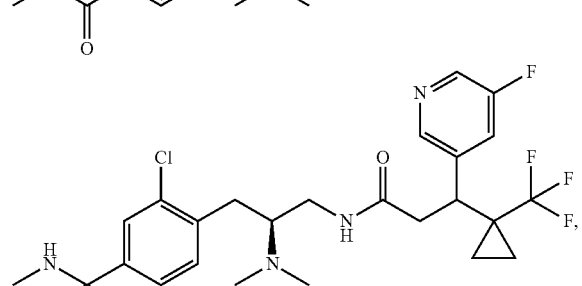
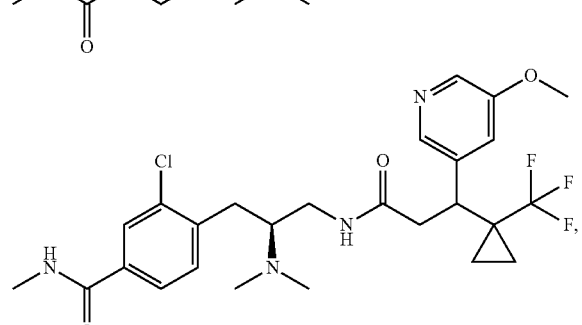

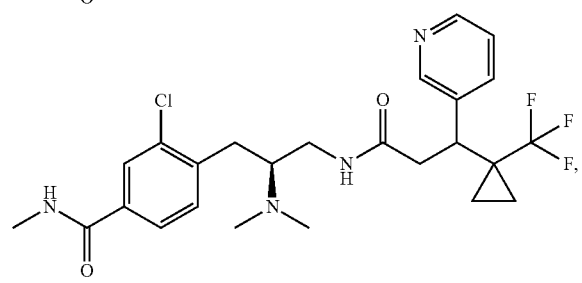
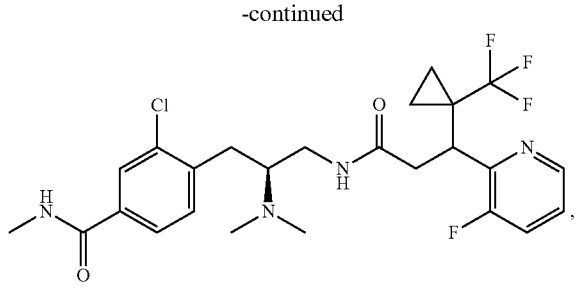
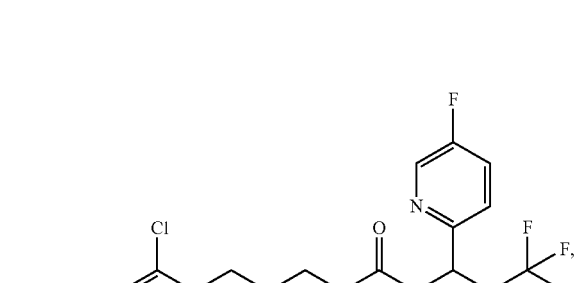
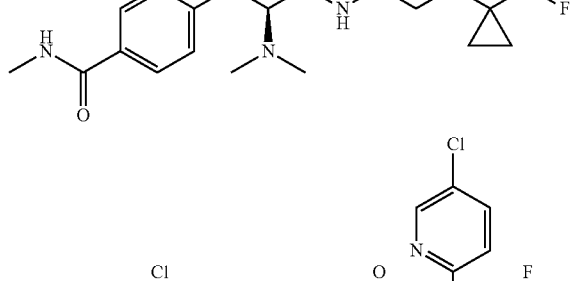
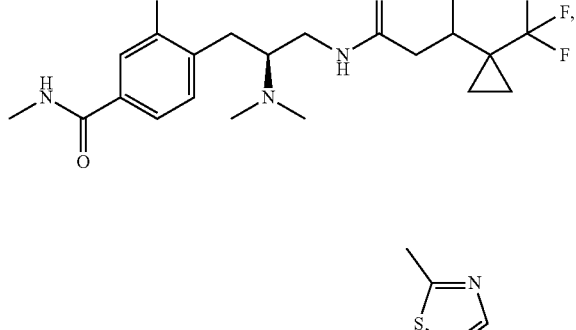
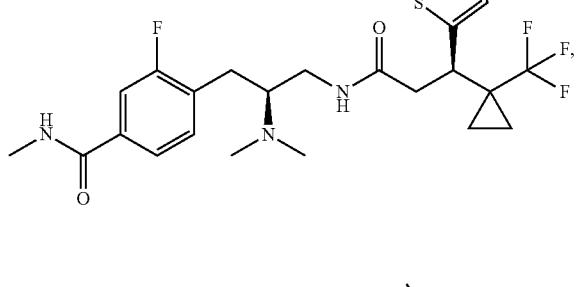
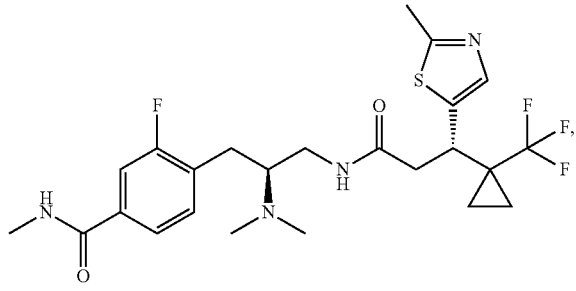

-continued
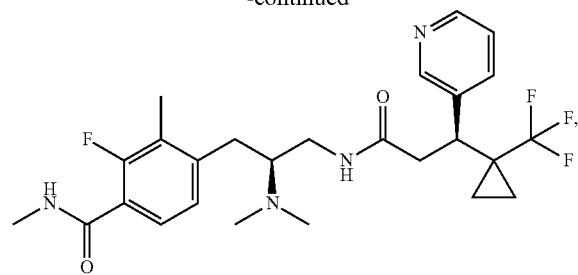
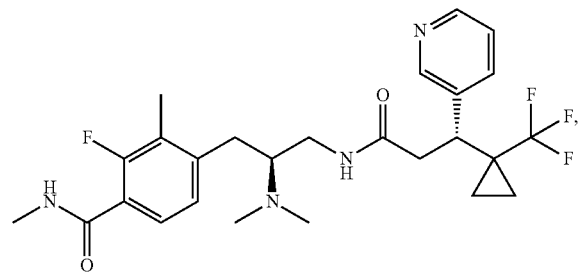
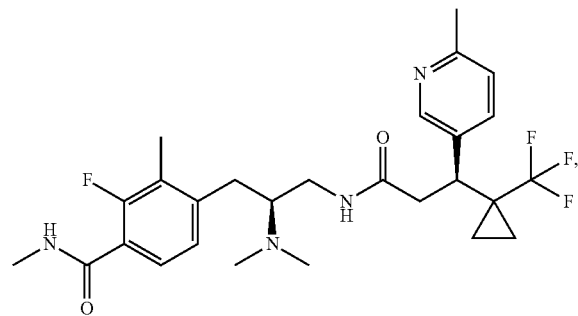
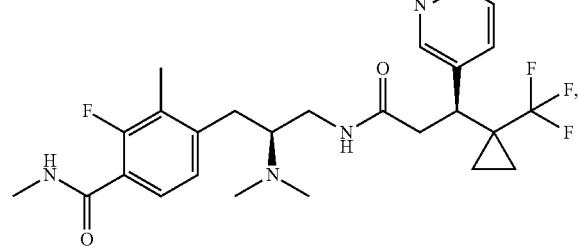
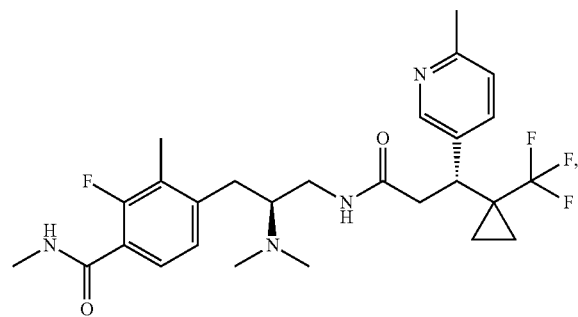
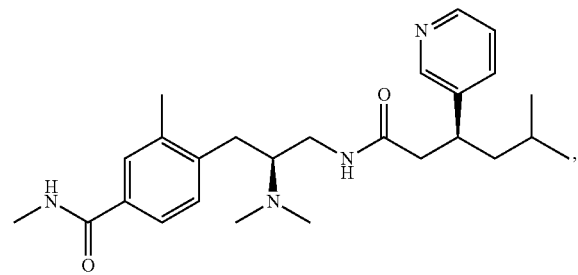
-continued
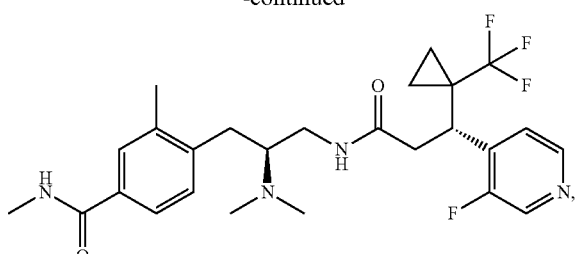
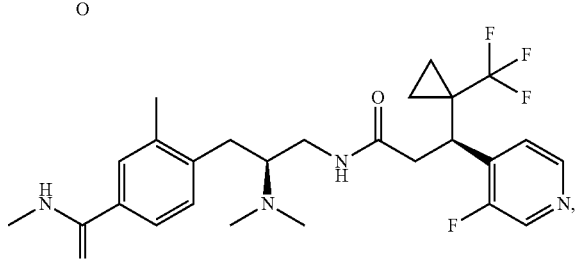
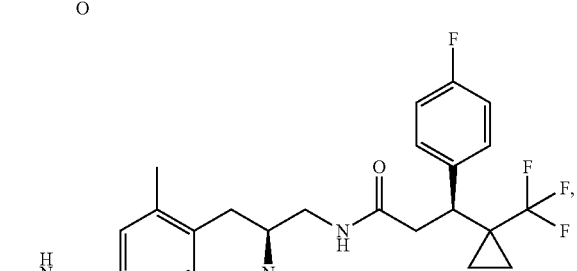
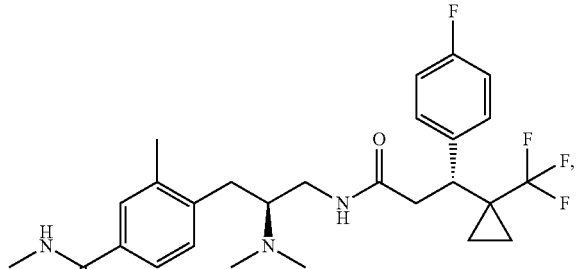
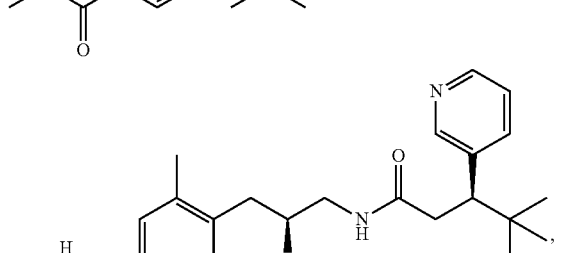
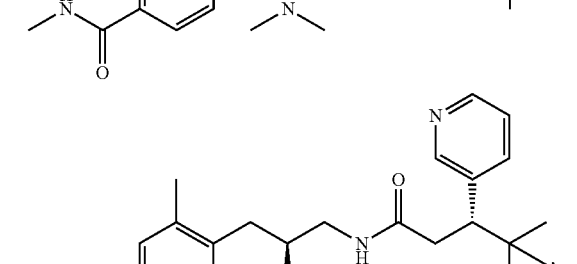

57
-continued
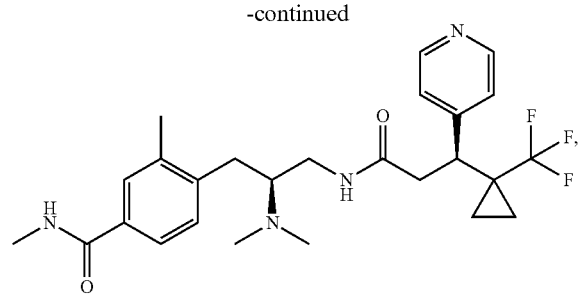
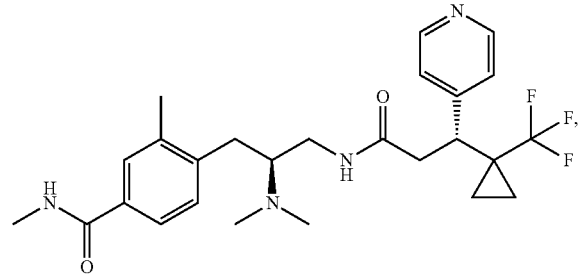
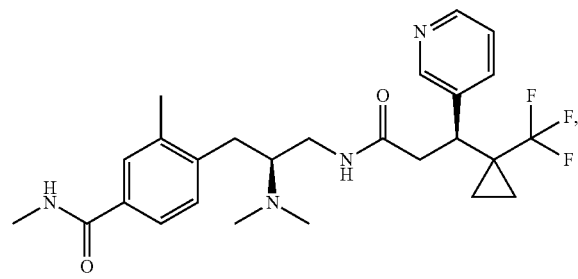
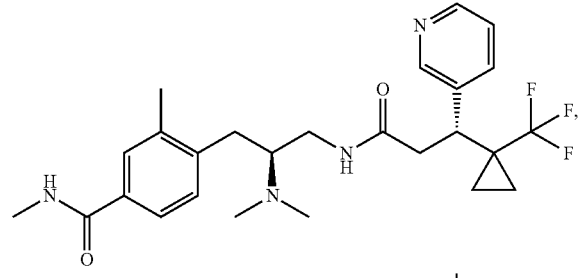
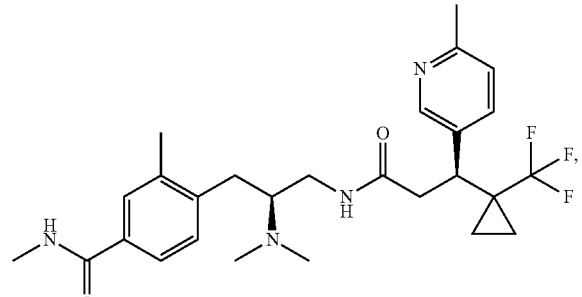
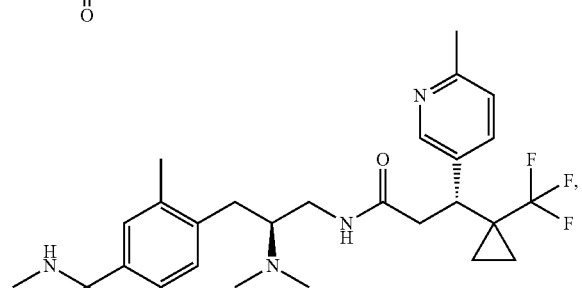
58
-continued
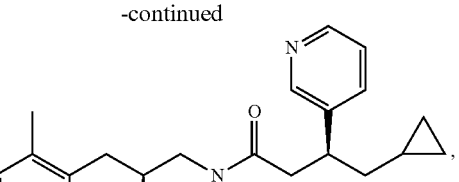
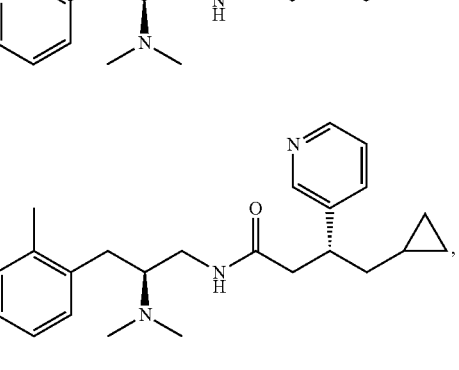
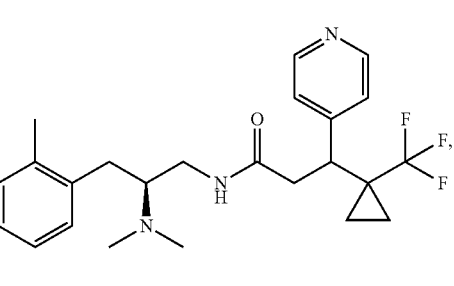
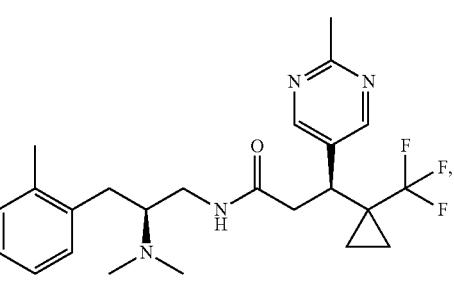
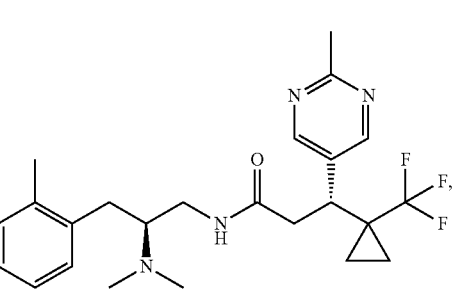
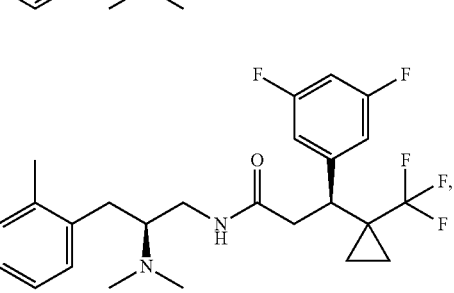

59
-continued
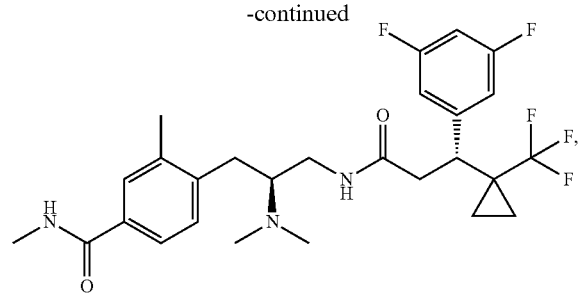
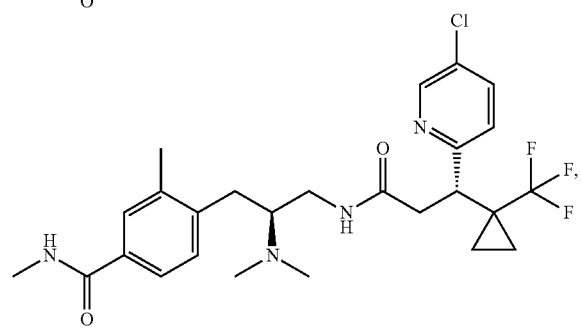
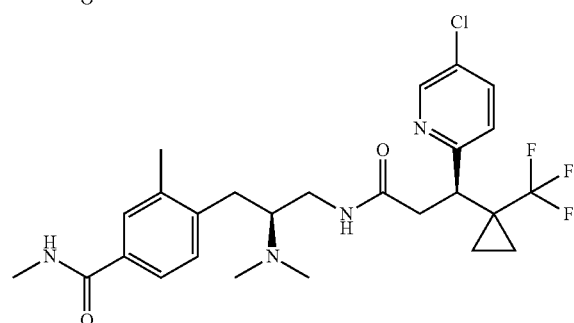
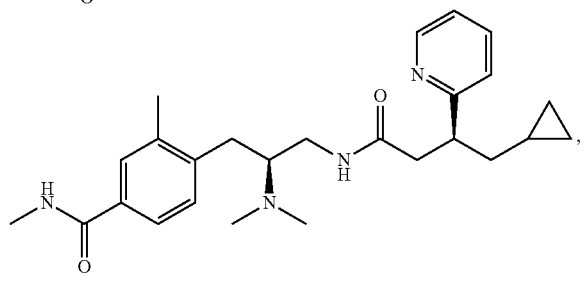
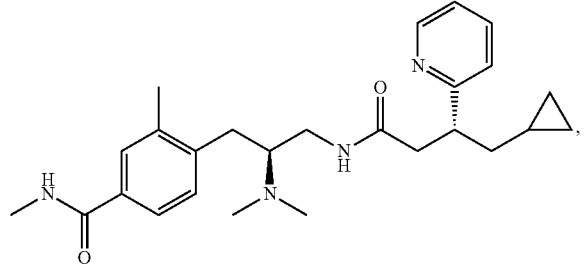
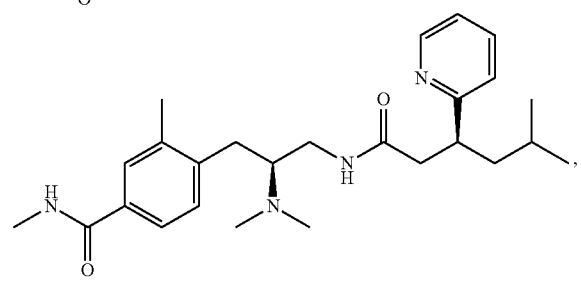
60
-continued
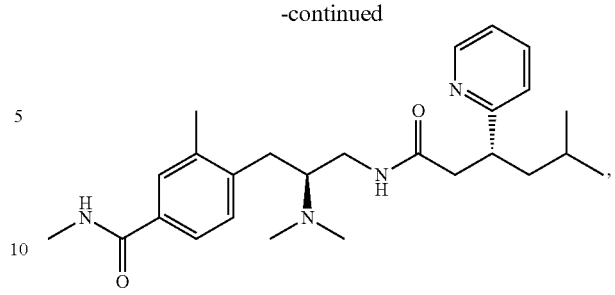
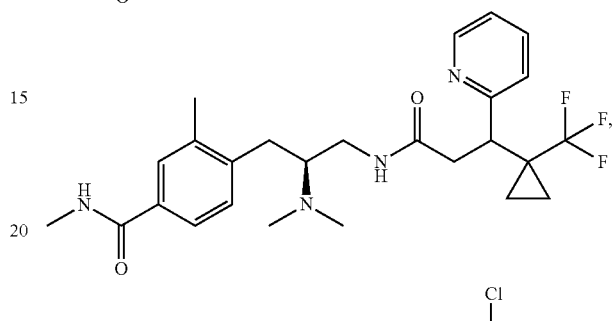
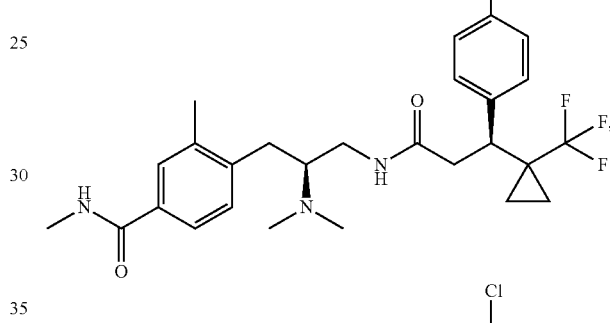
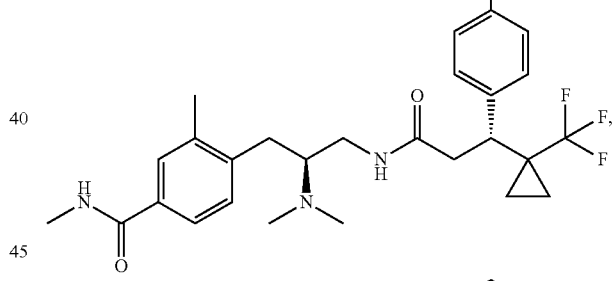
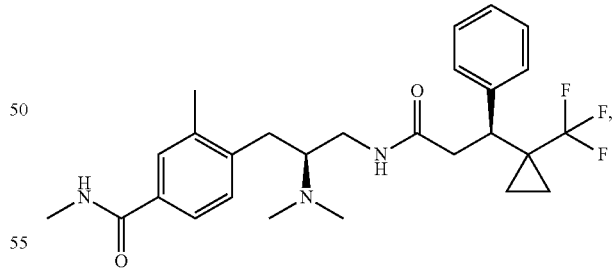
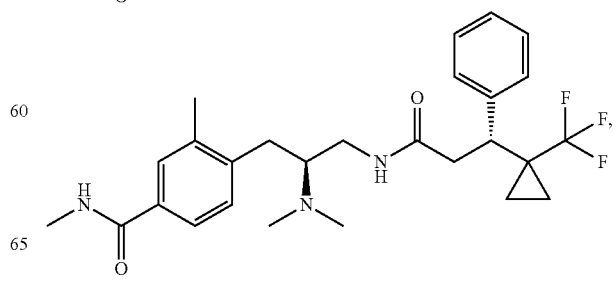

61
-continued
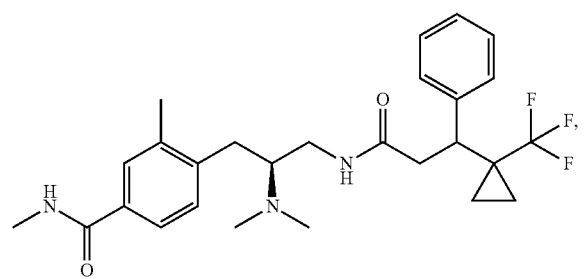
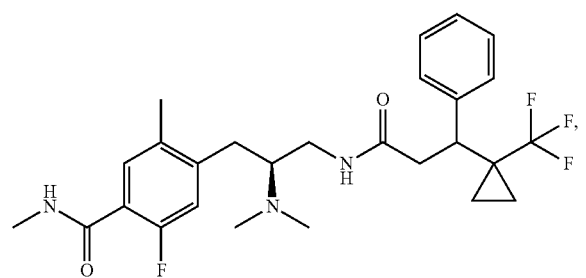
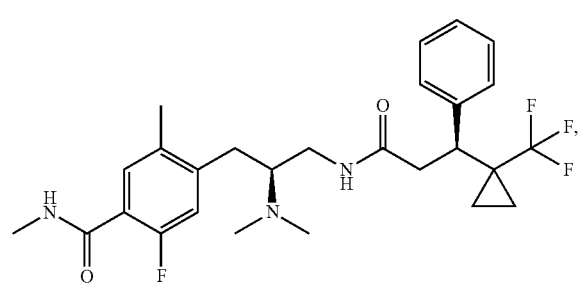
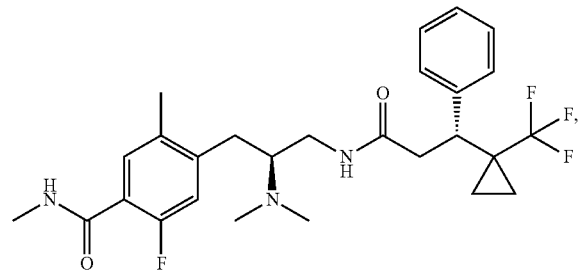
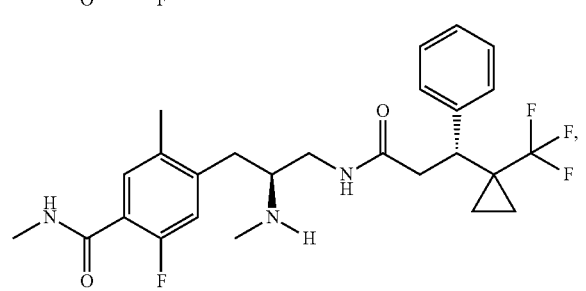
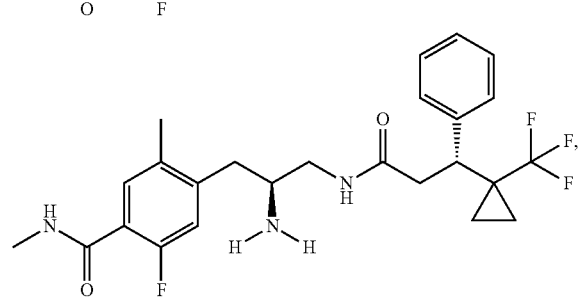
62
-continued
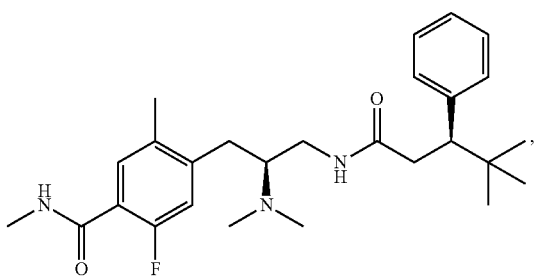
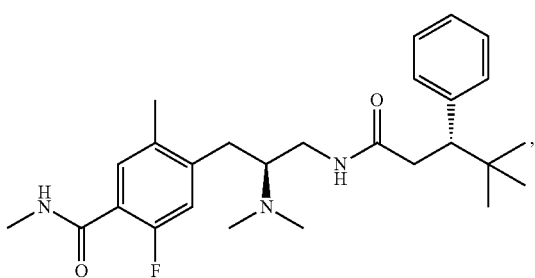
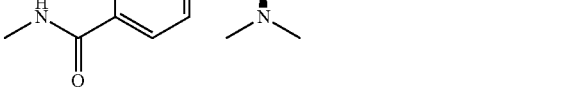
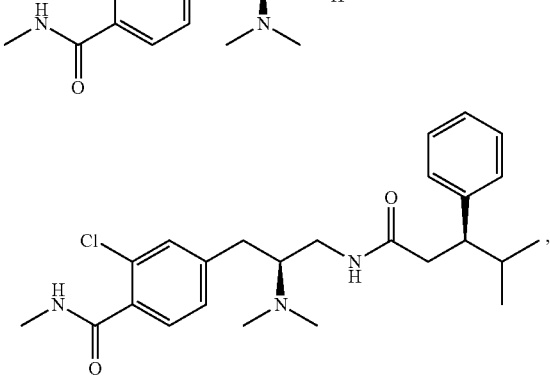
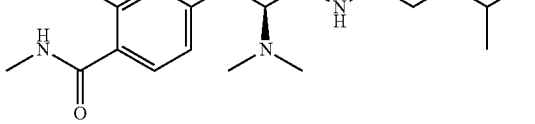

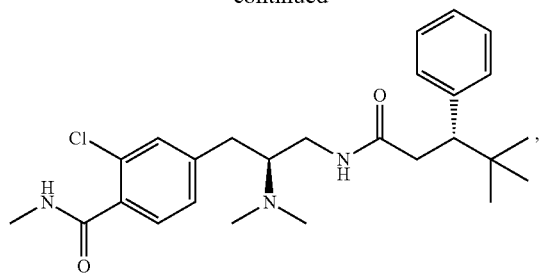
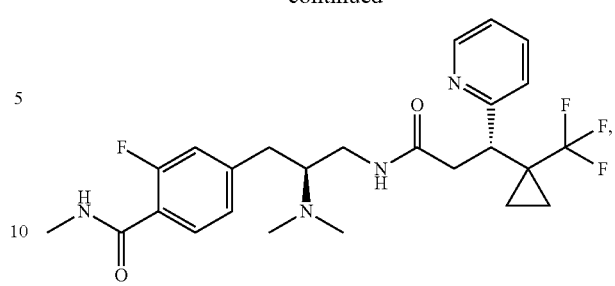

65
-continued
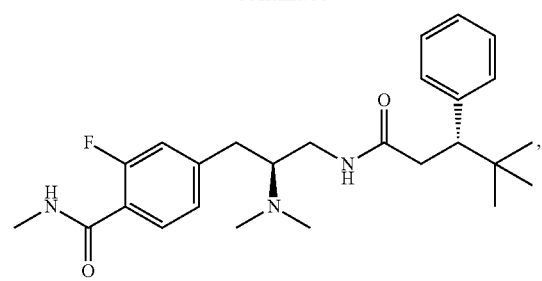
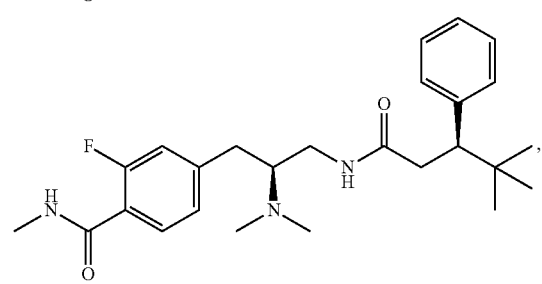
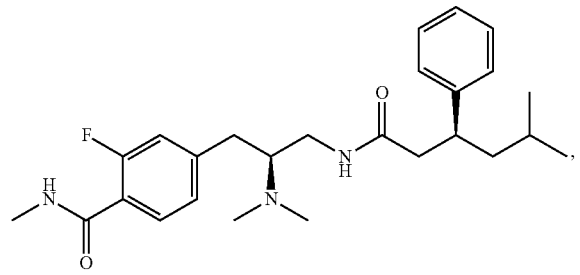
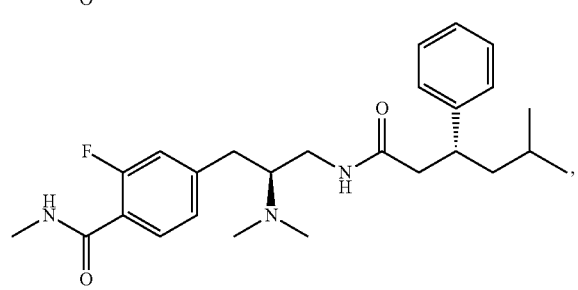
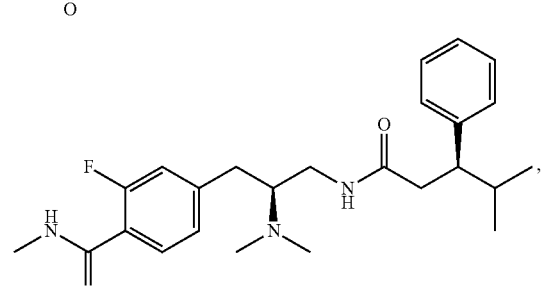
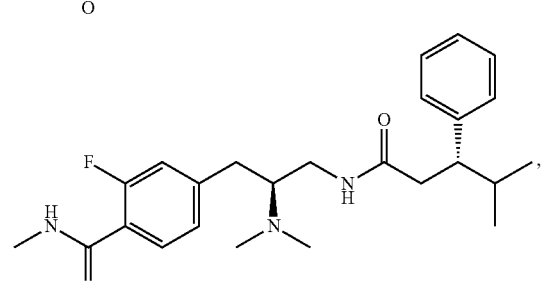
66
-continued
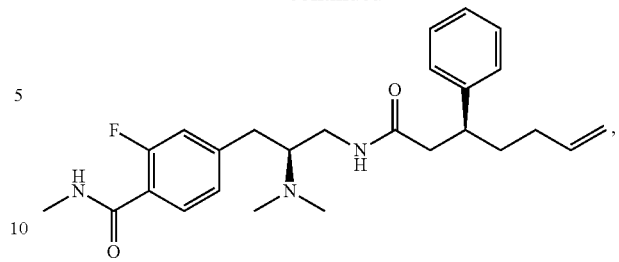
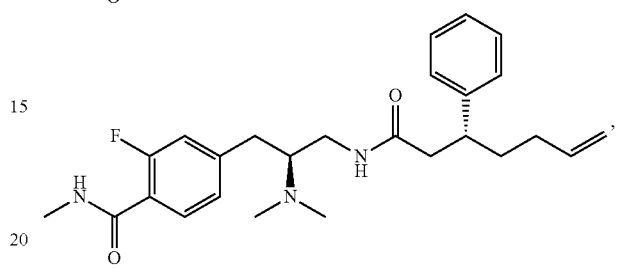
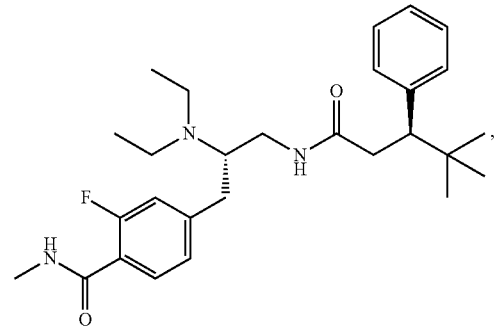
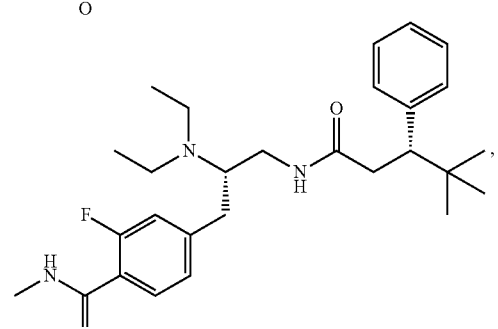
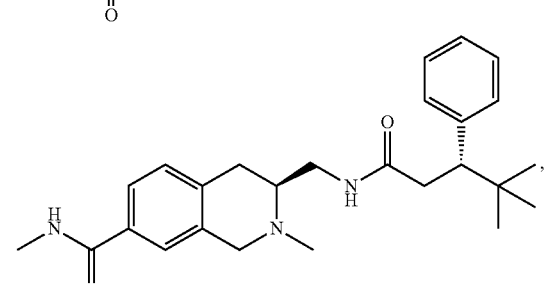
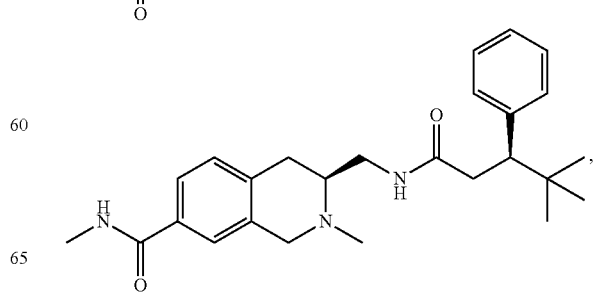

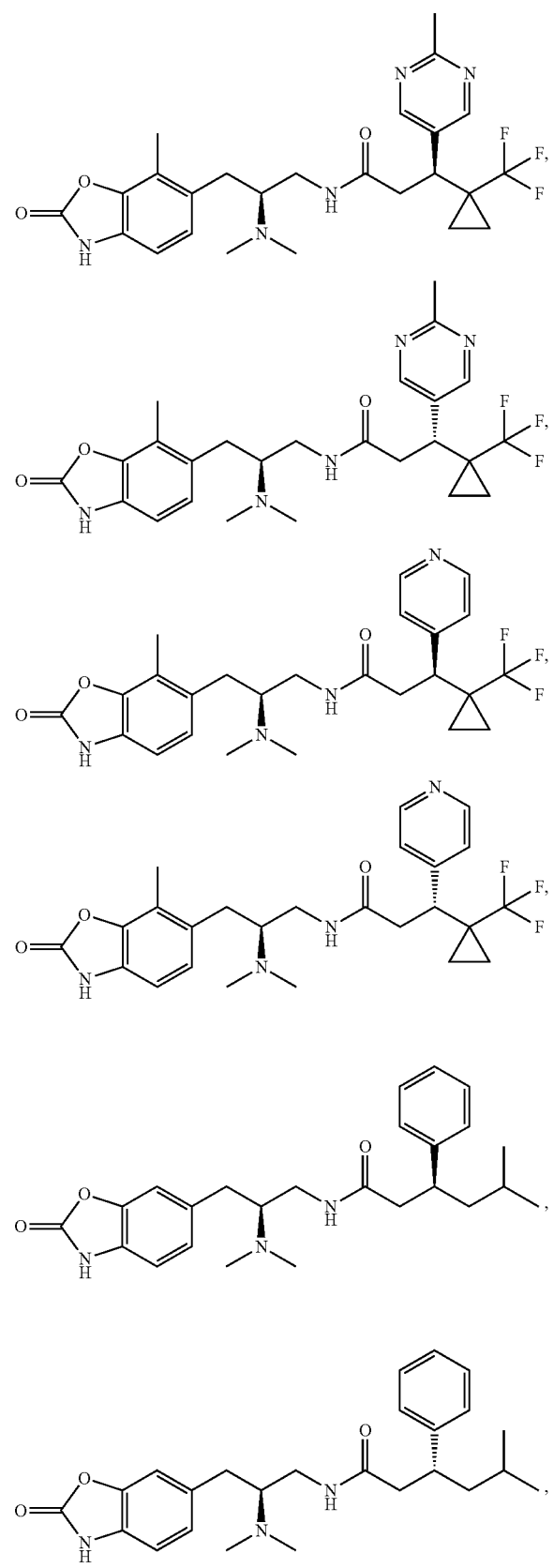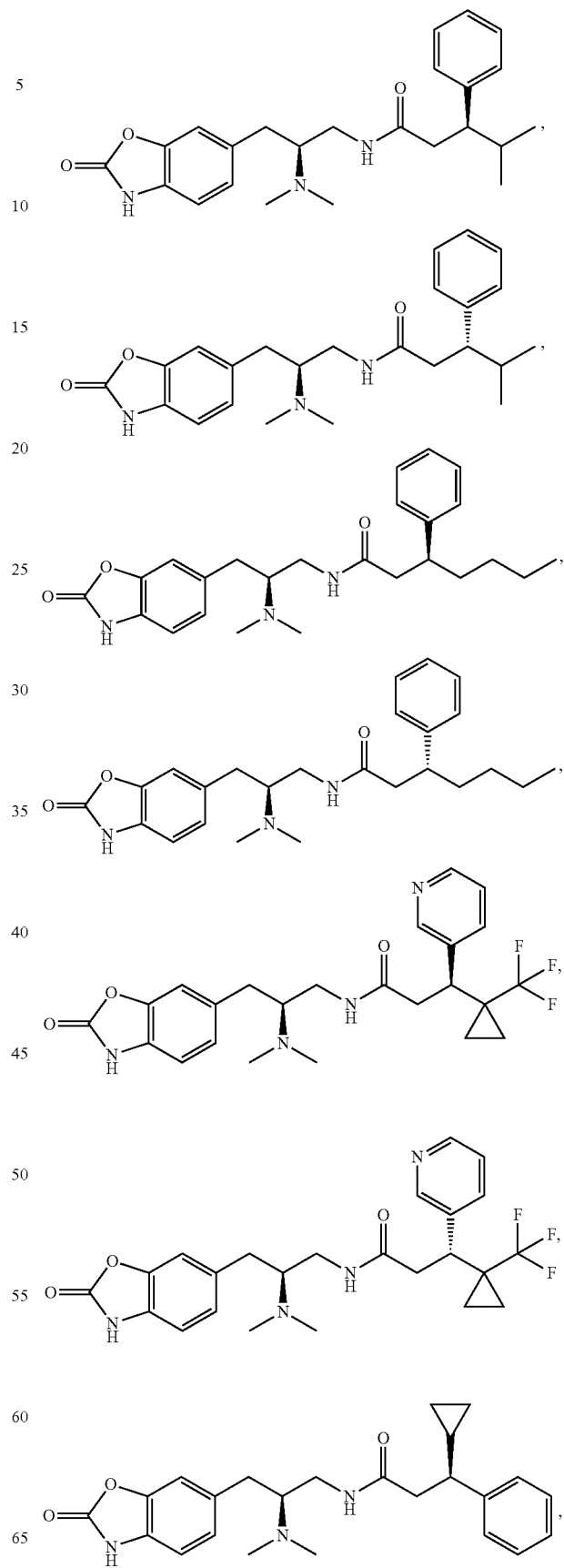

69
-continued
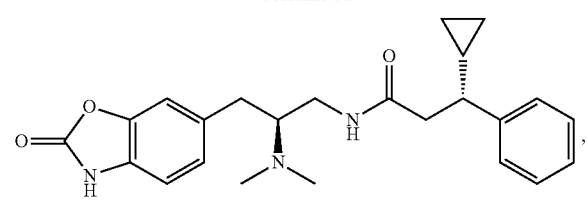
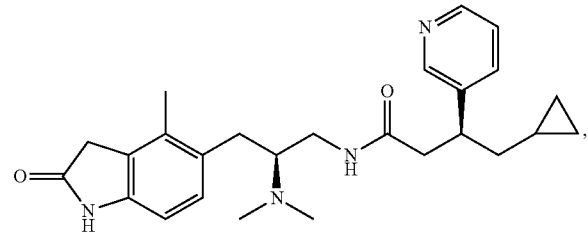
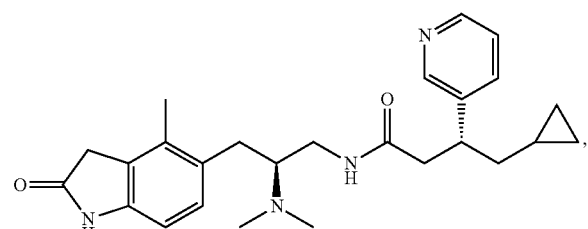
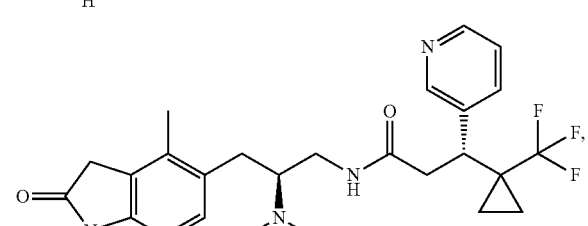
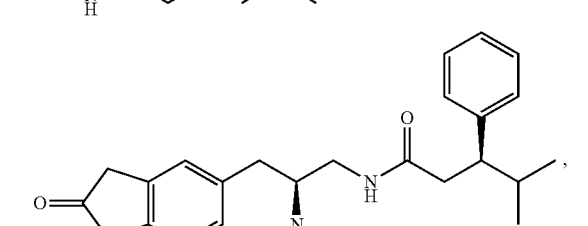
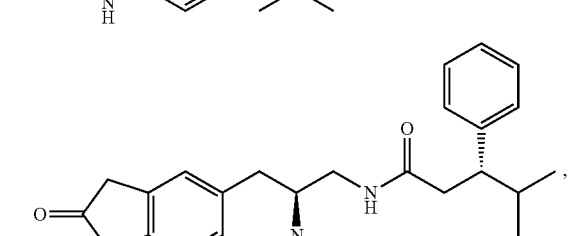
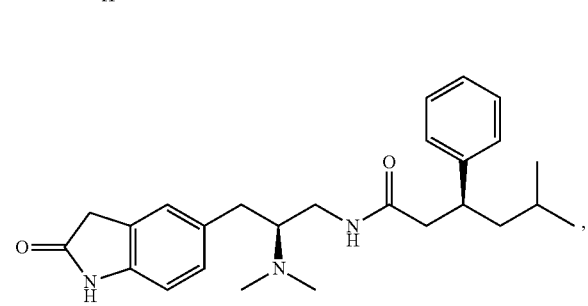
70
-continued
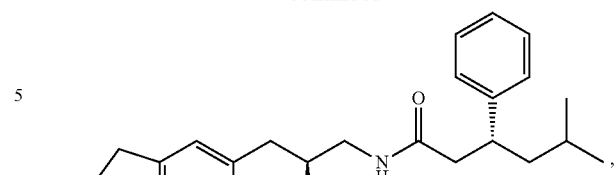
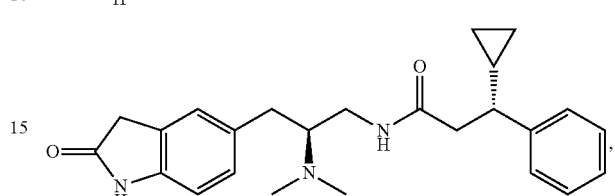
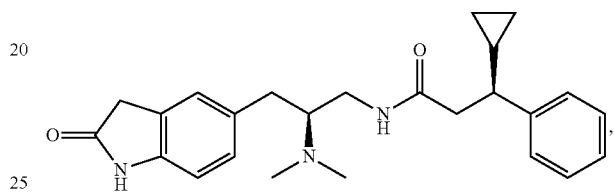
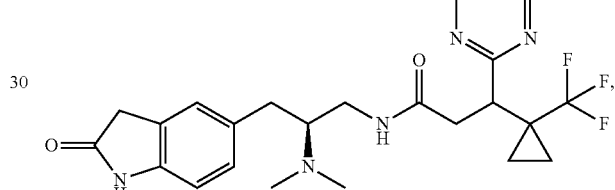
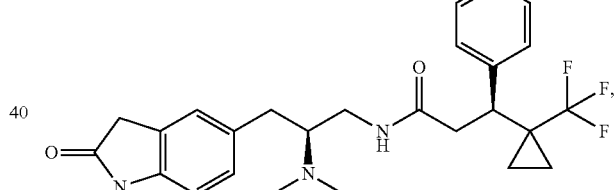
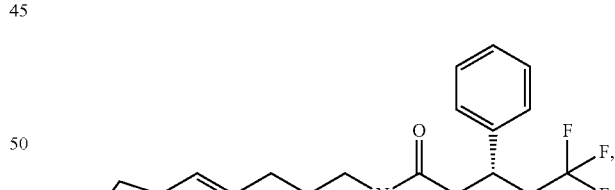
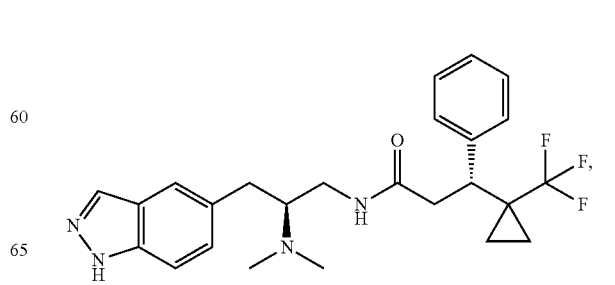

-continued
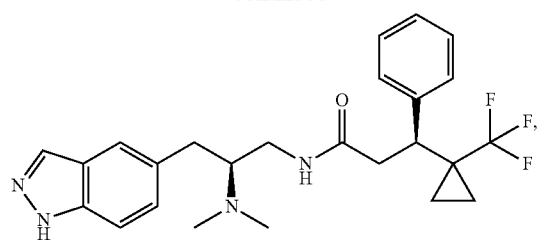
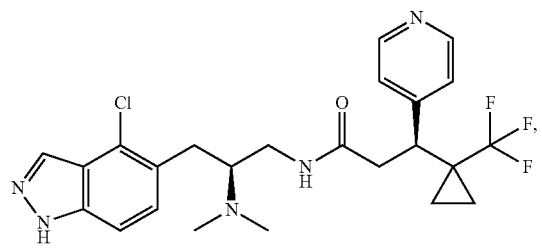
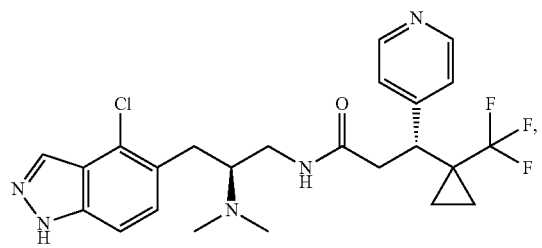
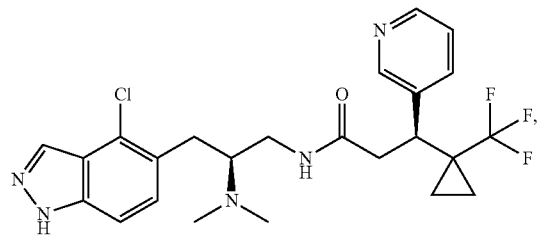
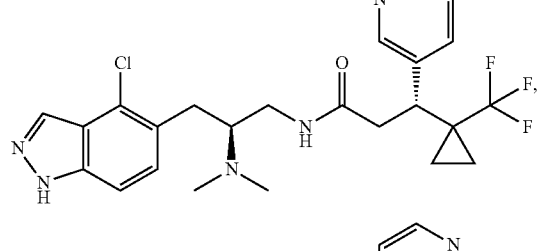
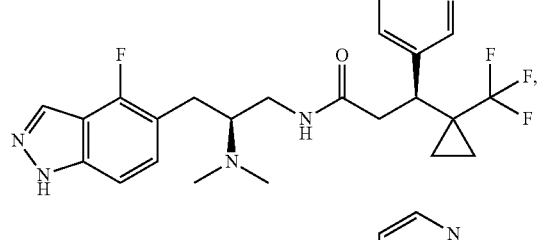
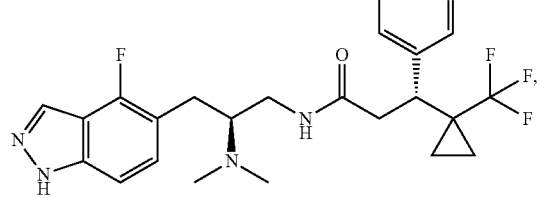
-continued
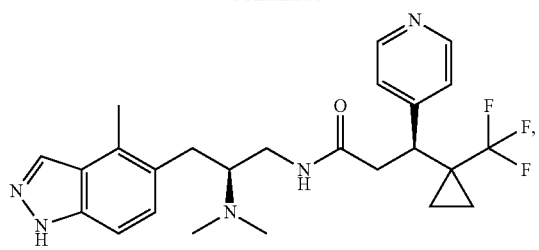
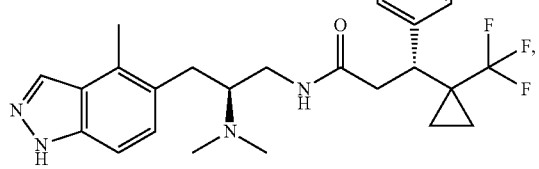
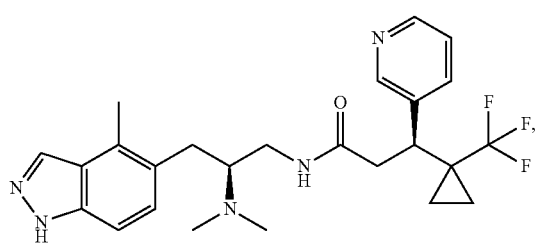
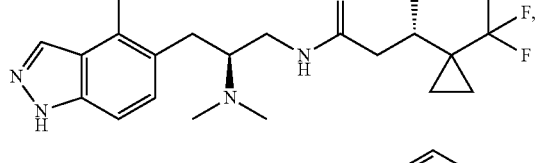
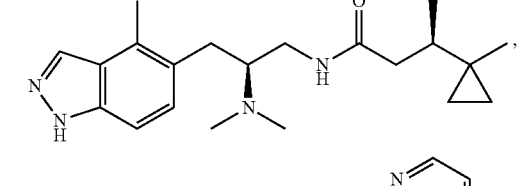
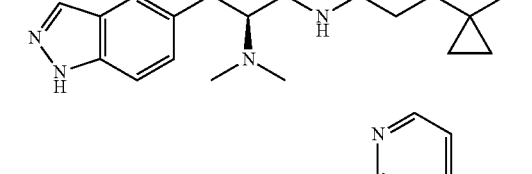
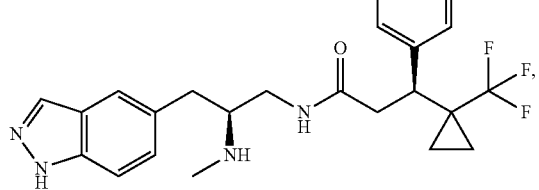

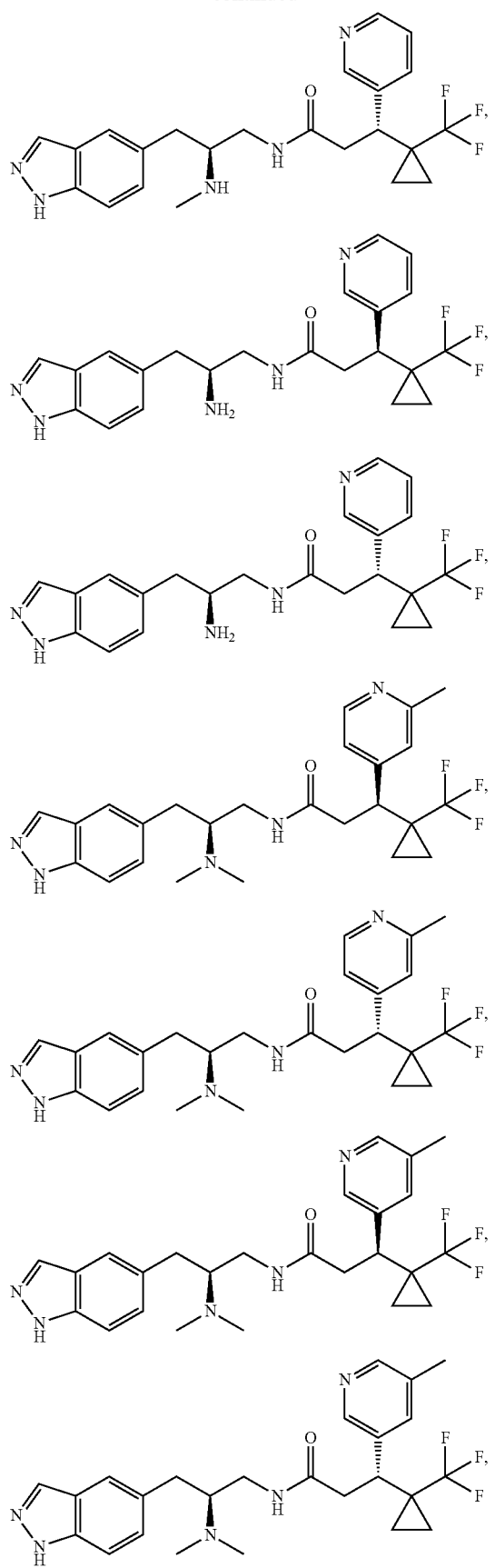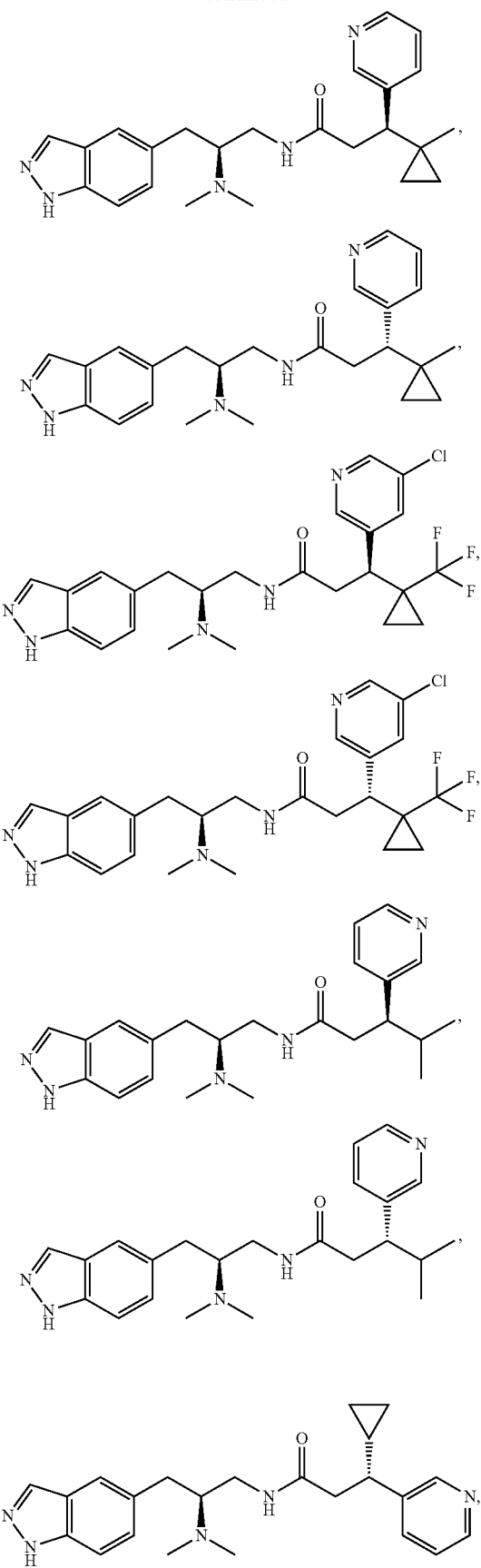

75
-continued
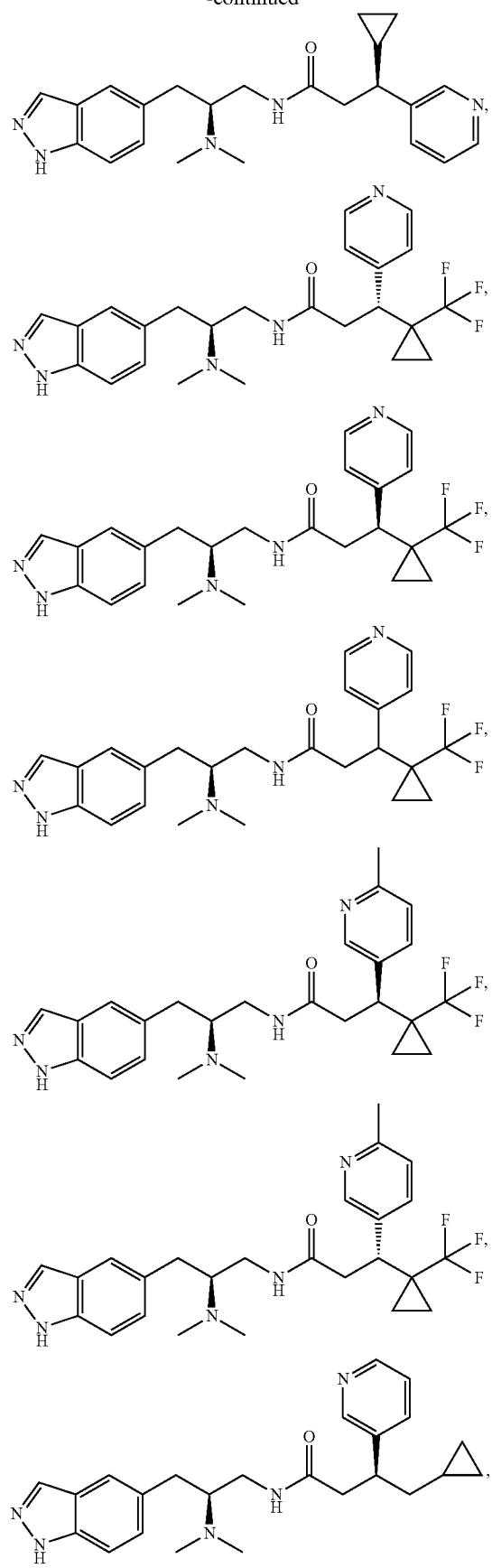
76
-continued
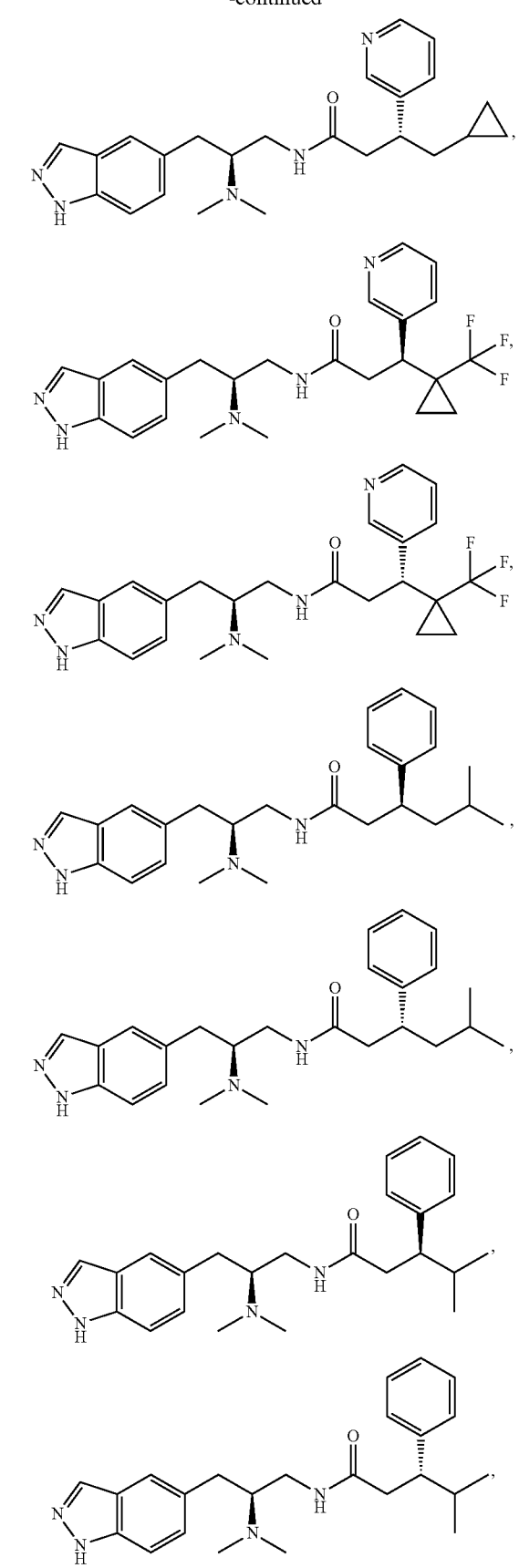

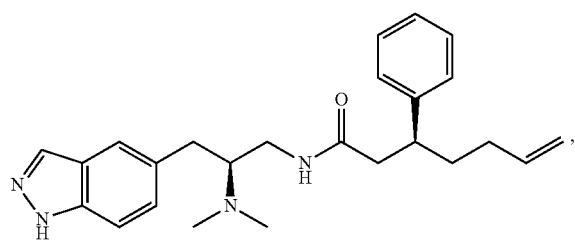
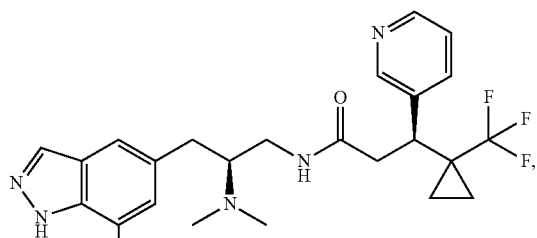
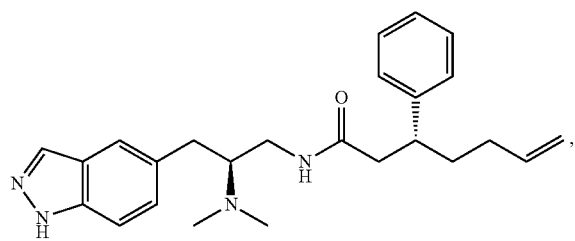
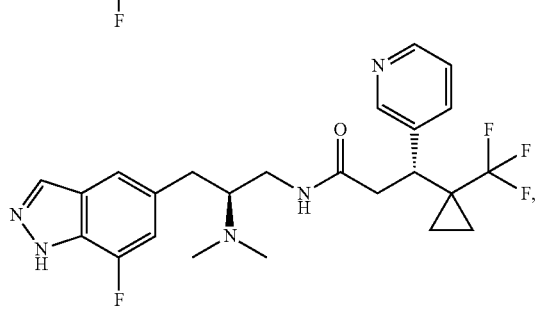
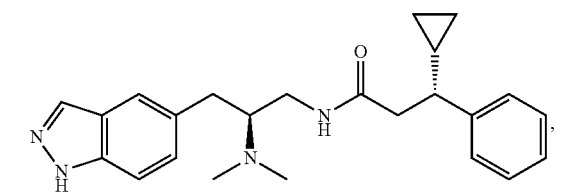
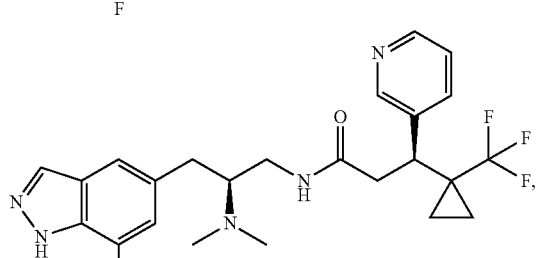
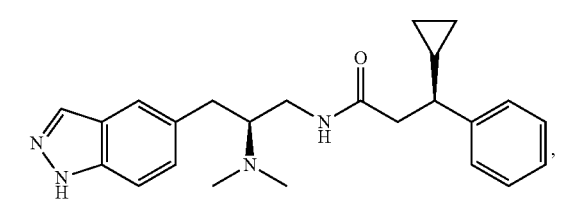
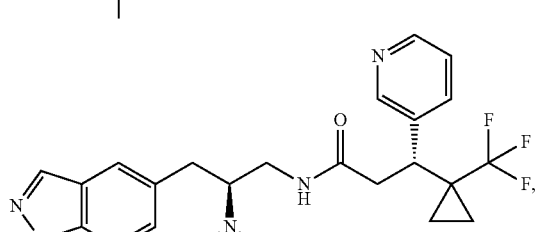
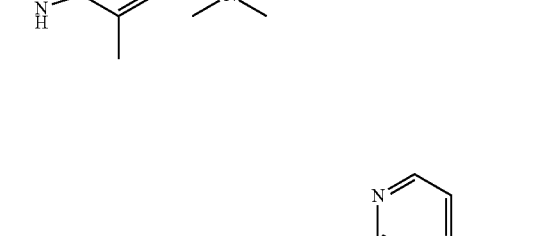
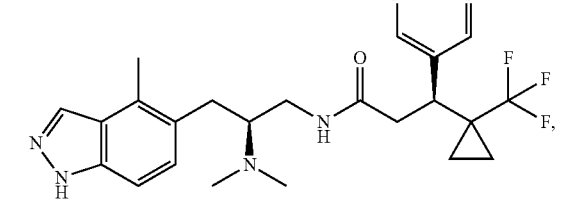

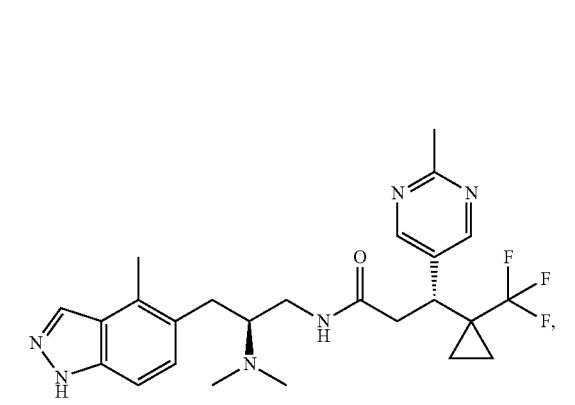
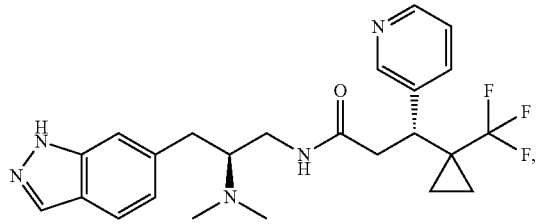

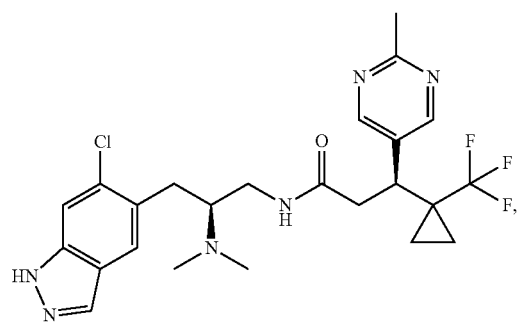
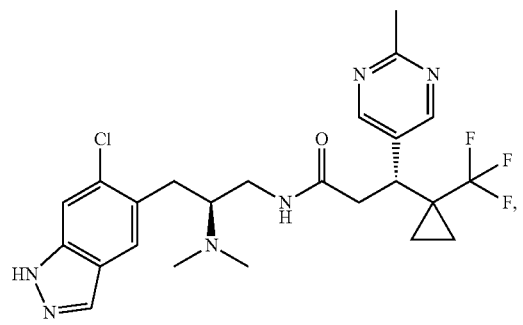
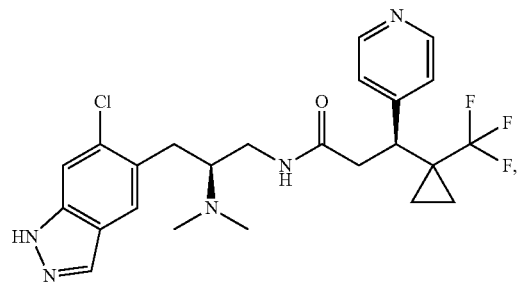
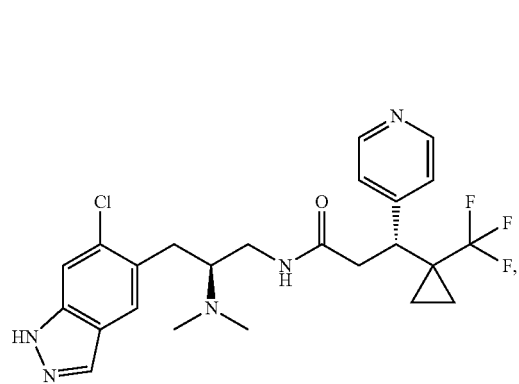
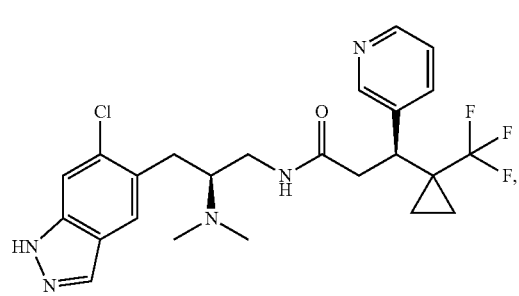
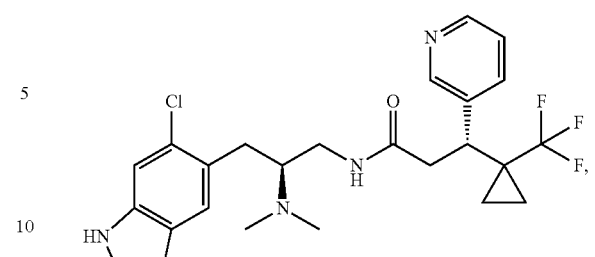

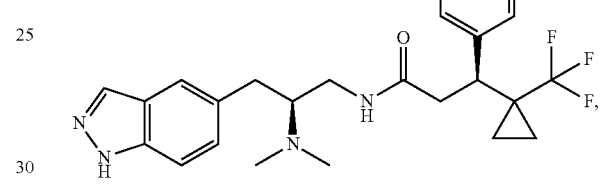
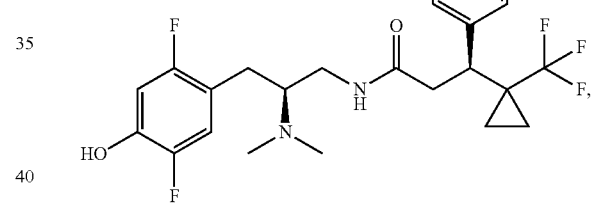
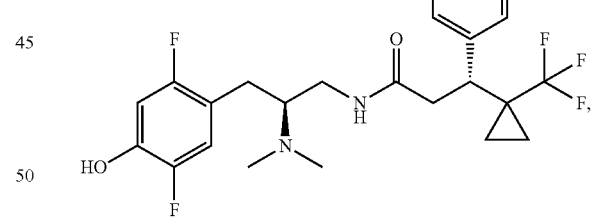
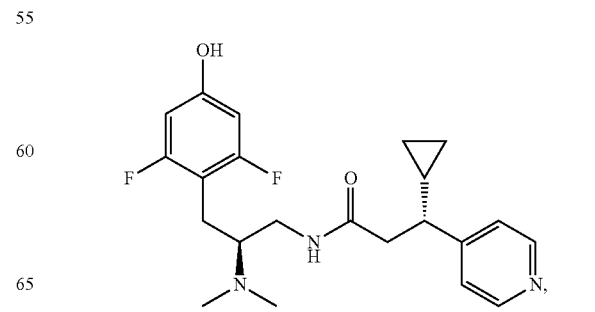

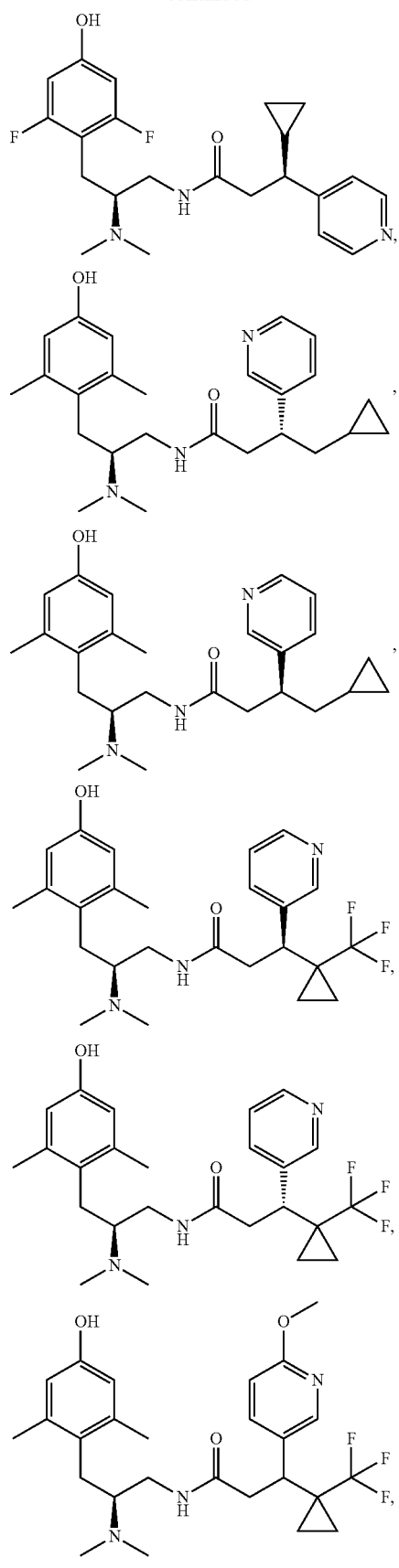
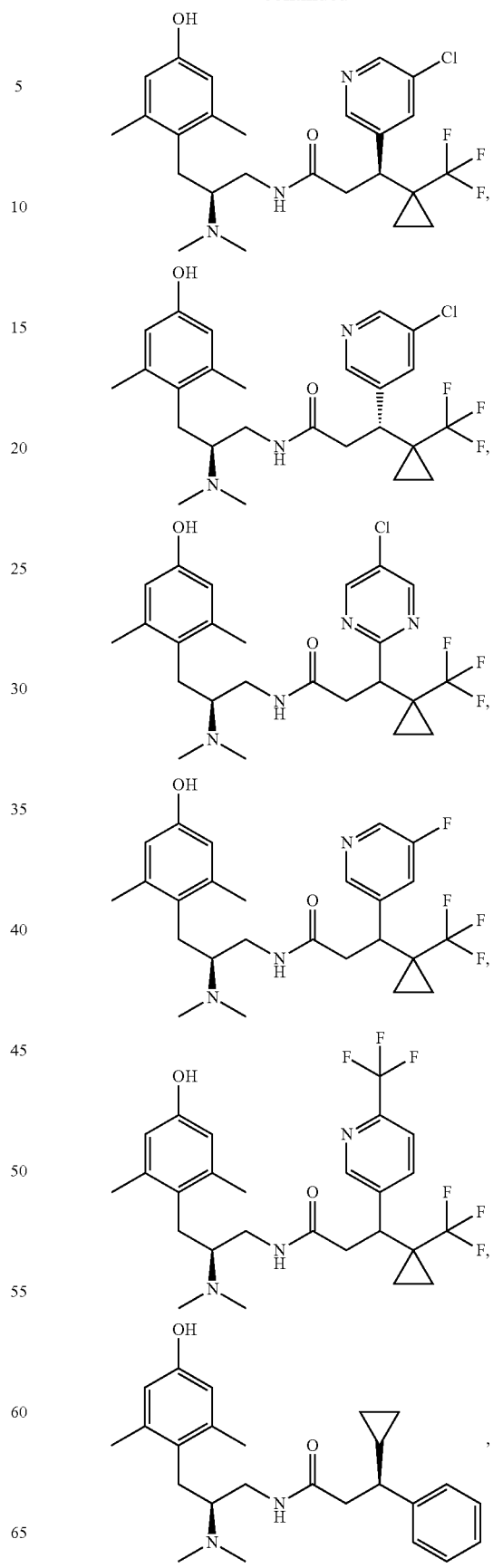

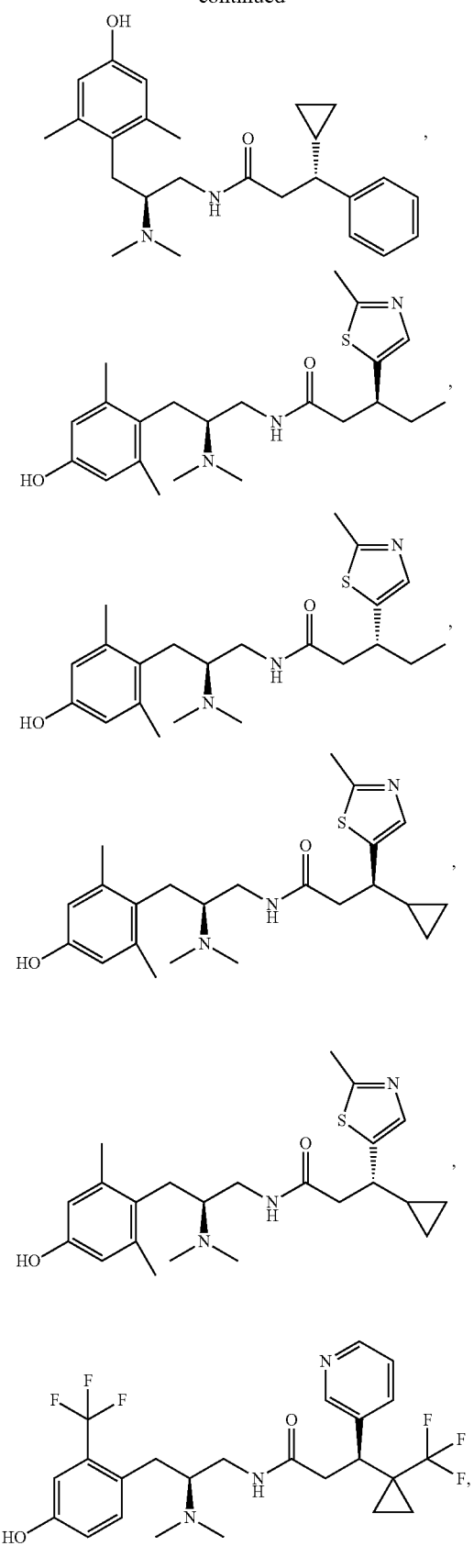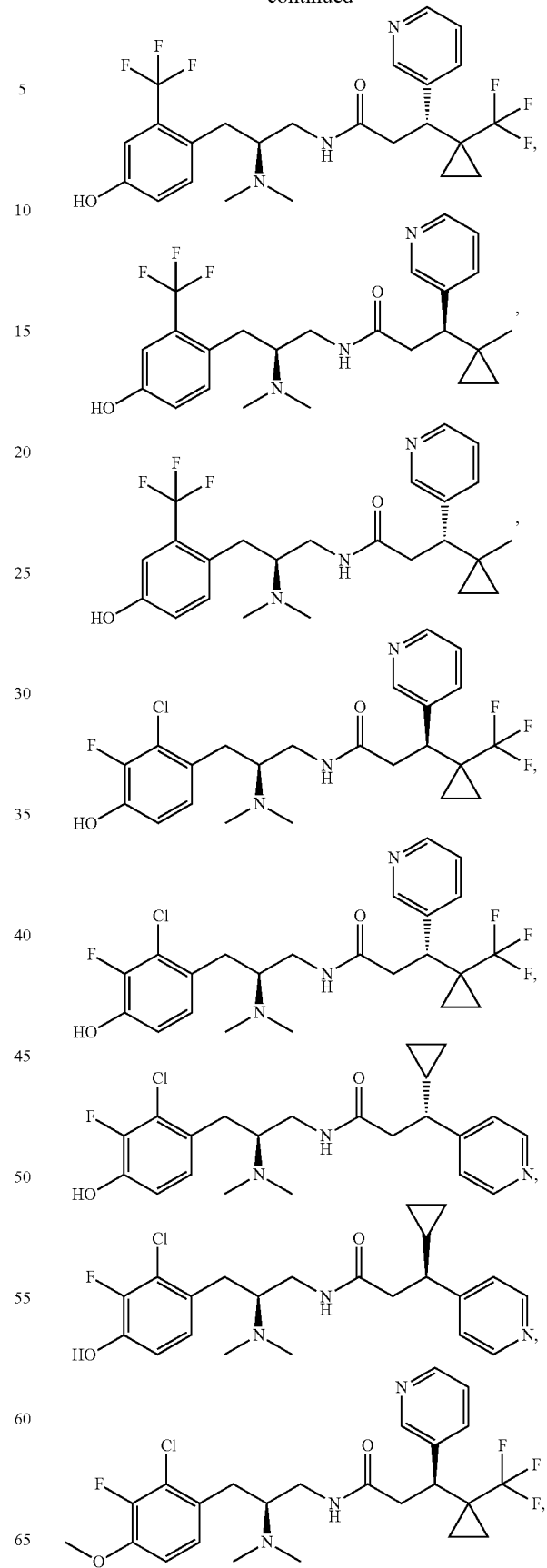

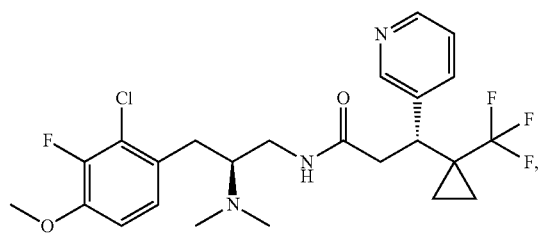
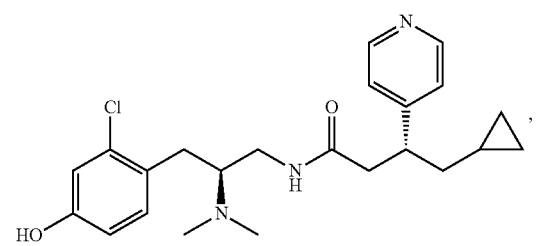
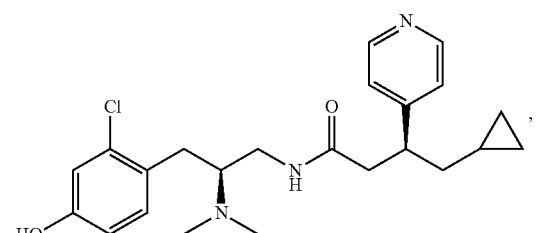
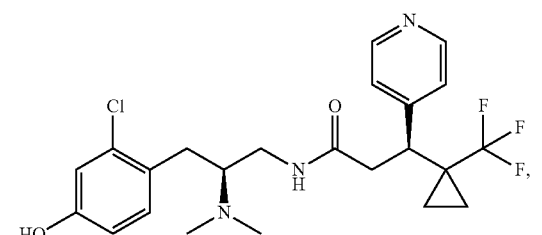
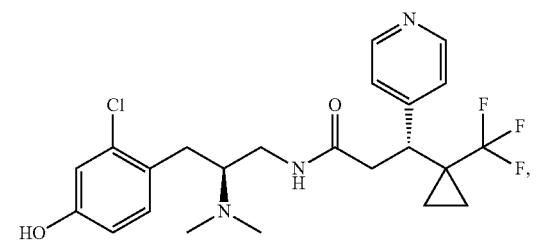
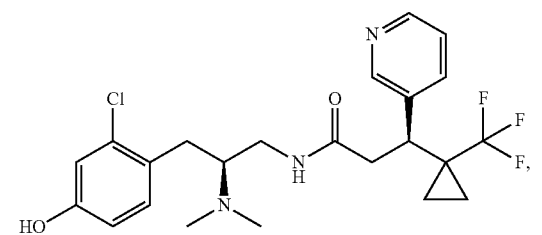
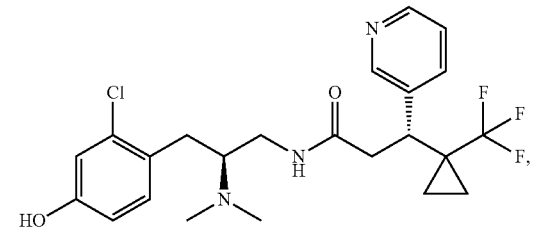
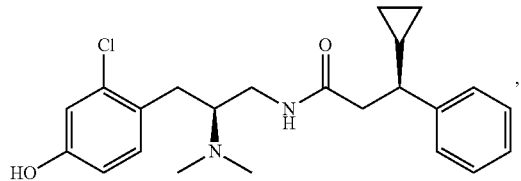
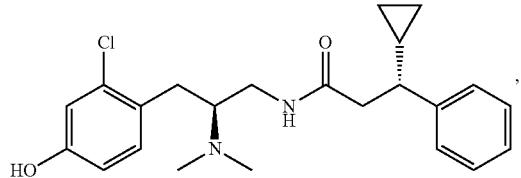
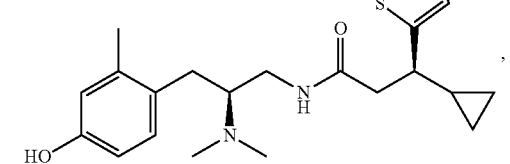
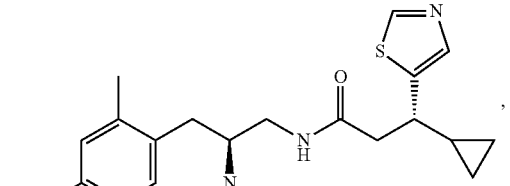
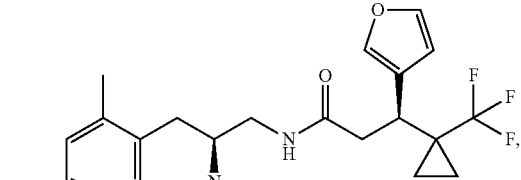
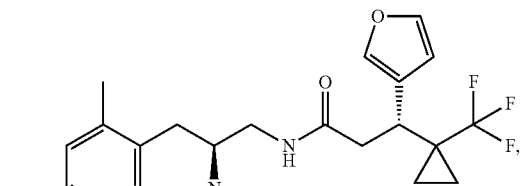
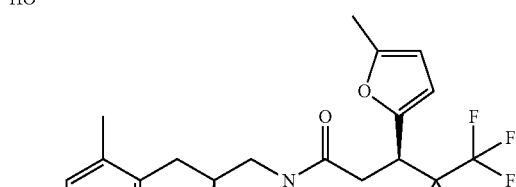
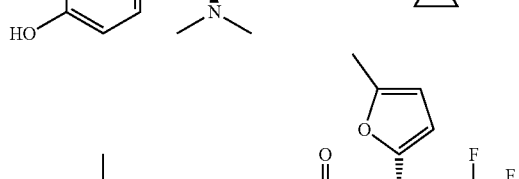

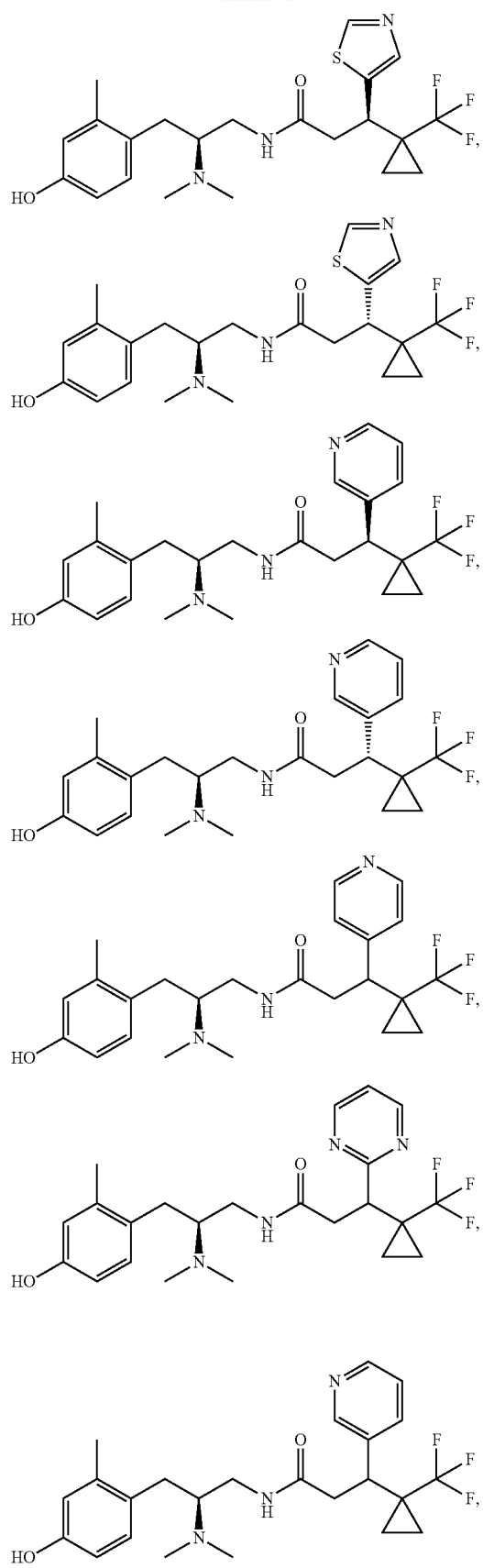
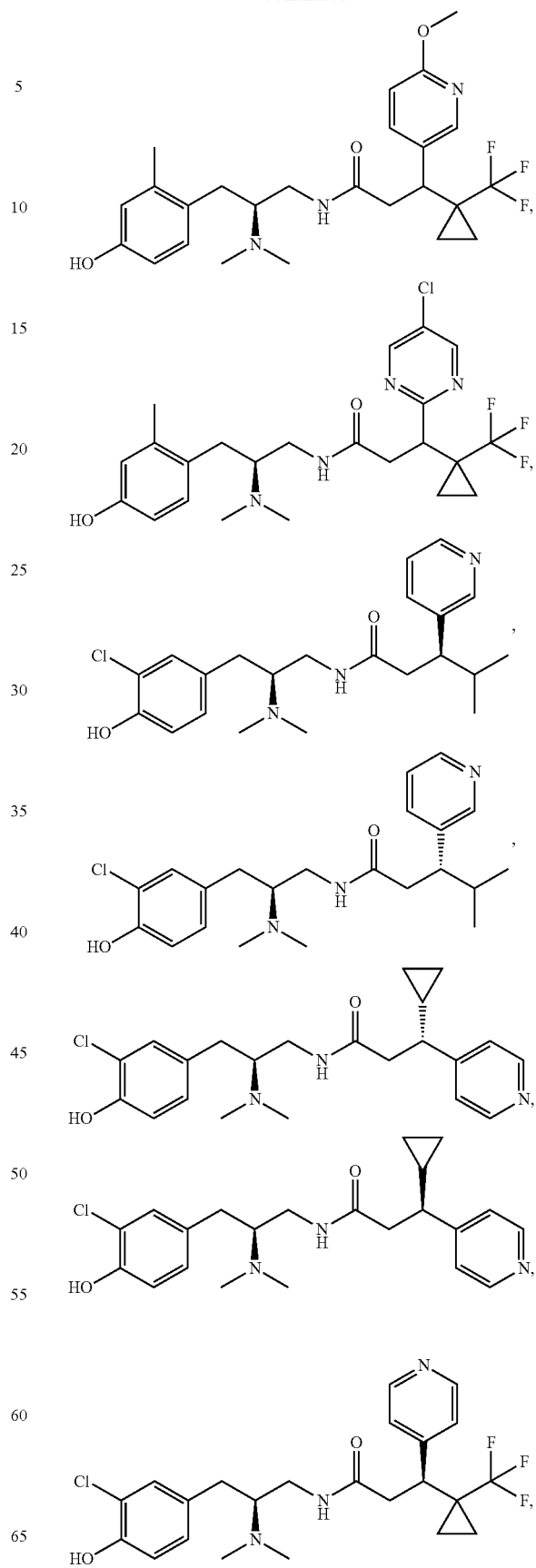

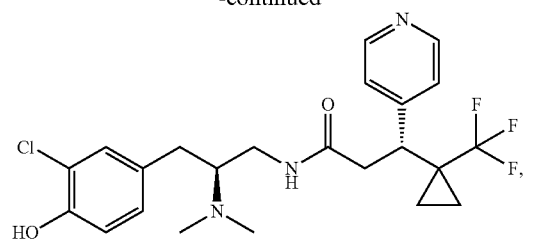
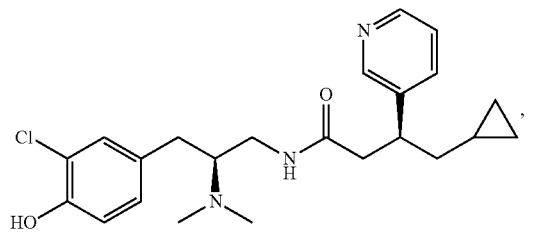
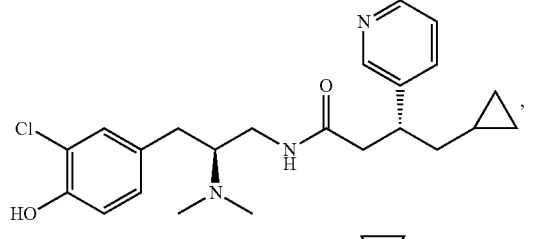
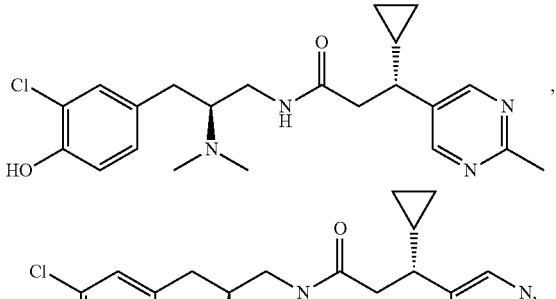
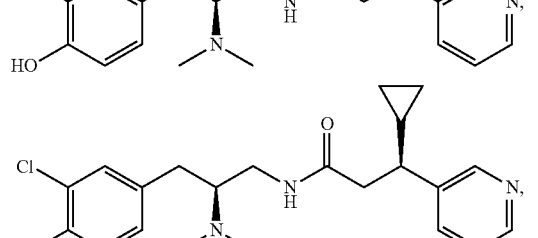

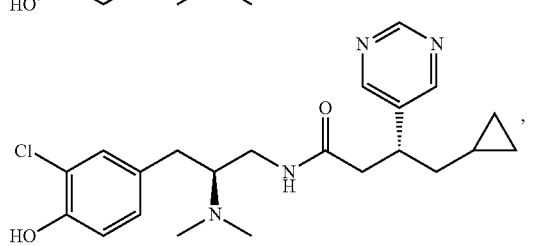
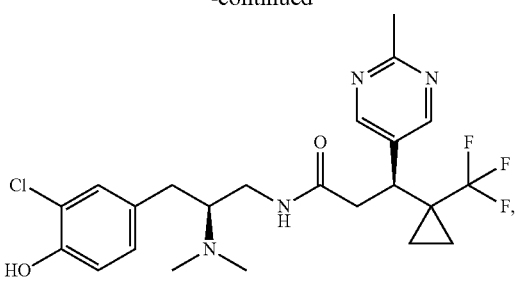
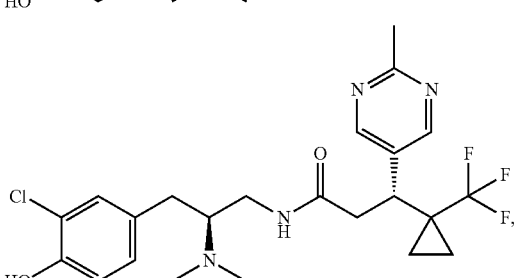
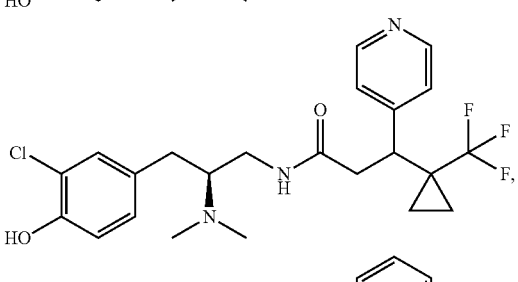
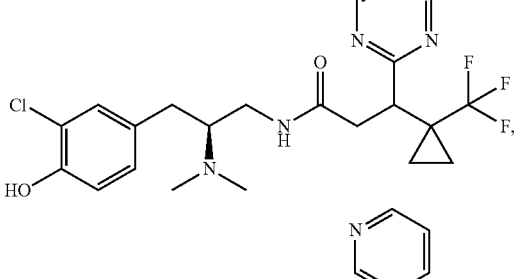
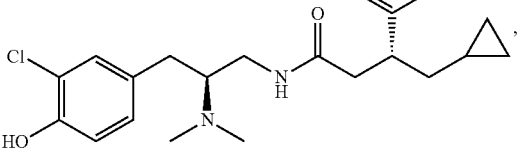
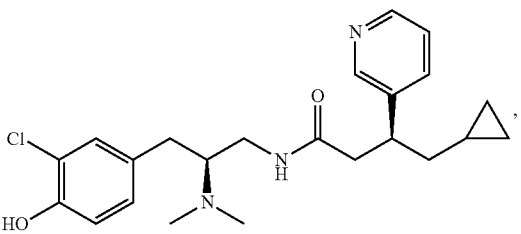
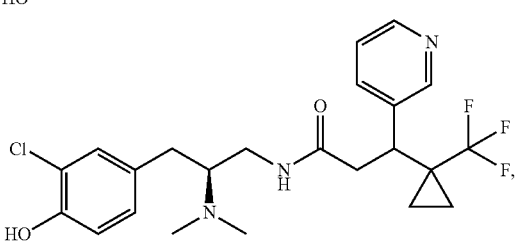

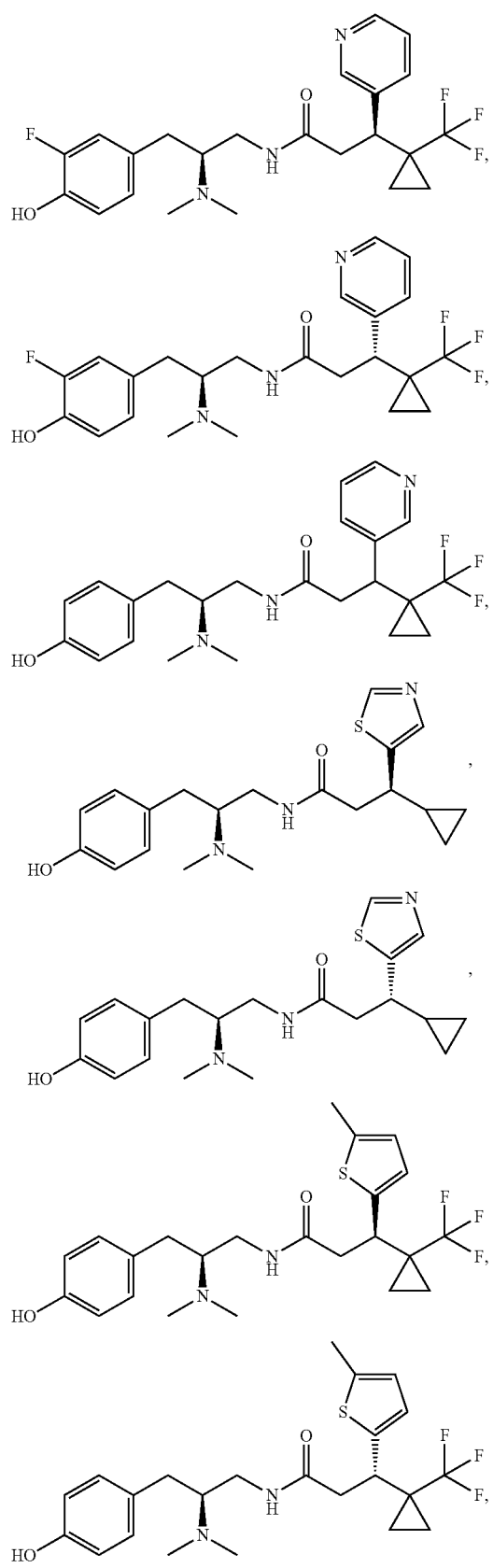
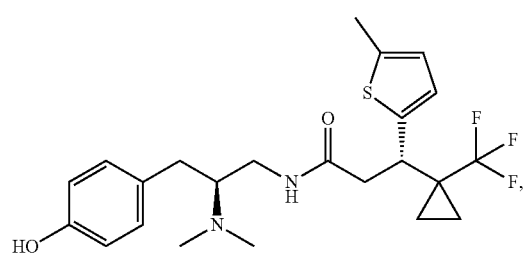
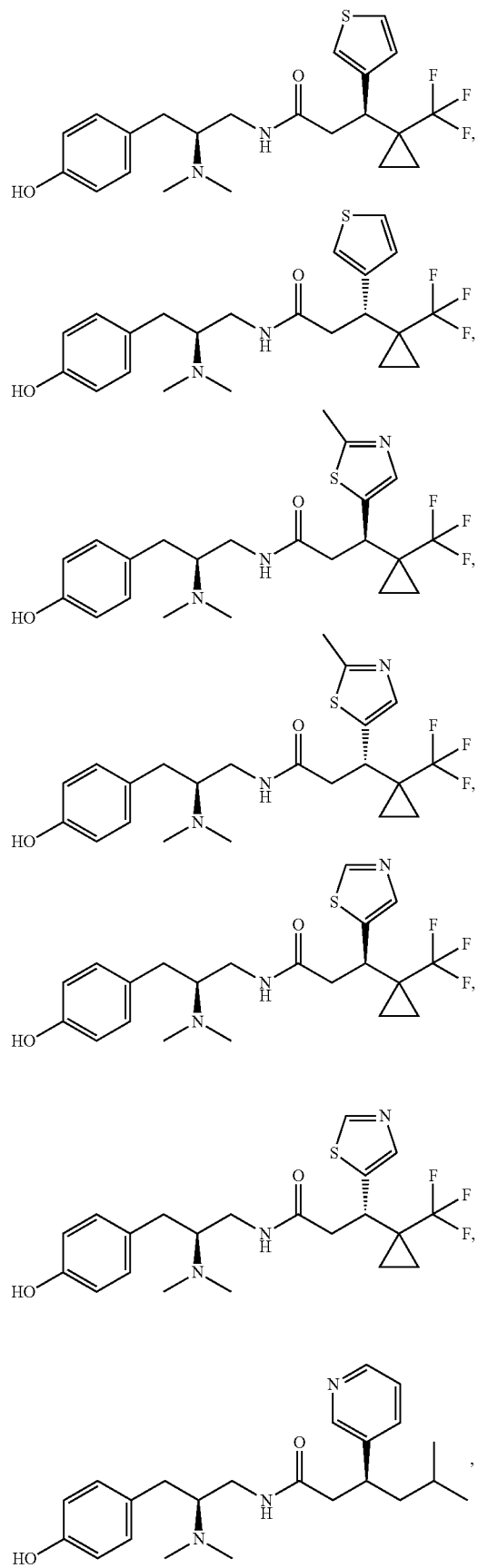

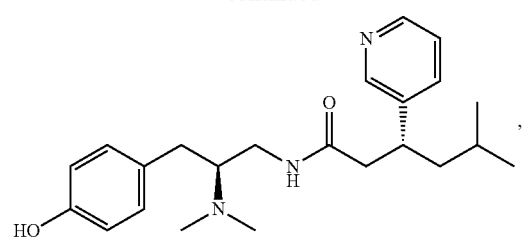
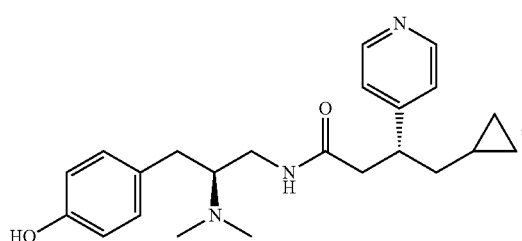
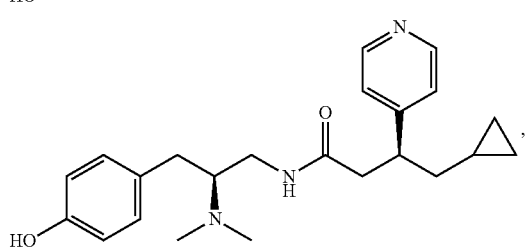
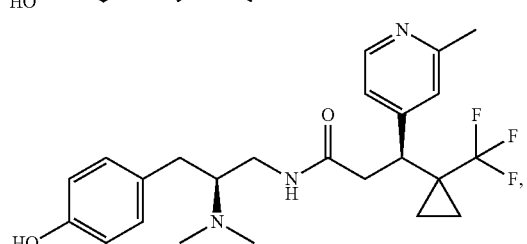
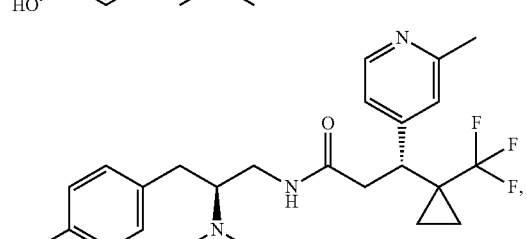
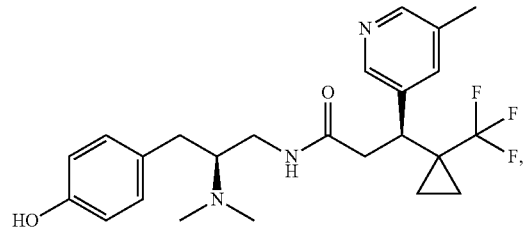
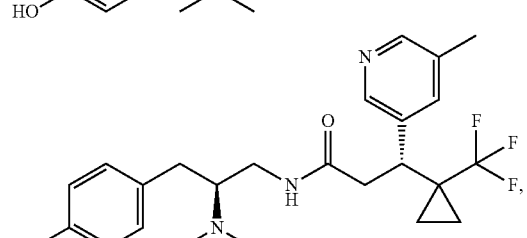
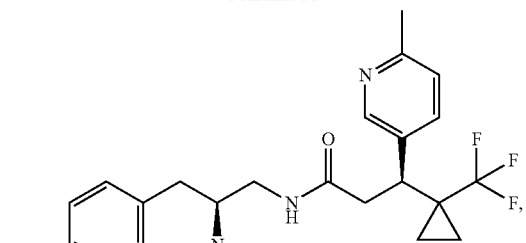
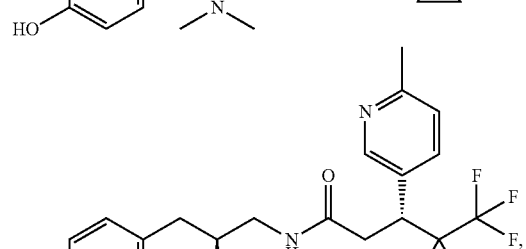
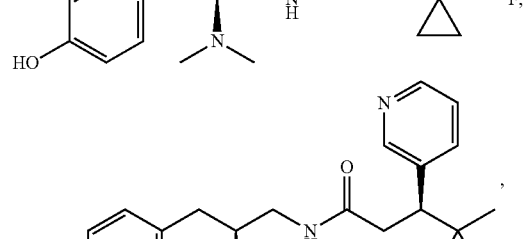
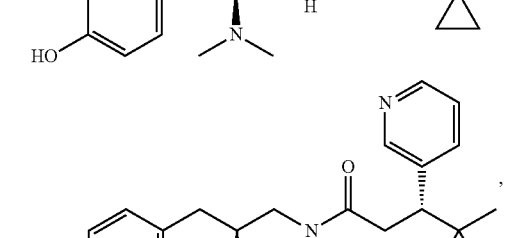
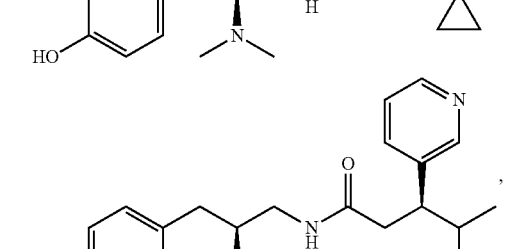
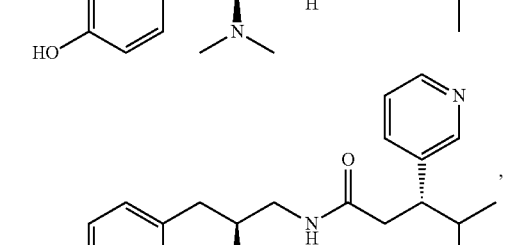
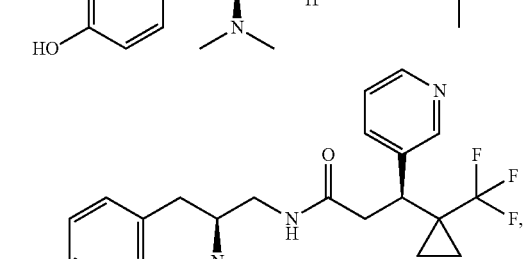

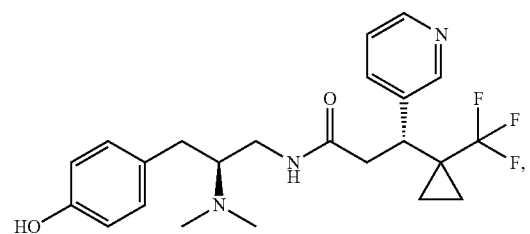

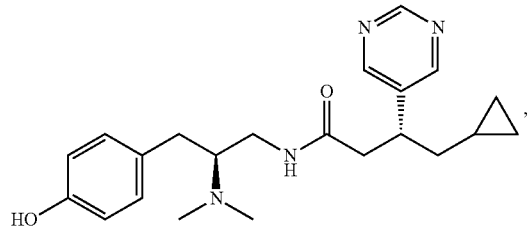
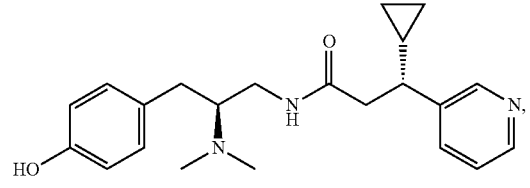
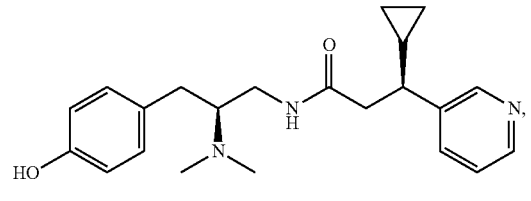
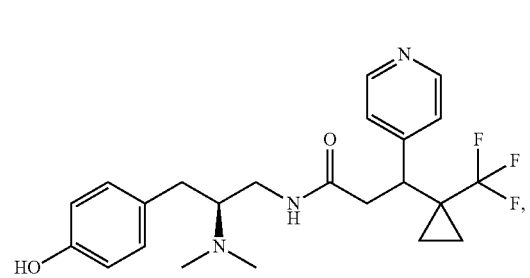
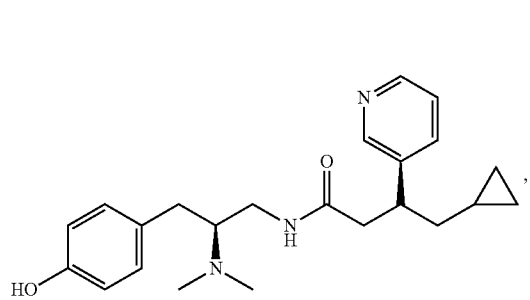
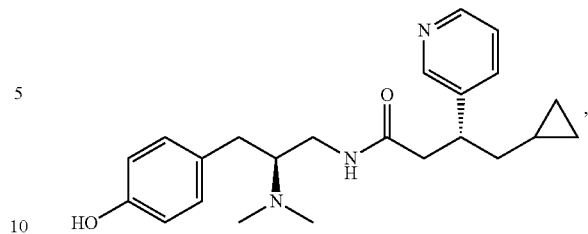

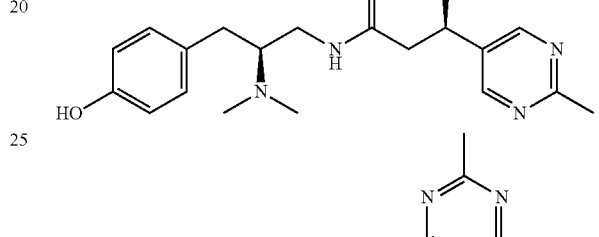
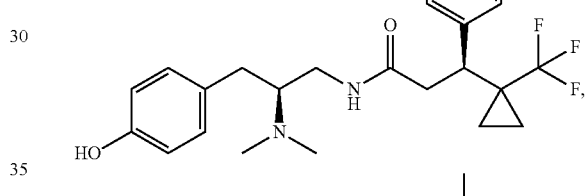
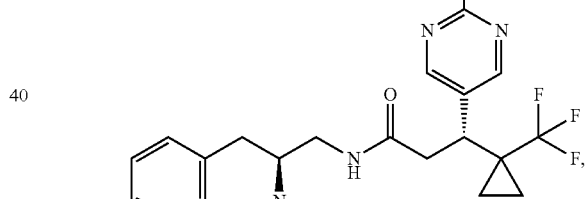
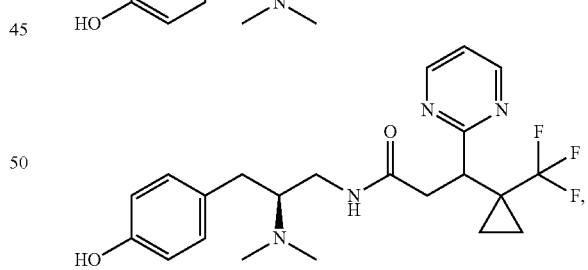
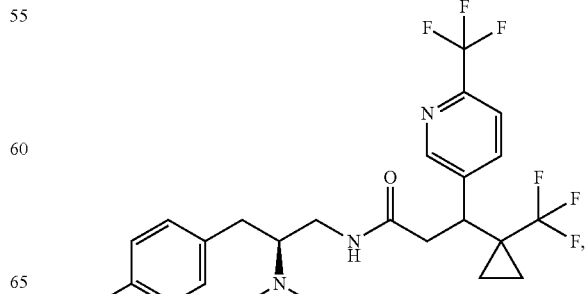

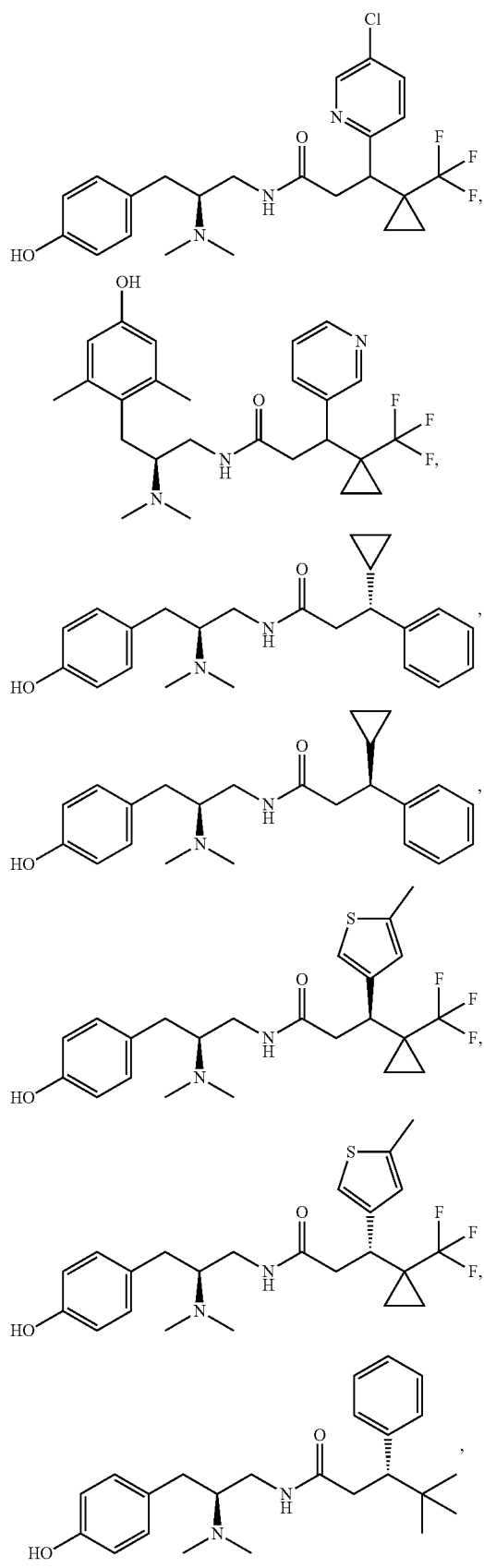
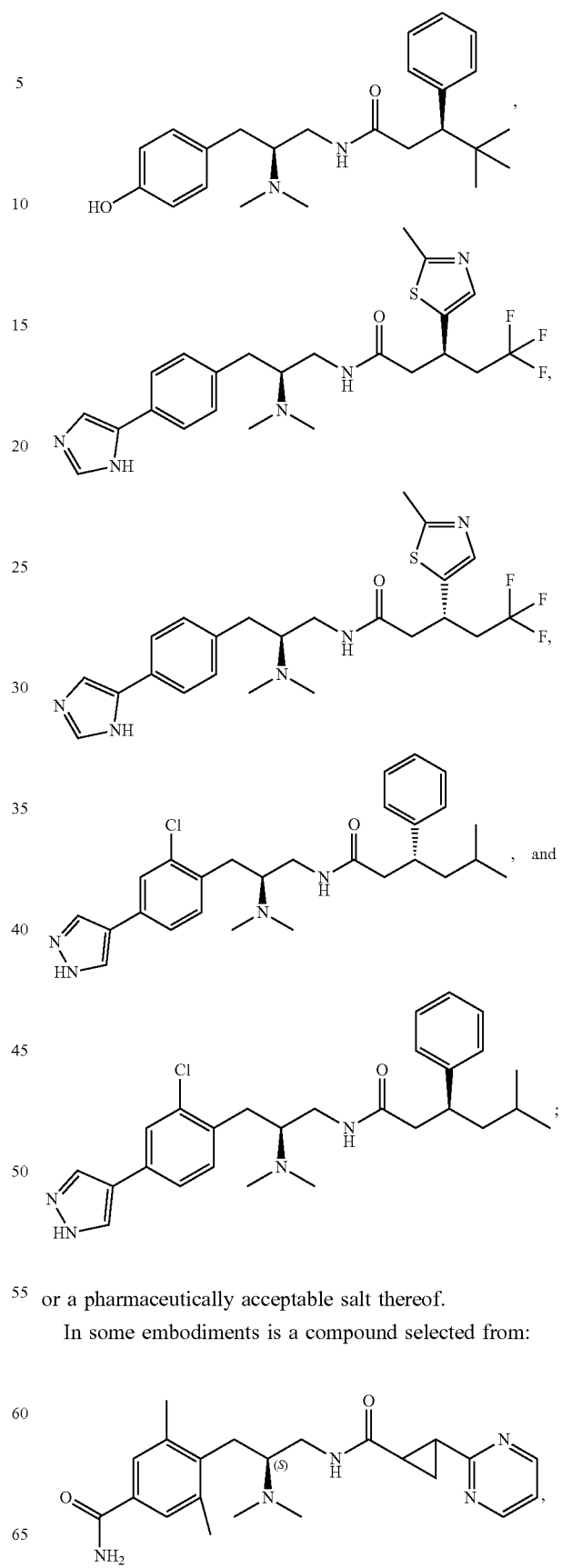
or a pharmaceutically acceptable salt thereof.
In some embodiments is a compound selected from:

99
-continued

100
-continued

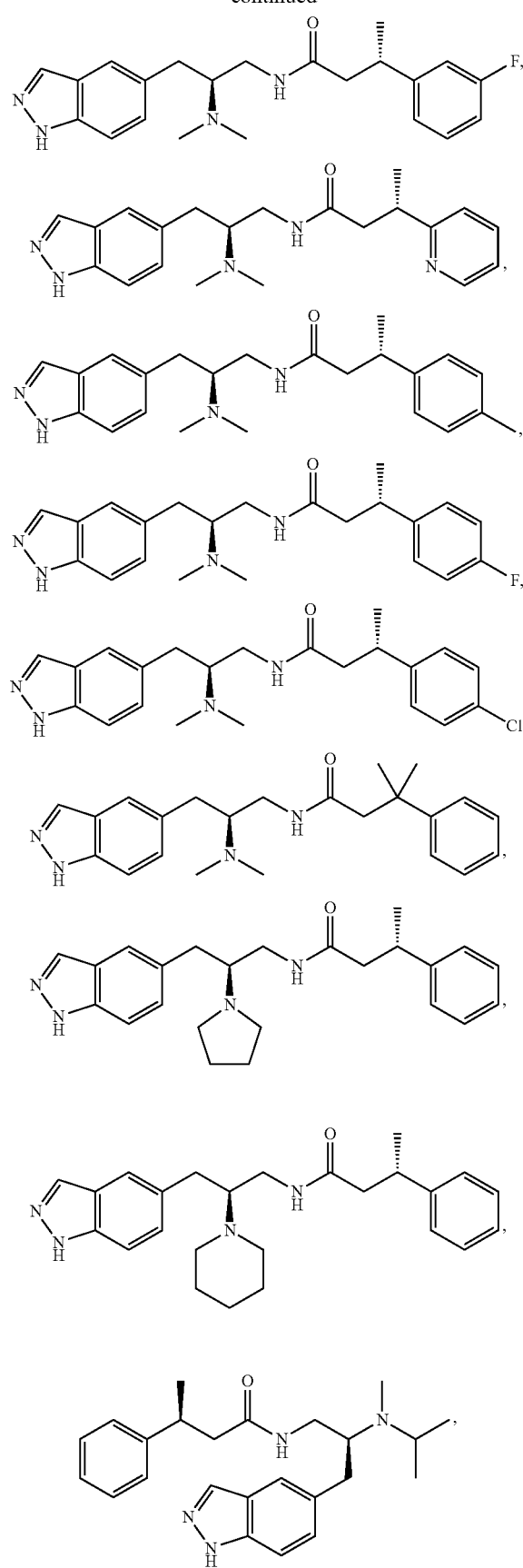
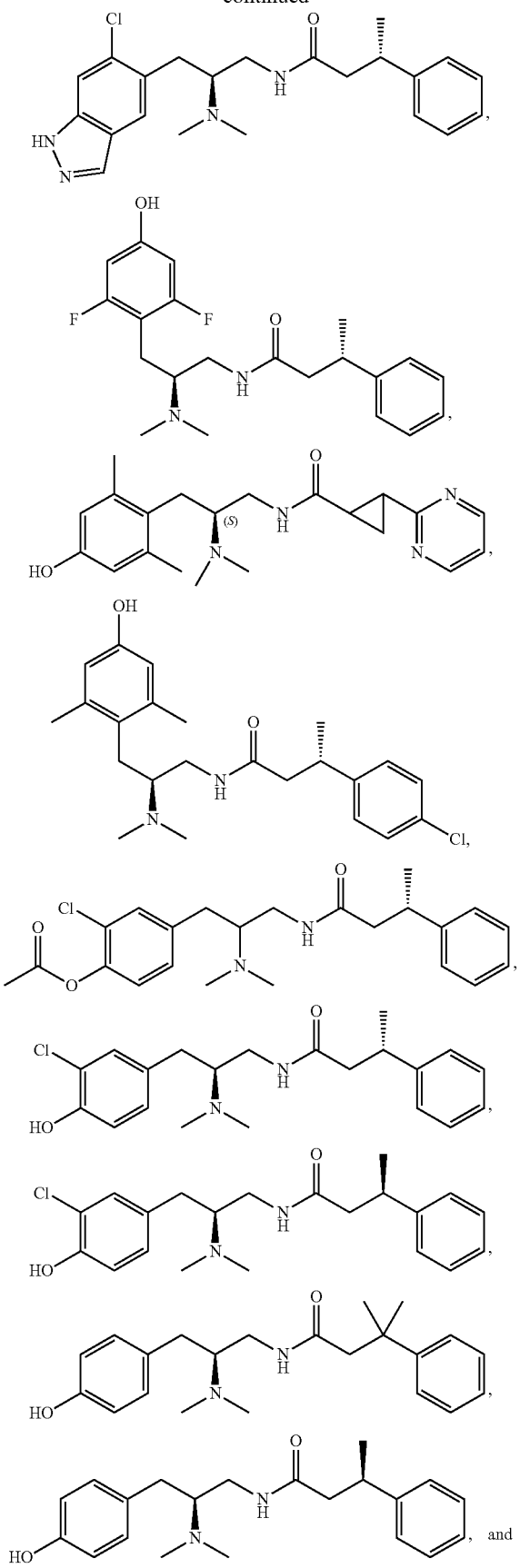

-continued

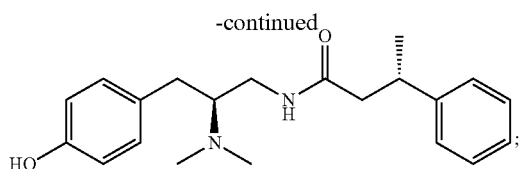

or a pharmaceutically acceptable salt thereof.

In some embodiments, the compounds of Formula (I), (Ia), (Ib), (Ic), (Id), (Ie), (If), (Ig), or (Ih), described herein are mu opioid receptor modulators. In some embodiments, the compounds described herein are mu opioid receptor super-agonists. In some embodiments, the compounds described herein are mu opioid receptor agonists. In some embodiments, the compounds described herein are mu opioid receptor partial agonists. In some embodiments, the compounds described herein are mu opioid receptor weak partial agonists. In some embodiments, the compounds described herein are mu opioid receptor weak partial agonists/antagonists. In some embodiments, the compounds described herein are mu opioid receptor antagonists.

In some embodiments, the compounds described herein are mu opioid receptor partial agonists having a cAMP activation of at least about 10%, about 20%, about 30%, about 40%, about 50%, about 60%, about 70%, about 80%, or more, compared to a standard full agonist (e.g., DAMGO). In some embodiments, the compounds described herein are mu opioid receptor weak partial agonists having a cAMP activation of about 10% to about 50% (e.g., about 10% to about 30%), compared to a standard full agonist (e.g., DAMGO). In some embodiments, the compounds described herein are mu opioid receptor partial agonists having a cAMP activation of about 30% to about 70%, compared to a standard full agonist (e.g., DAMGO). In some embodiments, the compounds described herein are mu opioid receptor partial agonists having a cAMP activation of about 50% to about 70%, compared to a standard full agonist (e.g., DAMGO). In some embodiments, the compounds described herein are mu opioid receptor partial agonists having a cAMP activation of about 40%, compared to a standard full agonist (e.g., DAMGO). In some embodiments, the compounds described herein are mu opioid receptor agonists having a cAMP activation of about 50%, compared to a standard full agonist (e.g., DAMGO). In some embodiments, the compounds described herein are mu opioid receptor agonists having a cAMP activation of about 60%, compared to a standard full agonist (e.g., DAMGO). In some embodiments, the compounds described herein are mu opioid receptor agonists having a cAMP activation of about 70/%, compared to a standard full agonist (e.g., DAMGO). In some embodiments, the compounds described herein are mu opioid receptor agonists having a cAMP activation of about 80%, compared to a standard full agonist (e.g., DAMGO).

In some embodiments, the compounds described herein are mu opioid receptor antagonist/weak partial agonists with efficacy less than that of buprenorphine. In some embodiments, the compounds described herein are mu opioid receptor antagonist/weak partial agonists with efficacy greater than that of naltrexone. In some embodiments, the compounds described herein are mu opioid receptor antagonist/weak partial agonists with efficacy below buprenorphine and above naltrexone. In some embodiments, the compounds described herein are mu opioid receptor antagonist/weak partial agonists with efficacy below morphine and above buprenorphine.

In some embodiments, the compounds of Formula (I), (Ia), (Ib), (Ic), (Id), (Ie), (If), (Ig), or (Ih), described herein are biased mu opioid receptor modulators (e.g., agonists, partial agonists, weak partial agonists, antagonists, etc.). In some embodiments, the compounds described herein are G-protein biased mu opioid receptor modulators. In some embodiments, the compounds described herein are β-arrestin biased mu opioid receptor modulators.

In some embodiments, the compounds of Formula (I), (Ia), (Ib), (Ic), (Id), (Ie), (If), (Ig), or (Ih), described herein are delta opioid receptor modulators. In some embodiments, the compounds described herein are delta opioid receptor agonists. In some embodiments, the compounds described herein are delta opioid receptor partial agonists. In some embodiments, the compounds described herein are delta opioid receptor weak partial agonists/antagonists. In some embodiments, the compounds described herein are delta opioid receptor antagonists.

In some embodiments, the compounds of Formula (I), (Ia), (Ib), (Ic), (Id), (Ie), (If), (Ig), or (Ih), described herein are kappa opioid receptor modulators. In some embodiments, the compounds described herein are kappa opioid receptor agonists. In some embodiments, the compounds described herein are kappa opioid receptor partial agonists. In some embodiments, the compounds described herein are kappa opioid receptor weak partial agonists/antagonists. In some embodiments, the compounds described herein are kappa opioid receptor antagonists.

In some embodiments, the compounds of Formula (I), (Ia), (Ib), (Ic), (Id), (Ie), (If), (Ig), or (Ih), described herein are selective opioid receptor modulators. In some embodiments, the compounds of Formula (I), (Ia), (Ib), (Ic), (Id), (Ie), (If), (Ig), or (Ih), described herein are selective mu opioid receptor modulators.

In some embodiments, the compounds of Formula (I), (Ia), (Ib), (Ic), (Id), (Ie), (If), (Ig), or (Ih), described herein, and compositions comprising these compounds, are useful for the treatment of one or more conditions selected from neuropsychiatric disorders, depression, obsessive compulsive disorder, alcohol addiction, gambling addiction, pain, opioid overdose, opioid use disorders and addiction. In some embodiments, the compounds of Formula (I), (Ia), (Ib), (Ic), (Id), (Ie), (If), (Ig), or (Ih), described herein, and compositions comprising these compounds, are useful for the treatment of one or more diseases or conditions without substantial respiratory suppression (i.e., less than about 75%, less than about 50%, less than about 25%, less than about 20%, less than about 10%, or less than about 5% compared to a standard-of-care opiate, e.g., fentanyl, morphine, oxycodone, or the like). In some embodiments, compounds described herein do not suppress respiration (e.g., at a dose effective for treating one or more diseases or conditions described herein). In some embodiments, compounds described herein do not substantially suppress respiration at a dose effective for treating one or more conditions selected from neuropsychiatric disorders, depression, obsessive compulsive disorder, alcohol addiction, gambling addiction, pain, opioid overdose, opioid use disorders and addiction.

In some embodiments, compounds described herein are not self-administered. In some embodiments, compounds described herein are not self-administered at a dose effective for treating one or more diseases or disorders described herein, e.g., neuropsychiatric disorders, depression, obsessive compulsive disorder, alcohol addiction, gambling addiction, pain, opioid overdose, opioid use disorders, addiction, or any combination thereof. In some embodiments, compounds described herein are not habit-forming.

In some embodiments, compounds described herein are not rewarding. In some embodiments, compounds described herein are not self-administered. In some embodiments, compounds described herein are not addictive. In some embodiments, compounds described herein are not addictive at a dose effective for treating one or more diseases or disorders described herein, e.g., neuropsychiatric disorders, depression, obsessive compulsive disorder, alcohol addiction, gambling addiction, pain, opioid overdose, opioid use disorders, addiction, or any combination thereof. In some embodiments, compounds described herein are less addictive than standard-of-care opiates (e.g., morphine, oxycodone, and the like).

In some embodiments, compounds described herein have low respiratory suppression liability (e.g., relative to standard-of-care)(e.g., at a dose effective for treating one or more diseases or disorders described herein, e.g., neuropsychiatric disorders, depression, obsessive compulsive disorder, alcohol addiction, gambling addiction, pain, opioid overdose, opioid use disorders, addiction, or any combination thereof). In some embodiments, compounds described herein have low addiction liability (e.g., relative to standard-of-care)(e.g., at a dose effective for treating one or more diseases or disorders described herein, e.g., neuropsychiatric disorders, depression, obsessive compulsive disorder, alcohol addiction, gambling addiction, pain, opioid overdose, opioid use disorders, addiction, or any combination thereof). In some embodiments, compounds described herein have low tolerance liability (e.g., relative to standard-of-care) (e.g., at a dose effective for treating one or more diseases or disorders described herein. e.g., neuropsychiatric disorders, depression, obsessive compulsive disorder, alcohol addiction, gambling addiction, pain, opioid overdose, opioid use disorders, addiction, or any combination thereof). In some embodiments, compounds described herein have low sedation liability (e.g., relative to standard-of-care) (e.g., at a dose effective for treating one or more diseases or disorders described herein, e.g., neuropsychiatric disorders, depression, obsessive compulsive disorder, alcohol addiction, gambling addiction, pain, opioid overdose, opioid use disorders, addiction, or any combination thereof). In some embodiments, compounds described herein are analgesics with reduced respiratory suppression, tolerance, addiction, and/or sedation liabilities (e.g., relative to standard-of-care) (e.g., at a dose effective for treating one or more diseases or disorders described herein, e.g., neuropsychiatric disorders, depression, obsessive compulsive disorder, alcohol addiction, gambling addiction, pain, opioid overdose, opioid use disorders, addiction, or any combination thereof).

In some embodiments, the compounds of Formula (I), (Ia), (Ib), (Ic), (Id), (Ie), (If), (Ig), or (Ih), described herein, have high CNS exposure. In some embodiments, compounds described herein are orally bioavailable. In some embodiments, compounds described herein have 3 H-bond donors or less (e.g., 2 H-bond donors or less (e.g., 1H-bond donor or less)). In some embodiments, compounds described herein have high permeability (e.g., cell permeability, tissue permeability, blood-brain barrier permeability). In some embodiments, compounds described herein have high stability (e.g., thermal stability, shelf stability, solution stability, plasma stability, lysosomal stability, hepatic stability, etc.). In some embodiments, compounds described herein have high metabolic stability. In some embodiments, compounds described herein have low efflux.

Preparation of Compounds

The compounds used in the reactions described herein are made according to organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.). Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.). Sundia Meditech, (Shanghai, China). TCI America (Portland, Oreg.). Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York., 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J, and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (19%) Oxford University Press, ISBN 0-19-509618-5; Larock, R. C. "Comprehensive Organic Transformations: A Guide to Functional Group Preparations" 2nd Edition (1999) Wiley—VCH, ISBN: 0-471-19031-4; March, J. "Advanced Organic Chemistry: Reactions, Mechanisms, and Structure" 4th Edition (1992) John Wiley & Sons, ISBN: 0-471-60180-2: Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons. T. W. G. "Organic Chemistry" 7th Edition (2000) John Wiley & Sons, ISBN: 0471-19095-0; Stowell, J. C., "Intermediate Organic Chemistry" 2nd Edition (1993) Wiley-Interscience, ISBN: 0471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on line databases (the American Chemical Society. Washington, D.C.). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

In some embodiments, the following synthetic methods may be utilized.

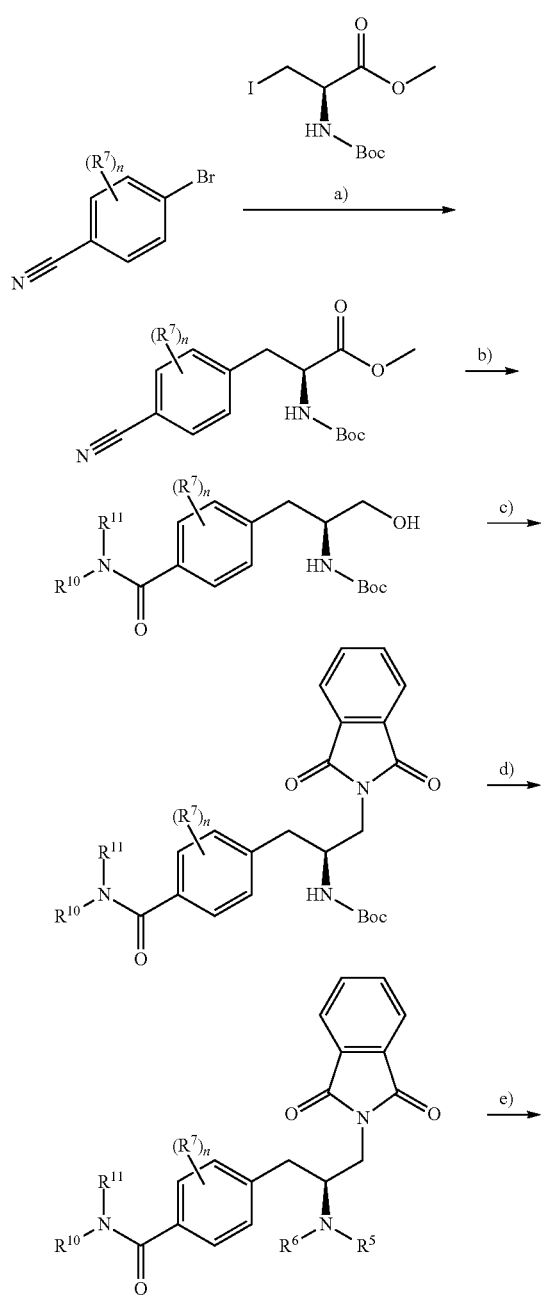

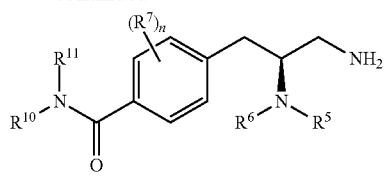

Synthesis of compounds comprising an amide-substituted aryl group such as those described in Formula (Ia) can be achieved according to General Scheme I. Generally, a suitable aryl halide (e.g., aryl bromide) is submitted to conditions sufficient for coupling to a functionalized amino acid as indicated in step (a). This may be achieved through means known to those skilled in the art, including but not limited to Negishi coupling. In some embodiments, suitable reagents for step (a) include Zn, $I_2$, $Pd_2(dba)_3$, and S-Phos in a suitable solvent (e.g., DMF), and at a temperature (e.g., −80° C.). Subsequently, the methyl ester can be reduced to an alcohol, and the nitrile hydrolyzed (preferably in that order) as indicated in step (b). The reduction may be carried out with a number of hydride reagents including, for example, $LiBH_4$. The hydrolysis may be carried out using a suitable base and aqueous solvent (e.g., NaOH and $H_2O$). In step (c) of General Scheme I, the alcohol functionality may be substituted with a suitable nucleophile (e.g., a phthalimide) using various conditions. In some instances, those conditions include Mitsunobu conditions (e.g., $PPh_3$ and DIAD in THF at 0° C. to room temperature). This transformation can be affected using a variety of suitable reagents, solvents, and temperatures known to those skilled in the art. In step (d), the Boc group on the nitrogen can be removed under acidic conditions, for example, 4N HCl dioxane. Subsequent to Boc deprotection, the amine can be further-functionalized to introduce R and $R^6$ substituents. In some embodiments, the nitrogen is functionalized using formaldehyde, acetic acid, and sodium cyanoborohydride. In other embodiments, the nitrogen is functionalized using a di-bromide (e.g., Br—$(CH_2)_n$—Br, where n is an integer between 2 and 10, preferably n is 4 or 5 and the nitrogen forms a pyrrolidine or piperidine). Such a di-bromide functionalization is typically carried out with a suitable base (e.g., potassium carbonate) with a suitable solvent system (e.g., DMF). The phthalimide group may, in some embodiments, be removed using a hydrazine reagent (e.g., $N_2H_4$) in a suitable solution (e.g., $H_2O$), optionally diluted in another solvent (e.g., EtOH).

General Scheme II

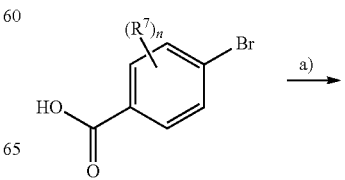

-continued

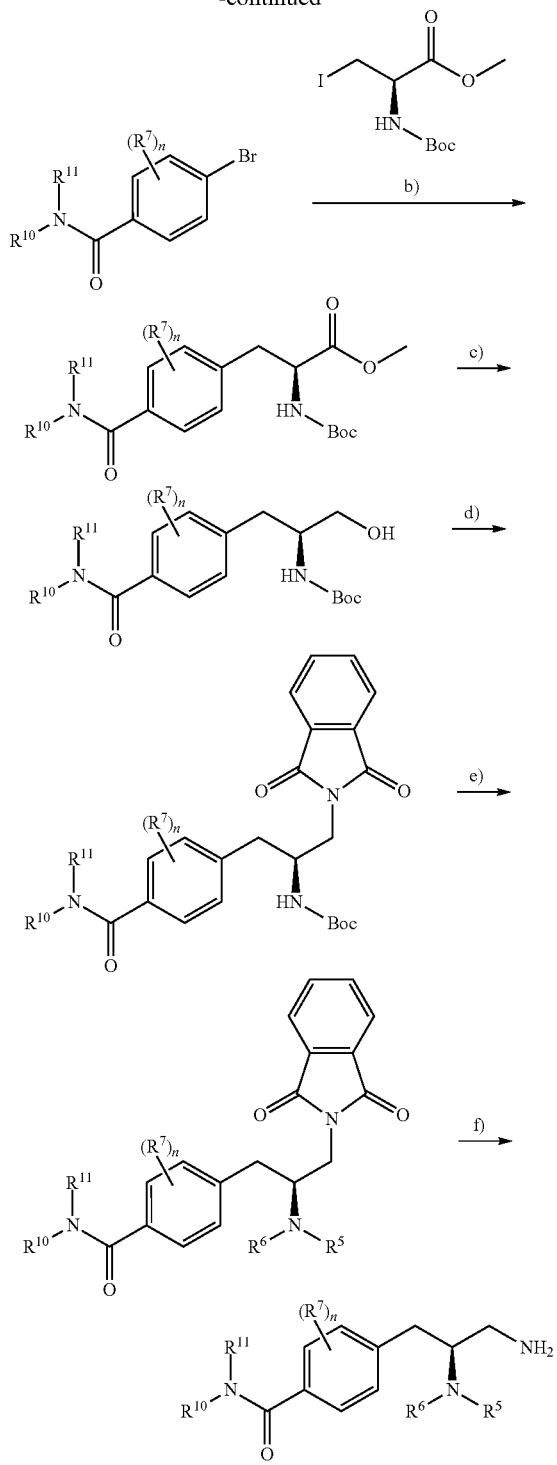

In addition to General Scheme I, compounds of Formula (Ia) may also be synthesized using an optionally substituted benzoic acid as outlined in General Scheme II. In step (a) of General Scheme II, a bromo-benzoic acid can be transformed to an amide (e.g., a primary amide) by reaction with a suitable amine. $NHR^{10}R^{11}$ or a cation thereof (e.g., $NH_4OH$, $NH_2CH_3$, $NH(CH_3)_2$, and the like). In some embodiments, such a transformation is preceded by an activating step, whereby the acid forms an activated ester upon coupling with a suitable coupling reagent (e.g., CDI). Other coupling agents (e.g., peptide coupling reagents) are commercially available and may be exchanged in order to optimize yield or kinetics. Alternate amines may also be used in step (a), as known to those skilled in the art. The amide coupling of step (a) may, in some embodiments, also include use of abase (e.g., triethylamine and the like) in a suitable solvent (e.g., dichloromethane). Steps (b)-(f) of General Scheme II can be performed using similar methods to those previously described in General Scheme I, or other suitable methods known to those skilled in the art. The steps described herein can be implemented in order to produce either primary, secondary, or tertiary amides, depending on the amine used in step (a). Alternatively, a primary amide may be further substituted at a later stage.

General Scheme III

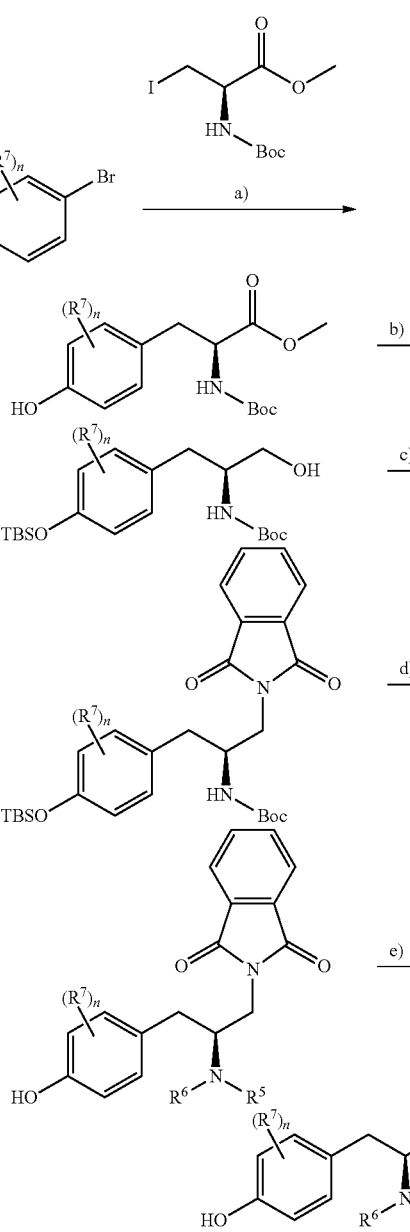

Compounds of Formula (Ib) can be prepared using similar methodologies to those described above, using a suitable phenol starting material. For example, Negishi coupling conditions (e.g., Zn, I$_2$, Pd$_2$(dba)$_3$, and S-Phos in DMF at 80° C.) can be used in step (a) to introduce a modified amino acid as described previously. In some instances, it is advantageous or necessary to protect the phenol to prevent side-reactions. In some embodiments, step (b) comprises protecting the phenol (e.g., with TBSCl and imidazole) prior to reduction of the ester, in order to prevent unwanted coupling to multiple alcohols. In some embodiments, the TBS protecting group is removed after the Mitsunobu reaction of step (c). In other embodiments of General Scheme III (not shown), a phenolic alcohol may be functionalized with additional substituents. In some embodiments, the phenol is not substituted and the —OH group participates in relevant receptor-ligand interactions.

General Scheme IV

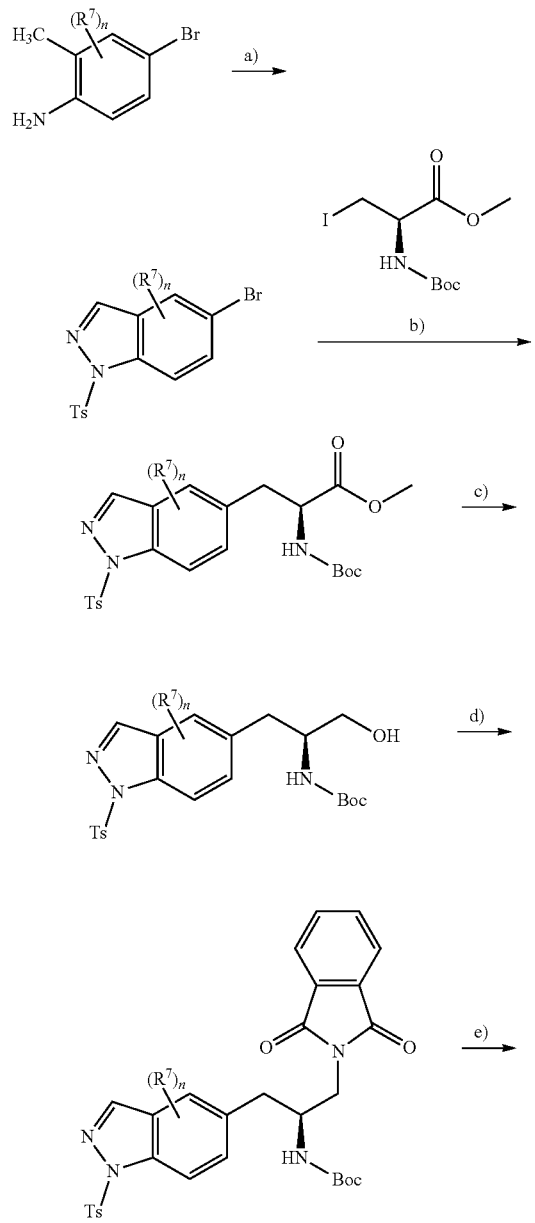

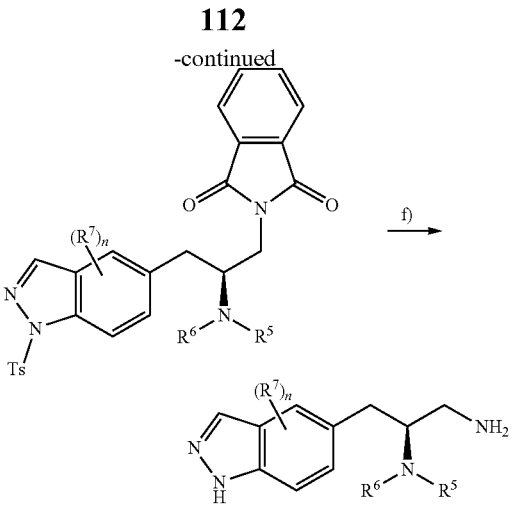

In the preparation of compounds of Formula (Ic), steps such as those described in General Scheme IV may be implemented to achieve the desired chemical scaffold and substituents. For example, in the preparation of compounds of Formula (Ic), an optionally substituted aniline may be functionalized (e.g., cyclized) in an initial step. Such cyclization conditions may include t-Bu-nitrile and acetic anhydride in combination with a suitable base (e.g., potassium acetate). Step (a) may additionally include use of a crown ether (e.g., 18-C-6). In some embodiments, step (a) further comprises use of a base or hydride reagent (e.g., NaH) with a sulfonyl chloride (e.g., tosyl chloride) in a suitable solvent (e.g., DMF), which yields a tosylated indazole as shown in General Scheme IV. The starting material may be further substituted with additional R$^7$ groups. Following cyclization of the optionally substituted indazole as outlined in step (a), compounds of Formula (Ic) may be prepared following similar steps to those described herein.

General Scheme V

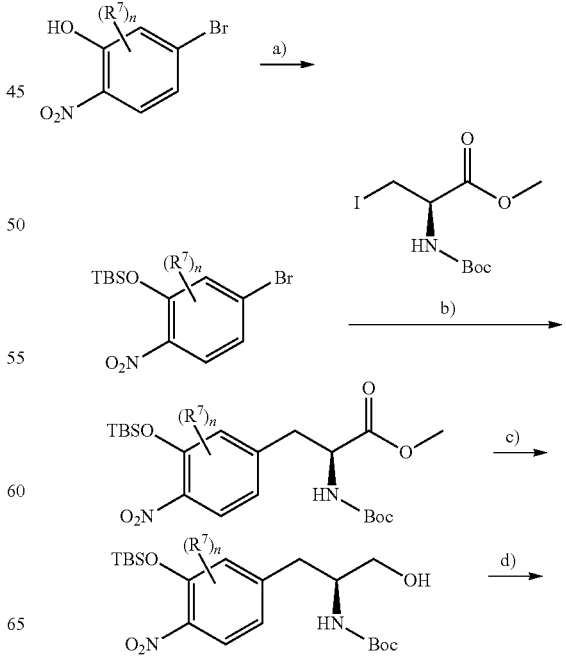

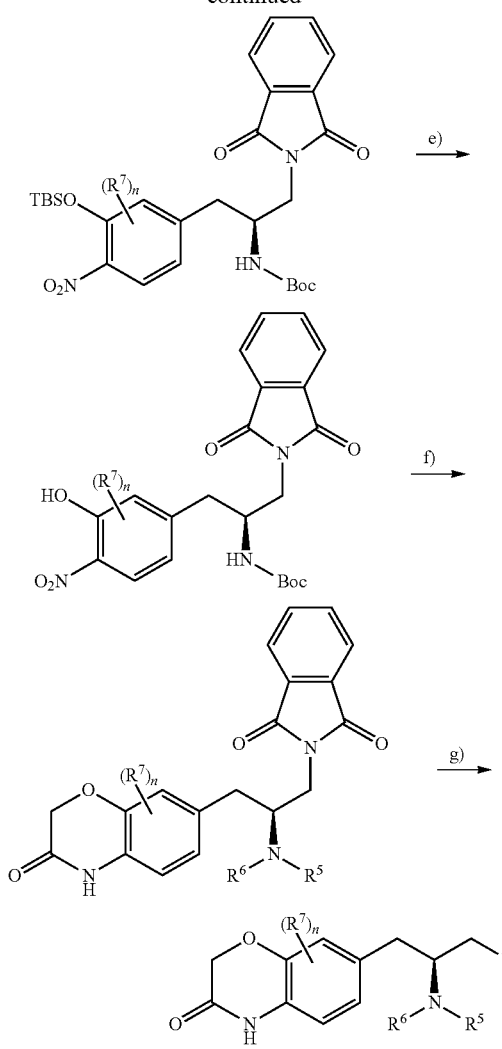

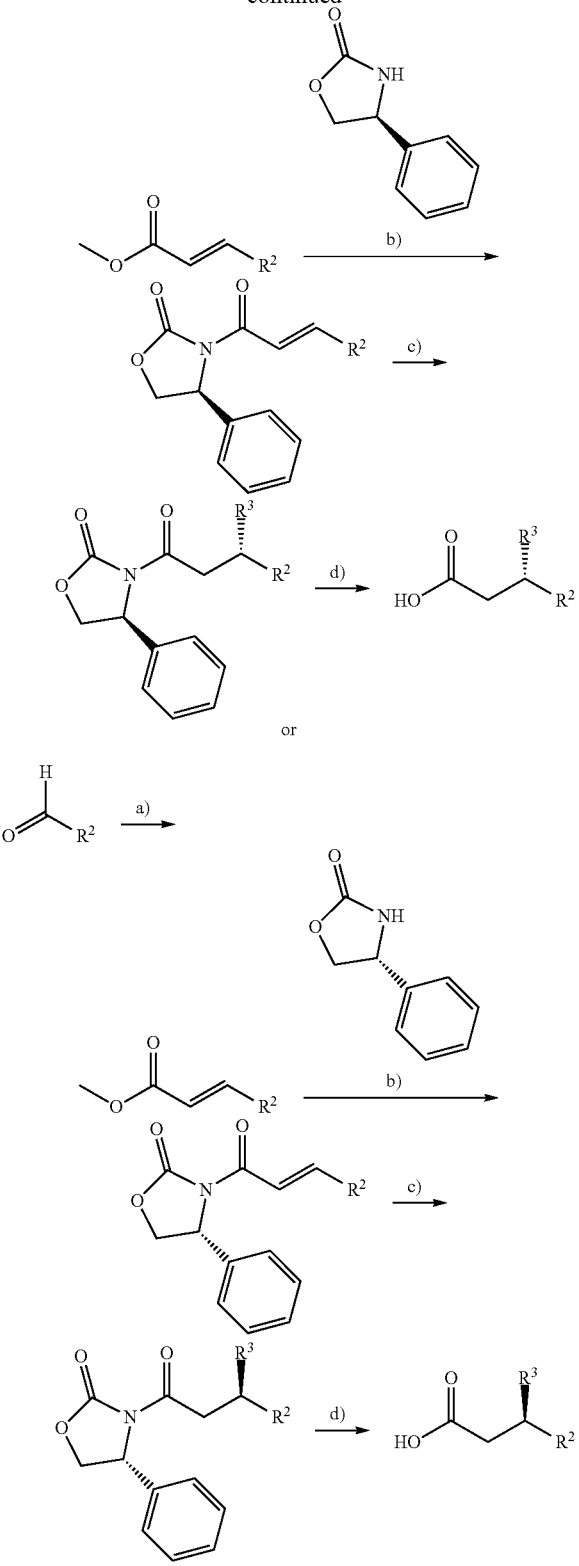

In the preparation of compounds of Formula (Id) a nitrophenol such as the one indicated in General Scheme V may be functionalized using reagents and conditions known to those skilled in the art. In some embodiments, the phenol moiety of the nitrophenol starting reagent is first protected (e.g., with TBSCl) prior to Negishi coupling, which takes place in step (b) of General Scheme V (as described herein). Subsequent steps (c)-(e) are as described herein, with appropriate modifications as understood by those skilled in the art. Following reduction of the nitro group, the resulting amine is treated with 2-chloroacetyl chloride which is then deprotected as described previously.

General Scheme VI

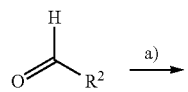

In some embodiments, compounds of the present disclosure have chiral centers at the position corresponding to $R^8$ of Formula (I). In some embodiments, the chirality is installed by use of achiral oxaxolidinone, commonly known as an Evans auxiliary. In some embodiments, the chirality is known and assigned. In other embodiments, the chirality is known to be a single isomer, though the precise (R) or (S) stereochemical assignment is unknown. In some embodiments, the compounds disclosed herein are a single diastereomer or enantiomer. As outlined in General Scheme VI, an aldehyde can be converted to an alpha-beta unsaturated carbonyl compound as described in step (a). In some embodiments, step (a) comprises a Horner-Wadsworth-Emmons or Wittig-type reaction. For example, in some instances, step (a) comprises treatment with a phosphonoacetate (e.g., trimethyl phosphonoacetate), and a suitable base (e.g., sodium hydride) in an appropriate solvent (e.g., THF). The alpha-beta unsaturated ester of General Scheme VI can be hydrolyzed to the corresponding carboxylic acid (e.g., using LiOH in THF/H$_2$O), and subsequently coupled to the chiral auxiliary using appropriate amide coupling conditions. Either the (R) or the (S) chiral auxiliary may be used according to General Scheme VI. Appropriate amide coupling conditions for step (b) may include the use of coupling reagents (e.g., DIC and DMAP) in a suitable solvent (e.g., dichloromethane). The alpha-beta unsaturated amide may subsequently be alkylated using any appropriate alkylation conditions, including conjugate additions (e.g., via a Grignard or magnesium bromide reagent). In some embodiments, the alkylation reaction also includes use of a copper(I) halide (e.g., CuI). In some embodiments, the alkylation reaction further comprises dimethyl sulfide. Such reactions may be carried out at low temperatures (e.g., −40° C.) and in a suitable solvent (e.g., THF). In step (d) of General Scheme VI, the chiral auxiliary is cleaved under conditions that result in a terminal carboxylic acid (e.g., LiOH/H$_2$O$_2$ in THF).

General Scheme VII

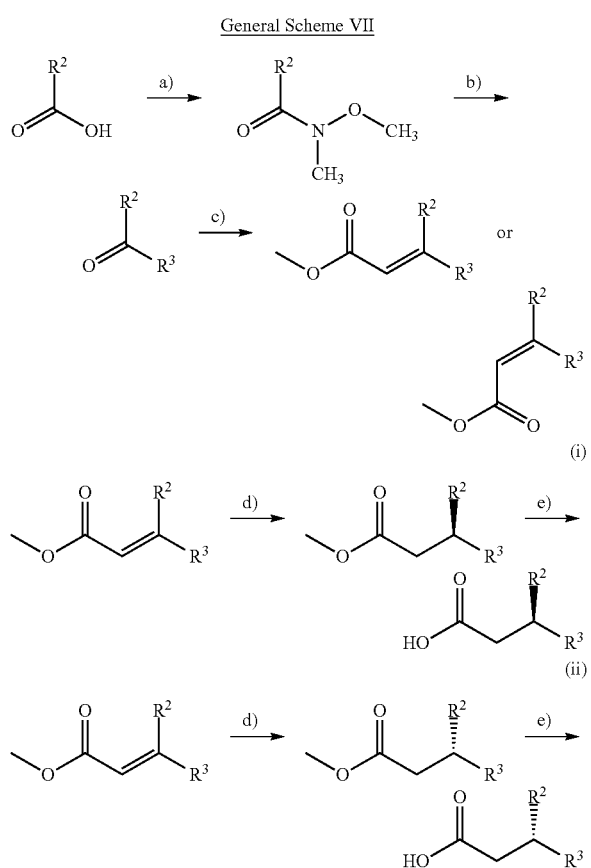

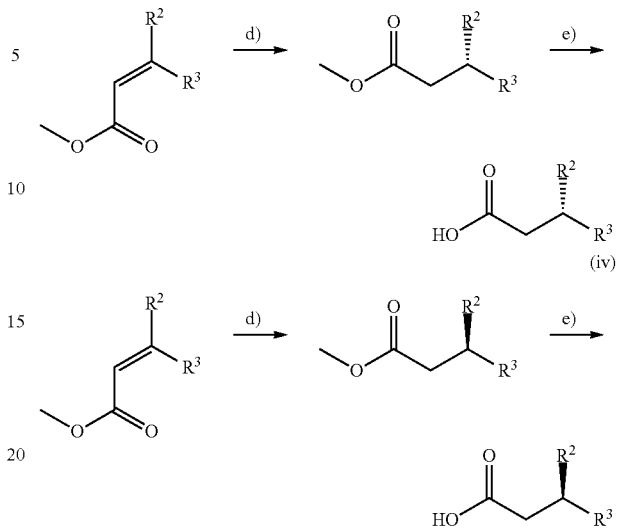

In some embodiments, the chirality of R$^3$ is installed starting from an appropriate carboxylic acid as shown in General Scheme VII. In some embodiments, the chirality is known and assigned. In other embodiments, the chirality is known to be a single isomer, though the precise (R) or (S) stereochemical assignment is unknown. In some embodiments, the compounds disclosed herein are a single diastereomer or enantiomer. In some embodiments, the carboxylic acid is activated (e.g., via CDI) to form an activated ester to facilitate amide coupling. Such activation reaction is carried out in a suitable solvent system (e.g., dichloromethane). Subsequently, the activated acid can be converted to a Weinreb amide as shown in step (a) of General Scheme VII. Step (b) involves alkylation of the Weinreb amide with an R$^3$ group. In some embodiments, R$^3$ is added via a organolithium or organomagnesium species. Step (c) of General Scheme VII includes an addition reaction to the ketone such as a Horner-Wadsworth-Emmons or Wittig-type reaction as described previously. In some embodiments, this reaction is facilitated by use of trimethylphosphonoacetate. In some embodiments, a suitable base (e.g., NaH or KHMDS) is also used. In some embodiments, the reaction further comprises use of a crown ether (e.g., 18-C-6). The conformation of the double bond (e.g., E or Z, and subsequent stereochemical orientation) can be controlled using techniques known to those skilled in the art. Step (d) provides the stereochemistry indicated in Formula (I) by use of a chiral ligand (e.g., R-DTBM-SEGPHOS or S-DTBM-SEGPHOS). Referring to General Scheme VII, in lines (i) and (iii), the reagent R-DTBM SEGPHOS is used, and in lines (ii) and (iv), S-DTBM SEGPHOS is used, resulting in the specific enantiomers shown above. In some embodiments, step (d) further comprises use of a copper species (e.g., Cu(OAc)$_2$). In some embodiments, step (d) further comprises DMMS, tert-BuOH, and/or toluene. In some embodiments, the alkene(s) produced in step (c) of General Scheme VII are reduced using hydrogen (H$_2$) over a catalyst (e.g., Pd/C) in a suitable solvent (e.g., EtOH). In some embodiments, the resulting ester is a mixture of R and S isomers. In some embodiments, the mixture of isomers is unresolved. In some embodiments, the mixture of isomers is resolved by chiral chromatography in a subsequent step. The final step of General Scheme VII, step (e), involves cleavage of the ester to provide the indicated carboxylic acid. In some embodiments, the ester is cleaved under basic conditions (e.g., with LiOH) in a suitable solvent or solvent system (e.g., MeOH/THF/H$_2$O).

The amines and acids disclosed herein can be combined in any combination, resulting in a wide range of compounds that fall within the genus of Formula (I). The methods described herein are by way of example only. Additional methods may be utilized to provide additional compounds disclosed herein.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z)isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^2$H, $^3$H, $^{13}$C, $^{14}$C, $^{15}$N, $^{19}$O, $^{17}$O, $^{31}$P, $^{32}$P, $^{35}$S, $^{18}$F, and $^{36}$Cl, respectively. Compounds described herein, and pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i. e., $^3$H and carbon-14, i. e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or MeOH. In addition, the compounds provided herein exist in unsolvated as well as solvated forms. In general, the solvated forms are considered equivalent to the unsolvated forms for the purposes of the compounds and methods provided herein.

Pharmaceutical Compositions

In certain embodiments, the compound of Formula (I), (Ia), (Ib), (Ic), (Id), (Ie), (If), (Ig), or (Ih), as described herein is administered as a pure chemical. In some embodiments, the compound of Formula (I), (Ia), (Ib), (Ic), (Id), (Ie), (If), (Ig), or (Ih), described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$, Ed. Mack Pub. Co., Easton, Pa. (2005)).

Accordingly, provided herein is a pharmaceutical composition comprising at least one compound of Formula (I), (Ia), (Ib), (Ic), (Id), (Ie), (If), (Ig), or (Ih), described herein, or a stereoisomer, pharmaceutically acceptable salt, hydrate, solvate, or N-oxide thereof, together with one or more pharmaceutically acceptable carriers. The carrier(s)(or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt or solvate thereof. Another embodiment provides a pharmaceutical composition comprising a pharmaceutically acceptable excipient and a compound of Formula (Ia), or a pharmaceutically acceptable salt or solvate thereof. Another embodiment provides a pharmaceutical composition comprising a pharmaceutically acceptable excipient and a compound of Formula (Ib), or a pharmaceutically acceptable salt or solvate thereof. Another embodiment provides a pharmaceutical composition comprising a pharmaceutically acceptable excipient and a compound of Formula (Ic), or a pharmaceutically acceptable salt or solvate thereof. Another embodiment provides a pharmaceutical composition comprising a pharmaceutically acceptable excipient and a compound of Formula (Id), or a pharmaceutically acceptable salt or solvate thereof. Another embodiment provides a pharmaceutical composition comprising a pharmaceutically acceptable excipient and a compound of Formula (Ie), or a pharmaceutically acceptable salt or solvate thereof. Another embodiment provides a pharmaceutical composition comprising a pharmaceutically acceptable excipient and a compound of Formula (If), or a pharmaceutically acceptable salt or solvate thereof. Another embodiment provides a pharmaceutical composition comprising a pharmaceutically acceptable excipient and a compound of Formula (Ig), or a pharmaceutically acceptable salt or solvate thereof. Another embodiment provides a pharmaceutical composition comprising a pharmaceutically acceptable excipient and a compound of Formula (Ih), or a pharmaceutically acceptable salt or solvate thereof.

Another embodiment provides a pharmaceutical composition consisting essentially of a pharmaceutically acceptable excipient and a compound of Formula (I), or a pharmaceutically acceptable salt thereof. Another embodiment provides a pharmaceutical composition consisting essentially of a pharmaceutically acceptable excipient and a compound of Formula (Ia), or a pharmaceutically acceptable salt thereof. Another embodiment provides a pharmaceutical composition consisting essentially of a pharmaceutically acceptable excipient and a compound of Formula (Ib), or a pharmaceutically acceptable salt thereof. Another embodiment provides a pharmaceutical composition consisting essentially of a pharmaceutically acceptable excipient and a compound of Formula (Ic), or a pharmaceutically acceptable salt thereof. Another embodiment provides a pharmaceutical composition consisting essentially of a pharmaceutically acceptable excipient and a compound of Formula (Id), or a pharmaceutically acceptable salt thereof. Another embodiment provides a pharmaceutical composition consisting essentially of a pharmaceutically acceptable excipient and a compound of Formula (Ie), or a pharmaceutically acceptable salt thereof. Another embodiment provides a pharmaceutical composition consisting essentially of a pharmaceutically acceptable excipient and a compound of Formula (If), or a pharmaceutically acceptable salt thereof. Another embodiment provides a pharmaceutical composition consisting essentially of a pharmaceutically acceptable excipient and a compound of Formula (Ig), or a pharmaceutically acceptable salt thereof. Another embodiment provides a pharmaceutical composition consisting essentially of a pharmaceutically acceptable excipient and a compound of Formula (Ih), or a pharmaceutically acceptable salt thereof.

In certain embodiments, the compound of Formula (I), (Ia), (Ib), (Ic), (Id), (Ie), (If), (Ig), or (Ih), as described herein is substantially pure, in that it contains less than about 5%, or less than about 1%, or less than about 0.1%, of other organic small molecules, such as contaminating intermediates or by-products that are created, for example, in one or more of the steps of a synthesis method.

In certain embodiments, the compound of Formula (I), (Ia), (Ib), (Ic), (Id), (Ie), (If). (Ig), or (Ih), described herein is formulated for oral, rectal, topical, buccal, parenteral (e.g., subcutaneous, intramuscular, intradermal, or intravenous), vaginal, ophthalmic, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tables, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills, and granules, are scored or prepared with coatings and shells, such as enteric coatings and other coatings.

Compositions for inhalation or insufflation include solutions and suspensions in pharmaceutically acceptable aqueous or organic solvents, or mixtures thereof, and powders. Liquid dosage forms for oral administration include pharmaceutically acceptable emulsions, microemulsions, solutions, suspensions, syrups, and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (optionally, cottonseed, groundnut, corn, germ, olive, castor and sesame oils), glycerol, tetrahydrofuryl alcohol, polyethylene glycols and fatty acid esters of sorbitan, cyclodextrins, and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), sorbitan esters, oleic acid, lecithin, amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils such as olive oil, and injectable organic esters such as ethyl oleate and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound, an enteric material, and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethactylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L 100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Methods

In another aspect, described herein are methods of using a compound of Formula (I), (Ia), (Ib), (Ic), (Id), (Ie), (If), (Ig), or (Ih), described herein, or a pharmaceutically acceptable salt thereof, for example, in a method of treating a disease or condition. In some embodiments is a method of treating a disease or condition selected from neuropsychiatric disorders, depression, obsessive compulsive disorder, alcohol addiction, gambling addiction, pain, opioid overdose, opioid use disorders and addiction in a patient in need thereof, comprising administering to the patient a therapeutically effective amount of a compound of Formula (I), (Ia), (Ib), (Ic), (Id), (Ie), (If), (Ig), or (Ih), described herein, or a pharmaceutically acceptable salt or solvate thereof. In some embodiments is a method of treating a neuropsychiatric disorder in a patient in need thereof, comprising administering to the patient a therapeutically effective amount of a compound of Formula (I), (Ia), (Ib), (Ic), (Id), (Ie), (If), (Ig), or (Ih), described herein, or a pharmaceutically acceptable salt or solvate thereof. In some embodiments is a method of treating depression in a patient in need thereof, comprising administering to the patient a therapeutically effective amount of a compound of Formula (I), (Ia), (Ib), (Ic), (Id), (Ie), (If), (Ig), or (Ih), described herein, or a pharmaceutically acceptable salt thereof. In some embodiments is a method of treating obsessive compulsive disorder in a patient in need thereof, comprising administering to the patient a therapeutically effective amount of a compound of Formula (I), (Ia), (Ib), (Ic), (Id), (Ie), (If), (Ig), or (Ih), described herein, or a pharmaceutically acceptable salt thereof. In some embodiments is a method of treating alcohol addiction in a patient in need thereof, comprising administering to the patient a therapeutically effective amount of a compound of Formula (I), (Ia), (Ib), (Ic), (Id), (Ie), (If), (Ig), or (Ih), described herein, or a pharmaceutically acceptable salt thereof. In some embodiments is a method of treating gambling addiction in a patient in need thereof, comprising administering to the patient a therapeutically effective amount of a compound of Formula (I), (Ia), (Ib), (Ic), (Id), (Ie), (If), (Ig), or (Ih), described herein, or a pharmaceutically acceptable salt thereof. In some embodiments is a method of treating pain in a patient in need thereof, comprising administering to the patient a therapeutically effective amount of a compound of Formula (I), (Ia), (Ib), (Ic), (Id), (Ie), (If), (Ig), or (Ih), described herein, or a pharmaceutically acceptable salt thereof. In some embodiments is a method of treating an opioid overdose in a patient in need thereof, comprising administering to the patient a therapeutically effective amount of a compound of Formula (I), (Ia), (Ib), (Ic), (Id), (Ie), (If), (Ig), or (Ih), described herein, or a pharmaceutically acceptable salt thereof. In some embodiments is a method of treating opioid use disorders in a patient in need thereof, comprising administering to the patient a therapeutically effective amount of a compound of Formula (I), (Ia), (Ib), (Ic), (Id), (Ie), (If). (Ig), or (Ih), described herein, or a pharmaceutically acceptable salt thereof. In some embodiments is a method of treating addiction in a patient in need thereof, comprising administering to the patient a therapeutically effective amount of a compound of Formula (I), (Ia), (Ib), (Ic), (Id), (Ie), (If), (Ig), or (Ih), described herein, or a pharmaceutically acceptable salt thereof.

In certain embodiments, a disclosed compound utilized by one or more of the foregoing methods is one of the generic, subgeneric, or specific compounds described herein, such as a compound of Formula (I), (Ia), (Ib), (Ic), (Id), (Ie), (If), (Ig), or (Ih).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray, or rectally in dosage unit formulations containing conventional non-toxic pharmaceutically acceptable carriers, adjuvants and vehicles. Parenteral administration include subcutaneous injections, intravenous, or intramuscular injections or infusion techniques.

The following examples are provided merely as illustrative of various embodiments and shall not be construed to limit the invention in any way.

EXAMPLES

Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (S) and coupling constants, J are reported in Hertz. For proton spectra the solvent peak was used as the reference peak.

Synthesis Examples A: Intermediates

Example A1: Preparation of (S)-4-(3-amino-2-(dimethylamino)propyl)-2-fluorobenzamide (1G, "Intermediate 1")

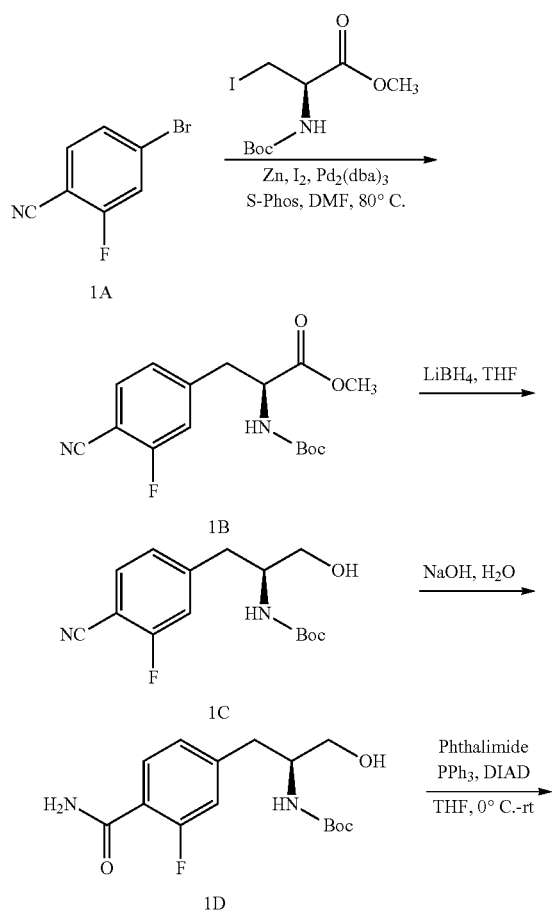

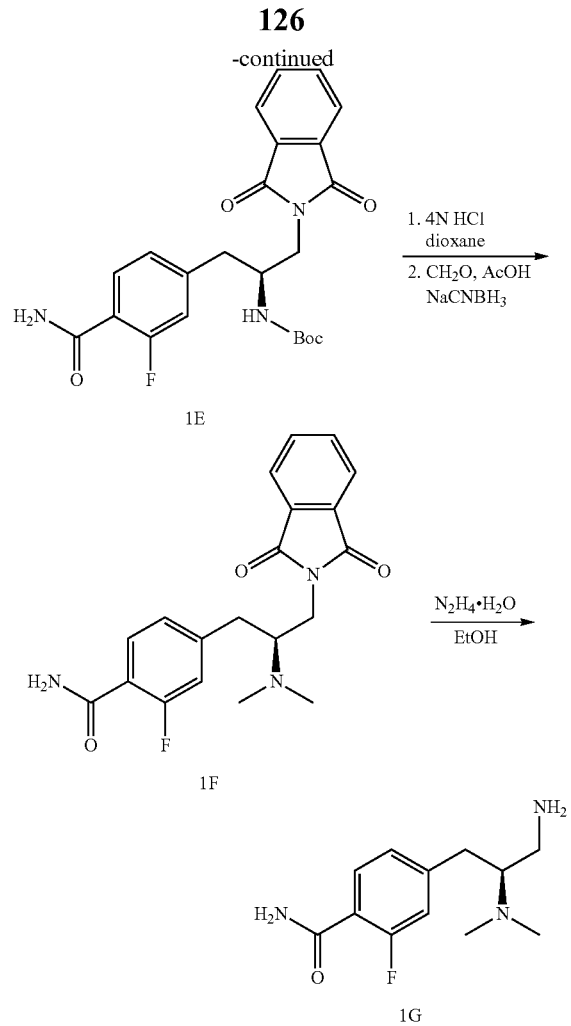

Preparation of methyl (S)-2-((tert-butoxycarbonyl)amino)-3-(4-cyano-3-fluorophenyl)propanoate (1B): To an oven-dried 100 mL RBF was added zinc (2.29 g, 35 mmol) and dry DMF (4 mL). To the reaction mixture was added a solution of iodine (159 mg, 1.25 mmol) in DMF (0.5 mL). The reaction mixture was stirred for 10 min, followed by the addition of a solution of methyl (2R)-2-{[(tert-butoxy)carbonyl]amino}-3-iodopropanoate (3.95 g, 12 mmol) in DMF (10 mL) and a solution of iodine (159 mg, 1.25 mmol) in DMF (0.5 mL), which resulted in an exotherm. The reaction mixture was stirred cooling to room temperature for 20 minutes, and 4-bromo-2-fluorobenzonitrile (2.00 g, 10 mmol), Pd$_2$(dba)$_3$ (458 mg, 0.50 mmol), and SPhos (411 mg, 1 mmol) were added to the reaction mixture. The reaction mixture was stirred at 70° C. for 16 h. The crude reaction mixture was cooled to room temperature, quenched with water, diluted with EtOAc, and filtered through celite. The organic layer was then washed with brine (5×), dried over MgSO$_4$, then concentrated. The resulting residue was adsorbed onto silica, then purified by column chromatography (100 g silica, 0-30% EtOAc/hex) to yield the title compound as a white solid (2.75 g, 85%). MS (m/z)=345.1 [M+H].

Preparation of tert-butyl (S)-(1-(4-cyano-3-fluorophenyl)-3-hydroxypropan-2-yl)carbamate (1C): To a 250 mL round bottom flask was added methyl (2S)-2-{[(tert-butoxy)carbonyl]amino}-3-(4-cyano-3-fluorophenyl)propanoate (2.75 g, 8.53 mmol) and THF (30 mL). The reaction mixture was cooled to 0° C., and a solution of lithium borohydride (4M in THF, 5.0 mL) was added in a dropwise fashion. The reaction mixture was stirred at 0° C. for 30 min. then stirred warming to room temperature for 16 h. The reaction mixture was then cooled to 0° C., and was quenched with the dropwise addition of water. The crude reaction mixture was diluted with brine, and the product was extracted with EtOAc (3×). The combined organic layers were washed with brine, dried over Na$_2$SO$_4$, then concentrated. The resulting residue was purified by column chromatography (80 g silica, 10-70% EtOAc/hex) to afford the title compound as a white solid (1.77 g, 60%). MS (m/z)=317.1 [M+Na].

Preparation tert-butyl (S)-(1-(4-carbamoyl-3-fluorophenyl)-3-hydroxypropan-2-yl)carbamate (1D): To a 250 mL round bottom flask was added tert-butyl N-[(2S)-1-(4-cyano-3-fluorophenyl)-3-hydroxypropan-2-yl]carbamate (1.45 g, 4.93 mL), MeOH (30 mL), aqueous 10 M NaOH (1.45 mL), and 27% H$_2$O$_2$ in water (4.8 mL). The reaction mixture was stirred at 50° C. for 1 h, then additional aqueous 10 M NaOH (0.64 mL), and 27% H$_2$O$_2$ in water (1.9 mL) was added. The crude reaction mixture was neutralized with sat. NH$_4$Cl(aq), and MeOH was removed under reduced pressure. The product was extracted with EtOAc (3×), and the combined organic layers were washed with brine, dried over MgSO$_4$, then concentrated. The product was further dried via toluene azeotrope to yield the title compound as a white solid (1.35 g, 88%).

Preparation of tert-butyl (S)-(1-(4-carbamoyl-3-fluorophenyl)-3-(1,3-dioxoisoindolin-2-yl)propan-2-yl)carbamate (1E): To a 250 mL round bottom flask was added tert-butyl N-[(2S)-1-(4-carbamoyl-3-fluorophenyl)-3-hydroxypropan-2-yl]carbamate (1.35 g, 4.32 mmol), triphenyl phosphine (1.25 g, 4.75 mmol), phthalimide (0.70 g, 4.75 mmol), and anhydrous THF (30 mL). The reaction mixture was cooled to 0° C., and DIAD (0.94 mL, 4.75 mmol) was added in a dropwise fashion. The reaction mixture was stirred at 0° C. for 1 h, then stirred at room temperature for 16 h. The resulting in the formation of a white precipitate. The precipitate was filtered, washed with THF, and dried to yield the title compound as a white solid (2.03 g, 106%). MS (m/z)=442.1 [M+H].

Preparation of (S)-4-(2-(dimethylamino)-3-(1,3-dioxoisoindolin-2-yl)propyl)-2-fluorobenzamide (1F): Step 1: To a 250 mL round bottom flask was added tert-butyl N-[(2S)-1-(4-carbamoyl-3-fluorophenyl)-3-(1,3-dioxo-2,3-dihydro-1H-isoindol-2-yl)propan-2-yl]carbamate (2.03 g, 4.6 mmol), MeOH (25 mL), and formic acid (50 mL). The reaction mixture was stirred at 50° C. for 1 h. The reaction mixture was concentrated, and the resulting residue was used directly for the next step. MS (m/z)=342.1 [M+H].

Step 2: To the crude reaction mixture was dissolved in MeCN/H$_2$O (5:1, 22 mL), then added 37 wt % formaldehyde in water (1.03 mL, 13.8 mmol). The reaction mixture was stirred for 30 minutes, then NaB(CN)H$_3$ (1.03 g, 16.1 mmol) was added to the reaction mixture in one portion, and continue to stir for another 30 minutes. The reaction mixture was cooled to 0° C. and quenched with sat. aqueous sodium bicarbonate (~50 mL). The product was extracted with EtOAc (7×), and the combined organic layers were dried over MgSO$_4$, then concentrated. The resulting residue was used without further purification in the next step. MS (m/z)=370.1 [M+H].

Preparation of (S)-4-(3-amino-2-(dimethylamino)propyl)-2-fluorobenzamide (1G): To a the crude product of (S)-4-(2-(dimethylamino)-3-(1,3-dioxoisoindolin-2-yl)propyl)-2-fluorobenzamide (1F) was added absolute EtOH (50 mL) and aqueous 80 wt % hydrazine hydrate (1.40 mL, 23 mmol). The reaction mixture was stirred at 75° C. for 3 h. The crude reaction mixture was then concentrated, adsorbed onto silica, then purified by column chromatography (40 g silica, 0-20% MeOH/DCM+1% NH4OH) to yield the title compound as a white solid (0.46 g, 42%). MS (m/z): 240.2 [M+H].

Example A2: Preparation of (S)-4-(3-amino-2-(dimethylamino)propyl)-2-fluorobenzamide (2H, "Intermediate 2")

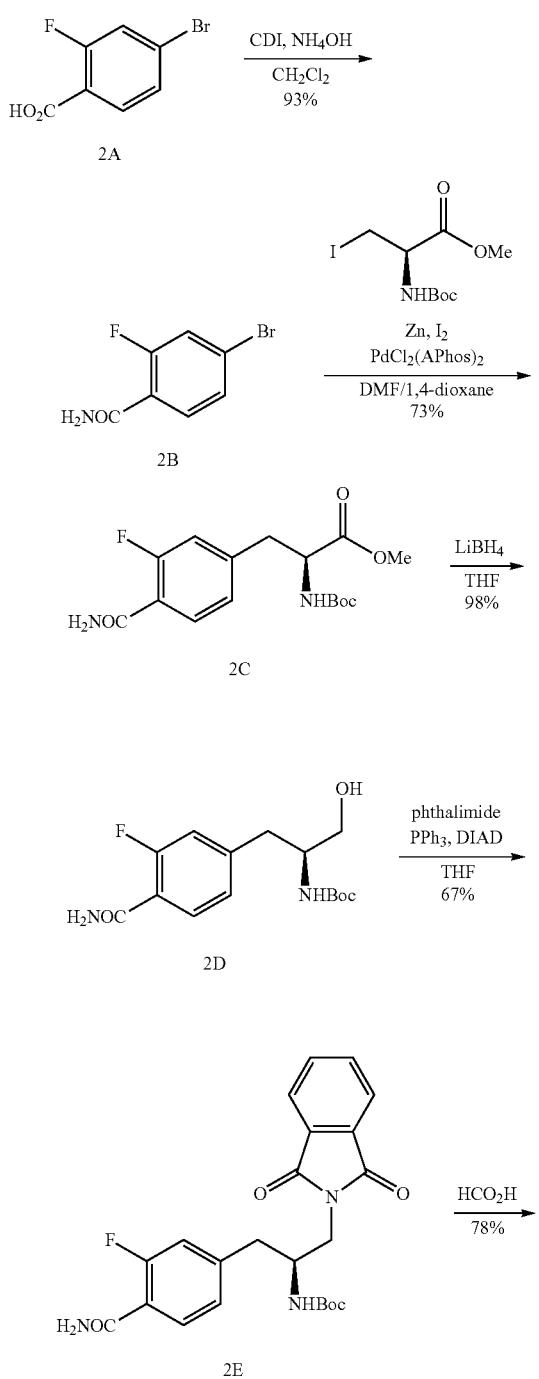

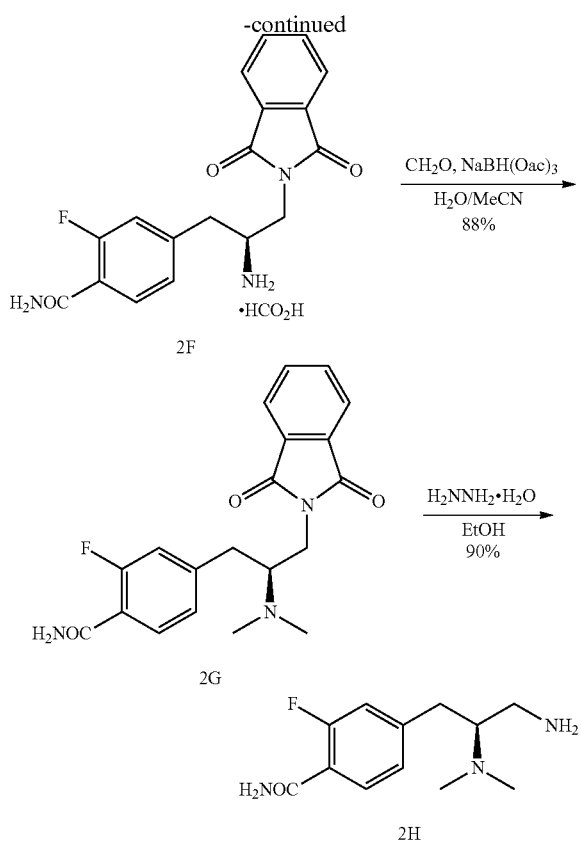

Preparation of 4-bromo-2-fluorobenzamide (2B): 4-Bromo-2-fluorobenzoic acid (44 g, 200 mmol) was taken in dichloromethane (500 ml) and carbonyldiimidazole (65 g, 200 mmol) was added to it in small portions over 15 mins. The suspension became a thick solid and then gradually cleared up over the next 45 mins. Ammonium hydroxide solution (150 ml) was then added very slowly over 15 mins. The biphasic solution was then stirred for the next 14 hrs. The two layers were separated, and the organic layer was then washed with 2 N HCl solution and then with water. The organic layer was then filtered through magnesium sulfate and the filtrate was concentrated to give the product as a white powder (40.9 g, 94%). MS (m/z): 218, 220 [M+H].

Preparation of methyl (S)-2-((tert-butoxycarbonyl)amino)-3-(4-carbamoyl-3-fluorophenyl)propanoate (2C): Granular zinc (37 g, 560 mmol, 20 mesh) was taken in DMF (190 ml) under nitrogen and iodine (1.2 g, 9.4 mmol) was added to it. The suspension was stirred for 15 mins during which time the initial brown color dissipated. Solid methyl (2R)-2-{[(tert-butoxy)carbonyl]amino} 1-3-iodopropanoate (93 g, 281 mmol) was then added along with iodine (1.2 g, 9.4 mmol), the suspension turned brown and then dark with increase in temperature. It was stirred for 1 hr when the temperature returned back to room temperature and the color disappeared as well. In a separate flask, 4-bromo-2-fluorobenzamide (40.9 g, 188 mmol) was taken with bis(di-tert-butyl(4-dimethylaminophenyl)phosphine)dichloropalladium(II)(8.0 g, 11.3 mmol) in 1,4-dioxane (190 ml). The solution of "N-Boc-beta-Zn-Ala-OMe" generated in the first flask was transferred into the second flask via cannula and the solution was bubbled with nitrogen for 15 min. The solution was then heated at 100° C. for the next 18 hrs. TLC and LCMS indicated that the reaction was completed. The solution was cooled to rt and then saturated ammonium hydroxide solution (6×60 ml) was added to it. This led to precipitation of a white solid. Water (3×60 ml) was added and the suspension was stirred for 30 mins. The solids were then collected by filtration and washed with hexanes to give the product as an off-white powder (47.1 g, 74%). MS (m/z): 363 [M+Na].

Preparation of tert-butyl (S)-(1-(4-carbamoyl-3-fluorophenyl)-3-hydroxypropan-2-yl)carbamate (2D): methyl (2S)-2-{[(tert-butoxy)carbonyl]amino}-3-(4-carbamoyl-3-fluorophenyl)propanoate (47.1 g, 138 mmol) was taken in THF (500 ml) under nitrogen and cooled in an ice-bath. A solution of lithium borohydride (70 ml, 4 M in THF, 280 mmol) was then added drop wise to it over 20 mins. The ice-bath was removed after 30 mins and the solution was stirred overnight at room temperature. TLC and LCMS indicated that the reaction was completed. The flask was cooled in an ice-bath and the reaction was quenched by adding saturated ammonium chloride solution slowly. The reaction mixture was filtered to remove black insoluble material. The solution was extracted into ethyl acetate (4×150 mL). The organic layer was dried with magnesium sulfate and the filtrate was concentrated. The light brown solids were then dried under high vacuum to give the product (41.9 g, 97%) as a light-brown powder. MS (m/z): 335 [M+Na].

Preparation of tert-butyl (S)-(1-(1,3-dioxoisoindolin-2-yl)-3-(3-fluoro-4-((oxo-13-methyl)-14-azaneyl)phenyl)propan-2-yl)carbamate(2E): tert-butyl N-[(2S)-1-(4-carbamoyl-3-fluorophenyl)-3-hydroxypropan-2-yl]carbamate (41.9 g, 134 mmol) was taken in THF (700 ml) with phthalimide (23.7, 161 mmol) and triphenylphosphine (42.2 g, 161 mmol). The solution was cooled in an ice-bath and then diisopropylazodicarboxylate (31.7 ml, 161 mmol) was added dropwise to it. The ice-bath was removed, and the solution was stirred for 24 hr. It was diluted with MTBE (500 ml) and the precipitated solids were collected by filtration. The solids were washed with a mixture of 1:1 MTBE and ethyl acetate to give the product as a white solid (41.1 g, 70%). MS (m/z): 464 [M+Na].

Preparation of (S)-4-(2-amino-3-(1,3-dioxoisoindolin-2-yl)propyl)-2-fluorobenzamide formic acid salt (2F): tert-butyl N-[(2S)-1-(4-carbamoyl-3-fluorophenyl)-3-(1,3-dioxo-2,3-dihydro-1H-isoindol-2-yl)propan-2-yl]carbamate (41.1 g, 93 mmol) taken in 1,4-dioxane (500 ml) and then formic acid (200 ml) was added to it. The solution was stirred for the next 18 hrs. Acetonitrile (500 ml) was added slowly and the precipitated solids were collected by filtration to give the product as a white powder (28.1 g, 78%). MS (M/z): 342 [M+H].

Preparation of (S)-4-(2-(dimethylamino)-3-(1,3-dioxoisoindolin-2-yl)propyl)-2-fluorobenzamide (2G): 4-[(2S)-2-amino-3-(1,3-dioxo-2,3-dihydro-1H-isoindol-2-yl)propyl]-2-fluorobenzamide; formic acid (28.1 72.7 mmol) was taken in acetonitrile/water (50 ml/10 ml). Aqueous formaldehyde solution (6.0 ml, 37% solution, 218 mmol) was then added and the solution was stirred at room temperature for 1 hr. Sodium triacetoxyborohydride (61 g, 291 mmol) was then added, which led to effervescence. The solution was stirred for the next 45 mins. LCMS indicated that the reaction was completed. The solution was quenched by slow addition of sodium bicarbonate solution and then extracted into ethyl acetate (3 times). The combined organic layers were filtered through magnesium sulfate and the filtrate was concentrated to give the product (23.6 g, 88%). MS (m/z): 370.2 [M+H].

Preparation of (S)-4-(3-amino-2-(dimethylamino)propyl)-2-fluorobenzamide (2H): 4-[(2S)-2-(dimethylamino)-3-

(1,3-dioxo-2,3-dihydro-1H-isoindol-2-yl)propyl]-2-fluorobenzamide (23.6 g, 64 mmol) was taken in ethanol (500 ml) and hydrazine hydrate solution (11.7 ml, 35% solution, 128 mmol) was added to it. The solution was heated at reflux for 3 hrs. LCMS indicated that the reaction was completed. The solution was diluted with ethyl acetate and the precipitated solids were removed by filtration. The filtrate was concentrated and the residue was purified on Combiflash using dichloromethane/methanol/ammonium hydroxide gradient to give the product (13.6 g, 89%). MS (m/z): 240.2 [M+H].

The following intermediates were synthesized in analogous methods to those described in Example A2: Int. 2 & General Scheme H:

| Intermediate (Int.) No. | Structure | LC/MS (m/z) | Name |
|---|---|---|---|
| Int. 13 | 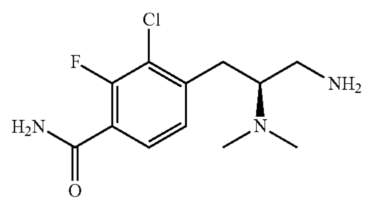 [SMILES: CN(C)[C@H](CN)Cc1ccc(C(N)=O)c(F)c1Cl] | 274.1 (M + H) | (S)-4-(3-amino-2-(dimethylamino)propyl)-3-chloro-2-fluorobenzamide |
| Int. 16 | 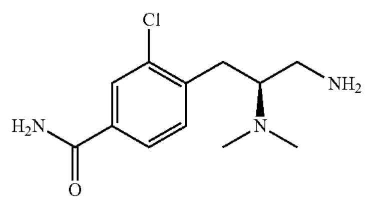 [SMILES: CN(C)[C@H](CN)Cc1ccc(C(N)=O)cc1Cl] | 256.3 (M + H) | 4-[(2S)-3-amino-2-(dimethylamino)propyl]-3-chlorobenzamide |
| Int. 17 | 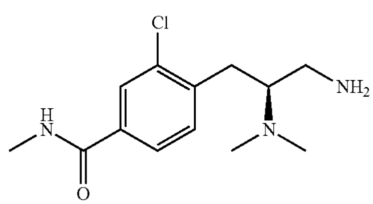 [SMILES: CNC(=O)c1ccc(C[C@@H](CN)N(C)C)c(Cl)c1] | 270.0 (M + H) | (S)-4-(3-amino-2-(dimethylamino)propyl)-3-chloro-N-methylbenzamide |
| Int. 30 | 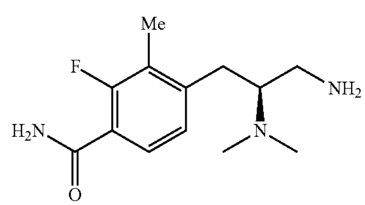 [SMILES: Cc1c(C[C@@H](CN)N(C)C)ccc(C(N)=O)c1F] | 254.1 (M + H) | 4-[(2S)-3-amino-2-(dimethylamino)propyl]-2-fluoro-3-methylbenzamide |
| Int. 31 | 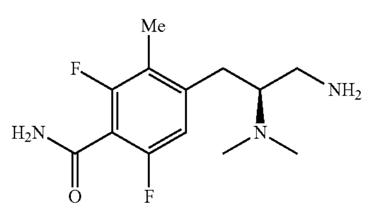 [SMILES: Cc1c(C[C@@H](CN)N(C)C)cc(F)c(C(N)=O)c1F] | 271.9 (M + H) | 4-[(2S)-3-amino-2-(dimethylamino)propyl]-2,6-difluoro-3-methylbenzamide |
| Int. 32 | 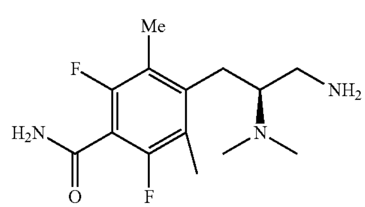 [SMILES: Cc1c(F)c(C(N)=O)c(F)c(C)c1C[C@@H](CN)N(C)C] | 286.1 (M + H) | 4-[(2S)-3-amino-2-(dimethylamino)propyl]-2,6-difluoro-3,5-dimethylbenzamide |

-continued

| Intermediate (Int.) No. | Structure | LC/MS (m/z) | Name |
|---|---|---|---|
| Int. 33 | 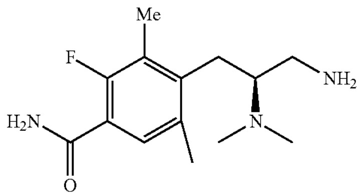 [SMILES: Cc1cc(C(N)=O)c(F)c(C)c1C[C@@H](CN)N(C)C] | | 4-[(2S)-3-amino-2-(dimethylamino)propyl]-2-fluoro-3,5-dimethylbenzamide |
| Int. 35 | 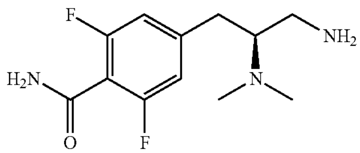 [SMILES: CN(C)[C@H](CN)Cc1cc(F)c(C(N)=O)c(F)c1] | 258.1 (M + H) | 4-[(2S)-3-amino-2-(dimethylamino)propyl]-2,6-difluorobenzamide |
| Int. 41 | 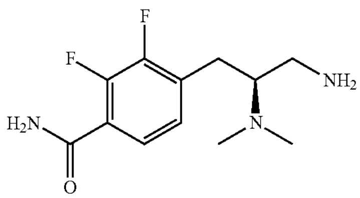 [SMILES: CN(C)[C@H](CN)Cc1ccc(C(N)=O)c(F)c1F] | 258.1 (M + H) | 4-[(2S)-3-amino-2-(dimethylamino)propyl]-2,3-difluorobenzamide |
| Int. 53 | 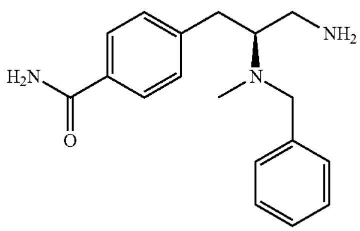 [SMILES: CN(Cc1ccccc1)[C@H](CN)Cc1ccc(C(N)=O)cc1] | 298.2 (M + H) | 4-[(2S)-3-amino-2-[benzyl(methyl)amino]propyl]benzamide |
| Int. 73 | 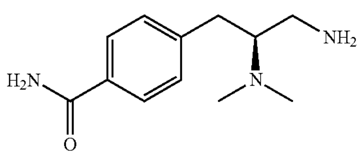 [SMILES: CN(C)[C@H](CN)Cc1ccc(C(N)=O)cc1] | 222.2 (M + H) | (S)-4-(3-amino-2-(dimethylamino)propyl)benzamide |
| Int. 74 | 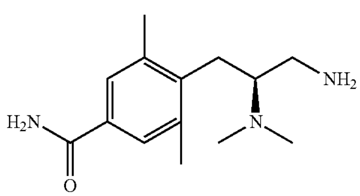 [SMILES: Cc1cc(C(N)=O)cc(C)c1C[C@@H](CN)N(C)C] | 250.2 (M + H) | (S)-4-(3-amino-2-(dimethylamino)propyl)-3,5-dimethylbenzamide |
| Int. 94 | 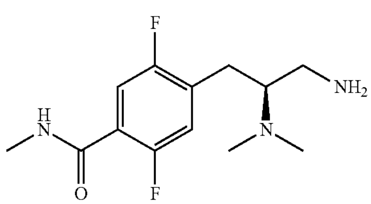 | 194.1 (M + H) | (S)-4-(3-amino-2-(dimethylamino)propyl)-2,5-difluoro-N-methylbenzamide |
| Int. 95 | 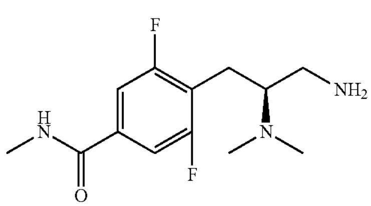 [SMILES: CNC(=O)c1cc(F)c(C[C@@H](CN)N(C)C)c(F)c1] | 272.1 (M + H) | (S)-4-(3-amino-2-(dimethylamino)propyl)-3,5-difluoro-N-methylbenzamide |

-continued

| Intermediate (Int.) No. | Structure | LC/MS (m/z) | Name |
|---|---|---|---|
| Int. 96 | 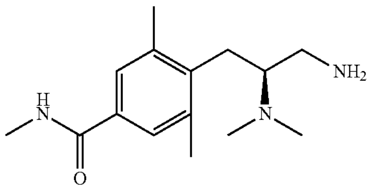 [SMILES: CNC(=O)c1cc(C)c(C[C@@H](CN)N(C)C)c(C)c1] | 264.2 (M + H) | (S)-4-(3-amino-2-(dimethylamino)propyl)-N,3,5-trimethylbenzamide |
| Int. 97 | 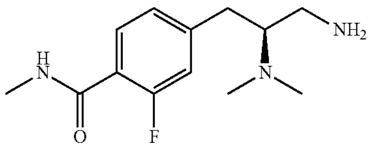 [SMILES: CNC(=O)c1ccc(C[C@@H](CN)N(C)C)cc1F] | 254.2 (M + H) | (S)-4-(3-amino-2-(dimethylamino)propyl)-2-fluoro-N-methylbenzamide |
| Int. 99 | 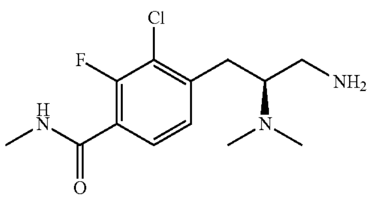 [SMILES: CNC(=O)c1ccc(C[C@@H](CN)N(C)C)c(Cl)c1F] | 288.2 (M + H) | (S)-4-(3-amino-2-(dimethylamino)propyl)-2-fluoro-N-methylbenzamide |
| Int. 102 | 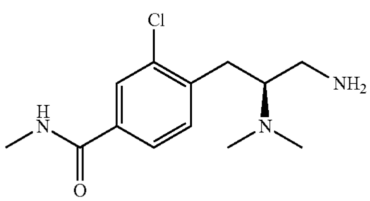 [SMILES: CNC(=O)c1ccc(C[C@@H](CN)N(C)C)c(Cl)c1] | 270.3 (M + H) | (S)-4-(3-amino-2-(dimethylamino)propyl)-3-chloro-N-methylbenzamide |
| Int. 110 | 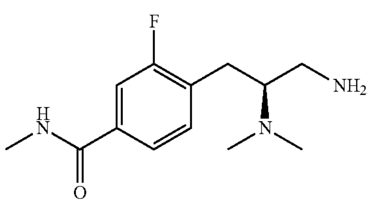 [SMILES: CNC(=O)c1ccc(C[C@@H](CN)N(C)C)c(F)c1] | 254.3 (M + H) | (S)-4-(3-amino-2-(dimethylamino)propyl)-3-fluoro-N-methylbenzamide |
| Int. 111 | 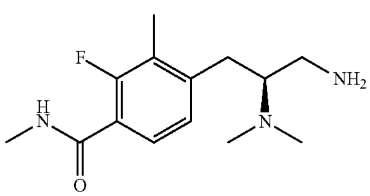 [SMILES: CNC(=O)c1ccc(C[C@@H](CN)N(C)C)c(C)c1F] | 268.3 (M + H) | (S)-4-(3-amino-2-(dimethylamino)propyl)-2-fluoro-N,3-dimethylbenzamide |
| Int. 112 | 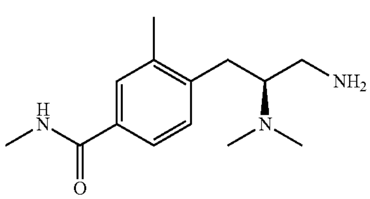 [SMILES: CNC(=O)c1ccc(C[C@@H](CN)N(C)C)c(C)c1] | 250.2 (M + H) | (S)-4-(3-amino-2-(dimethylamino)propyl)-N,3-dimethylbenzamide |
| Int. 122 | 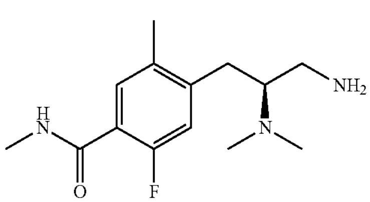 [SMILES: CNC(=O)c1cc(C)c(C[C@@H](CN)N(C)C)cc1F] | 268.2 (M + H) | (S)-4-(3-amino-2-(dimethylamino)propyl)-2-fluoro-N,5-dimethylbenzamide |

| Intermediate (Int.) No. | Structure | LC/MS (m/z) | Name |
|---|---|---|---|
| Int. 123 | 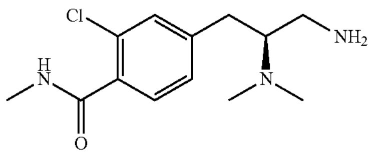 [SMILES: CNC(=O)c1ccc(C[C@@H](CN)N(C)C)cc1Cl] | 270.2 (M + H) | (S)-4-(3-amino-2-(dimethylamino)propyl)-2-chloro-N-methylbenzamide |
| Int. 128 | 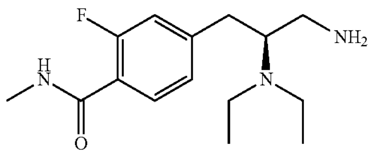 [SMILES: CCN(CC)[C@H](CN)Cc1ccc(C(=O)NC)c(F)c1] | 282.2 (M + H) | (S)-4-(3-amino-2-(dimethylamino)propyl)-2-fluoro-N-methylbenzamide |
| Int. 129 | 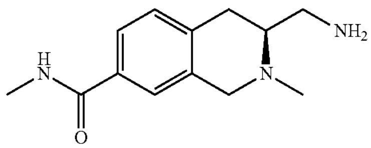 | 282.2 (M + H) | (S)-3-(aminomethyl)-N,2-dimethyl-1,2,3,4-tetrahydroisoquinoline-7-carboxamide |
| Int. 131 | 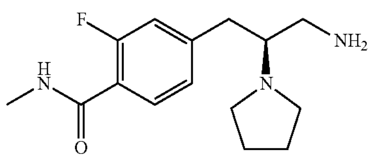 [SMILES: CNC(=O)c1ccc(C[C@@H](CN)N2CCCC2)cc1F] | 280.2 (M + H) | 4-[(2S)-3-amino-2-(pyrrolidin-1-yl)propyl]-2-fluoro-N-methylbenzamide |

Example A3: Preparation of (R)-3-Phenyl-3-(1-(trifluoromethyl)cyclopropyl)propanoic acid (3F, "Intermediate 3")

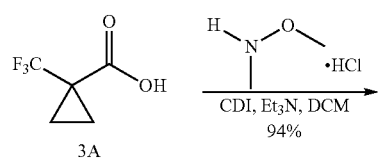

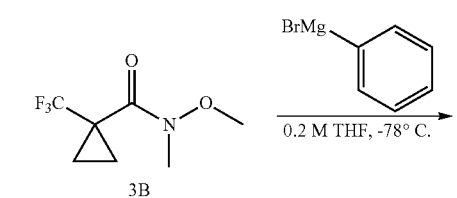

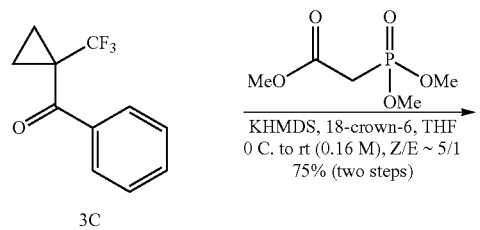

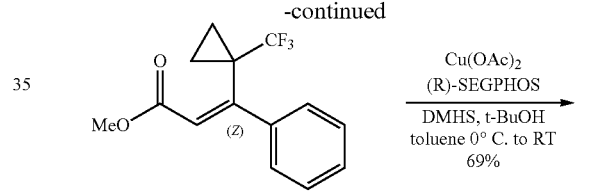

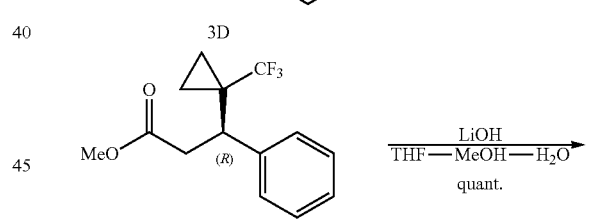

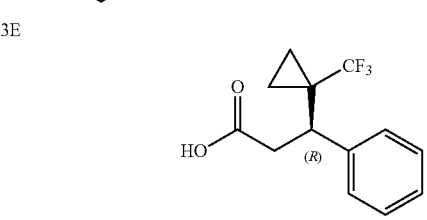

Preparation of N-Methoxy-N-methyl-1-(trifluoromethyl)cyclopropane-1-carboxamide(3B): 1-(trifluoromethyl)cyclopropane-1-carboxylic acid (25 g, 162 mmol) was taken in dichloromethane (250 ml) and carbonyldiimidazole (32 g, 200 mmol) was added in portions to it, which led to rapid effervescence. The solution was stirred for the next 30 mins at room temperature. Triethylamine (45 ml, 324 mmol) was then added followed by N,O-dimethylhydroxylamine hydrochloride (17.4 g, 180 mmol) was added and the solution was stirred for the next 24 hrs. TLC indicated that the reaction was completed. The reaction was quenched by adding 2 N HCl solution. After stirring for 15 mins, the two layers were separated. The organic layer was then washed with saturated sodium bicarbonate layer and then with brine. The organic layer was filtered through magnesium sulfate and the filtrate was concentrated to give the title compound as an oil (30 g, 94%).

Preparation of phenyl(1-(trifluoromethyl)cyclopropyl)methanone (3C): To an oven-dried 500 mL of RBF and egg-shaped stir bar with N-methoxy-N-methyl-1-(trifluoromethyl)cyclopropane-1-carboxamide (20.6 g, 104 mmol) was added THF (200 mL) under $N_2$ balloon atmosphere. The resulting mixture was cooled to −78° C. in a dry ice acetone bath for about 15 minutes. Pale yellow solution was observed. Phenylmagnesium bromide (41.8 mL, 3M in ether, 125 mmol) was added dropwise in 10 minutes with shaking vigorously to prevent gumming up the stir-bar. The reaction mixture was kept at −78° C. for 20 min, then stirred at 0° C. for 30 min. After that, the mixture was stirred at rt overnight. Most of the volatiles were then evaporated, the resulting crude was cooled to 0° C., added $NH_4Cl$ (80 mL) and water (100 mL). Then extracted by EtOAc twice, washed with water for three times and brine. After dried over $MgSO_4$ and concentrated. The crude product was obtained as a slightly yellow oil (27.7 g, ~80% purity). The crude was used directly in the next step without further purification.

Preparation of methyl (Z)-3-phenyl-3-(1-(trifluoromethyl)cyclopropyl)acrylate (3D): To a 500 mL of RBF with methyl 2-(dimethoxyphosphoryl)acetate (13.3 g, 73.2 mmol) and 18-crown-6 (19.3 g, 73.2 mmol) was added dry THF (200 mL). Then the reaction mixture was cooled to 0° C., potassium bis(trimethylsilyl)amide (73.2 mL, 1 M in THF) was added dropwise in 10 minutes. After the addition (yellow clear solution), the reaction mixture was warmed and stirred at rt for 40 minutes. Then a solution of phenyl [1-(trifluoromethyl)cyclopropyl]methanone (14.0 g) in THF (25 mL) was added to the solution dropwise in 2 minutes at rt. After the addition, more THF (30 mL) was added. The reaction mixture was stirred at rt overnight and H-NMR showed complete conversion (in $CDCl_3$, ratio of Z/E~5/1). Then the crude was evaporated to remove about half of the THF, the residue was worked up with EtOAc & water, the aqueous layer was extracted with EtOAc three times. The combined organic layers were dried over $MgSO_4$, concentrated, and purified by 220 g silica gel column (sample was mixed with silica gel and eluding the column with: 0-25% 10% EtOAc in Hexanes/Hexanes) to give the top spot (major product) methyl (2Z)-3-phenyl-3-[1-(trifluoromethyl)cyclopropyl]prop-2-enoate (10.6 g, 75% for two steps) as a colorless oil. MS (m/z): 271.2 (M+H). NOE between alkene CH and phenyl ring H confirmed the double-bond geometry.

Preparation of methyl (R)-3-phenyl-3-(1-(trifluoromethyl)cyclopropyl)propanoate (3E): To a stirred mixture of (R)-DTBM-SEGPHOS® (375 mg, 0.32 mmol) and $Cu(OAc)_2$ (173 mg, 0.955 mmol) in toluene (40 mL) at 0° C. under $N_2$ balloon, was added (dimethoxymethyl)silane (9.7 mL, 79 mmol), followed by t-BuOH (6 mL, 63 mmol). Then a solution of methyl (2Z)-3-phenyl-3-[1-(trifluoromethyl)cyclopropyl]prop-2-enoate (8.6 g, 31.8 mmol) in toluene (15 mL) was added dropwise in 5 minutes. The mixture was stirred at 0° C. for 45 min then rt for another 45 min, then LC-MS & H-NMR showed complete conversion. Saturated ammonium chloride solution (100 mL) was added. After stirring for 30 minutes, extracted with EtOAc (2×). The combined extracts were washed with water, 1 N HCl, water, sat. $NaHCO_3$ sol. & brine. After dried over $MgSO_4$, concentrated and purified by 220 g silica gel column (0-100% 10% EtOAc in Hexanes/Hexanes) using ESLD detecting combi-flash to provide methyl (3R)-3-phenyl-3-[1-(trifluoromethyl)cyclopropyl]propanoate as a colorless oil (6 g, 69%). MS (m/z): 273.2 (M+H).

Preparation of (R)-3-Phenyl-3-(1-(trifluoromethyl)cyclopropyl)propanoic acid (3F): Lithium hydroxide monohydrate (2.78 g, 66 mmol) was added into a solution of methyl (3S)-3-phenyl-3-[1-(trifluoromethyl)cyclopropyl]propanoate (6.0 g, 22 mmol) in THF-MeOH-water (v/v/v 1:1:1, 75 mL) at rt. The mixture was stirred at rt overnight. LC-MS showed complete conversion. Most of the volatiles were removed on rota-vapor. Water (30 mL) was added to the crude. After cooled with ice-water bath, 1N HCl (~72 mL) was added dropwise to adjust pH to 5. Extracted with EtOAc for four times, the combined extract layers were washed with brine. After dried over anhydrous $Na_2SO_4$, filtered and concentrated to provide (3R)-3-phenyl-3-[1-(trifluoromethyl)cyclopropyl]propanoic acid (5.65 g, 99%) as a colorless oil. MS (m/z): 259.1 M+H).

Example A4: Preparation of (S)-3-phenyl-3-(1-(trifluoromethyl)cyclopropyl)propanoic acid (4D, "Intermediate 4")

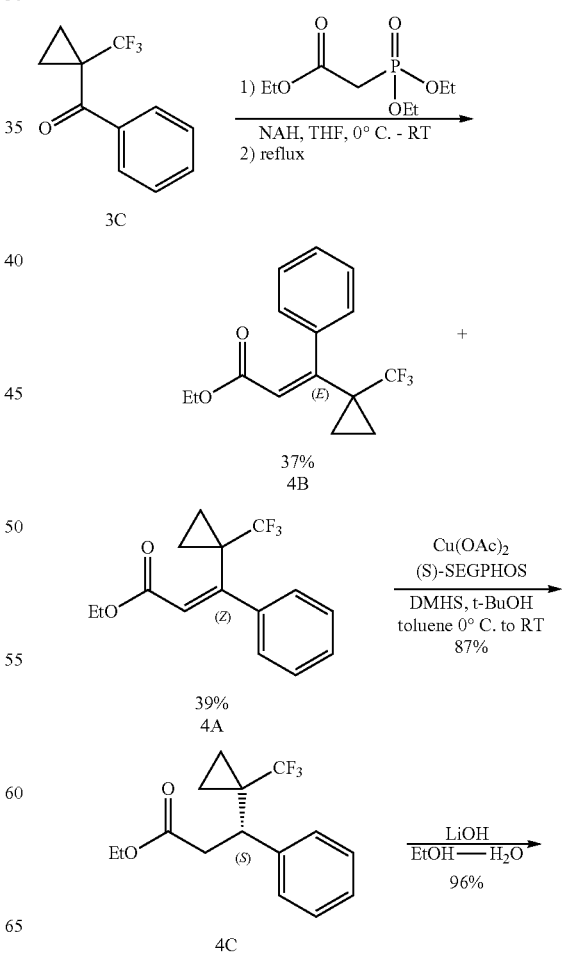

-continued

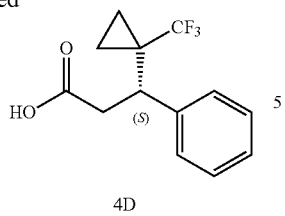

4D

Preparation of ethyl (Z)-3-phenyl-3-(1-(trifluoromethyl)cyclopropyl)acrylate (4A): To a stirred suspension of NaH (60%, 1.51 g, 37.8 mmol) in THF (50 mL) at 0° C. was added ethyl 2-(diethoxyphosphoryl)acetate (9.68 g, 43.2 mmol) dropwise. After the addition was completed, the ice bath was removed and the mixture was stirred at RT for 1h. Phenyl[1-(trifluoromethyl)cyclopropyl]methanone (5.64 g, 21.6 mmol) in THF (20 mL) was added. The reaction mixture was then heated to reflux in 16 h. The reaction mixture was cooled to RT, saturated aqueous NH$_4$Cl was added, extracted with EtOAc (3×). The combined extracts were dried over MgSO4, concentrated, and purified by flash chromatography (0-5% EtOAc/Hexanes) to give ethyl (2Z)-3-phenyl-3-[1-(trifluoromethyl)cyclopropyl]prop-2-enoate (4A, 2.41 g, 39%) and ethyl (2E)-3-phenyl-3-[1-(trifluoromethyl)cyclopropyl]prop-2-enoate (4B, 2.27 g, 37%). MS (m/z): 285.1 (M+H).

Preparation of ethyl (3S)-3-phenyl-3-[1-(trifluoromethyl)cyclopropyl]propanoate (4C): To a stirred mixture of (S)-DTBM-SEGPHOS® (20.7 mg, 0.017 mmol) and Cu(OAc)$_2$ (16 mg, 0.088 mmol) in toluene (4 mL) at 0° C. under N$_2$ balloon, was added (dimethoxymethyl)silane (0.645 mL, 5.28 mmol), followed by t-BuOH (0.334 mL, 3.52 mmol). Then a solution of ethyl (2Z)-3-phenyl-3-[1-(trifluoromethyl)cyclopropyl]prop-2-enoate (0.5 g, 1.76 mmol, compound 4A) in toluene (4 mL) was added dropwise in 5 minutes. The mixture was stirred at 0° C. for 45 min then rt for another 45 min, then LC-MS & H-NMR showed complete conversion. Saturated ammonium chloride solution (10 mL) was added. After stirring for 30 minutes, extracted with EtOAc (2×). The combined extracts were washed with water, 1 N HCl, water, sat. NaHCO$_3$ sol. & brine. After dried over MgSO$_4$, concentrated and purified by silica gel column (0-100% 10% EtOAc in Hexanes/Hexanes) using ESLD detecting combi-flash to provide ethyl (3S)-3-phenyl-3-[1-(trifluoromethyl)cyclopropyl]propanoate as a colorless oil (0.546 g, 87%). MS (m/z): 287.1 (M+H).

Preparation of (3S)-3-phenyl-3-[1-(trifluoromethyl)cyclopropyl]propanoic acid (4D): Lithium hydroxide monohydrate (2.78 g, 66 mmol) was added into a solution of ethyl (3R)-3-phenyl-3-[1-(trifluoromethyl)cyclopropyl]propanoate (0.5 g, 1.41 mmol) in EtOH-water (1:1; 4 mL) at rt. The mixture was stirred at rt overnight. LC-MS showed complete conversion. Most of the volatiles were removed on rota-vapor. Water (5 mL) was added to the crude. After cooled with ice-water bath, 1N HCl (~72 mL) was added dropwise to adjust pH to 5. Extracted with EtOAc for four times, the combined extract layers were washed with brine. After dried over anhydrous Na$_2$SO$_4$, filtered and concentrated to provide (3S)-3-phenyl-3-[1-(trifluoromethyl)cyclopropyl]propanoic acid (0.354 g, 96%) as a colorless oil. MS (m/z): 259.1 (M+H).

Example A5: Preparation of (S)-4-(3-amino-2-(dimethylamino)propyl)-2,3-difluorobenzamide (5E, "Intermediate 5")

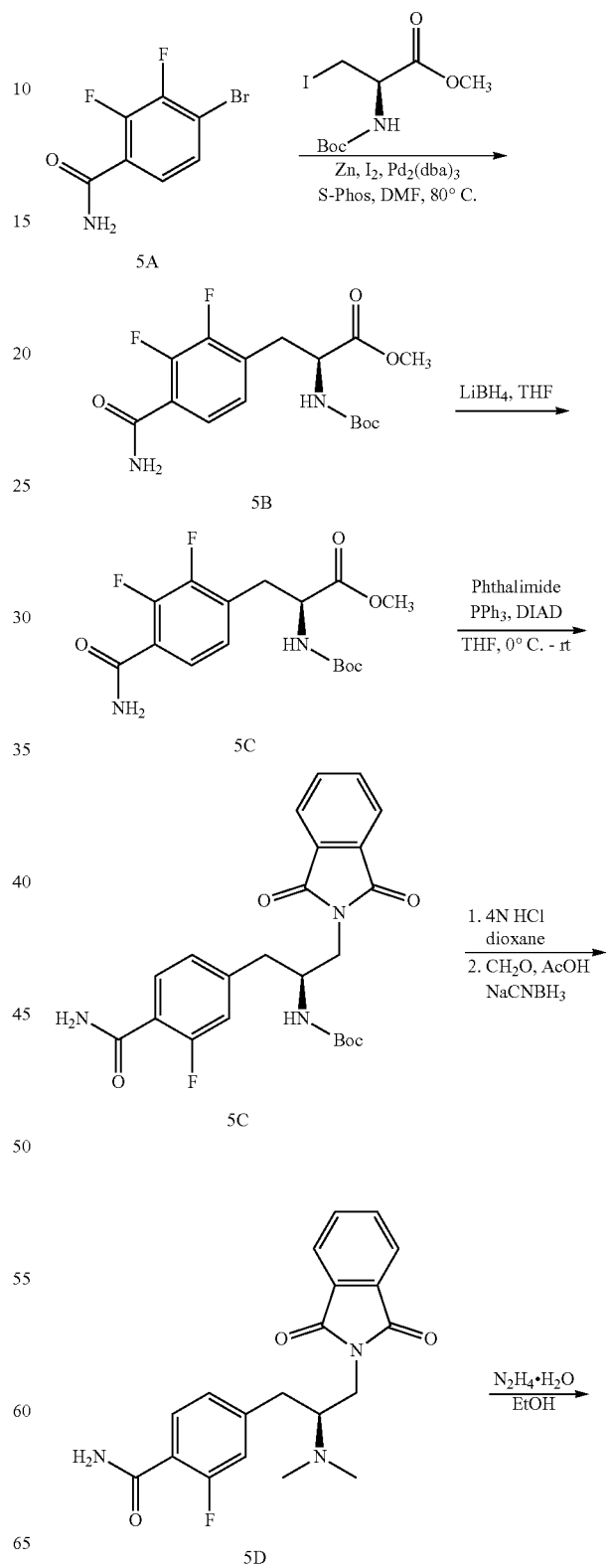

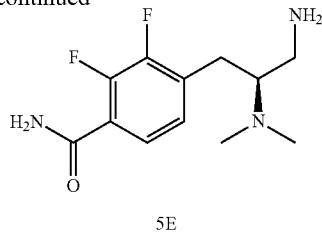

5E

Preparation of (S)-4-(3-amino-2-(dimethylamino)propyl)-2,3-difluorobenzamide (5E): The title compound (670 mg, 67%) was prepared in the same method as Intermediate 1, as described in Example A1. MS (m/z): 258.1 (M+H).

Example A6: Preparation of(S)-3-(2-methylthiazol-5-yl)-3-(1-(trifluoromethyl)cyclopropyl)propanoic acid (6D, "Intermediate 6")

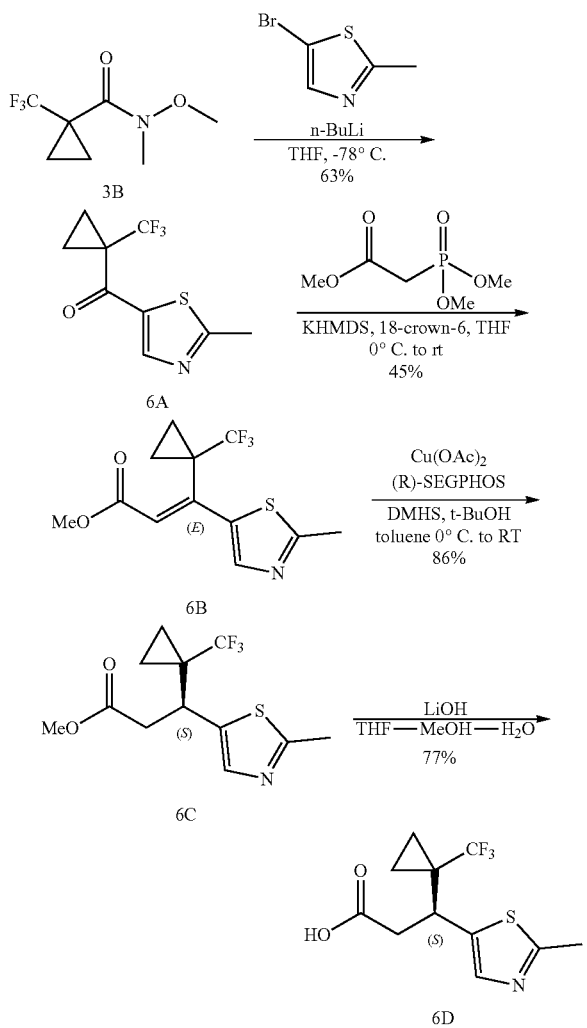

Preparation of (2-methylthiazol-5-yl)(1-(trifluoromethyl)cyclopropyl)methanone (6A): 5-bromo-2-methy-1,3-thiozole (7.67 g, 43.1 mmol) in THF (30 mL) was injected dropwise (over 20 minutes) into a solution of n-BuLi in hexanes (2.5M, 19.0 mL, 47.4 mmol) in THF (30 mL) at −78° C. The reaction turned into light brown cloudy. Intermediate 3B (9.34 g, 47.4 mmol) was injected dropwise, stirred for 2 hours at −78° C. The reaction was quenched with saturated NH$_4$Cl(aq)(150 mL), extracted with EtOAc (3×), dried over MgSO$_4$, filtered, concentrated, and purified on 330 g gold silica gel column, 0-50% EtOAc/hexanes to give the title compound as brown oil (6.47 g, 63%). MS (m/z): 236.0 (M+H).

Preparation of methyl (E)-3-(2-methylthiazol-5-yl)-3-(1-(trifluoromethyl)cyclopropyl)acrylate (6B): To a stirred solution of trimethyl phosphonoacetate (6.49 g, 35.6 mmol) and 18-crown-6-ether (Combi-Blocks, SS-7385, B43822, FW 264.3, 9.41 g, 35.6 mmol) in THF (40 mL) at 0° C., was injected KHMDS in THF (Oakwood Chemical, Lot 104258M05H, 1.0M, 35.6 mL) dropwise. The reaction mixture was warmed up to room temperature for 30 minutes. A solution of ketone (6 A, 6.45 g, 27.4 mmol) in THF (20 mL) was added dropwise. After the addition was completed, continued at 0° C. to rt for 16 hours. The reaction mixture was cooled, added NaHCO$_3$ (30 mL), extracted with EtOAc (3×). The combined extracts were washed with water (1×), brine (1×), dried over MgSO$_4$, concentrated, and purified by 220 g silica gel column (0-100% MTBE/Hexanes) to give the title compound (3.67 g, 45%). MS (m/z): 292.0 (M+H).

Preparation of methyl (3S)-3-(2-methyl-1,3-thiazol-5-yl)-3-[1-(trifluoromethyl)cyclopropyl]propanoate (6C): To a stirred mixture of (R)-DTBM-SEGPHOS® (MW 1180, 22.8 mg, 0.0193 mmol, 0.01 eq) and Cu(OAc)$_2$ (MW181.6, 10.5 mg, 0.0580 mmol, 0.03 eq) in toluene (5 mL) at 0° C. under N$_2$ balloon, was added DMHS (508 mg, 4.83 mmol, 2.5 eq), followed by t-BuOH (MW 74.12, d=0.781, 0.367 mL, 3.87 mmol, 2.0 eq). Then a solution of 6B (563 mg, 1.93 mmol) in toluene (5 mL) was added dropwise in 3 minutes. The mixture was stirred from 0° C. to rt for 30 minutes. The color changed from light blue to green to dark brown. Saturated NaHCO$_3$ (5 mL) was added and stirred for 30 minutes at rt, extracted with EtOAc (2×). The combined extracts were washed with water, brine, dried over MgSO$_4$, concentrated, and purified by 40 g silica gel column (0-50% EtOAc in Hexanes) to give the title compound (491 mg, 87%). MS (m/z): 294.0 (M+H).

Preparation of (S)-3-(2-methylthiazol-5-yl)-3-(1-(trifluoromethyl)cyclopropyl)propanoic acid (6D): A solution of 6C (486 mg, 1.66 mmol) in MeOH (3 mL)/THF (3 mL) was treated with LiOH (2N, 2.6 mL) at rt. The reaction mixture was stirred at RT for 1 h. LCMS: the reaction was completed. The solvents were removed on rota-vapor. Water (3 mL) was added, cooled with ice-water bath, adjusted pH ~4 by adding 1N HCl, extracted with DCM (3×). The combined extracts were dried over MgSO$_4$, filtered, and concentrated to provide the title compound (360 mg, 78%). MS (m/z): 280.0 (M+H).

The following intermediates were synthesized in analogous methods to those described in Example A6: Int. 6 & General Scheme VII:

| Intermediate (Int.) No. | Structure | LC/MS (m/z) | Name |
|---|---|---|---|
| Int. 9 | 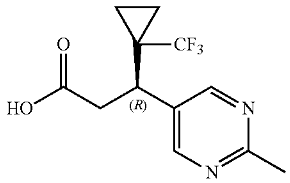 | 303.1 (M + H) | (R)-3-(2-methylpyrimidin-5-yl)-3-(1-(trifluoromethyl)cyclopropyl)propanoic acid |
| Int. 10 | 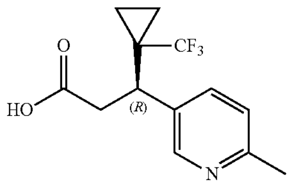 | 288.1 (M + H) | (R)-3-(6-methylpyridin-3-yl)-3-(1-(trifluoromethyl)cyclopropyl)propanoic acid |
| Int. 11 | 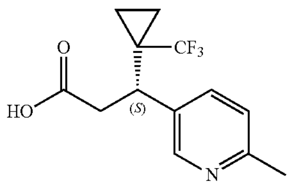 | 288.1 (M + H) | (S)-3-(6-methylpyridin-3-yl)-3-(1-(trifluoromethyl)cyclopropyl)propanoic acid |
| Int. 12 | 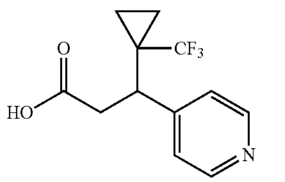 [SMILES: O=C(O)CC(c1ccncc1)C1(C(F)(F)F)CC1] | 260.1 (M + H) | 3-(pyridin-4-yl)-3-[1-(trifluoromethyl)cyclopropyl)propanoic acid |
| Int. 14 | 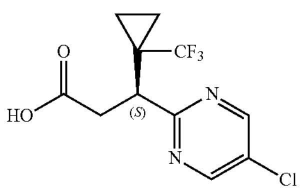 | 295.0 (M + H) | (3S)-3-(5-chloropyrimidin-2-yl)-3-[1-(trifluoromethyl)cyclopropyl)propanoic acid |
| Int. 15 | 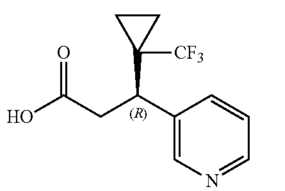 | 260.1 (M + H) | (R)-3-(pyridin-3-yl)-3-(1-(trifluoromethyl)cyclopropyl)propanoic acid |
| Int. 18 | 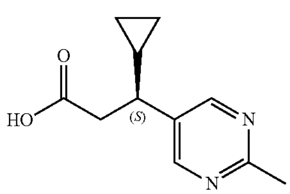 | 207.1 (M + H) | (3S)-3-cyclopropyl-3-(2-methylpyrimidin-5-yl)propanoic acid |
| Int. 19 | 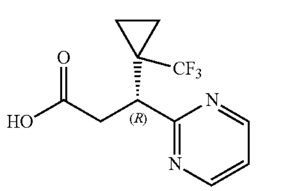 | 260.1 (M + H) | (3R)-3-(pyrimidin-2-yl)-3-[1-(trifluoromethyl)cyclopropyl)propanoic acid |

-continued

| Intermediate (Int.) No. | Structure | LC/MS (m/z) | Name |
| --- | --- | --- | --- |
| Int. 20 | 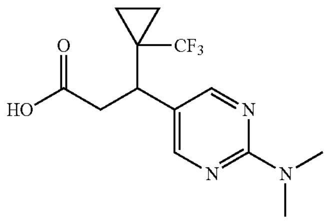 [SMILES: CN(C)c1ncc(C(CC(=O)O)C2(C(F)(F)F)CC2)cn1] | 304.1 (M + H) | 3-[2-(dimethylamino)pyrimidin-5-yl]-3-[1-(trifluoromethyl)cyclopropyl]propanoic acid |
| Int. 21 | 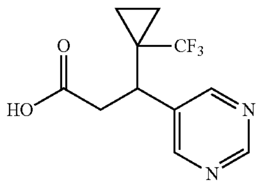 [SMILES: O=C(O)CC(c1cncnc1)C1(C(F)(F)F)CC1] | 261.0 (M + H) | 3-(pyrimidin-5-yl)-3-[1-(trifluoromethyl)cyclopropyl]propanoic acid |
| Int. 22 | 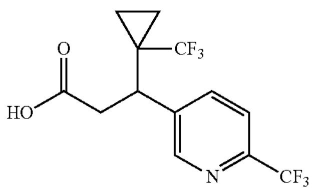 [SMILES: O=C(O)CC(c1ccc(C(F)(F)F)nc1)C1(C(F)(F)F)CC1] | 328.1 (M + H) | 3-[1-(trifluoromethyl)cyclopropyl]-3-[6-(trifluoromethyl)pyridin-3-yl]propanoic acid |
| Int. 23 | 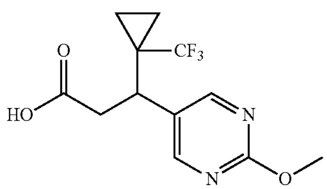 [SMILES: COc1ncc(C(CC(=O)O)C2(C(F)(F)F)CC2)cn1] | 291.1 (M + H) | 3-(2-methoxypyrimidin-5-yl)-3-[1-(trifluoromethyl)cyclopropyl]propanoic acid |
| Int. 24 | 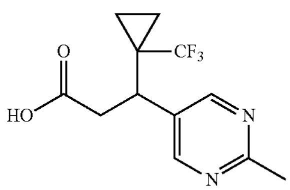 [SMILES: Cc1ncc(C(CC(=O)O)C2(C(F)(F)F)CC2)cn1] | 275.1 (M + H) | 3-(2-methylpyrimidin-5-yl)-3-[1-(trifluoromethyl)cyclopropyl]propanoic acid |
| Int. 25 | 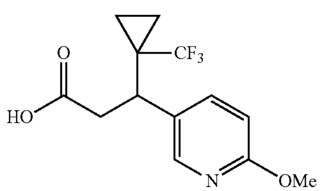 [SMILES: COc1ccc(C(CC(=O)O)C2(C(F)(F)F)CC2)cn1] | 290.1 (M + H) | 3-(6-methoxypyridin-3-yl)-3-[1-(trifluoromethyl)cyclopropyl]propanoic acid |
| Int. 26 | 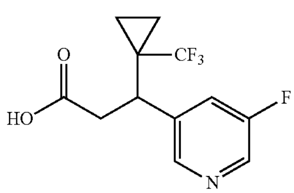 [SMILES: O=C(O)CC(c1cncc(F)c1)C1(C(F)(F)F)CC1] | 278.1 (M + H) | 3-(5-fluoropyridin-3-yl)-3-[1-(trifluoromethyl)cyclopropyl]propanoic acid |
| Int. 27 | 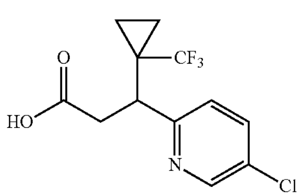 [SMILES: O=C(O)CC(c1ccc(Cl)cn1)C1(C(F)(F)F)CC1] | 294.1 (M + H) | 3-(5-chloropyridin-2-yl)-3-(1-(trifluoromethyl)cyclopropyl]propanoic acid |

-continued

| Intermediate (Int.) No. | Structure | LC/MS (m/z) | Name |
|---|---|---|---|
| Int. 28 | 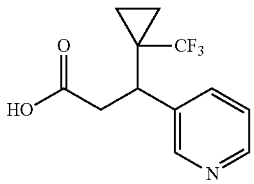 [SMILES: O=C(O)CC(c1cccnc1)C1(C(F)(F)F)CC1] | 260.1 (M + H) | 3-(pyridin-3-yl)-3-[1-(trifluoromethyl)cyclopropyl]propanoic acid |
| Int. 29 | 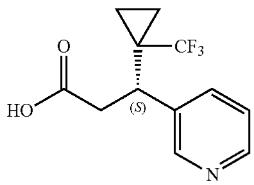 | 260.1 (M + H) | (3S)-3-(pyridin-3-yl)-3-[1-(trifluoromethyl)cyclopropyl]propanoic acid |
| Int. 34 | 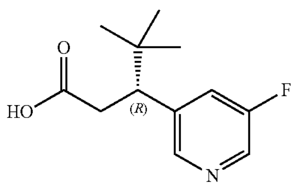 | 226.1 (M + H) | (3R)-3-(5-fluoropyridin-3-yl)-4,4-dimethylpentanoic acid |
| Int. 36 | 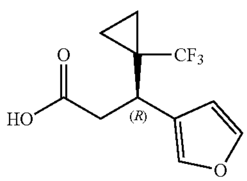 | 249.1 (M + H) | (R)-3-(furan-3-yl)-3-(1-(trifluoromethyl)cyclopropyl)propanoic acid |
| Int. 37 | 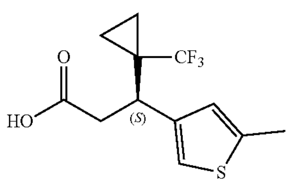 | 279.0 (M + H) | (3S)-3-(5-methylthiophen-3-yl)-3-[1-(trifluoromethyl)cyclopropyl]propanoic acid |
| Int. 38 | 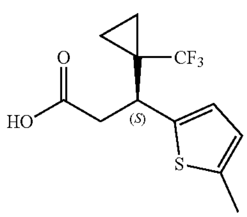 | 279.0 (M + H) | (S)-3-(5-methylthiophen-2-yl)-3-(1-(trifluoromethyl)cyclopropyl)propanoic acid |
| Int. 39 | 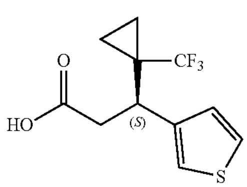 | 265.1 (M + H) | (3S)-3-(thiophen-3-yl)-3-[1-(trifluoromethyl)cyclopropyl]propanoic acid |
| Int. 40 | 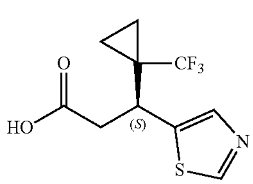 | 266.0 (M + H) | (3S)-3-(1,3-thiazol-5-yl)-3-[1-(trifluoromethyl)cyclopropyl]propanoic acid |

-continued

| Intermediate (Int.) No. | Structure | LC/MS (m/z) | Name |
|---|---|---|---|
| Int. 42 | 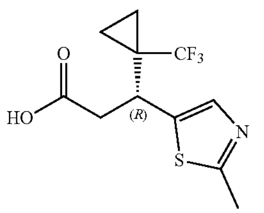 | 280.0 (M + H) | (3R)-3-(2-methyl-1,3-thiazol-5-yl)-3-[1-(trifluoromethyl)cyclopropyl]propanoic acid |
| Int. 43 | 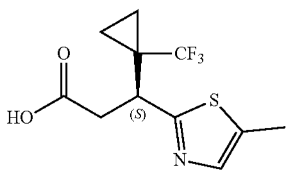 | 280.0 (M + H) | (3S)-3-(5-methyl-1,3-thiazol-2-yl)-3-[1-(trifluoromethyl)cyclopropyl]propanoic acid |
| Int. 44 | 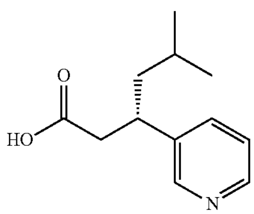 | 208.1 (M + H) | (3S)-5-methyl-3-(pyridin-3-yl)hexanoic acid |
| Int. 45 | 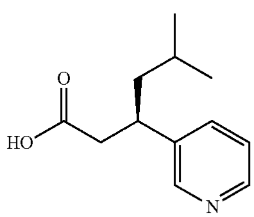 | 208.1 (M + H) | (3S)-5-methyl-3-(pyridin-3-yl)hexanoic acid |
| Int. 46 | 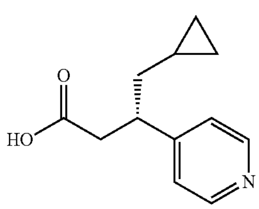 [SMILES: O=C(O)C[C@H](CC1CC1)c1ccncc1] | 206.1 (M + H) | (S)-4-cyclopropyl-3-(pyridin-4-yl)butanoic acid |
| Int. 47 | 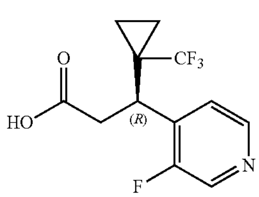 | 278.2 (M + H) | (3R)-3-(3-fluoropyridin-4-yl)-3-[1-(trifluoromethyl)cyclopropyl]propanoic acid |
| Int. 48 | 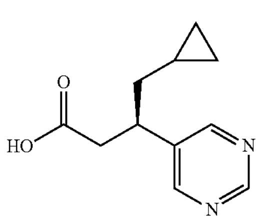 [SMILES: O=C(O)C[C@@H](CC1CC1)c1cncnc1] | 207.1 (M + H) | (3R)-4-cyclopropyl-3-(pyrimidin-5-yl)butanoic acid |

-continued

| Intermediate (Int.) No. | Structure | LC/MS (m/z) | Name |
|---|---|---|---|
| Int. 49 | 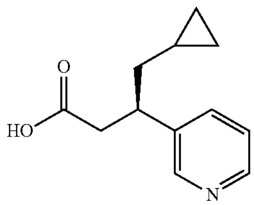 [SMILES: O=C(O)C[C@@H](CC1CC1)c1cccnc1] | 206.1 (M + H) | (3R)-4-cyclopropyl-3-(pyridin-3-yl)butanoic acid |
| Int. 50 | 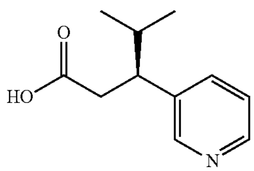 | 194.1 (M + H) | (3S)-4-methyl-3-(pyridin-3-yl)pentanoic acid |
| Int. 51 | 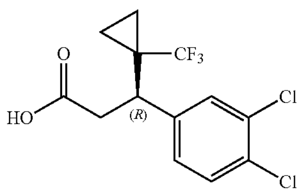 | 327.1 (M + H) | (3R)-3-(3,4-dichlorophenyl)-3-[1-(trifluoromethyl)cyclopropyl]propanoic acid |
| Int. 52 | 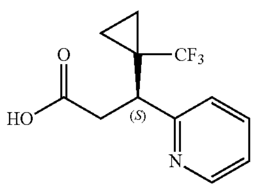 | 260.1 (M + H) | (3S)-3-(pyridin-2-yl)-3-[1-(trifluoromethyl)cyclopropyl]propanoic acid |
| Int. 54 | 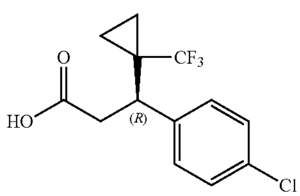 | 315.0 (M + H) | (3R)-3-(4-chlorophenyl)-3-[1-(trifluoromethyl)cyclopropyl]propanoic acid |
| Int. 55 | 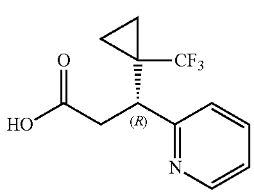 | 260.1 (M + H) | (3R)-3-(pyridin-2-yl)-3-[1-(trifluoromethyl)cyclopropyl]propanoic acid |
| Int. 56 | 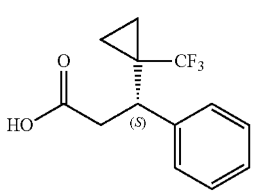 | 259.2 (M + H) | (3S)-3-phenyl-3-[1-(trifluoromethyl)cyclopropyl]propanoic acid |
| Int. 59 | 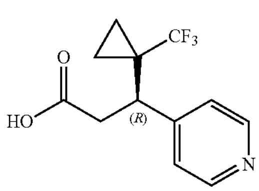 | 260.1 (M + H) | (3R)-3-(pyridin-4-yl)-3-[1-(trifluoromethyl)cyclopropyl]propanoic acid |

-continued

| Intermediate (Int.) No. | Structure | LC/MS (m/z) | Name |
|---|---|---|---|
| Int. 71 | 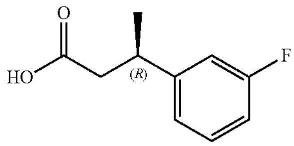 | 165.1 (M + H) | (R)-3-(3-fluorophenyl)butanoic acid |
| Int. 72 | 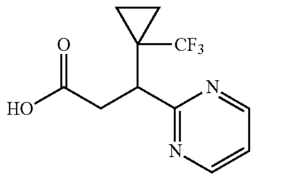 [SMILES: O=C(O)CC(c1ncccn1)C1(C(F)(F)F)CC1] | 261.1 (M + H) | 3-(pyrimidin-2-yl)-3-(1-(trifluoromethyl)cyclopropyl)propanoic acid |
| Int. 77 | 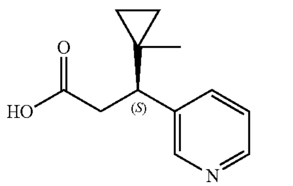 | 205.1 (M + H) | (3S)-3-(1-methylcyclopropyl)-3-(pyridin-3-yl)propanoic acid |
| Int. 89 | 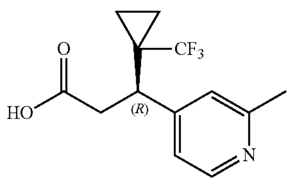 | 274.1 (M + H) | (3R)-3-(2-methylpyridin-4-yl)-3-[1-(trifluoromethyl)cyclopropyl]propanoic acid |
| Int. 90 | 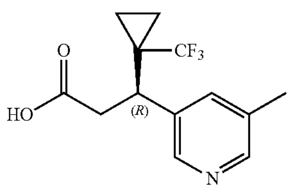 | 274.1 (M + H) | (3R)-3-(5-methylpyridin-3-yl)-3-[1-(trifluoromethyl)cyclopropyl]propanoic acid |
| Int. 91 | 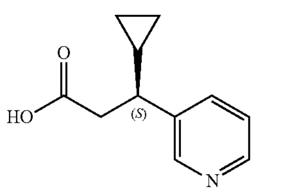 | 192.1 (M + H) | (3S)-3-cyclopropyl-3-(pyridin-3-yl)propanoic acid |
| Int. 93 | 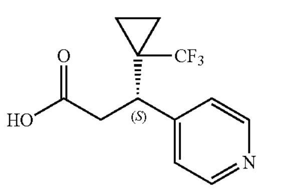 | 260.1 (M + H) | (3S)-3-(pyridin-4-yl)-3-[1-(trifluoromethyl)cyclopropyl]propanoic acid |
| Int. 98 | 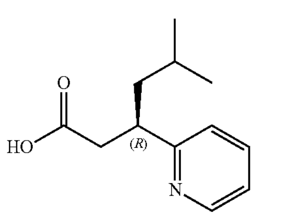 | 208.2 (M + H) | (R)-5-methyl-3-(pyridin-2-yl)hexanoic acid |

-continued

| Intermediate (Int.) No. | Structure | LC/MS (m/z) | Name |
|---|---|---|---|
| Int. 100 | 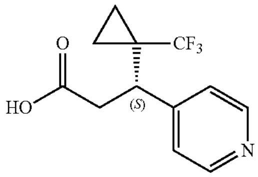 | 260.2 (M + H) | (S)-3-(pyridin-4-yl)-3-(1-(trifluoromethyl)cyclopropyl)propanoic acid |
| Int. 101 | 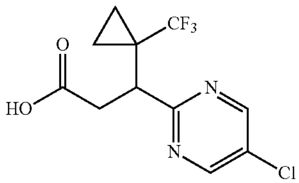 [SMILES: O=C(O)CC(c1ncc(Cl)cn1)C1(C(F)(F)F)CC1] | 294.2 (M + H) | 3-(5-chloropyrimidin-2-yl)-3-(1-(trifluoromethyl)cyclopropyl)propanoic acid |
| Int. 103 | 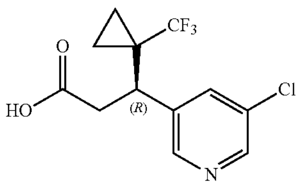 | 294.2 (M + H) | (R)-3-(5-chloropyridin-3-yl)-3-(1-(trifluoromethyl)cyclopropyl)propanoic acid |
| Int. 104 | 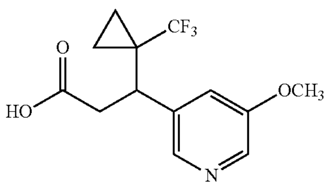 [SMILES: COc1cncc(C(CC(=O)O)C2(C(F)(F)F)CC2)c1] | 290.2 (M + H) | 3-(5-methoxypyridin-3-yl)-3-(1-(trifluoromethyl)cyclopropyl)propanoic acid |
| Int. 105 | 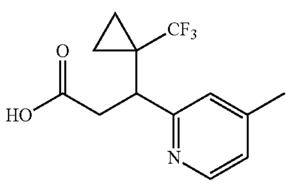 [SMILES: Cc1ccnc(C(CC(=O)O)C2(C(F)(F)F)CC2)c1] | 274.2 (M + H) | 3-(4-methylpyridin-2-yl)-3-(1-(trifluoromethyl)cyclopropyl)propanoic acid |
| Int. 106 | 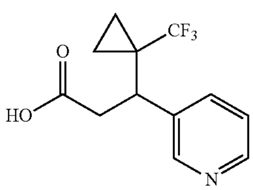 [SMILES: O=C(O)CC(c1cccnc1)C1(C(F)(F)F)CC1] | 260.2 (M + H) | 3-(pyridin-3-yl)-3-(1-(trifluoromethyl)cyclopropyl)propanoic acid |
| Int. 107 | 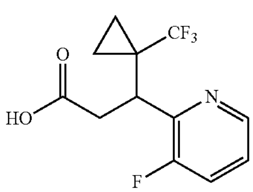 [SMILES: O=C(O)CC(c1ncccc1F)C1(C(F)(F)F)CC1] | 278.2 (M + H) | 3-(3-fluoropyridin-2-yl)-3-(1-(trifluoromethyl)cyclopropyl)propanoic acid |
| Int. 108 | 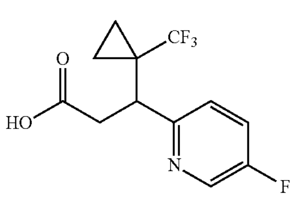 [SMILES: O=C(O)CC(c1ccc(F)cn1)C1(C(F)(F)F)CC1] | 278.2 (M + H) | 3-(5-fluoropyridin-2-yl)-3-(1-(trifluoromethyl)cyclopropyl)propanoic acid |

-continued

| Intermediate (Int.) No. | Structure | LC/MS (m/z) | Name |
|---|---|---|---|
| Int. 109 | 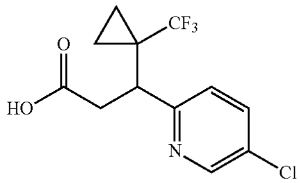 [SMILES: O=C(O)CC(c1ccc(Cl)cn1)C1(C(F)(F)F)CC1] | 294.2 (M + H) | 3-(5-chloropyridin-2-yl)-3-(1-(trifluoromethyl)cyclopropyl)propanoic acid |
| Int. 113 | 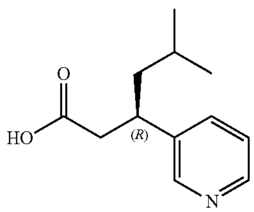 | 208.2 (M + H) | (R)-5-methyl-3-(pyridin-3-yl)hexanoic acid |
| Int. 114 | 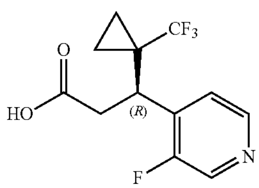 | 278.2 (M + H) | (R)-5-methyl-3-(pyridin-3-yl)hexanoic acid |
| Int. 115 | 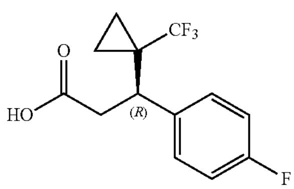 | 277.2 (M + H) | ((R)-3-(4-fluorophenyl)-3-(1-(trifluoromethyl)cyclopropyl)propanoic acid |
| Int. 116 | 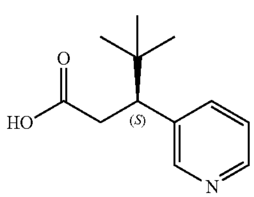 | 208.2 (M + H) | (S)-4,4-dimethyl-3-(pyridin-3-yl)pentanoic acid |
| Int. 117 | 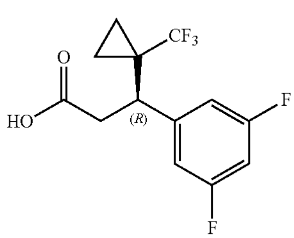 | 295.2 (M + H) | (R)-3-(3,5-difluorophenyl)-3-(1-(trifluoromethyl)cyclopropyl)propanoic acid |
| Int. 118 | 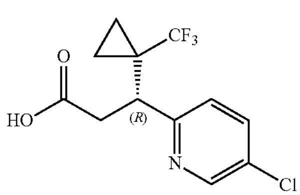 | 294.2 (M + H) | (R)-3-(5-chloropyridin-2-yl)-3-(1-(trifluoromethyl)cyclopropyl)propanoic acid |

-continued

| Intermediate (Int.) No. | Structure | LC/MS (m/z) | Name |
|---|---|---|---|
| Int. 119 | 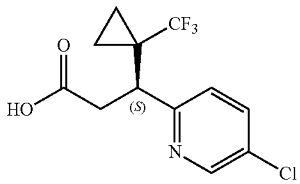 | 294.2 (M + H) | (S)-3-(5-chloropyridin-2-yl)-3-(1-(trifluoromethyl)cyclopropyl)propanoic acid |
| Int. 121 | 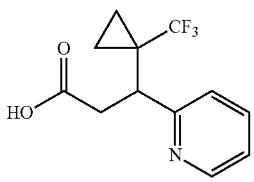 [SMILES: O=C(O)CC(c1ccccn1)C1(C(F)(F)F)CC1] | 260.2 (M + H) | 3-(pyridin-2-yl)-3-(1-(trifluoromethyl)cyclopropyl)propanoic acid |
| Int. 130 | 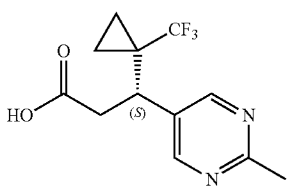 | 303.1 (M + H) | (S)-3-(2-methylpyrimidin-5-yl)-3-(1-(trifluoromethyl)cyclopropyl)propanoic acid |
| Int. 145 | 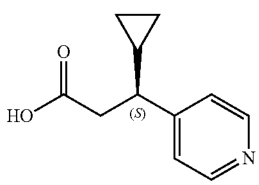 | 192.2 (M + H) | (S)-3-cyclopropyl-3-(pyridin-4-yl)propanoic acid |
| Int. 146 | 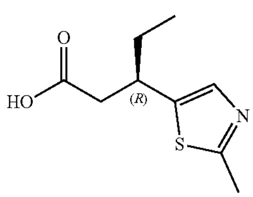 | 200.1 (M + H) | (R)-3-(2-methylthiazol-5-yl)pentanoic acid |
| Int. 147 | 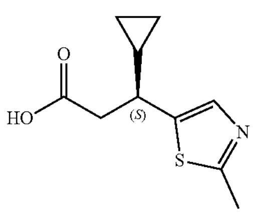 | 212.2 (M + H) | (S)-3-cyclopropyl-3-(2-methylthiazol-5-yl)propanoic acid |
| Int. 148 | 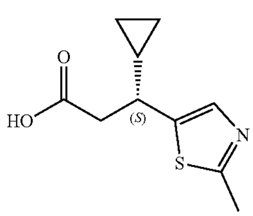 | 212.2 (M + H) | (R)-3-cyclopropyl-3-(2-methylthiazol-5-yl)propanoic acid |

-continued

| Intermediate (Int.) No. | Structure | LC/MS (m/z) | Name |
|---|---|---|---|
| Int. 149 | 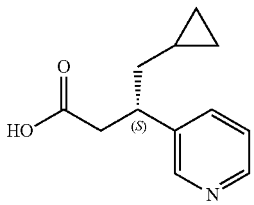 | 206.1 (M + H) | (3S)-4-cyclopropyl-3-(pyridin-3-yl)butanoic acid |
| Int. 150 | 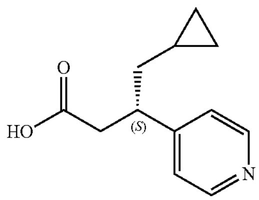 | 206.1 (M + H) | (S)-4-cyclopropyl-3-(pyridin-4-yl)butanoic acid |
| Int. 151 | 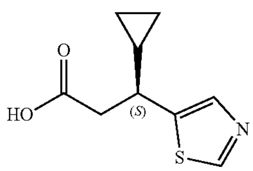 | 198.1 (M + H) | (3S)-3-cyclopropyl-3-(1,3-thiazol-5-yl)propanoic acid |
| Int. 152 | 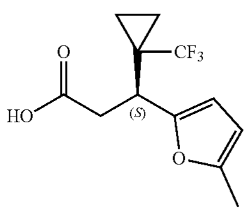 | 263.1 (M + H) | (S)-3-(5-methylfuran-2-yl)-3-(1-(trifluoromethyl)cyclopropyl)propanoic acid |

Example A7: Preparation of 2-(pyrimidin-2-yl)cyclopropane-1-carboxylic acid (7D, "Intermediate 7")

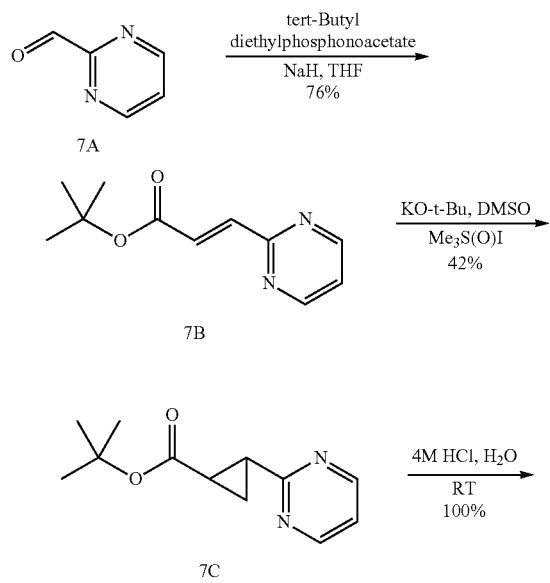

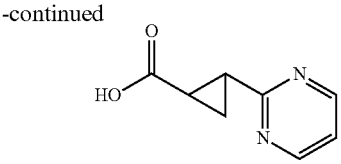

Preparation of tert-butyl (2E)-3-(pyrimidin-2-yl)prop-2-enoate (7B). To a stirred suspension of NaH (1.69 g, 42.2 mmol) in THF (50 mL) at 0° C. was added tert-butyl-2-(diethoxyphosphoryl)acetate (9.75 g, 38.7 mmol) dropwise. After the addition was completed, the reaction mixture was stirred at 0° C. for 30 minutes. Then pyrimidine-2-carbaldehyde (3.8 g, 35.2 mmol) was added and continued to stir at RT for 2 h. The reaction was diluted with EtOAc and quenched with saturated NH$_4$Cl. The organic layer was separated, dried over MgSO$_4$, concentrated and purified by flash chromatography (0-60% EtOAc/Hexanes) to give 7B, tert-butyl (2E)-3-(pyrimidin-2-yl)prop-2-enoate (5.5 g, 75.9%). MS (m/z): 207.1 (M+H).

Preparation of tert-butyl 2-(pyrimidin-2-yl)cyclopropane-1-carboxylate (7C). To a stirred solution of trimethylsulfoxonium iodide (3.07 g, 14.0 mmol) in DMSO (20 mL) was added KOt-Bu in single portion. The stirring was continued in 30 minutes, then tert-butyl (2E)-3-(pyrimidin-2-yl)prop-2-enoate (2.40 g, 11.6 mmol) was added also in single portion. The reaction mixture was stirred at RT for 2 h. Saturated aqueous NH₄Cl was added, extracted with EtOAc (3×). The extracts were dried over MgSO₄, concentrated, and purified by flash chromatography (040% EtOAc/Hexanes) to give tert-butyl 2-(pyrimidin-2-yl)cyclopropane-1-carboxylate (1.1 g, 42.9%). MS (m/z): 221.2 (M+H).

Preparation of 2-(pyrimidin-2-yl)cyclopropane-1-carboxylic acid (7D). A solution of tert-butyl 2-(pyrimidin-2-yl)cyclopropane-1-carboxylate (1.1 g, 4.99 mmol) in 4M HCl (10 mL) and H₂O (0.3 mL) was stirred at RT for 3 h. The mixture was concentrated to dryness to give 2-(pyrimidin-2-yl)cyclopropane-1-carboxylic acid hydrochloride salt (1.2 g, 100%). MS (m/z): 165.1 (M+H).

Example A8: Preparation of (S)-3-cyclopropyl-3-phenylpropanoic acid (8D, "Intermediate 8")

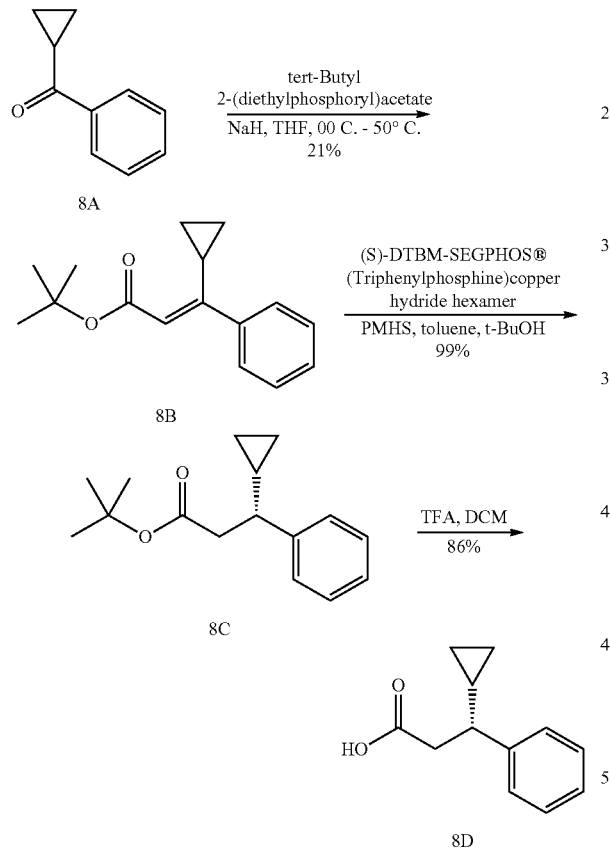

Preparation of tert-butyl (2E)-3-cyclopropyl-3-phenyl-prop-2-enoate (8B). To a stirred suspension of NaH (60%, 2.05 g, 51.3 mmol) in THF (50 mL) at 0° C. was added tert-butyl 2-(diethoxyphosphoryl)acetate (12 mL, 51.3 mmol). After the addition, the mixture was stirred for 30 minutes, cyclopropyl(phenyl)methanone (5 g, 34.2 mmol) was added and the reaction mixture was stirred at 50° C. for 16 h. The mixture was cooled to RT, saturated NH₄Cl was added, extracted with EtOAc (3×). The combined extracts were washed with H₂O, brine, dried over MgSO₄, concentrated, and purified by flash chromatography (0-20% MTBE/hexanes) to give tert-butyl (2E)-3-cyclopropyl-3-phenyl-prop-2-enoate (1.76 g, 21%).

Preparation of tert-butyl (3R)-3-cyclopropyl-3-phenyl-propanoate (8C). To a stirred mixture of (S)-DTBM-SEG-PHOS® (164 mg, 6.96 mmol) and (Triphenylphosphine)copper hydride hexamer (95.5 mg, 0.139 mmol) in toluene (8 mL) at 0 C was added PMHS (1.6 g, 139 mmol), followed by t-BuOH (567 mg, 7.76 mmol), and a solution of tert-butyl (2E)-3-cyclopropyl-3-phenylprop-2-enoate (1.7 g, 6.96 mmol) in toluene (5 mL) dropwise. The mixture was then stirred at 0° C. in 16 h. LC/MS showed only 50% conversion. The same amount of catalyst and solvent was added this time and gradually warmed to RT. After the second addition was completed, the reaction mixture was stirred for 4 h. saturated NH₄Cl was added slowly and stirred for 1 h. extracted with EtOAc (3×). The combined extracts were dried over MgSO₄, filtered, concentrated, and purified by flash chromatography (0-20% EtOAc/Hexanes) to give tert-butyl (3R)-3-cyclopropyl-3-phenylpropanoate (1.7 g, 99%). MS (m/z): 247.1 (M+H).

Preparation of (3R)-3-cyclopropyl-3-phenylpropanoic acid (8D). To the stirred solution of tert-butyl (3R)-3-cyclopropyl-3-phenylpropanoate (1.7 g, 6.9 mmol) in DCM (10 mL) was added TFA (7.9 g, 69.6 mmol). The stirring was continued for 4 h. The mixture was concentrated to dryness to give (3R)-3-cyclopropyl-3-phenylpropanoic acid (1.15 g, 86%).

Example A9: Preparation of (3S)-4-cyclobutyl-3-phenylbutanoic acid (57C, "Intermediate 57")

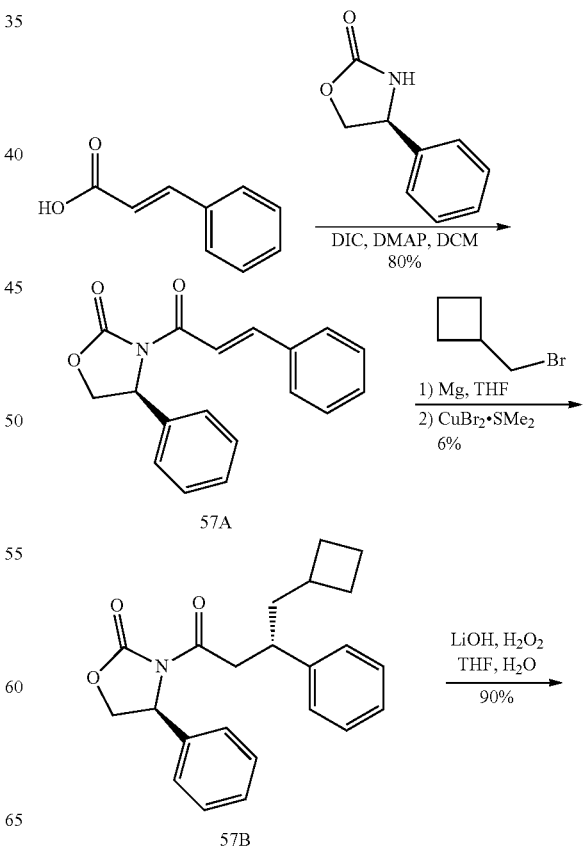

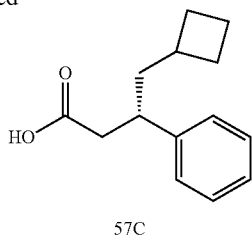

57C

Preparation of (4S)-4-phenyl-3-[(2E)-3-phenylprop-2-enoyl]-1,3-oxazolidin-2-one (57A). To a stirred mixture of (2E)-3-phenylprop-2-enoic acid (5 g, 33.7 mmol), DMAP (412 mg, 3.37 mmol), and (S)-4-phenyloxazolidin-2-one (5.5 g, 33.7 mmol) in DCM (80 mL) was added N,N'-Diisopropylcarbodiimide (6.39 g, 50.6 mmol) dropwise at 0° C. The stirring was continued for 16 h, the precipitated solid was filtered off. The filtrate was washed with 2N HCl, saturated NaHCO₃, brine, dried over Na₂SO₄, concentrated to dryness. The crude product was triturated in i-PrOH. The precipitated solid was collected, dried to give (4S)-4-phenyl-3-[(2E)-3-phenylprop-2-enoyl]-1,3-oxazolidin-2-one (8.01 g, 80.9%). MS (m/z): 294.2 (M+H).

Preparation of (4S)-3-[(3S)-4-cyclobutyl-3-phenylbutanoyl]-4-phenyl-1,3-oxazolidin-2-one (57B). To a 2 neck RBF, stirred suspension of Mg (1.1 g, 45.1 mmol) in THF (20 mL) equipped with condenser was added iodine (382 mg, 1.5 mmol). After the addition was completed, the mixture was stirred for 10 minutes, then (bromomethyl)cyclobutane (2.69 g, 18 mmol), then another iodine (382 mg, 1.5 mmol). The stirring was continued for 1 h. The mixture was then added dropwise to a stirred partial suspension of Copper(I) bromide dimethyl sulfide (4.02 g, 19.5 mmol) in THF (20 mL) at −40° C. After the addition, the mixture was stirred for 1 h at −40° C. Finally, the solution of (4S)-4-phenyl-3-[(2E)-3-phenylprop-2-enoyl]-1,3-oxazolidin-2-one (4.41 g, 15 mmol) in THF (40 mL) was added dropwise from dropping funnel to the stirring mixture at −40° C. After the addition was completed, the reaction mixture was stirred at −40° C. in 1 h, then gradually warmed to RT and stirred overnight. Saturated aq. NH₄Cl was added and stirred for 15 minutes, extracted with EtOAc (3×). The combined extracted was dried over MgSO₄, concentrated, and purified by flash chromatography (0-20% EtOAc/Hexanes) to give (4S)-3-[(3S)-4-cyclobutyl-3-phenylbutanoyl]-4-phenyl-1,3-oxazolidin-2-one (354 mg, 6.5%). MS (m/z): 364.2 (M+H).

Preparation of (3S)-4-cyclobutyl-3-phenylbutanoic acid (57C). To a stirred solution of (4S)-3-[(3S)-4-cyclobutyl-3-phenylbutanoyl]-4-phenyl-1,3-oxazolidin-2-one (1.20 g, 3.30 mmol) in THF (20 mL) was added lithium hydroxide monohydrate (2.64 mL, 1.6 eq., 5.28 mmol), followed by H₂O₂ (1.51 mL, 4 eq., 13.2 mmol). After the addition was completed, the reaction mixture was stirred at rt for 3 h. diluted with MTBE and water, and the layers were separated. The aqueous layer was cooled in an ice bath, acidified with 2N HCl, extracted with DCM (3×). The combined extracts were dried over Na₂SO₄, concentrated, and purified by flash chromatography (0-50% EtOAc/DCM) to give (3S)-4-cyclobutyl-3-phenylbutanoic acid (650 mg, 90%).

The following intermediates were synthesized in analogous methods to those described in Example A9: Int. 57 & General Scheme VI:

| Intermediate (Int.) No. | Structure | LC/MS (m/z) | Name |
|---|---|---|---|
| Int. 60 | 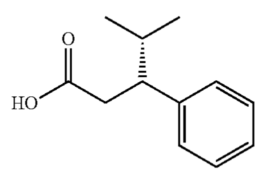 | 193.2 (M + H) | (R)-4-methyl-3-phenylpentanoic acid |
| Int. 61 | 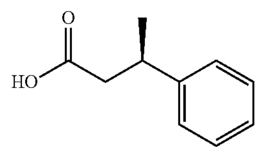 | 165.1 (M + H) | (R)-3-phenylbutanoic acid |
| Int. 62 | 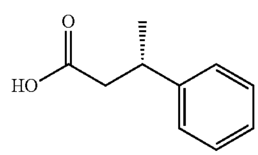 | 165.1 (M + H) | (S)-3-phenylbutanoic acid |
| Int. 63 | 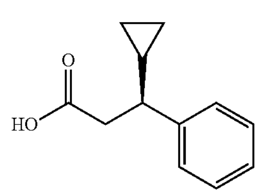 [SMILES: O=C(O)C[C@H](c1ccccc1)C1CC1] | 191.2 (M + H) | (S)-3-cyclopropyl-3-phenylpropanoic acid |

-continued

| Intermediate (Int.) No. | Structure | LC/MS (m/z) | Name |
|---|---|---|---|
| Int. 64 | 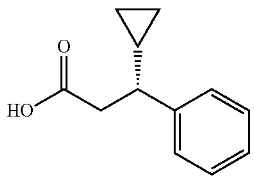 [SMILES: O=C(O)C[C@@H](c1ccccc1)C1CC1] | 191.2 (M + H) | (R)-3-cyclopropyl-3-phenylpropanoic acid |
| Int. 65 | 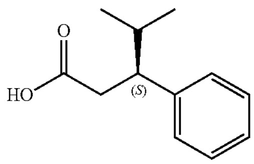 | 193.2 (M + H) | (S)-4-methyl-3-phenylpentanoic acid |
| Int. 66 | 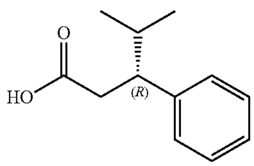 | 193.2 (M + H) | (R)-4-methyl-3-phenylpentanoic acid |
| Int. 67 | 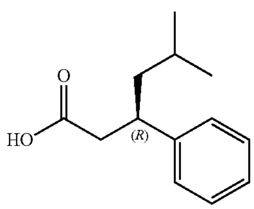 | 207.2 (M + H) | (R)-5-methyl-3-phenylhexanoic acid |
| Int. 68 | 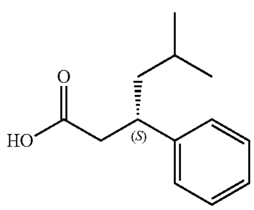 | 207.2 (M + H) | (S)-5-methyl-3-phenylhexanoic acid |
| Int. 69 | 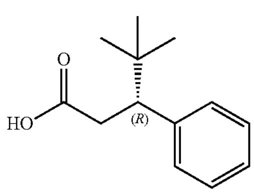 | 207.2 (M + H) | (R)-4,4-dimethyl-3-phenylpentanoic acid |
| Int. 70 | 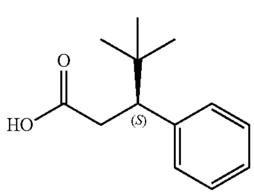 | 207.2 (M + H) | (S)-4,4-dimethyl-3-phenylpentanoic acid |
| Int. 120 | 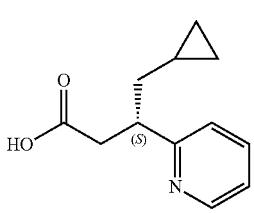 | 206.2 (M + H) | (S)-4-cyclopropyl-3-(pyridin-2-yl)butanoic acid |

-continued
| Intermediate (Int.) No. | Structure | LC/MS (m/z) | Name |
|---|---|---|---|
| Int. 124 | 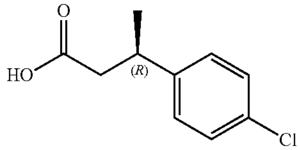 | 199.1 (M + H) | (R)-3-(4-chlorophenyl)butanoic acid |
| Int. 125 | 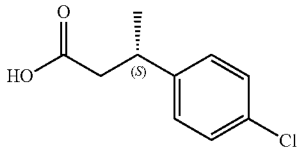 | 199.1 (M + H) | (S)-3-(4-chlorophenyl)butanoic acid |
| Int. 126 | 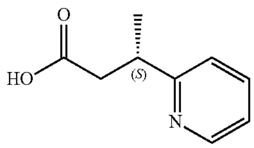 | 166.1 (M + H) | (S)-3-(4-chlorophenyl)butanoic acid |
| Int. 127 | 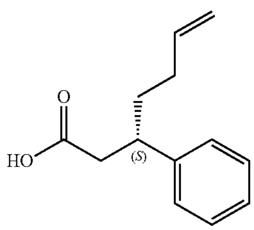 | 205.2 (M + H) | (S)-3-phenylhept-6-enoic acid |
| Int. 132 | 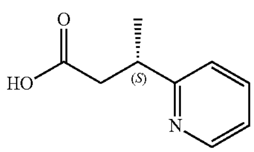 | 166.1 (M + H) | (S)-3-(pyridin-2-yl)butanoic acid |
Example A10: [(2S)-1-amino-3-(2-methoxyquinolin-6-yl)propan-2-yl]dimethylamine (58H, "Intermediate 58")
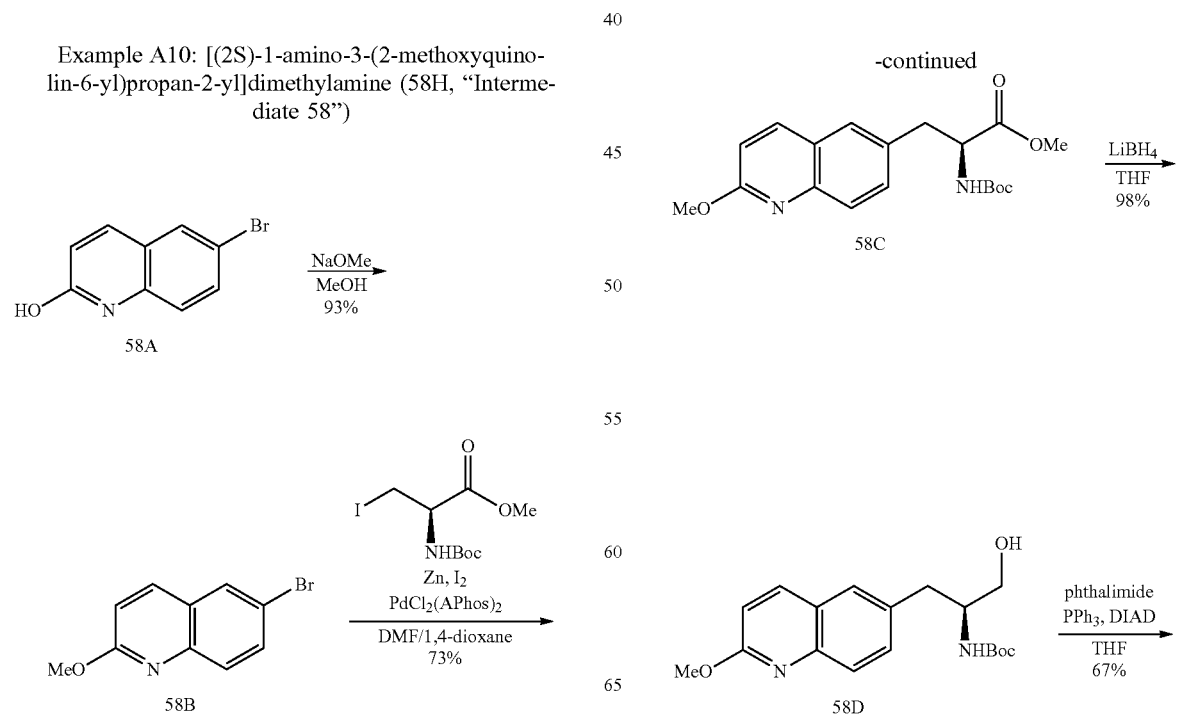

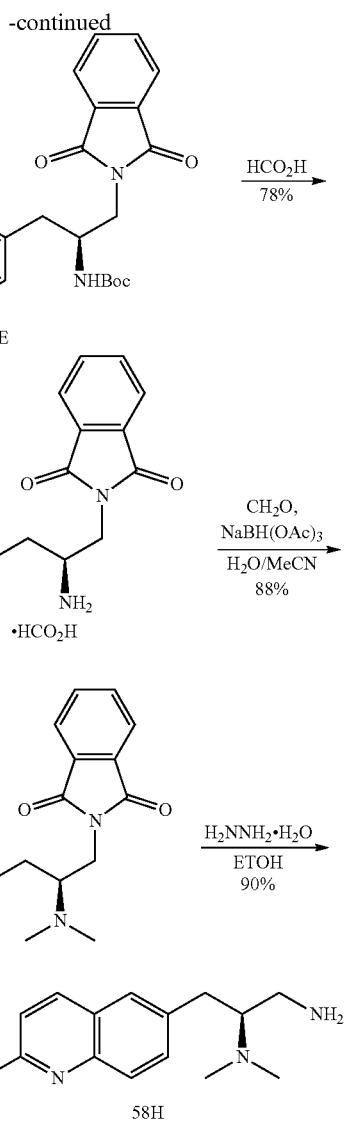

Preparation of 6-bromo-2-methoxyquinoline (58B): A mixture of 6-bromo-2-chloroquinoline (5.00 g, 20.6 mmol) and Sodium methoxide (1.34 g, 1.2 eq., 24.7 mmol) in MeOH (50 mL) was heated at reflux for 24 h. The reaction mixture was cooled to RT, poured onto ice water beaker. The precipitated solid was collected, washed with H₂O, dried to give the title compound (4.5 g, 92%), and used in the next step.

Preparation of methyl (2S)-2-{[(tert-butoxy)carbonyl]amino}-3-(2-methoxyquinolin-6-yl)propanoate (58C). Step 1: To a stirred suspension of zinc (3.71 g, 3 eq., 56.7 mmol) in DMF (20 mL) was added iodine (480 mg, 0.1 eq., 1.89 mmol). The stirring was continued for 15 minutes until all became clear color, then methyl (2R)-2-{1[(tert-butoxy)carbonyl]amino}-3-iodopropanoate (7.47 g, 1.2 eq., 22.7 mmol) was added in single portions, followed by another iodine (480 mg, 0.1 eq., 1.89 mmol). The mixture became warmed and was continued to stir for 1 h at RT. Step 2: The mixture from the Step 1 was added onto a stirred mixture of 6-bromo-2-methoxyquinoline (4.50 g, 18.9 mmol), S-Phos (543 mg, 0.07 eq., 1.32 mmol), and Pd₂(dba)₃ (519 mg, 0.03 eq., 567 μmol) in DMF (20 mL). After the addition was completed, the reaction mixture was degassed for 5 minutes, then heated to 70° C. in 24 h. The reaction mixture was cooled to RT, saturated NH₄Cl was added, stirred for 15 minutes, diluted with EtOAc. The layers were separated. The aqueous layer was extracted with EtOAc (2×). The combined extracts were dried over MgSO₄, concentrated and purified by flash chromatography (0-30% EtOAc Hexanes) to give methyl (2S)-2-{[(tert-butoxy)carbonyl]amino}-3-(2-methoxyquinolin-6-yl)propanoate (2.50 g, 36%).

Preparation of tert-butyl N-[(2S)-1-hydroxy-3-(2-methoxyquinolin-6-yl)propan-2-yl]carbamate (58D). To a stirred solution of methyl (2S)-2-{[(tert-butoxy)carbonyl]amino}-3-(2-methoxyquinolin-6-yl)propanoate (2.50 g, 6.94 mmol) in THF (20 mL) at 0° C. was added Lithium borohydride (2.60 mL, 1.5 eq., 10.4 mmol) dropwise. After the addition was completed, the reaction mixture was stirred at 0° C. for 1 h, then RT for 2 h. The reaction mixture was cooled in an ice bath and slowly quenched with saturated NH₄Cl, extracted with EtOAc (3×). The combined extracts were dried over MgSO₄, concentrated to give tert-butyl N-[(2S)-1-hydroxy-3-(2-methoxyquinolin-6-yl)propan-2-yl]carbamate (2.01 g, 87%) and used in the next step.

Preparation of tert-butyl N-[(2S)-1-(1,3-dioxo-2,3-dihydro-1H-isoindol-2-yl)-3-(2-methoxyquinolin-6-yl)propan-2-yl]carbamate (58E). To a stirred mixture of tert-butyl N-[(2S)-1-hydroxy-3-(2-methoxyquinolin-6-yl)propan-2-yl]carbamate (1.99 g, 5.99 mmol), triphenylphosphine (1.88 g, 1.2 eq., 7.18 mmol), and phthalimide (1.06 g, 1.2 eq., 7.18 mmol) in THF (30 mL) at 00C was added DIAD (1.42 mL, 1.2 eq., 7.18 mmol) dropwise. After the addition was completed, the reaction mixture was stirred at RT in 16 h. The mixture was concentrated to dryness, and purified by flash chromatography (40% EtOAc/Hexanes) to give tert-butyl N-[(2S)-1-(1,3-dioxo-2,3-dihydro-1H-isoindol-2-yl)-3-(2-methoxyquinolin-6-yl)propan-2-yl]carbamate (1.50 g, 54%). MS (m/z): 462.2.

Preparation of 2-[(2S)-2-amino-3-(2-methoxyquinolin-6-yl)propyl]-2,3-dihydro-1H-isoindole-1,3-dione (58F). A solution of tert-butyl N-[(2S)-1-(1,3-dioxo-2,3-dihydro-1H-isoindol-2-yl)-3-(2-methoxyquinolin-6-yl)propan-2-yl]carbamate (1.50 g, 3.25 mmol) in formic acid (20 mL) was stirred at RT in 16 h. The reaction mixture was concentrated to dryness to give the title compound (1.1 g, 100%), and used in the next step. MS (m/z): 362.1 (M+H).

Preparation of 2-[(2S)-2-(dimethylamino)-3-(2-methoxyquinolin-6-yl)propyl]-2,3-dihydro-1H-isoindole-1,3-dione (58G). To a stirred solution of 2-[(2S)-2-amino-3-(2-methoxyquinolin-6-yl)propyl]-2,3-dihydro-1H-isoindole-1,3-dione (2.00 g, 5.53 mmol) in MeCN/H₂O (5:1, 24 mL) was added formaldehyde (1.28 mL, 3 eq., 16.6 mmol). The stirring was continued for 30 minutes, followed by sodium cyanoborohydride (696 mg, 2 eq., 11.1 mmol). After the addition was completed, the reaction mixture was stirred at rt for 1 h. saturated NaHCO₃ was added to adjusted to PH=7-8, extracted with EtOAc (3×). The combined extracts were dried over MgSO₄, concentrated to dryness to give the title compound (2 g, 92%), and used in the next step. MS (m/z): 390.1 (M+H).

Preparation of [(2S)-1-amino-3-(2-methoxyquinolin-6-yl)propan-2-yl]dimethylamine (58H). To a stirred solution of 2-[(2S)-2-(dimethylamino)-3-(2-methoxyquinolin-6-yl)propyl]-2,3-dihydro-1H-isoindole-1,3-dione (2.00 g, 5.14 mmol) in EtOH (20 mL) was added hydrazine (1.57 mL, 5 eq., 25.7 mmol). The reaction mixture was then heated to 80° C. in 2 h. cooled to RT, diluted with EtOAc. The precipitated solid was filtered off and the filtrate was concentrated and purified by flash chromatography (0-15%

MeOH/DCM in 1% NH₄OH) to give [(2S)-1-amino-3-(2-methoxyquinolin-6-yl)propan-2-yl]dimethylamine (180 mg, 14%). MS (m/z): 260.2 (M+H).

Example A11: Preparation of 6-[(2S)-3-amino-2-(dimethylamino)propyl]-3-{[2-(trimethylsilyl)ethoxy]methyl}-2,3-dihydro-1,3-benzoxazol-2-one (75G, "Intermediate 75")

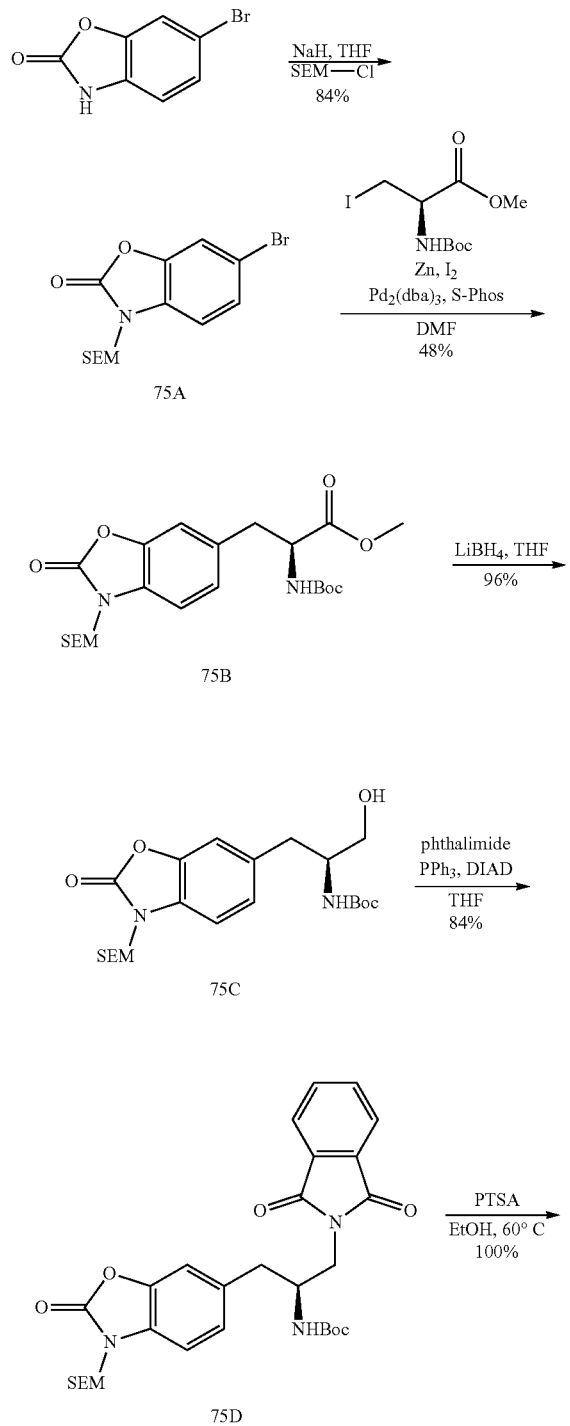

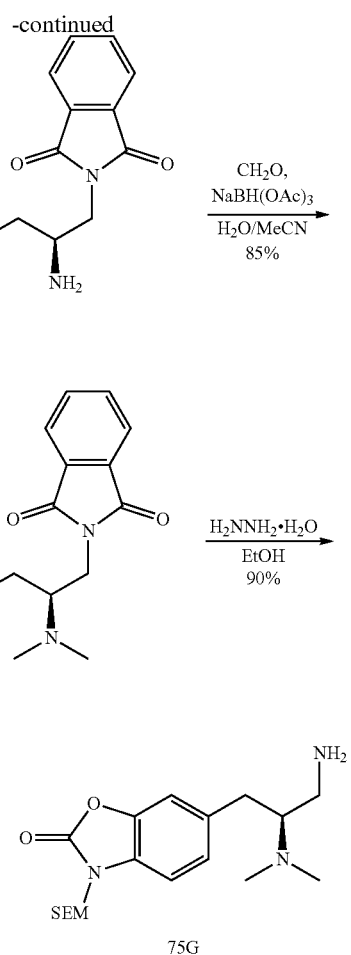

Preparation of 6-bromo-3-((2-(trimethylsilyl)ethoxy)methyl)benzo[d]oxazol-2(3H)-one (75A): To a stirred suspension of NaH (0.45 g, 11.21 mmol) in DMF (20 mL) was added 6-bromobenzo[d]oxazol-2(3H)-one (2 g, 9.34 mmol). After the addition was completed, the mixture was stirred at RT for 30 minutes, then SEM-Cl was added dropwise. The reaction mixture was then stirred at RT for 16 h. Saturated NH₄Cl was added, extracted with EtOAc (3×). The combined extracts were dried over Na₂SO₄, filtered, concentrated, and purified by flash chromatography (0-30% EtOAc/Hexanes) to give the title compound (7.85 g, 84%). MS (m/z): 345.1 (M+H).

Preparation of methyl (S)-2-((tert-butoxycarbonyl)amino)-3-(2-oxo-3-((2-(trimethylsilyl)ethoxy)methyl)-2,3-dihydrobenzo[d]oxazol-6-yl)propanoate (75B). The title compound (5.0 g, 48%) was prepared in the same method as described in Intermediate 1, Step 1. MS (m/z): 489.3 (M+Na).

Preparation of tert-butyl (S)-(1-hydroxy-3-(2-oxo-3-((2-(trimethylsilyl)ethoxy)methyl)-2,3-dihydrobenzo[d]oxazol-6-yl)propan-2-yl)carbamate (75C). The title compound (3.0 g, 96%) was prepared in the same method as described in Intermediate 1, Step 2. MS (m/z): 461.2 (M+Na).

Preparation of tert-butyl N-[(2S)-1-(1,3-dioxo-2,3-dihydro-1H-isoindol-2-yl)-3-(2-oxo-3-{[2-(trimethylsilyl)ethoxy]methyl}-2,3-dihydro-1,3-benzoxazol-6-yl)propan-2-yl]carbamate (75D). The title compound (3.3 g, 84%) was prepared in the same method as described in Intermediate 1, Step 3. MS (m/z): 568.2 (M+H).

Preparation of 2-[(2S)-2-amino-3-(2-oxo-3-{[2-(trimethylsilyl)ethoxy]methyl}-2,3-dihydro-1,3-benzoxazol-6-yl)propyl]-2,3-dihydro-1H-isoindole-1,3-dione (75E). A mixture of tert-butyl N-[(2S)-1-(1,3-dioxo-2,3-dihydro-1H-isoindol-2-yl)-3-(2-oxo-3-{[2-(trimethylsilyl)ethoxy]methyl}-2,3-dihydro-1,3-benzoxazol-6-yl)propan-2-yl]carbamate (2.05 g, 3.61 mmol) and 4-methylbenzene-1-sulfonic acid hydrate (756 mg, 1.1 eq., 3.97 mmol) in EtOH (40 ml) was heated at 60° C. in 2 h. The mixture was cooled to RT, concentrated to dryness to give 2-[(2S)-2-amino-3-(2-oxo-3-{[2-(trimethylsilyl)ethoxy]methyl}-2,3-dihydro-1,3-benzoxazol-6-yl)propyl]-2,3-dihydro-1H-isoindole-1,3-dione (2.30 g, 100%) as PTSA salt.

Preparation of 2-[(2S)-2-(dimethylamino)-3-(2-oxo-3-{[2-(trimethylsilyl)ethoxy]methyl}-2,3-dihydro-1,3-benzoxazol-6-yl)propyl]-2,3-dihydro-1H-isoindole-1,3-dione (75F). To a stirred solution of 2-[(2S)-2-amino-3-(2-oxo-3-{[2-(trimethylsilyl)ethoxy]methyl}-2,3-dihydro-1,3-benzoxazol-6-yl)propyl]-2,3-dihydro-1H-isoindole-1,3-dione (2.1 g, 4.49 mmol) in MeCN/H$_2$O (10:1, 22 mL) was added acetic acid (0.809 g, 13.5 mmol), formaldehyde (0.405 mL, 13.5 mmol). The mixture was stirred for 30 minutes, sodium cyanoborohydride (0.423 g, 6.74 mmol) was added. After the addition was completed, the reaction mixture was stirred for 30 minutes. Saturated aqueous NH$_4$CL was added, extracted with EtOAc (3×). The combined extracts were dried over MgSO$_4$, concentrated to give 2-[(2S)-2-(dimethylamino)-3-(2-oxo-3-{[2-(trimethylsilyl)ethoxy]methyl}-2,3-dihydro-1,3-benzoxazol-6-yl)propyl]-2,3-dihydro-1H-isoindole-1,3-dione (1.9 g, 85.3%). MS (m/z): 496.2 (M+H).

Preparation of 6-[(2S)-3-amino-2-(dimethylamino)propyl]-3-{[2-(trimethylsilyl)ethoxy]methyl}-2,3-dihydro-1,3-benzoxazol-2-one (75G). A mixture of 2-[(2S)-2-(dimethylamino)-3-(2-oxo-3-{[2-(trimethylsilyl)ethoxy]methyl}-2,3-dihydro-1,3-benzoxazol-6-yl)propyl]-2,3-dihydro-1H-isoindole-1,3-dione (380 mg, 0.767 mmol) and hydrazine (246 mg, 3.83 mmol) in EtOH (4 mL) was heated to 70° C. in 2 h. The reaction mixture was cooled to RT. Silica gel was added, concentrated to dryness, and dried loaded and purified by flash chromatography (0-25% MeOH/DCM in 1% NH$_4$OH) to give the title compound (1.15 g, 50%). MS (m/z): 366.3 (M+H).

The following intermediates were synthesized in analogous methods to those described in Example A11: Int. 77:

Example A12: Preparation of (S)-5-(3-amino-2-(dimethylamino)propyl)-4-methylindolin-2-one (78F, "Intermediate 78")

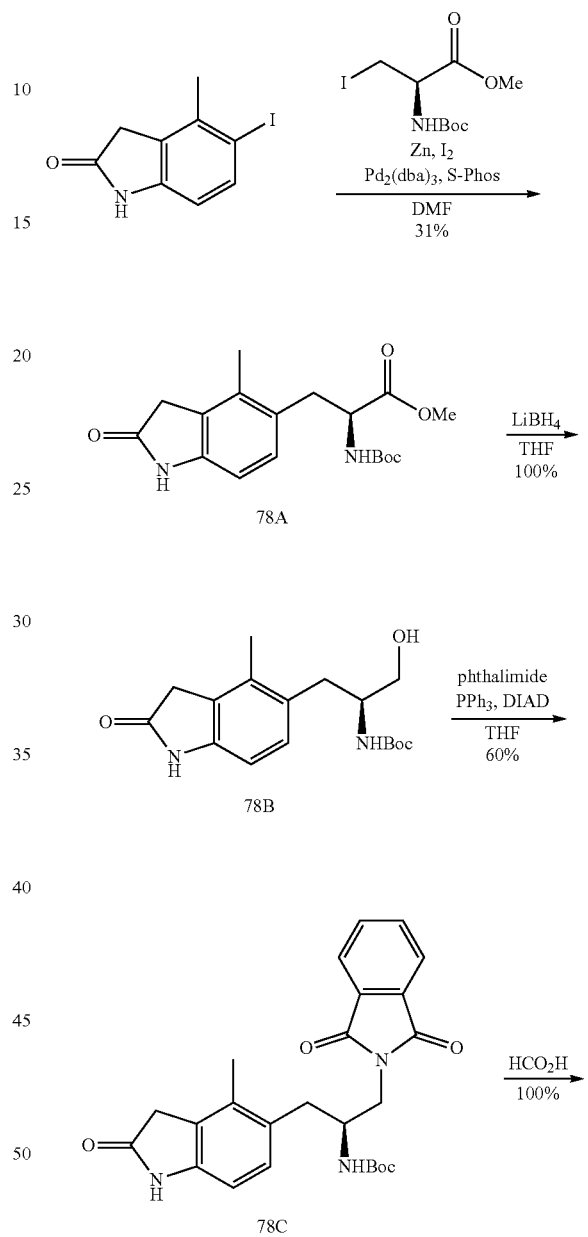

| Intermediate (Int.) No. | Structure | LC/MS (m/z) | Name |
|---|---|---|---|
| Int. 76 | 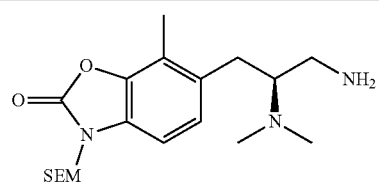 [SMILES: Cc1c(C[C@@H](CN)N(C)C)ccc2c1oc(=O)n2COCC[Si](C)(C)C] | 380.2 (M + H) | (S)-6-(3-amino-2-(dimethylamino)propyl-7-methyl-3-((2-(trimethylsilyl)ethoxy)methyl)benzo[d]oxazol-2(3H)-one |

-continued

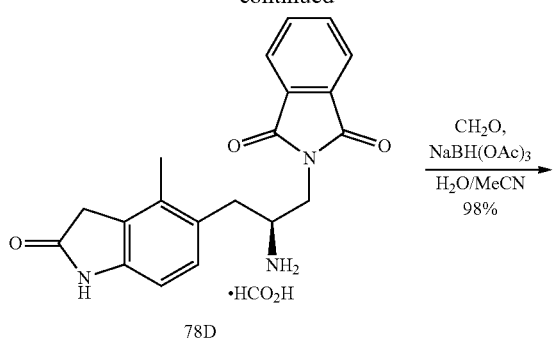

78D

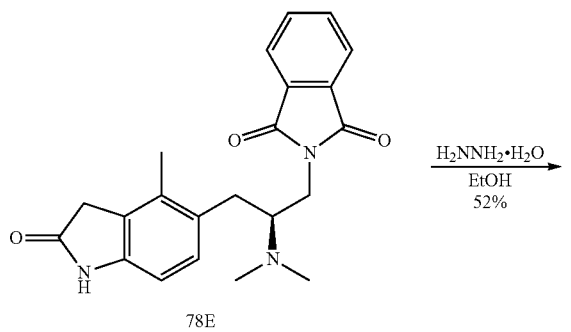

78E

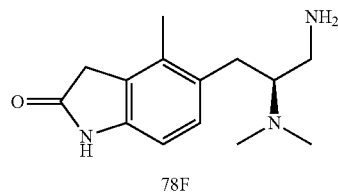 [SMILES: Cc1c(C[C@@H](CN)N(C)C)ccc2c1CC(=O)N2]

78F

Preparation of methyl (2S)-2-{[(tert-butoxy)carbonyl]amino}-3-(4-methyl-2-oxo-2,3-dihydro-1H-indol-5-yl)propanoate (78A): Step 1: To a stirred suspension of Zinc dust (1.4 g, 21.4 mmol), 3 eq) in DMF (20 mL) was added iodine (310 mg, 0.1 eq., 1.2 mmol) After stirring for 15 minutes, methyl (2R)-2-{[(tert-butoxy)carbonyl]amino}-3-iodopropanoate (2.62 g, 1.3 eq., 7.95 mmol) was added in single portion, followed by another iodine (310 mg 0.1 eq., 1.2 mmol). The resulting mixture was stirred at RT for 1 h. Step 2: The mixture of the Step 1 was added to a stirred mixture of 5-iodo-4-methyl-2,3-dihydro-1H-indol-2-one (1.67 g, 6.12 mmol), S-Phos (251 mg, 0.1 eq., 1.2 mmol), and $Pd_2(dba)_3$ (280 mg, 0.05 eq., 0.306 mmol) in DMF (20 mL). The reaction mixture was then heated to 70° C. in 16 h. The reaction was cooled to RT and added saturated $NH_4Cl$, extracted with EtOAc (3×). The extracts were dried over $MgSO_4$, filtered, concentrated and purified by flash chromatography (0-40% EtOAc/Hexanes) to give methyl (2S)-2-{[(tert-butoxy)carbonyl]amino}-3-[4-methyl-1-(4-methylbenzenesulfonyl)-1H-indazol-5-yl]propanoate (681 mg, 31%). MS (488.2)(M+H).

Preparation of tert-butyl N-[(2S-hydroxy-3-(4-methyl-2-oxo-2,3-dihydro-1H-indol-5-yl)propan-2-yl]carbamate (78B): methyl (2S)-2-{[(tert-butoxy)carbonyl]amino}-3-(4-methyl-2-oxo-2,3-dihydro-1H-indol-5-yl)propanoate (681 mg, 1.95 mmol) was dissolved in anhydrous THF (20 mL) under nitrogen and cooled in an ice-bath. Lithium borohydride (4M in THF, 0.7 mL, 5.85 mmol) was added dropwise and the mixture allowed to stir at rt overnight. After completion of reaction, the mixture was cooled in an ice-bath and quenched with saturated aqueous $NH_4Cl$. The aqueous layer was extracted with EtOAc (3×). The combined extracts were dried over $MgSO_4$, filtered, concentrated, and purified via silica gel chromatography (0-60% EtOAc/Hexanes) to give the title compound (710 mg, 110%). MS (m/z): 321.2 (M+H).

Preparation of tert-butyl N-[(2S)-1-(1,3-dioxo-2,3-dihydro-1H-isoindol-2-yl)-3-(4-methyl-2-oxo-2,3-dihydro-1H-indol-5-yl)propan-2-yl]carbamate (78C): To a stirred mixture of tert-butyl N-[(2S)-1-hydroxy-3-(4-methyl-2-oxo-2,3-dihydro-1H-indol-5-yl)propan-2-yl]carbamate (714 mg, 2.23 mmol), triphenylphosphine (701 mg, 2.67 mmol), and phthalimide (393 mg, 2.67 mmol) in THF (20 mL) at 0° C. was added DIAD (0.52 mL, 2.67 mmol) dropwise. After the addition was completed, the reaction mixture was stirred at RT for 16 h. The reaction mixture was then concentrated to dryness, and purified by flash chromatography (0-60% EtOAc:Hexanes) to give the title compound (600 mg, 60%). MS (m/z): 450.2 (M+H).

Preparation of 2-[(2S)-2-amino-3-(4-methyl-2-oxo-2,3-dihydro-1H-indol-5-yl)propyl]-2,3-dihydro-1H-isoindole-1,3-dione (78D): A solution of tert-butyl N-[(2S)-1-(1,3-dioxo-2,3-dihydro-1H-isoindol-2-yl)-3-(4-methyl-2-oxo-2,3-dihydro-1H-indol-5-yl)propan-2-yl]carbamate (600 mg, 1.33 mmol) in formic acid (10 mL) was heated to 50° C. in 1 h. The reaction mixture was cooled to RT, concentrated to dryness to give the title compound (600 mg, 100%) and used in the next step. (MS (m/z): 350.2 (M+H).

Preparation of 2-[(2S)-2-(dimethylamino)-3-(4-methyl-2-oxo-2,3-dihydro-1H-indol-5-yl)propyl]-2,3-dihydro-1H-isoindole-1,3-dione (78E): To a stirred solution of 2-[(2S)-2-amino-3-(4-methyl-2-oxo-2,3-dihydro-1H-indol-5-yl)propyl]-2,3-dihydro-1H-isoindole-1,3-dione (600 mg, 1.33 mmol) in MeCN/$H_2O$ (5:1, 24 mL) was added formaldehyde (300 µL, 3 eq., 10.7 mmol). The mixture was stirred for 30 minutes, then sodium cyanoborohydride (162 mg, 2 eq., 2.66 mmol) was added in single portion. The resulting mixture was stirred for another 30 minutes. Saturated aqueous $NaHCO_3$ was slowly added to adjust pH=7-8, extracted with EtOAc (3×). The combined extracts were dried over $MgSO_4$, concentrated to dryness to give the title compound (360 mg, 65%) and used in the next step without further purification. MS (m/z): 378.2 (M+H).

Preparation of (S)-5-(3-amino-2-(dimethylamino)propyl)-4-methylindolin-2-one (78F): To a stirred solution of 2-[(2S)-2-(dimethylamino)-3-(4-methyl-2-oxo-2,3-dihydro-1H-indol-5-yl)propyl]-2,3-dihydro-1H-isoindole-1,3-dione (360 mg, 0.954 mmol) in EtOH (10 mL) was added hydrazine (238 mL, Seq., 4.44 mmol). The reaction mixture was then heated to 80° C. in 2 h. The reaction mixture was cooled to RT, the precipitated solid was filtered off, washed with EtOH. The filtrate was concentrated to dryness and purified by flash chromatography (0-15% MeOH/DCM in 1% $NH_4OH$) to give the title compound (125 mg, 52%). MS (m/z): 248.1 (M+H).

The following intermediates were synthesized in analogous methods to those described in Example A12: Int. 78:

| Intermediate (Int.) No. | Structure | LC/MS (m/z) | Name |
|---|---|---|---|
| Int. 79 | 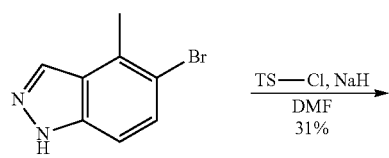 | 234.1 (M + H) | (S)-5-(3-amino-2-(dimethylamino)propyl)indolin-2-one |

Example A13: Preparation of (2S)-1-amino-3-[4-methyl-1-(4-methylbenzenesulfonyl)-1H-indazol-5-yl]propan-2-yl]dimethylamine (81G, "Intermediate 81")

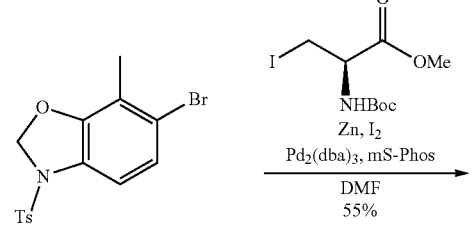

81A

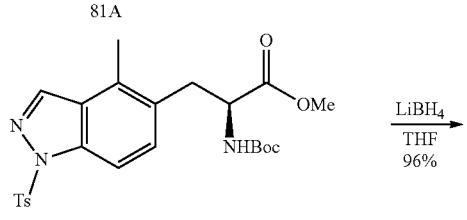

81B

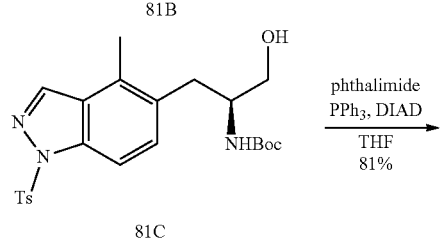

81C

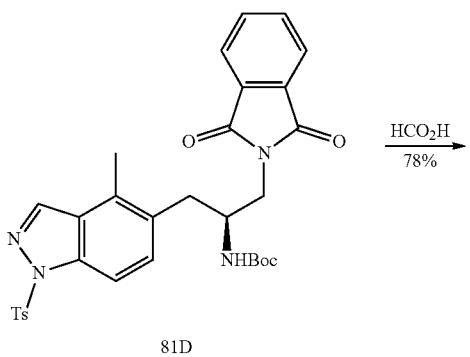

81D

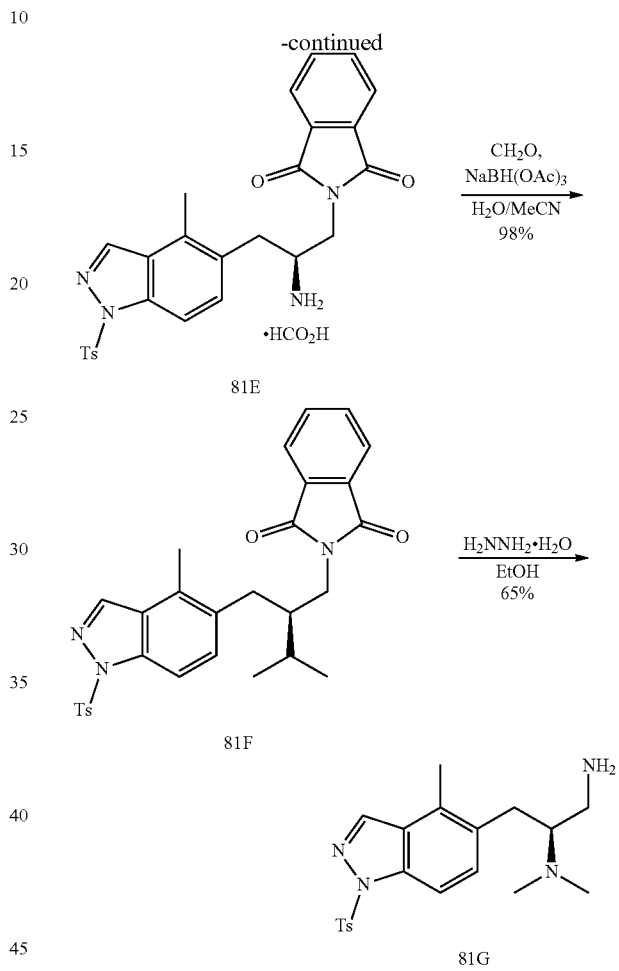

Preparation of 5-bromo-4-methyl-1-(4-methylbenzenesulfonyl)-1H-indazole (81A): To a stirred solution of 5-bromo-4-methyl-1H-indazole (5.50 g, 26.1 mmol) in DMF (40 mL) at 0° C. was added sodium hydride (1.25 g, 1.2 eq., 31.3 mmol) in portions. After the addition was completed, the mixture was continued to stir for 30 minutes, then 4-methylbenzene-1-sulfonyl chloride (5.96 g, 1.2 eq., 31.3 mmol) was added in single portion. The ice bath was removed, and the reaction mixture was stirred at RT for 16 h. The reaction mixture was cooled with an ice bath and added saturated NH$_4$Cl. The precipitated solid was collected, washed with H$_2$O, and purified by flash chromatography (50% DCM/Hexanes) to give 5-bromo-4-methyl-1-(4-methylbenzenesulfonyl)-1H-indazole (3.00 g, 31%).

Preparation of methyl (2S)-2-{[(tert-butoxy)carbonyl]amino}-3-[4-methyl-1-(4-methylbenzenesulfonyl)-1H-indazol-5-yl]propanoate (81B): Step 1: To a stirred suspension of Zinc dust (1.61 g, 24.6 mmol), 3 eq) in DMF (20 mL) was added iodine (208 mg, 0.1 eq., 821 μmol) After stirring for 15 minutes, methyl (2R)-2-{[(tert-butoxy)carbonyl]amino}-

3-iodopropanoate (3.24 g, 1.2 eq., 9.86 mmol) was added in single portion, followed by another iodine (208 mg, 0.1 eq., 821 µmol). The resulting mixture was stirred at RT for 1 h. Step 2: The mixture of the Step 1 was added to a stirred mixture of 5-bromo-4-methyl-1-(4-methylbenzenesulfonyl)-1H-indazole (3.00 g, 8.21 mmol). S-Phos (337 mg, 0.1 eq., 821 µmol), and Pd$_2$(dba)$_3$ (376 mg, 0.05 eq., 411 µmol) in DMF (20 mL). The reaction mixture was then heated to 70° C. in 16 h. The reaction was cooled to RT and added saturated NH$_4$Cl, extracted with EtOAc (3×). The extracts were dried over MgSO4, filtered, concentrated and purified by flash chromatography (0-40% EtOAc/Hexanes) to give methyl (2S)-2-{[(tert-butoxy)carbonyl]amino}-3-[4-methyl-1-(4-methylbenzenesulfonyl)-1H-indazol-5-yl]propanoate (2.20 g, 55%). MS (m/z): 488.2 (M+H).

Preparation of tert-butyl N-[(2S)-1-hydroxy-3-[14-methyl-1-(4-methylbenzenesulfonyl)-1H-indazol-5-yl]propan-2-yl]carbamate (81C). To a stirred solution of methyl (2S)-2-{[(tert-butoxy)carbonyl]amino}-3-[4-methyl-1-(4-methylbenzenesulfonyl)-1H-indazol-5-yl]propanoate (2.20 g, 4.51 mmol) in THF (20 mL) at 0° C. was added Lithium borohydride (1.69 mL, 1.5 eq., 6.77 mmol) dropwise. After the addition was completed, the reaction mixture was stirred at RT in 16 h, cooled in an ice bath, slowly quenched with saturated NH$_4$Cl, stirred for 10 minutes, diluted with H$_2$O, extracted with EtOAc (3×). The combined extracts were dried over MgSO$_4$, filtered, concentrated to dryness to give tert-butyl N-[(2S)-1-hydroxy-3-[4-methyl-1-(4-methylbenzenesulfonyl)-1H-indazol-5-yl]propan-2-yl]carbamate (2.00 g, 96%) and used in the next step without further purification.

Preparation of tert-butyl N-[(2S)-1-(1,3-dioxo-2,3-dihydro-1H-isoindol-2-yl)-3-[4-methyl-1-(4-methylbenzenesulfonyl)-1H-indazol-5-yl]propan-2-yl]carbamate (81D). To a stirred mixture of tert-butyl N-[(2S)-1-hydroxy-3-[4-methyl-(4-methylbenzenesulfonyl)-1H-indazol-5-yl]propan-2-yl]carbamate (2 g, 4.35 mmol), triphenylphosphine (1.37 g, 5.22 mmol), and phthalimide (0.768 g, 5.22 mmol) in THF (40 mL) at 0° C. was added DIAD (1.06 g, 5.22 mmol) dropwise. After the addition was completed, the reaction mixture was stirred at RT for 16 h. The reaction mixture was then concentrated to dryness and purified by flash chromatography (0-60% EtOAc/Hexanes) to give the title compound (2.1 g, 81%).

Preparation of 2-[(2S)-2-amino-3-[4-methyl-1-(4-methylbenzenesulfonyl)-1H-indazol-5-yl]propyl]-2,3-dihydro-1H-isoindole-1,3-dione (81E). A solution of tert-butyl N-[(2S)-1-(1,3-dioxo-2,3-dihydro-1H-isoindol-2-yl)-3-[4-methyl-1-(4-methylbenzenesulfonyl)-1H-indazol-5-yl]propan-2-yl] carbamate (2.10 g 3.57 mmol) in formic acid (20 mL) was heated to 50° C. in 1 h. The reaction mixture was cooled to RT, concentrated to dryness to give the title compound (1.74 g, 99.8%) and used in the next step. MS (m/z): 489.2 (M+H).

Preparation of 2-[(2S)-2-(dimethylamino)-3-[4-methyl-1-(4-methylbenzenesulfonyl)-1H-indazol-5-yl]propyl]-2,3-dihydro-1H-isoindole-1,3-dione (81F). To a stirred solution of 2-[(2S)-2-amino-3-[4-methyl-1-(4-methylbenzenesulfonyl)-1H-indazol-5-yl]propyl]-2,3-dihydro-1H-isoindole-1,3-dione (1.74 g, 3.56 mmol) in MeCN/H$_2$O (5:1, 24 mL) was added formaldehyde (827 µL, 3 eq., 10.7 mmol). The mixture was stirred for 30 minutes, then sodium cyanoborohydride (448 mg, 2 eq., 7.13 mmol) was added in single portion. The resulting mixture was stirred for another 30 minutes. Saturated aqueous NaHCO$_3$ was slowly added to adjust pH=7-8, extracted with EtOAc (3×). The combined extracts were dried over MgSO4, concentrated to dryness to give the title compound (1.84 g, 99.8%) and used in the next step without further purification. MS (m/z): 517.2 (M+H).

Preparation of [(2S)-1-amino-3-[4-methyl-1-(4-methylbenzenesulfonyl)-1H-indazol-5-yl]propan-2-yl]dimethylamine (81 G). To a stirred solution of 2-[(2S)-2-(dimethylamino)-3-[4-methyl-1-(4-methylbenzenesulfonyl)-1H-indazol-5-yl]propyl]-2,3-dihydro-1H-isoindole-1,3-dione (1.84 g, 3.56 mmol) in EtOH (20 mL) was added hydrazine (1.14 g, 5 eq., 17.8 mmol). The reaction mixture was then heated to 80° C. in 2 h. The reaction mixture was cooled to RT, the precipitated solid was filtered off, washed with EtOH. The filtrate was concentrated to dryness, and purified by flash chromatography (0-15% MeOH/DCM in 1% NH$_4$OH) to give [(2S)-1-amino-3-[4-methyl-1-(4-methylbenzenesulfonyl)-1H-indazol-5-yl]propan-2-yl]dimethylamine (900 mg, 65%). MS (m/z): 387.1 (M+H).

The following intermediates were synthesized in analogous methods to those described in Example A13: Int. 81 & General Scheme IV:

| Intermediate (Int.) No. | Structure | LC/MS (m/z) | Name |
|---|---|---|---|
| Int. 80 | 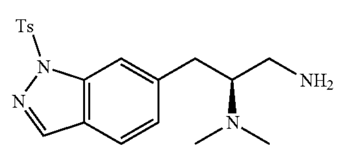 [SMILES: Cc1ccc(S(=O)(=O)n2ncc3ccc(C[C@@H](CN)N(C)C)cc32)cc1] | 373.2 (M + H) | [(2S)-1-amino-3-[1-(4-methylbenzenesulfonyl)-1H-indazol-6-yl]propan-2-yl]dimethylamine |
| Int. 82 | 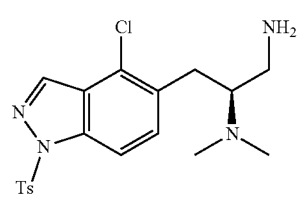 [SMILES: Cc1ccc(S(=O)(=O)n2ncc3c(Cl)c(C[C@@H](CN)N(C)C)ccc32)cc1] | 407.1 (M + H) | (S)-3-(4-chloro-1-tosyl-1H-indazol-5-yl)-N2,N2-dimethylpropane-1,2-diamine |

| Intermediate (Int.) No. | Structure | LC/MS (m/z) | Name |
|---|---|---|---|
| Int. 83 | 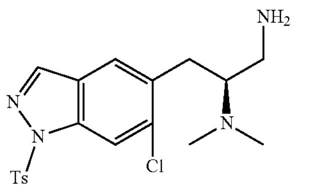 [SMILES: Cc1ccc(S(=O)(=O)n2ncc3cc(C[C@@H](CN)N(C)C)c(Cl)cc32)cc1] | 407.1 (M + H) | (S)-3-(6-chloro-1-tosyl-1H-indazol-5-yl)-N2,N2-dimethylpropane-1,2-diamine |
| Int. 84 | 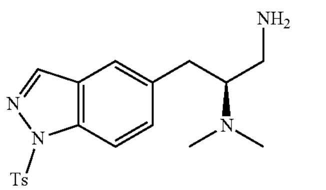 [SMILES: Cc1ccc(S(=O)(=O)n2ncc3cc(C[C@@H](CN)N(C)C)ccc32)cc1] | 373.2 (M + H) | (S)-N2,N2-dimethyl-3-(1-tosyl-1H-indazol-5-yl)propane-1,2-diamine |
| Int. 85 | 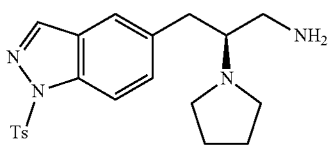 [SMILES: Cc1ccc(S(=O)(=O)n2ncc3cc(C[C@@H](CN)N4CCCC4)ccc32)cc1] | 399.4 (M + H) | (S)-2-(pyrrolidin-1-yl)-3-(1-tosyl-1H-indazol-5-yl)propan-1-amine |
| Int. 86 | 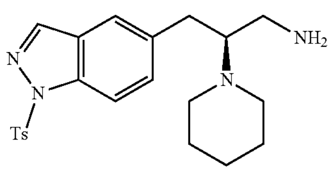 [SMILES: Cc1ccc(S(=O)(=O)n2ncc3cc(C[C@@H](CN)N4CCCCC4)ccc32)cc1] | 413.1 (M + H) | (S)-2-(piperidin-1-yl)-3-(1-tosyl-1H-indazol-5-yl)propan-1-amine |
| Int. 87 | 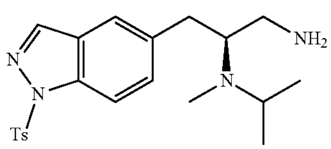 | 531.2 (M + H) | (S)-N2-isopropyl-N2-methyl-3-(1-tosyl-1H-indazol-5-yl)propane-1,2-diamine |
| Int. 88 | 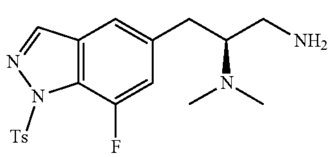 [SMILES: Cc1ccc(S(=O)(=O)n2ncc3cc(C[C@@H](CN)N(C)C)cc(F)c32)cc1] | 391.2 (M + H) | (S)-3-(7-fluoro-1-tosyl-1H-indazol-5-yl)-N2,N2-dimethylpropane-1,2-diamine |
| Int. 92 | 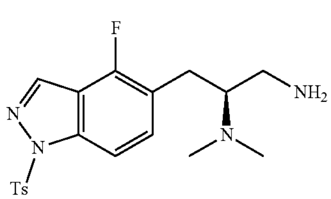 [SMILES: Cc1ccc(S(=O)(=O)n2ncc3c(F)c(C[C@@H](CN)N(C)C)ccc32)cc1] | 390.1 (M + H) | (S)-3-(4-fluoro-1-tosyl-1H-indazol-5-yl)-N2,N2-dimethylpropane-1,2-diamine |

Example A14: Preparation of (S)-4-(3-amino-2-(dimethylamino)propyl)phenol (133E, "Intermediate 133")

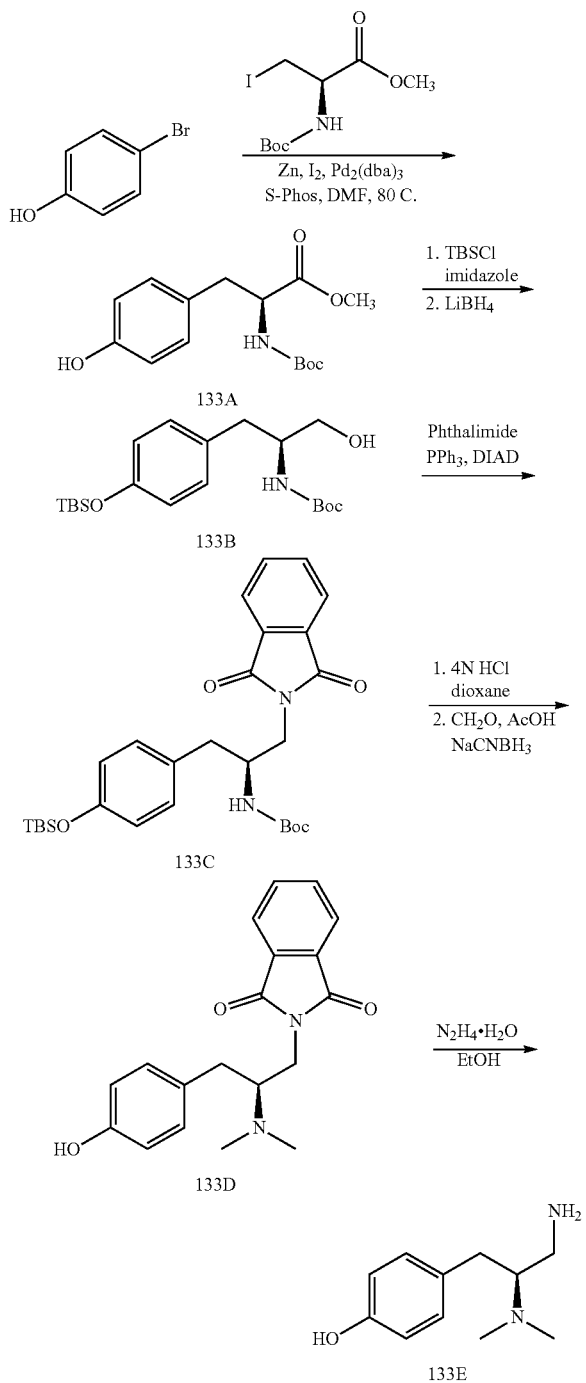

Preparation of methyl (S)-2-((tert-butoxycarbonyl)amino)-3-(2,5-difluoro-4-hydroxyphenyl)propanoate (133A): To an oven-dried RBF was added zinc (26 g, 35 mmol), dry DMF (140 mL) and iodine (1.8 g, 140 mmol). The reaction mixture was stirred for 10 min, followed by the addition of a solution of methyl (2R)-2-{[(tert-butoxy)carbonyl]amino}-3-iodopropanoate (46 g, 140 mmol) and iodine (1.8 g, 140 mmol) which resulted in an exotherm. The reaction mixture was stirred cooling to room temperature for 20 min, and then 4-bromo-phenol (20 g, 116 mmol), Pd₂(dba)₃ (5.3 g, 5.8 mmol), and SPhos (4.8 g, 12 mmol) were added to the reaction mixture. The reaction mixture was stirred at 75° C. for 16 h. The crude reaction mixture was cooled to room temperature, quenched with water, diluted with EtOAc, and filtered through celite. The organic layer was then washed with brine (5×), dried over MgSO₄, then concentrated. The resulting residue was adsorbed onto silica, then purified by column chromatography (silica, 0-50%/EtOAc/hex) to yield the title compound as a white solid (27 g, 78%). MS (m/z)=296.1 [M+H].

Preparation of tert-butyl (S)-(1-(4-((tert-butyldimethylsilyl)oxy)-2,5-difluorophenyl)-3-hydroxypropan-2-yl)carbamate (133B): Methyl (2S)-2-{[(tert-butoxy)carbonyl]amino}-3-(2,6-difluoro-4-hydroxyphenyl)propanoate (29 g, 98 mmol) was taken in dichloromethane (600 ml) with tert-butyl(chloro)dimethylsilane (16 g, 107 mmol) and 1H-imidazole (20 g 293 mmol). The solution was stirred at room temperature for 24 hrs. The solution was diluted with dichloromethane and then washed with saturated sodium bicarbonate solution. The organic layer was filtered through magnesium sulfate and the filtrate was concentrated to give the desired product (35 g). This product was dissolved in THF (300 mL), cooled to 0° C., and a solution of lithium borohydride (4M in THF, 43 mL, 170 mmol) was added in a dropwise fashion. The reaction mixture was stirred at 0° C. for 30 min, then stirred warming to room temperature for 6 h. The reaction mixture was then cooled to 0° C., and was quenched with the dropwise addition of ammonium chloride solution. The crude reaction mixture was diluted with brine, and the product was extracted with EtOAc (3×). The combined organic layers were washed with brine, dried over Na₂SO₄, then concentrated. The resulting residue was purified by column chromatography (80 g silica, 10% DCM/MeOH) to afford the title compound as an oil (33 g, 60%). MS (m/z)=382.1 [M+Na].

Preparation of tert-butyl (S)-(1-(4-((tert-butyldimethylsilyl)oxy)phenyl)-3-(1,3-dioxoisoindolin-2-yl)propan-2-yl) carbamate (133C): tert-Butyl N-[(2S)-1-(4-carbamoyl-3-fluorophenyl)-3-hydroxypropan-2-yl]carbamate (32 g, 84 mmol), triphenylphosphine (24 g, 92 mmol), phthalimide (13.6 g, 92 mmol) were dissolved in anhydrous THF (500 mL). The reaction mixture was cooled to 0° C., and DIAD (18.2 mL, 92 mmol) was added dropwise. The reaction mixture was stirred at 0° C. for 1 h, then stirred at room temperature for 16 h. The resulting in the formation of a white precipitate. The precipitate was filtered, washed with THF, and dried to yield the title compound as a white solid (28 g, 65%). MS (m/z)=511.1 [M+H].

Preparation of (S)-2-(3-(2,5-difluoro-4-hydroxyphenyl)-2-(dimethylamino)propyl)isoindoline-1,3-dione (133D): tert-butyl (S)-(1-(4-((tert-butyldimethylsilyl)oxy)phenyl)-3-(1,3-dioxoisoindolin-2-yl)propan-2-yl)carbamate (1.8 g, 3.2 mmol) was taken in methanol (200 ml) and then 4 M HCl in 1,4-dioxane (120 mL, 500 mmol) was added. The reaction mixture was stirred at 50° C. for 1 h; full conversion by LCMS. The reaction mixture was concentrated, and the resulting residue was triturated with ethyl acetate to give the product as a white solid (17 g, 94%) that was used directly for the next step. MS (m/z)=297.1 [M+H]. The solid was dissolved in MeCN/H₂O (240 ml/60 ml), then 37 wt % formaldehyde in water (15 mL, 207 mmol) was added. The reaction mixture was stirred for 30 min, then NaCNBH₃ (9.8 g, 156 mmol) was added to the reaction mixture in one portion. Full conversion after 1 h by LCMS. The reaction mixture was cooled to 0° C. and quenched with sat. aqueous sodium bicarbonate (500 mL). The product was extracted with EtOAc (7×), and the combined organic layers were dried over MgSO$_4$, then concentrated. The resulting residue was purification by silica gel chromatography to give the desired product as an oil. (8.4 g, 50%). MS (m/z)=325.1 [M+H].

Preparation of (S)-4-(3-amino-2-(dimethylamino)propyl)-2,5-difluorophenol (133E): (S)-2-(3-(2,5-difluoro-4-hydroxy phenyl)-2-(dimethylamino)propyl)isoindoline-1,3-dione (8.4 g, 26 mmol) was taken in absolute EtOH (250 mL) with aqueous 50 wt % hydrazine hydrate (12 mL, 130 mmol). The reaction mixture was stirred at 75° C. for 3 h. The crude reaction mixture was then concentrated, adsorbed onto silica, then purified by column chromatography (40 g silica, 0-20% MeOH/DCM+1% NH$_4$OH) to yield the title compound as a white solid (3.0 g, 60%); MS (m/z): 195.2 [M+H].

The following intermediates were synthesized in analogous method to those described in Example A14: Int. 133 & General Scheme III:

| Intermediate (Int.) No. | Structure | LC/MS (m/z) | Name |
|---|---|---|---|
| Int. 134 | 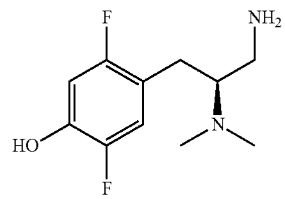 [SMILES: CN(C)[C@H](CN)Cc1cc(F)c(O)cc1F] | 231.2 (M + H) | (S)-4-(3-amino-2-(dimethylamino)propyl)-2,5-difluorophenol |
| Int. 135 | 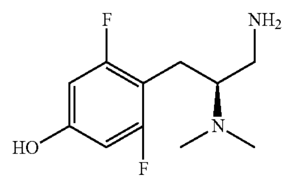 [SMILES: CN(C)[C@H](CN)Cc1c(F)cc(O)cc1F] | 231.2 (M + H) | (S)-4-(3-amino-2-(dimethylamino)propyl)-3,5-difluorophenol |
| Int. 136 | 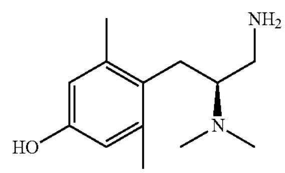 [SMILES: Cc1cc(O)cc(C)c1C[C@@H](CN)N(C)C] | 223.2 (M + H) | (S)-4-(3-amino-2-(dimethylamino)propyl)-3,5-dimethylphenol |
| Int. 137 | 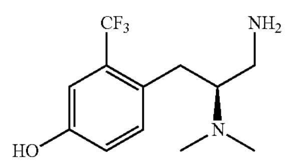 [SMILES: CN(C)[C@H](CN)Cc1ccc(O)cc1C(F)(F)F] | 263.2 (M + H) | (S)-4-(3-amino-2-(dimethylamino)propyl)-3-(trifluoromethyl)phenol |
| Int. 138 | 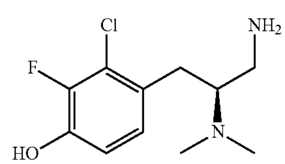 [SMILES: CN(C)[C@H](CN)Cc1ccc(O)c(F)c1Cl] | 247.2 (M + H) | (S)-4-(3-amino-2-(dimethylamino)propyl)-3-chloro-2-fluorophenol |
| Int. 139 | 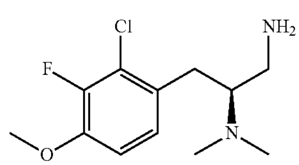 | 261.2 (M + H) | (S)-3-(2-chloro-3-fluoro-4-methoxyphenyl)-N2,N2-dimethylpropane-1,2-diamine |
| Int. 140 | 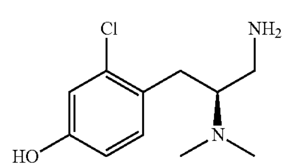 | 230.2 (M + H) | (S)-4-(3-amino-2-(dimethylamino)propyl)-3-chlorophenol |

| Intermediate (Int.) No. | Structure | LC/MS (m/z) | Name |
|---|---|---|---|
| Int. 141 | 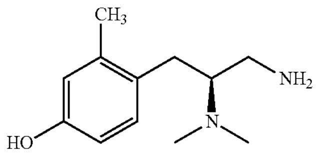 | 223.2 (M + H) | (S)-4-(3-amino-2-(dimethylamino)propyl)-3-methylphenol |
| Int. 142 | 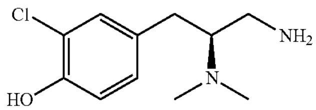 | 229.2 (M + H) | (S)-4-(3-amino-2-(dimethylamino)propyl)-2-chlorophenol |
| Int. 143 | 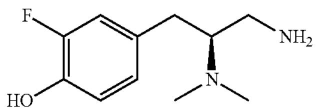 | 213.2 (M + H) | (S)-4-(3-amino-2-(dimethylamino)propyl)-2-fluorophenol |

Example A15: Preparation of (S)-3-(aminomethyl)-2-methyl-1,2,3,4-tetrahydroisoquinolin-7-ol ("Intermediate 144")

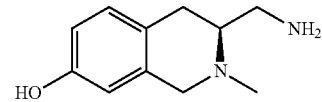

Intermediate 144 was synthesized as described in WO2019195634A1.

Synthesis Examples B: Compounds

Example B1: Preparation of 4-((S)-2-(dimethylamino)-3-((S)-3-(2-methylthiazol-5-yl)-3-(1-(trifluoromethyl)cyclopropyl)propanamido)propyl)-2,3-difluorobenzamide ("Compound 1")

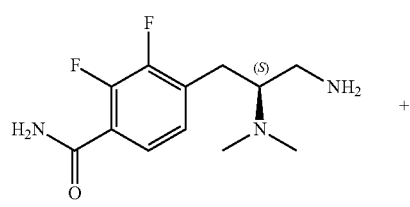
Int. 41

+

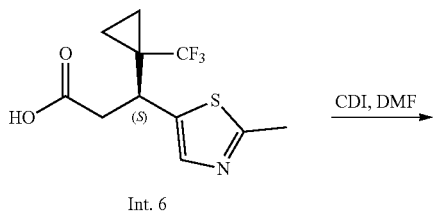
Int. 6

CDI, DMF →

-continued

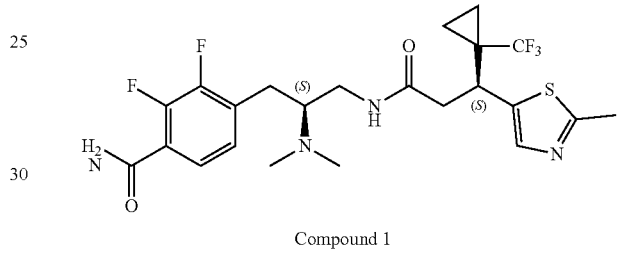
Compound 1

To a solution of the acid (Int. 6)(35 mg, 0.125 mmol) in DMF (0.25 mL), was added CDI (22 mg, 0.14 mmol). The mixture was stirred at room temperature for 1 h. To the mixture was added DIEA (0.043 mL, 0.25 mmol) and the amine (Int. 41.35 mg, 0.138 mmol), stirred for 1 h at room temperature. The reaction mixture was diluted with ethyl acetate (20 mL) and saturated NaHCO$_3$, water, and brine. The organic layer was dried over MgSO$_4$, filtered, and concentrated on rota-vapor. The crude material was purified on silica gel column, 0-25% MeOH/DCM with 1% NH$_4$OH. The pure fractions were concentrated and then triturated with MTBE to provide the title compound (44 mg, 67%). MS (m/z): 519.2 (M+H).

Example B2: Preparation of 4-((S)-2-(dimethylamino)-3-((S)-3-(thiazol-5-yl)-3-(1-(trifluoromethyl)cyclopropyl)propanamido)propyl)-2,3-difluorobenzamide ("Compound 2")

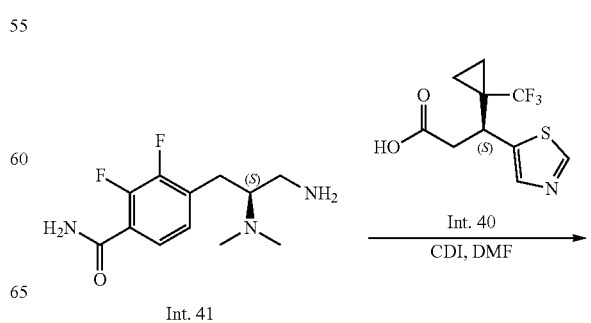
Int. 41      Int. 40
          CDI, DMF →

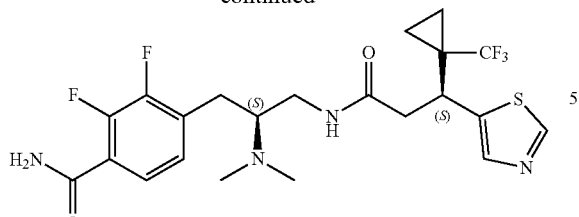

Compound 2

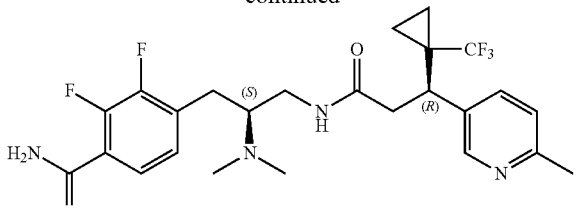

Compound 4

Compound 2 (78 mg, 70%) was synthesized from Int. 41 and Int. 40, as described in Example B1. MS (m/z): 505.1 (M+H).

Example B3: Preparation of 4-((S)-2-(dimethylamino)-3-((R)-3-(2-methylpyrimidin-5-yl)-3-(1-(trifluoromethyl)cyclopropyl)propanamido)propyl)-2,3-difluorobenzamide ("Compound 3")

Compound 4 (38 mg, 68%) was synthesized from Int. 41 and Int. 10 as described in Example B1. MS (m/z): 513.2 (M+H).

Example B5: Preparation of 4-[(2S)-3-[(3R)-3-(5-chloropyrimidin-2-yl)-3-[1-(trifluoromethyl)cyclopropyl]propanamido]-2-(dimethylamino)propyl]-2,5-difluorobenzamide ("Compound 5")

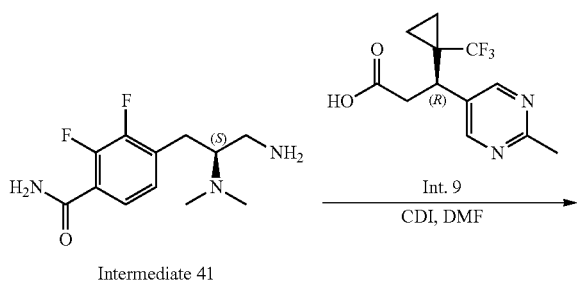

Intermediate 41

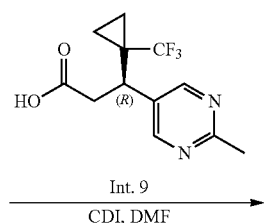

Int. 9
CDI, DMF

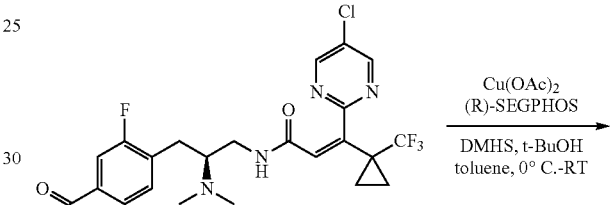

Cu(OAc)$_2$
(R)-SEGPHOS
DMHS, t-BuOH
toluene, 0° C.-RT

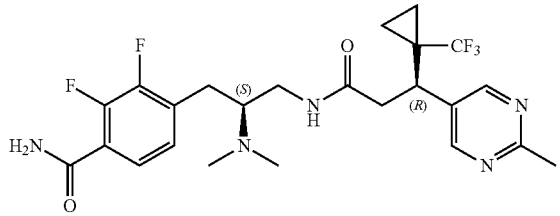

Compound 2  3

Compound 3 (19 mg, 51%) was synthesized from Int. 41 and Int. 9, as described in Example B1. MS (m/z): 514.2 (M+H).

Example B4 Preparation of 4-((S)-2-(dimethylamino)-3-((R)-3-(6-methylpyridin-3-yl)-3-(1-(trifluoromethyl)cyclopropyl)propanamido)propyl)-2,3-difluorobenzamide ("Compound 4")

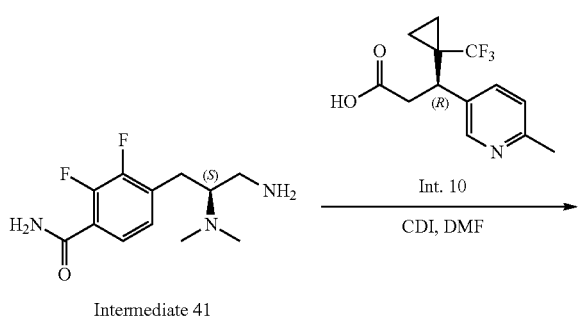

Intermediate 41

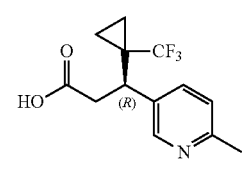

Int. 10
CDI, DMF

Compound 5

To a stirred mixture of (R)-DTBM-SEGPHOS (3.13 mg, 0.01 eq., 2.65 µmol) and copper (2+) diacetate (2.41 mg, 0.05 eq., 13.3 µmol) in toluene (1 mL) at 0° C. was added dimethoxy(methyl)silyl (81.0 µL, 2.5 eq., 663 µmol), followed by 2-methylpropan-2-ol (85.4 µL, 2 eq., 900 µmol). A solution of 4-[(2S)-3-[(2Z)-3-(5-chloropyrimidin-2-yl)-3-[1-(trifluoromethyl)cyclopropyl]prop-2-enamido]-2-(dimethylamino)propyl]-2,5-difluorobenzamide (141 mg, 265 µmol) in toluene (4 mL) was added dropwise. The reaction mixture was gradually stirred at RT overnight. LC/MS showed about 13% conversion. To mixture was cooled in an ice bath and added 10 mol % of (S-DTBM-SEGPHOS, 10 mol % Cu(OAc)$_2$, 5 eq of DMMS, and 4 eq t-BuOH. (a lot gas bubbles at this time). The ice bath was removed and stirred at RT for 3 h. LC/MS showed the >95% conversion of the expected product. NH$_4$F solid was added to the mixture and stirred vigorously for 15 minutes, then added H$_2$O, and stirred for 10 more minutes, and extracted with EtOAc (3×). The combined extracts were dried over MgSO$_4$, concentrated to dryness and purified by flash chromatography (0-15% MeOH/DCM) to give 4-[(2S)-3-[(3R)-3-(5-chloropyrimidin-2-yl)-3-[1-(trifluoromethyl)cyclopropyl]propanamido]-2-(dimethylamino)propyl]-2,5-difluorobenzamide (38.5 mg, 27%). MS (m/z): 534.1 (M+H).

Example B6: Preparation of 4-((2S)-2-(dimethylamino)-3-(2-(pyrimidin-2-yl)cyclopropane-1-carboxamido)propyl)-3,5-dimethylbenzamide ("Compound 6")

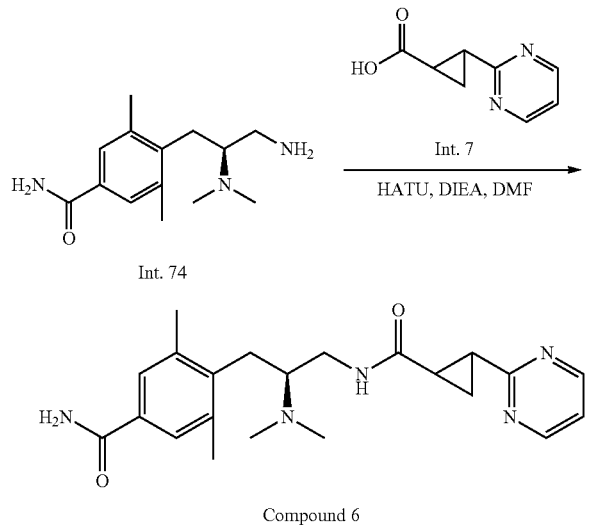

To a stirred mixture of (S)-4-(3-amino-2-(dimethylamino)propyl)-3,5-dimethylbenzamide (Int. 74, 120 mg, 0.48 mmol), 2-(pyrimidin-2-yl)cyclopropane-1-carboxylic acid (Int. 7, 95 mg, 0.58 mmol), and DIEA (0.17 ml, 2.5 eq, 1.2 mmol) in DMF (2 mL) was added HATU (220 mg, 1.2 eq., 0.58 mmol). After the addition was completed, the reaction mixture was stirred at rt in 1 h. H₂O was added, and the precipitated solid was collected, washed with H₂O, dried and purified by flash chromatography (0-10% MeOH/DCM) to give 4-((2S)-2-(dimethylamino)-3-(2-(pyrimidin-2-yl)cyclopropane-1-carboxamido)propyl)-3,5-dimethylbenzamide (108 mg, 65%). MS (m/z), 396.2 (M+H).

Example B7: Preparation of 4-((S)-2-(dimethylamino)-3-((S)-3-phenyl-3-(1-(trifluoromethyl)cyclopropyl)propanamido)propyl)-3,5-dimethylbenzamide ("Compound 7")

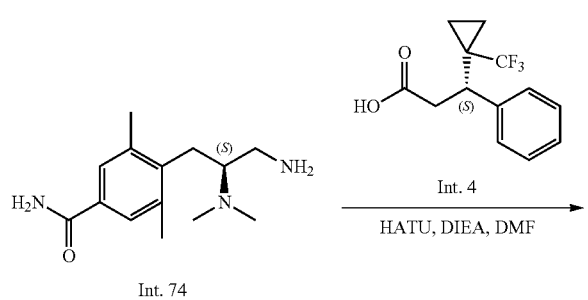

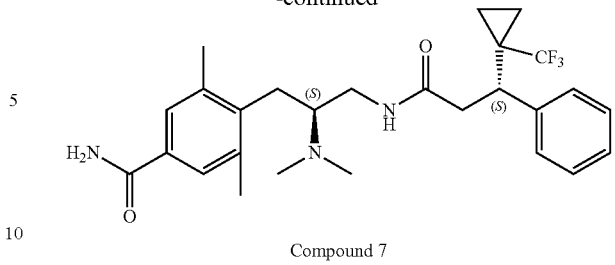

Compound 7

To a stirred mixture of 4-[(2S)-3-amino-2-(dimethylamino)propyl]-3,5-dimethylbenzamide (Int. 74, 56.2 mg, 1 eq., 225 μmol), (3S)-3-phenyl-3-[1-(trifluoromethyl)cyclopropyl]propanoic acid (Int. 4, 58.2 mg, 225 μmol), and DIEA (252 mg, 2.5 eq., 563 μmol) in DMF (2 mL) was added HATU (103 mg, 1.2 eq., 270 μmol). After the addition was completed, the reaction mixture was stirred at rt in 1 h. H₂O was added, and the precipitated solid was collected, washed with H₂O, dried and purified by flash chromatography (0-10% MeOH/DCM) to give 4-[(2S)-2-(dimethylamino)-3-[(3R)-3-phenyl-3-[1-(trifluoromethyl)cyclopropyl]propanamido]propyl]-3,5-dimethylbenzamide (37.3 mg, 76.2 μmol). MS (m/z): 490.3 (M+H).

Example B8: Preparation of 4-((S)-2-(dimethylamino)-3-((R)-3-phenyl-3-(1-(trifluoromethyl)cyclopropyl)propanamido)propyl)-3,5-dimethylbenzamide ("Compound 8")

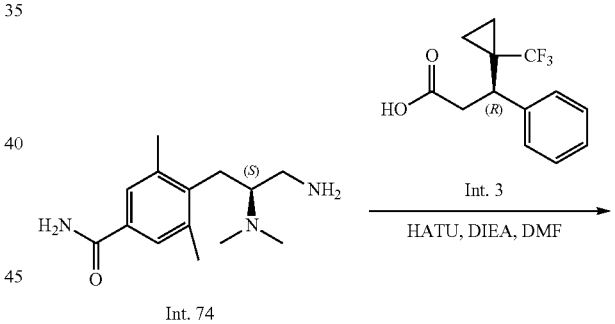

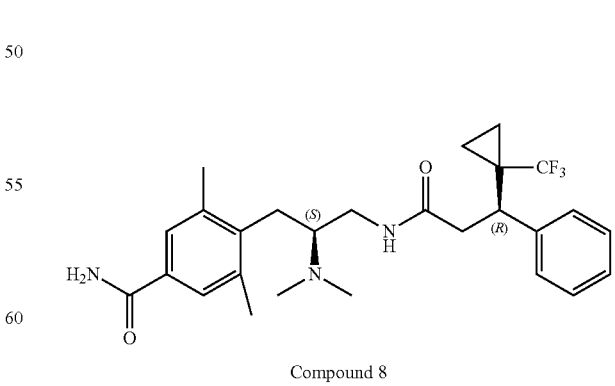

Compound 8 (67.5 mg, 64%) was synthesized from Int. 74 and Int. 3 as described in Example B7. MS (m/z): 490.3 (M+H).

Example B9: Preparation of 4-[(2S)-2-(dimethyl-amino)-3-[(3S)-5-methyl-3-phenylhexanamido]propyl]-3,5-dimethylbenzamide ("Compound 9")

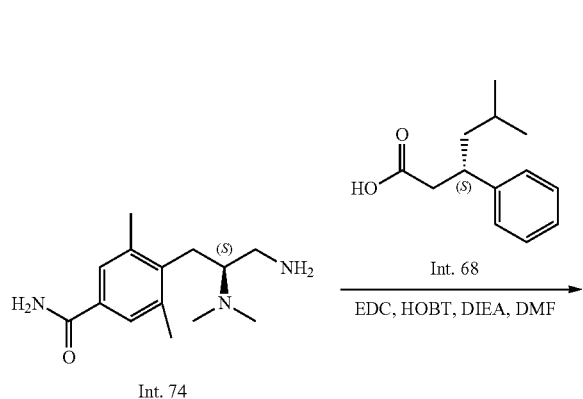

Int. 74

Compound 9

A solution of 4-[(2S)-3-amino-2-(dimethylamino)propyl]benzamide (Int. 74, 28.2 mg, 113 mmol) in DMF (1 ml) was added to (S)-5-methyl-3-phenylhexanoic acid (Int. 68, 25.6 mg, 124 mmol), EDC (24 mg, 124 mmol)), 1-hydroxybenzotriazole (15.3 mg, 113 mmol), and N,N'-diisopropylethylamine (16.1 mg, 124 mmol). The solution was stirred at room temperature for 3 hrs. It was then diluted with ethyl acetate and washed with water. The organic layer was filtered through magnesium sulfate and then concentrated. The residue was purified by flash chromatography (0-25% MeOH/DCM in 1% NH$_4$OH) to give the title compound (25 mg, 52%). MS (m/z): 438.3 (M+H).

Example B10: Preparation of 4-((S)-2-(dimethyl-amino)-3-((R)-4-methyl-3-phenylpentanamido)propyl)-3,5-dimethylbenzamide ("Compound 10")

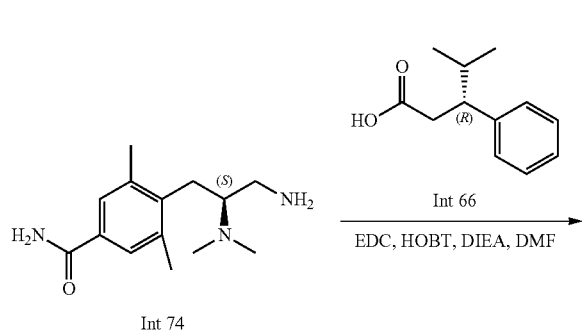

Int 74

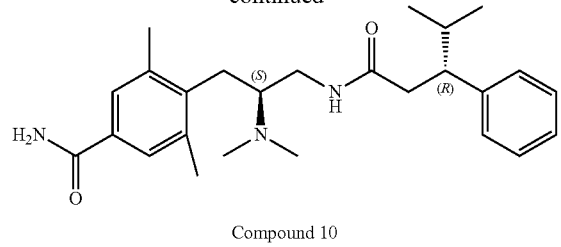

Compound 10

Compound 10 (24.6 mg, 51%) was synthesized from Int. 74 and Int. 66 as described in Example B9. MS (m/z): 424.3 (M+H).

Example B11: Preparation of 4-((S)-3-((R)-3-cyclo-propyl-3-phenylpropanamido)-2-(dimethylamino)propyl)-3,5-dimethylbenzamide ("Compound 11")

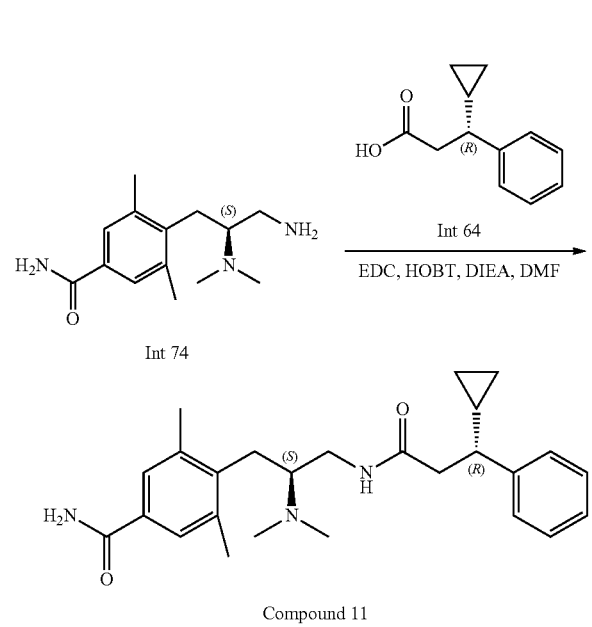

Int 74

Compound 11

Compound 11 (10 mg, 21%) was synthesized from Int. 74 and Int. 64 as described in Example B9. MS (m/z): 422.3 (M+H).

Example B12: Preparation of 4-[(2S)-2-(dimethyl-amino)-3-[(3R)-5-methyl-3-phenylhexanamido]propyl]-3,5-dimethylbenzamide ("Compound 12")

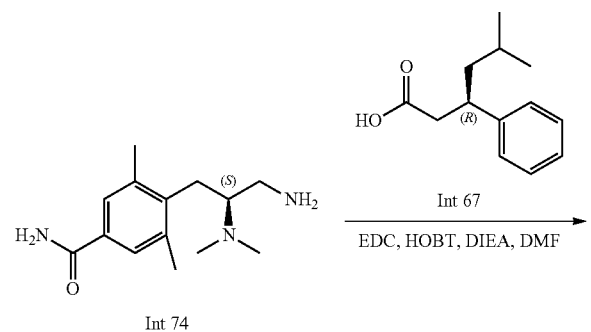

Int 74

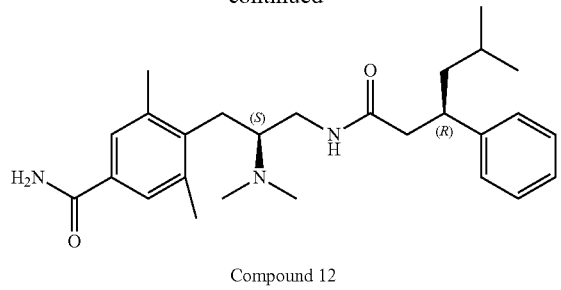

Compound 12

Compound 12 (5.1 mg, 7%) was synthesized from Int. 74 and Int. 67 as described in Example B9. MS (m/z): 438.5 (M+H).

Example B13: Preparation of 4-[(2S)-3-[(3S)-4,4-dimethyl-3-phenylpentanamido]-2-(dimethylamino)propyl]-3,5-dimethylbenzamide ("Compound 13")

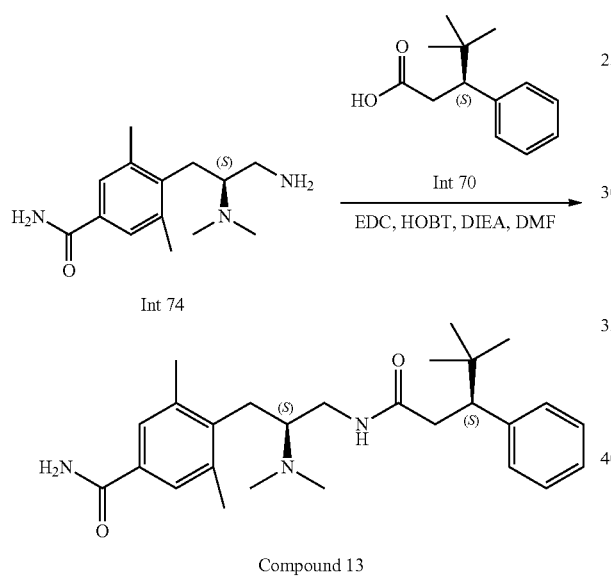

Compound 13

Compound 13 (25 mg, 35%) was synthesized from Int. 74 and Int. 70 as described in Example B9. MS (m/z): 438.3 (M+H).

Example B14: Preparation of 3-chloro-4-((S)-2-(dimethylamino)-3-((R)-3-phenylbutanamido)propyl)benzamide ("Compound 14")

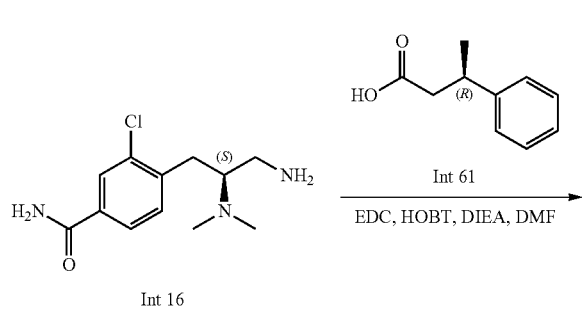

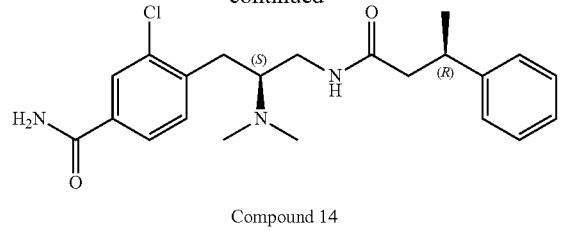

Compound 14

Compound 14 (17.1 mg, 17%) was synthesized from Int. 16 and Int. 61 as described in Example B9. MS (m/z): 402.2 (M+H).

Example B15: Preparation of 3-chloro-4-((S)-2-(dimethylamino)-3-((S)-3-phenylbutanamido)propyl)benzamide ("Compound 15")

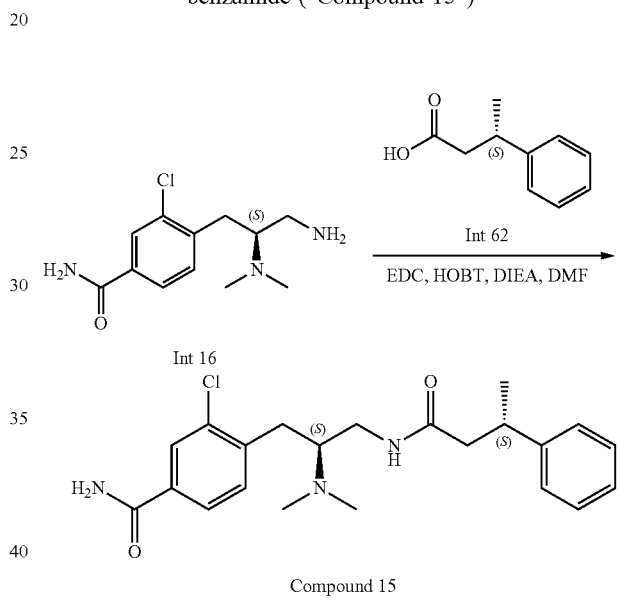

Compound 15

Compound 15 (32 mg, 37%) was synthesized from Int. 16 and Int. 62 as described in Example B9. MS (m/z): 402.2 (M+H).

Example B16: Preparation of 3-chloro-4-[(2S)-2-(dimethylamino)-3-[(3S)-3-(2-methyl-1,3-thiazol-5-yl)-3-[1-(trifluoromethyl)cyclopropyl]propanamido]propyl]-2-fluorobenzamide ("Compound 16")

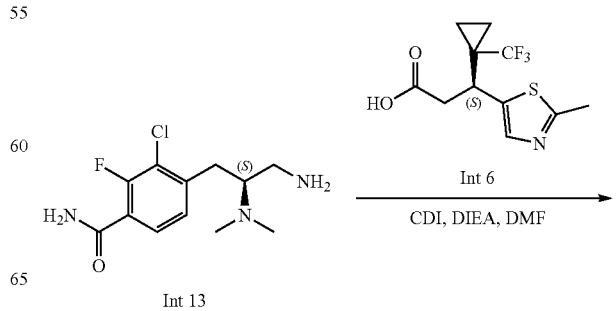

-continued

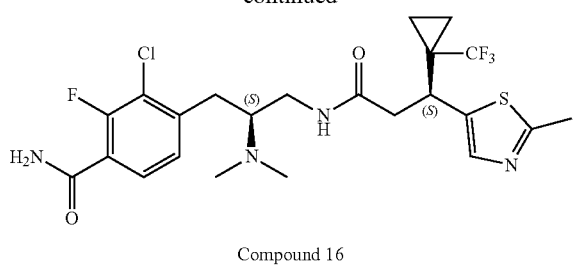

Compound 16

Compound 16 (46 mg, 74%) was synthesized from Int. 13 and Int. 6 as described in Example B1. MS (m/z): 535.2 (M+H).

Example B17: Preparation of 3-chloro-4-[(2S)-2-(dimethylamino)-3-[(3S)-3-(6-methylpyridin-3-yl)-3-[1-(trifluoromethyl)cyclopropyl]propanamido]propyl]-2-fluorobenzamide ("Compound 17")

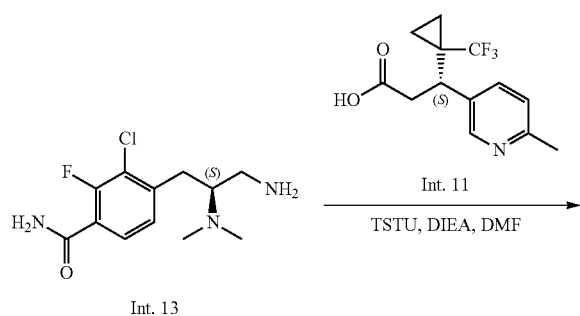

To a solution of Int. 11 (22.8 mg, 0.0834 mmol) and DIEA (29.1 uL, 0.167 mmol) in DMF (0.25 mL), was added TSTU (25.1 mg, 0.0834 mmol). The mixture was stirred at room temperature for 1 hour. Int. 13 (25.1 mg, 0.0918 mmol) was added in one portion, continued to stir for an hour at room temperature. The reaction mixture was diluted with ethyl acetate (15 mL) and saturated NaHCO₃, water, and brine. The organic layer was dried over MgSO₄, filtered and concentrated. The crude material was purified silica gel column (0-10% MeOH/DCM with 1% NH₄OH) to give the title compound (22 mg, 50%). MS (m/z): 529.2 (M+H).

Example B18: Preparation of 3-chloro-4-[(2S)-2-(dimethylamino)-3-[(3R)-3-(pyridin-3-yl)-3-[1-(trifluoromethyl)cyclopropyl]propanamido]propyl]-2-fluorobenzamide ("Compound 18")

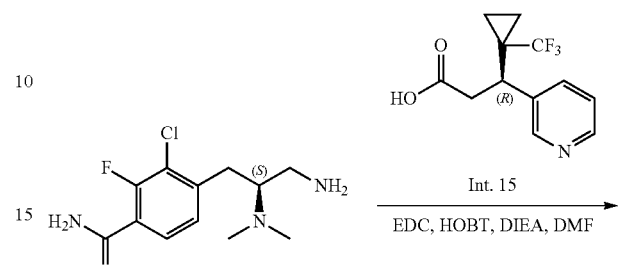

Compound 18

Compound 18 (20.1 mg, 53%) was synthesized from Int. 13 and Int. 15 as described in Example B9. MS (m/z): 515.2 (M+H).

Example B19: Preparation of 3-chloro-4-[(2S)-2-(dimethylamino)-3-[3-(pyridin-4-yl)-3-[1-(trifluoromethyl)cyclopropyl]propanamido]propyl]-2-fluorobenzamide ("Compound 19")

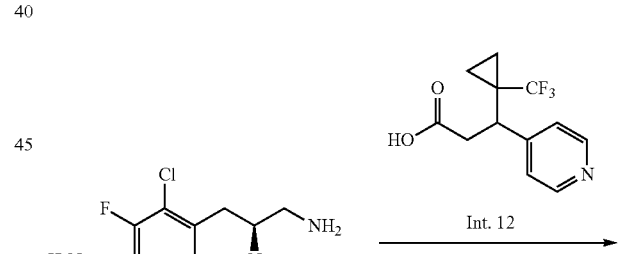

Compound 19

Compound 19 (30 mg, 56%) was synthesized from Int. 13 and Int. 12 as described in Example B9. MS (m/z): 515.2 (M+H).

Example B20: Preparation of 3-chloro-4-((S)-2-(dimethylamino)-3-((R)-3-(6-methylpyridin-3-yl)-3-(1-(trifluoromethyl)cyclopropyl)propanamido)propyl)-2-fluorobenzamide ("Compound 20")

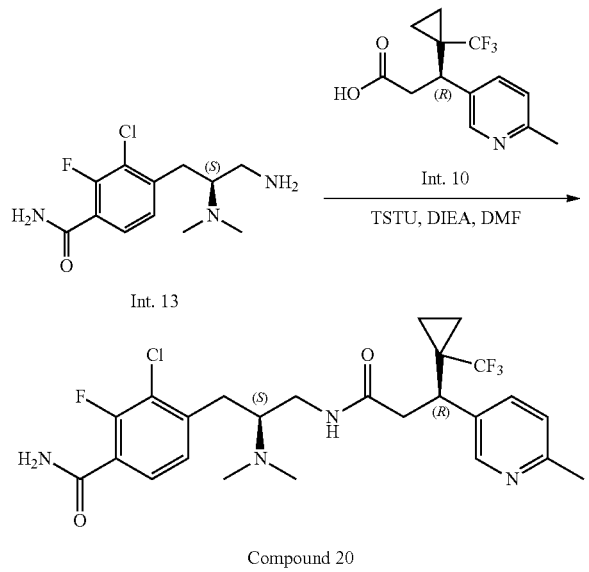

Compound 20

Compound 20 (42 mg, 77%) was synthesized from Int. 13 and Int. 10 as described in Example B17. MS (m/z): 529.1 (M+H).

Example B21: Preparation of 3-chloro-4-[(2S)-2-(dimethylamino)-3-[(3R)-3-(2-methylpyrimidin-5-yl)-3-[1-(trifluoromethyl)cyclopropyl]propanamido]propyl]-2-fluorobenzamide ("Compound 21")

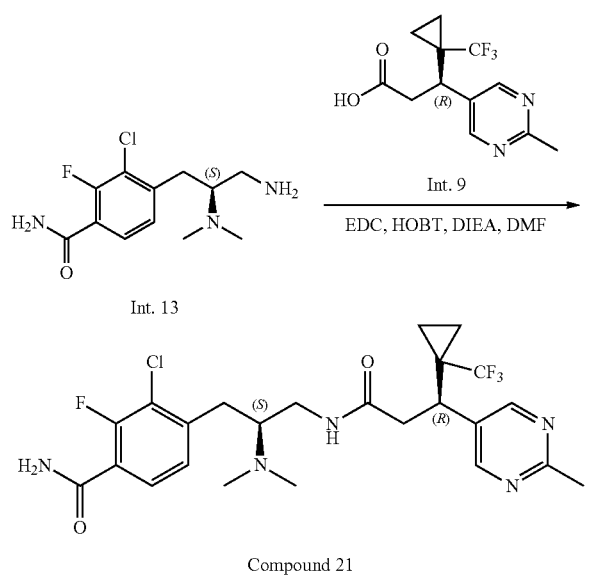

Compound 21

Compound 21 (15.8 mg, 37%) was synthesized from Int. 13 and Int. 9 as described in Example B9. MS (m/z): 530.2 (M+H).

Example B22: Preparation of 3-chloro-4-[(2S)-3-[3-(5-chloropyrimidin-2-yl)-3-[1-(trifluoromethyl)cyclopropyl]propanamido]-2-(dimethylamino)propyl]-2-fluorobenzamide ("Compound 22")

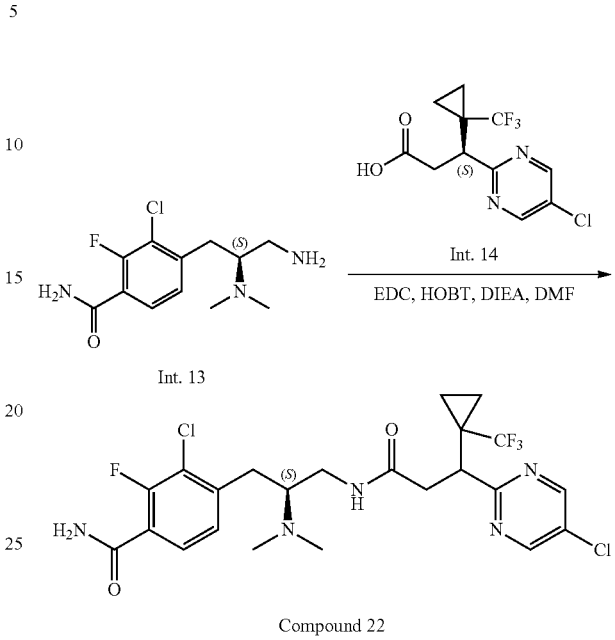

Compound 22

Compound 22 (25.1 mg, 55%) was synthesized from Int. 13 and Int. 14 as described in Example B9. MS (m/z): 550.1 (M+H).

Example B23: Preparation of 3-chloro-4-((S)-3-((R)-3-(pyridin-3-yl)-3-(1-(trifluoromethyl)cyclopropyl)propanamido)-2-(pyrrolidin-1-yl)propyl)benzamide ("Compound 23")

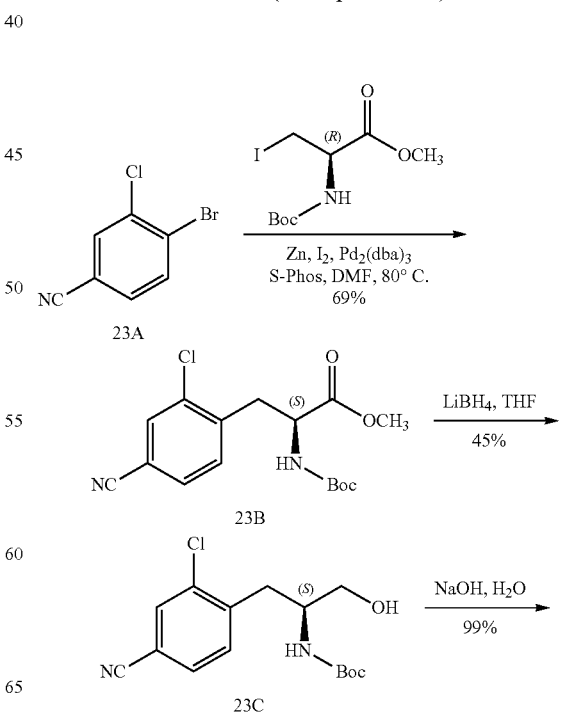

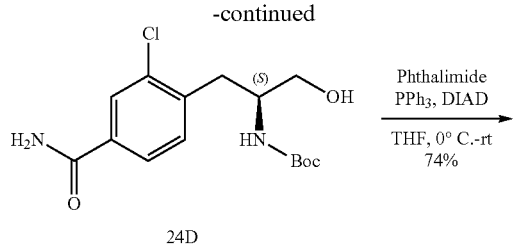

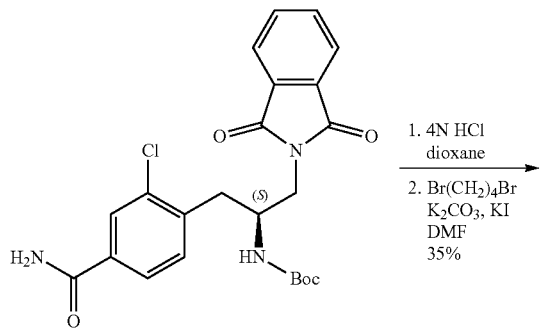

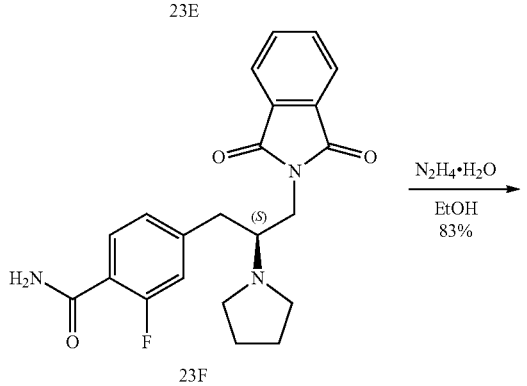

Step 3: Tert-butyl N-[(2S)-1-(4-carbamoyl-3-chlorophenyl)-3-hydroxypropan-2-yl]carbamate (23D) was prepared in the same method as described in Intermediate 1D.

Step 4: Tert-butyl N-[(2S)-1-(4-carbamoyl-3-chlorophenyl)-3-(1,3-dioxo-2,3-dihydro-1H-isoindol-2-yl)propan-2-yl]carbamate (23E) was prepared in the same method as described in Intermediate 1E.

Step 5: 3-chloro-4-[(2S)-3-(1,3-dioxo-2,3-dihydro-1H-isoindol-2-yl)-2-(pyrrolidin-1-yl)propyl]benzamide (23F) was prepared in the same method as described in Intermediate 1F. MS (m/z): 412.0 (M+H).

Step 6: 4-[(2S)-3-amino-2-(pyrrolidin-1-yl)propyl]-3-chlorobenzamide (23G) was prepared in the same method as described in Intermediate 1G. MS (m/z): 282.0 (M+H).

Step 7: 3-chloro-4-((S)-3-((R)-3-(pyridin-3-yl)-3-(1-(trifluoromethyl)cyclopropyl) propanamido)-2-(pyrrolidin-1-yl) propyl)benzamide ("Compound 23"). To a 1 dram vial was added (3R)-3-(2-methylpyrimidin-5-yl)-3-[1-(trifluoromethyl)cyclopropyl]propanoic acid (30.0 mg, 0.11 mmol), DIPEA (0.04 mL, 0.2 mmol), and DMF (0.4 mL). To the reaction mixture was added TSTU (32.9 mg, 0.11 mmol). After stirring the reaction mixture for 40 min, the reaction mixture was added to 4-[(2S)-3-amino-2-(pyrrolidin-1-yl)propyl]-2-fluorobenzamide (31.9 mg, 0.12 mmol) in DMF (0.4 mL). The reaction mixture was stirred at RT for 1 h, diluted with EtOAc (10 mL), then washed with sat. NaHCO₃, brine (3×), dried over MgSO₄, then concentrated. The resulting residue was purified by column chromatography (4 g silica, 0-25% MeOH/DCM plus 1% NH₄OH) Eluted at 20% MeOH in DCM) to give the title compound (30.1 mg, 53%). MS (m/z): 524.3 (M+H).

Example B24: Preparation of 3-chloro-4-[(2S)-2-(dimethylamino)-3-[(3R)-3-(2-methylpyrimidin-5-yl)-3-[1-(trifluoromethyl)cyclopropyl]propanamido] propyl]benzamide ("Compound 24")

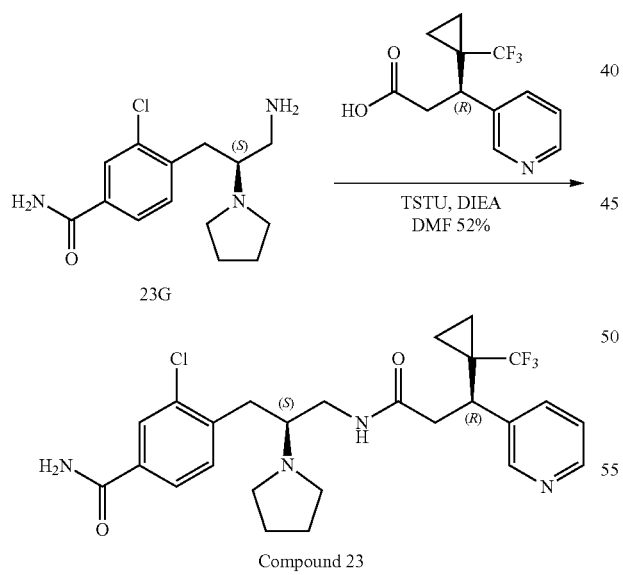

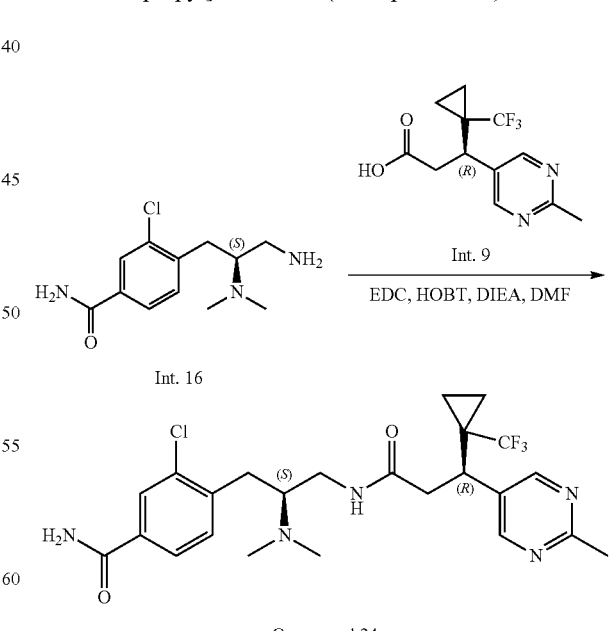

Step 1: Methyl (2S)-2-{[(tert-butoxy)carbonyl]amino}-3-(2-chloro-4-cyanophenyl)propanoate (23B) was prepared in the same method as described in Intermediate 1B.

Step 2: Tert-butyl N-[(2S)-1-(2-chloro-4-cyanophenyl)-3-hydroxypropan-2-yl]carbamate (23C) was prepared in the same method as described in Intermediate 1C.

Compound 24 (74.8 mg, 21%) was synthesized from Int. 16 and Int. 9 as described in Example B9. MS (m/z): 512.3 (M+H).

Example B25: Preparation of 3-chloro-4-[(2S)-3-[(3S)-3-cyclopropyl-3-(2-methylpyrimidin-5-yl)propanamido]-2-(dimethylamino)propyl]benzamide ("Compound 25")

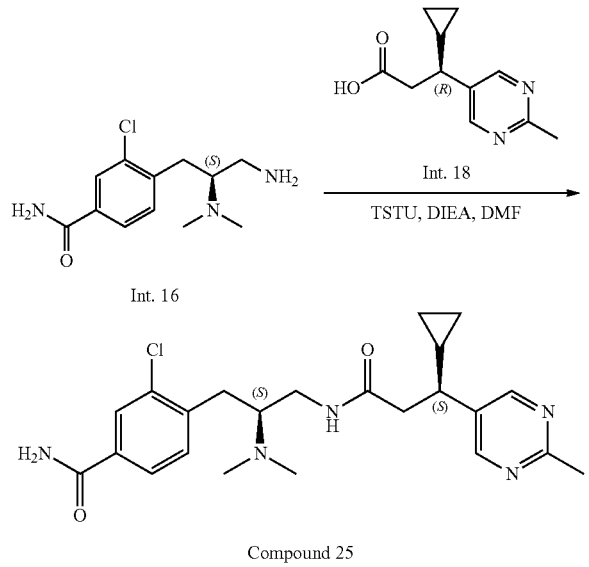

Compound 25

Compound 25 (35 mg, 70%) was synthesized from Int. 16 and Int. 18 as described in Example B17. MS (m/z): 444.2 (M+H).

Example B26: Preparation of 3-chloro-4-[(2S)-2-(dimethylamino)-3-[3-(pyridin-4-yl)-3-[1-(trifluoromethyl)cyclopropyl]propanamido]propyl]benzamide ("Compound 26")

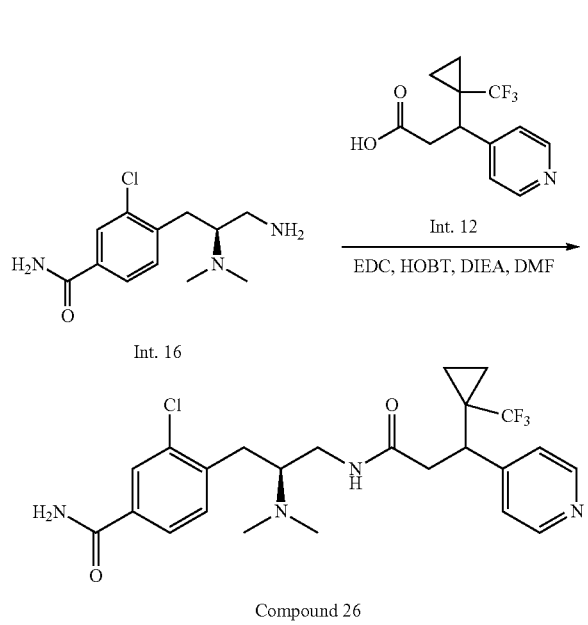

Compound 26

Compound 26 (34 mg, 64%) was synthesized from Int. 16 and Int. 12 as described in Example B9. MS (m/z): 497.2 (M+H).

Example B27: Preparation of 3-chloro-4-((2S)-2-(dimethylamino)-3-(3-(pyrimidin-2-yl)-3-(1-(trifluoromethyl) cyclopropyl)propanamido)propyl)benzamide ("Compound 27")

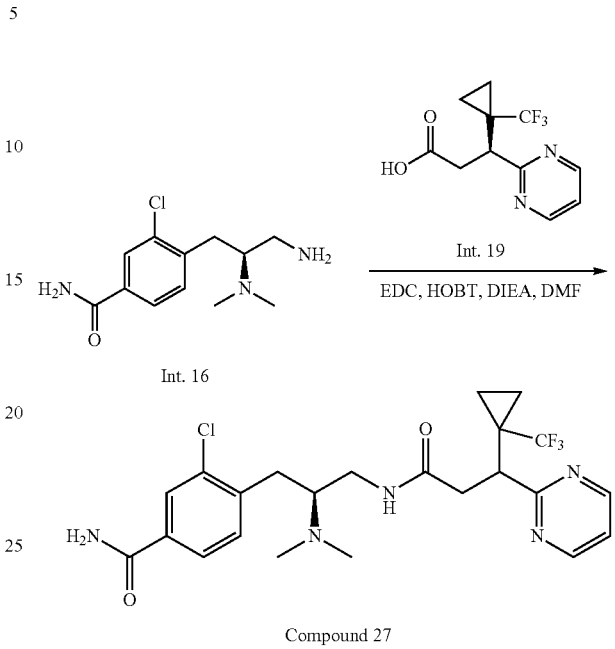

Compound 27

Compound 27 (26 mg, 54%) was synthesized from Int. 16 and Int. 19 as described in Example B9. MS (m/z): 498.1 (M+H).

Example B28: Preparation of 3-chloro-4-((S)-2-(dimethylamino)-3-((R)-3-(pyridin-3-yl)-3-(1-(trifluoromethyl)cyclopropyl)propanamido)propyl)benzamide ("Compound 28")

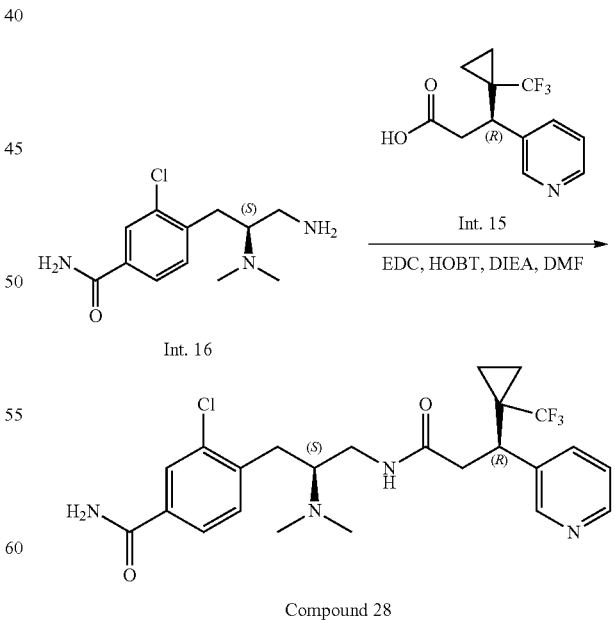

Compound 28

Compound 28 (226 mg, 60%) was synthesized from Int. 16 and Int. 15 as described in Example B9. MS (m/z): 497.2 (M+H).

Example B29: Preparation of 3-chloro-4-[(2S)-2-(dimethylamino)-3-{3-[2-(dimethylamino)pyrimidin-5-yl]-3-[1-(trifluoromethyl)cyclopropyl]propanamido}propyl]benzamide ("Compound 29")

Example B31: Preparation of 3-chloro-4-[(2S)-3-[3-(5-chloropyrimidin-2-yl)-3-[1-(trifluoromethyl)cyclopropyl]propanamido]-2-(dimethylamino)propyl]benzamide ("Compound 31")

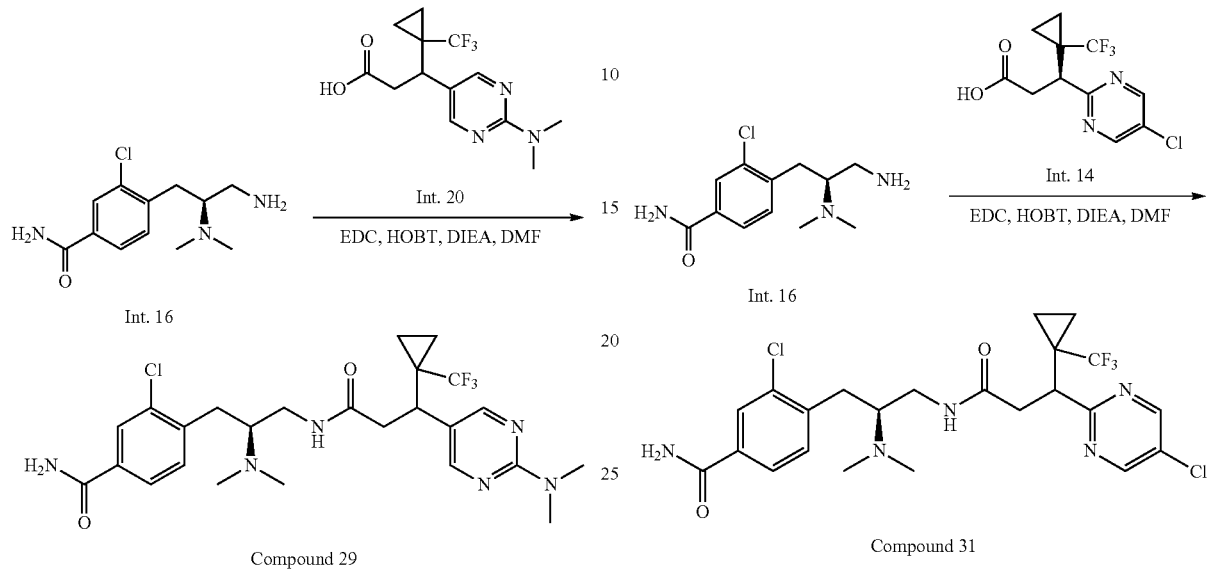

Compound 29 (17.5 mg, 64%) was synthesized from Int. 16 and Int. 20 as described in Example B9. MS (m/z): 541.2 (M+H).

Example B30: Preparation of 3-chloro-4-[(2S)-2-(dimethylamino)-3-[3-(pyrimidin-5-yl)-3-[1-(trifluoromethyl)cyclopropyl]propanamido]propyl]benzamide ("Compound 30")

Compound 31 (43.3 mg, 64%) was synthesized from Int. 16 and Int. 14 as described in Example B9. MS (m/z): 532.2 (M+H).

Example B32: Preparation of 3-chloro-4-[(2S)-2-(dimethylamino)-3-{3-[1-(trifluoromethyl)cyclopropyl]-3-[6-(trifluoromethyl)pyridin-3-yl]propanamido}propyl]benzamide ("Compound 32")

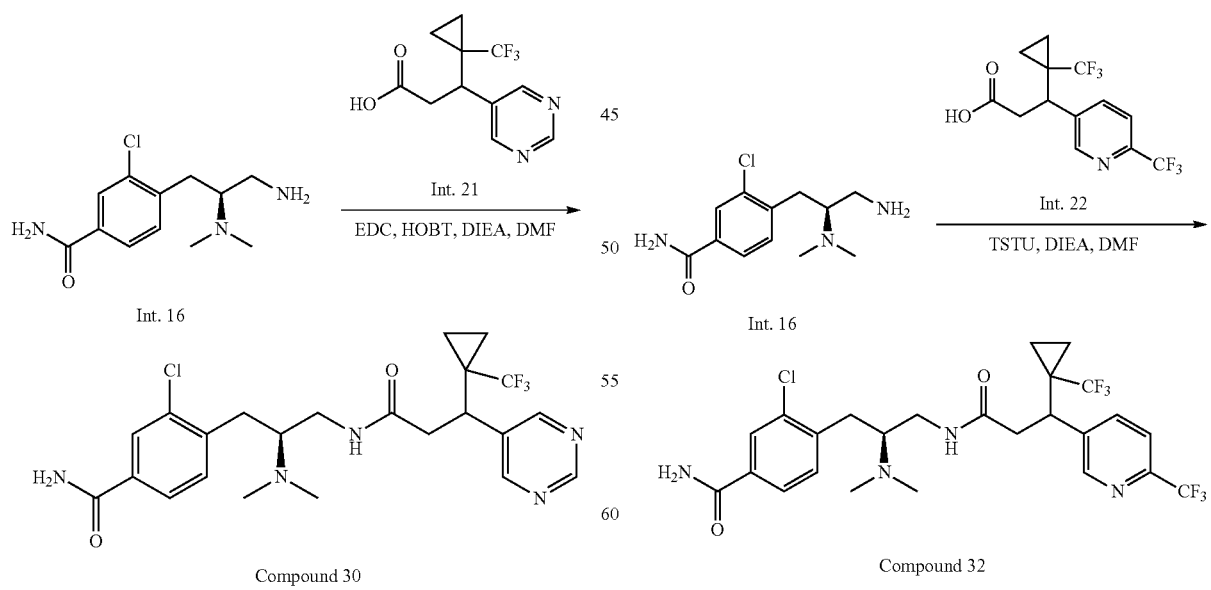

Compound 30 (39.8 mg, 84%) was synthesized from Int. 16 and Int. 21 as described in Example B9. MS (m/z): 498.2 (M+H).

Compound 32 (36.3, 70%) was synthesized from Int. 16 and Int. 22 as described in Example B17. MS (m/z): 565.2 (M+H).

Example B33: Preparation of 3-chloro-4-[(2S)-2-(dimethylamino)-3-[3-(2-methoxypyrimidin-5-yl)-3-[1-(trifluoromethyl)hydropropyl]propanamido]propyl]benzamide ("Compound 33")

Example B35: Preparation of 3-chloro-4-[(2S)-2-(dimethylamino)-3-[3-(6-methoxypyridin-3-yl)-3-[1-(trifluoromethyl)cyclopropyl]propanamido]propyl]benzamide ("Compound 35")

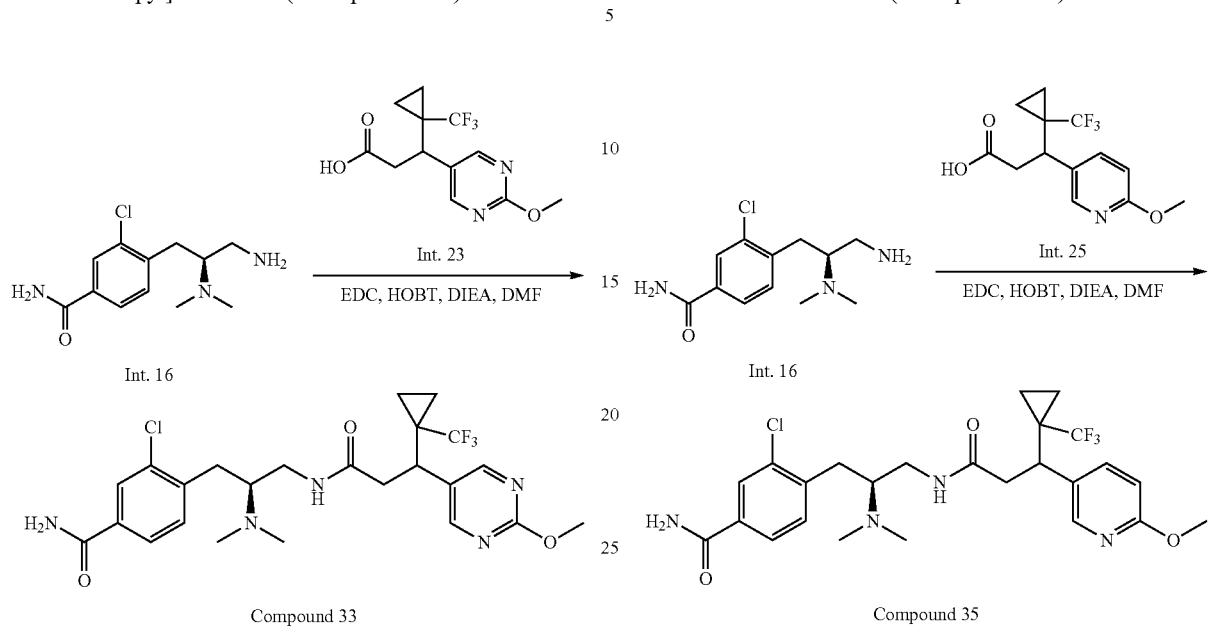

Compound 33 (28.9 mg, 39%) was synthesized from Int. 16 and Int. 23 as described in Example B9. MS (m/z): 528.2 (M+H).

Compound 35 (45 mg, 72%) was synthesized from Int. 16 and Int. 25 as described in Example B9. MS (m/z): 527.2 (M+H).

Example B34: Preparation of 3-chloro-4-[(2S)-2-(dimethylamino)-3-[3-(2-methylpyrimidin-5-yl)-3-[1-(trifluoromethyl)cyclopropyl]propanamido]propyl]benzamide ("Compound 34")

Example B36: Preparation of 3-chloro-4-[(2S)-2-(dimethylamino)-3-[3-(5-fluoropyridin-3-yl)-3-[1-(trifluoromethyl)cyclopropyl]propanamido]propyl]benzamide ("Compound 36")

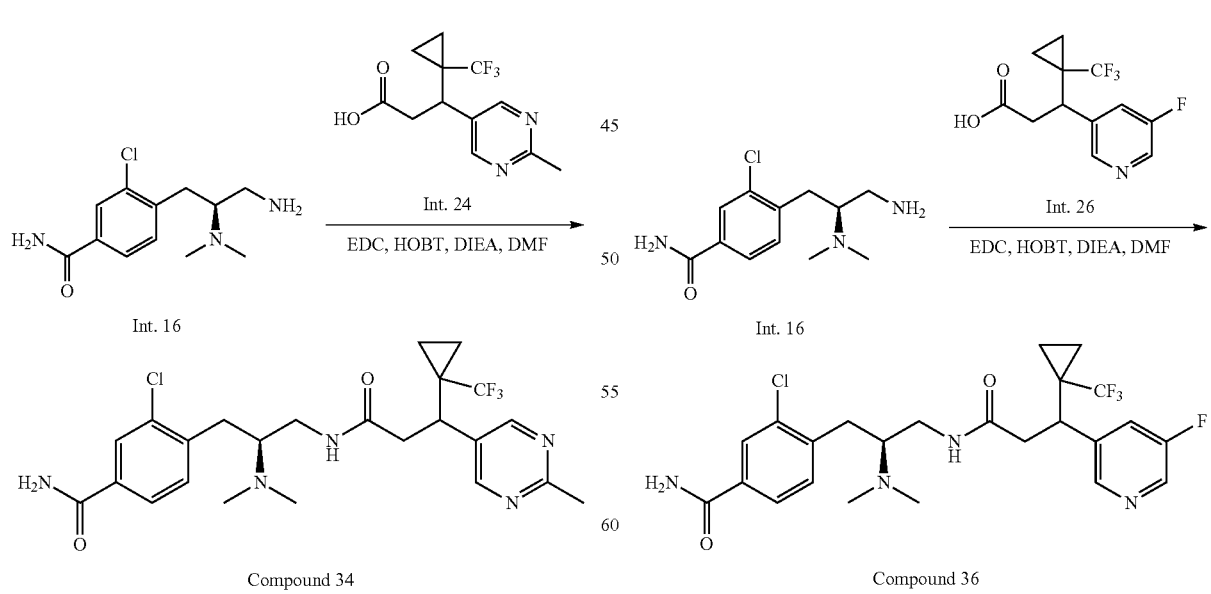

Compound 34 (15.7 mg, 26%) was synthesized from Int. 16 and Int. 24 as described in Example B9. MS (m/z): 512.2 (M+H).

Compound 36 (39.9 mg, 79%) was synthesized from Int. 16 and Int. 26 as described in Example B9. MS (m/z): 515.2 (M+H).

Example B37: Preparation of 3-chloro-4-[(2S)-3-[3-(5-chloropyridin-2-yl)-3-[1-(trifluoromethyl)cyclopropyl]propanamido]-2-(dimethylamino)propyl]benzamide ("Compound 37")

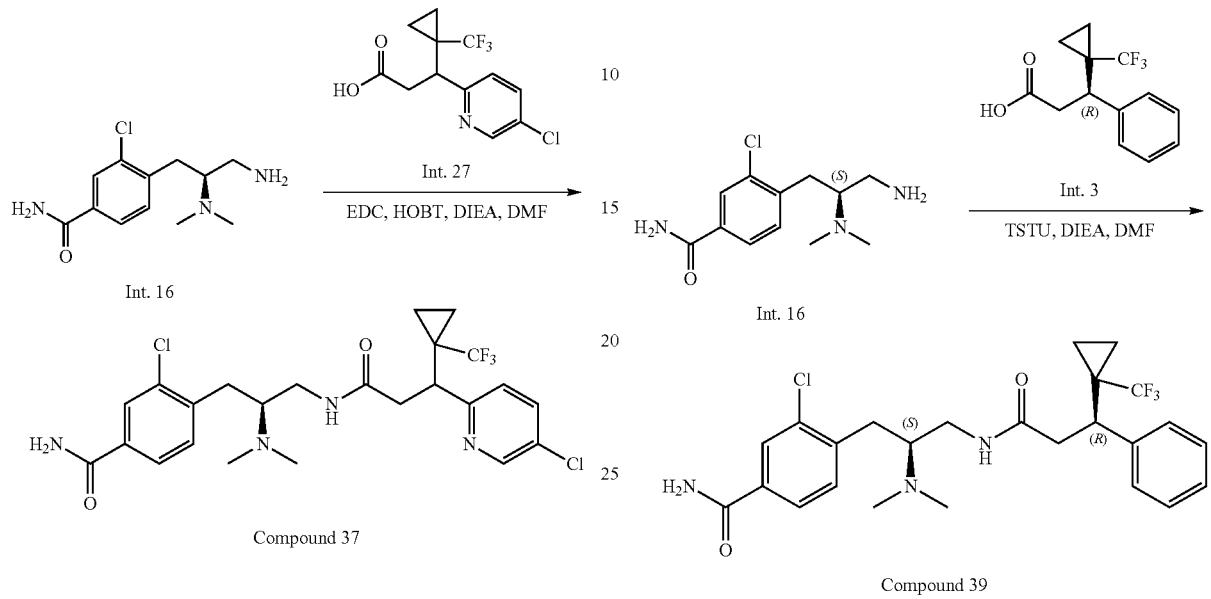

Compound 37

Compound 37 (39.9 mg, 79%) was synthesized from Int. 16 and Int. 27 as described in Example B9. MS (m/z): 531.2 (M+H).

Example B38: Preparation of 3-chloro-4-[(2S)-2-(dimethylamino)-3-[3-(pyridin-3-yl)-3-[1-(trifluoromethyl)cyclopropyl]propanamido]propyl]benzamide ("Compound 38")


Compound 38

Compound 38 (90 mg, 90%) was synthesized from Int. 16 and Int. 28 as described in Example B9. MS (m/z): 497.2 (M+H).

Example B39: Preparation of 3-chloro-4-[(2S)-2-(dimethylamino)-3-[(3R)-3-phenyl-3-[1-(trifluoromethyl)cyclopropyl]propanamido]propyl]benzamide ("Compound 39")

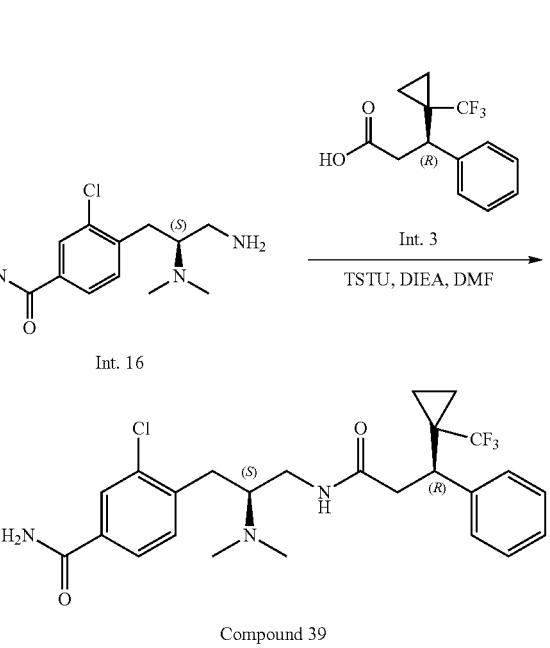

Compound 39

Compound 39 (36.3 mg, 70%) was synthesized from Int. 16 and Int. 3 as described in Example B17. MS (m/z): 496.2 (M+H).

Example B40: Preparation of 3-chloro-4-((S)-2-(dimethylamino)-3-((R)-4-methyl-3-phenylpentanamido)propyl)benzamide ("Compound 40")

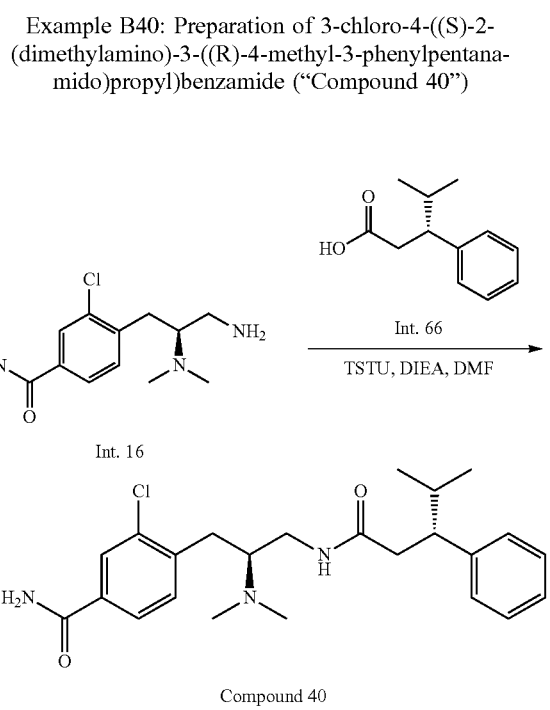

Compound 40

Compound 40 (10 mg, 15%) was synthesized from Int. 16 and Int. 66 as described in Example B17. MS (m/z): 430.2 (M+H).

Example B41: Preparation of 3-chloro-4-((S)-2-(dimethylamino)-3-((S)-3-(pyridin-3-yl)-3-(1-(trifluoromethyl)cyclopropyl)propanamido)propyl)benzamide ("Compound 41")

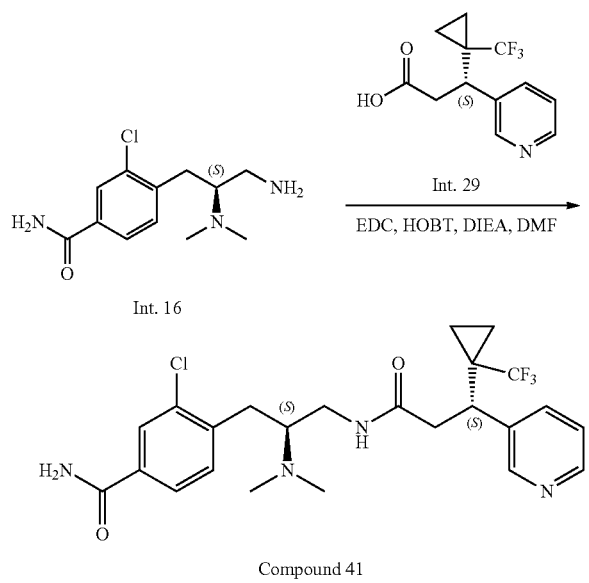

Compound 41

Compound 41 (220 mg, 56%) was synthesized from Int. 16 and Int. 29 as described in Example B9. MS (m/z): 497.2 (M+H).

Example B42: Preparation of 4-((S)-3-((S)-3-cyclopropyl-3-(2-methylpyrimidin-5-yl)propanamido)-2-(dimethylamino)propyl)-2-fluoro-3-methylbenzamide ("Compound 42")

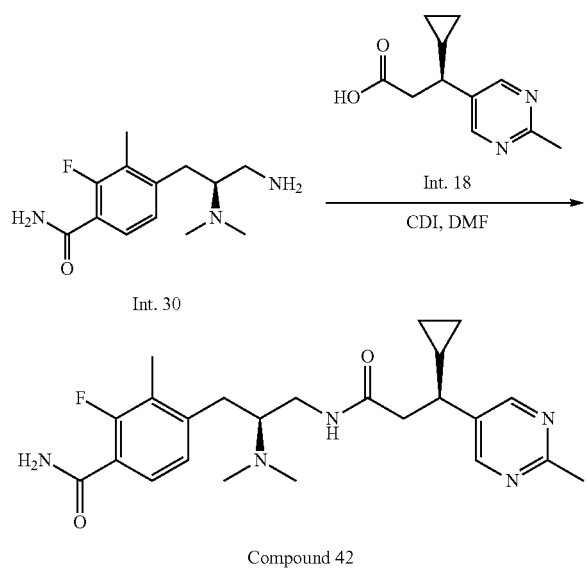

Compound 42

Compound 42 (10 mg, 28%) was synthesized from Int. 30 and Int. 18 as described in Example B1. MS (m/z): 442.2 (M+H).

Example B43: Preparation of 4-((S)-2-(dimethylamino)-3-((S)-3-(2-methylthiazol-5-yl)-3-(1-(trifluoromethyl)cyclopropyl)propanamido)propyl)-2-fluoro-3-methylbenzamide ("Compound 43")

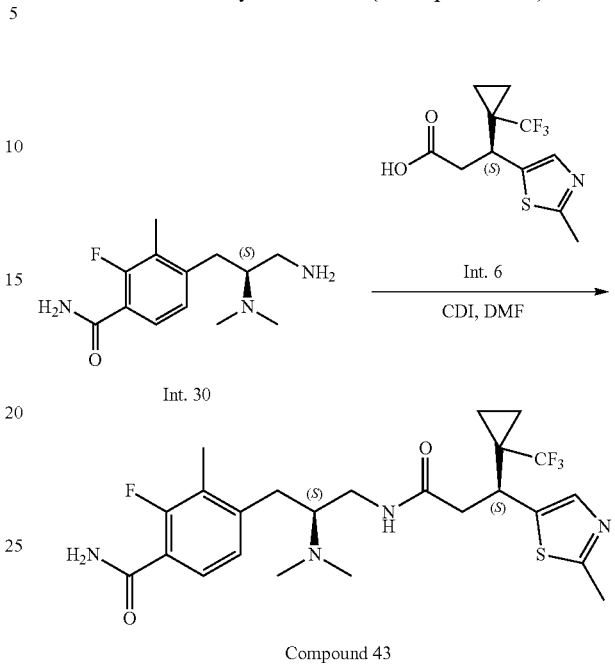

Compound 43

Compound 43 (38 mg, 59%) was synthesized from Int. 30 and Int. 6 as described in Example B1. MS (nm/z): 515.2 (M+H).

Example B44: Preparation of 4-((S)-2-(dimethylamino)-3-((R)-3-(2-methylpyrimidin-5-yl)-3-(1-(trifluoromethyl)cyclopropyl)propanamido)propyl)-2-fluoro-3-methylbenzamide ("Compound 44")

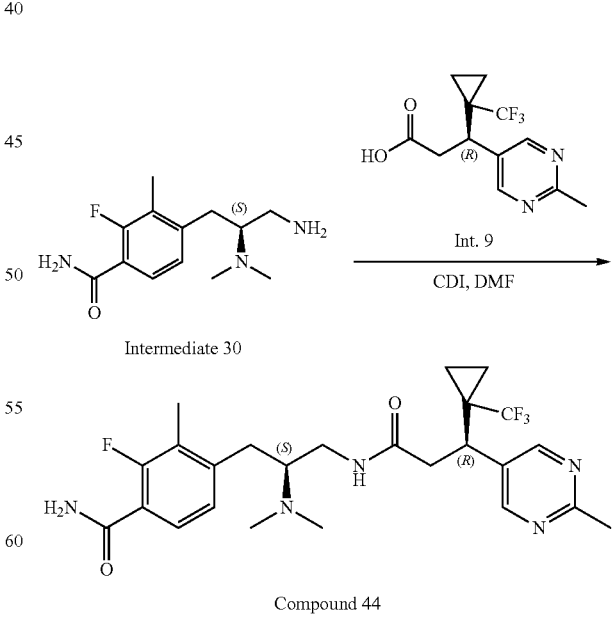

Compound 44

Compound 44 (18 mg, 49%) was synthesized from Int. 30 and Int. 9 as described in Example B1. MS (m/z): 510.2 (M+H).

Example B45: Preparation of 4-((S)-2-(dimethylamino)-3-((R)-3-(5-fluoropyridin-3-yl)-4,4-dimethylpentanamido)propyl)-2-fluoro-3-methylbenzamide ("Compound 45")

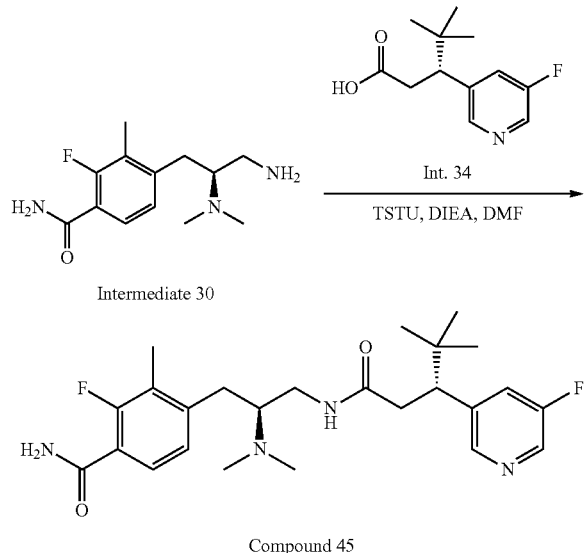

Compound 45

Compound 45 (18 mg, 36%) was synthesized from Int. 30 and Int. 34 as described in Example B17. MS (m/z): 461.2 (M+H).

Example B46: Preparation of 4-((S)-2-(dimethylamino)-3-((R)-3-(6-methylpyridin-3-yl)-3-(1-(trifluoromethyl)cyclopropyl)propanamido)propyl)-2-fluoro-3-methylbenzamide ("Compound 46")

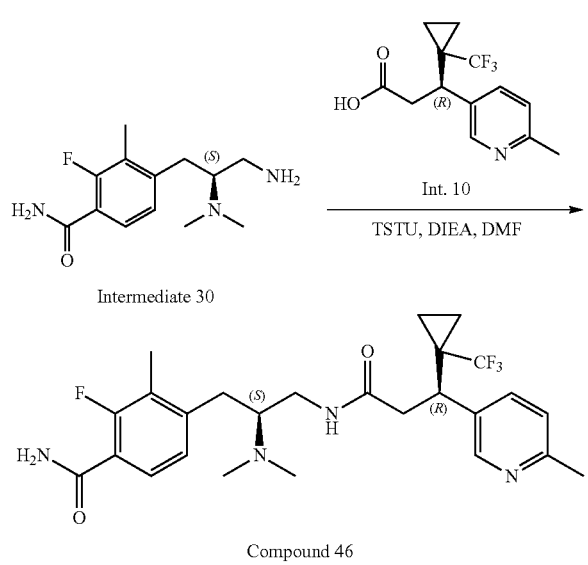

Compound 46

Compound 46 (33 mg, 71%) was synthesized from Int. 30 and Int. 10 as described in Example B17. MS (m/z): 509.3 (M+H).

Example B47: Preparation of 4-((S)-2-(dimethylamino)-3-((R)-3-(6-methylpyridin-3-yl)-3-(1-(trifluoromethyl)cyclopropyl)propanamido)propyl)-26-difluorobenzamide ("Compound 47")

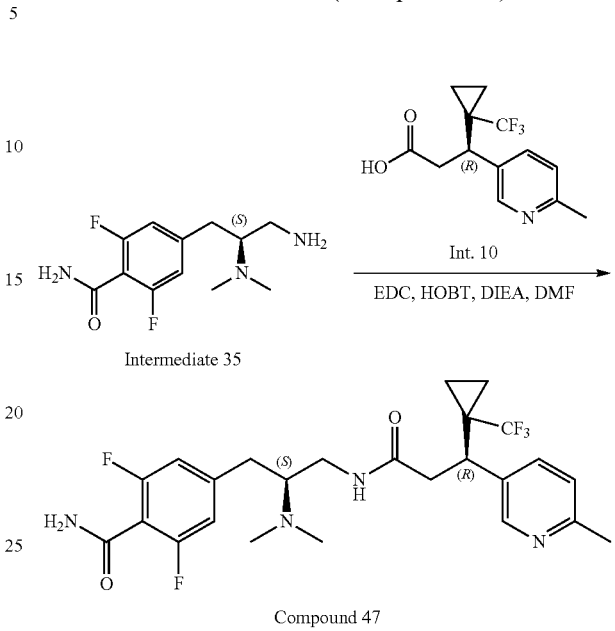

Compound 47

Compound 47 (5 mg, 10%) was synthesized from Int. 35 and Int. 10 as described in Example B9. MS (m/z): 513.2 (M+H).

Example B48: Preparation of 4-((S)-2-(dimethylamino)-3-((R)-3-(2-methylpyrimidin-5-yl)-3-(1-(trifluoromethyl)cyclopropyl)propanamido)propyl)-2,6-difluorobenzamide ("Compound 48")

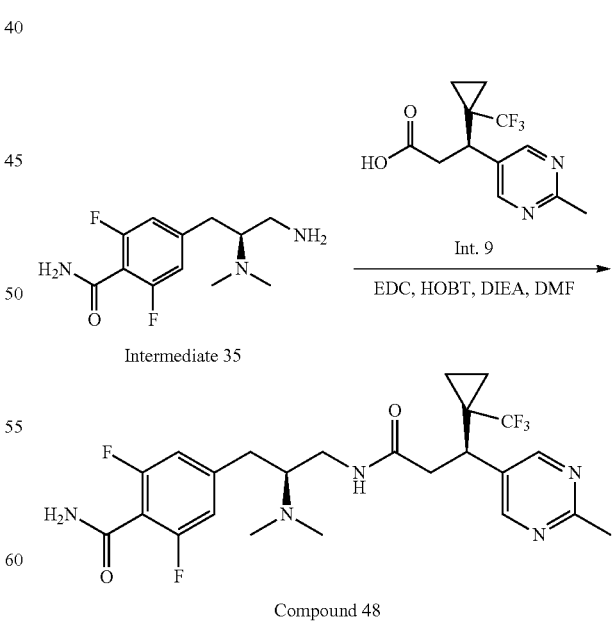

Compound 48

Compound 48 (12 mg, 20%) was synthesized from Int. 35 and Int. 9 as described in Example B9. MS (m/z): 514.2 (M+H).

Example B49: Preparation of 4-[(2S)-2-(dimethylamino)-3-[3-(6-methoxypyridin-3-yl)-3-[1-(trifluoromethyl)cyclopropyl]propanamido]propyl]-2,6-difluorobenzamide ("Compound 49")

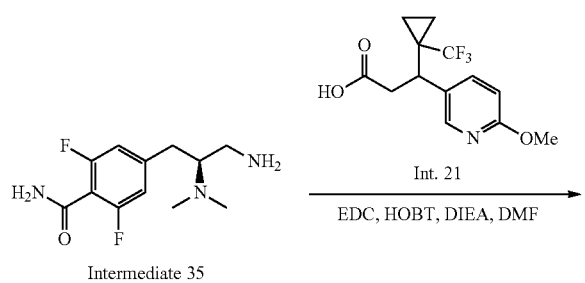

Compound 49

Compound 49 (15 mg, 45%) was synthesized from Int. 35 and Int. 25 as described in Example B9. MS (m/z): 529.3 (M+H).

Example B50: Preparation of 4-[(2S)-2-(dimethylamino)-3-[3-(pyridin-3-yl)-3-[1-(trifluoromethyl)cyclopropyl]propanamido]propyl]-2,6-difluorobenzamide ("Compound 50")

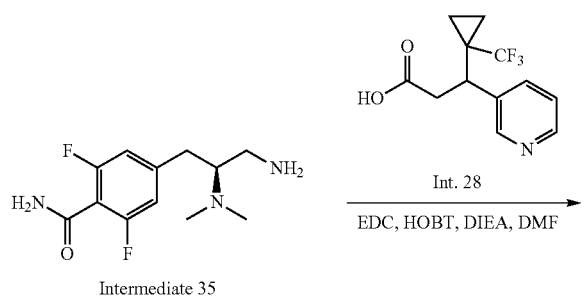

Compound 50

Compound 50 (30 mg, 51%) was synthesized from Int. 35 and Int. 28 as described in Example B9. MS (m/z): 499.2 (M+H).

Example B51: Preparation of 4-((S)-2-(dimethylamino)-3-((R)-3-(furan-3-yl)-3-(1-(trifluoromethyl)cyclopropyl)propanamido)propyl)-2-fluorobenzamide ("Compound 51")

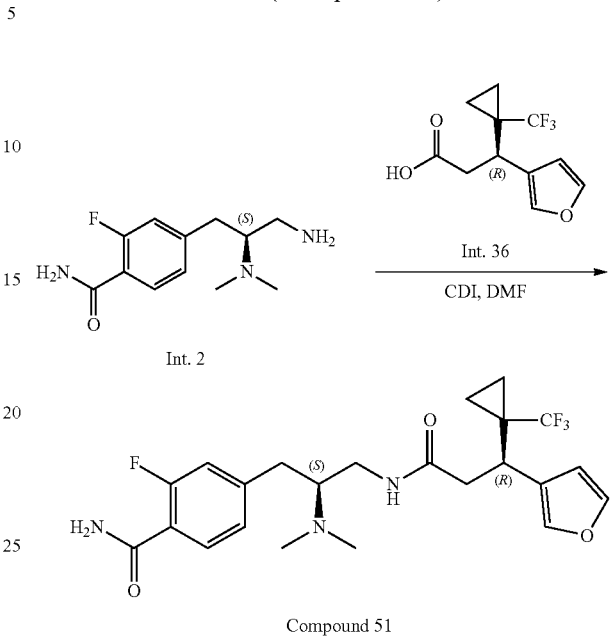

Compound 51

Compound 51 (155 mg, 69%) was synthesized from Int. 2 and Int. 36 as described in Example B1. MS (m/z): 470.2 (M+H).

Example B52: Preparation of 4-((S)-2-(dimethylamino)-3-((S)-3-(5-methylthiophen-3-yl)-3-(1-(trifluoromethyl)cyclopropyl)propanamido)propyl)-2-fluorobenzamide ("Compound 52")

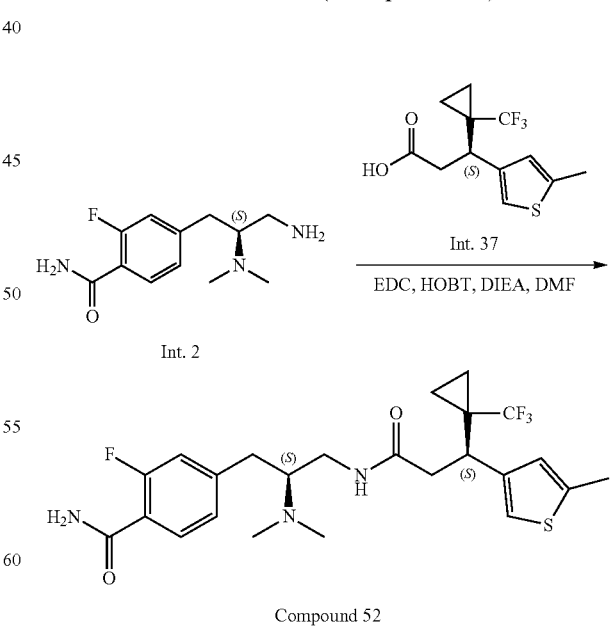

Compound 52

Compound 52 (155 mg, 69%) was synthesized from Int. 2 and Int. 37 as described in Example B9. MS (m/z): 500.2 (M+H).

Example B53: Preparation of 4-((S)-2-(dimethyl-amino)-3-((S)-3-(5-methylthiophen-2-yl)-3-(1-(trifluoromethyl)cyclopropyl)propanamido)propyl)-2-fluorobenzamide ("Compound 53")

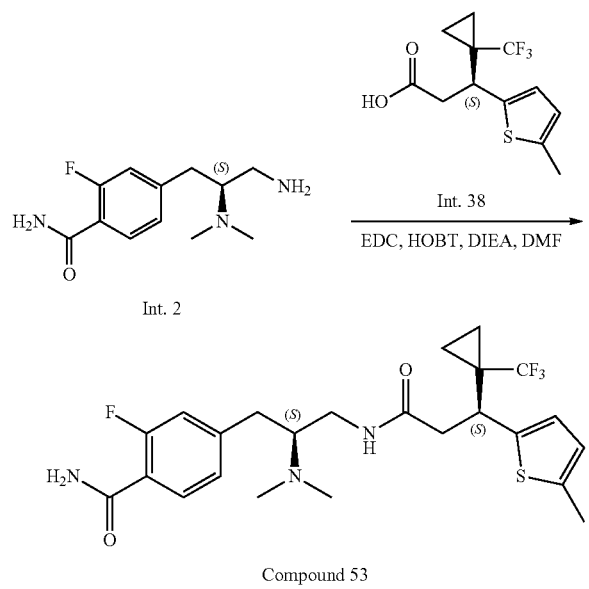

Compound 53

Compound 53 (15 mg, 34%) was synthesized from Int. 2 and Int. 38 as described in Example B9. MS (m/z): 500.2 (M+H).

Example B54: Preparation of 4-((S)-2-(dimethyl-amino)-3-((S)-3-(thiophen-3-yl)-3-(1-(trifluoromethyl)cyclopropyl)propanamido)propyl)-2-fluorobenzamide ("Compound 54")

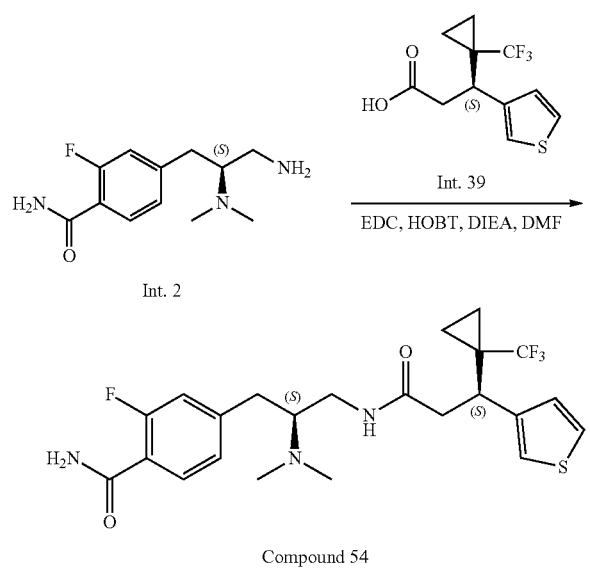

Compound 54

Compound 54 (40 mg, 79%) was synthesized from Int. 2 and Int. 39 as described in Example B9. MS (m/z): 486.1 (M+H).

Example B55: Preparation of 4-((S)-2-(dimethyl-amino)-3-((S)-3-(thiazol-5-yl)-3-(1-(trifluoromethyl)cyclopropyl)propanamido)propyl)-2-fluorobenzamide ("Compound 55")

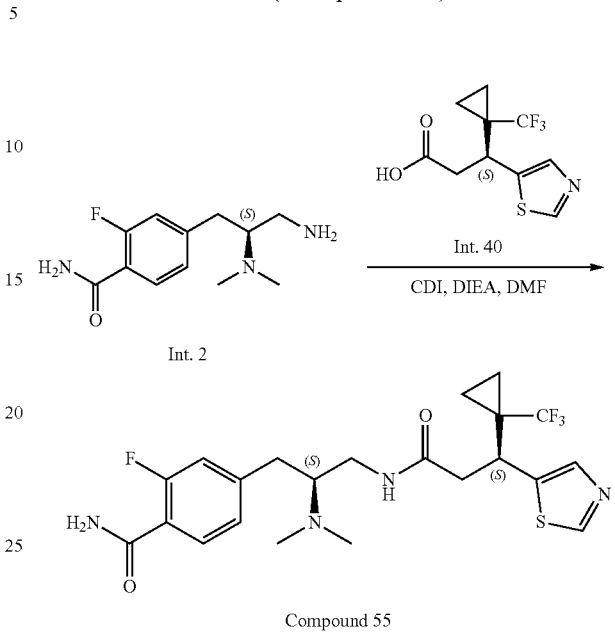

Compound 55

Compound 55 (34 mg, 74%) was synthesized from Int. 2 and Int. 40 as described in Example B1. MS (m/z): 487.2 (M+H).

Example B56: Preparation of 4-((S)-2-(dimethyl-amino)-3-((S)-3-(5-methylthiazol-2-yl)-3-(1-(trifluoromethyl)cyclopropyl)propanamido)propyl)-2-fluorobenzamide ("Compound 56")

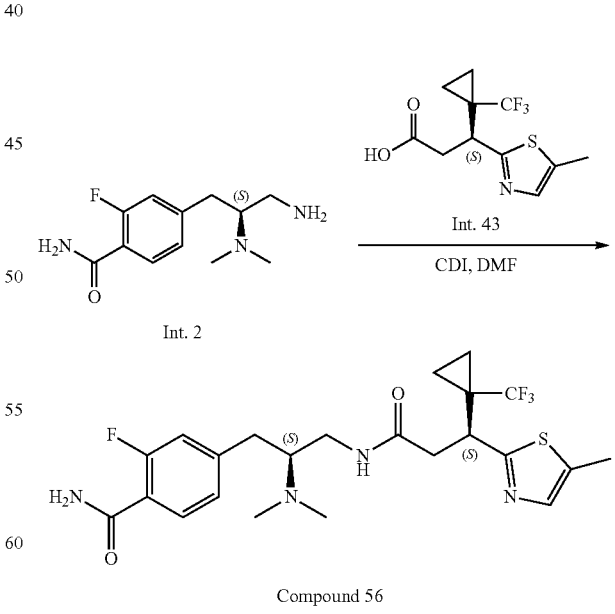

Compound 56

Compound 56 (72 mg, 81%) was synthesized from Int. 2 and Int. 43 as described in Example B1. MS (m/z): 501.1 (M+H).

Example B57: Preparation of 4-((S)-2-(dimethylamino)-3-((S)-3-(5-methylpyrimidin-2-yl)-3-(1-(trifluoromethyl)cyclopropyl)propanamido)propyl)-2-fluorobenzamide ("Compound 57")

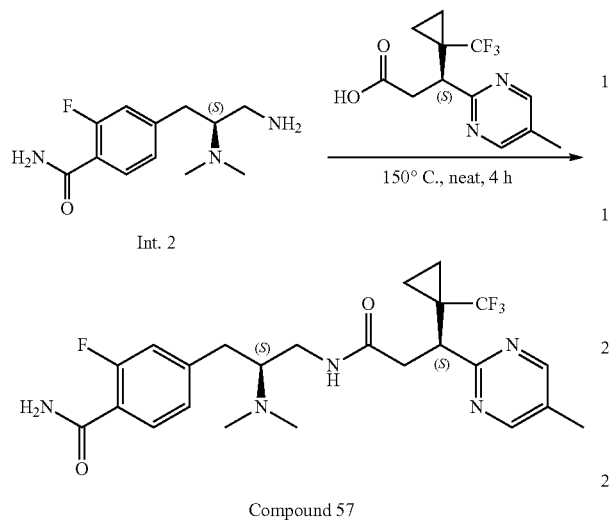

Compound 57

A mixture of Int. 2 (94.8 mg, 2 eq., 396 μmol) and methyl (3S)-3-(5-methylpyrimidin-2-yl)-3-[1-(trifluoromethyl)cyclopropyl]propanoate (57.1 mg, 198 μmol) was heated to 150° C. neat for 4 h by microwave. The mixture was cooled to RT, dissolved in DCM and purified by flash chromatography (0-15% MeOH/DCM) to give 4-[(2S)-2-(dimethylamino)-3-[(3R)-3-(5-methylpyrimidin-2-yl)-3-[1-(trifluoromethyl)cyclopropyl]propanamido]propyl]-2-fluorobenzamide (9.8 mg, 10%). MS (m/z): 496.2 (M+H).

Example B58: Preparation of 4-((S)-2-(dimethylamino)-3-((R)-3-(2-methylthiazol-5-yl)-3-(1-(trifluoromethyl)cyclopropyl)propanamido)propyl)-2-fluorobenzamide ("Compound 58")

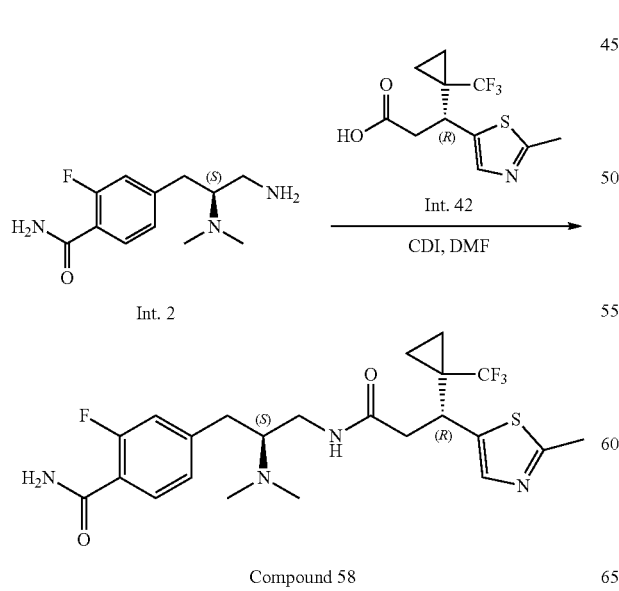

Compound 58

Compound 58 (59 mg, 68%) was synthesized from Int. 2 and Int. 42 as described in Example B1. MS (m/z): 501.2 (M+H).

Example B59: Preparation of 4-((S)-2-(dimethylamino)-3-((S)-3-(2-methylthiazol-5-yl)-3-(1-(trifluoromethyl)cyclopropyl)propanamido)propyl)-2-fluorobenzamide ("Compound 59")

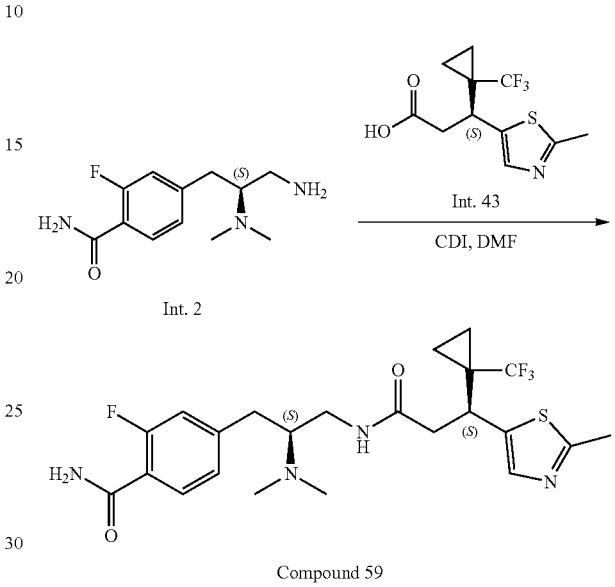

Compound 59

Compound 59 (72 mg, 81%) was synthesized from Int. 2 and Int. 43 as described in Example B1. MS (m/z): 501.2 (M+H).

Example B60: Preparation of 4-((S)-2-(dimethylamino)-3-((R)-5-methyl-3-(pyridin-3-yl)hexanamido)propyl)-2-fluorobenzamide ("Compound 60")

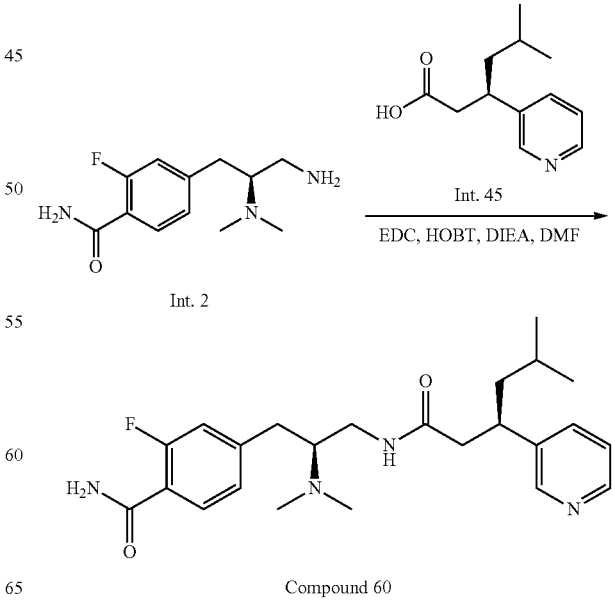

Compound 60

Compound 60 (31 mg, 68%) was synthesized from Int. 2 and Int. 45 as described in Example B9. MS (m/z): 429.2 (M+H).

Example B61: Preparation of 4-((S)-2-(dimethylamino)-3-((R)-3-(3-fluoropyridin-4-yl)-3-(1-(trifluoromethyl)cyclopropyl)propanamido)propyl)-2-fluorobenzamide ("Compound 61")

Compound 62 (28 mg, 63%) was synthesized from Int. 2 and Int. 46 as described in Example B9. MS (m/z): 427.2 (M+H).

Example B63: Preparation of 4-((S)-2-(dimethylamino)-3-((R)-3-(5-fluoropyridin-3-yl)-4,4-dimethylpentanamido)propyl)-2-fluorobenzamide ("Compound 63")

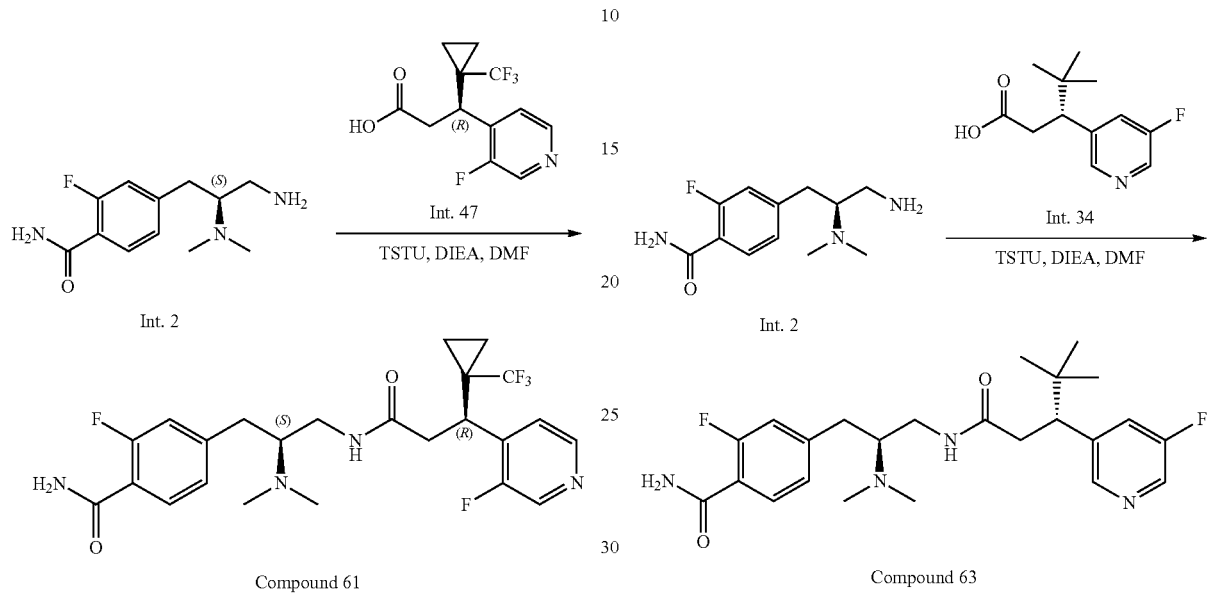

Compound 61 (31 mg, 68%) was synthesized from Int. 2 and Int. 47 as described in Example B9. MS (m/z): 499.2 (M+H).

Example B62: Preparation of 4-((S)-3-((S)-4-cyclopropyl-3-(pyridin-4-yl)butanamido)-2-(dimethylamino)propyl)-2-fluorobenzamide ("Compound 62")

Compound 63 (30 mg, 80%) was synthesized from Int. 2 and Int. 34 as described in Example B17. MS (m/z): 447.2 (M+H).

Example B64: Preparation of 4-((S)-3-((R)-4-cyclopropyl-3-(pyrimidin-5-yl)butanamido)-2-(dimethylamino)propyl)-2-fluorobenzamide ("Compound 64")

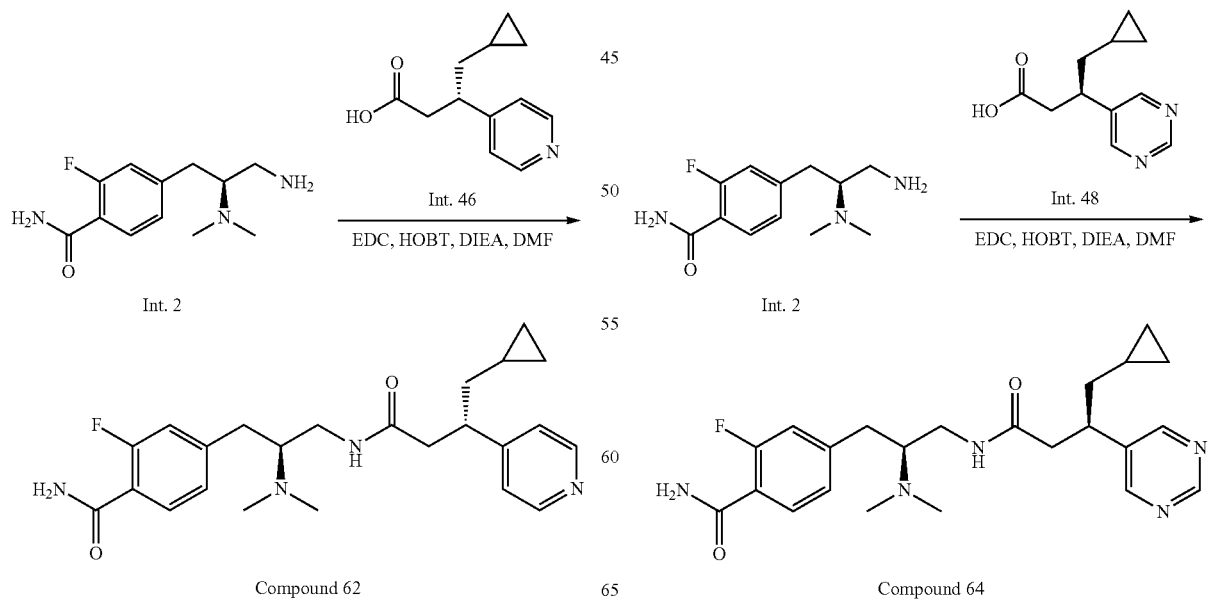

Compound 64 (24 mg, 54%) was synthesized from Int. 2 and Int. 48 as described in Example B9. MS (m/z): 427.2 (M+H).

Example B65: Preparation of 2-fluoro-4-((S)-3-((R)-3-(2-methylpyrimidin-5-yl)-3-(1-(trifluoromethyl)cyclopropyl)propanamido)-2-(pyrrolidin-1-yl)propyl)benzamide ("Compound 65")

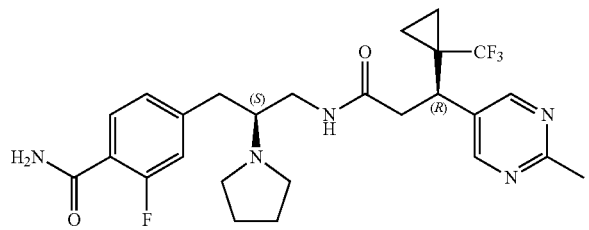

Compound 65 (41 mg, 71%) was synthesized from Int. 2 and 23G as described in Example B23. MS (m/z): 522.2 (M+H).

Example B66: Preparation of 4-((S)-3-((R)-4-cyclopropyl-3-(pyridin-3-yl)butanamido)-2-(dimethylamino)propyl)-2-fluorobenzamide ("Compound 66")

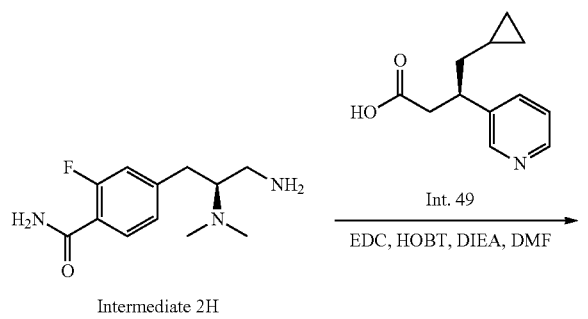

Compound 66

Compound 66 (14 mg, 43%) was synthesized from Int. 2 and Int. 49 as described in Example B9. MS (m/z): 427.3 (M+H).

Example B67: Preparation of 4-((S)-3-((S)-3-cyclopropyl-3-(2-methylpyrimidin-5-yl)propanamido)-2-(dimethylamino)propyl)-2-fluorobenzamide ("Compound 67")

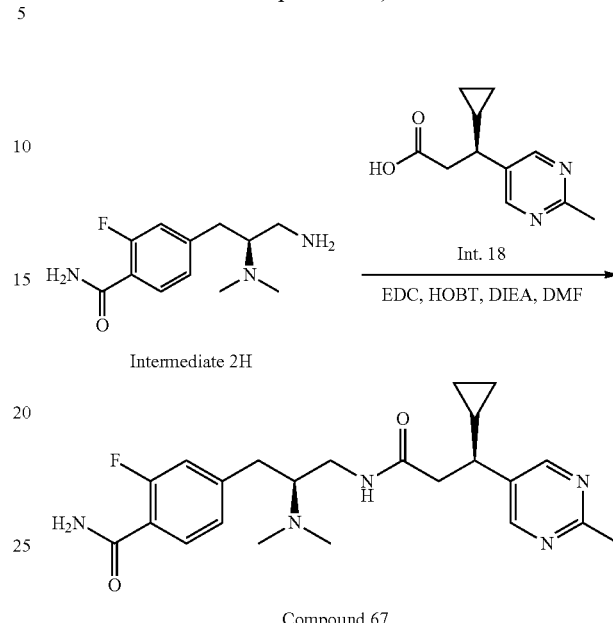

Compound 67

Compound 67 (14 mg, 43%) was synthesized from Int. 2 and Int. 18 as described in Example B9. MS (m/z): 428.0 (M+H).

Example B68: Preparation of 4-((S)-2-(dimethylamino)-3-((R)-3-(2-methylpyrimidin-5-yl)-3-(1-(trifluoromethyl)cyclopropyl)propanamido)propyl)-2-fluorobenzamide ("Compound 68")

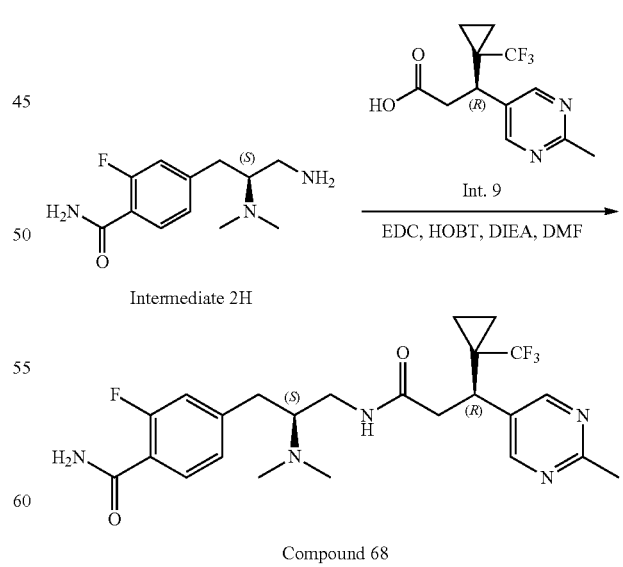

Compound 68

Compound 68 (14 mg, 43%) was synthesized from Int. 2 and Int. 9 as described in Example B9. MS (m/z): 496.3 (M+H).

Example B69: Preparation of 4-((2S)-3-(3-(5-chloropyridin-2-yl)-3-(1-(trifluoromethyl)cyclopropyl)propanamido)-2-(dimethylamino)propyl)-2-fluorobenzamide ("Compound 69")

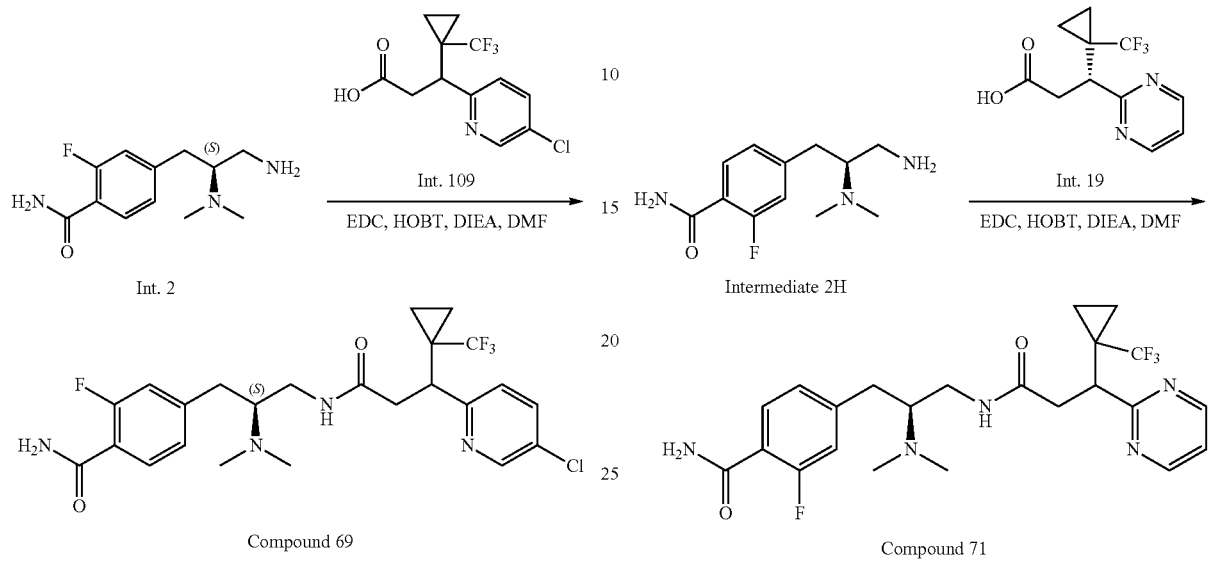

Compound 69

Compound 69 (28 mg, 72%) was synthesized from Int. 2 and Int. 109 as described in Example B9. MS (m/z): 515.2 (M+H).

Example B70: Preparation of 4-[(2S)-2-(dimethylamino)-3-[3-(pyridin-4-yl)-3-[1-(trifluoromethyl)cyclopropyl]propanamido]propyl]-2-fluorobenzamide ("Compound 70")

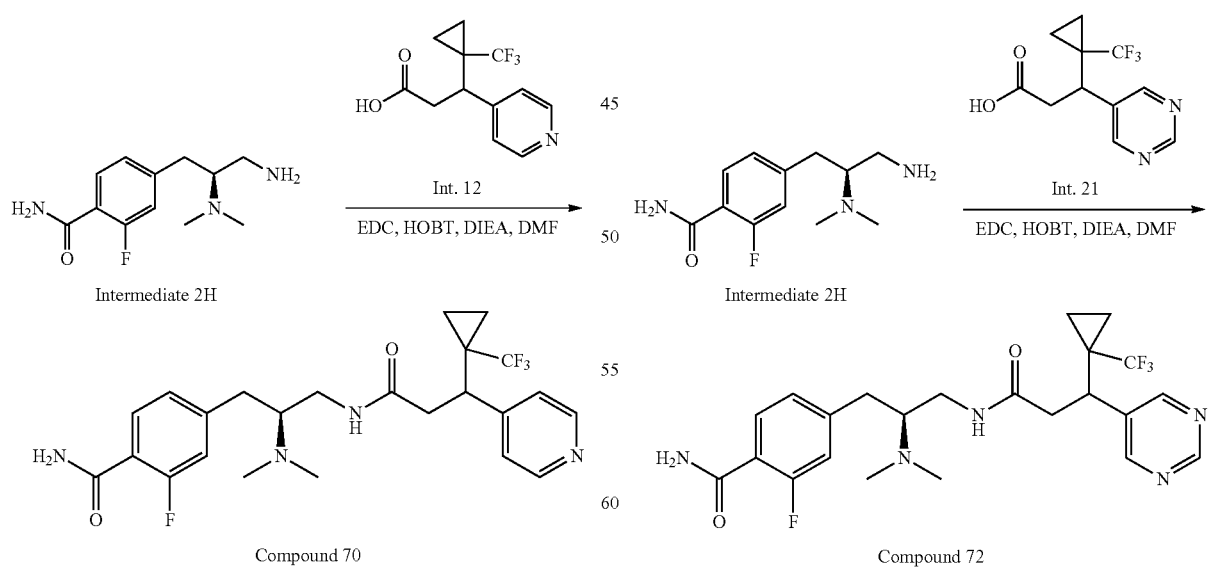

Compound 70

Compound 70 (31 mg, 61%) was synthesized from Int. 2 and Int. 12 as described in Example B9. MS (m/z): 481.2 (M+H).

Example B71: Preparation of 4-[(2S)-2-(dimethylamino)-3-[3-(pyrimidin-2-yl)-3-[1-(trifluoromethyl)cyclopropyl]propanamido]propyl]-2-fluorobenzamide ("Compound 71")

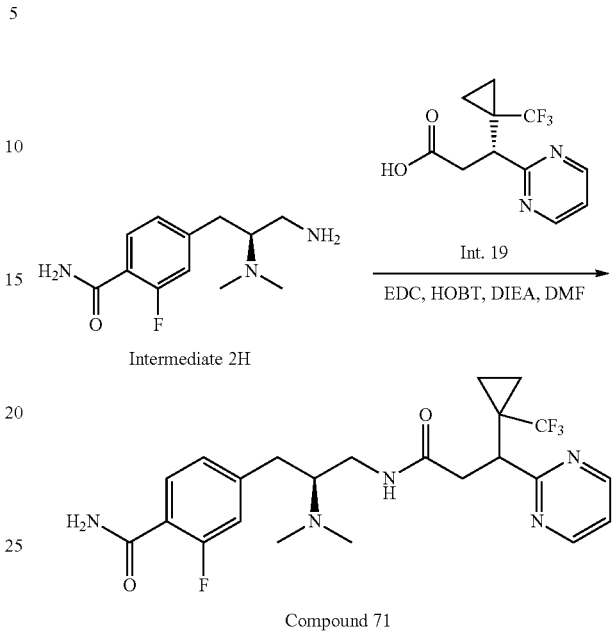

Compound 71

Compound 71 (25 mg, 67%) was synthesized from Int. 2 and Int. 19 as described in Example B9. MS (m/z): 482.3 (M+H).

Example B72: Preparation of 4-[(2S)-2-(dimethylamino)-3-[3-(pyrimidin-5-yl)-3-[1-(trifluoromethyl)cyclopropyl]propanamido]propyl]-2-fluorobenzamide ("Compound 72")

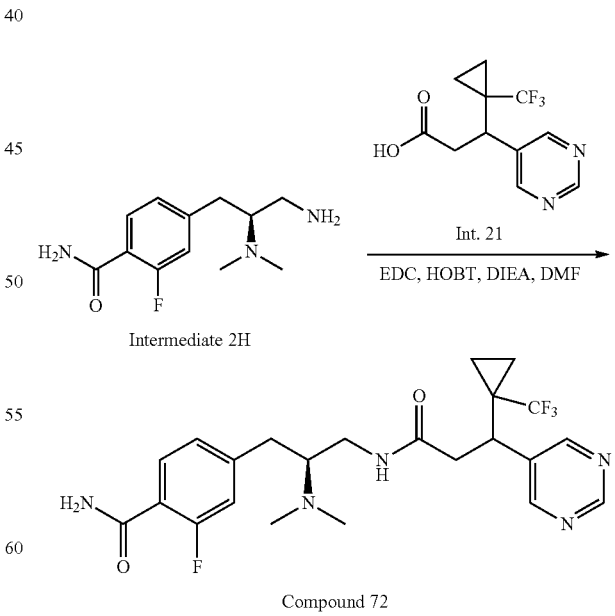

Compound 72

Compound 72 (17.2 mg, 43%) was synthesized from Int. 2 and Int. 21 as described in Example B9. MS (m/z): 482.2 (M+H).

Example B73: Preparation of 4-[(2S)-3-[3-(5-chloropyrimidin-2-yl)-3-[1-(trifluoromethyl)cyclopropyl]propanamido]-2-(dimethylamino)propyl]-2-fluorobenzamide ("Compound 73")

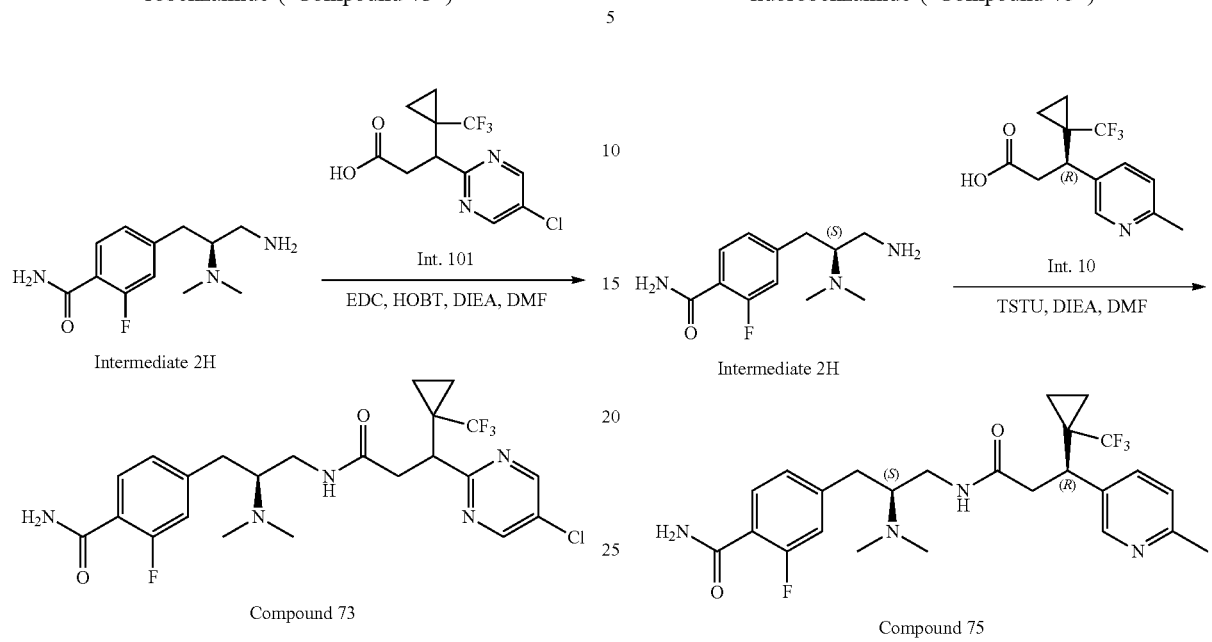

Compound 73

Compound 73 (10.2 mg, 17%) was synthesized from Int. 2 and Int. 101 as described in Example B9. MS (m/z): 516.2 (M+H).

Example B74: Preparation of 4-[(2S)-2-(dimethylamino)-3-[3-(pyridin-3-yl)-3-[1-(trifluoromethyl)cyclopropyl]propanamido]propyl]-2-fluorobenzamide ("Compound 74")

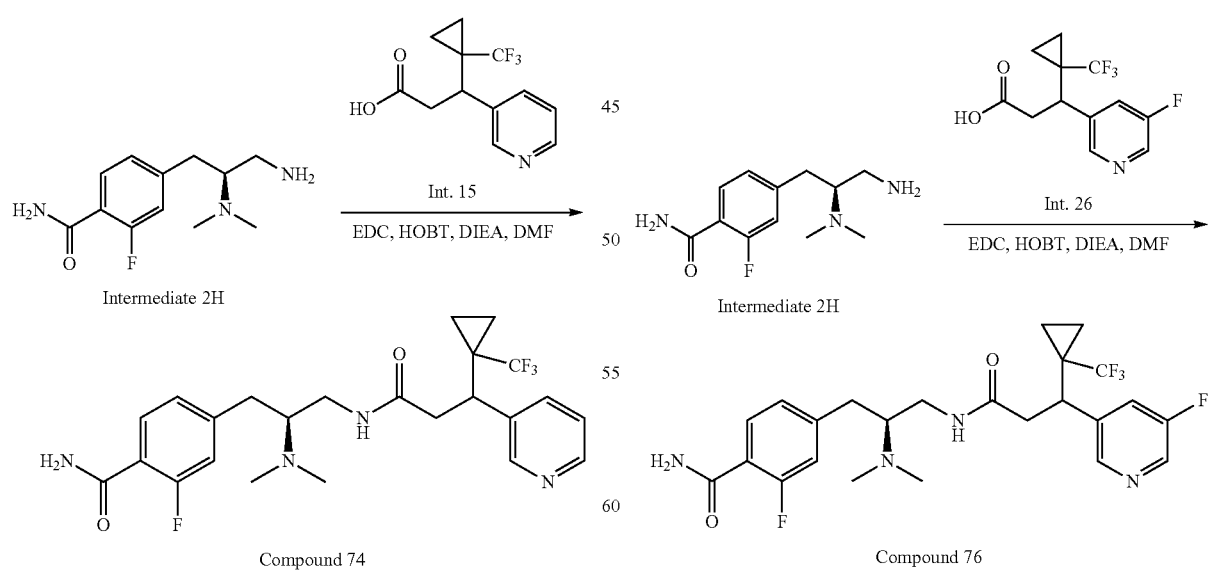

Compound 74

Compound 74 (34 mg, 70%) was synthesized from Int. 2 and Int. 15 as described in Example B9. MS (m/z): 481.2 (M+H).

Example B75: Preparation of 4-[(2S)-2-(dimethylamino)-3-[(3R)-3-(6-methylpyridin-3-yl)-3-[1-(trifluoromethyl)cyclopropyl]propanamido]propyl]-2-fluorobenzamide ("Compound 75")

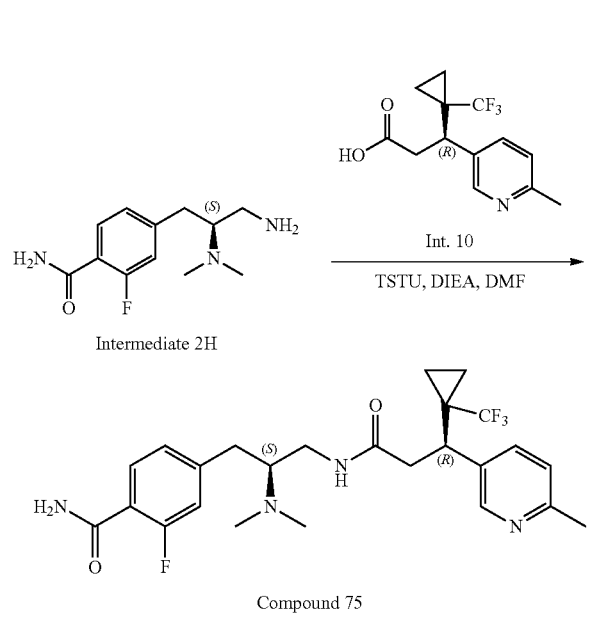

Compound 75

Compound 75 (34 mg, 70%) was synthesized from Int. 2 and Int. 10 as described in Example B17. MS (m/z): 495.2 (M+H).

Example B76: Preparation of 4-[(2S)-2-(dimethylamino)-3-[3-(5-fluoropyridin-3-yl)-3-[1-(trifluoromethyl)cyclopropyl]propanamido]propyl]-2-fluorobenzamide ("Compound 76")

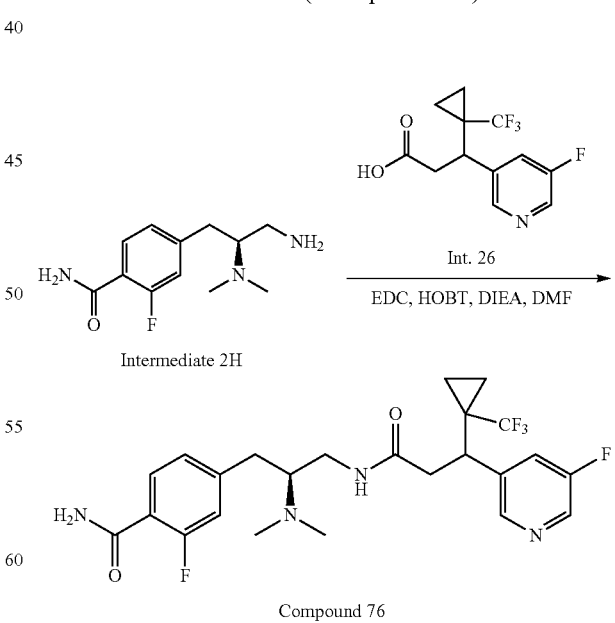

Compound 76

Compound 76 (36.4 mg, 67%) was synthesized from Int. 2 and Int. 26 as described in Example B9. MS (m/z): 499.2 (M+H).

Example B77: Preparation of 4-((S)-2-(dimethylamino)-3-((R)-3-phenyl-3-(1-(trifluoromethyl)cyclopropyl)propanamido)propyl)-2-fluorobenzamide ("Compound 77")

Example B79: Preparation of 4-((S)-2-(dimethylamino)-3-((R)-3-(2-methylpyrimidin-5-yl)-3-(1-(trifluoromethyl)cyclopropyl)propanamido)propyl)benzamide ("Compound 79")

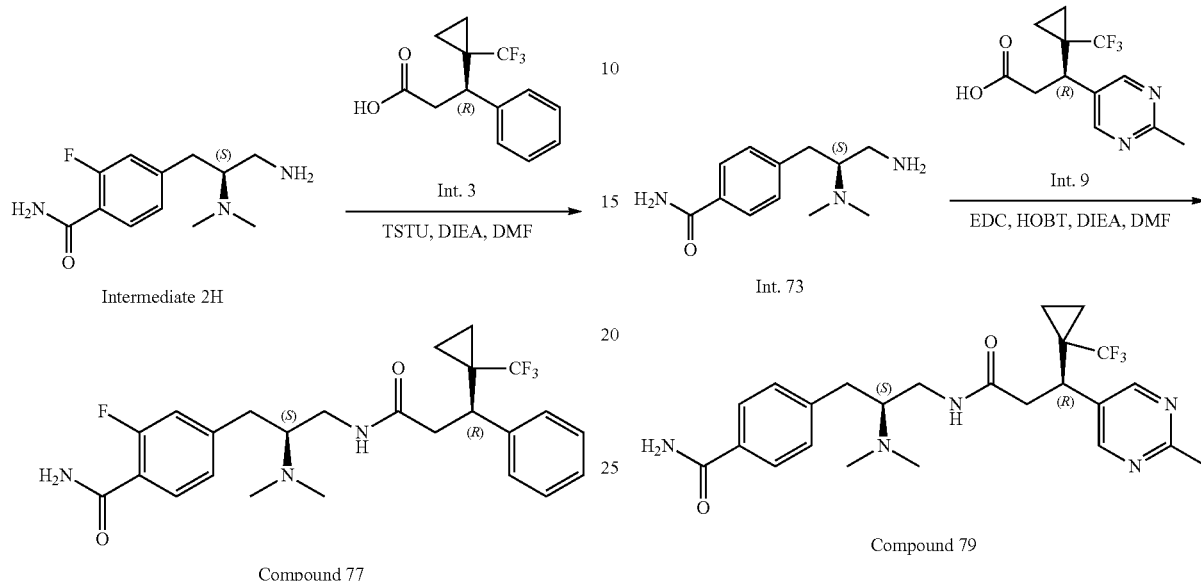

Compound 77 (27 mg, 58%) was synthesized from Int. 2 and Int. 3 as described in Example B17. MS (m/z): 480.3 (M+H).

Example B78: Preparation of 4-[(2S)-2-(dimethylamino)-3-[(3S)-4-methyl-3-(pyridin-3-yl)pentanamido]propyl]-2-fluorobenzamide ("Compound 78")

Compound 79 (20 mg, 32%) was synthesized from Int. 73 and Int. 9 as described in Example B9. MS (m/z): 478.2 (M+H).

Example B80: Preparation of 4-((S)-3-((R)-3-(3,4-dichlorophenyl)-3-(1-(trifluoromethyl)cyclopropyl)propanamido)-2-(dimethylamino)propyl)benzamide ("Compound 80")

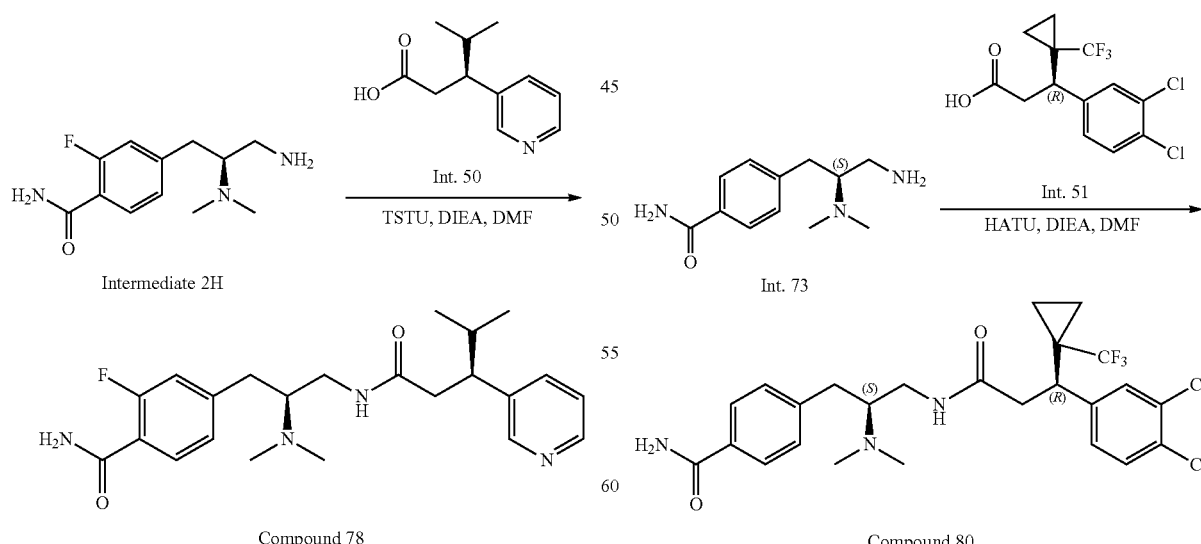

Compound 78 (20 mg, 32%) was synthesized from Int. 2 and Int. 50 as described in Example B17. MS (m/z): 415.2 (M+H).

Compound 80 (23.1 mg, 46%) was synthesized from Int. 73 and Int. 51 as described in Example B9. MS (m/z): 530.1 (M+H).

Example B81: Preparation of 4-((S)-2-(dimethylamino)-3-((S)-3-(pyridin-2-yl)-3-(1-(trifluoromethyl)cyclopropyl)propanamido)propyl)benzamide ("Compound 81")

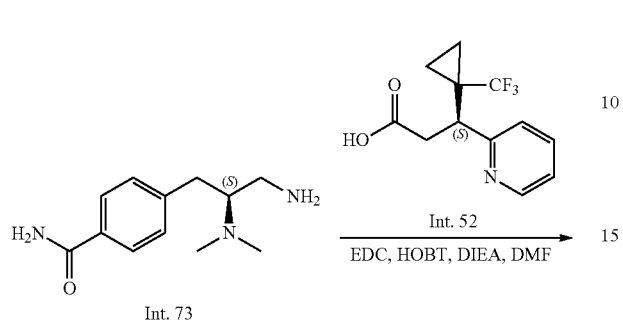

Int. 73

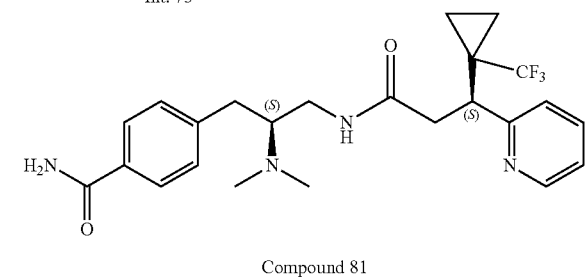

Compound 81

Compound 81 (20 mg, 32%) was synthesized from Int. 73 and Int. 52 as described in Example B9. MS (m/z): 463.2 (M+H).

Example B82: Preparation of 4-((S)-2-(methylamino)-3-((S)-3-phenyl-3-(1-(trifluoromethyl)cyclopropyl)propanamido)propyl)benzamide ("Compound 82")

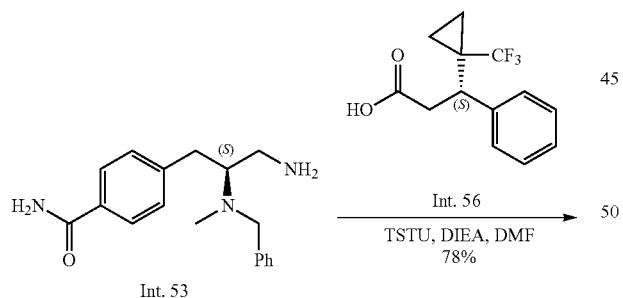

Int. 53

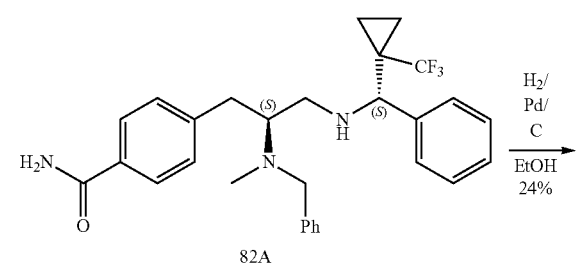

82A

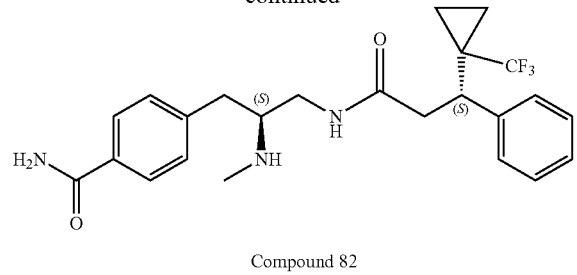

Compound 82

Step 1: Preparation of 4-((S)-2-(benzyl(methyl)amino)-3-((S)-3-phenyl-3-(1-(trifluoromethyl)cyclopropyl)propanamido)propyl)benzamide. To a solution of (3S)-3-phenyl-3-[1-(trifluoromethyl)cyclopropyl] propanoic acid (Int. 56, 31.0 mg, 0.120 mmol) and DIEA (31.4 uL, 0.180 mmol) in DMF (0.45 mL), was added TSTU (36.1 mg, 0.120 mmol) in one portion. The mixture was stirred at room temperature for an hour. To the reaction mixture was then added 4-[(2S)-3-amino-2-[benzyl(methyl)amino]propyl] benzamide (Int. 53, 35.4 mg, 0.120 mmol), continued to stir for another hour. The reaction mixture was diluted with ethyl acetate, and saturated NaHCO$_3$, water, and brine. The organic layer was dried over MgSO$_4$, filtered, and concentrated. The crude material was purified on silica gel column (0-10% MeOH/DCM with 1% NH$_4$OH) to provide the title compound (49 mg, 77%). MS (m/z): 538.2 (M+H).

Step 2: Preparation of 4-((S)-2-(methylamino)-3-((S)-3-phenyl-3-(1-(trifluoromethyl)cyclopropyl)propanamido)propyl)benzamide. Compound 82A (44 mg, 0.0818 mmol) and 20% Pd(OH)$_2$ on carbon (44 mg) in EtOH (10 mL) was treated with H$_2$ at 55 psi for 6 hours. The catalyst was removed by filtration, rinsed with EtOH, and concentrated. The crude product was purified by reverse phase preparative HPLC on C-18 column, 0-100% ACN with 0.1% TFA/water with 0.1% TFA. The pure fractions were combined, adjusted pH=9 by adding saturated NaHCO$_3$(aq), extracted with DCM (3×), dried over MgSO$_4$, filtered and concentrated to provide the title compound (9 mg, 24%). MS (m/z): 448.2 (M+H).

Example B83: Preparation of 4-((S)-3-((R)-3-(4-chlorophenyl)-3-(1-(trifluoromethyl)cyclopropyl)propanamido)-2-(dimethylamino)propyl)benzamide ("Compound 83")

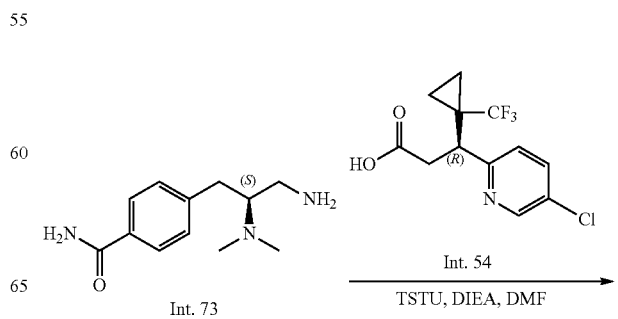

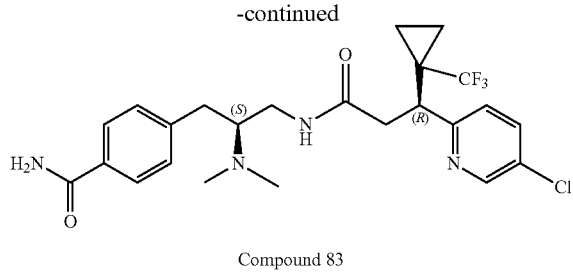

Compound 83

Compound 83 (51 mg, 84%) was synthesized from Int. 73 and Int. 54 as described in Example B17. MS (m/z): 496.2 (M+H).

Example B84: Preparation of 4-[(2S)-2-(dimethylamino)-3-[(3R)-3-(pyridin-2-yl)-3-[1-(trifluoromethyl)cyclopropyl] propanamido]propyl]benzamide ("Compound 84")

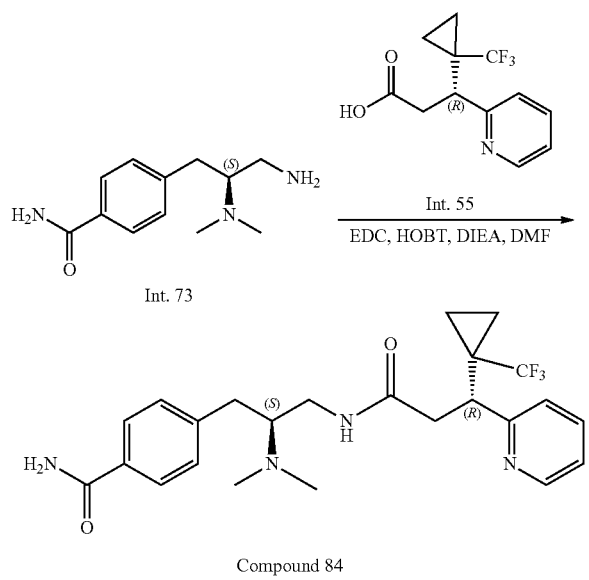

Compound 84

Compound 84 (151 mg, 54%) was synthesized from Int. 73 and Int. 55 as described in Example B9. MS (m/z): 463.2 (M+H).

Example B85: Preparation of 4-[(2S)-2-(methylamino)-3-[(3R)-3-phenyl-3-[1-(trifluoromethyl)cyclopropyl]propanamido]propyl]benzamide ("Compound 85")

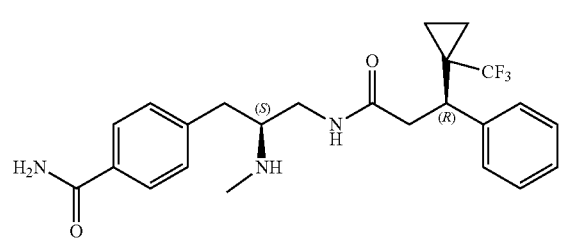

Compound 85 (9 mg, 24%) was synthesized as described in Example B82. MS (m/z): 448.2 (M+H).

Example B86: Preparation of 4-[(2S)-2-[benzyl(methyl)amino]-3-[(3R)-3-phenyl-3-[1-(trifluoromethyl)cyclopropyl]propanamido] propyl]benzamide ("Compound 86")

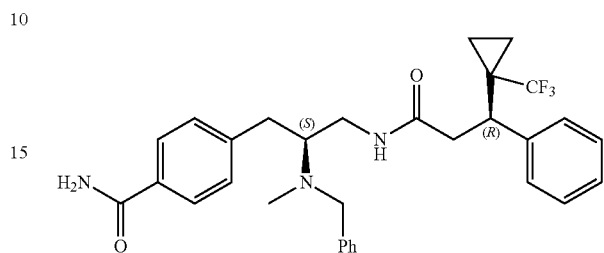

Compound 86 (49 mg, 77%) was synthesized as described in Example B82. MS (m/z): 538.2 (M+H).

Example B87: Preparation of 4-[(2S)-2-amino-3-[(3R)-3-phenyl-3-[1-(trifluoromethyl)cyclopropyl] propanamido]propyl]benzamide ("Compound 87")

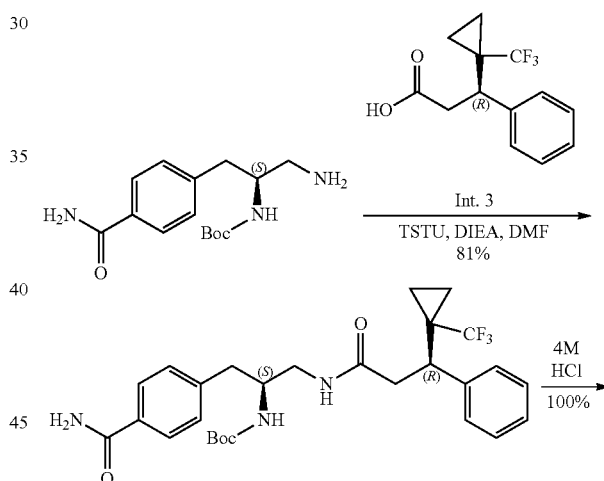

Compound 87

Step 1: Preparation of tert-butyl N-[(2S)-1-(4-carbamoylphenyl)-3-[(3R)-3-phenyl-3-[1-(trifluoromethyl)cyclopropyl]propanamido]propan-2-yl]carbamate (87A). To a solution of the acid (Int. 3.31.0 mg, 0.120 mmol) and DIEA (31.4 uL, 0.180 mmol) in DMF (0.45 mL), was added TSTU (36.1 mg, 0, 120 mmol) in one portion. The mixture was stirred at room temperature for an hour. To the reaction mixture was then added amine (35.2 mg, 0.120 mmol), continued to stir for another hour. The reaction mixture was diluted with ethyl acetate (15 mL) and saturated NaHCO₃, water, and brine. The organic layer was dried over MgSO₄, filtered, and concentrated. The crude material was purified on silica gel column (0-10% MeOH/DCM with 1% NH₄OH) to provide the title compound (52 mg, 81%). MS (m/z): 556.3 (M+H).

Step 2: Preparation of 4-[(2S)-2-amino-3-[(3R)-3-phenyl-3-[1-(trifluoromethyl)cyclopropyl]propanamido] propyl] benzamide (Compound 87). Compound 87A (50 mg, 0.0937 mmol) in MeOH (0.5 mL) was treated with 4N HCl in dioxane (0.5 mL) at room temperature for 2 hours. The solvents were removed on rota-vapor, triturated with ethyl ether, The precipitated solid was filtered, washed with ether, dried in vacuo to provide the title compound as HCl salt (48 mg, 100%). MS (m/z): 434.2 (M+H).

Example B88: Preparation of 4-[(2S)-2-(dimethylamino)-3-[(3S)-3-phenyl-3-[1-(trifluoromethyl)cyclopropyl]propanamido] propyl]benzamide ("Compound 88")

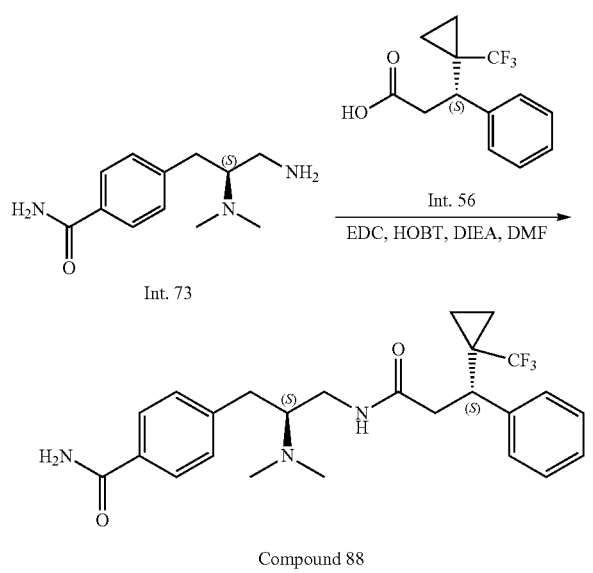

Compound 88

Compound 88 (77.2 mg, 41%) was synthesized from Int. 73 and Int. 56 as described in Example B9. MS (m/z): 462.2 (M+H).

Example B89: Preparation of 4-[(2S)-2-(dimethylamino)-3-[(3R)-3-phenyl-3-[1-(trifluoromethyl)cyclopropyl]propanamido] propyl]benzamide ("Compound 89")

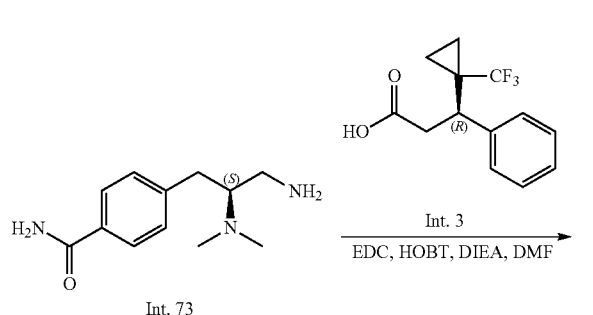

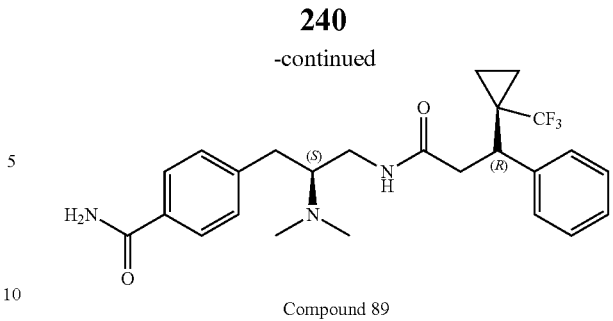

Compound 89

Compound 89 (377 mg, 86%) was synthesized from Int. 73 and Int. 3 as described in Example B9. MS (m/z): 462.2 (M+H).

Example B90: Preparation of 4-[(2S)-3-[(3S)-4-cyclobutyl-3-phenylbutanamido]-2-(dimethylamino) propyl]benzamide ("Compound 90")

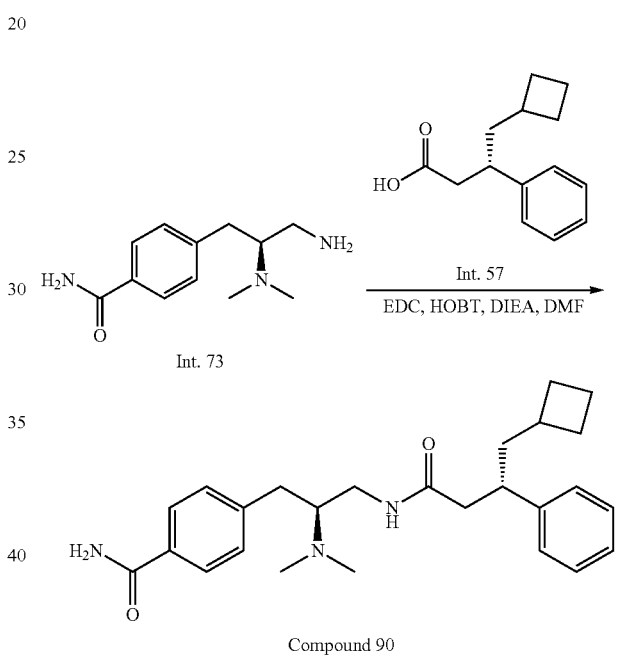

Compound 90

Compound 90 (89.9 mg, 27%) was synthesized from Int. 73 and Int. 57 as described in Example B9. MS (m/z): 422.2 (M+H).

Example B91: Preparation of 4-[(2S)-2-(dimethylamino)-3-[(3S)-5-methyl-3-phenylhexanamido]propyl]benzamide ("Compound 91")

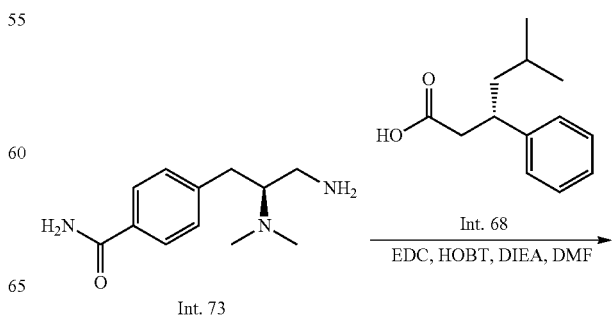

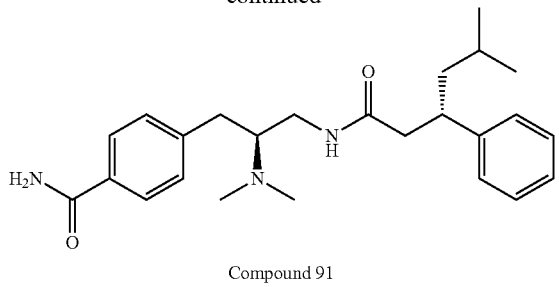

Compound 91

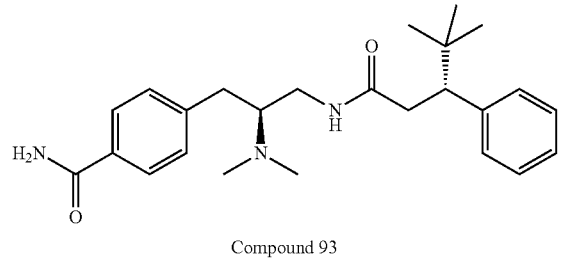

Compound 93

Compound 91 (620 mg, 60%) was synthesized from Int. 73 and Int. 68 as described in Example B9. MS (m/z): 410.3 (M+H).

Compound 93 (49 mg, 66%) was synthesized from Int. 73 and Int. 69 as described in Example B9. MS (m/z): 410.2 (M+H).

Example B92: Preparation of 4-((S)-2-(dimethylamino)-3-((R)-4-methyl-3-phenylpentanamido)propyl)benzamide ("Compound 92")

Example B94: Preparation of 4-[(2S)-2-(dimethylamino)-3-[(3S)-4-methyl-3-phenylpentanamido]propyl]benzamide ("Compound 94")

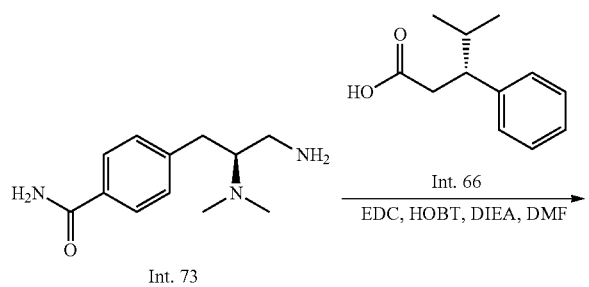

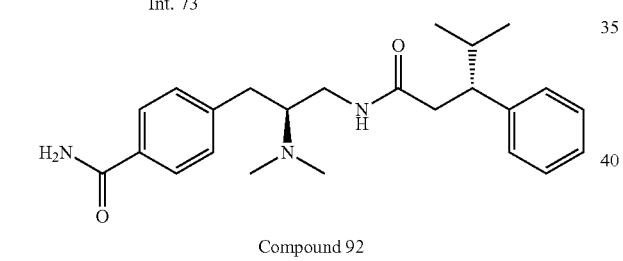

Compound 92

Compound 94

Compound 92 (26 mg, 58%) was synthesized from Int. 73 and Int. 66 as described in Example B9. MS (m/z): 396.3 (M+H).

Compound 94 (45 mg, 72%) was synthesized from Int. 73 and Int. 94 as described in Example B9. MS (m/z): 396.5 (M+H).

Example B93: Preparation of 4-[(2S)-3-[(3R)-4,4-dimethyl-3-phenylpentanamido]-2-(dimethylamino)propyl]benzamide ("Compound 93")

Example B95: Preparation of 4-((S)-3-((R)-4,4-dimethyl-3-phenylpentanamido)-2-(dimethylamino)propyl)benzamide ("Compound 95")

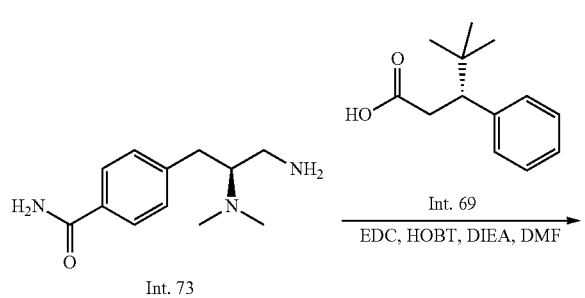

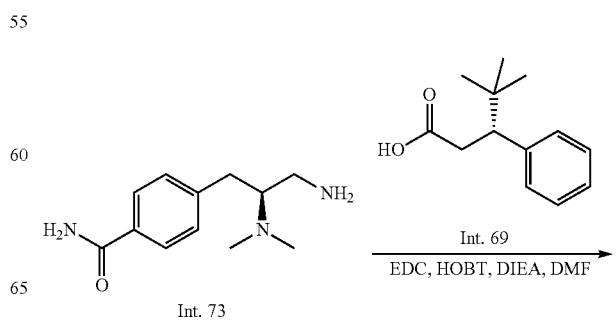

-continued

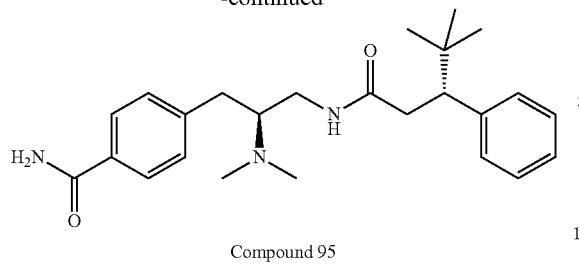

Compound 95

Compound 95 (51 mg, 69%) was synthesized from Int. 73 and Int. 69 as described in Example B9. MS (m/z): 410.3 (M+H).

Example B96: Preparation of 4-((S)-2-(dimethylamino)-3-((R)-5-methyl-3-phenyl hexanamido)propyl)benzamide ("Compound 96")

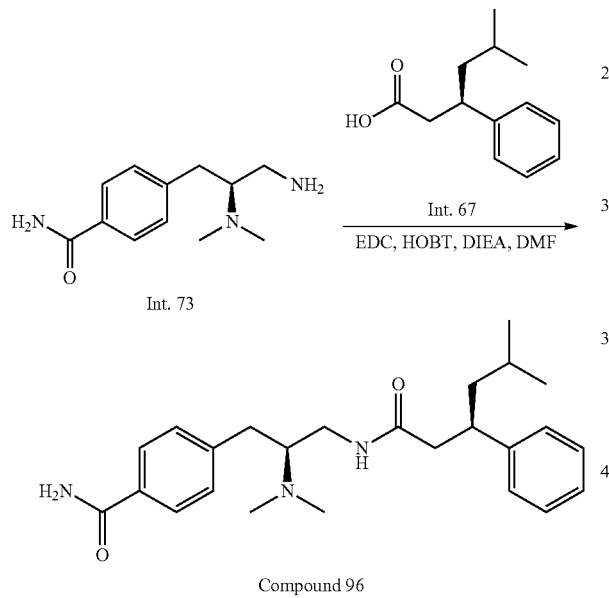

Compound 96

Compound 96 (48 mg, 74%) was synthesized from Int. 73 and Int. 67 as described in Example B9. MS (m/z): 410.3 (M+H).

Example B97: Preparation of 4-((S)-3-((R)-3-cyclopropyl-3-phenylpropanamido)-2-(dimethylamino)propyl)benzamide ("Compound 97")

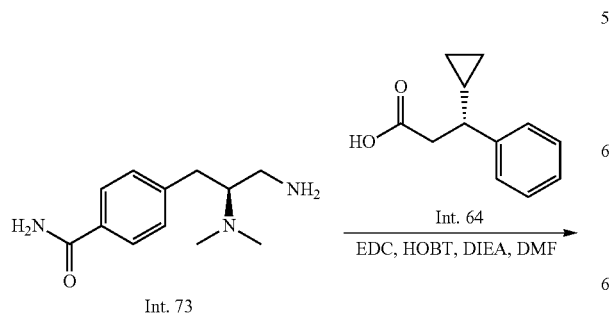

-continued

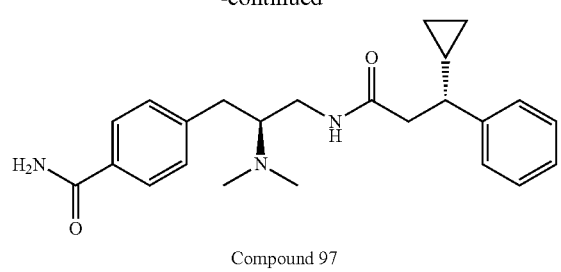

Compound 97

Compound 97 (10 mg, 21%) was synthesized from Int. 73 and Int. 64 as described in Example B9. MS (m/z): 394.3 (M+H).

Example B98: Preparation of 4-((S)-2-(dimethylamino)-3-((R)-3-phenylbutanamido)propyl)benzamide ("Compound 98")

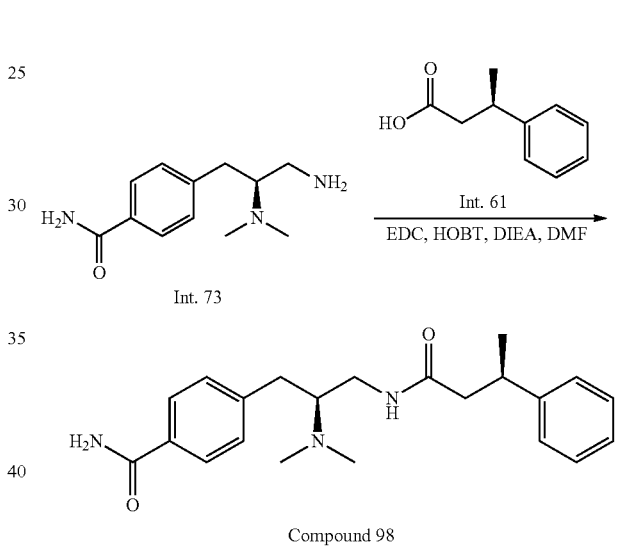

Compound 98

Compound 98 (152 mg, 55%) was synthesized from Int. 73 and Int. 61 as described in Example B9. MS (m/z): 368.2 (M+H).

Example B99: Preparation of 4-((S)-2-(dimethylamino)-3-((S)-3-phenylbutanamido)propyl)benzamide ("Compound 99")

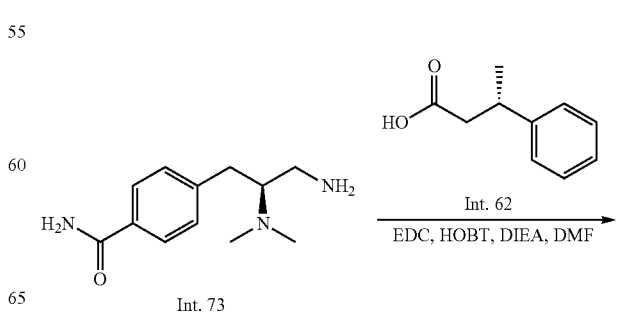

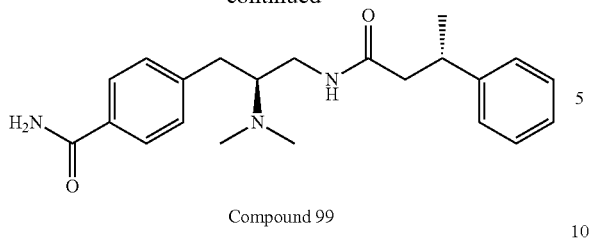

Compound 99

Compound 99 (118 mg, 65%) was synthesized from Int. 73 and Int. 62 as described in Example B9. MS (m/z): 368.2 (M+H).

Example B100: Preparation of 4-((S)-2-(dimethylamino)-3-((S)-3-phenylbutanamido)propyl)-3,5-dimethylbenzamide ("Compound 100")

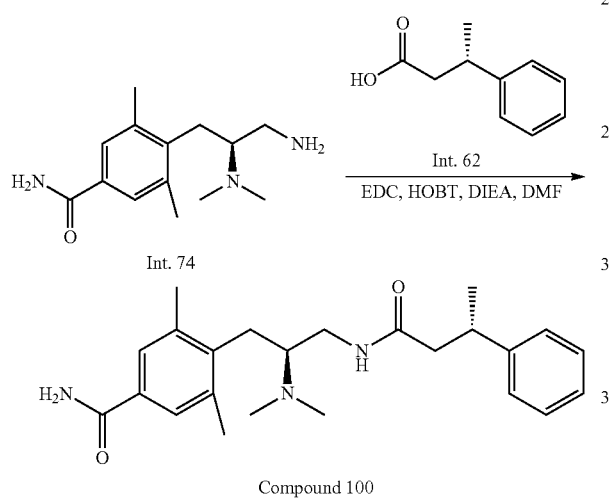

Compound 100 (190 mg, 52%) was synthesized from Int. 74 and Int. 62 as described in Example B9. MS (m/z): 396.3 (M+H).

Example B101: Preparation of 4-((S)-3-((S)-4,4-dimethyl-3-phenylpentanamido)-2-(dimethylamino)propyl)-2-fluoro-N-(2,2,2-trifluoroethyl)benzamide ("Compound 101")

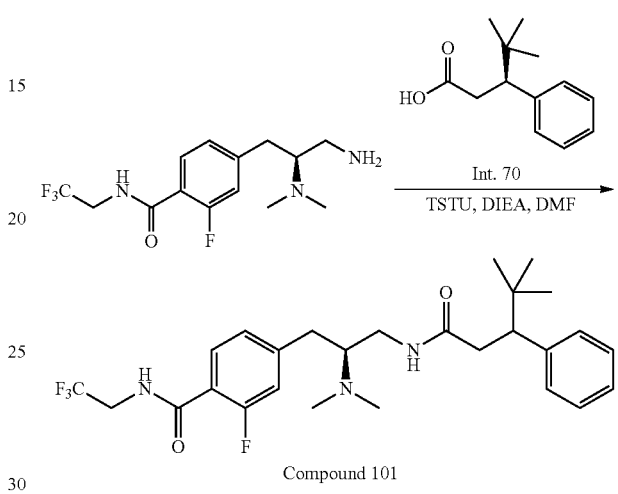

Compound 101 (59 mg, 45%) was synthesized as described in Example B17. MS (m/z): 510.3 (M+H).

Example B102: Preparation of (R)-N-((S)-2-(dimethylamino)-3-(2-oxo-1,2-dihydroquinolin-6-yl)propyl)-3-(pyridin-3-yl)-3-(1-(trifluoromethyl)cyclopropyl) propanamide ("Compound 102")

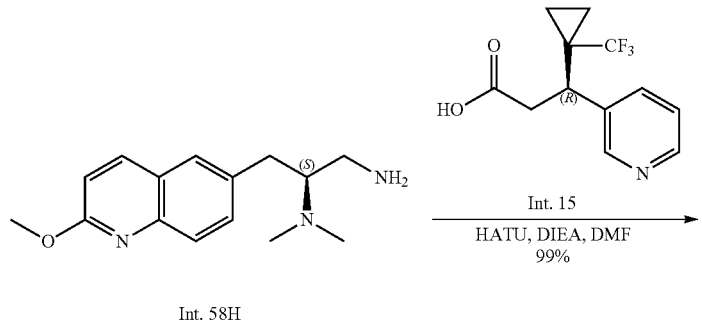

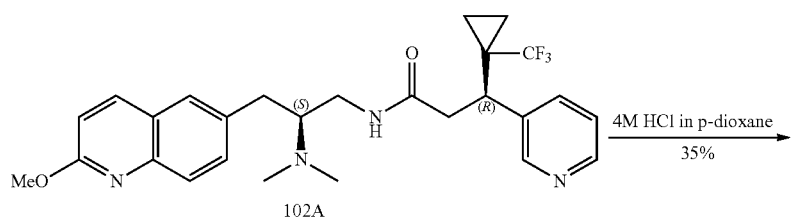

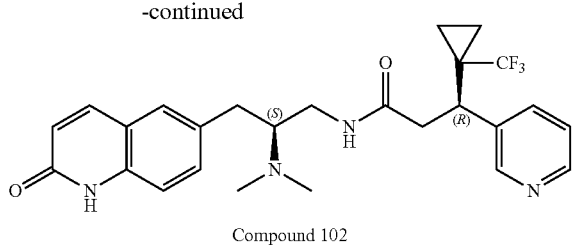

Compound 102

Step 1: Preparation of (R)-N-((S)-2-(dimethylamino)-3-(2-methoxyquinolin-6-yl)propyl)-3-(pyridin-3-yl)-3-(1-(trifluoromethyl)cyclopropyl)propanamide (102A). To a stirred mixture of [(2S)-1-amino-3-(2-methoxyquinolin-6-yl)propan-2-yl]dimethylamine (29.3 mg, 113 µmol), (3S)-3-(pyridin-3-yl)-3-[1-(trifluoromethyl)cyclopropyl]propanoic acid (30.8 mg, 1.1 eq., 119 µmol), and DIEA (30.0 µL, 1.5 eq., 169 µmol) in DMF (1 mL) at RT was added HATU (51.5 mg, 1.2 eq., 136 µmol). The reaction mixture was then stirred at RT for 1 h. H₂O was added, extracted with EtOAc (3×). The combined extracts were dried over MgSO₄, concentrated and purified by flash chromatography (0-10% MeOH/DCM) to give (3S)-N-[(2S)-2-(dimethylamino)-3-(2-methoxyquinolin-6-yl)propyl]-3-(pyridin-3-yl)-3-[1-(trifluoromethyl)cyclopropyl]propanamide (56.0 mg, 99%). MS (m/z). 501.1 (M+H).

Step 2: Preparation of (R)-N-((S)-2-(dimethylamino)-3-(2-oxo-1,2-dihydroquinolin-6-yl)propyl)-3-(pyridin-3-yl)-3-(1-(trifluoromethyl)cyclopropyl)propanamide (Compound 102): To a stirred solution of (3S)-N-[(2S)-2-(dimethylamino)-3-(2-methoxyquinolin-6-yl)propyl]-3-(pyridin-3-yl)-3-[1-(trifluoromethyl)cyclopropyl]propanamide (56.0 mg, 112 µmol) in p-dioxane (2 mL) was added hydrogen chloride (186 µL, 10 eq., 1.12 mmol). The reaction mixture was then stirred at 60° C. in 16 h, then increased to 100° C. in 4 h. LC/MS showed no SM left. The mixture was cooled, concentrated to dryness, diluted with H₂O, basified with 10N NaOH until pH=5-6, extracted with DCM (3×). The combined extracts were dried over MgSO₄, concentrated and purified by flash chromatography (0-15% MeOH/DCM) to give Compound 102 (18.9 mg, 35%). MS (m/z): 487.2 (M+H).

Example B103: Preparation of (R)-N-((S)-2-(dimethylamino)-3-(2-oxo-1,2-dihydroquinolin-6-yl)propyl)-3-(pyridin-4-yl)-3-(1-(trifluoromethyl)cyclopropyl) propanamide ("Compound 103")

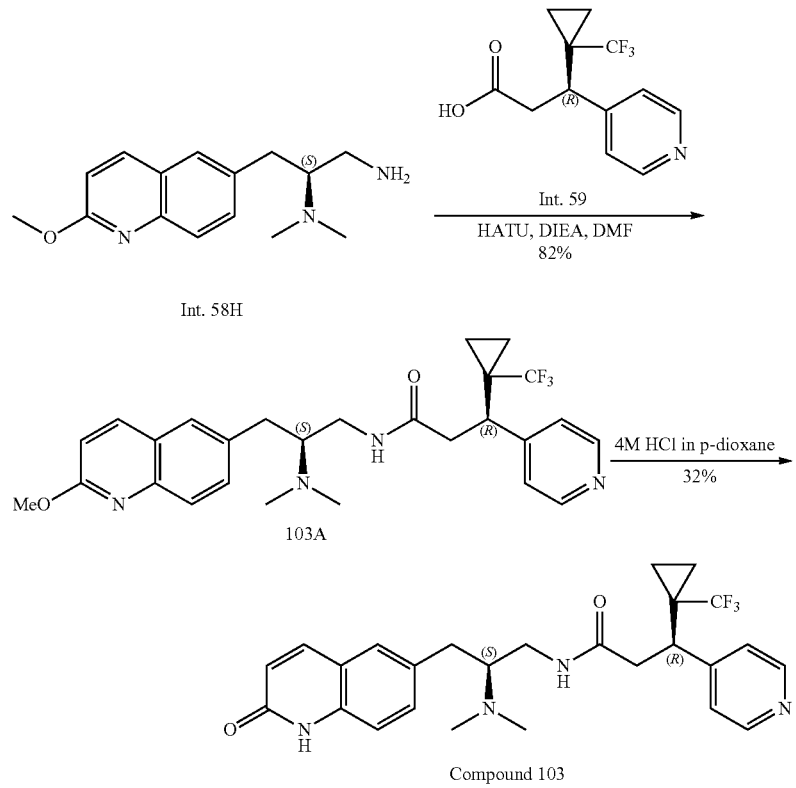

Compound 103 (23.7 mg, 32%) was synthesized as described in Example B102. MS (m/z): 487.2 (M+H).

Example B104: Preparation of 4-((S)-3-((S)-4,4-dimethyl-3-phenylpentanamido)-2-(dimethylamino)propyl)-2,5-difluoro-N-methylbenzamide ("Compound 104")

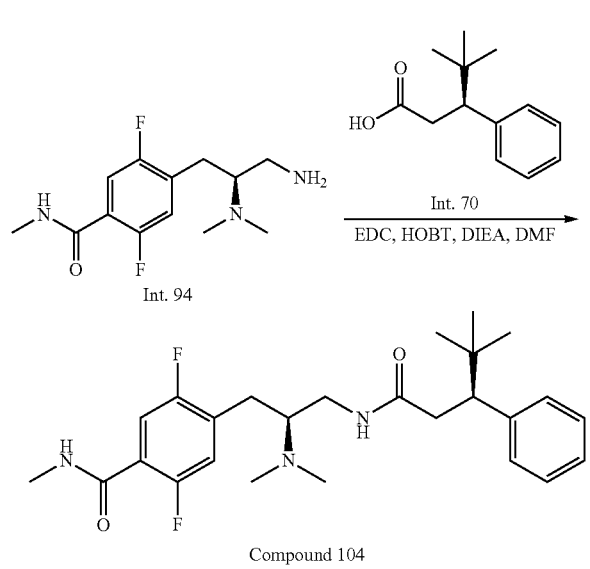

Compound 104

Compound 104 (226 mg, 60%) was synthesized from Int. 94 and Int. 70 as described in Example B9. MS (m/z): 460.2 (M+H).

Example B105: Preparation of 4-((S)-2-(dimethylamino)-3-((R)-3-(2-methylpyrimidin-5-yl)-3-(1-(trifluoromethyl)cyclopropyl)propanamido)propyl)-3,5-difluoro-N-methylbenzamide ("Compound 105")

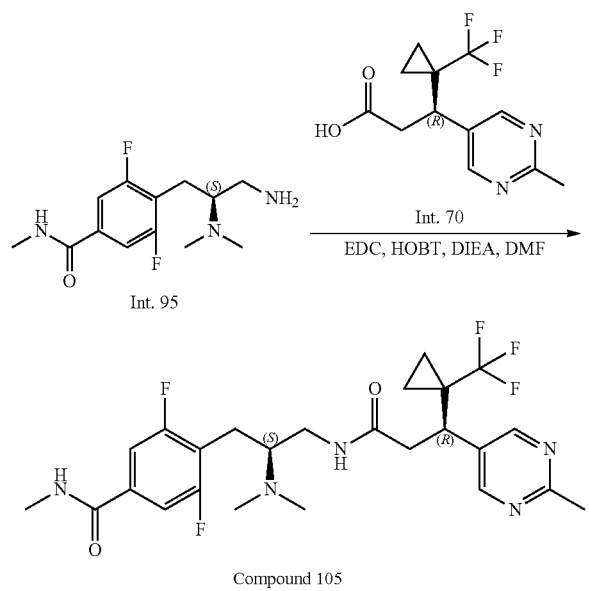

Compound 105

Compound 105 (226 mg, 60%) was synthesized from Int. 95 and Int. 9 as described in Example B9. MS (m/z): 528.2 (M+H).

Example B106: Preparation of 4-((S)-3-((R)-3-(4-chlorophenyl)-3-(1-(trifluoromethyl)cyclopropyl)propanamido)-2-(dimethylamino)propyl)-3,5-trimethylbenzamide ("Compound 106")

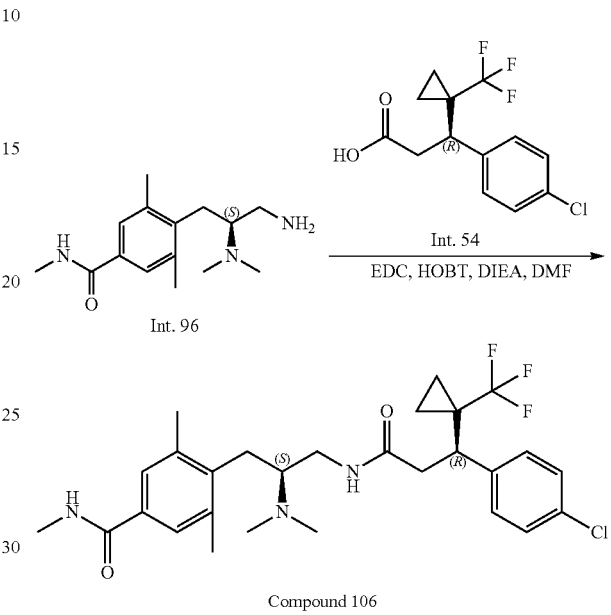

Compound 106

Compound 106 (36 mg, 78%) was synthesized from Int. 96 and Int. 54 as described in Example B9. MS (m/z): 539.2 (M+H).

Example B107: Preparation of 4-((S)-3-((R)-3-(4-chlorophenyl)-3-(1-(trifluoromethyl)cyclopropyl)propanamido)-2-(dimethylamino)propyl)-2-fluoro-N-methylbenzamide ("Compound 107")

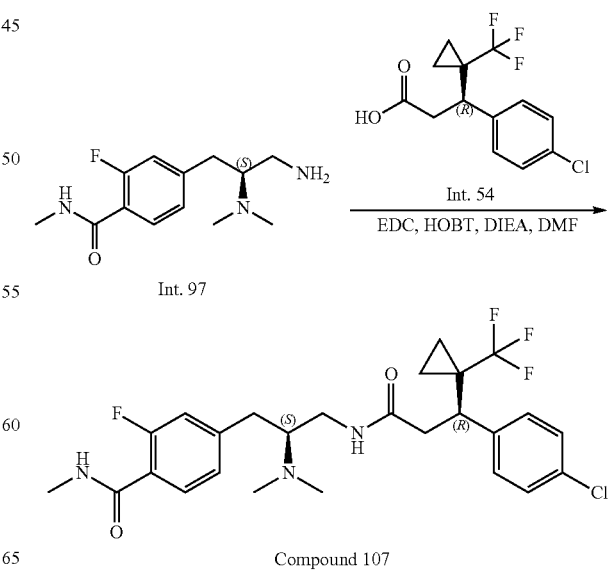

Compound 107

Compound 107 (33 mg, 75%) was synthesized from Int. 97 and Int. 54 as described in Example B9. MS (m/z): 529.2 (M+H).

Example B108: Preparation of 4-((S)-2-(dimethylamino)-3-((R)-5-methyl-3-(pyridin-2-yl)hexanamido)propyl)-N,3,5-trimethylbenzamide ("Compound 108")

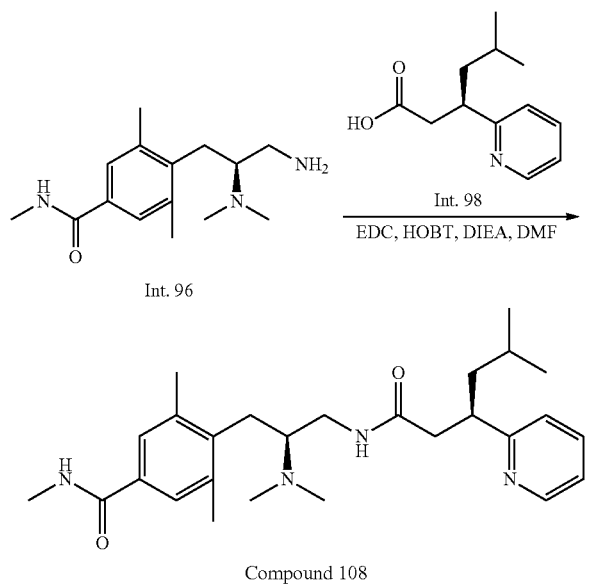

Compound 108 (9 mg, 18%) was synthesized from Int. 96 and Int. 98 as described in Example B9. MS (m/z): 453.2 (M+H).

Example B109: Preparation of 3-chloro-4-((S)-2-(dimethylamino)-3-((S)-3-(pyridin-3-yl)-3-(1-(trifluoromethyl)cyclopropyl) propanamido)propyl)-2-fluoro-N-methylbenzamide ("Compound 109")

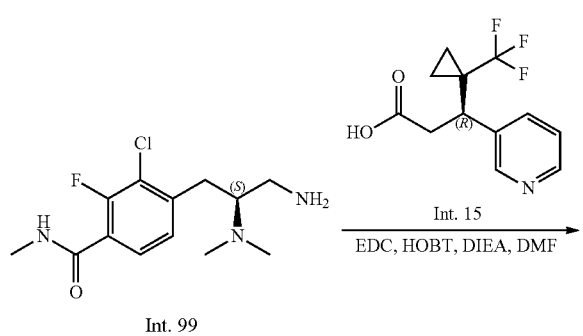

Compound 109 (15 mg, 45%) was synthesized from Int. 99 and Int. 15 as described in Example B9. MS (m/z): 529.2 (M+H).

Example B110: Preparation of 3-chloro-4-((S)-2-(dimethylamino)-3-((S)-3-(pyridin-4-yl)-3-(1-(trifluoromethyl)cyclopropyl)propanamido)propyl)-2-fluoro-N-methylbenzamide ("Compound 110")

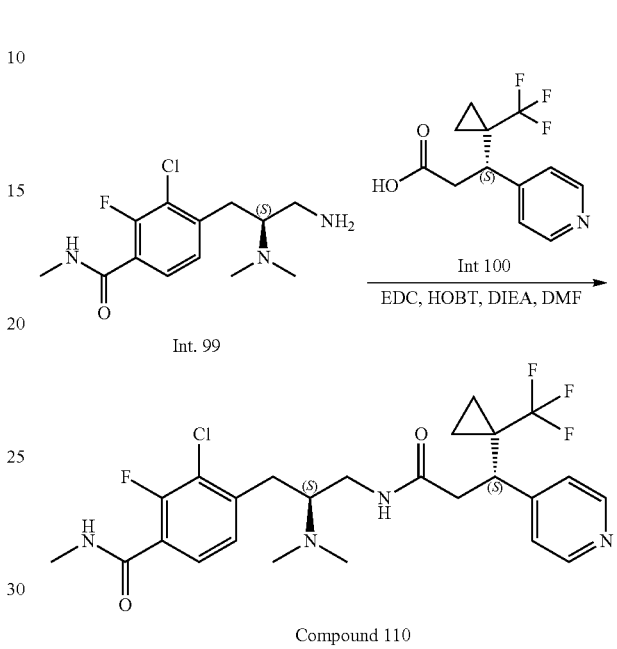

Compound 110 (15 mg, 63%) was synthesized from Int. 99 and Int. 100 as described in Example B9. MS (m/z): 529.2 (M+H).

Example B111: Preparation of 3-chloro-4-((S)-2-(dimethylamino)-3-((R)-3-(pyridin-4-yl)-3-(1-(trifluoromethyl)cyclopropyl)propanamido)propyl)-2-fluoro-N-methylbenzamide ("Compound 111")

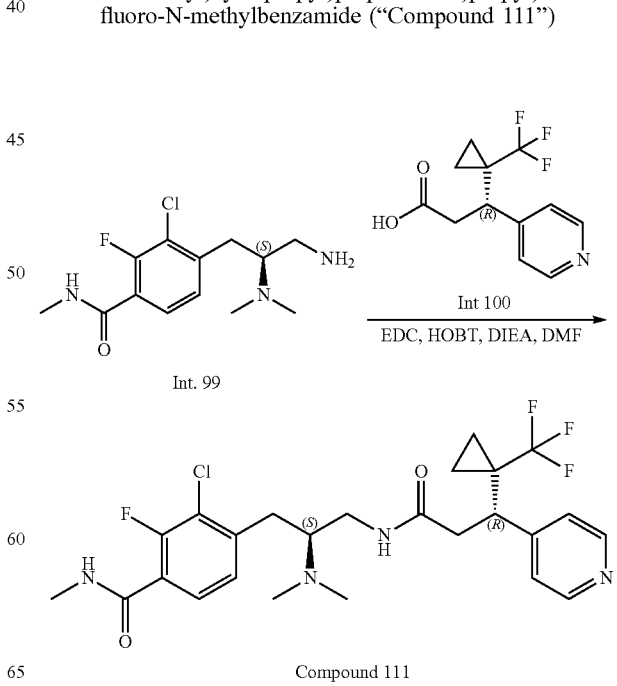

Compound 111 (46 mg, 82%) was synthesized from Int. 99 and Int. 59 as described in Example B9. MS (m/z): 529.2 (M+H).

Example B112: Preparation of 3-chloro-4-((2S)-3-(3-(5-chloropyrimidin-2-yl)-3-(1-(trifluoromethyl) cyclopropyl)propanamido)-2-(dimethylamino)propyl)-2-fluoro-N-methylbenzamide ("Compound 112")

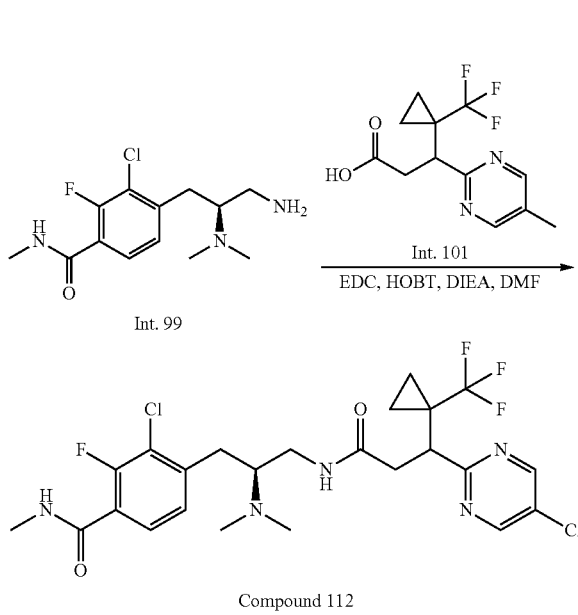 [SMILES: CNC(=O)c1ccc(C[C@@H](CN)N(C)C)c(Cl)c1F ; Cc1cnc(C(CC(=O)O)C2(C(F)(F)F)CC2)nc1 ; CNC(=O)c1ccc(C[C@@H](CNC(=O)CC(c2ncc(Cl)cn2)C2(C(F)(F)F)CC2)N(C)C)c(Cl)c1F]

Compound 112

Compound 112 (33 mg, 78%) was synthesized from Int. 99 and Int. 101 as described in Example B9. MS (m/z): 564.2 (M+H).

Example 3113: Preparation of 3-chloro-4-((S)-2-(dimethylamino)-3-((R)-3-(6-methylpyridin-3-yl)-3-(1-(trifluoromethyl)cyclopropyl)propanamido)propyl)-N-methylbenzamide ("Compound 113")

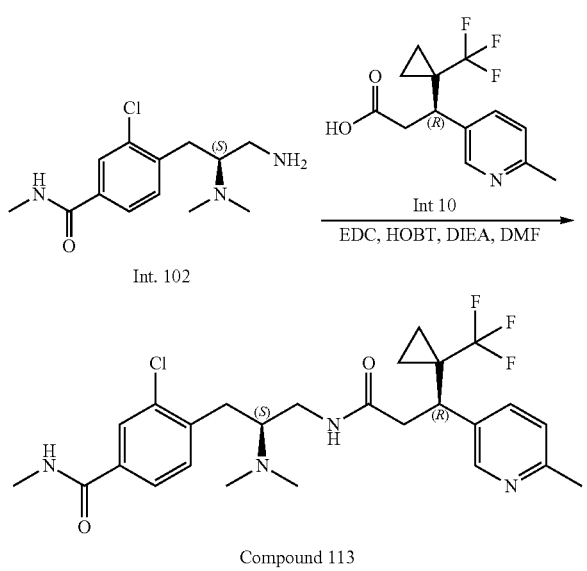

Compound 113

Compound 113 (42 mg, 74%) was synthesized from Int. 102 and Int. 10 as described in Example B9. MS (m/z): 525.2 (M+H).

Example 3114: Preparation of 3-chloro-4-((S)-3-((R)-3-(5-chloropyridin-3-yl)-3-(1-(trifluoromethyl) cyclopropyl)propanamido)-2-(dimethylamino)propyl)-N-methylbenzamide ("Compound 114")

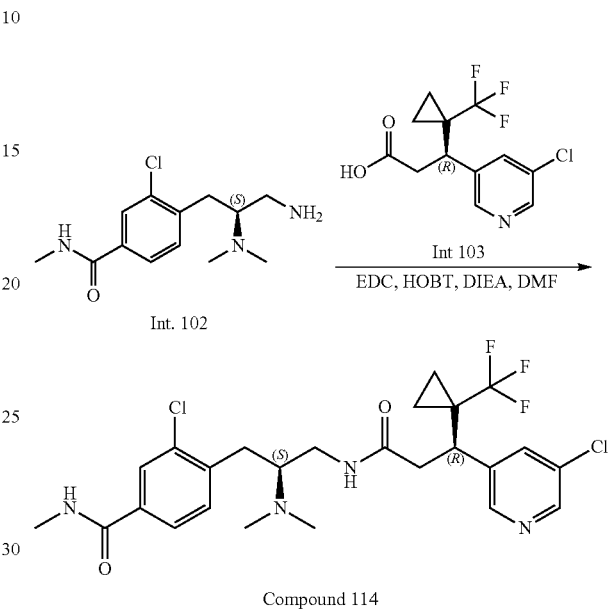

Compound 114

Compound 114 (47 mg, 54%) was synthesized from Int. 102 and Int. 103 as described in Example B9. MS (m/z): 545.2 (M+H).

Example B115: Preparation of 3-chloro-4-((2S)-2-(dimethylamino)-3-(3-(6-methoxypyridin-3-yl)-3-(1-(trifluoromethyl)cyclopropyl) propanamido)propyl)-N-methylbenzamide ("Compound 115")

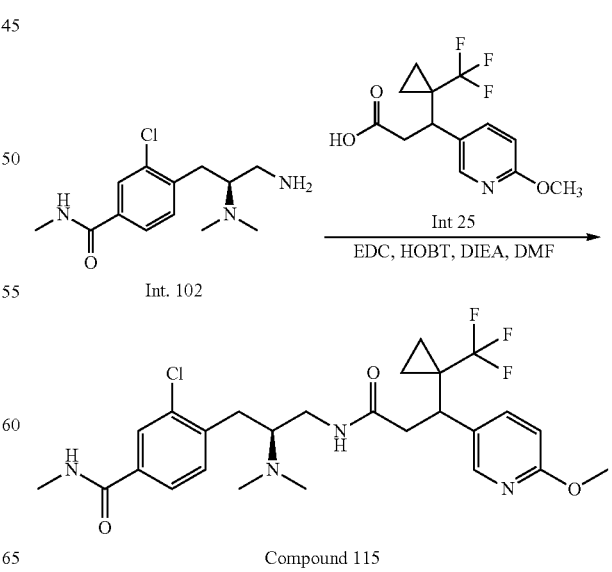

Compound 115

Compound 115 (50 mg, 65%) was synthesized from Int. 102 and Int. 25 as described in Example B9. MS (m/z): 541.2 (M+H).

Example B116: Preparation of 3-chloro-4-((2S)-2-(dimethylamino)-3-(3-(6-methoxy pyridin-3-yl)-3-(1-(trifluoromethyl)cyclopropyl)propanamido)propyl)-N-methylbenzamide ("Compound 116")

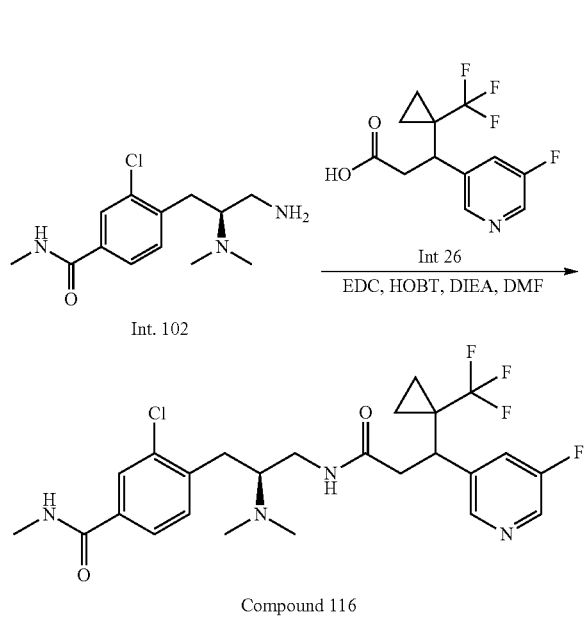 [SMILES: CNC(=O)c1ccc(C[C@@H](CN)N(C)C)c(Cl)c1 ; O=C(O)CC(c1cncc(F)c1)C1(C(F)(F)F)CC1 ; CNC(=O)c1ccc(C[C@@H](CNC(=O)CC(c2cncc(F)c2)C2(C(F)(F)F)CC2)N(C)C)c(Cl)c1]

Compound 116

Compound 116 (45 mg, 65%) was synthesized from Int. 102 and Int. 26 as described in Example B9. MS (m/z): 529.3 (M+H).

Example B117: Preparation of 3-chloro-4-((2S)-2-(dimethylamino)-3-(3-(5-methoxypyridin-3-yl)-3-(1-(trifluoromethyl)cyclopropyl) propanamido)propyl)-N-methylbenzamide ("Compound 117")

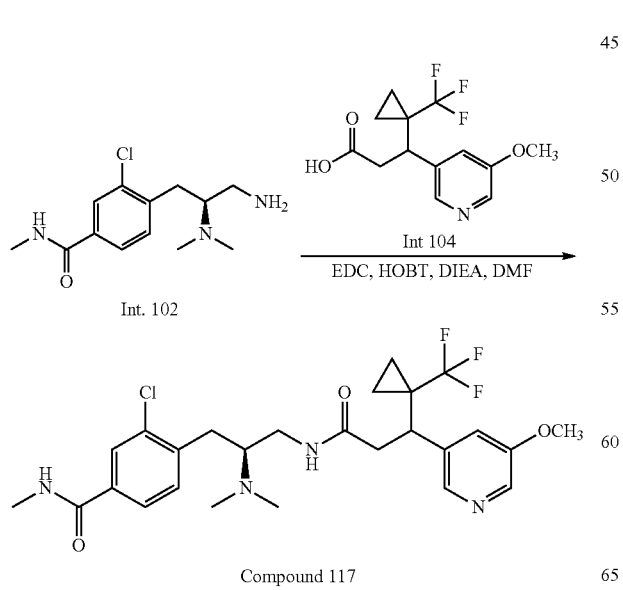

Compound 117

Compound 117 (25 mg, 42%) was synthesized from Int. 102 and Int. 104 as described in Example B9. MS (m/z): 541.3 (M+H).

Example B118: Preparation of 3-chloro-4-((2S)-2-(dimethylamino)-3-(3-(4-methylpyridin-2-yl)-3-(1-(trifluoromethyl)cyclopropyl) propanamido)propyl)-N-methylbenzamide ("Compound 118")

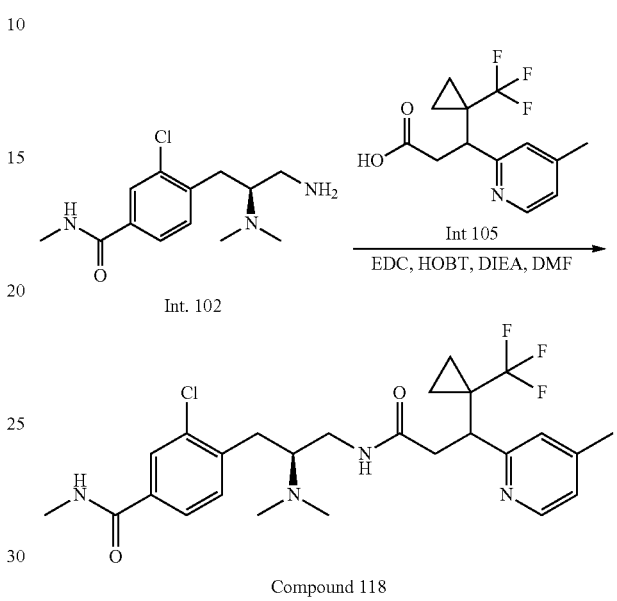

Compound 118

Compound 118 (25 mg, 42%) was synthesized from Int. 102 and Int. 105 as described in Example B9. MS (m/z): 525.2 (M+H).

Example 3119: Preparation of 3-chloro-4-((2S)-2-(dimethylamino)-3-(3-(pyridin-3-yl)-3-(1-(trifluoromethyl)cyclopropyl) propanamido)propyl)-N-methylbenzamide ("Compound 119")

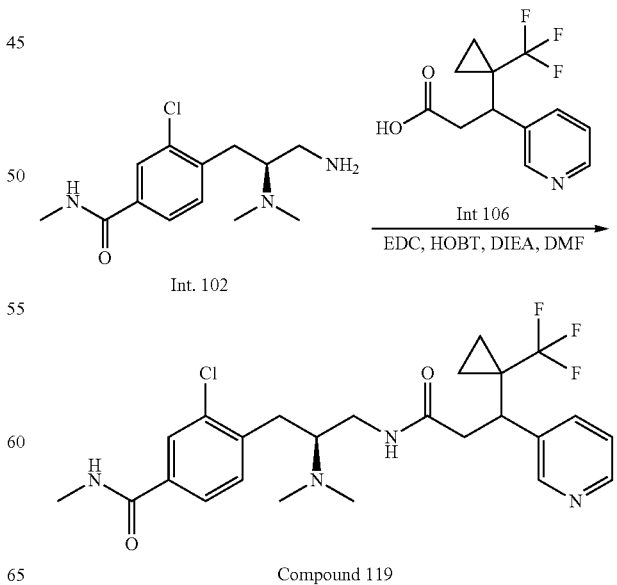

Compound 119

Compound 119 (36 mg, 74%) was synthesized from Int. 102 and Int. 106 as described in Example B9. MS (m/z): 511.2 (M+H).

Example B120: Preparation of 3-chloro-4-((2S)-2-(dimethylamino)-3-(3-(3-fluoropyridin-2-yl)-3-(1-(trifluoromethyl)cyclopropyl) propanamido)propyl)-N-methylbenzamide ("Compound 120")

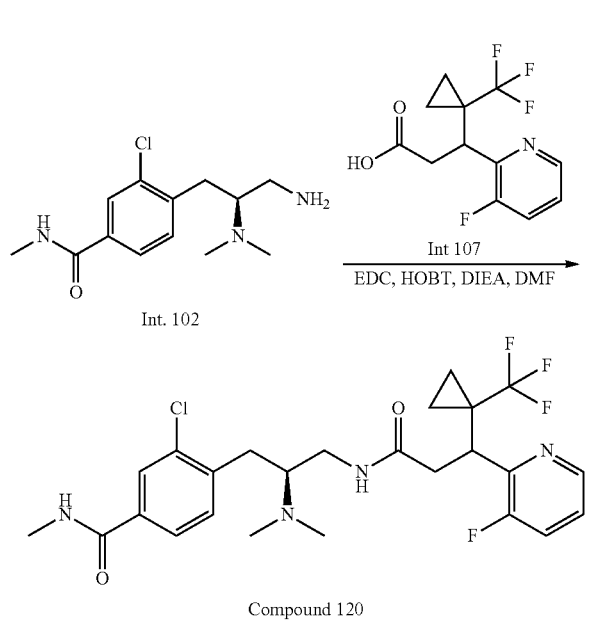 [SMILES: CNC(=O)c1ccc(C[C@@H](CN)N(C)C)c(Cl)c1 ; O=C(O)CC(c1ncccc1F)C1(C(F)(F)F)CC1 ; CNC(=O)c1ccc(C[C@@H](CNC(=O)CC(c2ncccc2F)C2(C(F)(F)F)CC2)N(C)C)c(Cl)c1]

Compound 120

Compound 120 (36 mg, 74%) was synthesized from Int. 102 and Int. 107 as described in Example B9. MS (m/z): 529.2 (M+H).

Example B121: Preparation of 3-chloro-4-((2S)-2-(dimethylamino)-3-(3-(5-fluoropyridin-2-yl)-3-(1-(trifluoromethyl)cyclopropyl) propanamido)propyl)-N-methylbenzamide ("Compound 121")

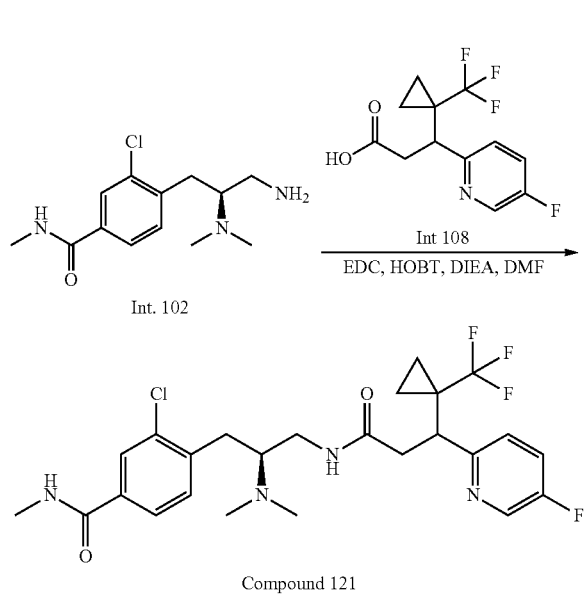 [SMILES: CNC(=O)c1ccc(C[C@@H](CN)N(C)C)c(Cl)c1 ; O=C(O)CC(c1ccc(F)cn1)C1(C(F)(F)F)CC1 ; CNC(=O)c1ccc(C[C@@H](CNC(=O)CC(c2ccc(F)cn2)C2(C(F)(F)F)CC2)N(C)C)c(Cl)c1]

Compound 121

Compound 121 (16 mg, 33%) was synthesized from Int. 102 and Int. 108 as described in Example B9. MS (m/z): 529.3 (M+H).

Example B122: Preparation of 3-chloro-4-((2S)-3-(3-(5-chloropyridin-2-yl)-3-(1-(trifluoromethyl)cyclopropyl)propanamido)-2-(dimethylamino)propyl)-N-methylbenzamide ("Compound 122")

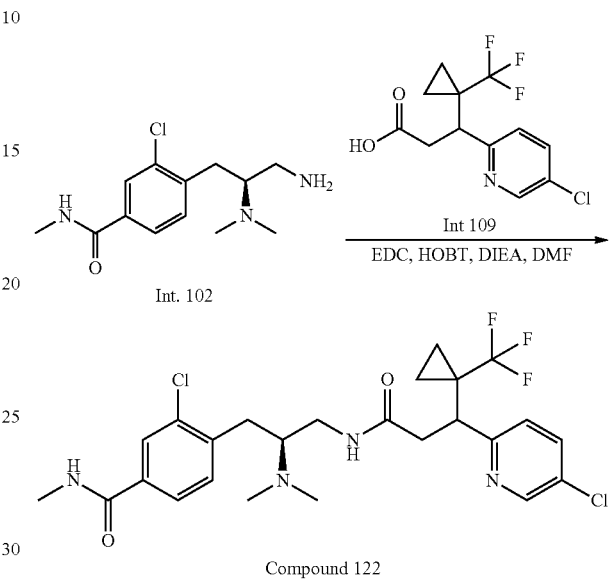

Compound 122

Compound 122 (16 mg, 35%) was synthesized from Int. 102 and Int. 109 as described in Example B9. MS (m/z): 545.2 (M+H).

Example B123: Preparation of 4-((S)-2-(dimethylamino)-3-((S)-3-(2-methylthiazol-5-yl)-3-(1-(trifluoromethyl)cyclopropyl)propanamido)propyl)-3-fluoro-N-methylbenzamide ("Compound 123")

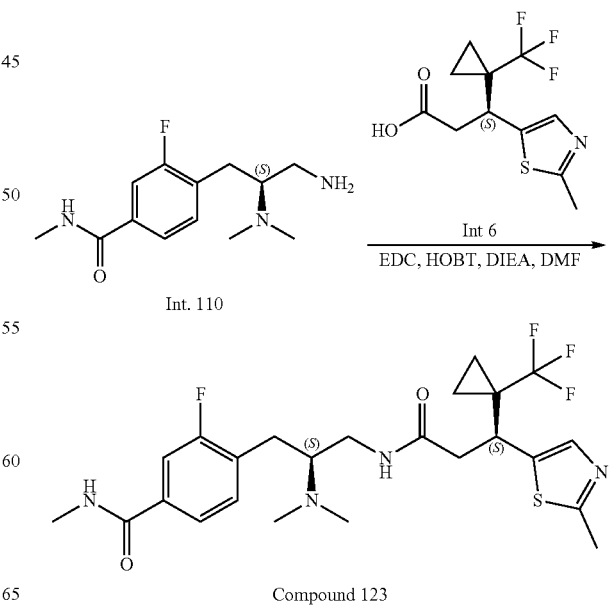

Compound 123

Compound 123 (33 mg, 63%) was synthesized from Int. 110 and Int. 6 as described in Example B9. MS (m/z): 515.2 (M+H).

Example B124: Preparation of 4-((S)-2-(dimethylamino)-3-((S)-3-(pyridin-3-yl)-3-(1-(trifluoromethyl)cyclopropyl)propanamido)propyl)-2-fluoro-N,3-dimethylbenzamide ("Compound 124")

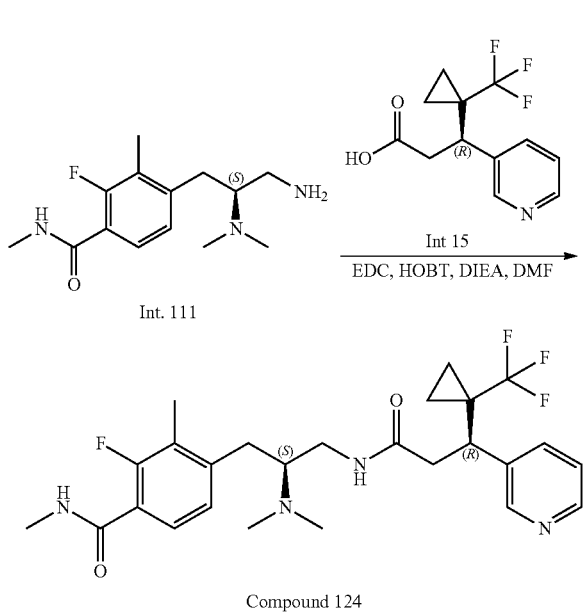

Compound 124

Compound 124 (35 mg, 71%) was synthesized from Int. 111 and Int. 15 as described in Example B9. MS (m/z): 509.2 (M+H).

Example B125: Preparation of 4-((S)-2-(dimethylamino)-3-((R)-3-(6-methylpyridin-3-yl)-3-(1-(trifluoromethyl)cyclopropyl)propanamido)propyl)-2-fluoro-N,3-dimethylbenzamide ("Compound 125")

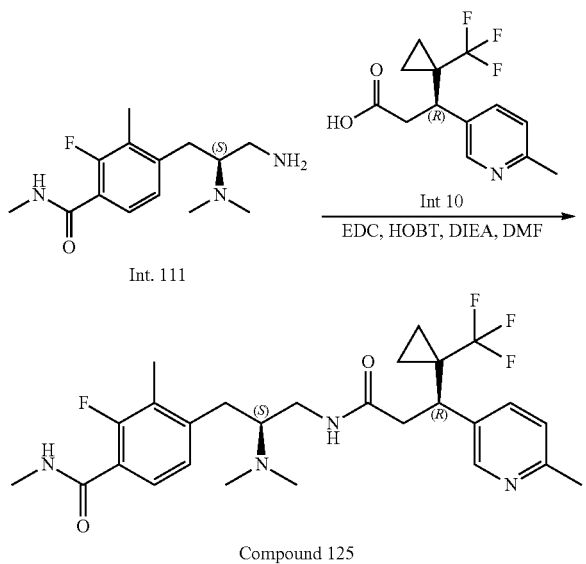

Compound 125

Compound 125 (26 mg, 56%) was synthesized from Int. 111 and Int. 10 as described in Example B9. MS (m/z): 523.2 (M+H).

Example B126: Preparation of 4-((S)-2-(dimethylamino)-3-((R)-5-methyl-3-(pyridin-3-yl)hexanamido)propyl)-N,3-dimethylbenzamide ("Compound 126")

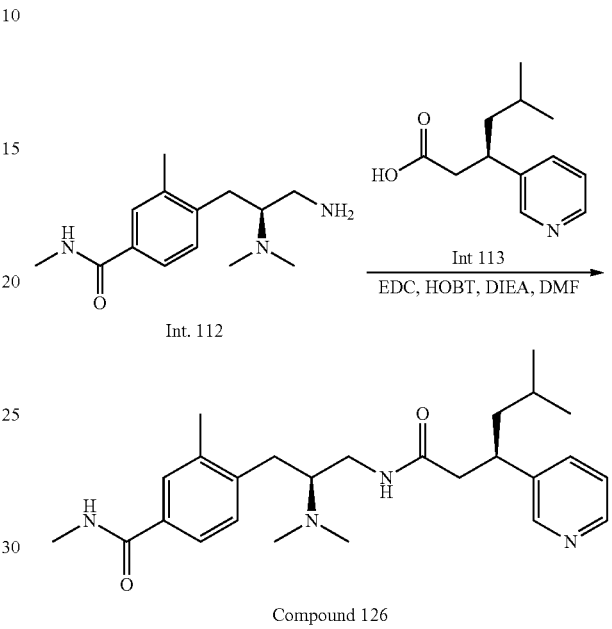

Compound 126

Compound 126 (30 mg, 59%) was synthesized from Int. 112 and Int. 113 as described in Example B9. MS (m/z): 439.3 (M+H).

Example B127: Preparation of 4-((S)-2-(dimethylamino)-3-((R)-3-(3-fluoropyridin-4-yl)-3-(1-(trifluoromethyl)cyclopropyl)propanamido)propyl)-N,3-dimethylbenzamide ("Compound 127")

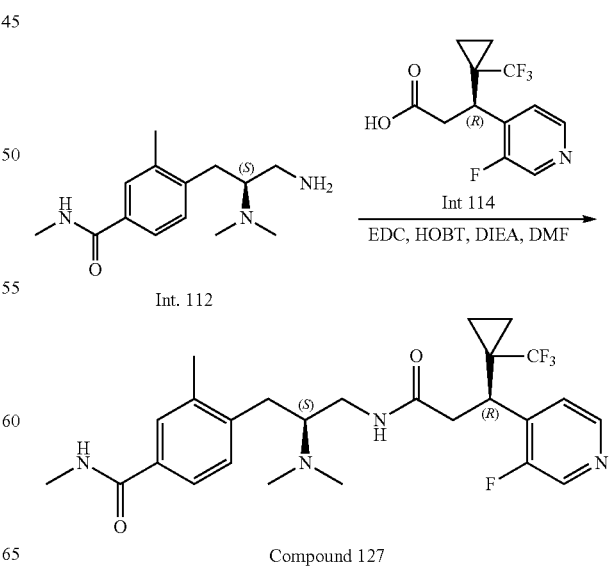

Compound 127

Compound 127 (10 mg, 39%) was synthesized from Int. 112 and Int. 114 as described in Example B9. MS (m/z): 509.2 (M+H).

Example B128: Preparation of 4-((S)-2-(dimethylamino)-3-((R)-3-(4-fluorophenyl)-3-(1-(trifluoromethyl)cyclopropyl)propanamido)propyl)-N,3-dimethylbenzamide ("Compound 128")

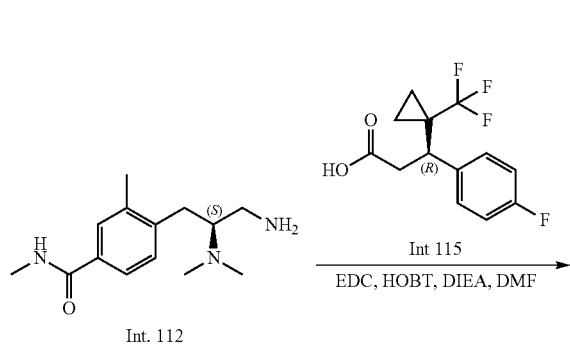

Compound 128

Compound 128 (32 mg, 78%) was synthesized from Int. 112 and Int. 115 as described in Example B9. MS (m/z): 508.3 (M+H).

Example B129: Preparation of 4-((S)-3-((S)-4,4-dimethyl-3-(pyridin-3-yl)pentanamido)-2-(dimethylamino)propyl)-N,3-dimethylbenzamide ("Compound 129")

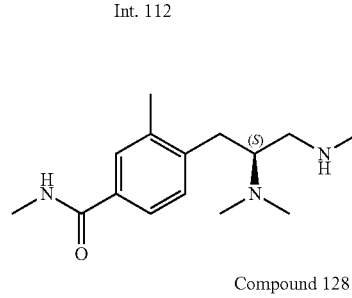

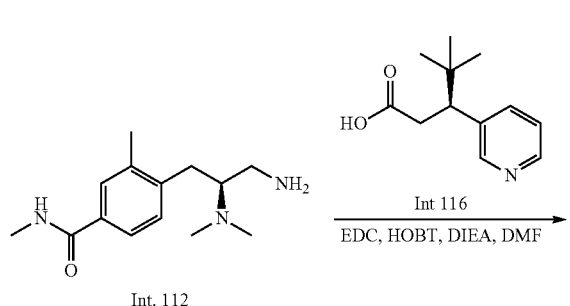

Compound 129

Compound 129 (14 mg, 63%) was synthesized from Int. 112 and Int. 116 as described in Example B9. MS (m/z): 439.3 (M+H).

Example B130: Preparation of 4-((S)-2-(dimethylamino)-3-((S)-3-(pyridin-4-yl)-3-(1-(trifluoromethyl)cyclopropyl)propanamido)propyl)-N,3-dimethylbenzamide ("Compound 130")

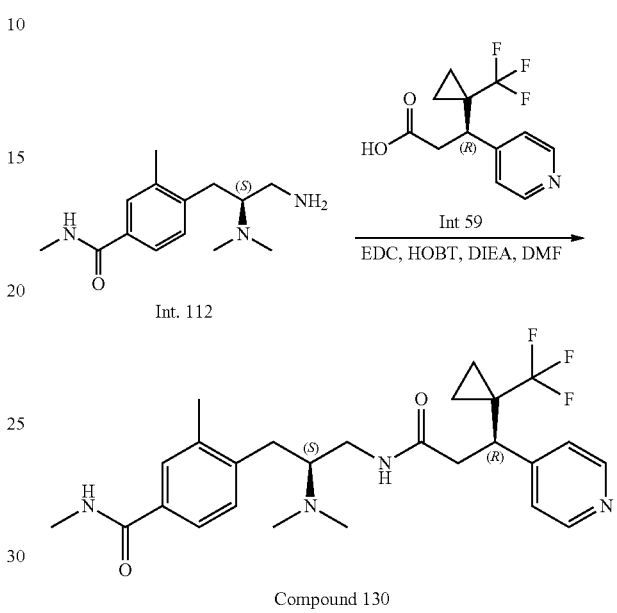

Compound 130

Compound 130 (32 mg, 78%) was synthesized from Int. 112 and Int. 59 as described in Example B9. MS (m/z): 491.3 (M+H).

Example B131: Preparation of 4-((S)-2-(dimethylamino)-3-((R)-3-(pyridin-3-yl)-3-(1-(trifluoromethyl)cyclopropyl)propanamido)propyl)-N,3-dimethylbenzamide ("Compound 131")

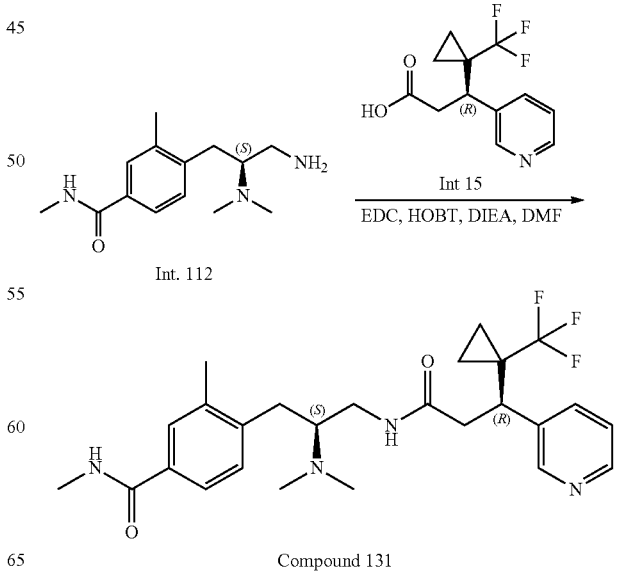

Compound 131

Compound 131 (32 mg, 78%) was synthesized from Int. 112 and Int. 15 as described in Example B9. MS (m/z): 491.3 (M+H).

Example B132: Preparation of 4-((S)-2-(dimethylamino)-3-((R)-3-(6-methylpyridin-3-yl)-3-(1-(trifluoromethyl)cyclopropyl)propanamido)propyl)-N,3-dimethylbenzamide ("Compound 132")

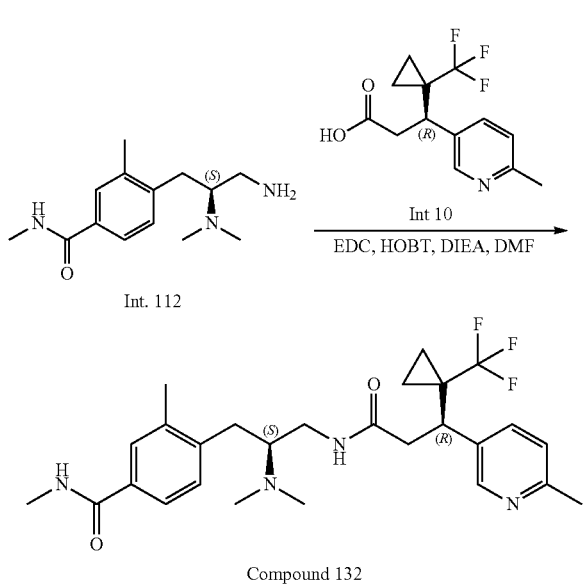

Compound 132

Compound 132 (32 mg, 78%) was synthesized from Int. 112 and Int. 10 as described in Example B9. MS (m/z): 505.3 (M+H).

Example B133: Preparation of 4-((S)-3-((R)-4-cyclopropyl-3-(pyridin-3-yl)butanamido)-2-(dimethylamino)propyl)-N,3-dimethylbenzamide ("Compound 133")

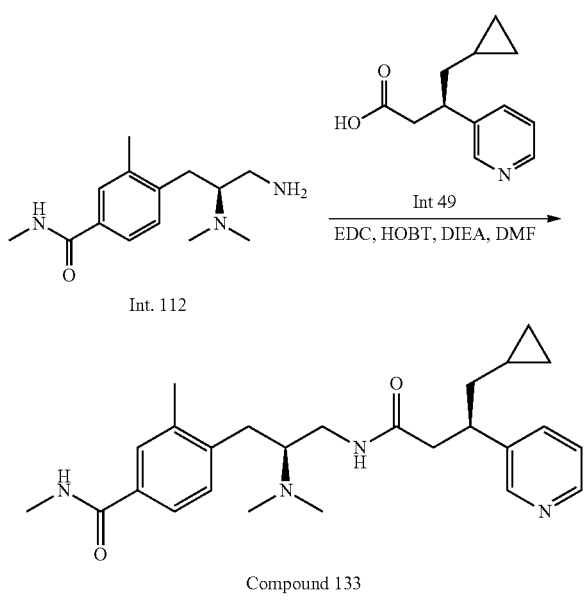 [SMILES: CNC(=O)c1ccc(C[C@@H](CN)N(C)C)c(C)c1 ; O=C(O)C[C@@H](CC1CC1)c1cccnc1 ; CNC(=O)c1ccc(C[C@@H](CNC(=O)C[C@@H](CC2CC2)c2cccnc2)N(C)C)c(C)c1]

Compound 133

Compound 133 (32 mg, 78%) was synthesized from Int. 112 and Int. 49 as described in Example B9. MS (m/z): 437.3 (M+H).

Example B134: Preparation of 4-((2S)-2-(dimethylamino)-3-(3-(pyridin-4-yl)-3-(1-(trifluoromethyl)cyclopropyl)propanamido)propyl)-N,3-dimethylbenzamide ("Compound 134")

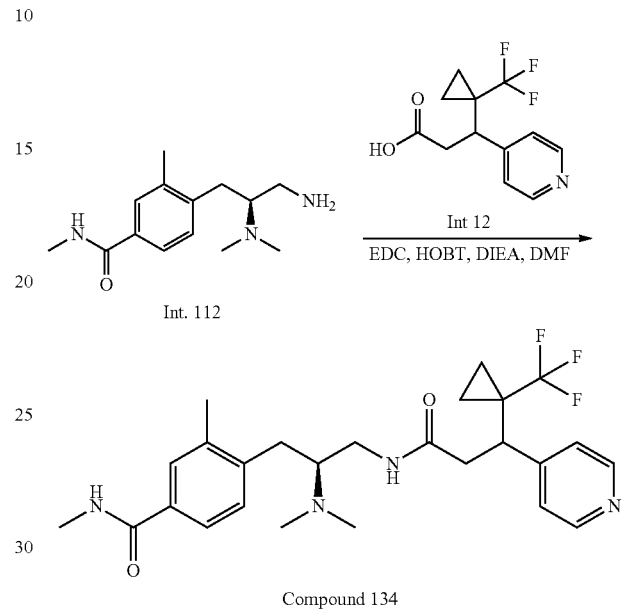

Compound 134

Compound 134 (28 mg, 70%) was synthesized from Int. 112 and Int. 12 as described in Example B9. MS (m/z): 491.2 (M+H).

Example B135: Preparation of 4-((S)-2-(dimethylamino)-3-((R)-3-(2-methylpyrimidin-5-yl)-3-(1-(trifluoromethyl)cyclopropyl)propanamido)propyl)-N,3-dimethylbenzamide ("Compound 135")

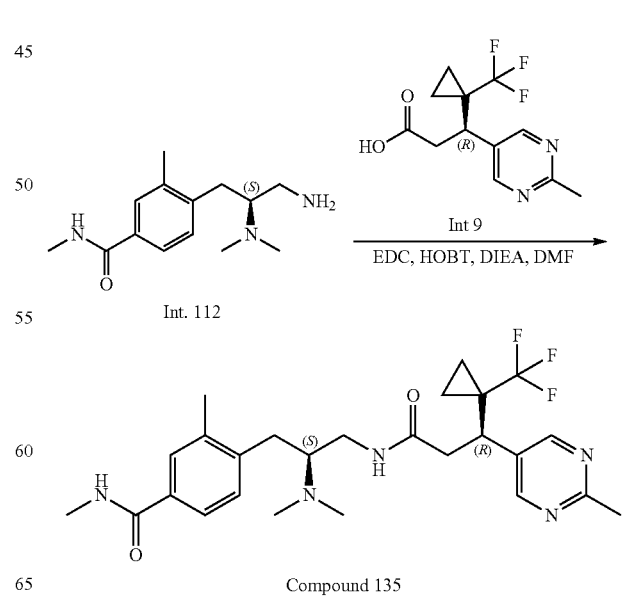

Compound 135

Compound 135 (28 mg, 70%) was synthesized from Int. 112 and Int. 9 as described in Example B9. MS (m/z): 506.3 (M+H).

Example B136: Preparation of 4-((S)-3-((R)-3-(3,5-difluorophenyl)-3-(1-(trifluoromethyl)cyclopropyl)propanamido)-2-(dimethylamino)propyl)-N,3-dimethylbenzamide ("Compound 136")

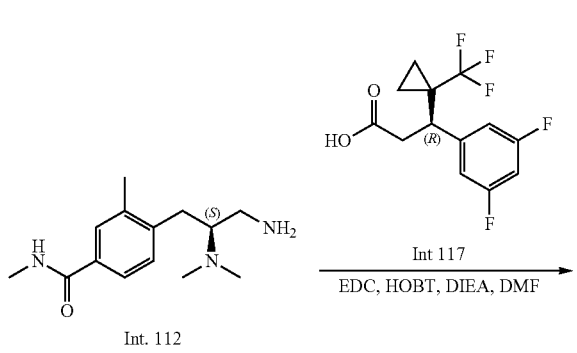

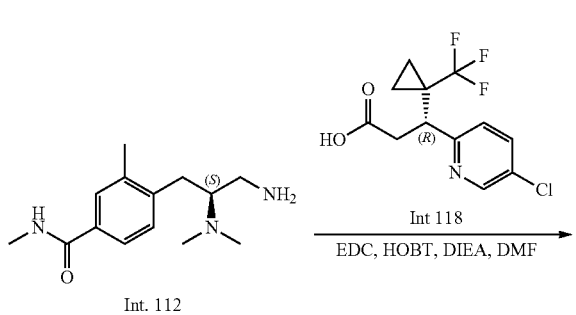

Compound 136

Compound 136 (18 mg, 64%) was synthesized from Int. 112 and Int. 117 as described in Example B9. MS (m/z): 526.2 (M+H).

Example B137: Preparation of 4-((S)-3-((R)-3-(5-chloropyridin-2-yl)-3-(1-(trifluoromethyl)cyclopropyl)propanamido)-2-(dimethylamino)propyl)-N,3-dimethylbenzamide ("Compound 137")

Compound 137 (18 mg, 64%) was synthesized from Int. 112 and Int. 118 as described in Example B9. MS (m/z): 525.2 (M+H).

Example B138: Preparation of 4-((S)-3-((S)-3-(5-chloropyridin-2-yl)-3-(1-(trifluoromethyl)cyclopropyl)propanamido)-2-(dimethylamino)propyl)-N,3-dimethylbenzamide ("Compound 138"

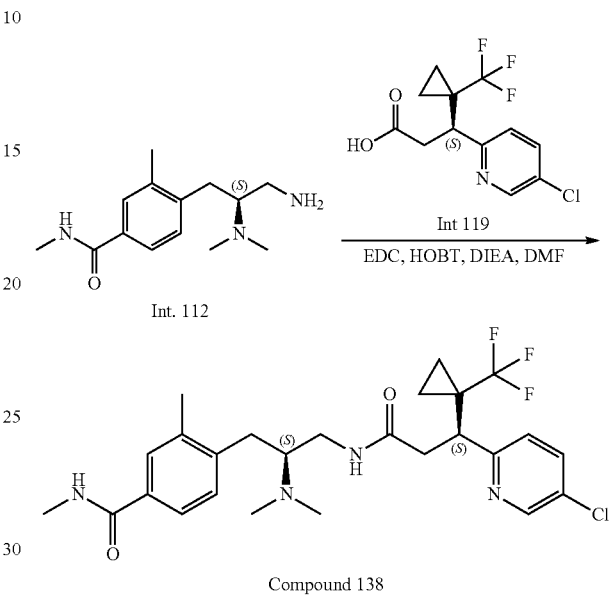

Compound 138

Compound 138 (27 mg, 74%) was synthesized from Int. 112 and Int. 119 as described in Example B9. MS (m/z): 525.2 (M+H).

Example B139: Preparation of 4-((S)-3-((S)-4-cyclopropyl-3-(pyridin-2-yl)butanamido)-2-(dimethylamino)propyl)-N,3-dimethylbenzamide ("Compound 139")

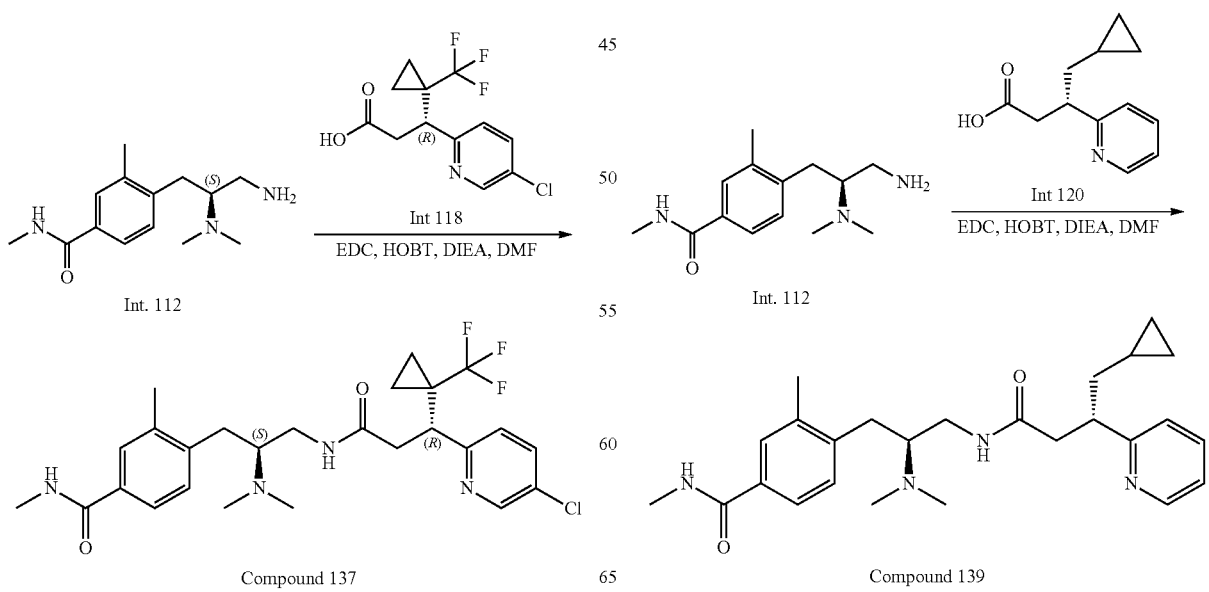

Compound 139

Compound 139 (10 mg, 67%) was synthesized from Int. 112 and Int. 120 as described in Example B9. MS (m/z): 437.2 (M+H).

Example B140: Preparation of 4-((S)-2-(dimethylamino)-3-((R)-5-methyl-3-(pyridin-2-yl)hexanamido)propyl)-N,3-dimethylbenzamide ("Compound 140")

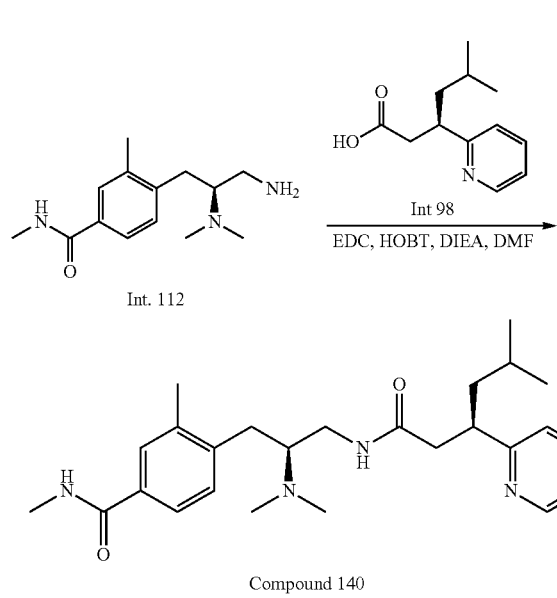

Compound 140

Compound 140 (32 mg, 83%) was synthesized from Int. 112 and Int. 98 as described in Example B9. MS (m/z): 439.3 (M+H).

Example B141: Preparation of 4-((2S)-2-(dimethylamino)-3-(3-(pyridin-2-yl)-3-(1-(trifluoromethyl)cyclopropyl)propanamido)propyl)-N,3-dimethylbenzamide ("Compound 141")

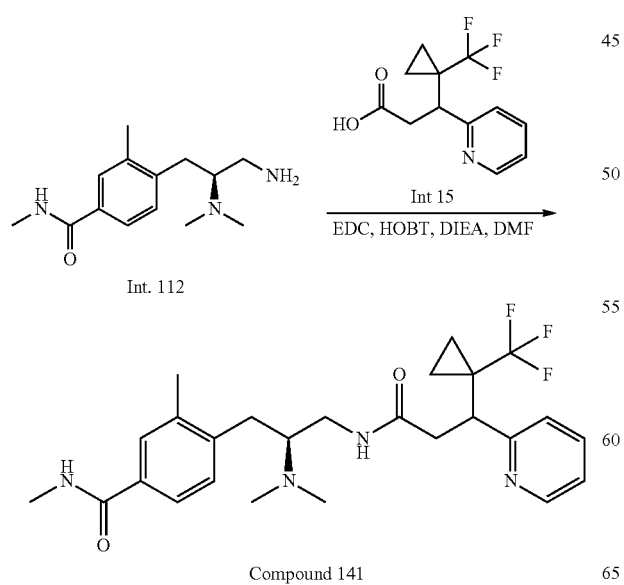

Compound 141

Compound 141 was synthesized from Int. 112 and Int. 121 as described in Example B9. MS (m/z): 491.3 (M+H).

Example B142: Preparation of 4-((S)-3-((R)-3-(4-chlorophenyl)-3-(1-(trifluoromethyl)cyclopropyl)propanamido)-2-(dimethylamino)propyl)-N,3-dimethylbenzamide ("Compound 142")

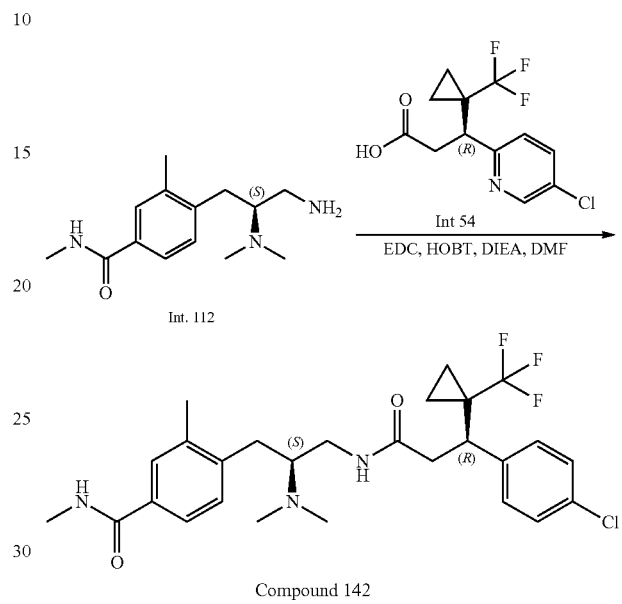

Compound 142

Compound 142 was synthesized from Int. 112 and Int. 54 as described in Example B9. MS (m/z): 524.2 (M+H).

Example B143: Preparation of 4-((S)-2-(dimethylamino)-3-((R)-3-phenyl-3-(1-(trifluoromethyl)cyclopropyl)propanamido)propyl)-N,3-dimethylbenzamide ("Compound 143")

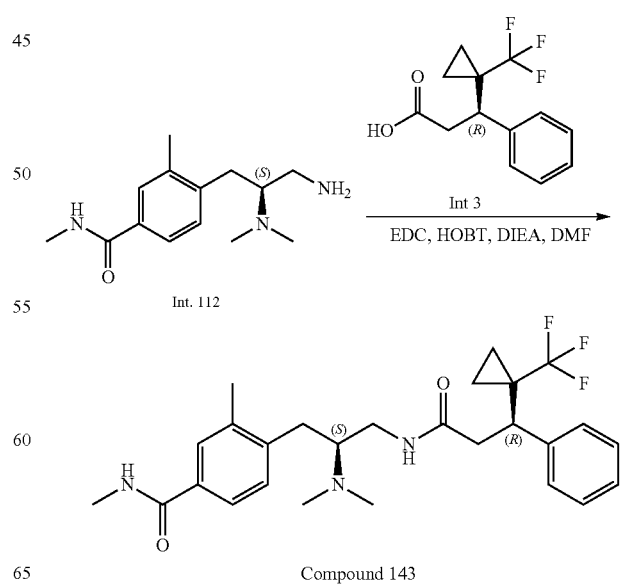

Compound 143

Compound 143 was synthesized from Int. 112 and Int. 3 as described in Example B9. MS (m/z): 490.3 (M+H).

Example B144: Preparation of 4-((S)-2-(dimethylamino)-3-((R)-3-phenyl-3-(1-(trifluoromethyl)cyclopropyl)propanamido)propyl)-2-fluoro-N,5-dimethylbenzamide ("Compound 144")

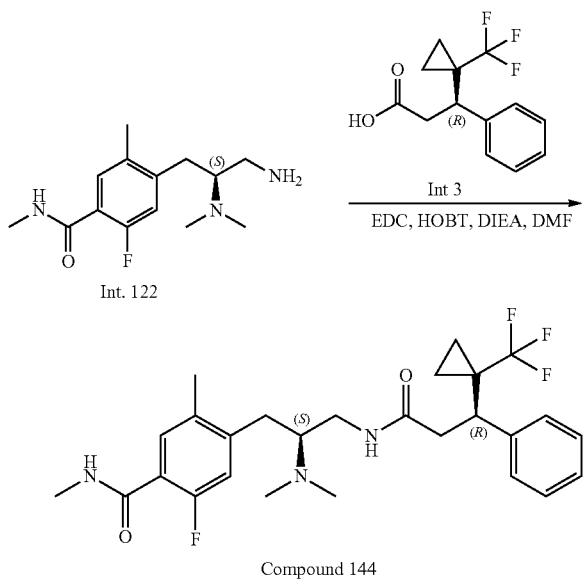

Compound 144

Compound 144 (25 mg, 79%) was synthesized from Int. 122 and Int. 3 as described in Example B9. MS (m/z): 508.2 (M+H).

Example B145: Preparation of 4-((S)-2-(dimethylamino)-3-((R)-3-phenyl-3-(1-(trifluoromethyl)cyclopropyl)propanamido)propyl)-2-fluoro-N,5-dimethylbenzamide ("Compound 145")

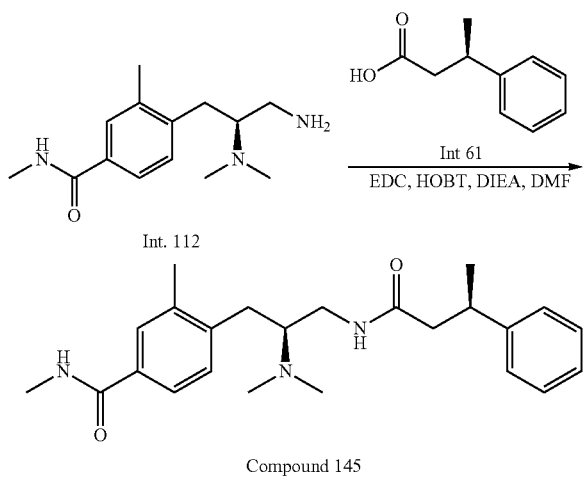

Compound 145

Compound 145 (43 mg, 71%) was synthesized from Int. 112 and Int. 61 as described in Example B9. MS (m/z): 396.3 (M+H).

Example B146: Preparation of 4-((S)-3-((R)-4,4-dimethyl-3-phenylpentanamido)-2-(dimethylamino)propyl)-2-fluoro-N,5-dimethylbenzamide ("Compound 146")

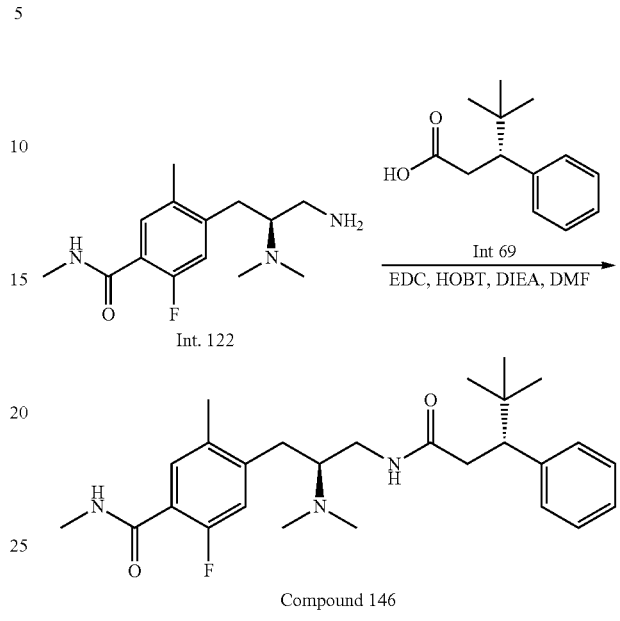

Compound 146

Compound 146 (52 mg, 76%) was synthesized from Int. 122 and Int. 69 as described in Example B9. MS (m/z): 456.3 (M+H).

Example B147: Preparation of 2-chloro-4-((S)-2-(dimethylamino)-3-((R)-5-methyl-3-phenylhexanamido)propyl)-N-methylbenzamide ("Compound 147")

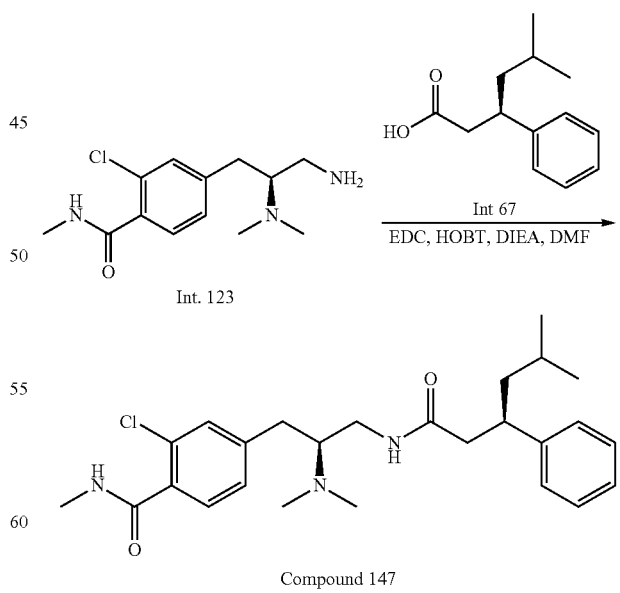

Compound 147

Compound 147 (35 mg, 63%) was synthesized from Int. 123 and Int. 67 as described in Example B9. MS (m/z): 458.3 (M+H).

Example B148: Preparation of 2-chloro-4-((S)-2-(dimethylamino)-3-((S)-4-methyl-3-phenylpentanamido)propyl)-N-methylbenzamide ("Compound 148")

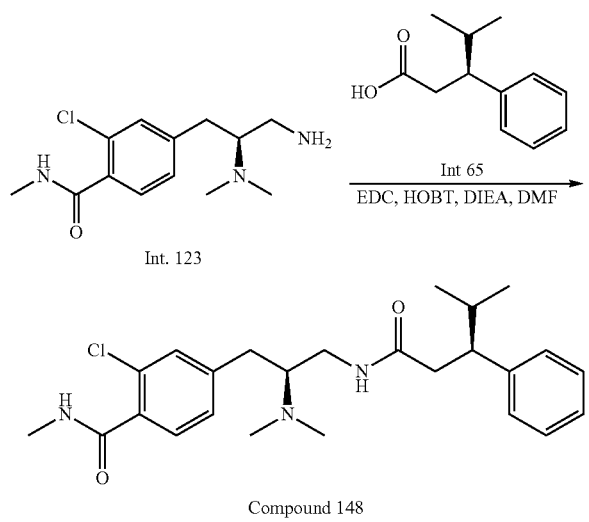

Compound 148 (35 mg, 67%) was synthesized from Int. 123 and Int. 65 as described in Example B9. MS (m/z): 444.3 (M+H).

Example B149: Preparation of 2-chloro-4-((S)-2-(dimethylamino)-3-((R)-3-phenylbutanamido)propyl)-N-methylbenzamide ("Compound 149")

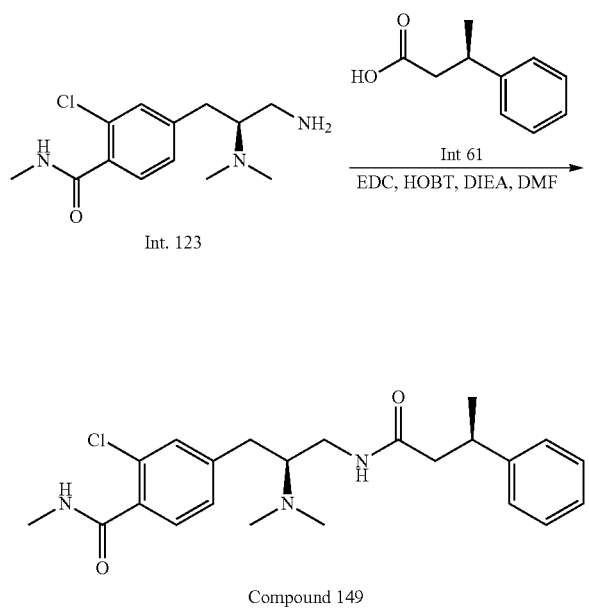 [SMILES: CNC(=O)c1ccc(C[C@@H](CN)N(C)C)cc1Cl ; C[C@H](CC(=O)O)c1ccccc1 ; CNC(=O)c1ccc(C[C@@H](CNC(=O)C[C@@H](C)c2ccccc2)N(C)C)cc1Cl]

Compound 149 (22 mg, 81%) was synthesized from Int. 123 and Int. 61 as described in Example B9. MS (m/z): 416.2 (M+H).

Example 3B150: Preparation of 2-chloro-4-((S)-3-((S)-4,4-dimethyl-3-phenylpentanamido)-2-(dimethylamino)propyl)-N-methylbenzamide ("Compound 150")

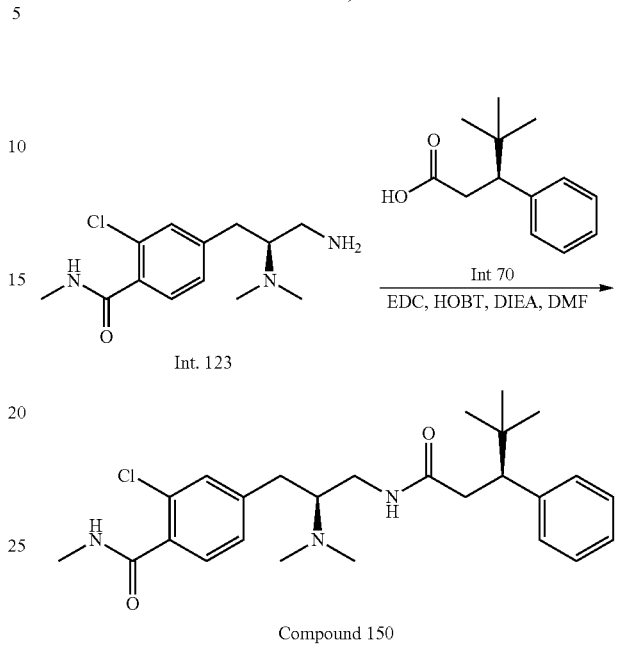

Compound 150 (22 mg, 81%) was synthesized from Int. 123 and Int. 70 as described in Example B9. MS (m/z): 458.3 (M+H).

Example B151: Preparation of 4-((S)-2-(dimethylamino)-3-((R)-3-(5-fluoropyridin-3-yl)-4,4-dimethylpentanamido)propyl)-2-fluoro-N-methylbenzamide ("Compound 151")

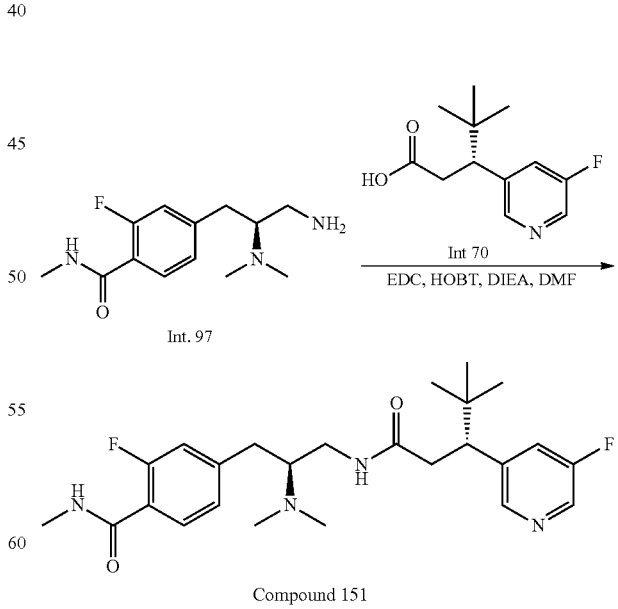

Compound 151 (22 mg, 81%) was synthesized from Int. 97 and Int. 34 as described in Example B9. MS (m/z): 461.3 (M+H).

Example B152: Preparation of 4-((S)-2-(dimethyl-amino)-3-((R)-3-(2-methylpyrimidin-5-yl)-3-(1-(trifluoromethyl)cyclopropyl)propanamido)propyl)-2-fluoro-N-methylbenzamide ("Compound 152")

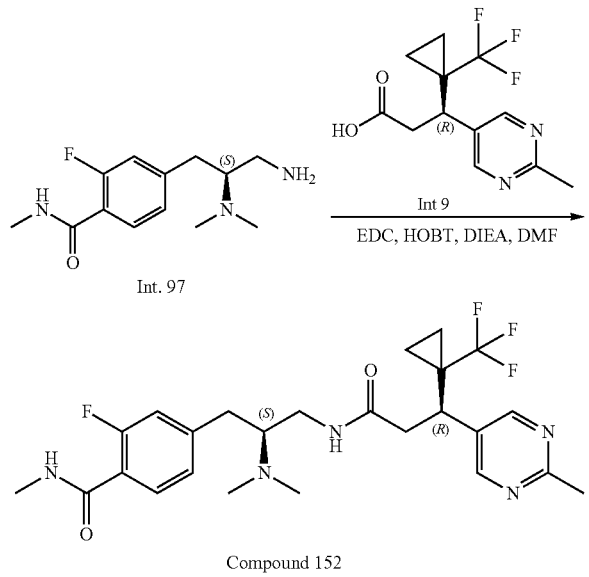

Compound 152

Compound 152 (40 mg, 74%) was synthesized from Int. 97 and Int. 9 as described in Example B9. MS (m/z): 510.3 (M+H).

Example B153: Preparation of 4-((S)-2-(dimethyl-amino)-3-((R)-3-(pyridin-2-yl)-3-(1-(trifluoromethyl)cyclopropyl)propanamido)propyl)-2-fluoro-N-methylbenzamide ("Compound 153")

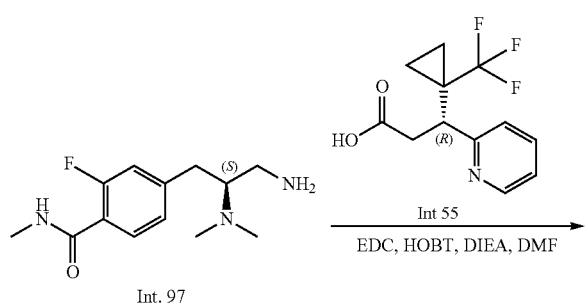

Compound 153

Compound 153 (19 mg, 54%) was synthesized from Int. 97 and Int. 55 as described in Example B9. MS (m/z): 495.2 (M+H).

Example B154: Preparation of 4-((S)-2-(dimethyl-amino)-3-((S)-3-phenyl-3-(1-(trifluoromethyl)cyclopropyl)propanamido)propyl)-2-fluoro-N-methylbenzamide ("Compound 154")

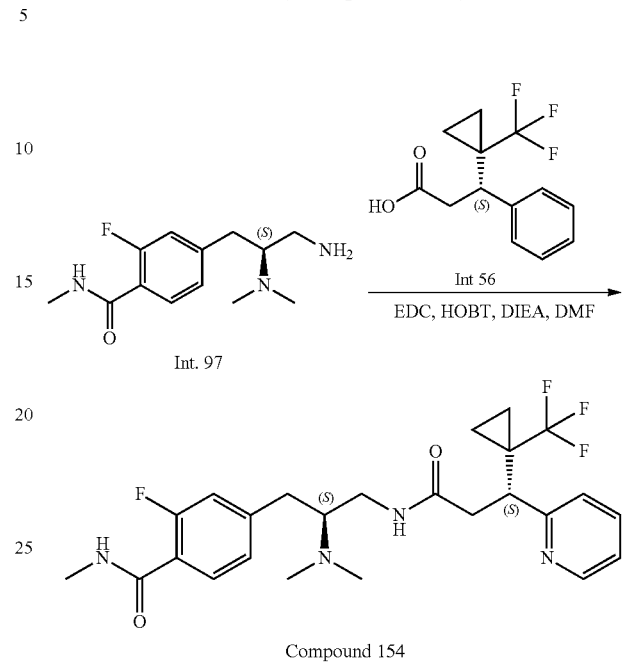

Compound 154

Compound 154 (25 mg, 77%) was synthesized from Int. 97 and Int. 56 as described in Example B9. MS (m/z): 494.3 (M+H).

Example B155: Preparation of 4-((S)-3-((R)-3-(4-chlorophenyl)butanamido)-2-(dimethylamino)propyl)-2-fluoro-N-methylbenzamide ("Compound 155")

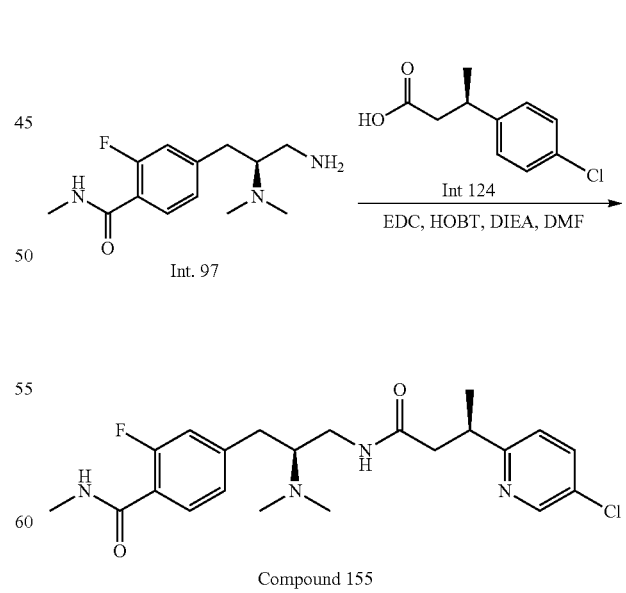

Compound 155

Compound 155 (71 mg, 83%) was synthesized from Int. 97 and Int. 124 as described in Example B9. MS (m/z): 434.2 (M+H).

Example B156: Preparation of 4-((S)-3-((S)-3-(4-chlorophenyl)butanamido)-2-(dimethylamino)propyl)-2-fluoro-N-methylbenzamide ("Compound 156")

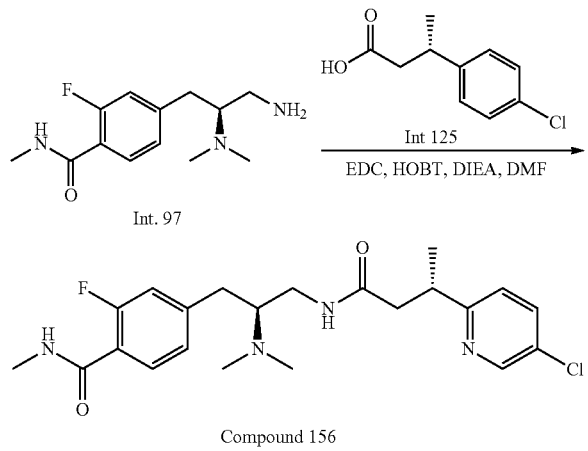

Compound 156 (41 mg, 63%) was synthesized from Int. 97 and Int. 125 as described in Example B9. MS (m/z): 434.2 (M+H).

Example B157: Preparation of 4-((S)-3-((S)-4,4-dimethyl-3-phenylpentanamido)-2-(pyrrolidin-1-yl)propyl)-2-fluoro-N-methylbenzamide ("Compound 157")

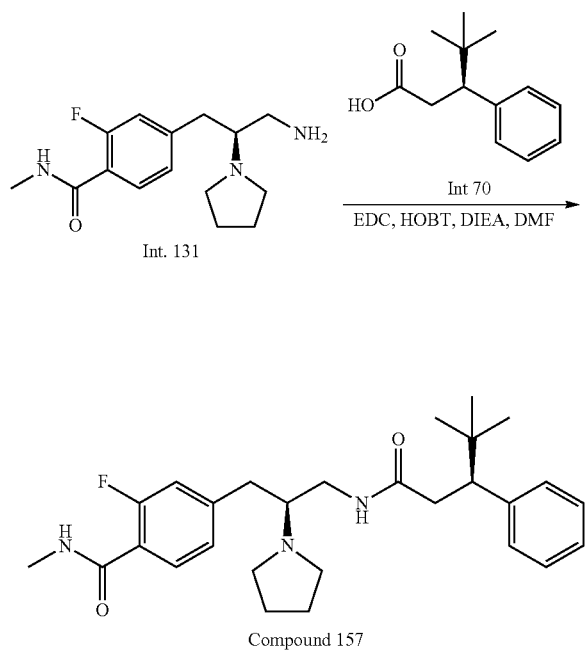 [SMILES: CNC(=O)c1ccc(C[C@@H](CN)N2CCCC2)cc1F ; CC(C)(C)[C@H](CC(=O)O)c1ccccc1 ; CNC(=O)c1ccc(C[C@@H](CNC(=O)C[C@H](c2ccccc2)C(C)(C)C)N2CCCC2)cc1F]

Compound 157 (41 mg, 63%) was synthesized from Int. 131 and Int. 70 as described in Example B9. MS (m/z): 468.3 (M+H).

Example B158: Preparation of 4-((S)-3-((S)-4,4-dimethyl-3-phenylpentanamido)-2-(dimethylamino)propyl)-2-fluoro-N-methylbenzamide ("Compound 158")

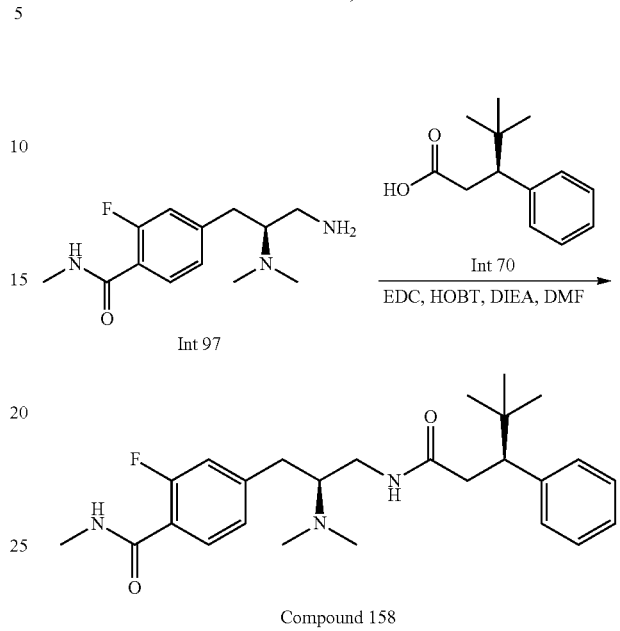

Compound 158 (42 mg, 77%) was synthesized from Int. 97 and Int. 70 as described in Example B9. MS (m/z): 442.3 (M+H).

Example B159: Preparation of 4-((S)-3-((R)-4,4-dimethyl-3-phenylpentanamido)-2-(dimethylamino)propyl)-2-fluoro-N-methylbenzamide ("Compound 159")

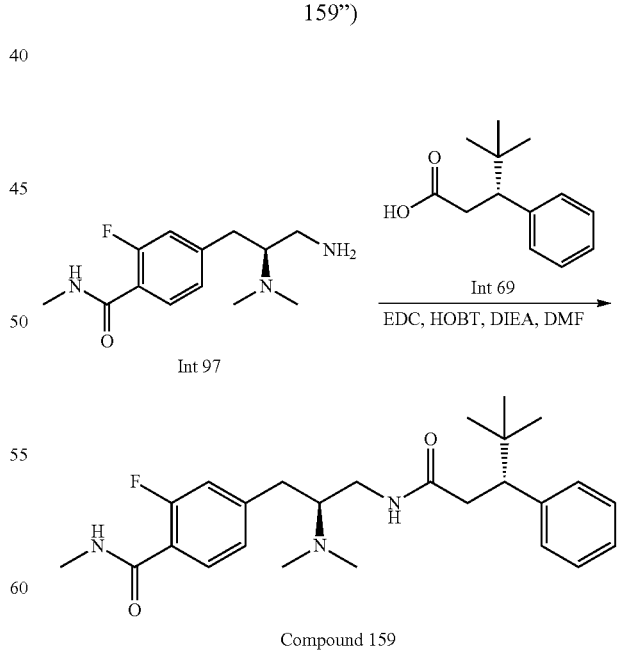

Compound 159 (600 mg, 83%) was synthesized from Int. 97 and Int. 69 as described in Example B9. MS (m/z): 442.3 (M+H).

Example B160: Preparation of 4-((S)-2-(dimethyl-amino)-3-((R)-5-methyl-3-phenylhexanamido)propyl)-2-fluoro-N-methylbenzamide ("Compound 160")

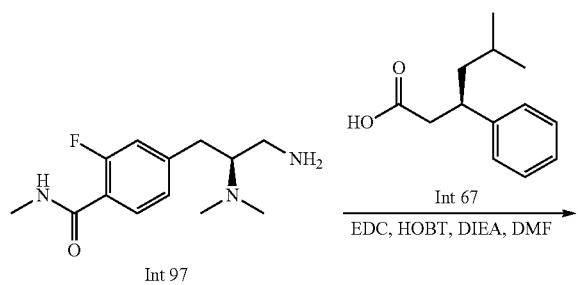

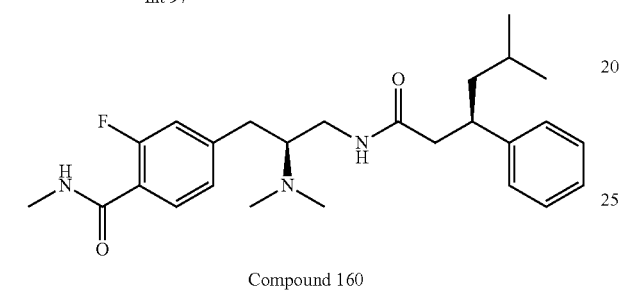

Compound 160

Compound 160 (9 mg, 43%) was synthesized from Int. 97 and Int. 67 as described in Example B9. MS (m/z): 442.3 (M+H).

Example B161: Preparation of 44-((S)-2-(1H-imidazol-1-yl)-3-((S)-3-phenylbutanamido)propyl)-2-fluoro-N-methylbenzamide ("Compound 161")

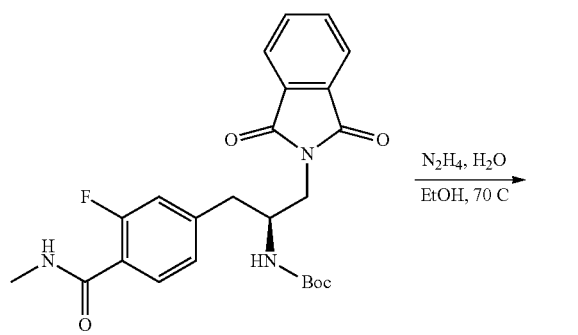

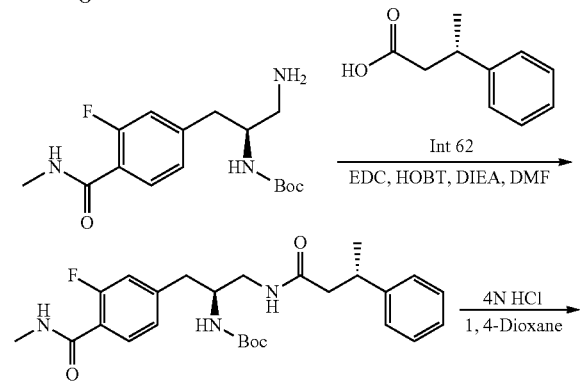

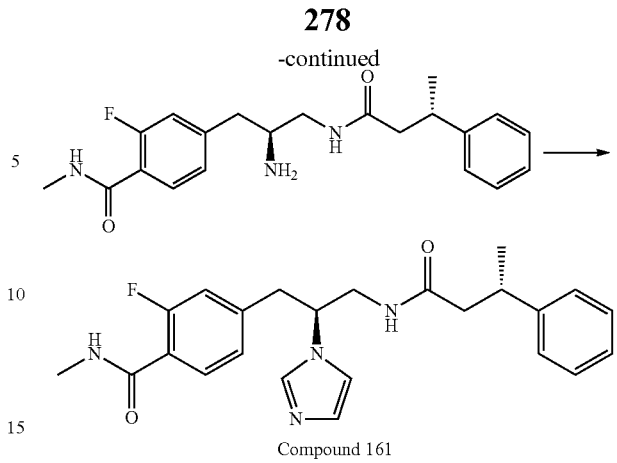

Compound 161

Compound 161 (15 mg, 56%) was synthesized as described in Example B9. MS (m/z): 423.2 (M+H).

Example B162: Preparation of 4-((S)-2-(dimethyl-amino)-3-((R)-4-methyl-3-phenylpentanamido)propyl)-2-fluoro-N-methylbenzamide ("Compound 162")

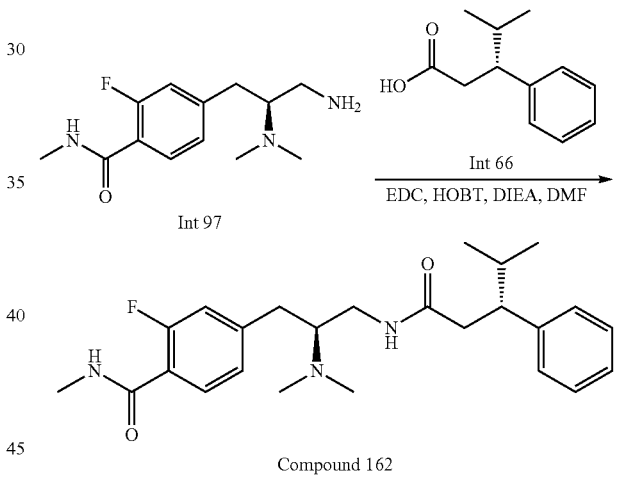

Compound 162

Compound 162 (44 mg, 69%) was synthesized from Int. 97 and Int. 66 as described in Example B9. MS (m/z): 428.3 (M+H).

Example B163: Preparation of 4-((S)-2-(dimethyl-amino)-3-((S)-3-(pyridin-2-yl)butanamido)propyl)-2-fluoro-N-methylbenzamide ("Compound 163")

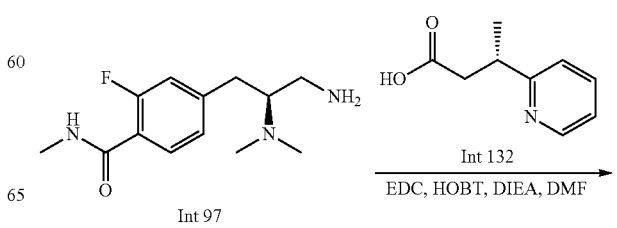

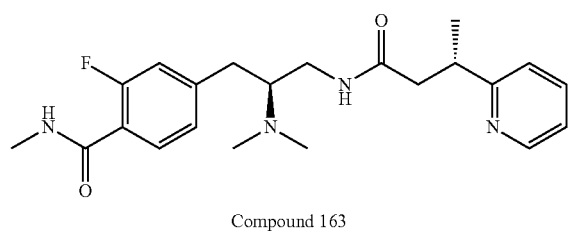

Compound 163

Compound 163 (44 mg, 69%) was synthesized from Int. 97 and Int. 132 as described in Example B9. MS (m/z): 401.2 (M+H).

Example B164: Preparation of 4-((S)-2-(dimethylamino)-3-((S)-3-phenylbutanamido)propyl)-2-fluoro-N-methylbenzamide ("Compound 164")

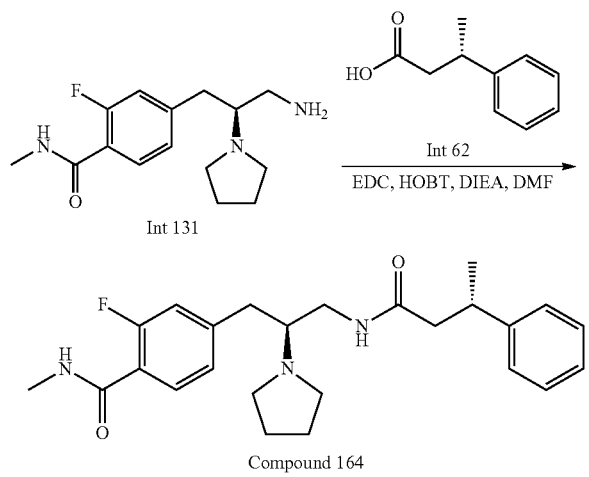

Compound 164

Compound 164 (45 mg, 82%) was synthesized from Int. 131 and Int. 62 as described in Example B9. MS (m/z): 426.3 (M+H).

Example B165: Preparation of 4-((S)-2-(dimethylamino)-3-((S)-3-phenylbutanamido)propyl)-2-fluoro-N-methylbenzamide ("Compound 165")

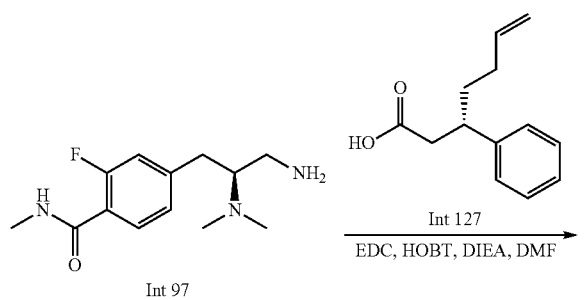

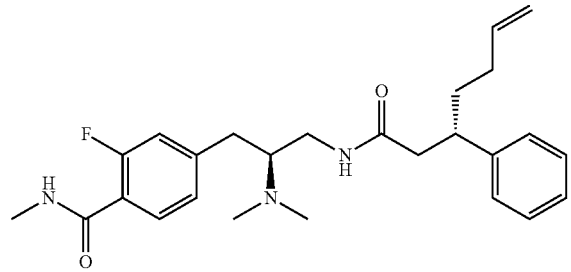

Compound 165

Compound 165 (35 mg, 72%) was synthesized from Int. 97 and Int. 127 as described in Example B9. MS (m/z): 440.3 (M+H).

Example B166: Preparation of 4-((S)-2-(diethylamino)-3-((R)-4,4-dimethyl-3-phenylpentanamido)propyl)-2-fluoro-N-methylbenzamide ("Compound 166")

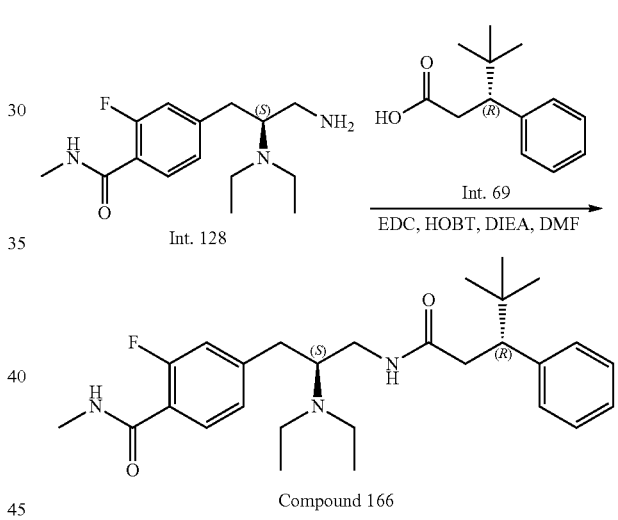

Compound 166

Compound 166 (47 mg, 62%) was synthesized from Int. 128 and Int. 69 as described in Example B9. MS (m/z): 470.3 (M+H).

Example B167: Preparation of 4-((S)-2-(dimethylamino)-3-((S)-3-phenylbutanamido)propyl)-2-fluoro-N-methylbenzamide ("Compound 167")

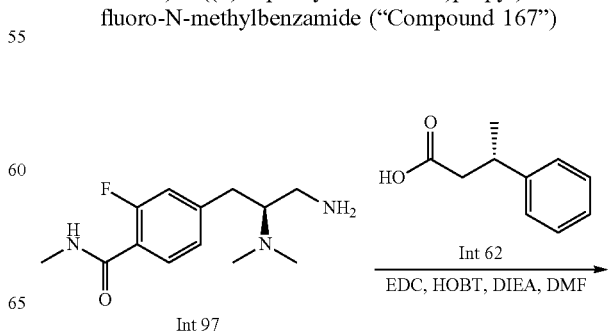

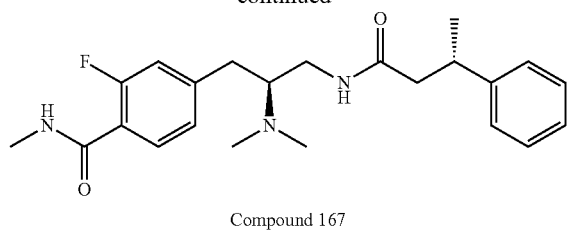

Compound 167

Compound 167 (35 mg, 62%) was synthesized from Int. 97 and Int. 62 as described in Example B9. MS (m/z): 400.3 (M+H).

Example B168: Preparation of (S)-3-(((S)-4,4-dimethyl-3-phenylpentanamido)methyl)-N,2-dimethyl-1,2,3,4-tetrahydroisoquinoline-7-carboxamide ("Compound 168")

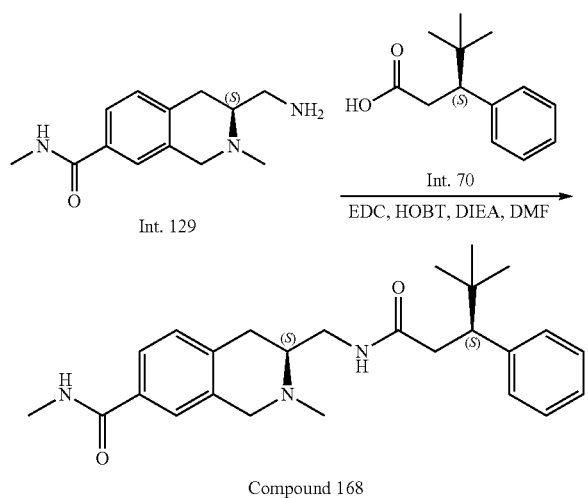

Compound 168

Compound 168 (40 mg, 75%) was synthesized from Int. 129 and Int. 70 as described in Example B9. MS (m/z). 422.2 (M+H).

Example B169: Preparation of (R)-N-((S)-2-(dimethylamino)-3-(7-methyl-2-oxo-2,3-dihydrobenzo[d]oxazol-6-yl)propyl)-3-(2-methylpyrimidin-5-yl)-3-(1-(trifluoromethyl)cyclopropyl)propanamide ("Compound 169")

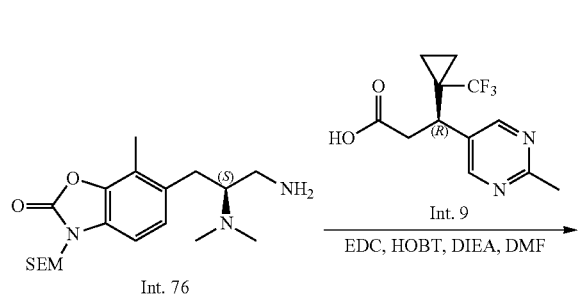

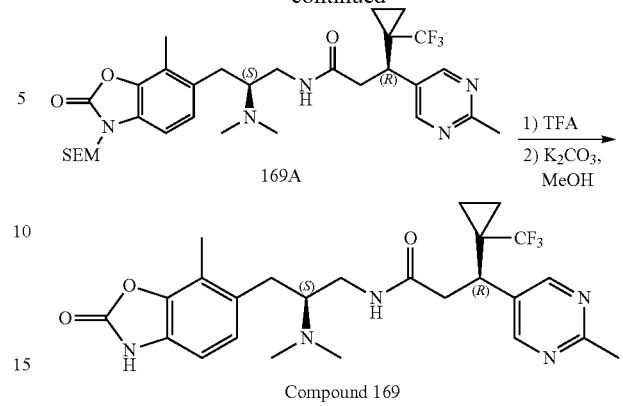

169A

Compound 169

Compound 169 (9 mg, 10%) was synthesized from Int. 76 and Int. 9 as described in Example B9. MS (m/z): 506.2 (M+H).

Example B170: Preparation of (R)-N-((S)-2-(dimethylamino)-3-(7-methyl-2-oxo-2,3-dihydrobenzo[d]oxazol-6-yl)propyl)-3-(pyridin-4-yl)-3-(1-(trifluoromethyl)cyclopropyl)propanamide ("Compound 170")

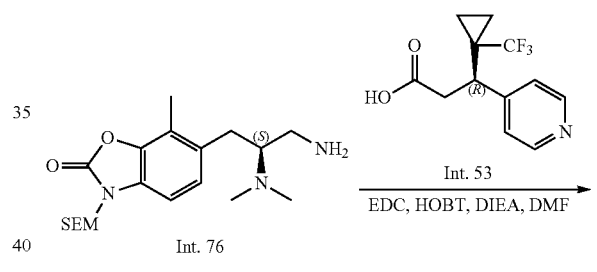

Int. 76

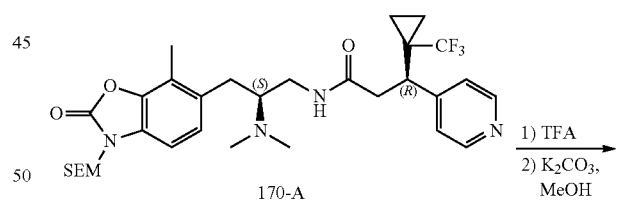

170-A

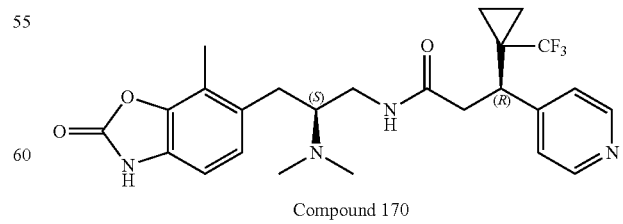

Compound 170

Compound 170 (27.4 mg, 41%) was synthesized from Int. 76 and Int. 59 as described in Example B9. MS (m/z): 491.2 (M+H).

Example B171: Preparation of (3S)-N-[(2S)-2-(dimethylamino)-3-(7-methyl-2-oxo-2,3-dihydro-1,3-benzoxazol-6-yl)propyl]-3-phenylbutanamide ("Compound 171")

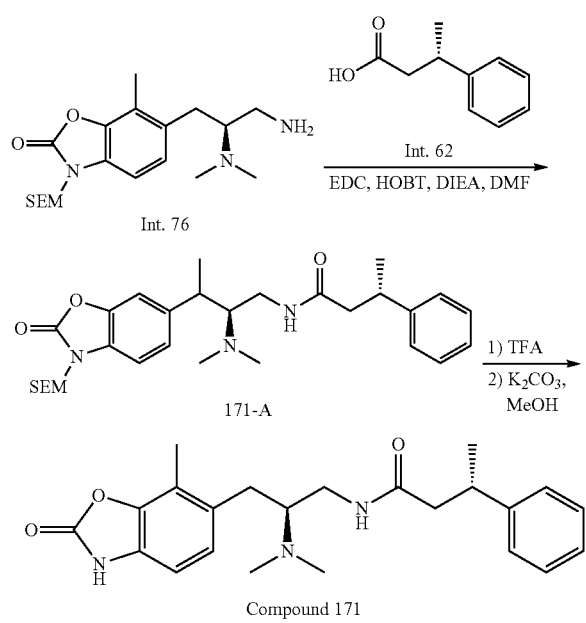

Compound 171 (14.5 mg, 18%) was synthesized from Int. 76 and Int. 62 as described in Example B9. MS (m/z): 396.2 (M+H).

Example B172: Preparation of (3S)-N-[(2S)-2-(dimethylamino)-3-(2-oxo-2,3-dihydro-1,3-benzoxazol-6-yl)propyl]-5-methyl-3-phenylhexanamide ("Compound 172")

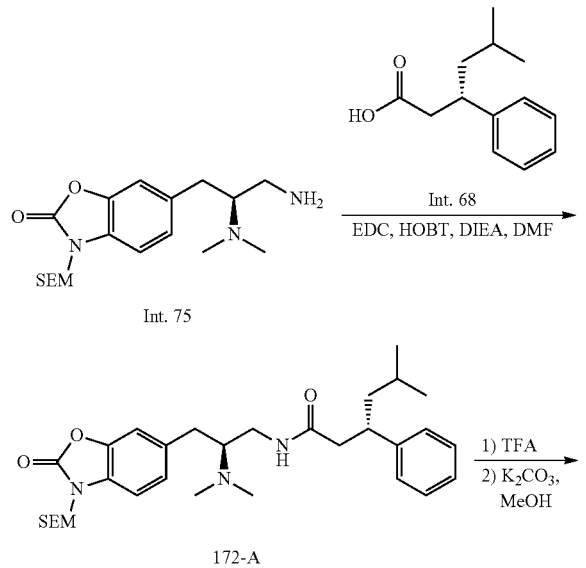

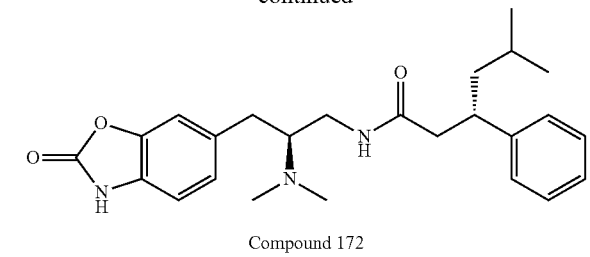

Compound 172

Step 1: Compound 172A was synthesized from Int. 75 and Int. 68 as described in Example B9.

Step 2: A solution of (1S,2S)-N-[(2S)-2-(dimethylamino)-3-(2-oxo-3-{[2-(trimethylsilyl)ethoxy]methyl}-2,3-dihydro-1,3-benzoxazol-6-yl)propyl]-2-phenylcyclopropane-1-carboxamide (172A, 950 mg, 1.86 mmol) in TFA (10 mL) was stirred at RT for 1 h. LC/MS showed completed conversion to the product 172-A. The mixture was concentrated to dryness, dissolved in MeOH (3 mL) and added potassium carbonate (99.9 mg, 0.723 mmol) and continued to stir at RT for 16 h. The mixture was concentrated to dryness, taken up water, acidified with 2N HCl to pH=6-7, extracted with DCM (3×). The combined extracts were dried over MgSO$_4$, concentrated and purified by flash chromatography (0-10% MeOH/DCM) to give (3S)-N-[(2S)-2-(dimethylamino)-3-(2-oxo-2,3-dihydro-1,3-benzoxazol-6-yl)propyl]-5-methyl-3-phenylhexanamide (40 mg, 63.7%). MS (m/z): 424.3 (M+H).

Example B173: Preparation of (R)-N-((S)-2-(dimethylamino)-3-(2-oxo-2,3-dihydrobenzo[d]oxazol-6-yl)propyl)-4-methyl-3-phenylpentanamide ("Compound 173")

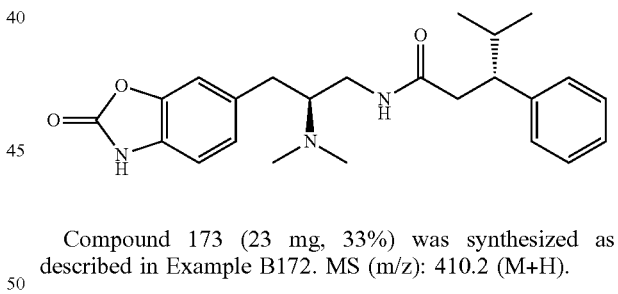

Compound 173 (23 mg, 33%) was synthesized as described in Example B172. MS (m/z): 410.2 (M+H).

Example B174: Preparation of (S)-N-((S)-2-(dimethylamino)-3-(2-oxo-2,3-dihydrobenzo[d]oxazol-6-yl)propyl)-3-phenylpentanamide ("Compound 174")

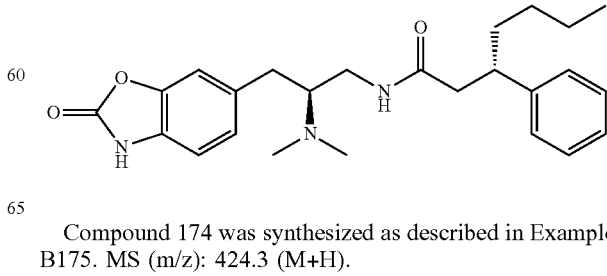

Compound 174 was synthesized as described in Example B175. MS (m/z): 424.3 (M+H).

Example B175: Preparation of (S)-N-((S)-2-(dimethylamino)-3-(2-oxo-2,3-dihydrobenzo[d]oxazol-6-yl)propyl)-3-phenylbutanamide ("Compound 175")

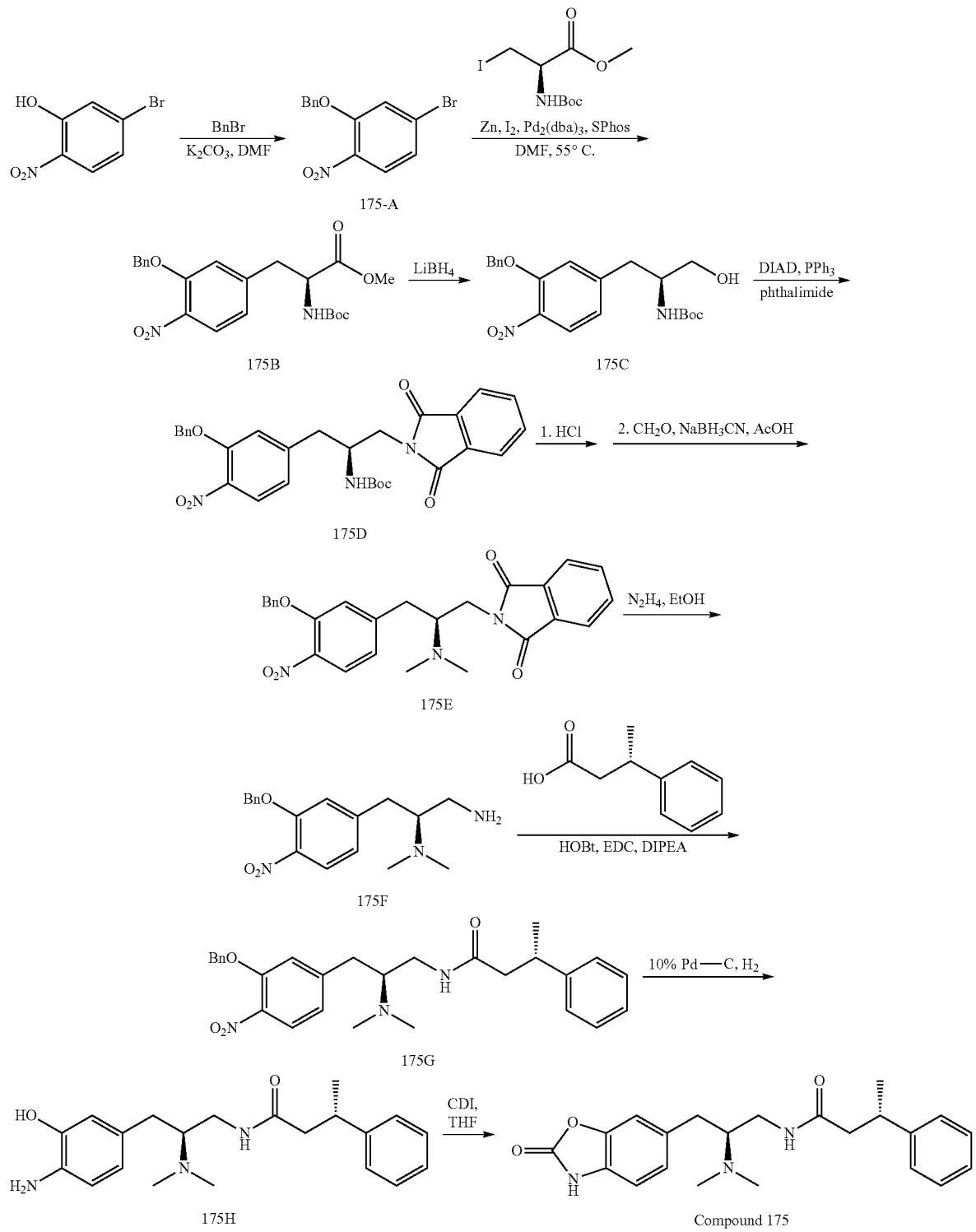

Step 1: Preparation of 2-(benzyloxy)-4-bromo-1-nitrobenzene (175A): A mixture of 5-bromo-2-nitrophenol (5 g, 22.9 mmol), benzyl bromide (3.0 mL, 25.2 mmol) and potassium carbonate (10 g, 72.3 mmol) was taken up in DMF (36 mL) and stirred at rt overnight. After cooling to ambient temperature, the reaction mixture was diluted with water and ethyl acetate. Then layers were separated, and the aqueous layer was extracted with ethyl acetate. The combined organic layers were washed with water and brine, dried over sodium sulfate and concentrated in vacuo. The crude material was purified by flash column chromatography (9:1 hexanes/ethyl acetate) to give 2-(benzyloxy)-4-bromo-1-nitrobenzene (8.25 g, 97%) as a light-yellow solid. LC-MS 332.0 (M+Na).

Step 2: Preparation of methyl (S)-3-(3-(benzyloxy)-4-nitrophenyl)-2-((tert-butoxycarbonyl)amino)propanoate (175B): Zinc dust (1.6 g, 24.5 mmol) was added to a flame dried round bottom flask (100 mL), then purged with nitrogen. Dry DMF (10 mL) was added via syringe followed by a solution of iodine (150 mg) in dry DMF (mL). A color change of the DMF was observed from colorless to yellow and back again. After 5 min. a solution of iodoalanine (2.47 g. 7.49 mmol) in dry DMF (5 mL) was added immediately followed by a solution of iodine (150 mg) in dry DMF (1 mL) The solution was stirred at room temperature and gave a noticeable exotherm. When the solution had cooled (~20 min), a mixture of $Pd_2(dba)_3$ (312 mg, 0.34 mmol), SPhos (279 mg, 0.68 mmol) and 2-(benzyloxy)-4-bromo-1-nitrobenzene (175A, 2.1 g, 681 mmol) in dry DMF (9 mL) were added via syringe to the flask. The reaction mixture was heated at 55° C. overnight, under positive pressure of nitrogen. After cooling to room temperature, ethyl acetate (100 mL) and water (30 mL) were added. After stirring at rt for 30 min, the mixture was then filtered via Celite (80 g) and washed with ethyl acetate (100 mL). The yellow filtrate was then washed with water (4×100 mL). After dried over anhydrous $MgSO_4$ and concentrated in vacuo, the crude reaction mixture was purified by flash chromatography, eluting with ethyl acetate-hexanes (0-35%, to afford the product as a white solid (2.1 g, 71%). MS (m/z): 453.2 (M+Na).

Step 3: To a solution of methyl (S)-3-(3-(benzyloxy)-4-nitrophenyl)-2-((tert-butoxycarbonyl)amino)propanoate (175B, 6 g, 13.9 mmol) in dry THF (60 mL) was added $LiBH_4$ (789 mg, 36.2 mmol) slowly at 0° C. over 15 min, the mixture was then stirred at 0° C. for 1 h. Then the reaction mixture was stirred at rt overnight (the reaction progress was monitored by TLC or LC-MS). Then it was cooled to 0° C., water (5 mL) and then saturated $NH_4Cl$ sol. (10 mL) were added dropwise (slow addition is necessary). Then water (30 mL) and ethyl acetate (200 mL) were added, the aqueous layer was separated and extracted further with ethyl acetate (100 mL). The combined organic layers were washed with water (40 mL), and then dried over anhydrous $Na_2SO_4$. After filtration and concentration, the crude product was put in lyophilization overnight and used in the next step without further purification (5.3 g). MS (m/z): 425.2 (M+Na).

Step 4: Preparation of tert-butyl (S)-(1-(3-(benzyloxy)-4-nitrophenyl)-3-(1,3-dioxoisoindolin-2-yl)propan-2-yl)carbamate (175D): To a mixture of tert-Butyl (S)-(1-(3-(benzyloxy)-4-nitrophenyl)-3-hydroxypropan-2-yl)carbamate (175C, crude, 5.3 g), triphenylphosphine (4.4 g. 16.7 mmol), and phthalimide (2.45 g, 16.7 mmol) in anhydrous THF (60 mL) at 0° C. under nitrogen, was added DIAD (3.3 mL, 16.7 mmol) dropwise over 20 min. The reaction mixture was then stirred from 0° C. to room temperature overnight. The crude reaction mixture was mixed with silica gel (20 g), concentrated to dryness on rota vapor, purified on 120 g silica gel column, eluted with EtOAc/hexanes (0-50%) to provide the desired product as a yellow solid (6.0 g, 81% for two steps). MS (m/z): 554.2 (M+Na).

Step 5: Preparation of (S)-2-(3-(3-(benzyloxy)-4-nitrophenyl)-2-(dimethylamino)propyl)isoindoline-1,3-dione (175E): To a solution of tert-butyl (S)-(1-(3-(benzyloxy)-4-nitrophenyl)-3-(1,3-dioxoisoindolin-2-yl)propan-2-yl)carbamate (175D, 4.5 g, 8.4 mmol) in dry MeOH (60 mL), was added 4M HCl in dioxane solution (19 mL). The mixture was stirred at rt overnight. Then the solvents were evaporated. The solid residue was used in the next step without further purification. To a suspension of above solid in $CH_3CN$ (60 mL) and water (3 mL), was added 37% formaldehyde (3.8 mL, 50.7 mmol), sodium cyanoborohydride (2.1 g, 33.8 mmol). After stirring at rt for 10 min, acetic acid (1.45 mL, 25.3 mmol) was added. The mixture was stirred at room temperature for 2 h. The reaction mixture was then partitioned between ethyl acetate (200 mL) and saturated sodium bicarbonate (40 mL). Layers were separated, and aqueous layer was extracted with more ethyl acetate (3×100 mL). The combined organic layers were dried over anhydrous $Na_2SO_4$, filtered and concentrated. The crude material was purified on 80 g silica gel column, eluted with 10% MeOH in DCM: DCM (0-100%) to provide the desired product (3.2 g), which was not pure (according to H-NMR and TLC) and used in the next step. MS (m/z)=460.2 (M+H).

Step 6: Preparation of (S)-3-(3-(benzyloxy)-4-nitrophenyl)-N2,N2-dimethylpropane-1,2-diamine (175F): To a solution of (S)-2-(3-(3-(benzyloxy)-4-nitrophenyl)-2-(dimethylamino)propyl)isoindoline-1,3-dione (175E, 3.2 g, 6.9 mmol) in 95% ethanol (50 mL), was added hydrazine hydrate (2.3 mL, 41.8 mmol). The mixture was heated at 70° C. for 3 h. The crude reaction mixture was diluted with MeOH (50 mL) and mixed with silica gel (~10 g), concentrated to dryness on rota vapor, and then purified on 40 g silica gel column, eluted with 10% MeOH in DCM (including 1% $NH_4OH$):DCM (0-100/100) to provide the desired product as a white solid (1.25 g, 45% over last 3 steps). MS (m/z): 330.2 M+H).

Step 7: Preparation of (S)-N-((S)-3-(3-(benzyloxy)-4-nitrophenyl)-2-(dimethylamino)propyl)-3-phenylbutanamide (175G): (S)-3-(3-(benzyloxy)-4-nitrophenyl)-N2,N2-dimethylpropane-1,2-diamine (175F, 200 mg, 0.6 mmol) and acid (0.67 mmol) were dissolved in dry DMF (5 mL), then EDCl (140 mg, 0.73 mmol), HOBT (98 mg, 0.73 mmol) and DIPEA (0.123 mL, 0.73 mmol) were added. The reaction mixture was stirred at rt overnight, then work-up with ethyl acetate and water. The organic layer was dried over anhydrous $MgSO_4$ and concentrated in vacuo, the crude reaction mixture was purified by flash chromatography, eluting with 10% MeOH in DCM (including 1% $NH_4OH$): DCM (0-40/100) to afford the corresponding product as a yellow solid (249 mg, 86%). MS (m/z): 476.2 (M+H).

Step 8: Preparation of (S)-N-((S)-3-(4-amino-3-hydroxyphenyl)-2-(dimethylamino)propyl)-3-phenylbutanamide (175H): (S)-N-((S)-3-(3-(benzyloxy)-4-nitrophenyl)-2-(dimethylamino)propyl)-3-phenylbutanamide (175G, 24) mg, 0.5 mmol) and 10% palladium on carbon (55 mg. Aldrich) in MeOH (12 mL) was stirred under $H_2$ atmosphere for 16 h. The mixture was filtered through a Celite® pad and the filtrate was evaporated under reduced pressure to give the title compound (185 mg, 100%). MS (m/z): 356.3 (M+H).

Step 9: Preparation of (S)-N-((S)-2-(dimethylamino)-3-(2-oxo-2,3-dihydrobenzo[d]oxazol-6-yl)propyl)-3-phenylbutanamide (Compound 175). 1,1'-Carbonyldiimidazole (230 mg, 1.68 mmol) was added to a 7 mL of THF solution of (S)-N-((S)-3-(4-amino-3-hydroxyphenyl)-2-(dimethylamino)propyl)-3-phenylbutanamide (175, 300 mg. 0.84 mmol), and the solution was heated at 60° C. for 2 h After cooling to room temperature, the reaction mixture was poured into 100 mL of water and then extracted twice with 100 mL of ethylacetate. After removal of water with sodium sulfate, the solvent was removed using a rotary flash evaporator, and the residual material was purified by silica gel column chromatography using 10% MeOH in DCM (including 1% NH₄OH):DCM (0-60/100) to provide the desired product as a white solid (94 mg, 52% over last 3 steps). MS (m/z): 382.2 (M+H).

Example B176: Preparation of (S)-N-((S)-2-(dimethylamino)-3-(2-oxo-2,3-dihydrobenzo[d]oxazol-6-yl)propyl)-3-(pyridin-3-yl)-3-(1-(trifluoromethyl)cyclopropyl)propanamide ("Compound 176")

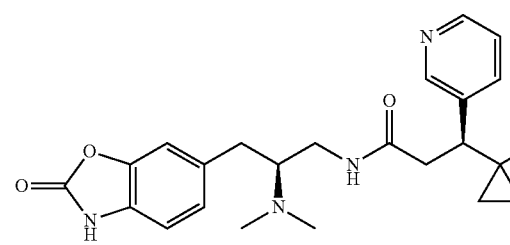

Compound 176 (20 mg, 45%) was synthesized from (S)-6-(3-amino-2-(dimethylamino)propyl)benzo[d]oxazol-2 (3H)-one (175F) and (S)-3-(pyridin-3-yl)-3-(1-(trifluoromethyl)cyclopropyl)propanoic acid, as described in Example B175. MS (m/z): 477.2 (M+H).

Example B177: Preparation of (S)-3-cyclopropyl-N-((S)-2-(dimethylamino)-3-(2-oxo-2,3-dihydrobenzo[d]oxazol-6-yl)propyl)-3-phenylpropanamide ("Compound 177")

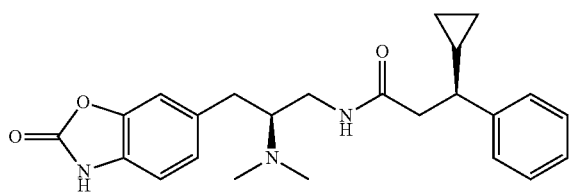 [SMILES: CN(C)[C@H](CNC(=O)C[C@H](c1ccccc1)C1CC1)Cc1ccc2[nH]c(=O)oc2c1]

Compound 177 (74 mg, 70%) was synthesized as described in Example B175. MS (m/z): 408.3 (M+H).

Example B178: Preparation of (R)-3-cyclopropyl-N-((S)-2-(dimethylamino)-3-(2-oxo-2,3-dihydrobenzo[d]oxazol-6-yl)propyl)-3-phenylpropanamide ("Compound 178")

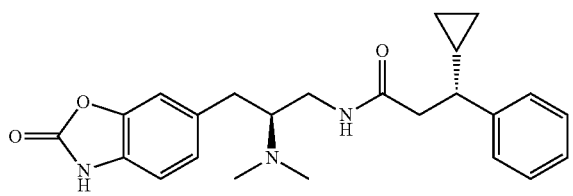 [SMILES: CN(C)[C@H](CNC(=O)C[C@@H](c1ccccc1)C1CC1)Cc1ccc2[nH]c(=O)oc2c1]

Compound 178 (40 mg, 65%) was synthesized as described in Example B175. MS (m/z): 408.2 (M+H).

Example B179: Preparation of (R)-4-cyclopropyl-N-((S)-2-(dimethylamino)-3-(4-methyl-2-oxoindolin-5-yl)propyl)-3-(pyridin-3-yl)butanamide ("Compound 179")

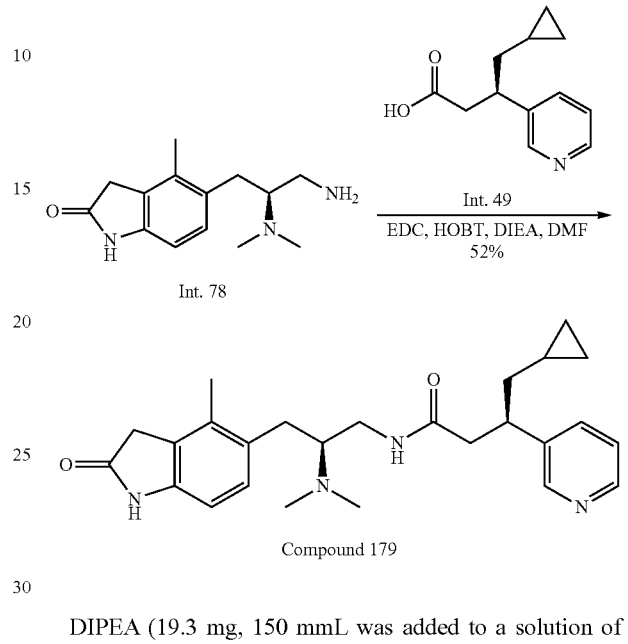

DIPEA (19.3 mg, 150 mmL was added to a solution of 5-[(2S)-3-amino-2-(dimethylamino)propyl]-4-methyl-2,3-dihydro-1H-indol-2-one (14.8 mg, 59.8 mmol), (3R)-3-(pyridin-3-yl)-3-[1-(trifluoromethyl)cyclopropyl]propanoic acid (12.3 mg, 59.8 mmol), EDC (13.8 mg, 71.8 mmol), and HOBt (4.04 mg, 29.9 mmol) in 1 mL of dry DMF. The reaction was stirred at rt for 16 h. After completion of reaction, the mixture was diluted with water and extracted with ethyl acetate (3×). The combined organic layers were washed with water and brine followed by drying over MgSO₄, filtered and concentrated. The crude was purified by SiO₂ chromatography (0-10% MeOH in DCM) to give the title compound (13.6 mg, 52%). MS (m/z): 435.3 (M+H).

Example B180: Preparation of (R)-N-((S)-2-(dimethylamino)-3-(4-methyl-2-oxoindolin-5-yl)propyl)-3-(pyridin-3-yl)-3-(1-(trifluoromethyl)cyclopropyl)propanamide ("Compound 180")

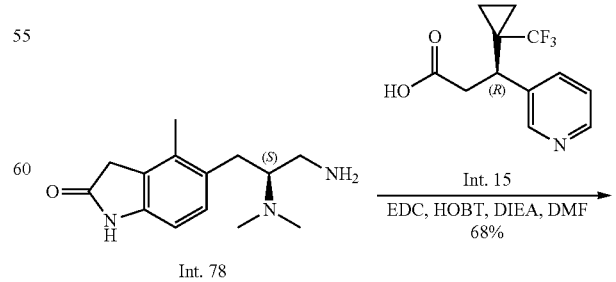

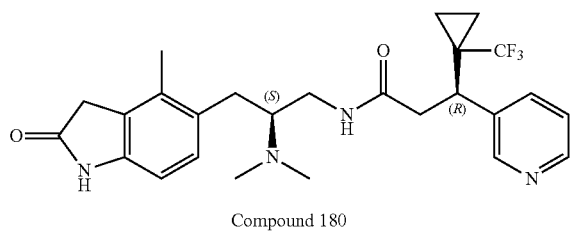

Compound 180

Compound 180 (20 mg, 68%) was synthesized from Int. 78 and Int. 15 as described in Example B179. MS (m/z): 489.2 (M+H).

Example B181: Preparation of (3S)-N-[(2S)-2-(dimethylamino)-3-(4-methyl-2-oxo-2,3-dihydro-1H-indol-5-yl)propyl]-3-phenylbutanamide ("Compound 181")

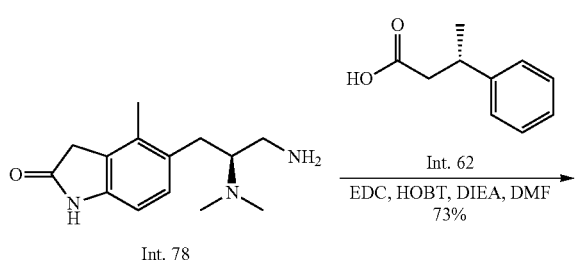

Compound 181

Compound 181 (35 mg, 73%) was synthesized from Int. 78 and Int. 62 as described in Example B179. MS (m/z): 394.2 (M+H).

Example B182: Preparation of (R)-N-((S)-2-(dimethylamino)-3-(2-oxoindolin-5-yl)propyl)-4-methyl-3-phenylpentanamide ("Compound 182")

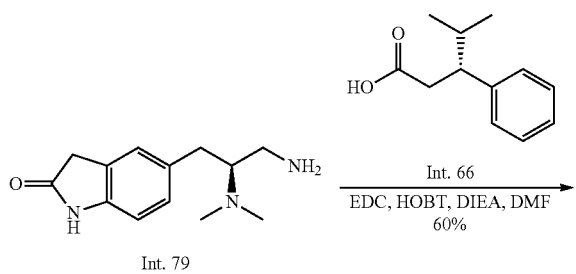

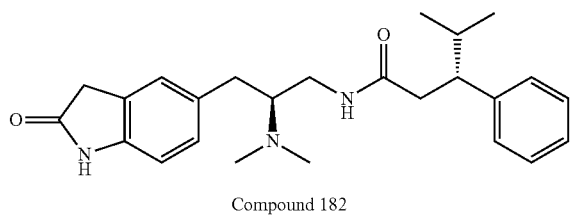

Compound 182

Compound 182 (28 mg, 60%) was synthesized from Int. 79 and Int. 66 as described in Example B179. MS (m/z): 408.3 (M+H).

Example B183: Preparation of (S)-N-((S)-2-(dimethylamino)-3-(2-oxoindolin-5-yl)propyl)-5-methyl-3-phenylhexanamide ("Compound 183")

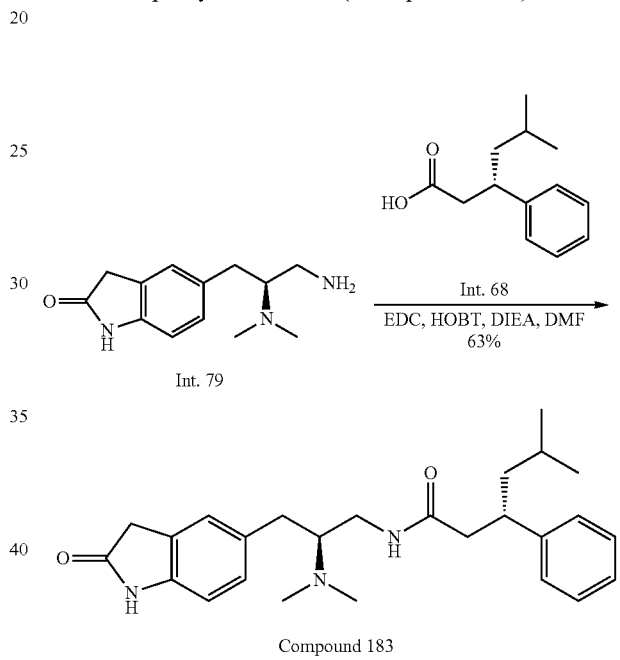

Compound 183

Compound 183 (22 mg, 63%) was synthesized from Int. 79 and Int. 68 as described in Example B179. MS (m/z): 422.2 (M+H).

Example B184: Preparation of (3S)-N-[(2S)-2-(dimethylamino)-3-(2-oxo-2,3-dihydro-1H-indol-5-yl)propyl]-3-phenylbutanamide ("Compound 184")

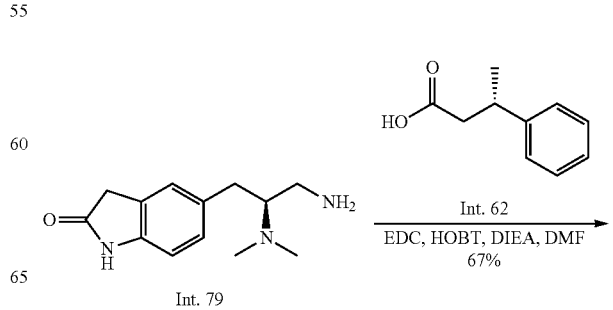

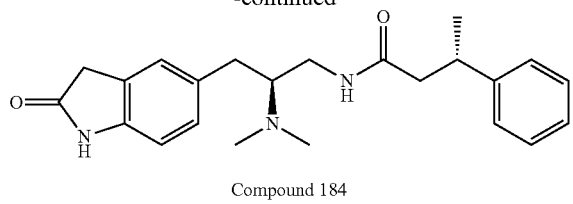

Compound 184

Compound 184 (706 mg, 67%) was synthesized from Int. 79 and Int. 62 as described in Example B179. MS (m/z): 380.2 (M+H).

Example B185: Preparation of (3R)-N-[(2S)-2-(dimethylamino)-3-(2-oxo-2,3-dihydro-1H-indol-5-yl)propyl]-3-phenylbutanamide ("Compound 185")

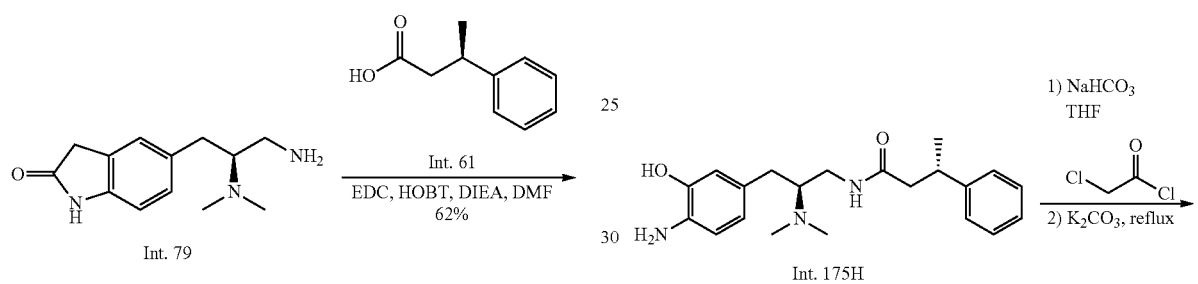

Compound 185

Compound 185 (31 mg, 62%) was synthesized from Int. 79 and Int. 61 as described in Example B179. MS (m/z): 380.2 (M+H).

Example B186: Preparation of (R)-3-cyclopropyl-N-((S)-2-(dimethylamino)-3-(2-oxoindolin-5-yl)propyl)-3-phenylpropanamide ("Compound 186")

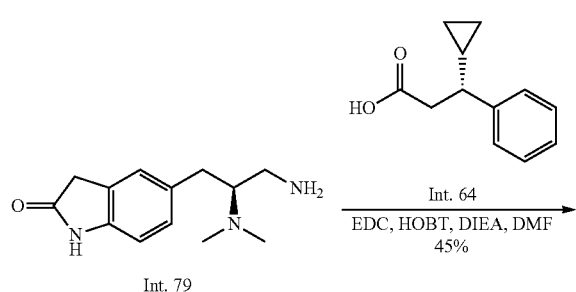

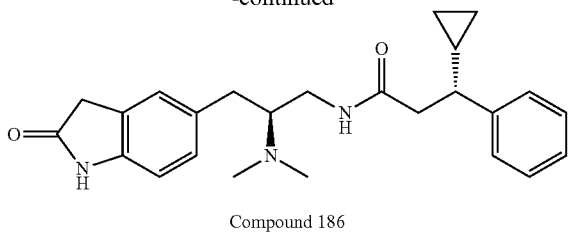

Compound 186

Compound 186 (31.6 mg, 45%) was synthesized from Int. 79 and Int. 64 as described in Example B179. MS (m/z): 406.3 (M+H).

Example B187: Preparation of (S)-N-((S)-2-(dimethylamino)-3-(3-oxo-3,4-dihydro-2H-benzo[b][1,4]oxazin-7-yl)propyl)-3-phenylbutanamide ("Compound 187")

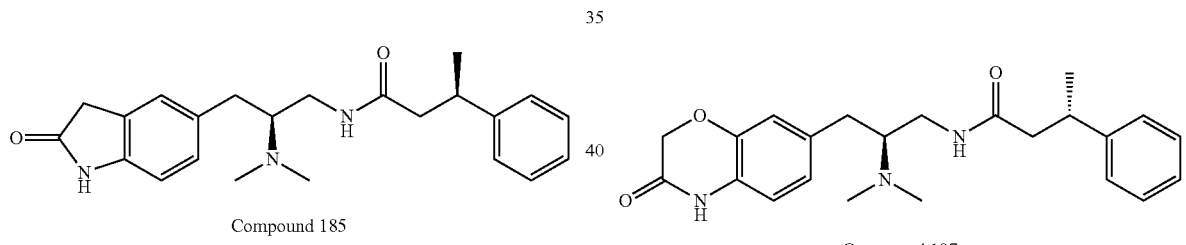

Compound 187

A solution of chloroacetyl chloride (142 mg, 1.26 mmol) in THF (2.5 mL) was added dropwise to a stirred suspension of sodium hydrogen carbonate (189 mg, 2.25 mmol) and (S)-N-((S)-3-(4-amino-3-hydroxyphenyl)-2-(dimethylamino)propyl)-3-phenylbutanamide (175H) (320 mg, 0.9 mmol) in THF (3 mL) at 0° C. under nitrogen over approximately 15 min. Vigorous effervescence was observed with an exotherm to approximately 25° C. The resulting yellow suspension was stirred at room temperature for 1.5 h. Potassium carbonate (311 mg, 2.25 mmol) was added and the mixture heated to reflux and stirred for 2 h. The mixture was allowed cool to 40° C., and diluted with ethyl acetate and water, the layers were separated, and the aqueous was extracted with ethyl acetate twice. The combined organic layers were washed with water and brine, dried over sodium sulfate and concentrated in vacuo. The crude material was purified by flash column chromatography using 10% MeOH in DCM: DCM (0-50%) as eluent to the product as a white solid (140 mg, 39%). MS (m/z): 396.2.

Example B188: Preparation of N-((S)-2-(dimethylamino)-3-(2-oxoindolin-5-yl)propyl)-3-(pyrimidin-2-yl)-3-(1-(trifluoromethyl)cyclopropyl)propenamide ("Compound 188")

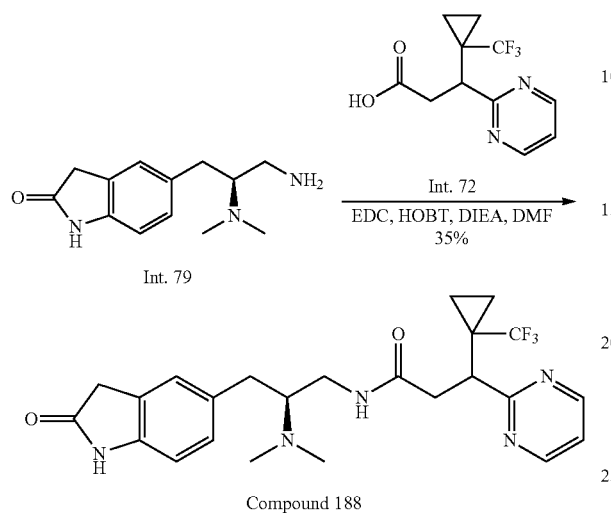

Compound 188 (13.1 mg, 25%) was synthesized from Int. 79 and Int. 72 as described in Example B179. MS (m/z): 476.2 (M+H).

Example B189: Preparation of (R)-N-((S)-2-(dimethylamino)-3-(2-oxoindolin-5-yl)propyl)-3-phenyl-3-(1-(trifluoromethyl)cyclopropyl)propanamide ("Compound 189")

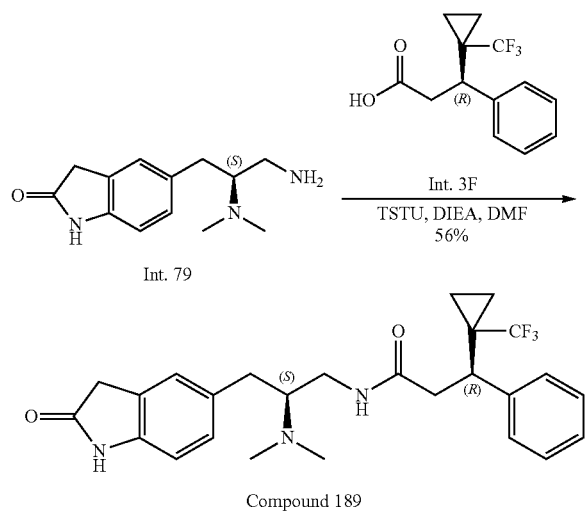

To a solution of the acid (Int. 72, 20.7 mg, 0.0802 mmol) and DIEA (20.9 uL, 0.120 mmol) in DMF (0.3 mL), was added TSTU (24.1 mg, 0.0802 mmol) in one portion. The mixture was stirred at room temperature for an hour. To the reaction mixture was then added amine (Int. 79, 18.7 mg, 0.0802 mmol), continued to stir for another hour. The reaction mixture was diluted with ethyl acetate (15 mL) and saturated NaHCO$_3$, water, and brine. The organic layer was dried over MgSO$_4$, filtered, and concentrated on rota-vapor. The crude material was purified on silica gel column (0-10% MeOH/DCM with 1% NH$_4$OH) to give the title compound (21.5 mg, 57). MS (m/z): 474.3.

Example B190: Preparation of (S)-N-((S)-2-(dimethylamino)-3-(1H-indazol-5-yl)propyl)-3-phenyl-3-(1-(trifluoromethyl)cyclopropyl)propanamide ("Compound 190")

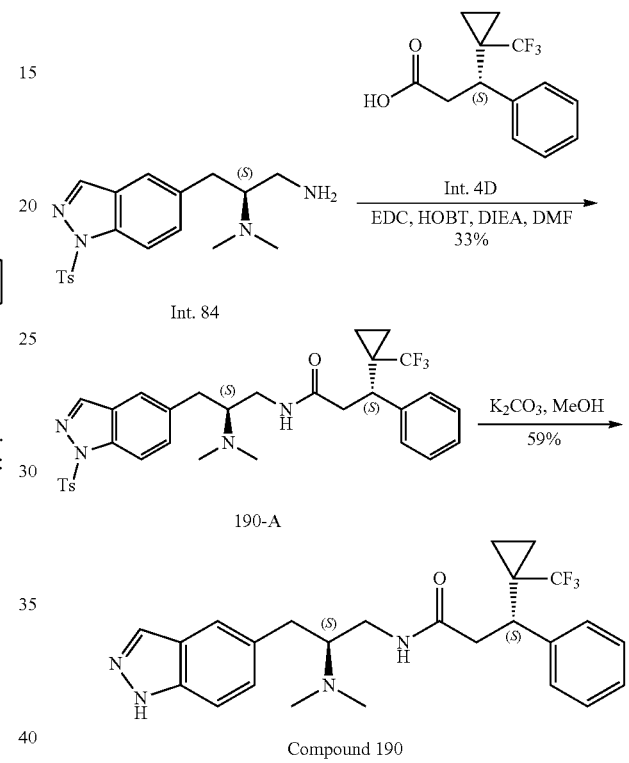

Step 1: Preparation of (S)-N-((S)-2-(dimethylamino)-3-(1-tosyl-1H-indazol-5-yl)propyl)-3-phenyl-3-(1-(trifluoromethyl)cyclopropyl)propenamide (190A). To a solution of the acid (Int. 4D, 49.0 mg, 0.190 mmol) and DIEA (49.7 uL, 0.286 mmol) in DMF (0.3 mL) at rt, was added TSTU (57.2 mg, 0.190 mmol). The mixture was stirred at room temperature for 40 minutes. The resulting solution was injected into a suspension of (Int 84, 70.7 mg, 0.190 mmol) and stirred for 1 h. The reaction mixture was diluted with ethyl acetate and washed with saturated NaHCO$_3$, water, and brine. The organic layer was dried over MgSO$_4$, filtered, and concentrated on rota-vapor. The crude material was purified on 12 g silica gel column, 0-10% MeOH/DCM with 1% NH$_4$OH to provide the title compound (38 mg, 33%). MS (m/z): 612.2 (M+H).

Step 2: Preparation of (S)-N-((S)-2-(dimethylamino)-3-(1H-indazol-5-yl)propyl)-3-phenyl-3-(1-(trifluoromethyl)cyclopropyl)propanamide (Compound 190): Compound 190A (36.0 mg, 0.0588 mmol) in MeOH (2 mL) was treated with K$_2$CO$_3$ (mg, mmol) at 70° C. for 40 minutes. LCMS showed that the reaction was completed. The reaction mixture was cooled to rt, concentrated to dryness. The crude material was dissolved in DMF (1 mL)/H$_2$O with 0.1% TFA (0.5 mL)/ACN with 0.1% TFA (0.5 mL), filtered, purified on C18 column, 0-100% ACN with 0.1% TFA/water with 0.1%

TFA. The pure fractions were combined, concentrated, adjusted pH ~ 9 by saturated NaHCO₃ (aq), extracted with DCM (3×). The combined extracts were dried and concentrated to provide the title compound (16 mg, 59%). MS (m/z): 459.2 (M+H).

Example B191: Preparation of (R)-N-((S)-3-(4-chloro-1H-indazol-5-yl)-2-(dimethylamino)propyl)-3-(pyridin-4-yl)-3-(1-(trifluoromethyl)cyclopropyl) propanamide ("Compound 191")

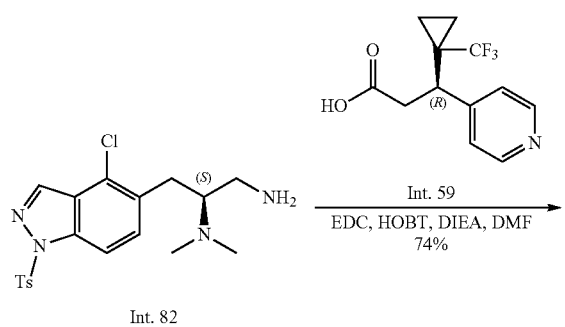

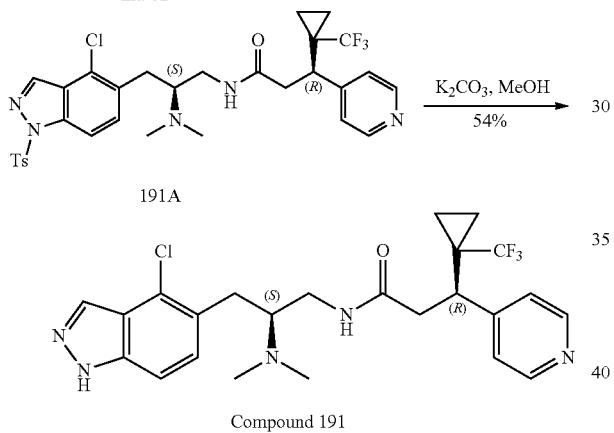

Compound 191 was synthesized from Int. 82 and Int. 69 as described in Example B190. MS (m/z): 494.2 (M+H).

Example B192: Preparation of (R)-N-((S)-3-(4-chloro-1H-indazol-5-yl)-2-(dimethylamino)propyl)-3-(pyridin-3-yl)-3-(1-(trifluoromethyl)cyclopropyl) propanamide ("Compound 192")

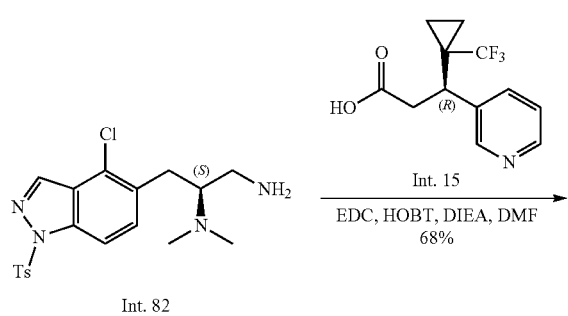

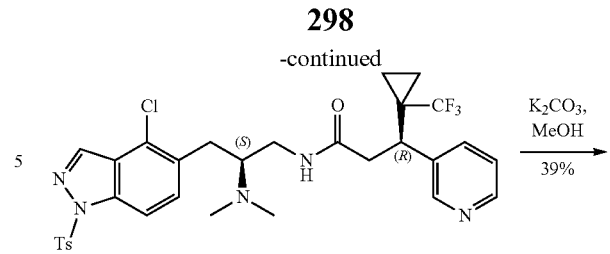

Compound 192 (25.8 mg, 39%) was synthesized from 192A, which was synthesized from Int. 82 and Int. 15 (59.7 mg, 68%) as described in Example B190. MS (m/z): 494.2 (M+H).

Example B193: Preparation of (R)-N-((S)-3-(4-chloro-1H-indazol-5-yl)-2-(dimethylamino)propyl)-3-phenylbutanamide ("Compound 193")

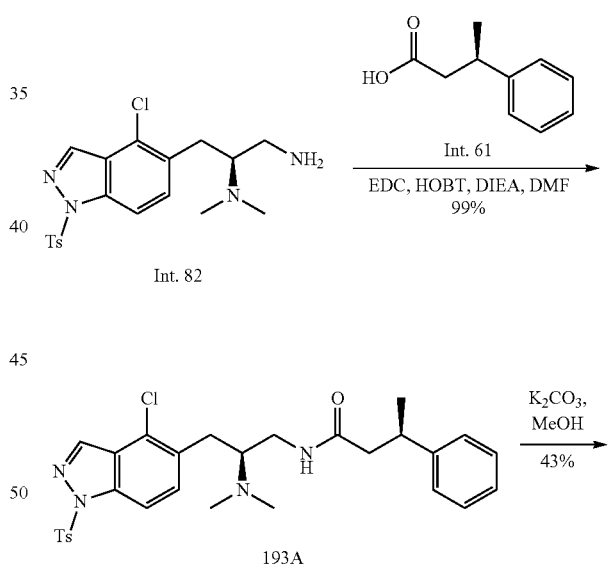

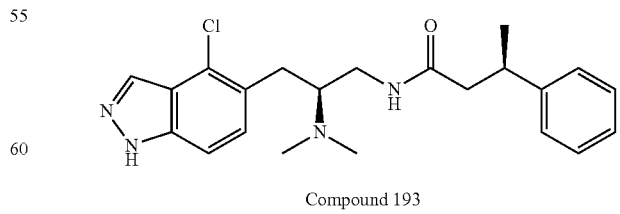

Compound 193 (29.5 mg, 43%) was synthesized from Int. 82 and Int. 61 as described in Example B190. MS (m/z): 399.2 (M+H).

Example B194: Preparation of (S)-N-((S)-3-(4-chloro-1H-indazol-5-yl)-2-(dimethylamino)propyl)-3-phenylbutanamide ("Compound 194")

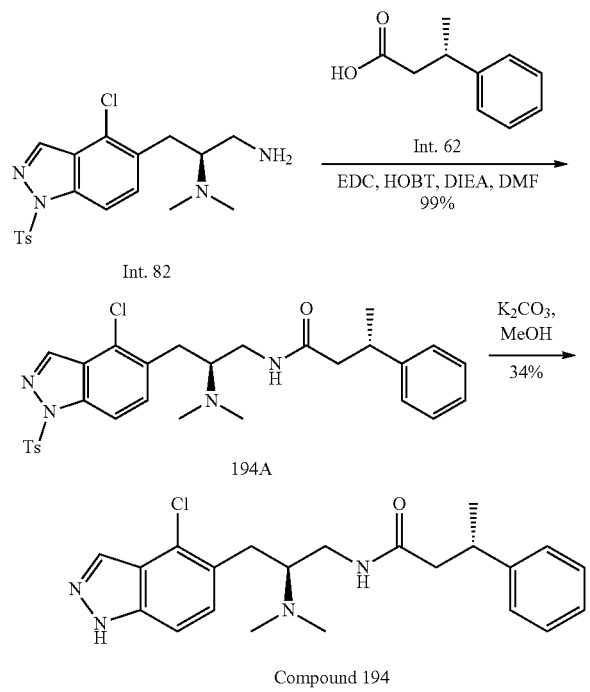

Compound 194 (23.5 mg, 34%) was synthesized from Int. 82 and Int. 62 as described in Example B190. MS (m/z): 399.2 (M+H).

Example B195: Preparation of (R)-N-((S)-2-(dimethylamino)-3-(4-fluoro-1H-indazol-5-yl)propyl)-3-(pyridin-3-yl)-3-(1-(trifluoromethyl)cyclopropyl)propanamide ("Compound 195")

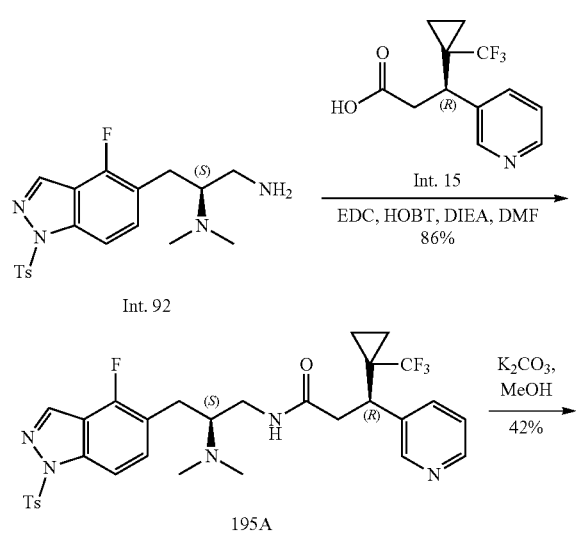

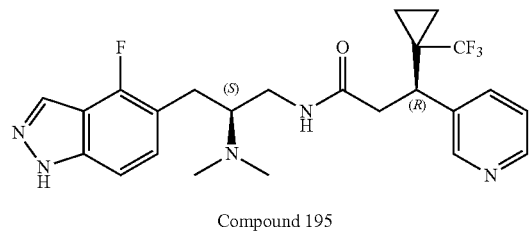

Compound 195 was synthesized from Int. 92 and Int. 15 as described in Example B190. MS (m/z): 478.2 (M+H).

Example B196: Preparation of (R)-N-((S)-2-(dimethylamino)-3-(4-methyl-1H-indazol-5-yl)propyl)-3-(pyridin-4-yl)-3-(1-(trifluoromethyl)cyclopropyl)propanamide ("Compound 196")

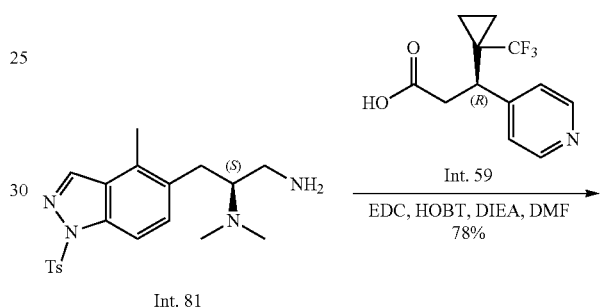

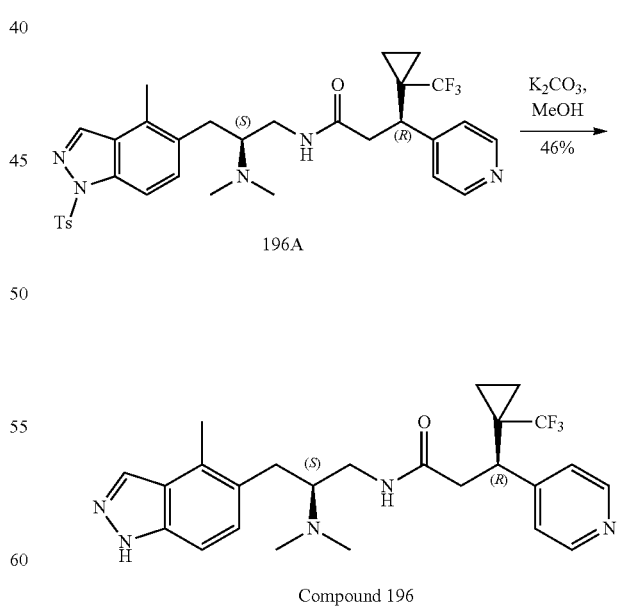

Compound 16 was synthesized from Int. 81 and Int. 59 as described in Example B190. MS (m/z): 474.3 (M+H).

Example B197: Preparation of (R)-N-((S)-2-(dimethylamino)-3-(4-methyl-1H-indazol-5-yl)propyl)-3-(pyridin-3-yl)-3-(1-(trifluoromethyl)cyclopropyl)propanamide ("Compound 197")

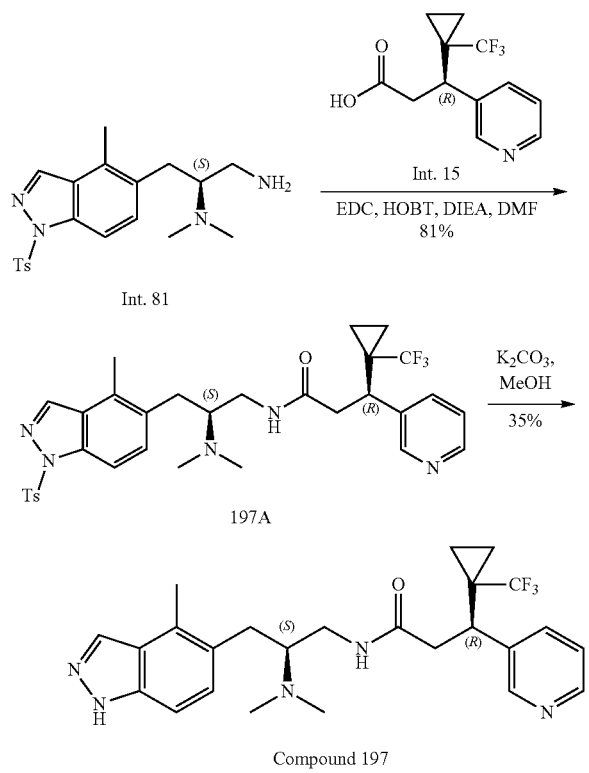

Compound 197

Compound 197 was synthesized from Int. 81 and Int. 15 as described in Example B190. MS (m/z): 474.3 (M+H).

Example B198: Preparation of (S)-N-((S)-2-(dimethylamino)-3-(4-methyl-1H-indazol-5-yl)propyl)-3-phenylbutanamide ("Compound 198")

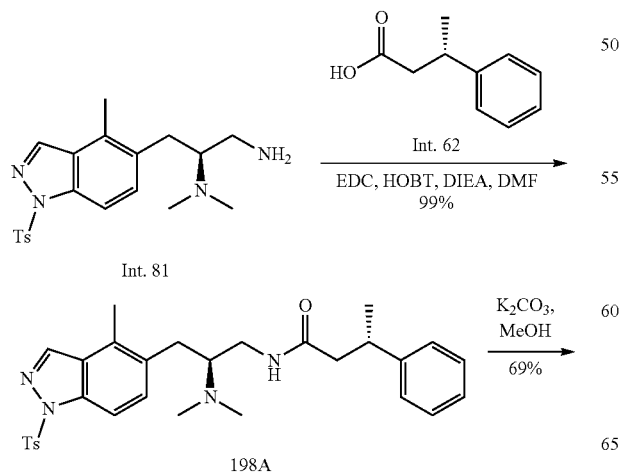

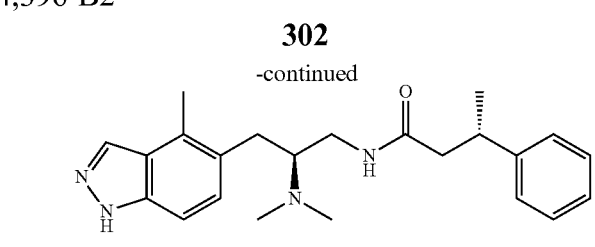

Compound 198

Compound 198 was synthesized from Int. 81 and Int. 62 as described in Example B190. MS (m/z): 379.3 (M+H).

Example B199: Preparation of (S)-N-((S)-2-(dimethylamino)-3-(4-methyl-1H-indazol-5-yl)propyl)-3-(1-methylcyclopropyl)-3-(pyridin-3-yl)propanamide ("Compound 199")

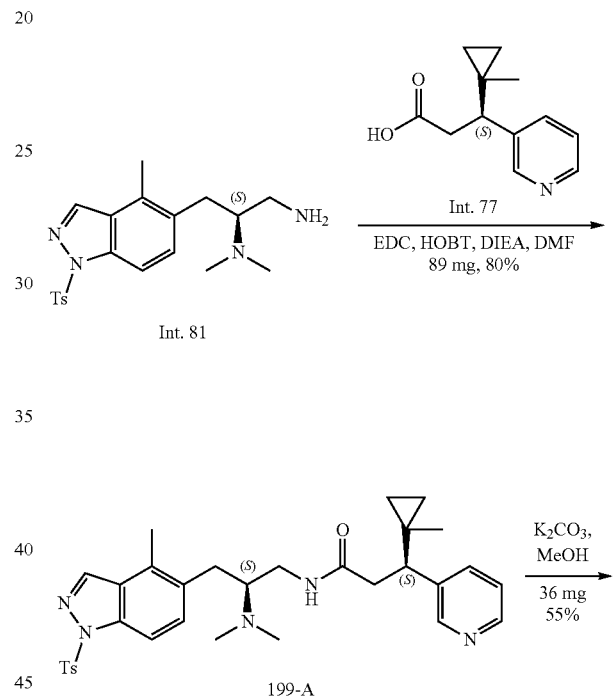

Compound 199

Compound 199 was synthesized from Int. 81 and Int. 77 as described in Example B190. MS (m/z): 420.3 (M+H).

Example B200: Preparation of (R)-N-((S)-3-(1H-indazol-5-yl)-2-(methylamino)propyl)-3-(pyridin-3-yl)-3-(1-(trifluoromethyl)cyclopropyl)propanamide ("Compound 200")

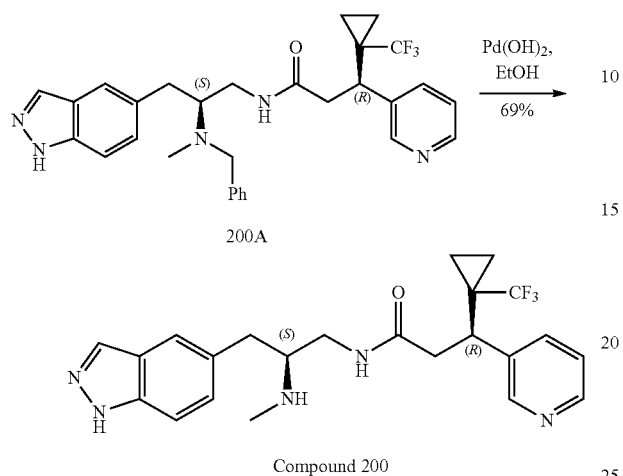

200A

Compound 200

(R)-N-((S)-2-(benzyl(methyl)amino)-3-(1H-indazol-5-yl)propyl)-3-(pyridin-3-yl)-3-(1-(trifluoromethyl)cyclopropyl)propanamide (200A, 120 mg, 0.224 mmol)) was taken with palladium(II)hydroxide (100 mg) and then ethanol (5 ml) was added. The flask was evacuated and then filled with hydrogen (balloon). The reaction was stirred under hydrogen balloon for the next 18 hrs. TLC and LCMS indicated formation of the product. The solution was filtered through packed celite to remove the palladium and the filtrate was concentrated. The residue was purified by flash chromatography (0-15% MeOH/DCM in 1% ammonium hydroxide) to give the title compound (55 mg, 53%). MS (m/z): 446.2 (M+H).

Example B201: Preparation of (R)-N-((S)-2-amino-3-(1H-indazol-5-yl)propyl)-3-(pyridin-3-yl)-3-(1-(trifluoromethyl)cyclopropyl)propenamide dihydrochloride salt ("Compound 201")

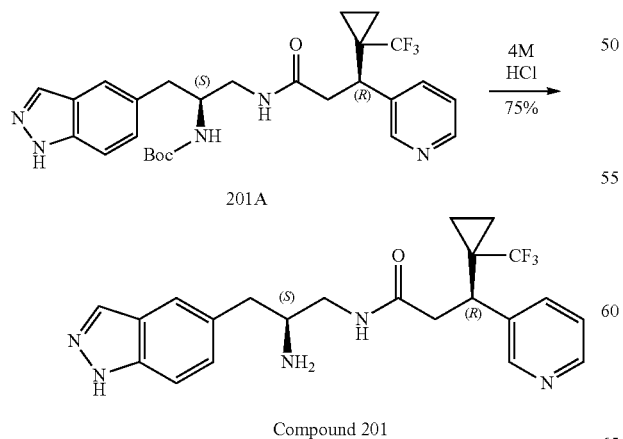

201A

Compound 201 tert-butyl ((S)-1-(1H-indazol-5-yl)-3-((R)-3-(pyridin-3-yl)-3-(1-(trifluoromethyl)cyclopropyl)propanamido)propan-2-yl)carbamate (201A, 125 mg, 0.23 mmol) was taken in 1,4-dioxane (3 ml) and then a solution of hydrogen chloride in 1,4-dioxane (2 ml, 4 M solution) was added to it dropwise. The suspension was stirred at room temperature for 18 hrs. TLC and LCMS indicated that the reaction was completed. The solution was partially concentrated and then MTBE was added. The precipitated solids were collected by filtration. The solids were then dried under vacuum to give the title compound as dihydrochloride salt (110 mg, 75%). MS (m/z): 432.2 (M+H).

Example B202: Preparation of (R)-N-((S)-2-(dimethylamino)-3-(1H-indazol-5-yl)propyl)-3-(2-methylpyridin-4-yl)-3-(1-(trifluoromethyl)cyclopropyl)propanamide ("Compound 202")

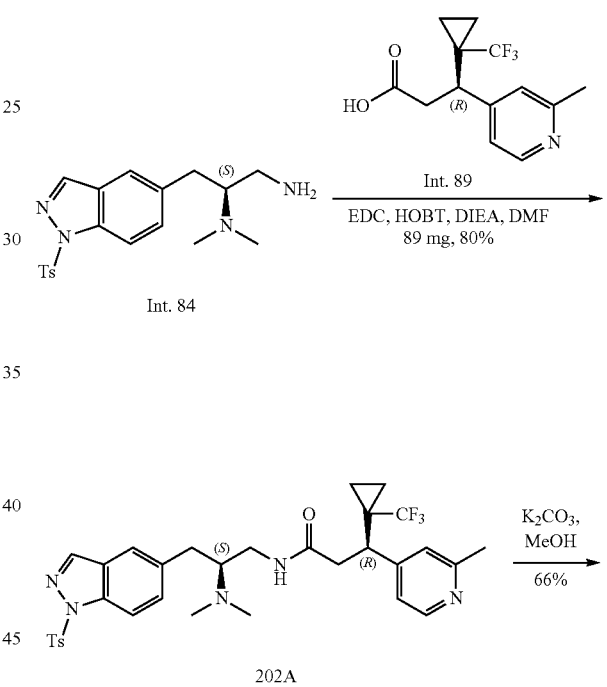

202A

Compound 202

Compound 202 was synthesized from Int. 84 and Int. 89 as described in Example B190. MS (m/z): 474.2 (M+H).

Example B203: Preparation of (S)-N-((S)-2-(dimethylamino)-3-(1H-indazol-5-yl)propyl)-3-(5-methylpyridin-3-yl)-3-(1-(trifluoromethyl)cyclopropyl)propanamide ("Compound 203")

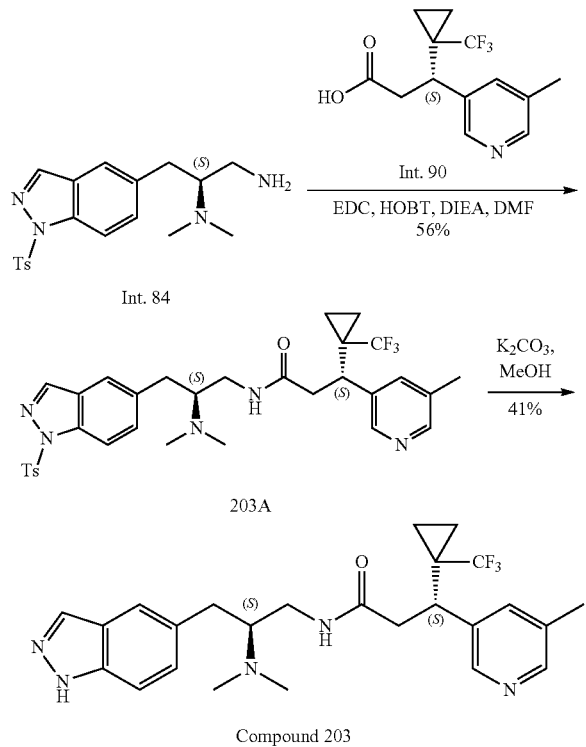

Compound 203 was synthesized from Int. 84 and Int. 90 as described in Example B190. MS (m/z): 474.3 (M+H).

Example B204: Preparation of (S)-N-((S)-2-(dimethylamino)-3-(1H-indazol-5-yl)propyl)-3-(1-methylcyclopropyl)-3-(pyridin-3-yl)propanamide ("Compound 204")

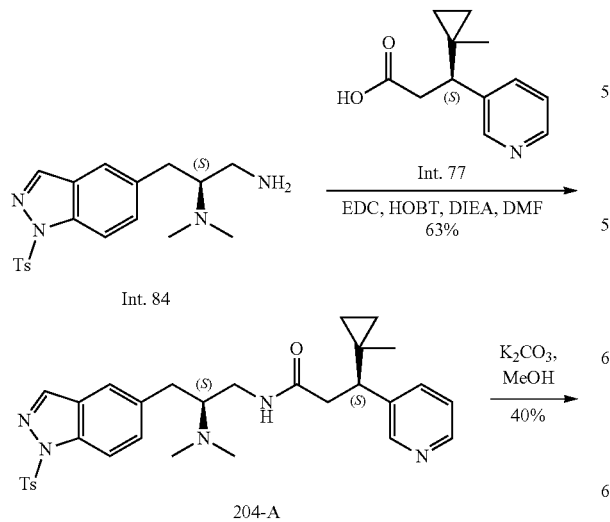

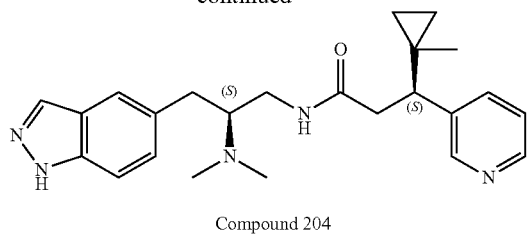

Compound 204 was synthesized from Int. 84 and Int. 77 as described in Example B190. MS (m/z): 406.3 (M+H).

Example B205: Preparation of (R)-3-(5-chloropyridin-3-yl)-N-((S)-2-(dimethylamino)-3-(1H-indazol-5-yl)propyl)-3-(1-(trifluoromethyl)cyclopropyl) propanamide ("Compound 205")

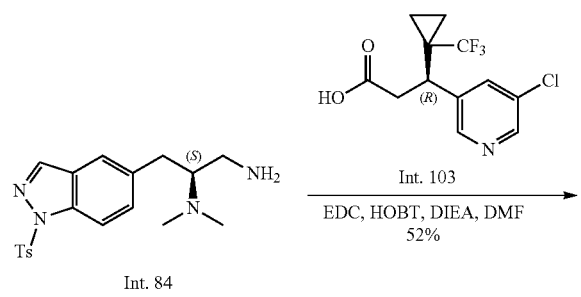

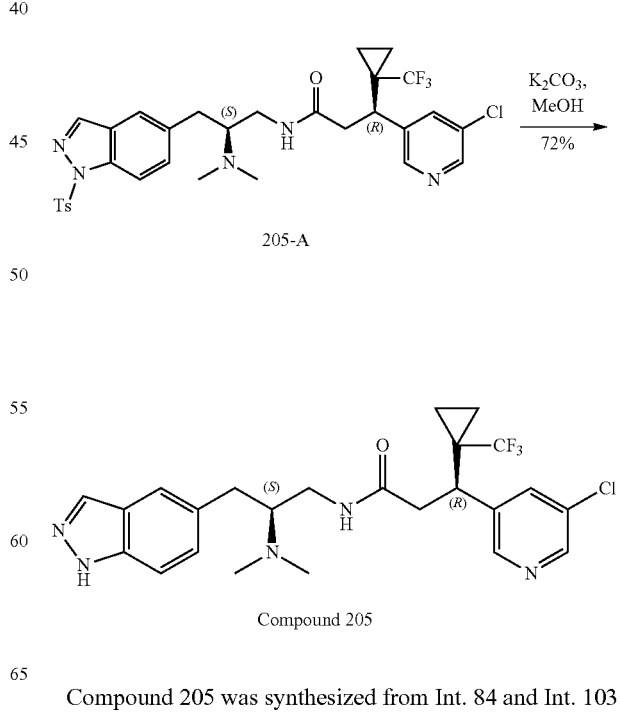

Compound 205 was synthesized from Int. 84 and Int. 103 as described in Example B190. MS (m/z): 494.2 (M+H).

Example B206: Preparation of (S)-N-((S)-2-(dimethylamino)-3-(1H-indazol-5-yl)propyl)-4-methyl-3-(pyridin-3-yl)pentanamide ("Compound 206")

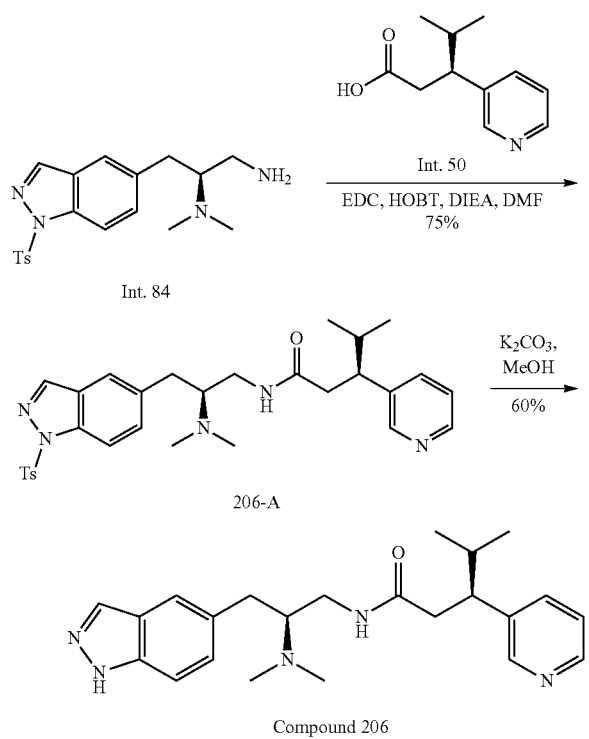

Compound 206 was synthesized from Int. 84 and Int. 50 as described in Example B190. MS (m/z): 394.2 (M+H).

Example B207: Preparation of (S)-3-cyclopropyl-N-((S)-2-(dimethylamino)-3-(1H-indazol-5-yl)propyl)-3-(pyridin-3-yl)propanamide ("Compound 207")

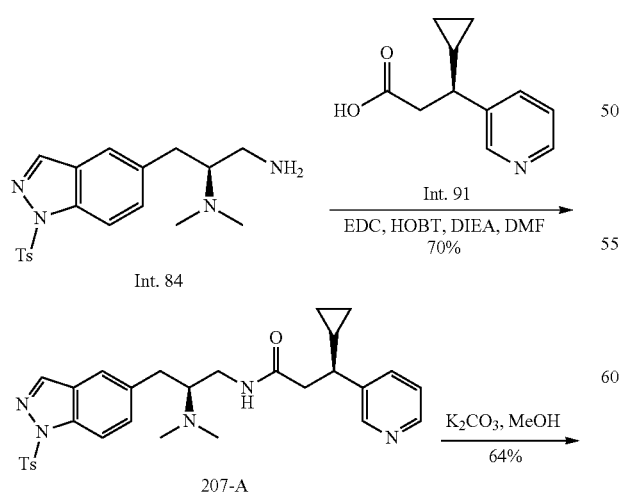

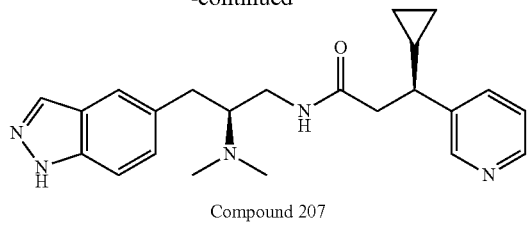

Compound 207 was synthesized from Int. 84 and Int. 91 as described in Example B190. MS (m/z): 392.1 (M+H).

Example B208: Preparation of (S)-N-((S)-2-(dimethylamino)-3-(1H-indazol-5-yl)propyl)-3-(pyridin-4-yl)-3-(1-(trifluoromethyl)cyclopropyl)propanamide ("Compound 208")

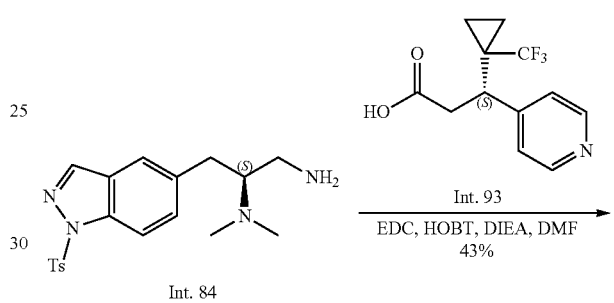

Compound 208 was synthesized from Int. 84 and Int. 93 as described in Example B190. MS (m/z): 460.2 (M+H).

Example B209: Preparation of (R)-N-((S)-2-(dimethylamino)-3-(1H-indazol-5-yl)propyl)-3-(pyridin-4-yl)-3-(trifluoromethyl)cyclopropyl)propanamide ("Compound 209")

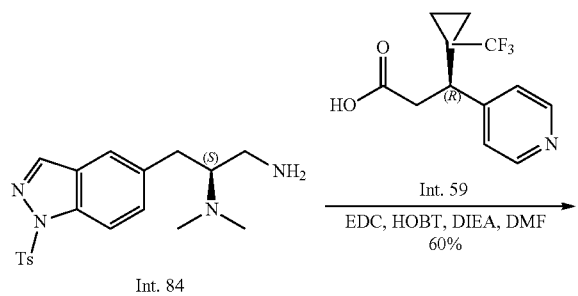

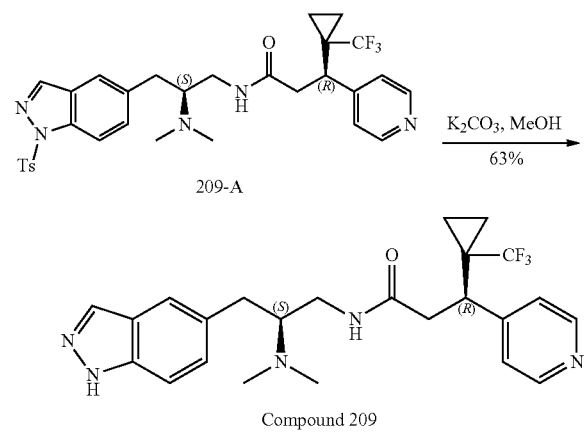

Compound 209 was synthesized from Int. 84 and Int. 59 as described in Example B190. MS (m/z): 460.2 (M+H).

Example B210: Preparation of (3S)-N-[(2S)-2-dimethylamino)-3-(1H-indazol-5-yl)propyl]-3-(pyridin-4-yl)-3-[1-(trifluoromethyl)cyclopropyl]propenamide ("Compound 210")

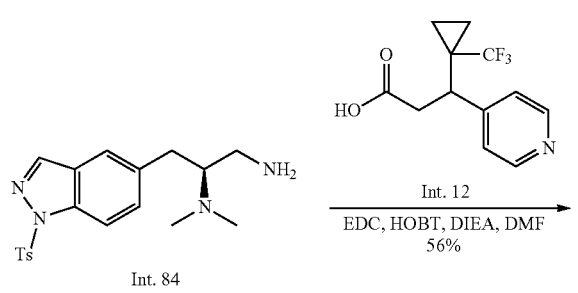

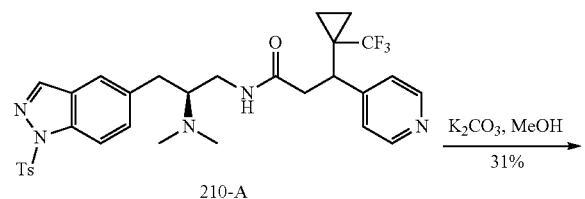

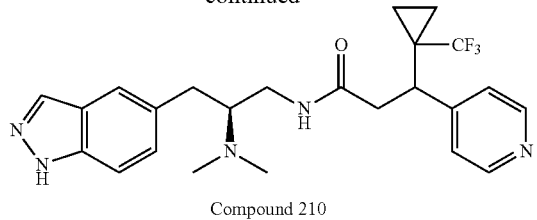

Compound 210 was synthesized from Int. 84 and Int. 12 as described in Example B190. MS (m/z): 460.2 (M+H).

Example B211: Preparation of (R)-N-((S)-2-(dimethylamino)-3-(1H-indazol-5-yl)propyl)-3-(6-methylpyridin-3-yl)-3-(1-(trifluoromethyl)cyclopropyl)propanamide ("Compound 211")

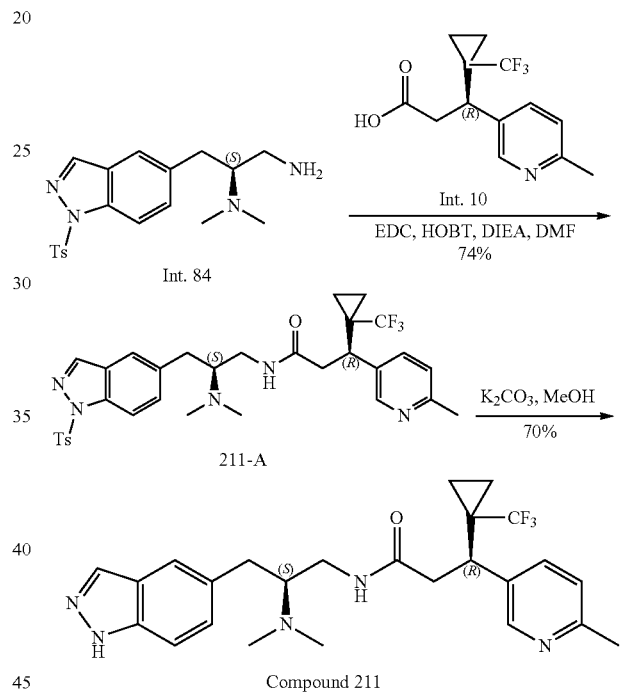

Compound 211 was synthesized from Int. 84 and Int. 10 as described in Example B190. MS (m/z): 474.3 (M+H).

Example B212: Preparation of (R)-4-cyclopropyl-N-((S)-2-(dimethylamino)-3-(1H-indazol-5-yl)propyl)-3-(pyridin-3-yl)butanamide ("Compound 212")

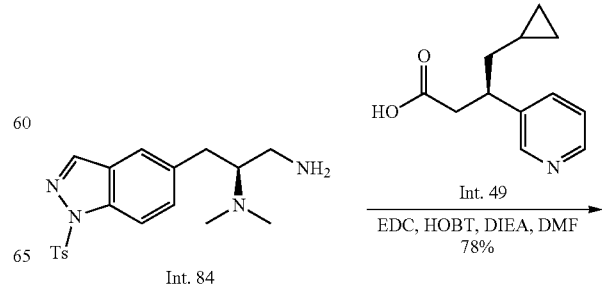

-continued

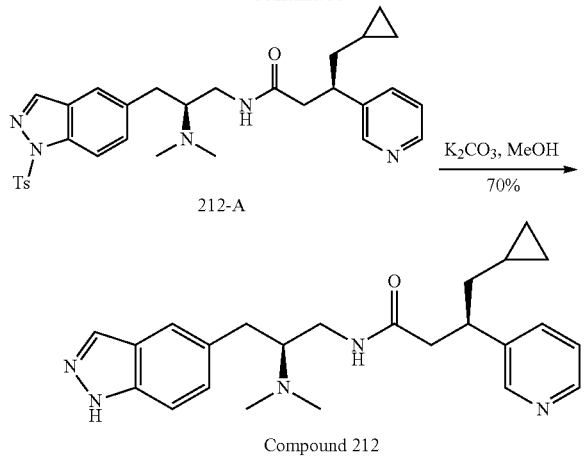

Compound 212

Compound 212 was synthesized from Int. 84 and Int. 49 as described in Example B190. MS (m/z): 406.2 (M+H).

Example B213: Preparation of (R)-N-((S)-2-(dimethylamino)-3-(1H-indazol-5-yl)propyl)-3-(pyridin-3-yl)-3-(1-(trifluoromethyl)cyclopropyl)propanamide ("Compound 213")

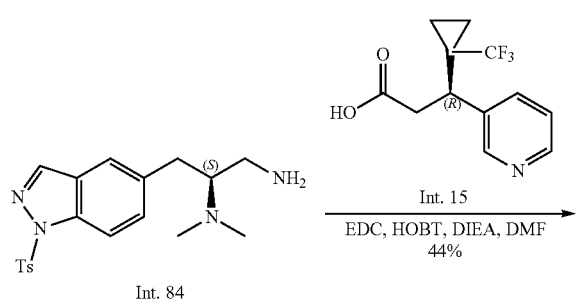

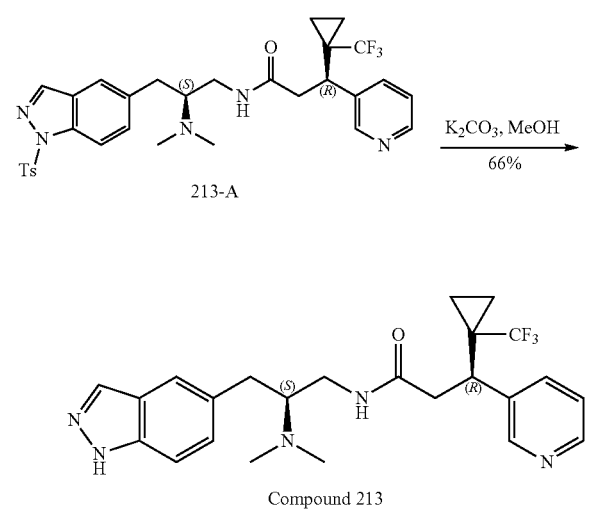

Compound 213

Compound 213 was synthesized from Int. 84 and Int. 15 as described in Example B190. MS (m/z): 460.2 (M+H).

Example B214: Preparation of (S)-N-((S)-2-(dimethylamino)-3-(1H-indazol-5-yl)propyl)-5-methyl-3-phenylhexanamide ("Compound 214")

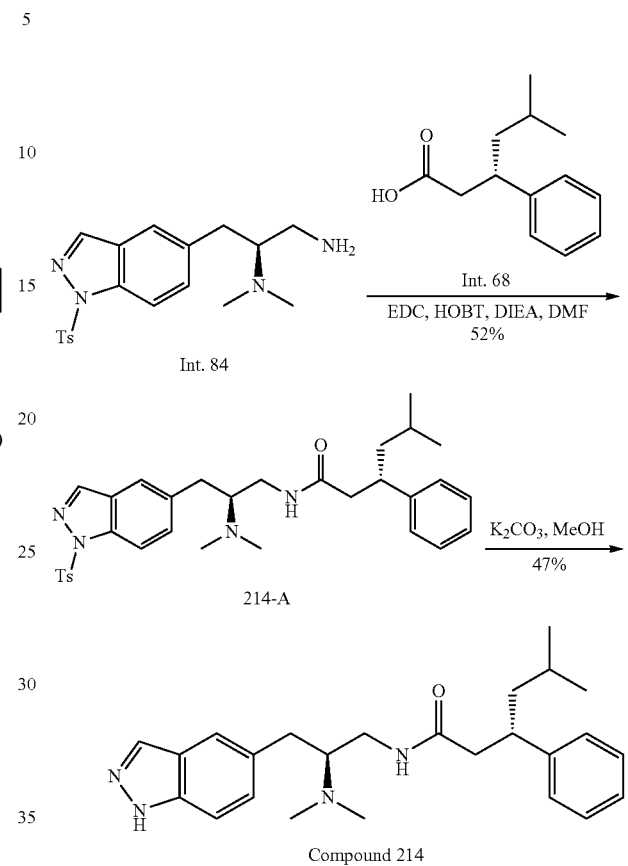

Compound 214

Compound 214 was synthesized from Int. 84 and Int. 68 as described in Example B190. MS (m/z): 407.3 (M+H).

Example B215: Preparation of (R)-N-((S)-2-(dimethylamino)-3-(1H-indazol-5-yl)propyl)-3-(3-fluorophenyl)butanamide ("Compound 215")

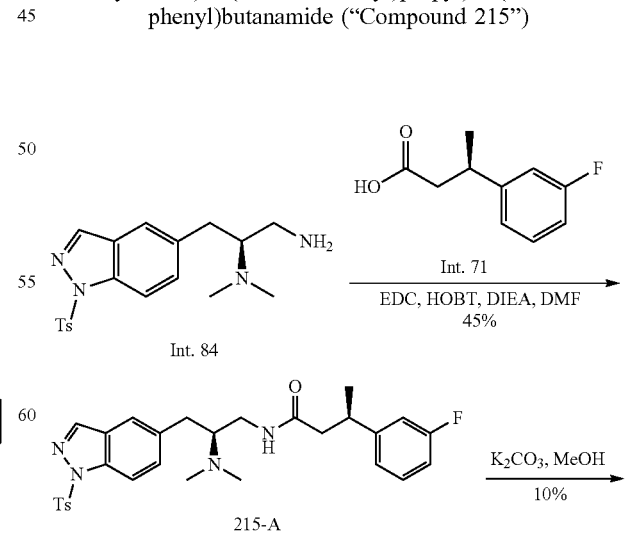

-continued

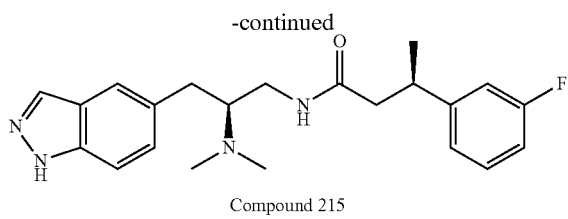

Compound 215

Compound 215 was synthesized from Int. 84 and Int. 71 as described in Example B190. MS (m/z): 383.2 (M+H).

Example B216: Preparation of (S)-N-((S)-2-(dimethylamino)-3-(1H-indazol-5-yl)propyl)-3-(pyridin-2-yl)butanamide ("Compound 216")

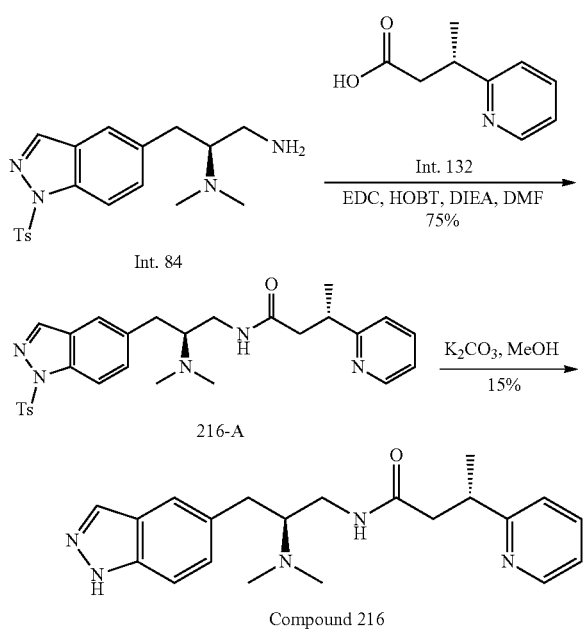

Compound 216

Compound 216 was synthesized from Int. 84 and Int. 132 as described in Example B190. MS (m/z): 366.3 (M+H).

Example B217: Preparation of (S)-N-((S)-2-(dimethylamino)-3-(1H-indazol-5-yl)propyl)-3-(p-tolyl)butanamide ("Compound 217")

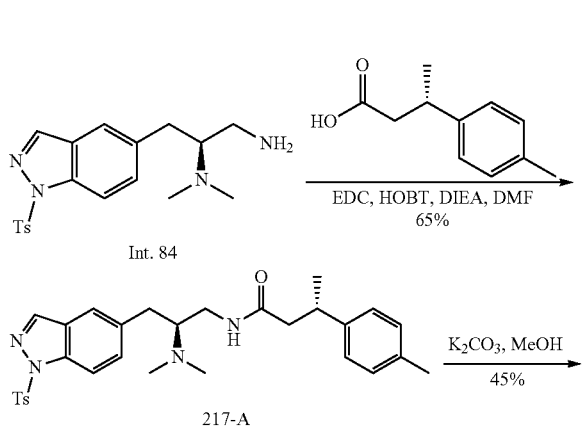

-continued

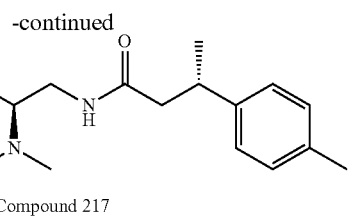

Compound 217

Compound 217 was synthesized from Int. 84 as described in Example B190. MS (m/z): 379.2 (M+H).

Example B218: Preparation of (S)-N-((S)-2-(dimethylamino)-3-(1H-indazol-5-yl)propyl)-3-(4-fluorophenyl)butanamide ("Compound 218")

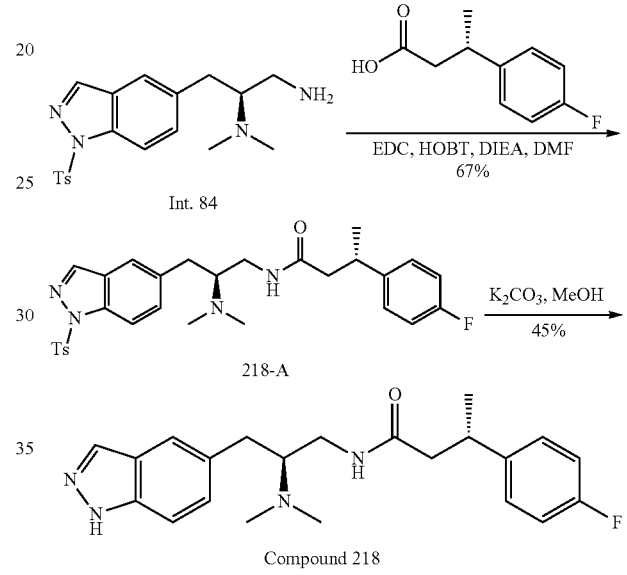

Compound 218

Compound 218 was synthesized from Int. 84 as described in Example B190. MS (m/z): 383.2 (M+H).

Example B219: Preparation of (R)-N-((S)-2-(dimethylamino)-3-(1H-indazol-5-yl)propyl)-4-methyl-3-phenylpentanamide ("Compound 219")

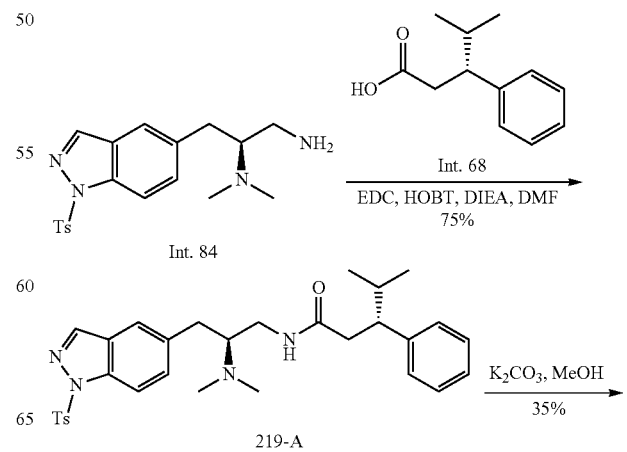

-continued

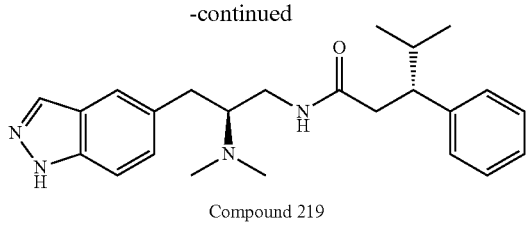

Compound 219

Compound 219 was synthesized from Int. 84 and Int. 66 as described in Example B190. MS (m/z): 393.3 (M+H).

Example B220: Preparation of (S)-3-(4-chlorophenyl)-N-((S)-2-(dimethylamino)-3-(1H-indazol-5-yl)propyl)butanamide ("Compound 220")

-continued

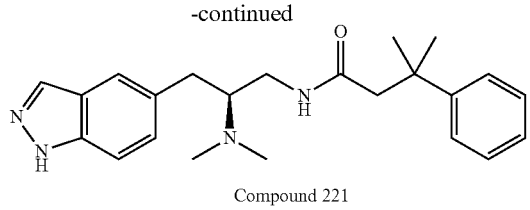

Compound 221

Compound 221 was synthesized from Int. 84 as described in Example B190. MS (m/z): 379.4 (M+H).

Example B222: Preparation of (S)-N-((S)-3-(1H-indazol-5-yl)-2-(pyrrolidin-1-yl)propyl)-3-phenylbutanamide ("Compound 222")

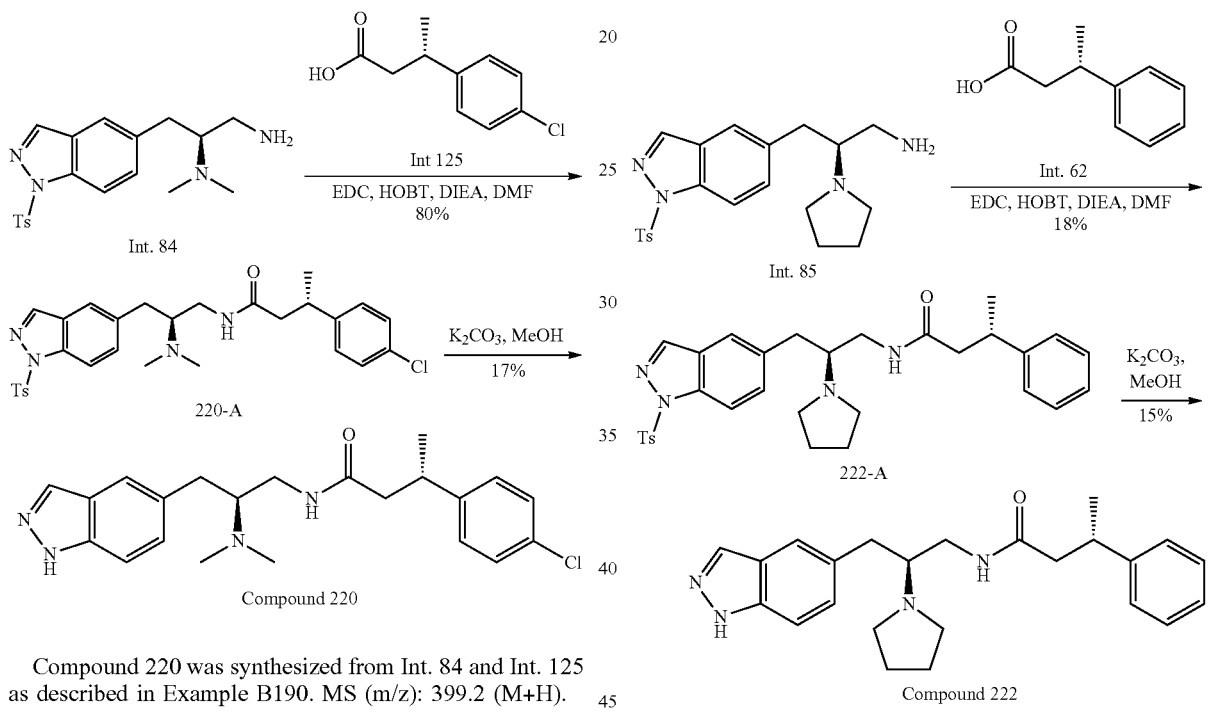

Compound 220

Compound 220 was synthesized from Int. 84 and Int. 125 as described in Example B190. MS (m/z): 399.2 (M+H).

Example B221: Preparation of (S)-N-(2-(dimethylamino)-3-(1H-indazol-5-yl)propyl)-3-methyl-3-phenylbutanamide ("Compound 221")

Compound 222 was synthesized from Int. 85 and Int. 62 as described in Example B190. MS (m/z): 391.2 (M+H).

Example B223: Preparation of (S)-N-((S)-2-(dimethylamino)-3-(1H-indazol-5-yl)propyl)-3-phenyl-hex-5-enamide ("Compound 223")

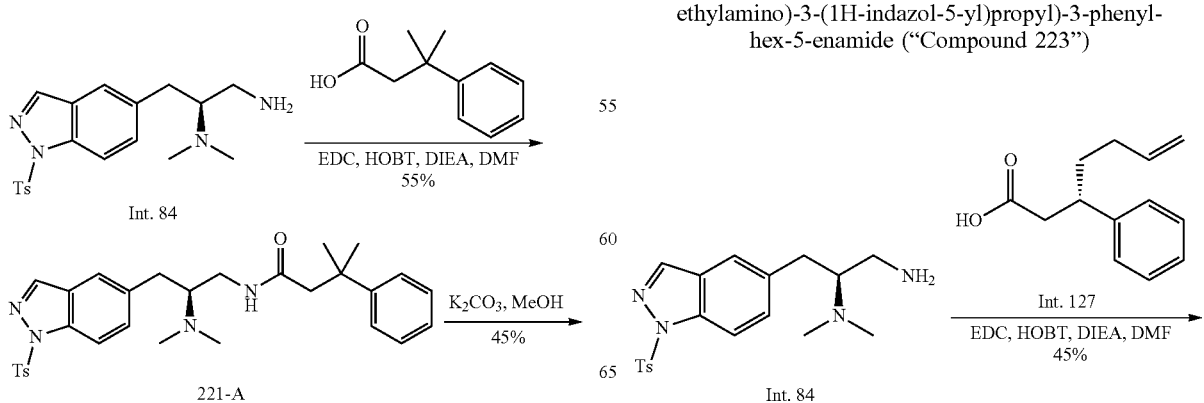

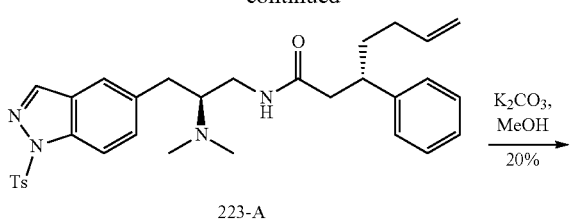

223-A

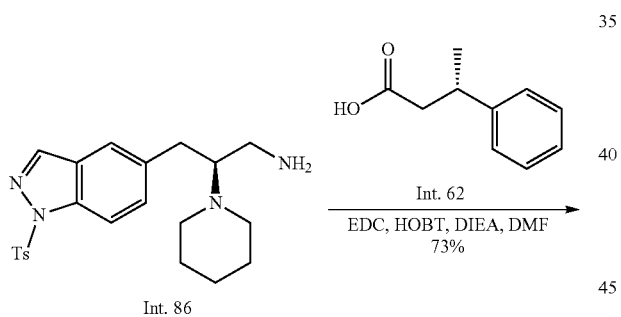

Compound 223

Compound 223 was synthesized from Int. 84 and Int. 127 as described in Example B190. MS (m/z): 405.3 (M+H).

Example B224: Preparation of (S)-N-((S)-3-(1H-indazol-5-yl)-2-(piperidin-1-yl)propyl)-3-phenylbutanamide ("Compound 224")

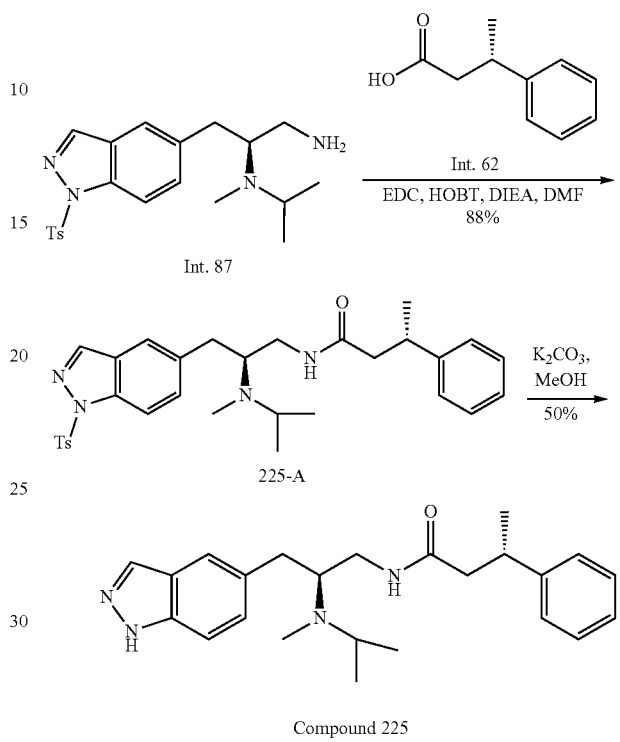

Compound 224 was synthesized from Int. 86 and Int. 62 as described in Example B190. MS (m/z): 405.2 (M+H).

Example B225: Preparation of (S)-N-((S)-3-(1H-indazol-5-yl)-2-(isopropyl(methyl)amino)propyl)-3-phenylbutanamide ("Compound 225")

Compound 225 was synthesized from Int. 87 and Int. 62 as described in Example B190. MS (m/z): 393.2 (M+H).

Example B226: Preparation of (3R)-3-cyclopropyl-N-[(2S)-2-(dimethylamino)-3-(1H-indazol-5-yl)propyl]-3-phenylpropanamide ("Compound 226")

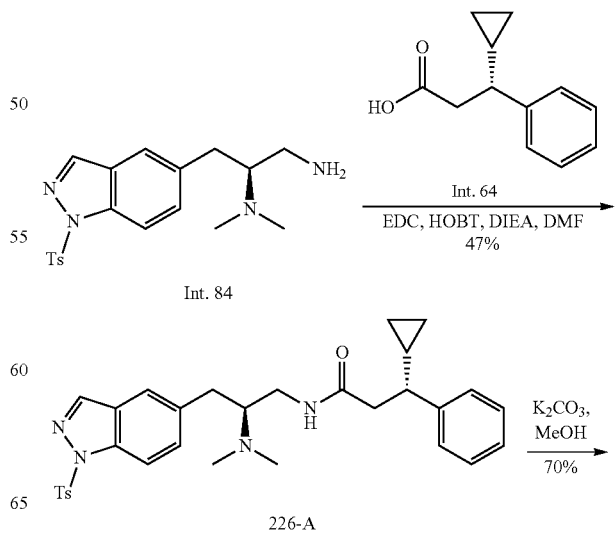

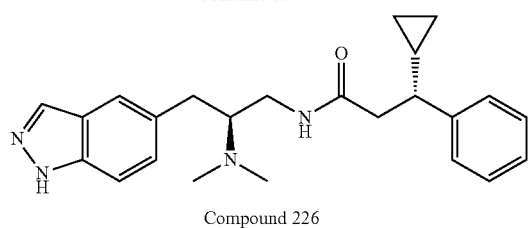

Compound 226

Compound 226 was synthesized from Int. 84 and Int. 64 as described in Example B190. MS (m/z): 391.3 (M+H).

Example B227: Preparation of (3S)-3-cyclopropyl-N-[(2S)-2-(dimethylamino)-3-(1H-indazol-5-yl)propyl]-3-phenylpropanamide ("Compound 227")

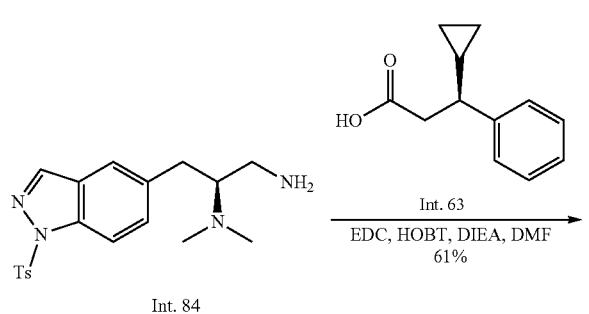

Compound 227

Compound 227 was synthesized from Int. 84 and Int. 63 as described in Example B190. MS (m/z): 391.3 (M+H).

Example B228: Preparation of (3R)-N-[(2S)-2-(dimethylamino)-3-(1H-indazol-1-yl)propyl]-3-phenylbutanamide ("Compound 228")

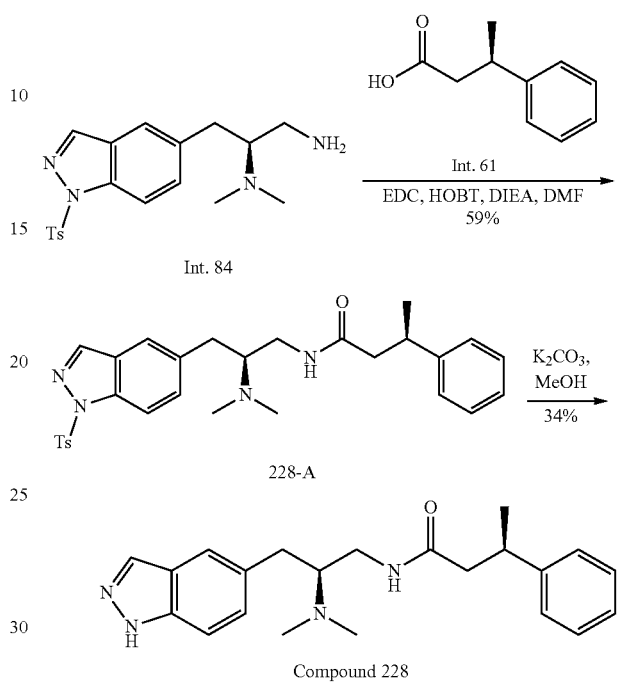

Compound 228

Compound 228 was synthesized from Int. 84 and Int. 61 as described in Example B190. MS (m/z): 365.2 (M+H).

Example B229: Preparation of (3R)-N-((2S)-2-(dimethylamino)-3-(1H-indazol-5-yl)butyl)-3-(2-methylpyrimidin-5-yl)-3-(1-(trifluoromethyl)cyclopropyl)propanamide ("Compound 229")

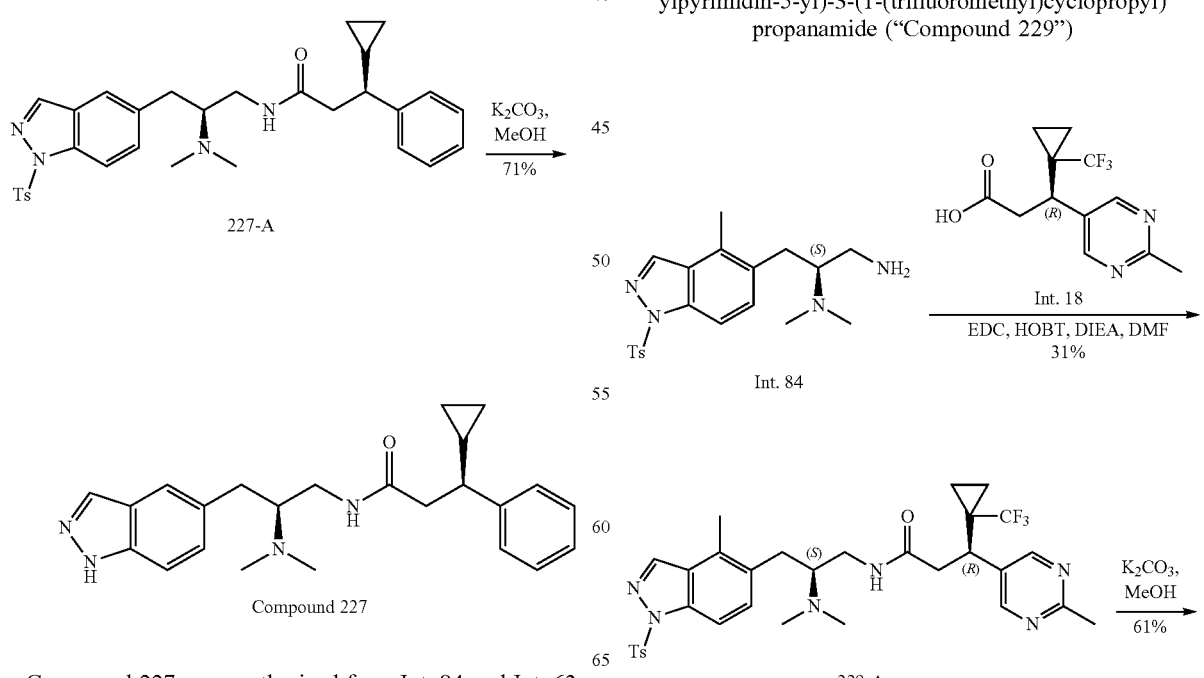

-continued

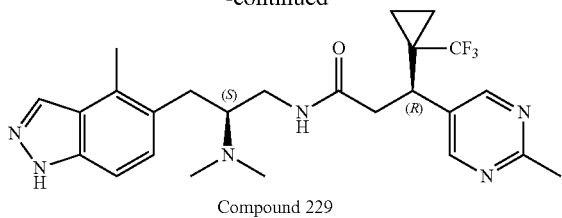

Compound 229

Compound 229 was synthesized from Int. 84 and Int. 18 as described in Example B190. MS (m/z): 489.3 (M+H).

Example B230: Preparation of (R)-N-((S)-2-(dimethylamino)-3-(7-fluoro-1H-indazol-5-yl)propyl)-3-(pyridin-3-yl)-3-(1-(trifluoromethyl)cyclopropyl) propanamide ("Compound 230")

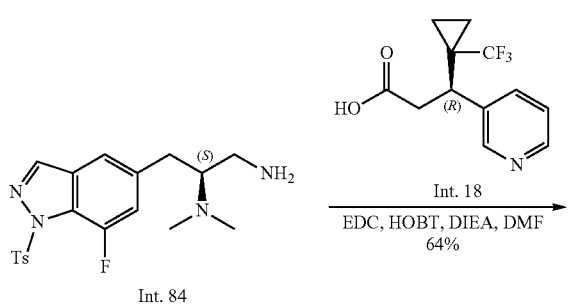

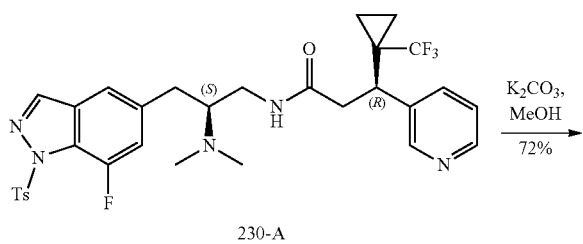

Compound 230

Compound 230 was synthesized from Int. 84 and Int. 18 as described in Example B190. MS (m/z): 478.2 (M+H).

Example B231: Preparation of (R)-N-((S)-2-(dimethylamino)-3-(7-methyl-1H-indazol-5-yl)propyl)-3-(pyridin-3-yl)-3-(1-(trifluoromethyl)cyclopropyl) propanamide; bis(trifluoroacetic acid) ("Compound 231")

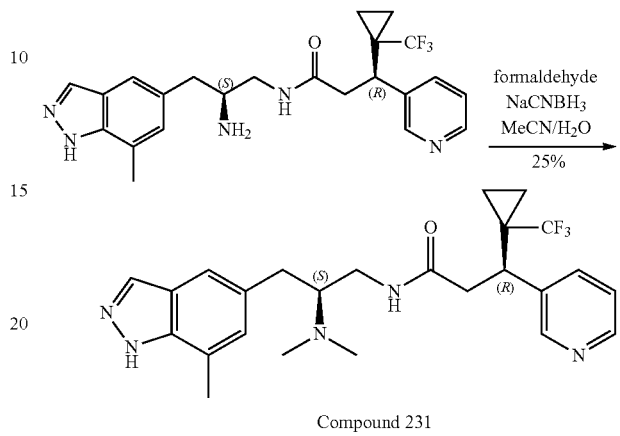

Compound 231

To a solution of (R)-N-((S)-2-amino-3-(7-methyl-1H-indazol-5-yl)propyl)-3-(pyridin-3-yl)-3-(1-(trifluoromethyl)cyclopropyl)propanamide hydrochloride (78.0 mg, 146 µmol) in 8:2 CH₃CN:water (1 mL) were added NaBH₃(CN) (27.5 mg, 3 eq., 437 µmol) and then Formaldehyde 37% w/w (47.3 mg, 4 eq., 583 µmol). LCMS showed complete conversion. Sat. NaHCO₃ was added (2 mL). Acetonitrile was removed in vac. The residue was added with more sat NaHCO₃ (an additional 10 mL) to pH 6-7, extracted with EtOAc (3×). The combined extracts were washed with brine, dried over Na₂SO₄, concentrated, and purified by flash chromatography (0-15% MeOH in DCM+1% NH₄OH), then purified again by reverse Prep. HPLC. The pure fractions were concentrated to dryness to give the title compound (27.5 mg, 25%) as di-TFA salt. MS (m/z): 474.2 (M+H).

Example B232: Preparation of (R)-N-((S)-2-(dimethylamino)-3-(1H-indazol-6-yl)propyl)-3-(pyridin-3-yl)-3-(1-(trifluoromethyl)cyclopropyl)propanamide ("Compound 232")

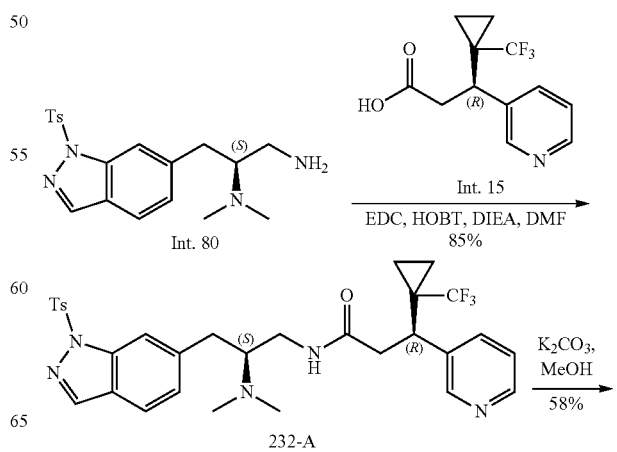

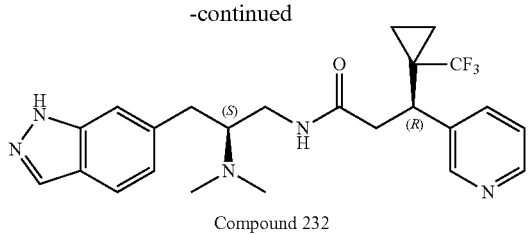

Compound 232

Compound 232 was synthesized from Int. 80 and Int. 15 as described in Example B190. MS (m/z): 460.2 (M+H).

Example B233: Preparation of (R)-N-((S)-3-(6-chloro-H-indazol-5-yl)-2-(dimethylamino)propyl)-3-(2-methylpyrimidin-5-yl)-3-(1-(trifluoromethyl)cyclopropyl) propanamide ("Compound 233")

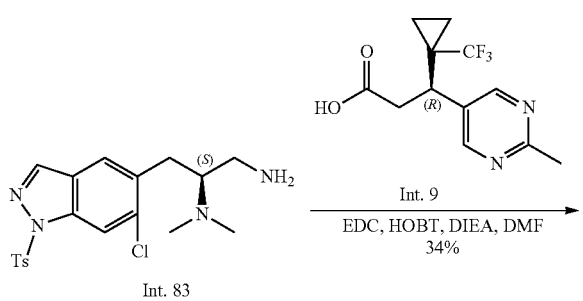

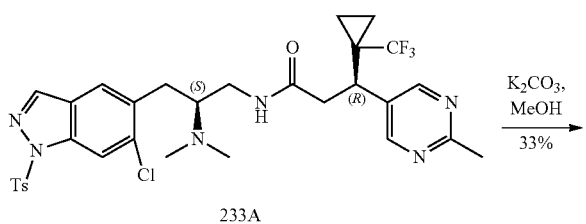

Compound 233

Compound 233 was synthesized from Int. 83 and Int. 9 as described in Example B190. MS (m/z): 509.2 (M+H).

Example B234: Preparation of (R)-N-((S)-3-(6-chloro-H-indazol-5-yl)-2-(dimethylamino)propyl)-3-(pyridin-4-yl)-3-(1-(trifluoromethyl)cyclopropyl) propanamide ("Compound 234")

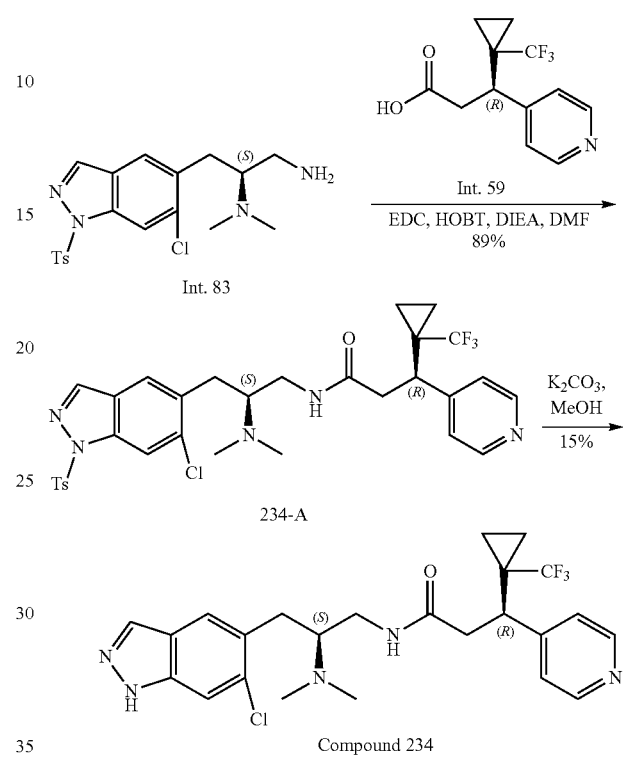

Compound 234

Compound 234 was synthesized from Int. 83 and Int. 59 as described in Example B190. MS (m/z): 494.2 (M+H).

Example B235: Preparation of (R)-N-((S)-3-(6-chloro-1H-indazol-5-yl)-2-(dimethylamino)propyl)-3-(pyridin-3-yl)-3-(1-(trifluoromethyl)cyclopropyl) propanamide ("Compound 235")

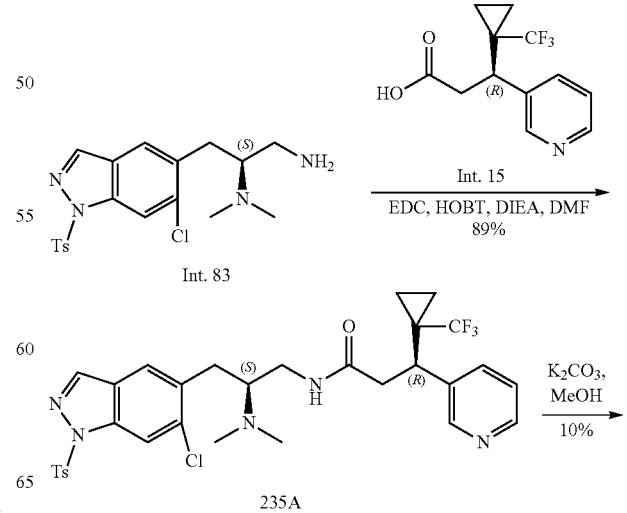

235A

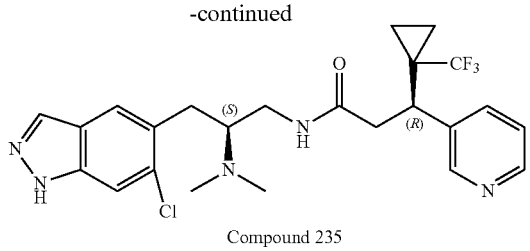

Compound 235

Compound 235 was synthesized from Int. 83 and Int. 15 as described in Example B190. MS (m/z): 494.2 (M+H).

Example B236: Preparation of (S)-N-((S)-3-(6-chloro-1H-indazol-5-yl)-2-(dimethylamino)propyl)-3-phenylbutanamide ("Compound 236")

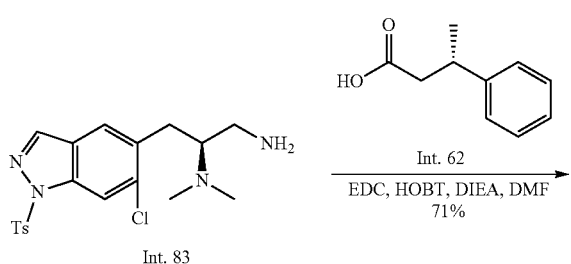

Int. 83

236-A

Compound 236

Compound 236 was synthesized from Int. 83 and Int. 62 as described in Example B190. MS (m/z): 399.2 (M+H).

Example B237: Preparation of (S)-N-((S)-2-(dimethylamino)-3-(1H-indazol-5-yl)propyl)-3-(pyridin-3-yl)-3-(1-(trifluoromethyl)cyclopropyl)propanamide ("Compound 237")

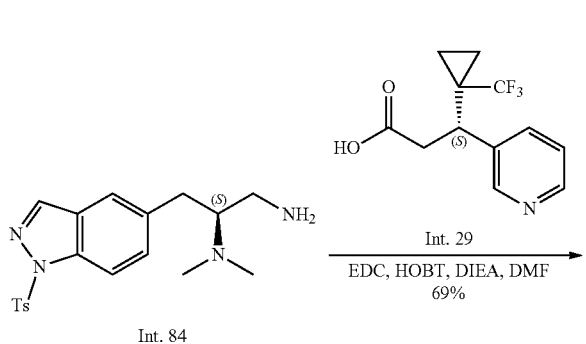

Int. 84

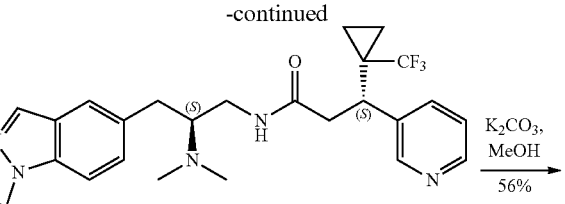

237A

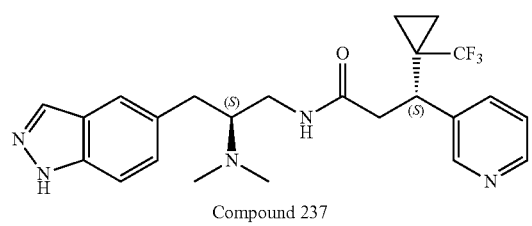

Compound 237

Compound 237 was synthesized from Int. 84 and Int. 29 as described in Example B190. MS (m/z): 460.2 (M+H).

Example B238: Preparation of (R)-N-((S)-3-(2,5-difluoro-4-hydroxyphenyl)-2-(dimethylamino)propyl)-3-(pyridin-3-yl)-3-(1-(trifluoromethyl)cyclopropyl)propanamide ("Compound 238")

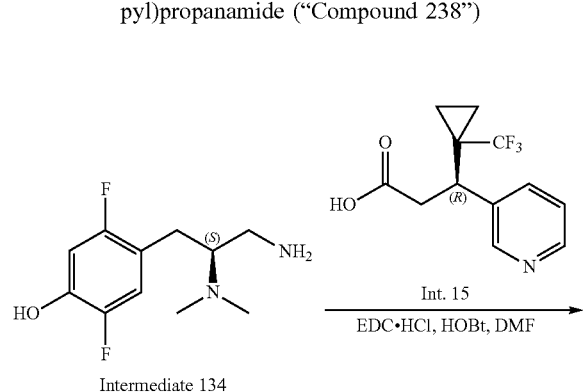

Intermediate 134

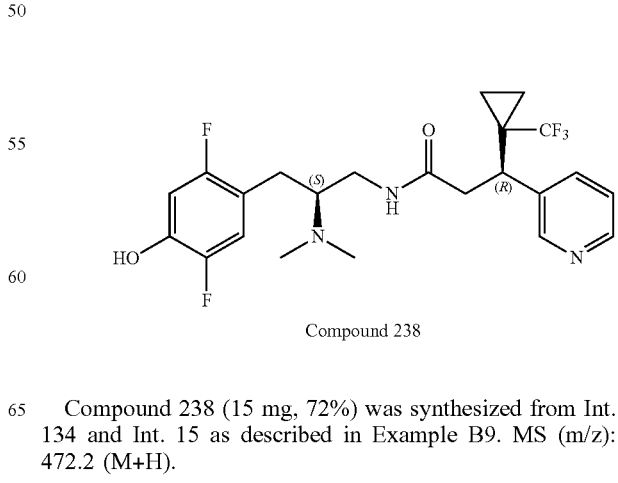

Compound 238

Compound 238 (15 mg, 72%) was synthesized from Int. 134 and Int. 15 as described in Example B9. MS (m/z): 472.2 (M+H).

Example B239: Preparation of (S)-3-cyclopropyl-N-((S)-3-(2,6-difluoro-4-hydroxyphenyl)-2-(dimethylamino)propyl)-3-(pyridin-4-yl)propanamide ("Compound 239")

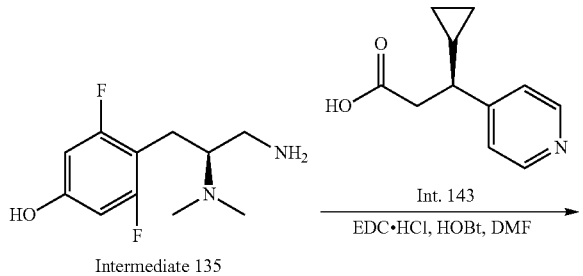

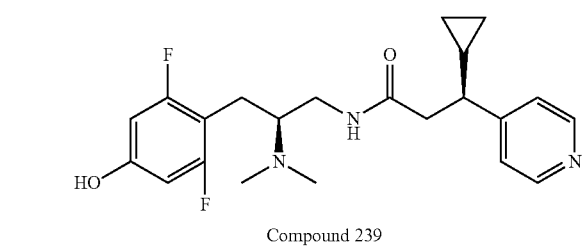

Compound 239

Compound 239 (24 mg, 68%) was synthesized from Int. 135 and Int. 143 as described in Example B9. MS (m/z): 404.2 (M+H).

Example B240: Preparation of (S)-N-((S)-3-(2,6-difluoro-4-hydroxyphenyl)-2-(dimethylamino)propyl)-3-phenylbutanamide ("Compound 240")

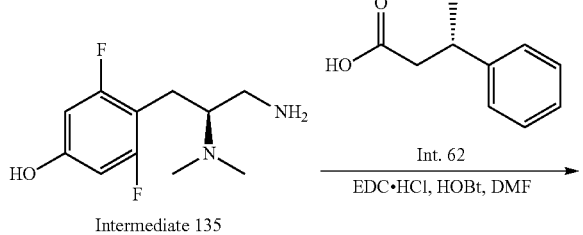

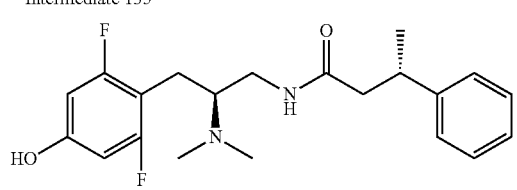

Compound 240

Compound 240 (8 mg, 42%) was synthesized from Int. 135 and Int. 62 as described in Example B9. MS (m/z): 377.2 (M+H).

Example B241: Preparation of (S)-4-cyclopropyl-N-((S)-2-(dimethylamino)-3-(4-hydroxy-2,6-dimethylphenyl)propyl)-3-(pyridin-3-yl)butanamide ("Compound 241")

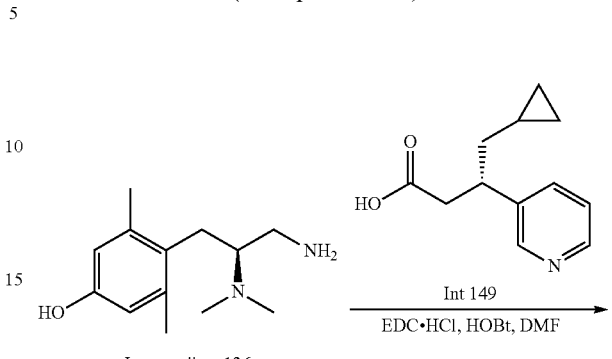

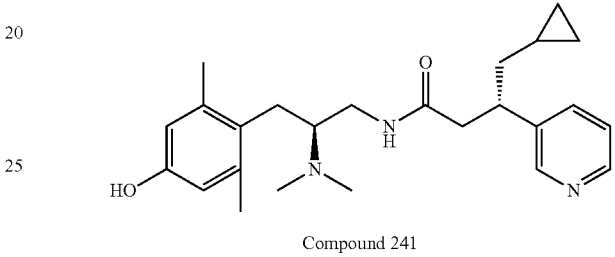

Compound 241

Compound 241 (78 mg, 82%) was synthesized from Int. 136 and Int. 149 as described in Example B9. MS (m/z): 410.3 (M+H).

Example B242: Preparation of (R)-N-((S)-2-(dimethylamino)-3-(4-hydroxy-2,6-dimethylphenyl)propyl)-3-(pyridin-3-yl)-3-(1-(trifluoromethyl)cyclopropyl)propanamide ("Compound 242")

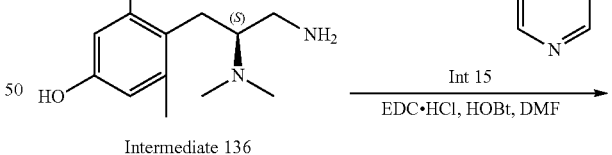

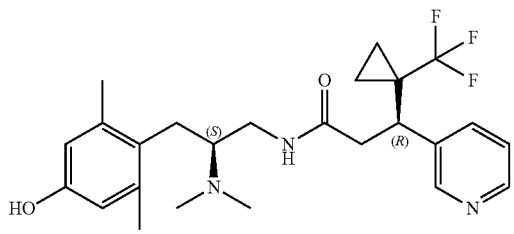

Compound 242

Compound 242 (32 mg, 63%) was synthesized from Int. 136 and Int. 15 as described in Example B9. MS (m/z): 464.2 (M+H).

Example B243: Preparation of (S)-N-((S)-2-(dimethylamino)-3-(4-hydroxy-2,6-dimethylphenyl)propyl)-3-(pyridin-3-yl)-3-(1-(trifluoromethyl)cyclopropyl)propanamide ("Compound 243")

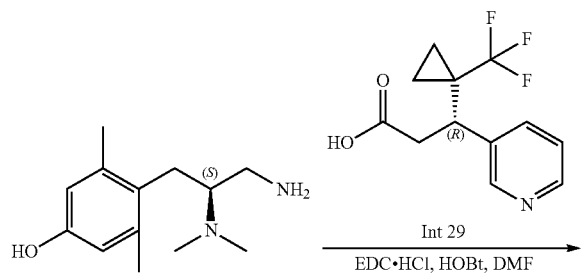

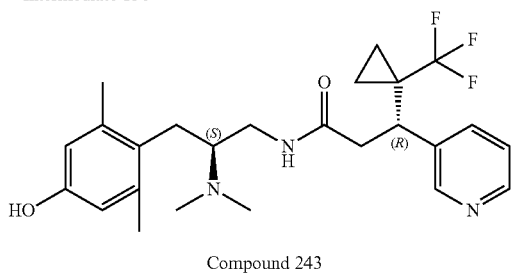

Compound 243

Compound 243 (72 mg, 66%) was synthesized from Int. 136 and Int. 29 as described in Example B9. MS (m/z): 464.2 (M+H).

Example B244: Preparation of N-((S)-2-(dimethylamino)-3-(4-hydroxy-2,6-dimethylphenyl)propyl)-3-(6-methoxypyridin-3-yl)-3-(1-(trifluoromethyl)cyclopropyl) propanamide ("Compound 244")

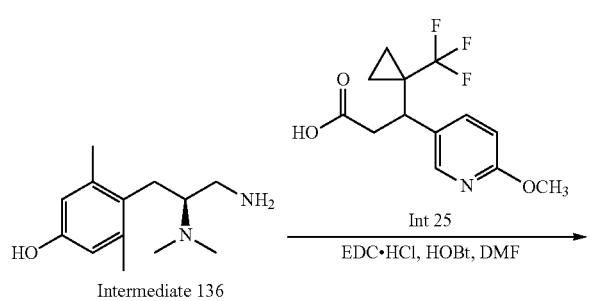

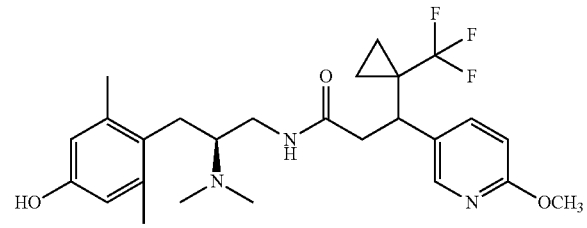

Compound 244

Compound 244 (9 mg, 62%) was synthesized from Int. 136 and Int. 25 as described in Example B9. MS (m/z): 494.2 (M+H).

Example B245: Preparation of (R)-3-(5-chloropyridin-3-yl)-N-((S)-2-(dimethylamino)-3-(4-hydroxy-2,6-dimethylphenyl)propyl)-3-(1-(trifluoromethyl)cyclopropyl)propanamide ("Compound 245")

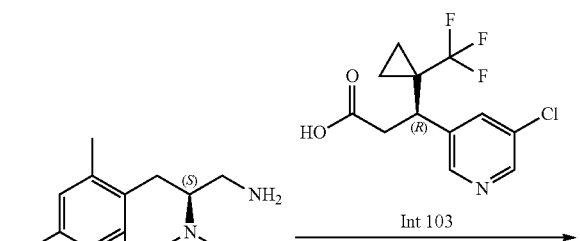

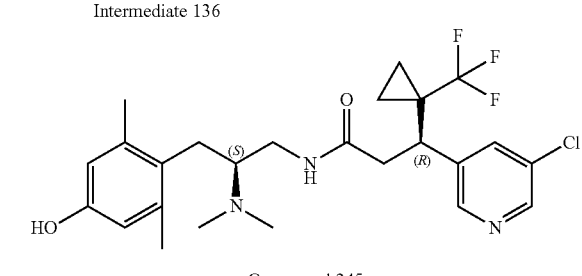

Compound 245

Compound 245 (35 mg, 57%) was synthesized from Int. 136 and Int. 103 as described in Example B9. MS (m/z): 498.2 (M+H).

Example B246: Preparation of 3-(5-chloropyrimidin-2-yl)-N-((S)-2-(dimethylamino)-3-(4-hydroxy-2,6-dimethylphenyl)propyl)-3-(1-(trifluoromethyl)cyclopropyl)propanamide ("Compound 246")

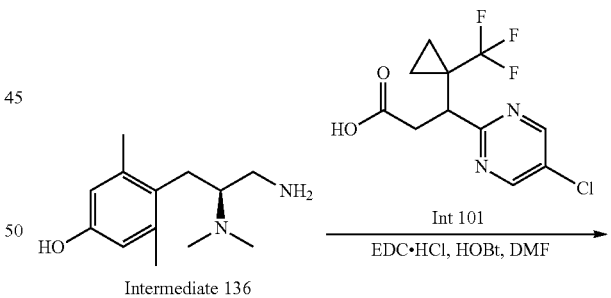

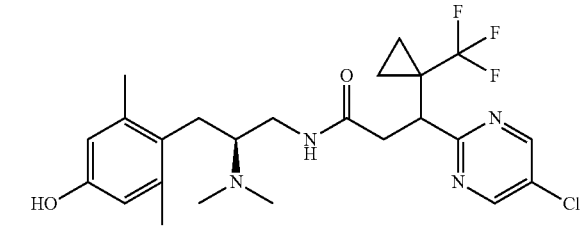

Compound 246

Compound 246 (31 mg, 71%) was synthesized from Int. 136 and Int. 101 as described in Example B9. MS (m/z): 499.2 (M+H).

Example B247: Preparation of N-((S)-2-(dimethyl-amino)-3-(4-hydroxy-2,6-dimethylphenyl)propyl)-3-(5-fluoropyridin-3-yl)-3-(1-(trifluoromethyl)cyclopropyl)propanamide ("Compound 247")

Example B249: Preparation of N-((S)-2-(dimethyl-amino)-3-(4-hydroxy-2,6-dimethylphenyl)propyl)-3-(1-(trifluoromethyl)cyclopropyl)-3-(6-(trifluoromethyl)pyridin-3-yl)propanamide ("Compound 249")

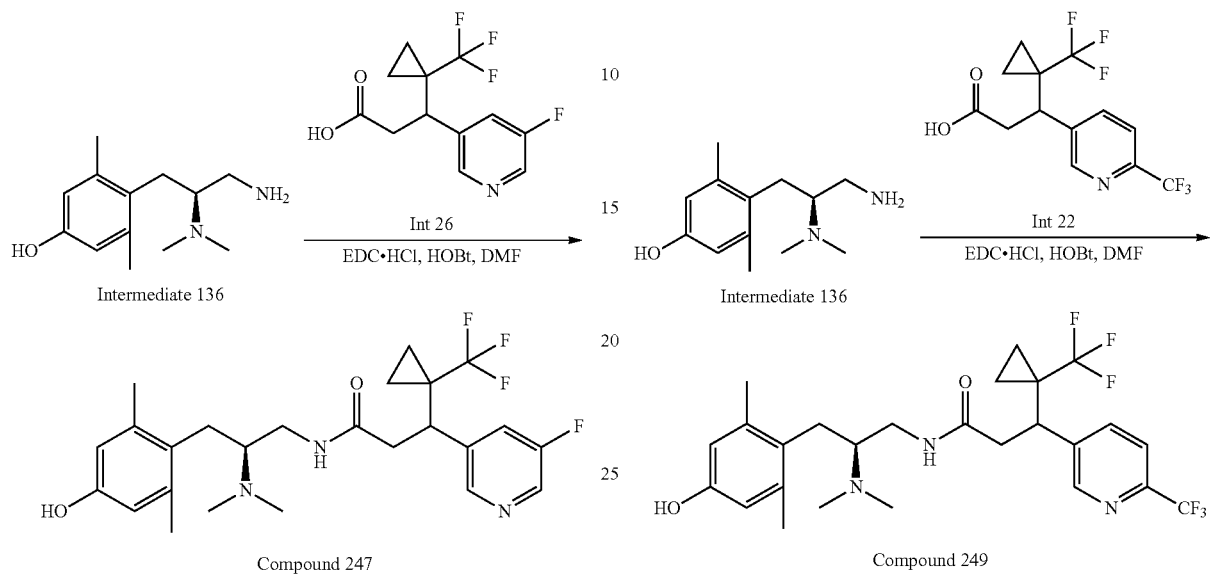

Compound 247 (20 mg, 58%) was synthesized from Int. 136 and Int. 26 as described in Example B9. MS (m/z): 482.2 (M+H).

Compound 249 (25 mg, 65%) was synthesized from Int. 136 and Int. 22 as described in Example B9. MS (m/z). 532.1 (M+H).

Example B248: Preparation of N-((S)-2-(dimethyl-amino)-3-(4-hydroxy-2,6-dimethylphenyl)propyl)-2-(pyrimidin-2-yl)cyclopropane-1-carboxamide ("Compound 248")

Example B250: Preparation of (S)-3-(4-chlorophenyl)-N-((S)-2-(dimethylamino)-3-(4-hydroxy-2,6-dimethylphenyl)propyl)butanamide ("Compound 250")

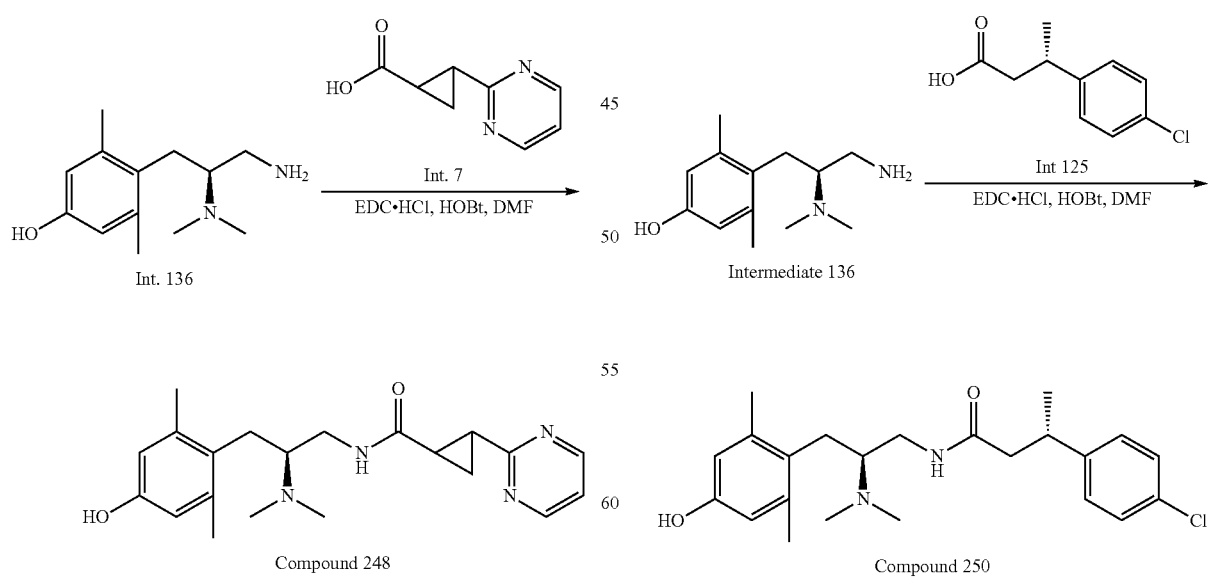

Compound 248 (11 mg, 78%) was synthesized from Int. 136 and Int. 7 as described in Example B9. MS (m/z): 369.1 (M+H).

Compound 250 (40 mg, 78%) was synthesized from Int. 136 and Int. 125 as described in Example B9. MS (m/z): 403.2 (M+H).

Example B251: Preparation of (S)-3-cyclopropyl-N-((S)-2-(dimethylamino)-3-(4-hydroxy-2,6-dimethylphenyl)propyl)-3-phenylpropanamide ("Compound 251")

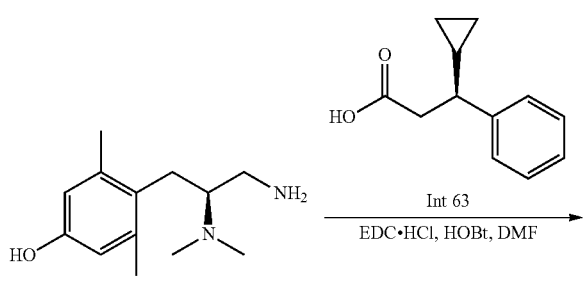

Compound 251 (560 mg, 75%) was synthesized from Int. 136 and Int. 63 as described in Example B9. MS (m/z): 395.3 (M+H).

Example B252: Preparation of (R)-N-((S)-2-(dimethylamino)-3-(4-hydroxy-2,6-dimethylphenyl)propyl)-3-(2-methylthiazol-5-yl)pentanamide ("Compound 252")

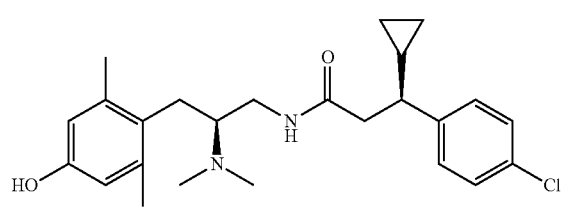
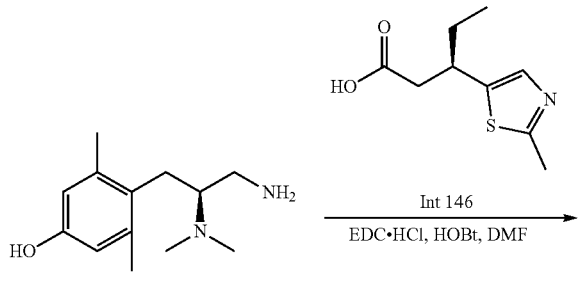

Compound 252 (120 mg, 78%) was synthesized from Int. 136 and Int. 146 as described in Example B9. MS (m/z): 404.2 (M+H).

Example B253: Preparation of (S)-3-cyclopropyl-N-((S)-2-(dimethylamino)-3-(4-hydroxy-2,6-dimethylphenyl)propyl)-3-(2-methylthiazol-5-yl)propanamide ("Compound 253")

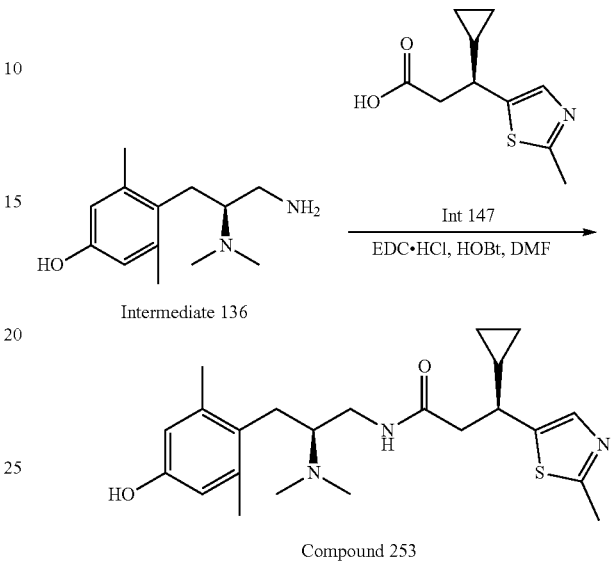

Compound 253 (43 mg, 59%) was synthesized from Int. 136 and Int. 147 as described in Example B9. MS (m/z): 416.2 (M+H).

Example B254: Preparation of (S)-3-cyclopropyl-N-((S)-2-(dimethylamino)-3-(4-hydroxy-2,6-dimethylphenyl)propyl)-3-(2-methylthiazol-5-yl)propanamide ("Compound 254")

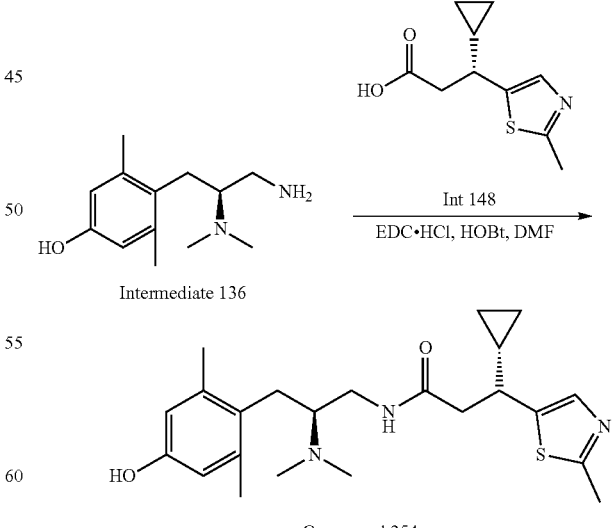

Compound 254 (39 mg, 60%) was synthesized from Int. 136 and Int. 148 as described in Example B9. MS (m/z): 416.2 (M+H).

Example B255: Preparation of (R)-N-((S)-2-(dimethylamino)-3-(4-hydroxy-2-(trifluoromethyl)phenyl)propyl)-3-(pyridin-3-yl)-3-(1-(trifluoromethyl)cyclopropyl) propanamide ("Compound 255")

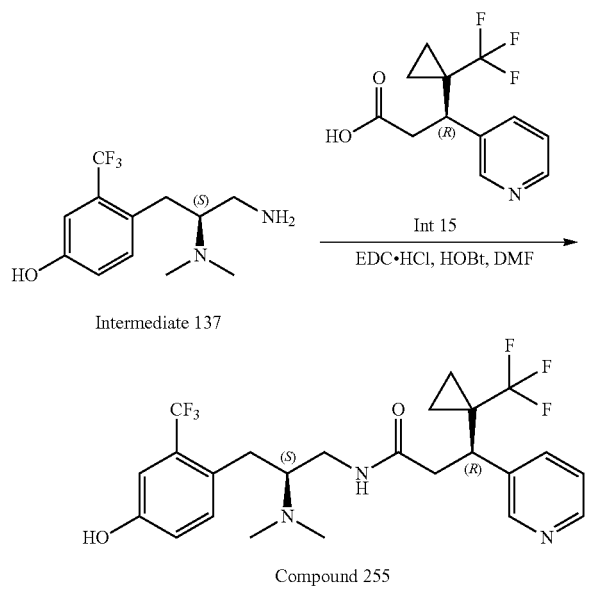

Compound 255 (15 mg, 78%) was synthesized from Int. 137 and Int. 15 as described in Example B9. MS (m/z): 505.2 (M+H).

Example B256: Preparation of (S)-N-((S)-2-(dimethylamino)-3-(4-hydroxy-2-(trifluoromethyl)phenyl)propyl)-3-(1-methylcyclopropyl)-3-(pyridin-3-yl)propanamide ("Compound 256")

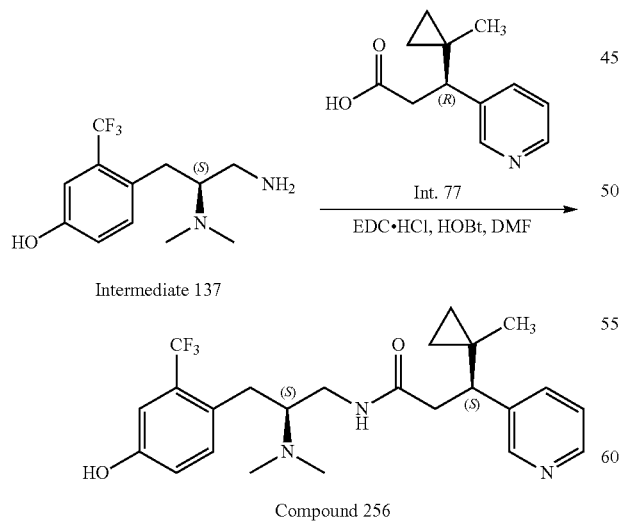

Compound 256 (12 mg, 89%) was synthesized from Int. 137 and Int. 77 as described in Example B9. MS (m/z): 450.2 (M+H).

Example B257: Preparation of (R)-N-((S)-3-(2-chloro-3-fluoro-4-hydroxyphenyl)-2-(dimethylamino)propyl)-3-(pyridin-3-yl)-3-(1-(trifluoromethyl)cyclopropyl)propanamide ("Compound 257")

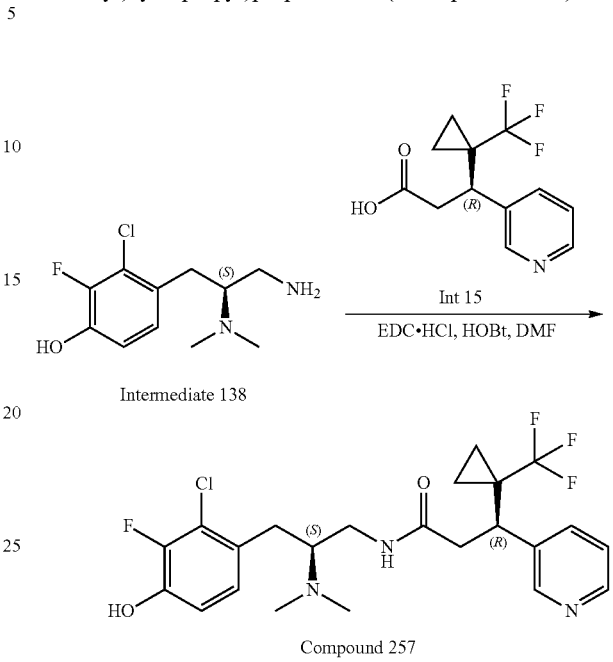

Compound 257 (50 mg, 55%) was synthesized from Int. 138 and Int. 15 as described in Example B9. MS (m/z): 488.2 (M+H).

Example B258: Preparation of (S)-N-((S)-3-(2-chloro-3-fluoro-4-hydroxy phenyl)-2-(dimethylamino)propyl)-3-cyclopropyl-3-(pyridin-4-yl)propanamide ("Compound 258")

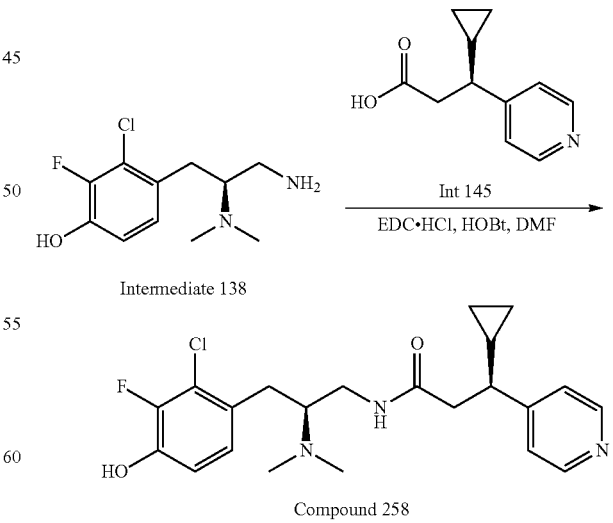

Compound 258 (11 mg, 69%) was synthesized from Int. 138 and Int. 145 as described in Example B9. MS (m/z): 420.2 (M+H).

Example B259: Preparation of (R)-N-((S)-3-(2-chloro-3-fluoro-4-methoxyphenyl)-2-(dimethylamino)propyl)-3-(pyridin-3-yl)-3-(1-(trifluoromethyl)cyclopropyl)propanamide ("Compound 259")

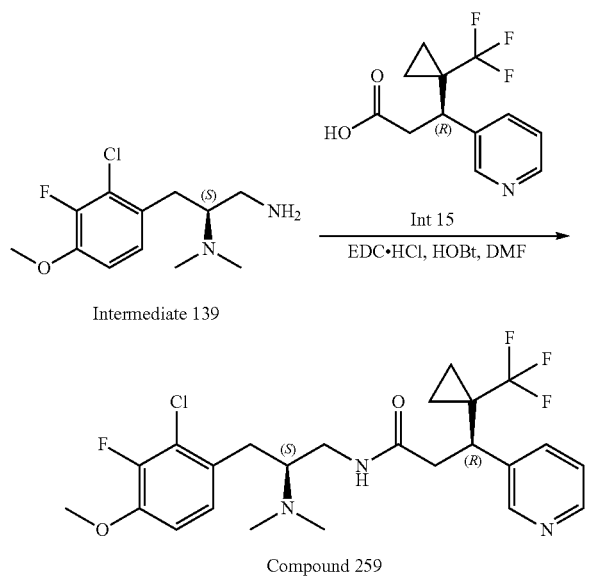

Compound 259 (53 mg, 58%) was synthesized from Int. 139 and Int. 15 as described in Example B9. MS (m/z): 502.2 (M+H).

Example B260: Preparation of (S)-N-((S)-3-(2-chloro-4-hydroxyphenyl)-2-(dimethylamino)propyl)-4-cyclopropyl-3-(pyridin-4-yl)butanamide ("Compound 260")

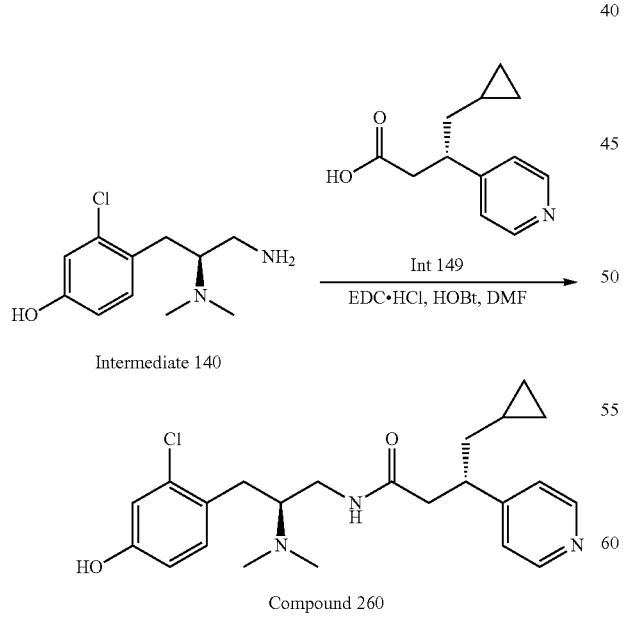

Compound 260 (35 mg, 47%) was synthesized from Int. 140 and Int. 149 as described in Example B9. MS (m/z): 416.2 (M+H).

Example B261: Preparation of (R)-N-((S)-3-(2-chloro-4-hydroxyphenyl)-2-(dimethylamino)propyl)-3-(pyridin-4-yl)-3-(1-(trifluoromethyl)cyclopropyl)propanamide ("Compound 261")

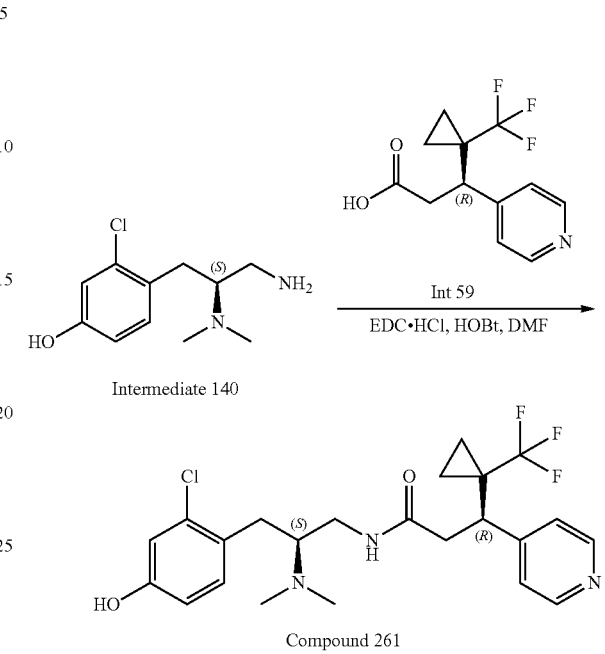

Compound 261 (12 mg, 35%) was synthesized from Int 140 and Int 59 as described in Example B9, MS (m/z): 470.1 (M+H).

Example B262: Preparation of (R)-N-((S)-3-(2-chloro-4-hydroxyphenyl)-2-(dimethylamino)propyl)-3-(pyridin-3-yl)-3-(1-(trifluoromethyl)cyclopropyl)propanamide ("Compound 262")

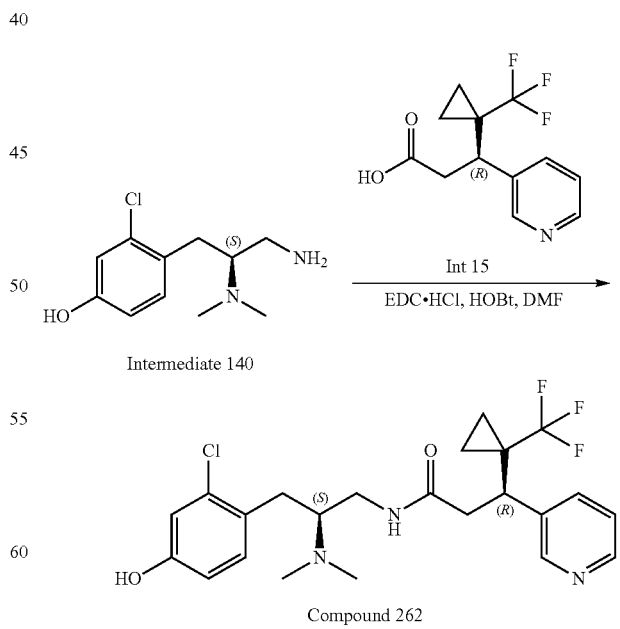

Compound 262 (14 mg, 62%) was synthesized from Int. 140 and Int. 15 as described in Example B9. MS (m/z): 470.2 (M+H).

Example B263: Preparation of (S)-N-((S)-3-(2-chloro-4-hydroxyphenyl)-2-(dimethylamino)propyl)-3-cyclopropyl-3-phenylpropanamide ("Compound 263")

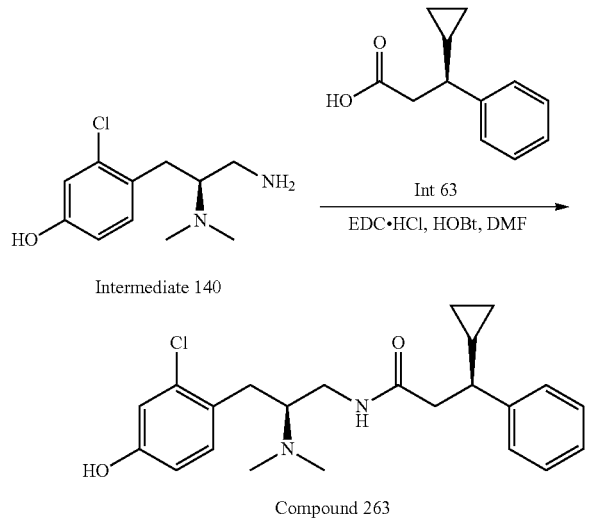

Compound 263

Compound 263 (298 mg, 81%) was synthesized from Int. 140 and Int. 63 as described in Example B9. MS (m/z): 401.2 (M+H).

Example B264: Preparation of (S)-3-cyclopropyl-N-((S)-2-(dimethylamino)-3-(4-hydroxy-2-methylphenyl)propyl)-3-(thiazol-5-yl)propanamide ("Compound 264")

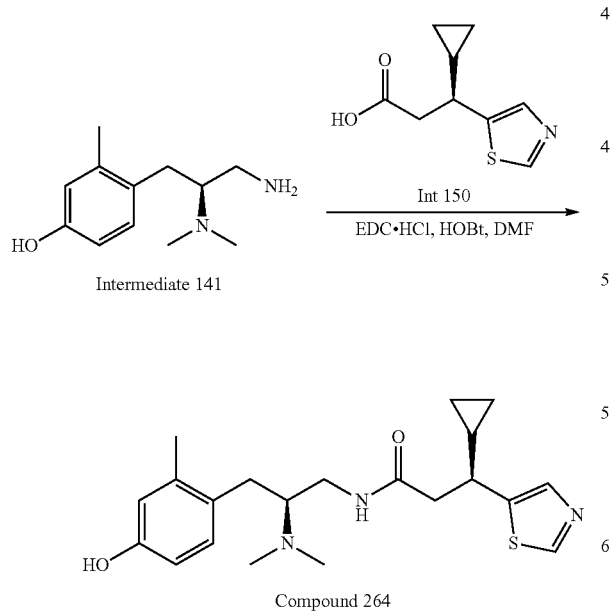

Compound 264

Compound 264 (54 mg, 66%) was synthesized from Int. 141 and Int. 150 as described in Example B9. MS (m/z): 388.2 (M+H).

Example B265: Preparation of (R)-N-((S)-2-(dimethylamino)-3-(4-hydroxy-2-methylphenyl)propyl)-3-(furan-3-yl)-3-(1-(trifluoromethyl)cyclopropyl)propanamide ("Compound 265")

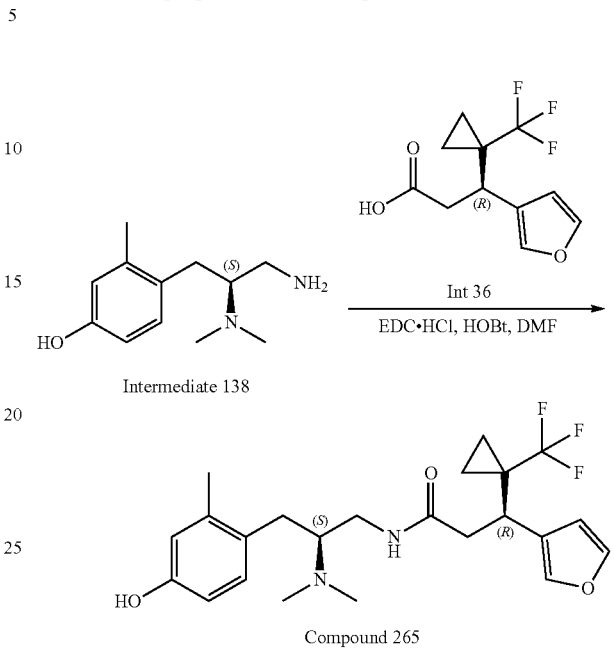

Compound 265

Compound 265 (45 mg, 64%) was synthesized from Int. 141 and Int. 36 as described in Example B9. MS (m/z): 439.2 (M+H).

Example B266: Preparation of (S)-N-((S)-2-(dimethylamino)-3-(4-hydroxy-2-methylphenyl)propyl)-3-(5-methylfuran-2-yl)-3-(1-(trifluoromethyl)cyclopropyl) propanamide ("Compound 266")

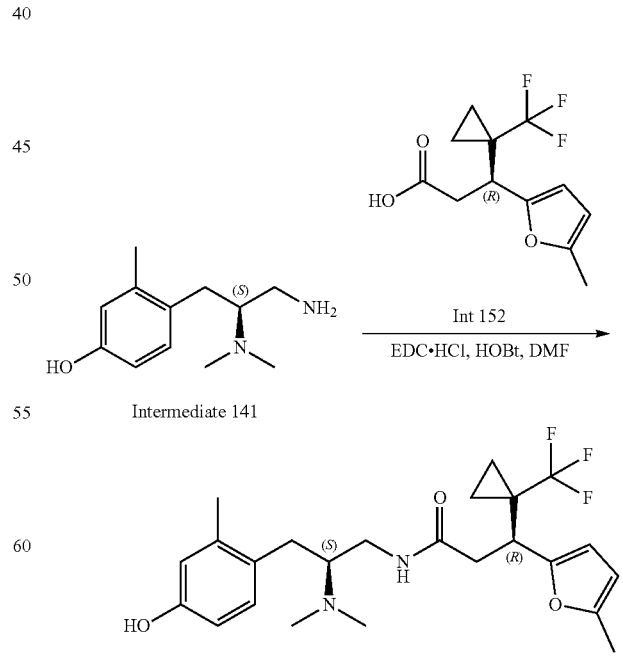

Compound 266

Compound 266 (35 mg, 79%) was synthesized from Int. 141 and Int. 152 as described in Example B9. MS (m/z): 453.2 (M+H).

Example B267: Preparation of 4-((S)-2-(dimethylamino)-3-((S)-3-(5-methylfuran-2-yl)-3-(1-(trifluoromethyl)cyclopropyl)propanamido)propyl)-2-fluorobenzamide ("Compound 267")

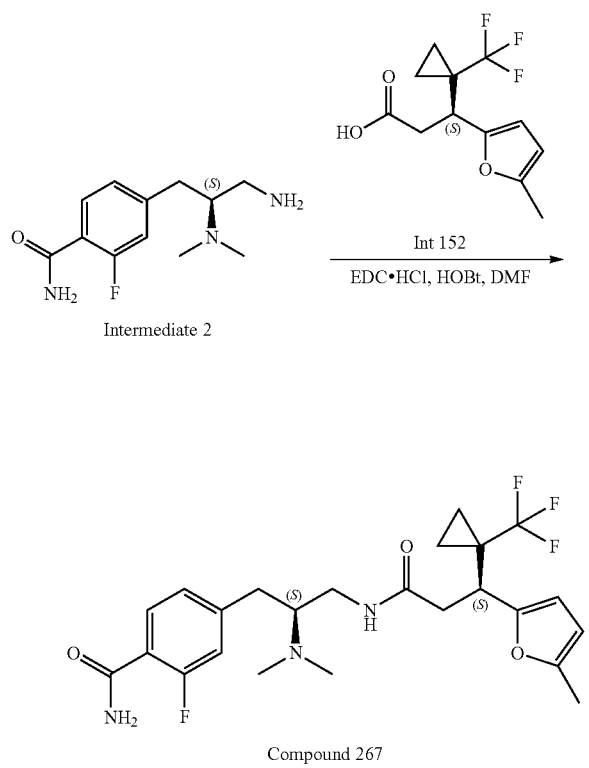

Compound 267 (91.7 mg, 81%) was synthesized from Int. 2 and Int. 152 as described in Example B9. MS (m/z): 484.2 (M+H).

Example B268: Preparation of (S)-N-((S)-2-(dimethylamino)-3-(4-hydroxy-2-methylphenyl)propyl)-3-(thiazol-5-yl)-3-(1-(trifluoromethyl)cyclopropyl)propanamide ("Compound 268")

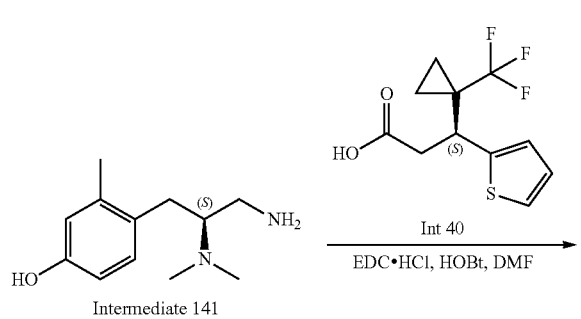

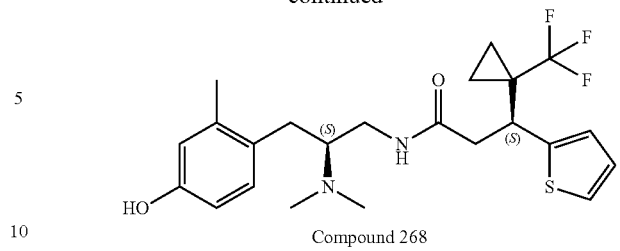

Compound 268 (26 mg, 77%) was synthesized from Int. 141 and Int. 40 as described in Example B9. MS (m/z): 456.2 (M+H).

Example B269: Preparation of (R)-N-((S)-2-(dimethylamino)-3-(4-hydroxy-2-methylphenyl)propyl)-3-(pyridin-3-yl)-3-(1-(trifluoromethyl)cyclopropyl)propanamide ("Compound 269")

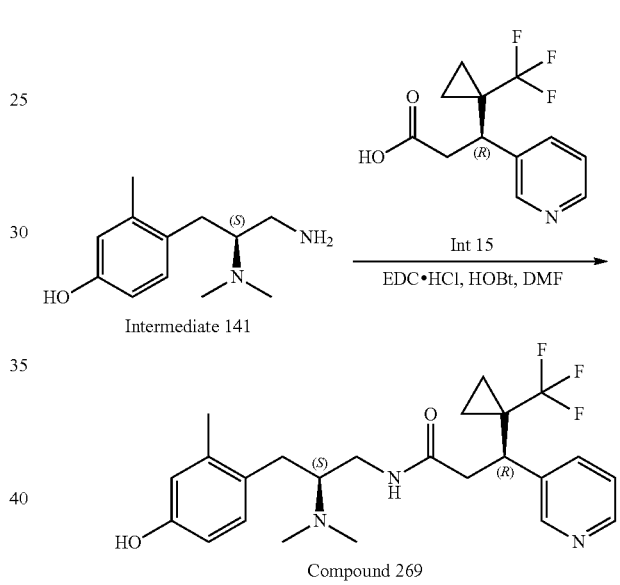

Compound 269 (20 mg, 57%) was synthesized from Int. 141 and Int. 15 as described in Example B9. MS (m/z): 450.3 (M+H).

Example B270: Preparation of N-((S)-2-(dimethylamino)-3-(4-hydroxy-2-methylphenyl)propyl)-3-(pyridin-4-yl)-3-(1-(trifluoromethyl)cyclopropyl)propanamide ("Compound 270")

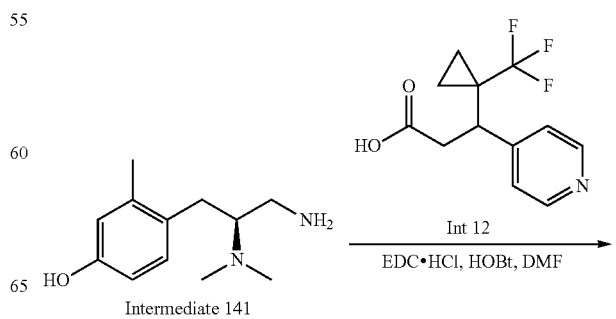

-continued

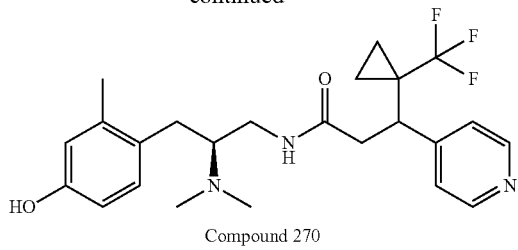

Compound 270

Compound 270 (25 mg, 59%) was synthesized from Int. 141 and Int. 12 as described in Example B9. MS (m/z): 450.3 (M+H).

Example B271: Preparation of N-((S)-2-(dimethylamino)-3-(4-hydroxy-2-methylphenyl)propyl)-3-(pyrimidin-2-yl)-3-(1-(trifluoromethyl)cyclopropyl) propanamide ("Compound 271")

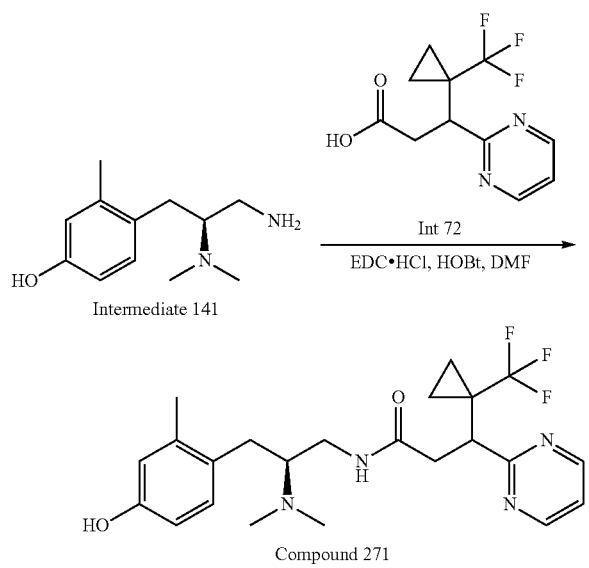

Compound 271

Compound 271 (46 mg, 87%) was synthesized from Int. 141 and Int. 72 as described in Example B9. MS (m/z): 451.2 (M+H).

Example B272: Preparation of N-((S)-2-(dimethylamino)-3-(4-hydroxy-2-methylphenyl)propyl)-3-(pyridin-3-yl)-3-(1-(trifluoromethyl)cyclopropyl) propanamide ("Compound 272")

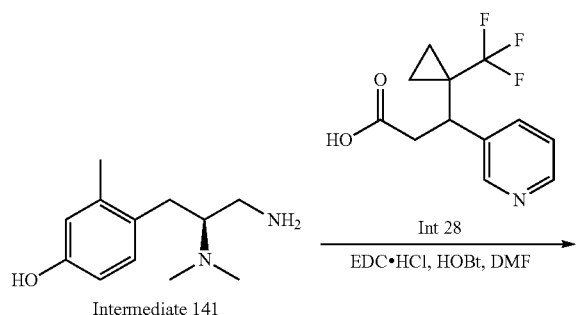

-continued

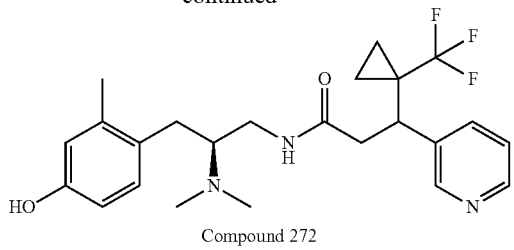

Compound 272

Compound 272 (14 mg, 67%) was synthesized from Int. 141 and Int. 28 as described in Example B9. MS (m/z): 450.2 (M+H).

Example B273: Preparation of N-((S)-2-(dimethylamino)-3-(4-hydroxy-2-methylphenyl)propyl)-3-(6-methoxypyridin-3-yl)-3-(1-(trifluoromethyl)cyclopropyl) propanamide ("Compound 273")

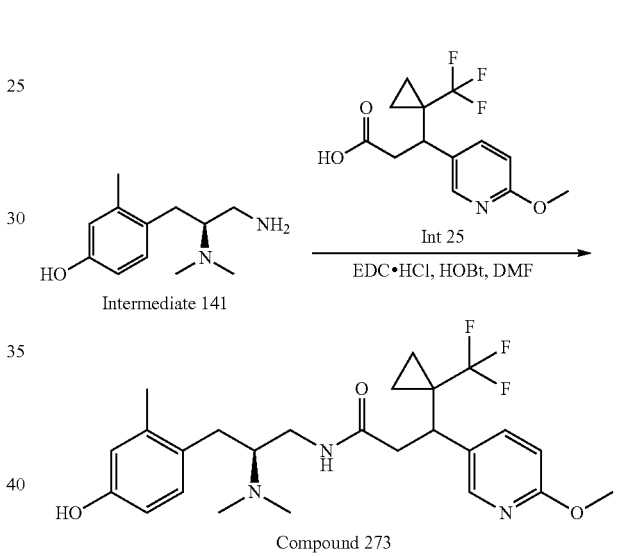

Compound 273

Compound 273 (20 mg, 67%) was synthesized from Int. 141 and Int. 25 as described in Example B9. MS (m/z): 480.2 (M+H).

Example B274: Preparation of 3-(5-chloropyridmidin-2-yl)-N-((S)-2-(dimethylamino)-3-(4-hydroxy-2-methylphenyl)propyl)-3-(1-(trifluoromethyl)cyclopropyl) propanamide ("Compound 274")

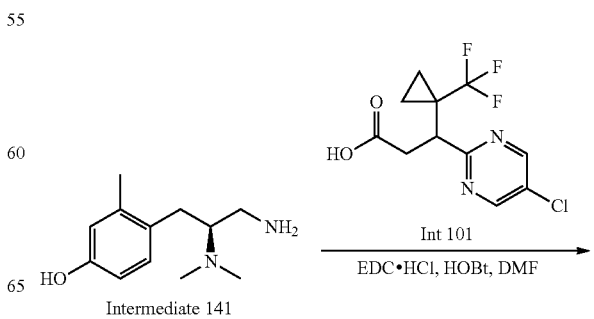

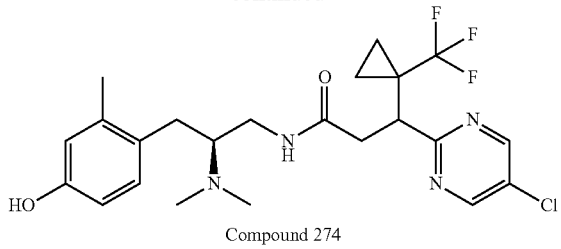
Compound 274

Compound 274 (35 mg, 72%) was synthesized from Int. 141 and Int. 101 as described in Example B9. MS (m/z): 485.2 (M+H).

Example B275: Preparation of 2-chloro-4-((S)-2-(dimethylamino)-3-((S)-3-phenylbutanamido)propyl) phenyl acetate ("Compound 275")

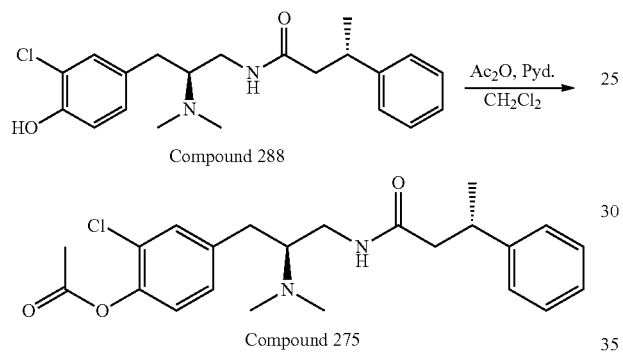

Compound 275 (500 mg, 92%) was synthesized was prepared by reacting the phenol of Compound 288 with acetic anhydride and pyridine in dichloromethane. MS (m/z): 417.2 (M+H).

Example B276: Preparation of (S)-N-((S)-3-(3-chloro-4-hydroxyphenyl)-2-(dimethylamino)propyl)-4-methyl-3-(pyridin-3-yl)pentanamide ("Compound 276")

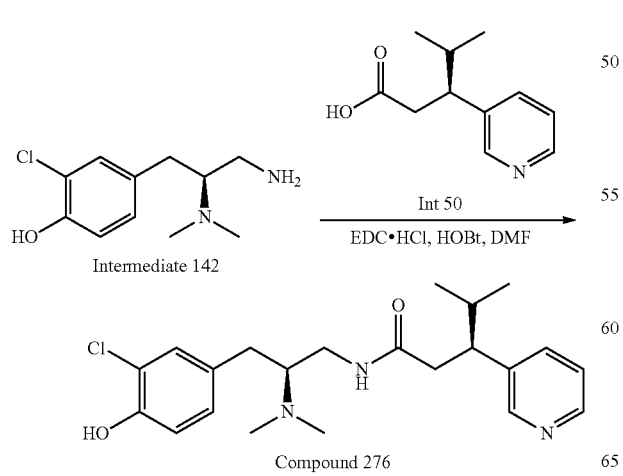

Compound 276 (15 mg, 68%) was synthesized from Int. 142 and Int. 50 as described in Example B9. MS (m/z): 404.2 (M+H).

Example B277: Preparation of (S)-N-((S)-3-(3-chloro-4-hydroxyphenyl)-2-(dimethylamino)propyl)-3-cyclopropyl-3-(pyridin-4-yl)propanamide ("Compound 277")

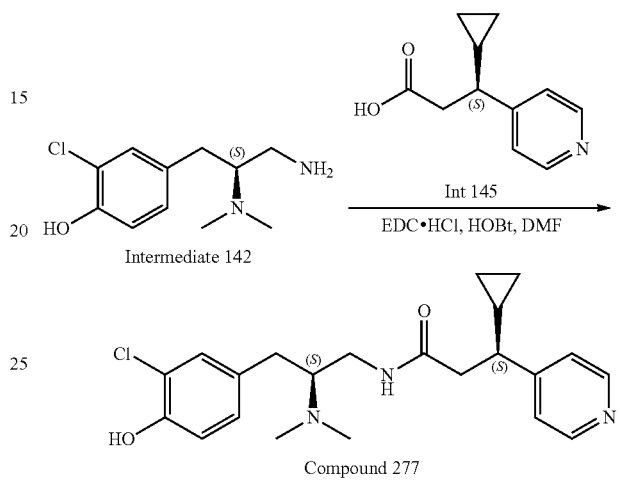

Compound 277 (16 mg, 78%) was synthesized from Int. 142 and Int. 145 as described in Example B9. MS (m/z): 402.1 (M+H).

Example B278: Preparation of (R)-N-((S)-3-(3-chloro-4-hydroxyphenyl)-2-(dimethylamino)propyl)-3-(pyridin-4-yl)-3-(1-(trifluoromethyl)cyclopropyl) propanamide ("Compound 278")

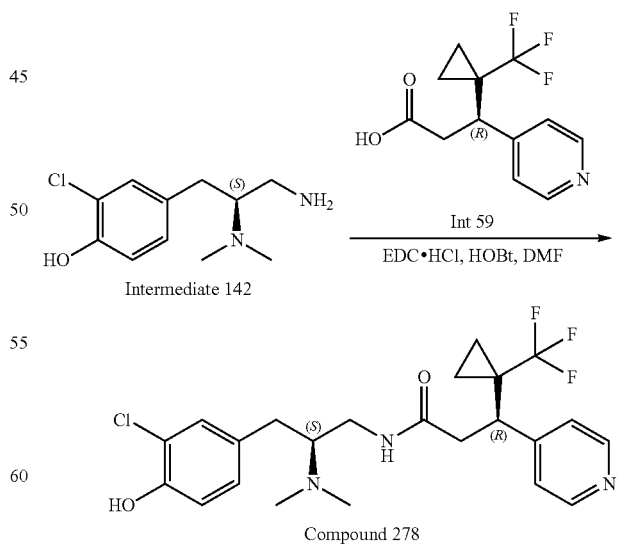

Compound 278 (28 mg, 56%) was synthesized from Int. 142 and Int. 59 as described in Example B9. MS (m/z): 470.1 (M+H).

Example B279: Preparation of (R)-N-((S)-3-(3-chloro-4-hydroxyphenyl)-2-(dimethylamino)propyl)-4-cyclopropyl-3-(pyridin-3-yl)butanamide ("Compound 279")

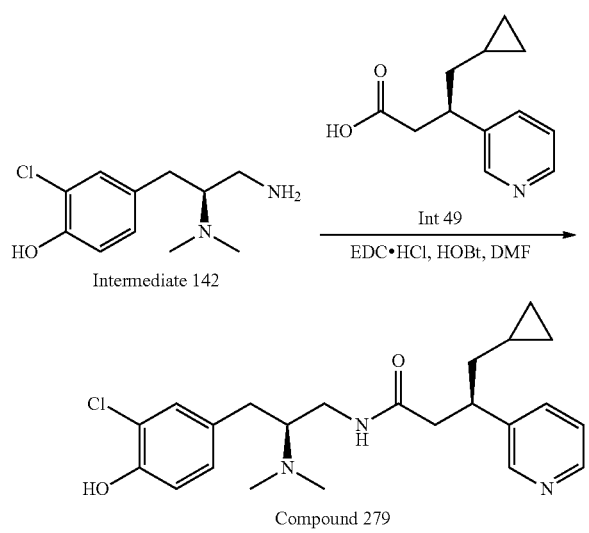

Compound 279 (27 mg, 70%) was synthesized from Int. 142 and Int. 49 as described in Example B9. MS (m/z): 416.2 (M+H).

Example B280: Preparation of N-((S)-3-(3-chloro-4-hydroxyphenyl)-2-(dimethylamino)propyl)-3-cyclopropyl-3-(5-methylpyrimidin-2-yl)propanamide ("Compound 280")

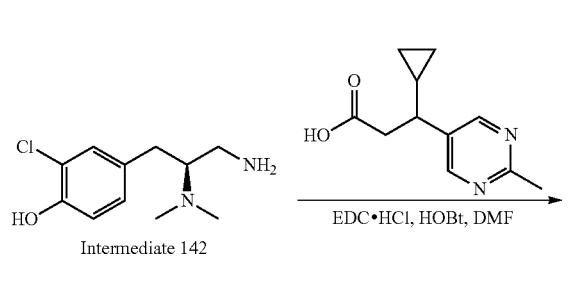

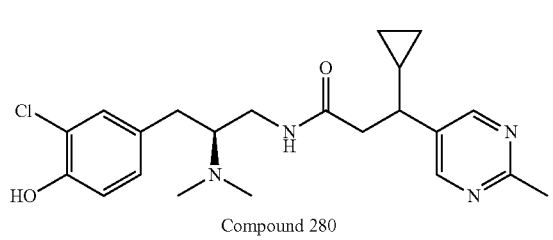

Compound 280 (19 mg, 62%) was synthesized from Int. 142 and Int. 18 (racemic) as described in Example B9. MS (m/z): 417.1 (M+H).

Example B281: Preparation of (S)-N-((S)-3-(3-chloro-4-hydroxyphenyl)-2-(dimethylamino)propyl)-3-cyclopropyl-3-(pyridin-3-yl)propanamide ("Compound 281")

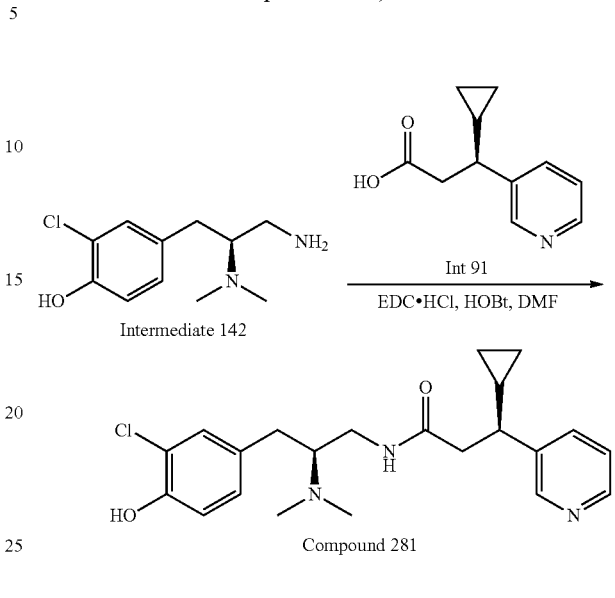

Compound 281 (10 mg, 52%) was synthesized from Int. 142 and Int. 91 as described in Example B9. MS (m/z): 402.1 (M+H).

Example B282: Preparation of (R)-N-((S)-3-(3-chloro-4-hydroxyphenyl)-2-(dimethylamino)propyl)-4-cyclopropyl-3-(pyrimidin-5-yl)butanamide ("Compound 282")

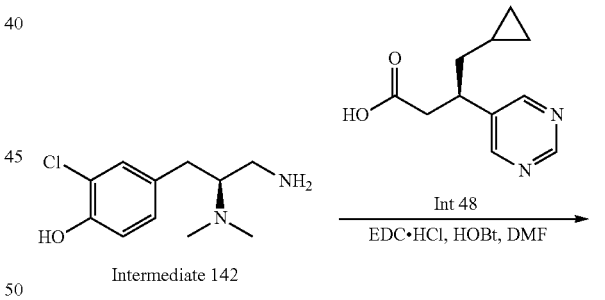

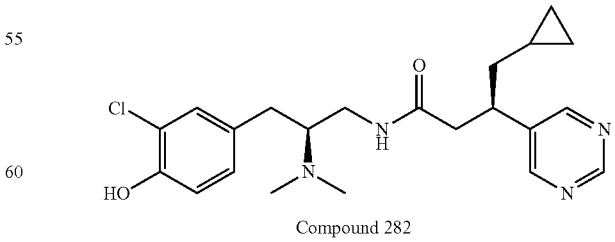

Compound 282 (19 mg, 76%) was synthesized from Int. 142 and Int. 48 as described in Example B9. MS (m/z): 417.2 (M+H).

Example B283: Preparation of (R)-N-((S)-3-(3-chloro-4-hydroxyphenyl)-2-(dimethylamino)propyl)-3-(2-methylpyrimidin-5-yl)-3-(1-(trifluoromethyl)cyclopropyl)propanamide ("Compound 283")

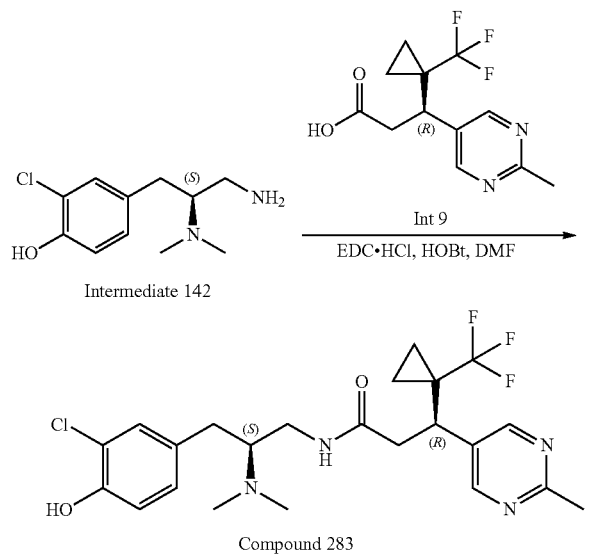

Compound 283 (22 mg, 67%) was synthesized from Int. 142 and Int. 9 as described in Example B9. MS (m/z): 485.2 (M+H).

Example B284: Preparation of N-((S)-3-(3-chloro-4-hydroxyphenyl)-2-(dimethylamino)propyl)-3-(pyridin-4-yl)-3-(1-(trifluoromethyl)cyclopropyl)propanamide ("Compound 284")

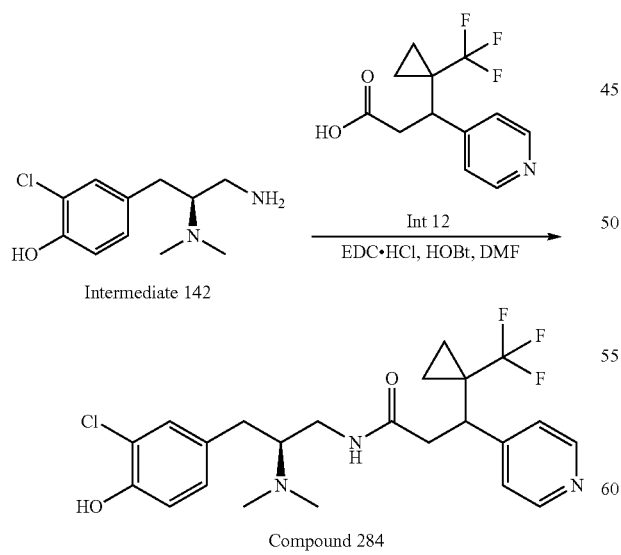

Compound 284 (18 mg, 67%) was synthesized from Int. 142 and Int. 12 as described in Example B9. MS (m/z): 470.2 (M+H).

Example B285: Preparation of N-((S)-3-(3-chloro-4-hydroxyphenyl)-2-(dimethylamino)propyl)-3-(pyrimidin-2-yl)-3-(1-(trifluoromethyl)cyclopropyl)propanamide ("Compound 285")

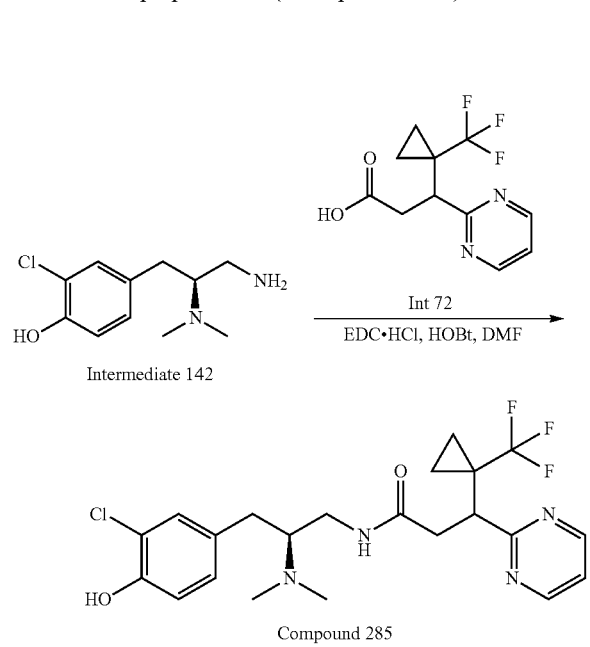

Compound 285 (18 mg, 72%) was synthesized from Int. 142 and Int. 72 as described in Example B9. MS (m/z): 471.1 (M+H).

Example B286: Preparation of (S)-N-((S)-3-(3-chloro-4-hydroxyphenyl)-2-(dimethylamino)propyl)-4-cyclopropyl-3-(pyridin-3-yl)butanamide ("Compound 286")

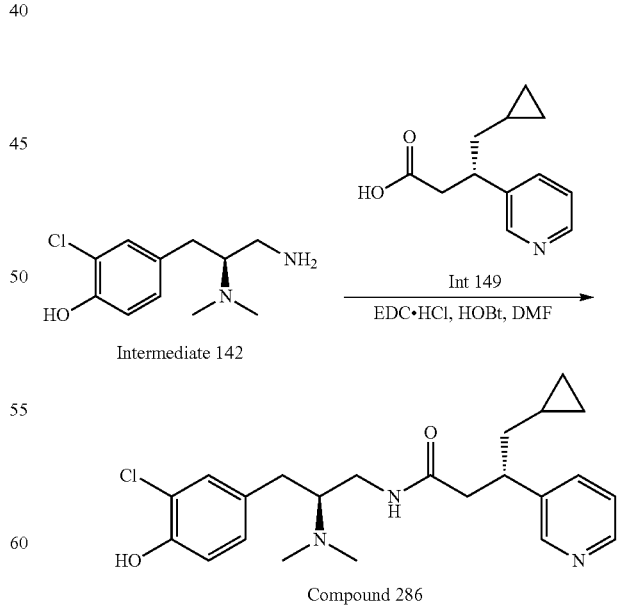

Compound 286 (20 mg, 72%) was synthesized from Int. 142 and Int. 149 as described in Example B9. MS (m/z): 416.2 (M+H).

Example B287: Preparation of N-((S)-3-(3-chloro-4-hydroxyphenyl)-2-(dimethylamino)propyl)-3-(pyridin-3-yl)-3-(1-(trifluoromethyl)cyclopropyl)propanamide ("Compound 287")

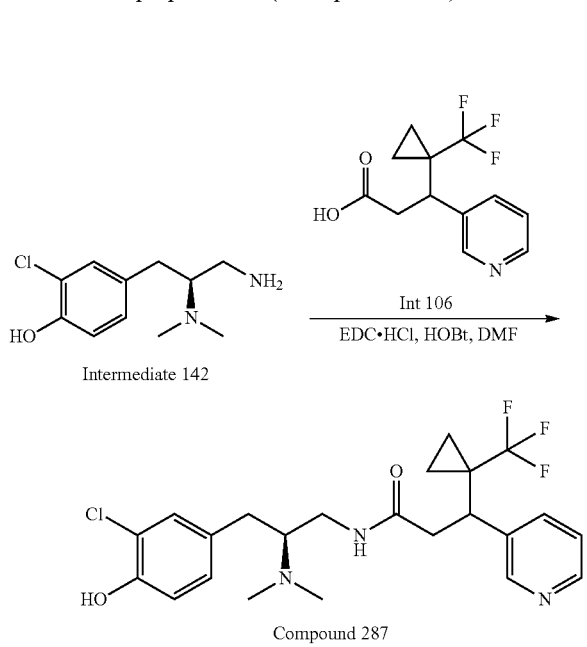

Compound 287 (28 mg, 73%) was synthesized from Int. 142 and Int. 106 as described in Example B9. MS (m/z): 470.2 (M+H).

Example B288: Preparation of (S)-N-((S)-3-(3-chloro-4-hydroxyphenyl)-2-(dimethylamino)propyl)-3-phenylbutanamide ("Compound 288")

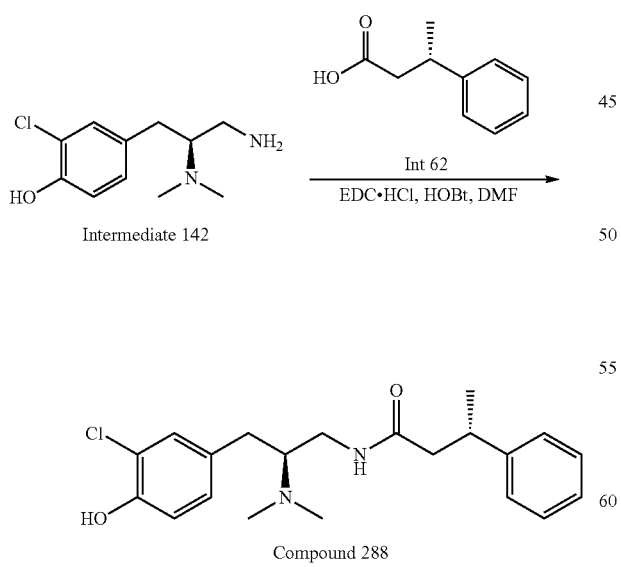

Compound 288 (480 mg, 82%) was synthesized from Int. 142 and Int. 62 as described in Example B9. MS (m/z): 375.2 (M+H).

Example B289: Preparation of (R)-N-((S)-3-(3-chloro-4-hydroxyphenyl)-2-(dimethylamino)propyl)-3-phenylbutanamide ("Compound 289")

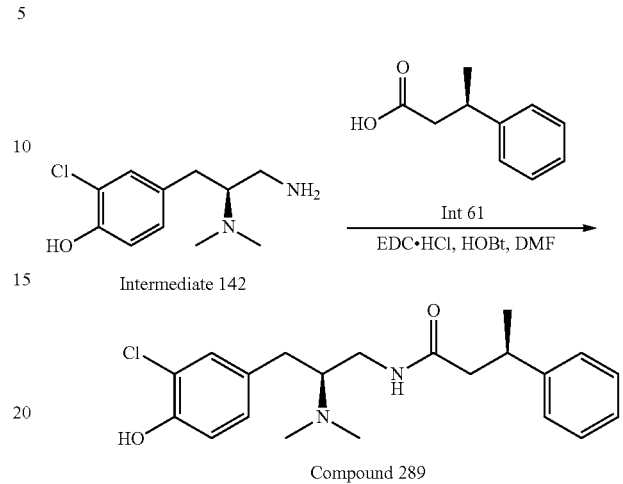

Compound 289 (52 mg, 63%) was synthesized from Int. 142 and Int. 61 as described in Example B9. MS (m/z): 375.2 (M+H).

Example B290: Preparation of (R)-N-((S)-2-(dimethylamino)-3-(3-fluoro-4-hydroxyphenyl)propyl)-3-(pyridin-3-yl)-3-(1-(trifluoromethyl)cyclopropyl)propanamide ("Compound 290")

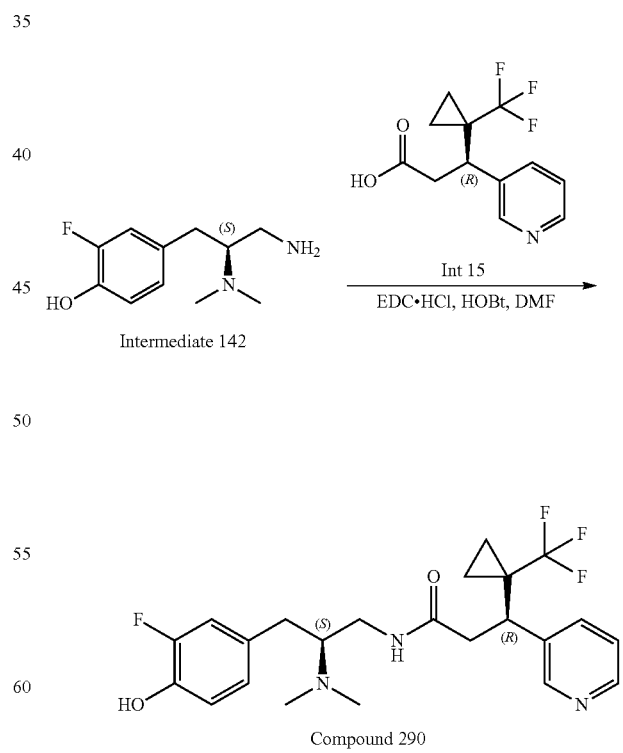

Compound 290 (40 mg, 73%) was synthesized from Int. 142 and Int. 15 as described in Example B9. MS (m/z): 454.2 (M+H).

Example B291: Preparation of N-((S)-2-(dimethylamino)-3-(4-hydroxyphenyl)propyl)-3-(pyridin-3-yl)-3-(1-(trifluoromethyl)cyclopropyl)propanamide ("Compound 291")

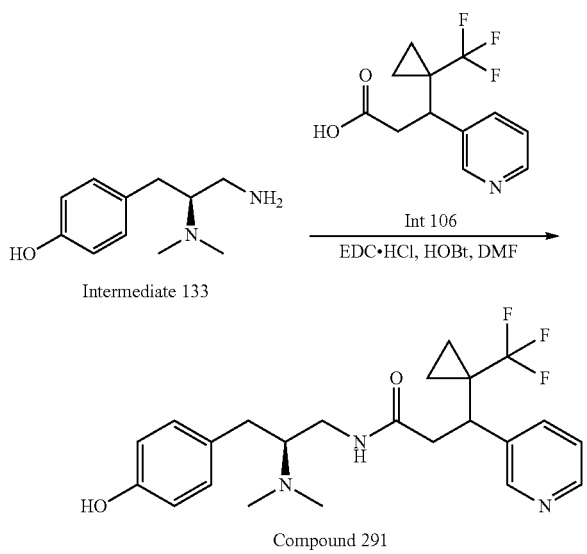

Compound 291

Compound 291 (34 mg, 72%) was synthesized from Int. 133 and Int. 106 as described in Example B9. MS (m/z): 436.2 (M+H).

Example B292: Preparation of (S)-3-cyclopropyl-N-((S)-2-(dimethylamino)-3-(4-hydroxyphenyl)propyl)-3-(thiazol-5-yl)propanamide ("Compound 292")

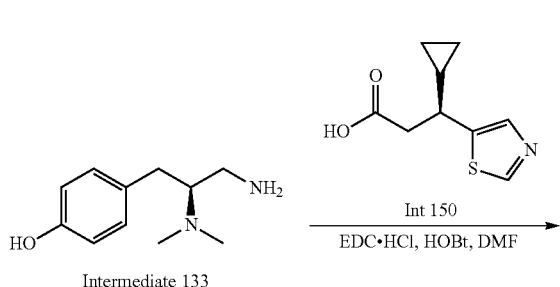

Compound 292

Compound 292 (35 mg, 70%) was synthesized from Int. 133 and Int. 150 as described in Example B9. MS (m/z): 374.3 (M+H).

Example B293: Preparation of (S)-N-((S)-2-(dimethylamino)-3-(4-hydroxyphenyl)propyl)-3-(5-methylthiophen-2-yl)-3-(1-(trifluoromethyl)cyclopropyl)propanamide ("Compound 293")

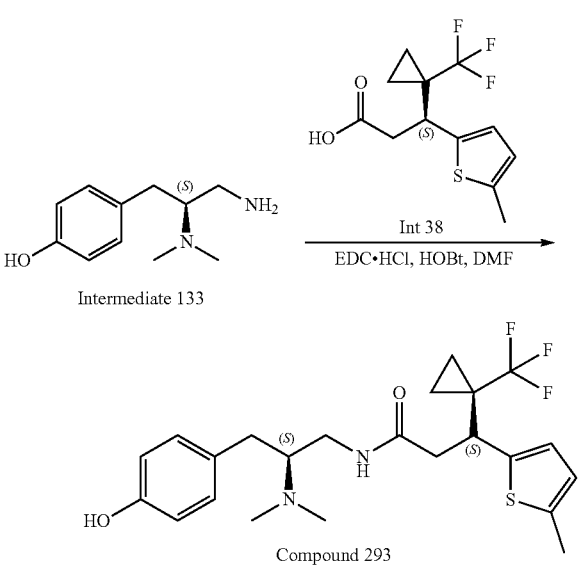

Compound 293

Compound 293 (18 mg, 75%) was synthesized from Int. 133 and Int. 38 as described in Example B9. MS (m/z): 455.2 (M+H).

Example B294: Preparation of (S)-N-((S)-2-(dimethylamino)-3-(4-hydroxyphenyl)propyl)-3-(thiophen-3-yl)-3-(1-(trifluoromethyl)cyclopropyl)propanamide ("Compound 294")

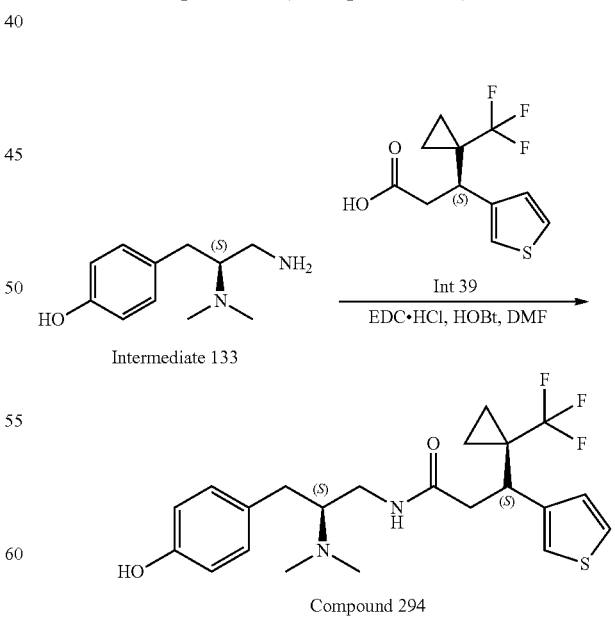

Compound 294

Compound 294 (28 mg, 70%) was synthesized from Int. 133 and Int. 39 as described in Example B9. MS (m/z): 441.2 (M+H).

Example B295: Preparation of (S)-N-((S)-2-(dimethylamino)-3-(4-hydroxy phenyl)propyl)-3-(2-methylthiazol-5-yl)-3-(1-(trifluoromethyl)cyclopropyl)propanamide ("Compound 295")

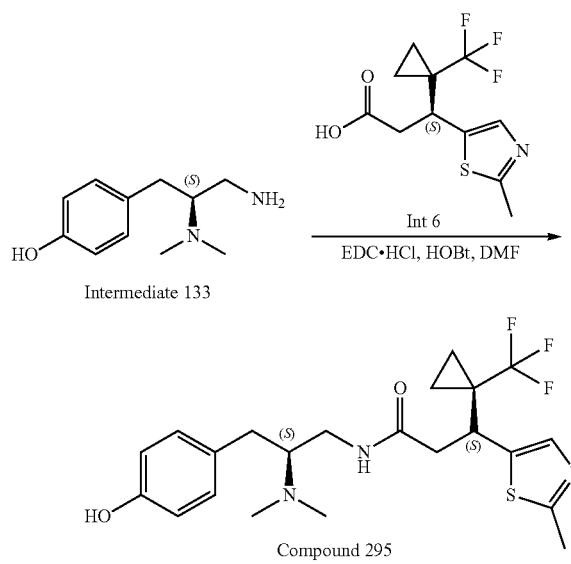

Compound 295 (27 mg, 49%) was synthesized from Int. 133 and Int. 6 as described in Example B9. MS (m/z): 456.1 (M+H).

Example B296: Preparation of (S)-N-((S)-2-(dimethylamino)-3-(4-hydroxyphenyl)propyl)-3-(thiazol-5-yl)-3-(1-(trifluoromethyl)cyclopropyl)propanamide ("Compound 296")

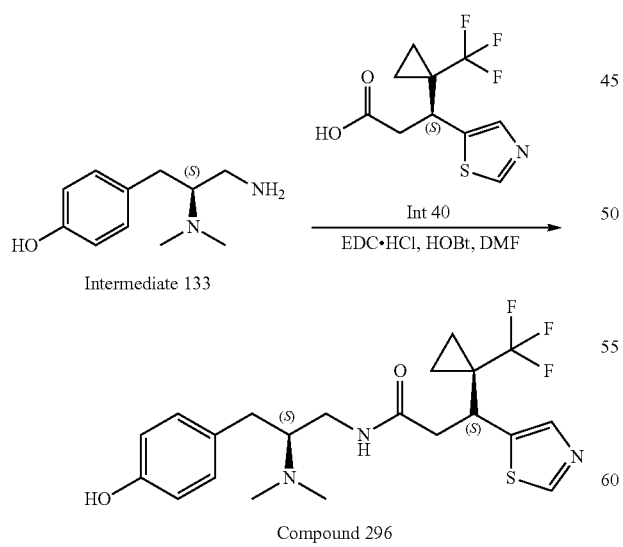

Compound 2% (34 mg, 72%) was synthesized from Int. 133 and Int. 40 as described in Example B9. MS (m/z): 442.1 (M+H).

Example B297: Preparation of (R)-N-((S)-2-(dimethylamino)-3-(4-hydroxyphenyl)propyl)-5-methyl-3-(pyridin-3-yl)hexanamide ("Compound 297")

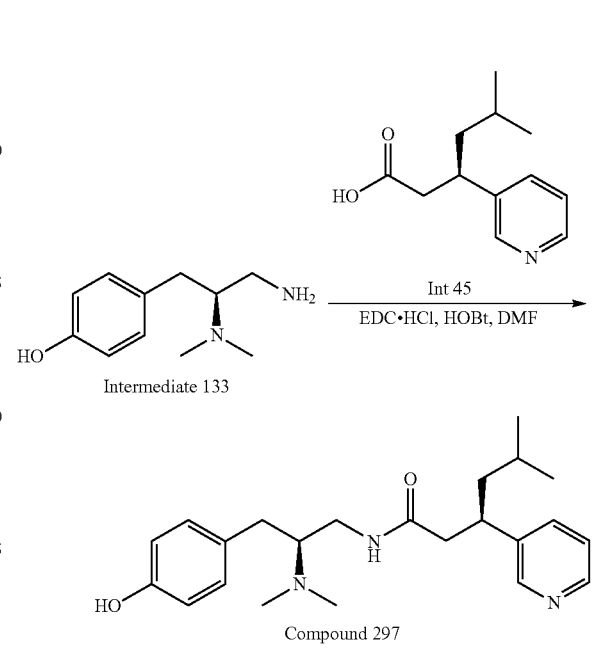

Compound 297 (28 mg, 73%) was synthesized from Int. 133 and Int. 45 as described in Example B9. MS (m/z): 384.3 (M+H).

Example B298: Preparation of (S)-4-cyclopropyl-N-((S)-2-(dimethylamino)-3-(4-hydroxyphenyl)propyl)-3-(pyridin-4-yl)butanamide ("Compound 298")

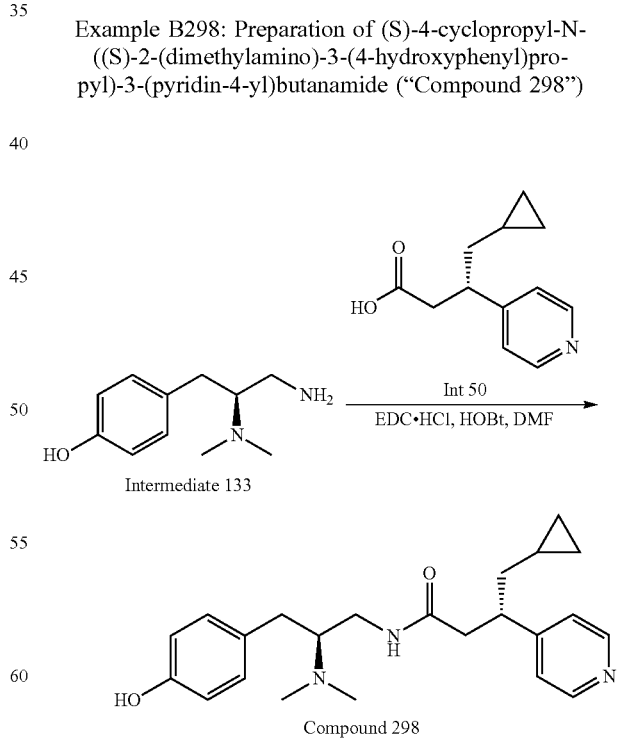

Compound 298 (28 mg, 73%) was synthesized from Int. 133 and Int. 150 as described in Example B9. MS (m/z): 382.2 (M+H).

Example B299: Preparation of (R)-N-((S)-2-(dimethylamino)-3-(4-hydroxyphenyl)propyl)-3-(2-methylpyridin-4-yl)-3-(1-(trifluoromethyl)cyclopropyl)propanamide ("Compound 299")

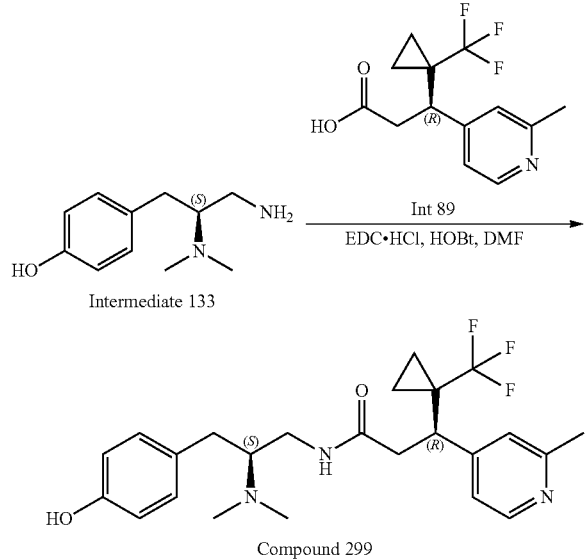

Compound 299 (30 mg, 63%) was synthesized from Int. 133 and Int. 89 as described in Example B9. MS (m/z): 450.2 (M+H).

Example B300: Preparation of (R)-N-((S)-2-(dimethylamino)-3-(4-hydroxyphenyl)propyl)-3-(5-methylpyridin-3-yl)-3-(1-(trifluoromethyl)cyclopropyl)propanamide ("Compound 300")

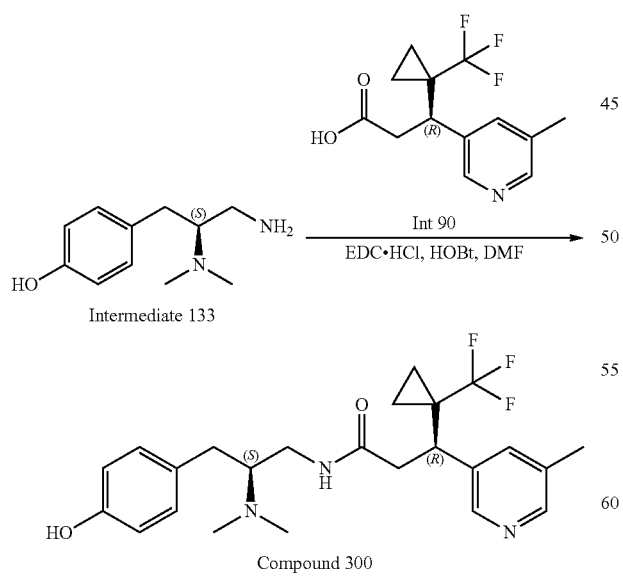

Compound 300 (28 mg, 73%) was synthesized from Int. 133 and Int. 90 as described in Example B9. MS (m/z): 450.2 (M+H).

Example B301: Preparation of (R)-N-((S)-3-(4-hydroxyphenyl)-2-methoxypropyl)-3-(pyridin-3-yl)-3-(1-(trifluoromethyl)cyclopropyl)propanamide ("Compound 301")

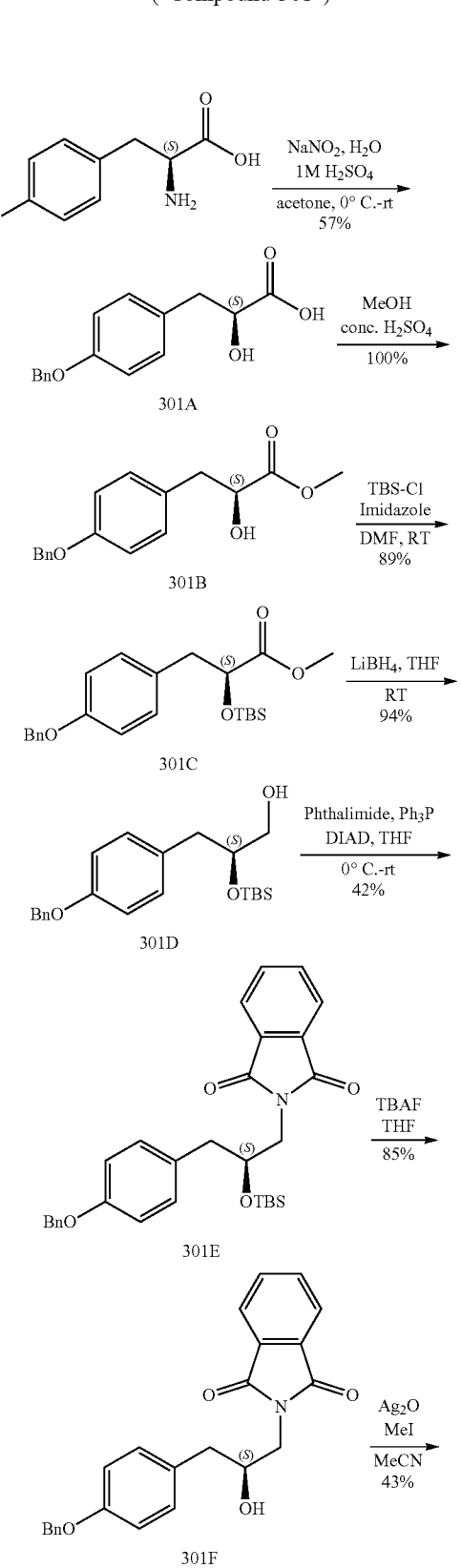

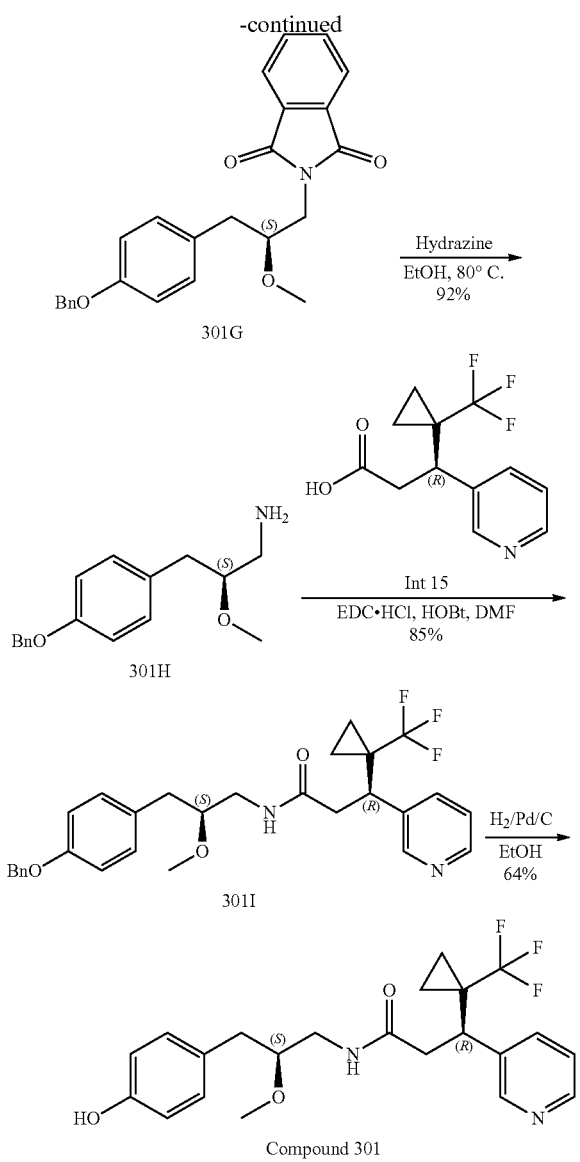

a stirred solution of methyl (S)-3-(4-(benzyloxy)phenyl)-2-hydroxypropanoate (8.05 g, 28.11 mmol) and imidazole (2.30 g, 33.73 mmol, 1.2 eq.) in DMF (50 mL) at RT was added TBS-Cl (5.08 g, 33.73 mmol). The reaction mixture was stirred at RT for 2 h. $H_2O$ was added, extracted with EtOAc (3×). The combined extracts were dried over $MgSO_4$, filtered, concentrated and purified by flash chromatography (0-20% EtOAc/Hexanes) to give 301C (10.1 g, 89%). MS (m/z): 423.2 (M+Na).

Step 4: Preparation of (S)-3-(4-(benzyloxy)phenyl)-2-((tert-butyldimethylsilyl)oxy)propan-1-ol (301 D). To a stirred solution of methyl (S)-3-(4-(benzyloxy)phenyl)-2-((tert-butyldimethylsilyl)oxy)propanoate (10.1 g. 25.21 mmol) in THF (50 mL) was added $LiBH_4$ in THF (4M, 9.5 mL, 37.81 mmol, 1.5 eq.) dropwise. The stirring was continued for 3 h, cooled in an ice bath, and slowly quenched with saturated aq. $NH_4Cl$, then diluted with $H_2O$, extracted with EtOAc (3×). The combined extracts were dried over $MgSO_4$, concentrated to give 301D (9.1 g. 94%). MS (m/z): 395.2 (M+Na).

Step 5: Preparation of (S)-2-(3-(4-(benzyloxy)phenyl)-2-((tert-butyldimethylsilyl)oxy)propyl)isoindoline-1,3-dione (301E). To a stirred mixture of phthalimide (4.31 g. 29.31 mmol, 1.2 eq.), $Ph_3P$ (7.7 g, 29.31 mmol, 1.2 eq.), and (S)-3-(4-(benzyloxy)phenyl)-2-((tert-butyldimethylsilyl) oxy)propan-1-ol (9.1 g, 24.42 mmol, 1 eq.) in THF (100 mL) at 0° C. was added DIAD (5.9 g, 29.31 mmol, 1.2 eq.) dropwise. After the addition was completed, the reaction mixture was stirred at RT in 16 h. The mixture was then concentrated to dryness and purified by flash chromatography (0-50% EtOAc/Hexanes) to give 301E (5.15 g, 42%). MS (m/z). 502.2 (M+H).

Step 6: Preparation of (S)-2-(3-(4-(benzyloxy)phenyl)-2-hydroxypropyl)isoindoline-1,3-dione 301F). To a stirred solution of (S)-2-(3-(4-(benzyloxy)phenyl)-2-((tert-butyldimethylsilyl)oxy)propyl)isoindoline-1,3-dione (2.5 g, 4.99 mmol) in THF (30 mL) at RT was added TBAF (1M in THF, 7.5 mL, 7.48 mmol, 1.5 eq.). The stirring was continued for 2 h at RT, $H_2O$ was added, extracted with EtOAc (3×). The combined extracts were dried over $MgSO_4$, concentrated, and purified by flash chromatography (0-50% EtOAc/DCM) to give 301F (1.64, 85%). MS (m/z): 388.1 (M+H).

Step 7: Preparation of (S)-2-(3-(4-(benzyloxy)phenyl)-2-methoxypropyl)isoindoline-1,3-dione (301G). To a stirred mixture of 2-[(2S)-3-[4-(benzyloxy)phenyl]-2-hydroxypropyl]-2,3-dihydro-1H-isoindole-1,3-dione (713 mg, 1.84 mmol) and silver oxide (2.15 g, 5 eq., 9.20 mmol) in MeCN (7 mL) was added iodomethane (573 μL, 5 eq., 9.20 mmol). The mixture was then stirred at rt for 72 h. The solid was removed through a pad of Celite. The filtrate was concentrated to dryness and purified by flash chromatography (0-20% EtOAc/DCM) to give 301G (320 mg, 43%). MS (m/z): 402.2 (M+H).

Step 8: Preparation of (2S)-3-[4-(benzyloxy)phenyl]-2-methoxypropan-1-amine (301H). To a stirred solution of 2-[(2S)-3-[4-(benzyloxy)phenyl]-2-methoxypropyl]-2,3-dihydro-1H-isoindole-1,3-dione (320 mg, 797 μmol) in EtOH (6 mL) was added hydrazine (255 mg, 5 eq., 3.99 mmol). The reaction mixture was stirred at 80° C. for 2 h, cooled to RT, filtered off the solid. The solid was rinsed with EtOAc. The filtrate was concentrated to dryness, then purified by flash chromatography (0-15% MeOH/DCM in 1% $NH_4OH$) to give 301H (179 mg, 82%).

Step 9: Preparation of (R)-N-((S)-3-(4-(benzyloxy)phenyl)-2-methoxypropyl)-3-(pyridin-3-yl)-3-(1-(trifluoromethyl)cyclopropyl)propanamide (301I). A mixture of (2S)-3-[4-(benzyloxy)phenyl]-2-methoxypropan-1-amine (45.0

Step 1: Preparation of (S)-3-(4-(benzyloxy)phenyl)-2-hydroxypropanoic acid (301A). To a stirred mixture of acetone/$H_2O$ (2:1, 150 mL) at RT was added (S)-2-amino-3-(4-(benzyloxy)phenyl)propanoic acid (13 g, 47.91 mmol) in several portions. After the addition was completed, the mixture was stirred at 0° C., then a solution of $NaNO_2$ (9.92 g, 143.75 mmol, 3 eq.) in $H_2O$ (20 mL) was added dropwise. After the addition was completed, the reaction mixture was stirred at RT for 16 h, extracted with EtOAc (3×). The extracts were dried over $MgSO_4$, concentrated to dryness, triturated with toluene. The precipitated solid was collected by filtration, dried to give 301A (7.5 g, 57%). MS (m/z): 295.1 (M+Na).

Step 2: Preparation of methyl (S)-3-(4-(benzyloxy)phenyl)-2-hydroxypropanoate (301B). To a stirred solution of (S)-3-(4-(benzyloxy)phenyl)-2-hydroxypropanoic acid (7.5 g, 27.55 mmol) in MeOH (100 mL) was added 1 mL of conc. $H_2SO_4$. The reaction mixture was then heated to reflux for 3 h, cooled to RT, concentrated to dryness to give 301B (8.05 g, 100%). MS (m/z): 309.1 (M+Na).

Step 3: Preparation of methyl (S)-3-(4-(benzyloxy)phenyl)-2-((tert-butyldimethylsilyl)oxy)propanoate (301C). To mg, 166 µmol), (3S)-3-(pyridin-3-yl)-3-[1-(trifluoromethyl) cyclopropyl]propanoic acid (43.0 mg, 166 µmol), HOBT (11.2 mg, 0.5 eq., 82.9 µmol), EDC HCl (38.1 mg, 1.2 eq., 199 µmol), and DIEA (44.0 µL, 1.5 eq., 249 µmol) in DMF (1 mL) was stirred at RT for 16 h. H₂O was added, extracted with EtOAc (3×). The combined extracts were dried over MgSO₄, concentrated to dryness to give 3011 (73.0 mg, 85%) which was used directly to the next step without further purification. MS (m/z): 513.2 (M+H).

Step 10: Preparation of (R)-N-((S)-3-(4-hydroxyphenyl)-2-methoxypropyl)-3-(pyridin-3-yl)-3-(1-(trifluoromethyl) cyclopropyl)propanamide (Compound 301). A solution of (3S)-N-[(2S)-3-[4-(benzyloxy)phenyl]-2-methoxypropyl]-3-(pyridin-3-yl)-3-[1-(trifluoromethyl)cyclopropyl]propanamide (73.0 mg, 142 µmol) in EtOH (5 mL) was hydrogenated in 10% palladium (30.3 mg, 0.2 eq., 28.5 µmol) at RT for 16 h. The catalyst was removed through a pad of celite, washed carefully with EtOAc. The filtrate was concentrated to dryness, and purified by flash chromatography (0-10% MeOH/DCM) to give Compound 301 (39.0 mg, 64%). MS (m/z): 423.2 (M+H).

Example B302: Preparation of (R)-N-((S)-2-(dimethylamino)-3-(4-hydroxyphenyl)propyl)-3-(6-methylpyridin-3-yl)-3-(1-(trifluoromethyl)cyclopropyl) propanamide ("Compound 302")

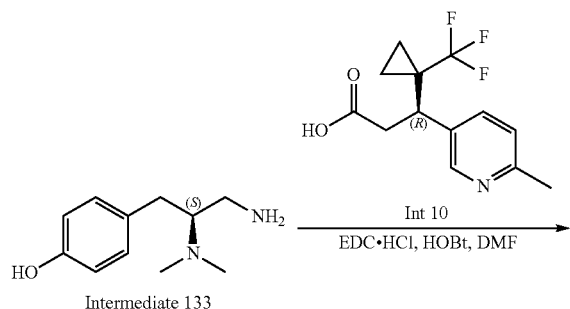

Compound 302

Compound 302 (39 mg, 79%) was synthesized from Int. 133 and Int. 302 as described in Example B9. MS (m/z): 450.3 (M+H).

Example B303: Preparation of (S)-N-((S)-2-(dimethylamino)-3-(4-hydroxyphenyl) propyl)-3-(1-methylcyclopropyl)-3-(pyridin-3-yl)propanamide ("Compound 303")

Compound 303

Compound 303 (25 mg, 53%) was synthesized from Int. 133 and Int. 77 as described in Example B9. MS (m/z): 382.2 (M+H).

Example B304: Preparation of (S)-N-((S)-2-(dimethylamino)-3-(4-hydroxyphenyl)propyl)-4-methyl-3-(pyridin-3-yl)pentanamide ("Compound 304")

Compound 304

Compound 304 (39 mg, 79%) was synthesized from Int. 133 and Int. 50 as described in Example B9. MS (m/z): 370.2 (M+H).

Example B305: Preparation of N-((S)-2-hydroxy-3-(4-hydroxyphenyl)propyl)-3-(pyridin-4-yl)-3-(1-(trifluoromethyl)cyclopropyl)propanamide ("Compound 305")

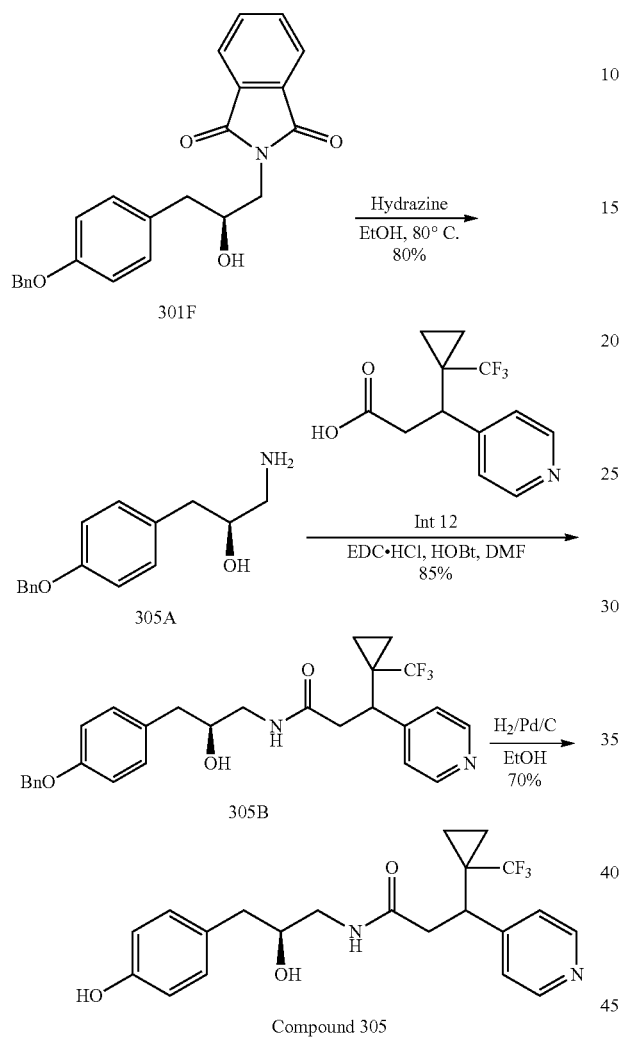

Step 1: Preparation of (S)-1-amino-3-(4-(benzyloxy)phenyl)propan-2-ol (305A). 305A (175 mg, 80%) was synthesized from Int. 301F as described in Example B310 Step 8. MS (m/z): 258.1 (M+H).

Step 2: Preparation of N-((S)-3-(4-(benzyloxy)phenyl)-2-hydroxypropyl)-3-(pyridin-4-yl)-3-(1-(trifluoromethyl)cyclopropyl)propenamide (305B). 305B (275 mg, 81%) was synthesized from Int. 305A and Int. 12 as described in Example B9. MS (m/z): 499.2 (M+H).

Step 3: Preparation of N-((S)-2-hydroxy-3-(4-hydroxyphenyl)propyl)-3-(pyridin-4-yl)-3-(1-(trifluoromethyl)cyclopropyl)propenamide (Compound 305). A solution of 305B (48.8 mg, 97.9 µmol) in EtOH (5 mL) was hydrogenated at RT in 10% palladium (20.8 mg, 0.2 eq., 19.6 µmol) for 16 h. The catalyst was filtered off through a pad of celite, washed with EtOH. The filtrate was concentrated to dryness, purified by flash chromatography (4% MeOH/DCM) to give Compound 305 (28.1 mg, 70%). MS (m/z): 409.2 (M+H).

Example B306: Preparation of (R)-N-((S)-2-(dimethylamino)-3-(4-hydroxyphenyl)propyl)-3-(pyridin-3-yl)-3-(1-(trifluoromethyl)cyclopropyl)propanamide ("Compound 306")

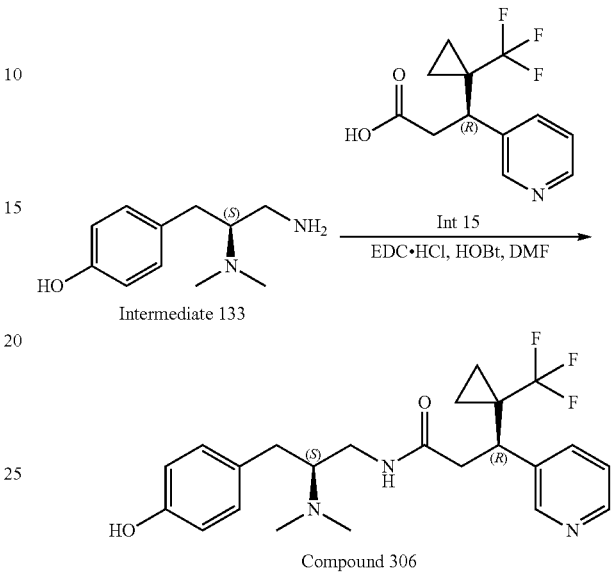

Compound 306 (292 mg, 73%) was synthesized from Int. 133 and Int. 15 as described in Example B9. MS (m/z): 436.2 (M+H).

Example B307: Preparation of (R)-4-cyclopropyl-N-((S)-2-(dimethylamino)-3-(4-hydroxyphenyl)propyl)-3-(pyrimidin-5-yl)butanamide ("Compound 307")

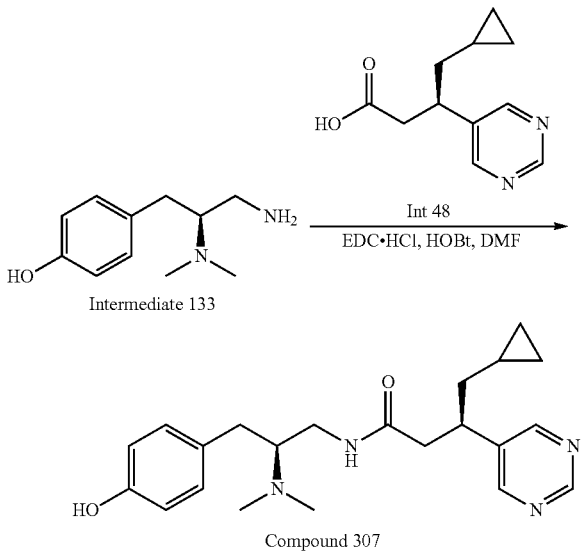 [SMILES: O=C(O)C[C@@H](CC1CC1)c1cncnc1 ; CN(C)[C@H](CN)Cc1ccc(O)cc1 ; CN(C)[C@H](CNC(=O)C[C@@H](CC1CC1)c1cncnc1)Cc1ccc(O)cc1]

Compound 307 (292 mg, 73%) was synthesized from Int. 133 and Int. 48 as described in Example B9. MS (m/z): 383.2 (M+H).

Example B308: Preparation of (S)-3-cyclopropyl-N-((S)-2-(dimethylamino)-3-(4-hydroxyphenyl)propyl)-3-(pyridin-3-yl)propanamide ("Compound 308")

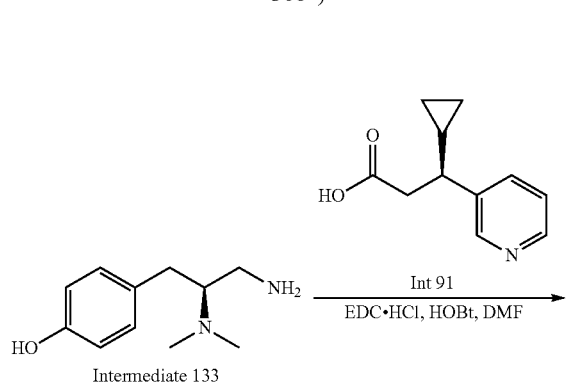

Compound 308

Compound 308 (292 mg, 73%) was synthesized from Int. 133 and Int. 91 as described in Example B9. MS (m/z): 368.2 (M+H).

Example B309: Preparation of N-((S)-2-(dimethylamino)-3-(4-hydroxyphenyl) propyl)-3-(pyridin-4-yl)-3-(1-(trifluoromethyl)cyclopropyl)propanamide ("Compound 309")

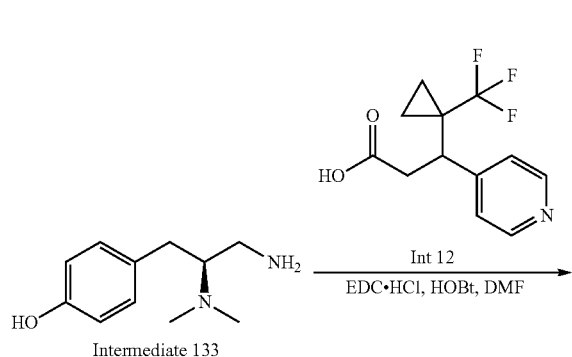

Compound 309

Compound 309 (34 mg, 74%) was synthesized from Int. 133 and Int. 12 as described in Example B9. MS (m/z): 436.2 (M+H).

Example B310: Preparation of (R)-4-cyclopropyl-N-((S)-2-(dimethylamino)-3-(4-hydroxyphenyl)propyl)-3-(pyridin-3-yl)butanamide ("Compound 310")

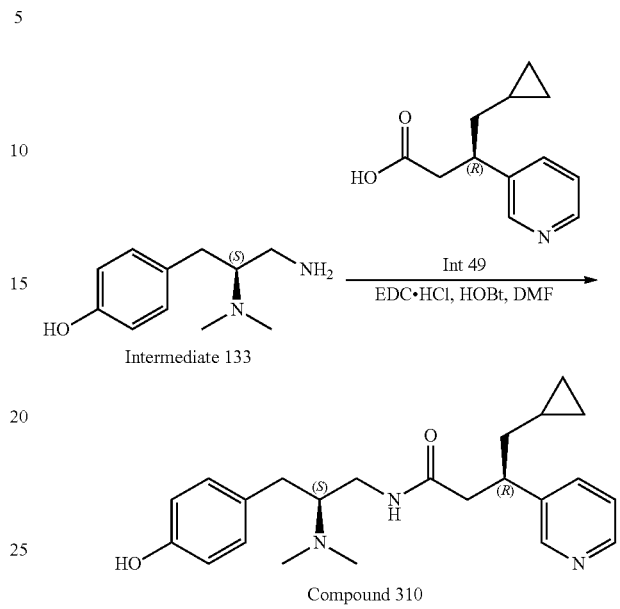

Compound 310

Compound 310 (12 mg, 50%) was synthesized from Int. 133 and Int. 49 as described in Example B9. MS (m/z): 382.2 (M+H).

Example B311: Preparation of (S)-3-cyclopropyl-N-((S)-2-(dimethylamino)-3-(4-hydroxyphenyl)propyl)-3-(2-methylpyrimidin-5-yl)propanamide ("Compound 311")

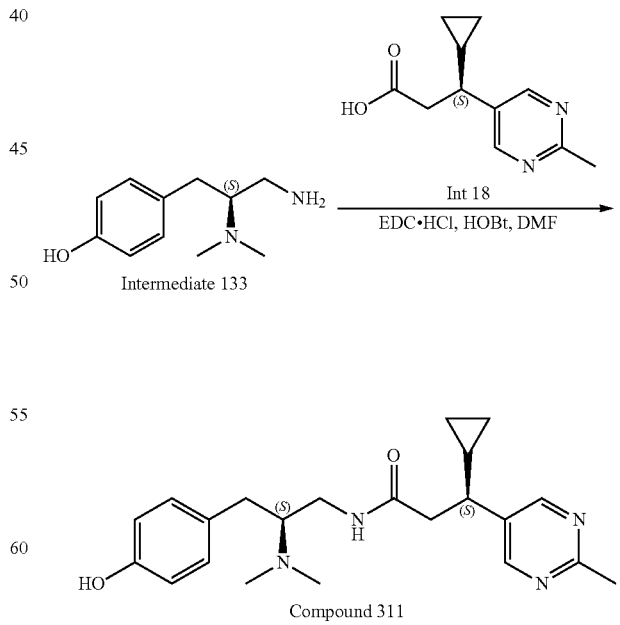

Compound 311

Compound 311 (34 mg, 59%) was synthesized from Int. 133 and Int. 18 as described in Example B9. MS (m/z): 383.3 (M+H).

Example B312: Preparation of (R)-N-((S)-2-(dimethylamino)-3-(4-hydroxyphenyl) propyl)-3-(2-methylpyrimidin-5-yl)-3-(1-(trifluoromethyl)cyclopropyl)propanamide ("Compound 312")

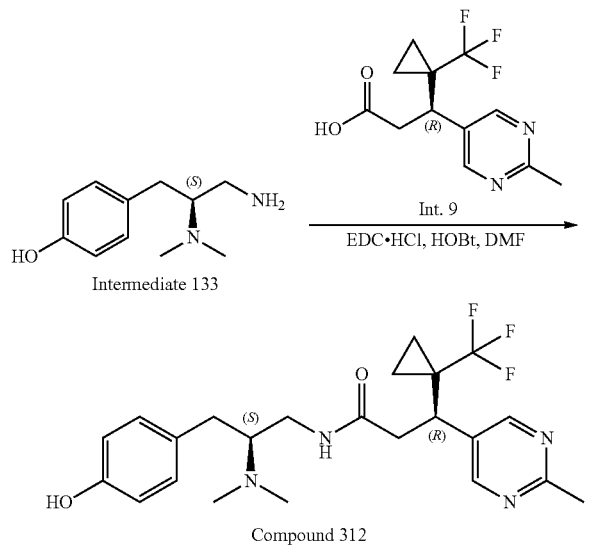

Compound 312 (12.1 mg, 26%) was synthesized from Int. 133 and Int. 9 as described in Example B9. MS (m/z): 451.3 (M+H).

Example B313: Preparation of N-((S)-2-(dimethylamino)-3-(4-hydroxyphenyl)propyl)-3-(pyrimidin-2-yl)-3-(1-(trifluoromethyl)cyclopropyl)propanamide ("Compound 313")

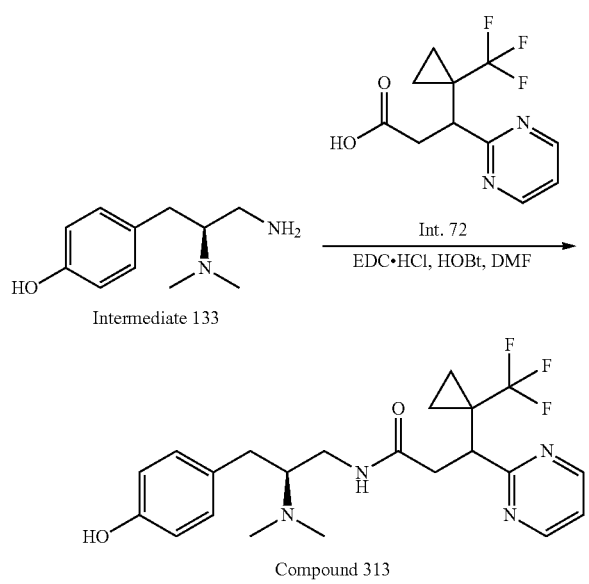

Compound 313 (34 mg, 59%) was synthesized from Int. 133 and Int. 72 as described in Example B9. MS (m/z): 437.2 (M+H).

Example B314: Preparation of N-((S)-2-(dimethylamino)-3-(4-hydroxyphenyl) propyl)-3-(1-(trifluoromethyl)cyclopropyl)-3-(6-(trifluoromethyl)pyridin-3-yl)propanamide ("Compound 314")

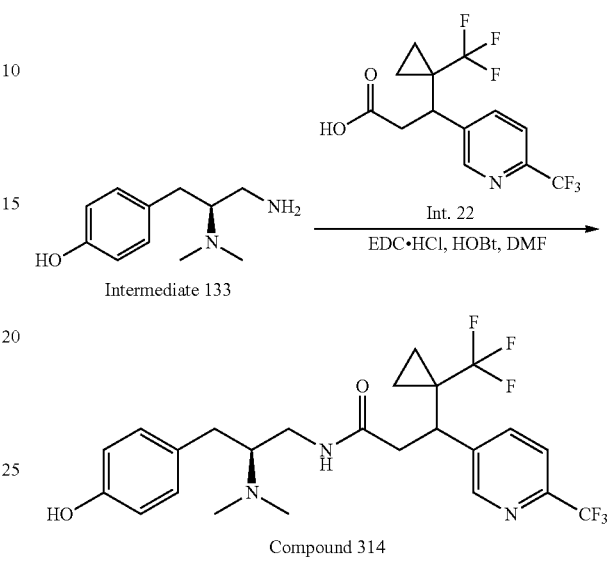

Compound 314 (17.5 mg, 37%) was synthesized from Int. 133 and Int. 22 as described in Example B9. MS (m/z): 504.2 (M+H).

Example B315: Preparation of N-((S)-2-(dimethylamino)-3-(4-hydroxyphenyl) propyl)-3-(1-(trifluoromethyl)cyclopropyl)-3-(6-(trifluoromethyl)pyridin-3-yl)propanamide ("Compound 315")

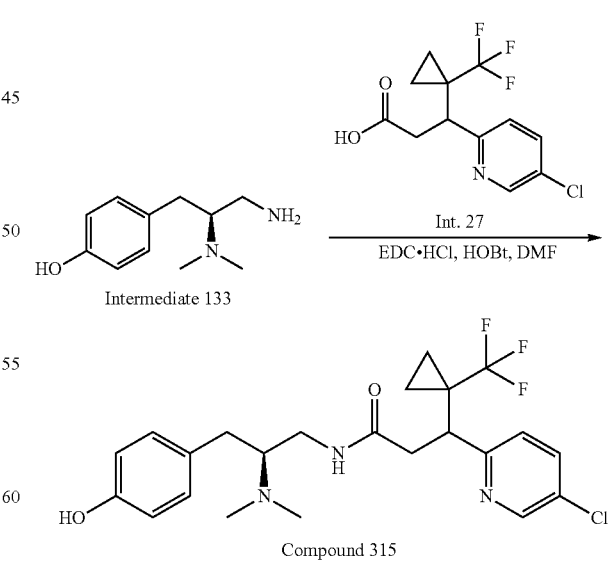

Compound 315 (9 mg, 28%) was synthesized from Int. 133 and Int. 27 as described in Example B9. MS (m/z): 470.2 (M+H).

Example B316: Preparation of N-((S)-2-(dimethylamino)-3-(4-hydroxy-2,6-dimethylphenyl)propyl)-3-(pyridin-3-yl)-3-(1-(trifluoromethyl)cyclopropyl)propanamide ("Compound 316")

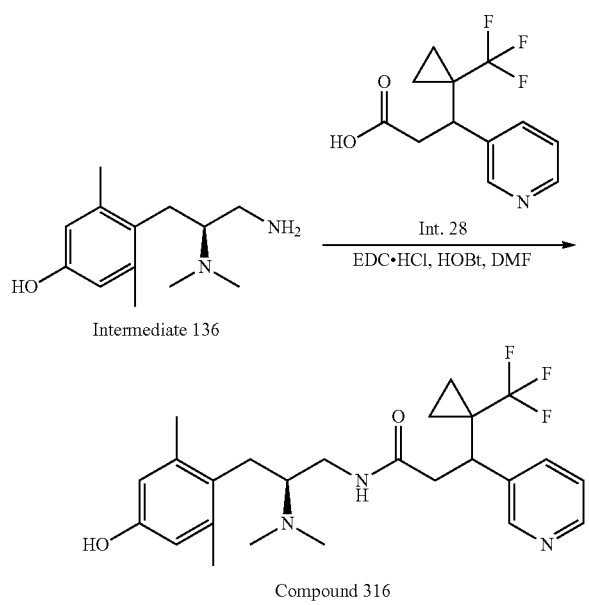

Compound 316

Compound 316 (22 mg, 43%) was synthesized from Int. 133 and Int. 28 as described in Example B9. MS (m/z): 464.2 (M+H).

Example B317: Preparation of (S)-N-(2-(dimethylamino)-3-(4-hydroxy-2,6-dimethylphenyl)propyl)-3-methyl-3-phenylbutanamide ("Compound 317")

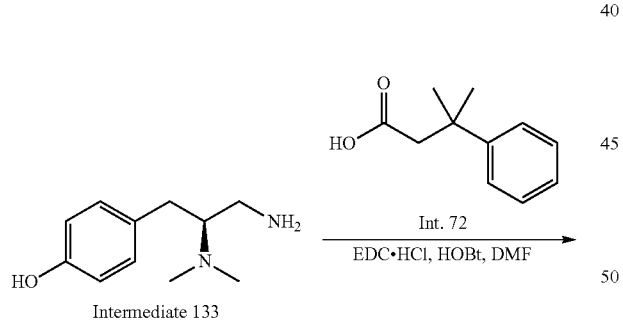

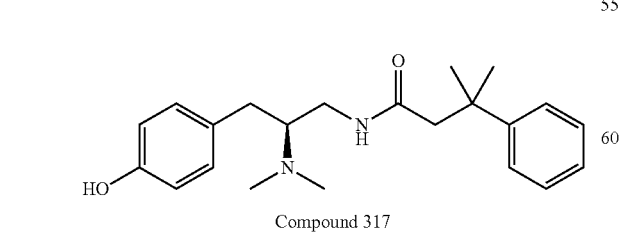

Compound 317

Compound 317 (39 mg, 69%) was synthesized from Int. 133 as described in Example B9. MS (m/z): 355.4 (M+H).

Example B318: Preparation of (R)-3-cyclopropyl-N-((S)-2-(dimethylamino)-3-(4-hydroxyphenyl)propyl)-3-phenylpropanamide ("Compound 318")

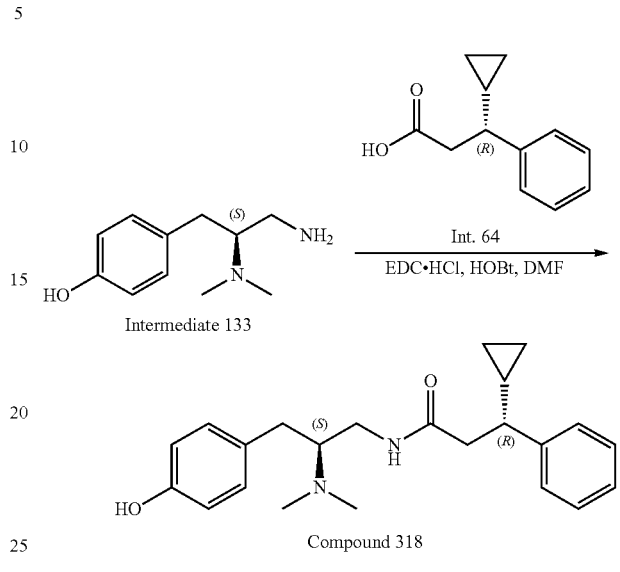

Compound 318

Compound 318 (678 mg, 80%) was synthesized from Int. 133 and Int. 64 as described in Example B9. MS (m/z): 367.2 (M+H).

Example B319: Preparation of (S)-3-cyclopropyl-N-((S)-2-(dimethylamino)-3-(4-hydroxyphenyl)propyl)-3-phenylpropanamide ("Compound 319")

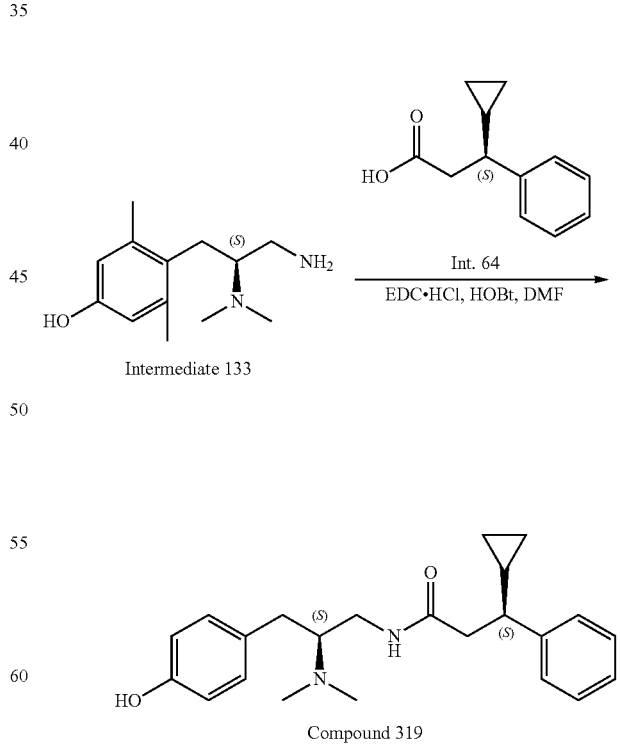

Compound 319

Compound 319 (510 mg, 75%) was synthesized from Int. 133 and Int. 63 as described in Example B9. MS (m/z): 367.5 (M+H).

Example B320: Preparation of (R)-N-((S)-2-(dimethylamino)-3-(4-hydroxyphenyl)propyl)-3-phenylbutanamide ("Compound 320")

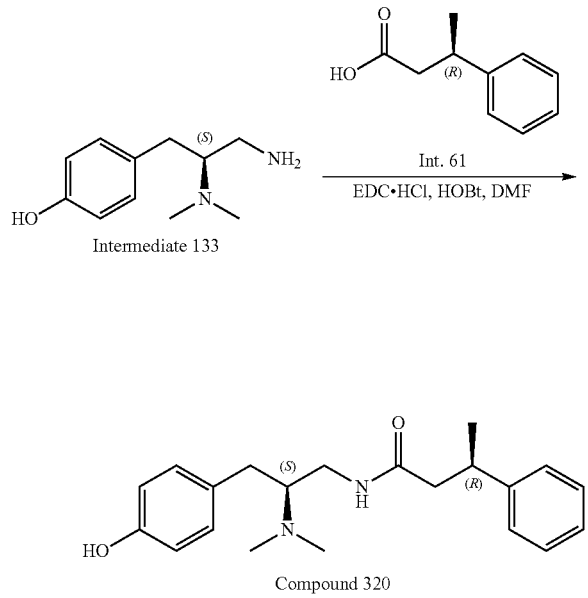

Compound 320 (39 mg, 70%) was synthesized from Int. 133 and Int. 61 as described in Example B9. MS (m/z): 341.2 (M+H).

Example B321: Preparation of (S)-N-((S)-2-(dimethylamino)-3-(4-hydroxyphenyl)propyl)-3-phenylbutanamide ("Compound 321")

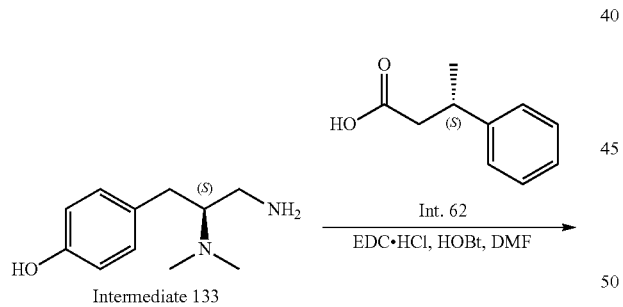

Compound 321 (104 mg, 69%) was synthesized from Int. 133 and Int. 62 as described in Example B9. MS (m/z): 341.2 (M+H).

Example B322: Preparation of (S)-N-((S)-2-(dimethylamino)-3-(4-hydroxyphenyl)propyl)-3-(5-methylthiophen-3-yl)-3-(1-(trifluoromethyl)cyclopropyl)propanamide ("Compound 322")

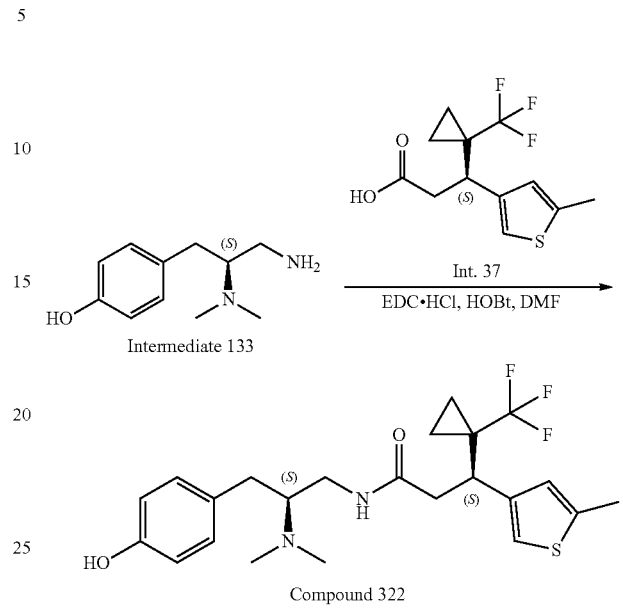

Compound 322 (22 mg, 46%) was synthesized from Int. 136 and Int. 37 as described in Example B9. MS (m/z): 455.1 (M+H).

Example B323: Preparation of (S)-N-(((S)-7-hydroxy-2-methyl-1,2,3,4-tetrahydroisoquinolin-3-yl)methyl)-4,4-dimethyl-3-phenylpentanamide ("Compound 323")

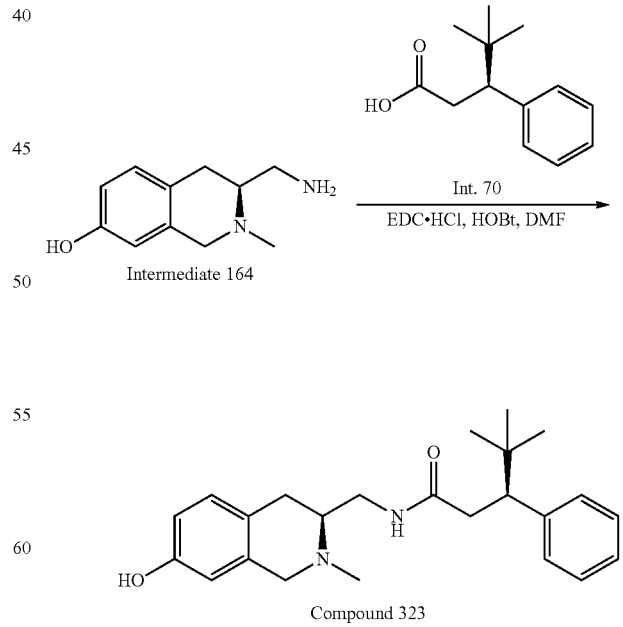

Compound 323 (22 mg, 49%) was synthesized from Int. 144 and Int. 70 as described in Example B9. MS (m/z): 381.2 (M+H).

Example B324: Preparation of (S)-N-(((S)-7-hydroxy-2-methyl-1,2,3,4-tetrahydroisoquinolin-3-yl)methyl)-3-phenylbutanamide ("Compound 324")

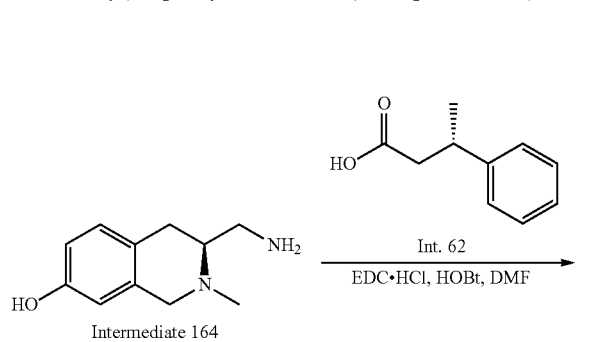

Compound 324 was synthesized from Int. 144 and Int. 62 as described in Example B9. MS (m/z): 339.2 (M+H).

Example B325: Preparation of (S)-N-((S)-3-(4-(4H-1,2,4-triazol-3-yl)phenyl)-2-(dimethylamino)propyl)-3-(5-methylthiazol-2-yl)-3-(1-(trifluoromethyl)cyclopropyl) propanamide ("Compound 325")

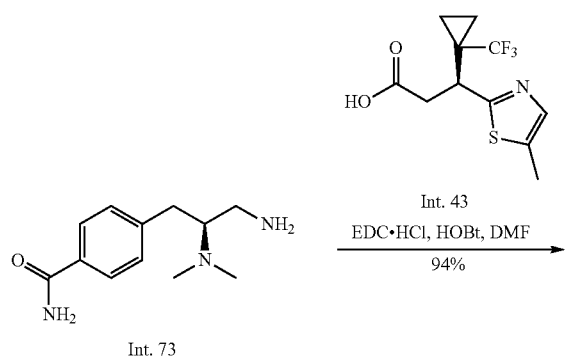

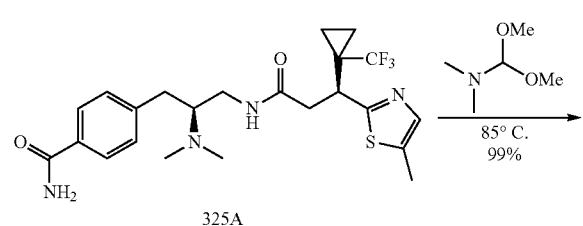

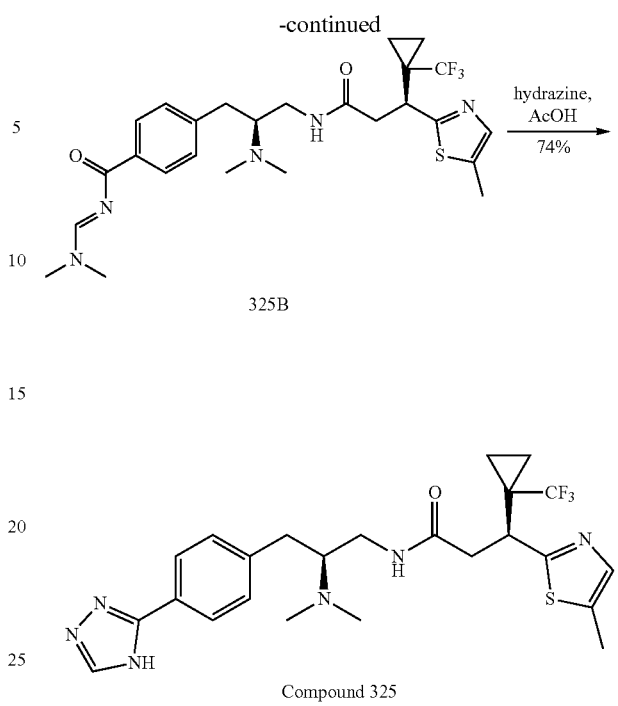

Step 1: Preparation of 4-((S)-2-(dimethylamino)-3-((S)-3-(5-methylthiazol-2-yl)-3-(1-(trifluoromethyl)cyclopropyl)propanamido)propyl)benzamide (325A). To a solution of the acid (Int. 43, 118 mg, 423 mmol), the amine (Int. 73, 98.2 mg, 444 mmol)) and HATU (177 mg, 465 mmol) in DMF (2 mL) was added DIEA (88.3 mL). After 10 minutes, the reaction was quenched by water. The aqueous solution was extracted with EtOAc (3×). The combined organic layers were dried, filtered, concentrated, and purified by silica gel column (0-20% MeOH/DCM with 1% NH₄OH) to give 325A (193 mg, 94%). MS (m/z): 483.2 M+H).

Step 2: Preparation of 4-((S)-2-(dimethylamino)-3-((S)-3-(5-methylthiazol-2-yl)-3-(1-(trifluoromethyl)cyclopropyl)propanamido)propyl)-N-((E)-(dimethylamino)methylene)benzamide (325B). A solution of 325A (193 mg, 400 mmol) in (dimethoxymethyl)dimethylamine (1.07 mL, 20 eq., 8.00 mmol) was heated at 85° C. in 2 h. The reaction mixture was cooled, concentrated to dryness, and used directly to the step.

Step 3: Preparation of (S)-N-((S)-3-(4-(4H-1,2,4-triazol-3-yl)phenyl)-2-(dimethylamino) propyl)-3-(5-methylthiazol-2-yl)-3-(1-(trifluoromethyl)cyclopropyl)propenamide (Compound 325). To a stirred solution of 325B (215 mg, 395 µmol) in acetic acid (5.90 mL) at RT was added hydrazine (95.3 µL, 5 eq., 2.00 mmol). The stirring was continued for 2 h, diluted with H₂O, adjust pH=4-5 with saturated aqueous NaHCO₃, extracted with DCM (3×). The combined extracts were dried over MgSO₄, concentrated, and purified by flash chromatography (0-20% MeOH containing 1% NH₄OH/DCM) to give Compound 325 (150 mg, 74%). MS (m/z): 507.1 (M+H).

Example B326: Preparation of (3R)-N-[(2S)-3-[2-chloro-4-(1H-pyrazol-4-yl)phenyl]-2-(dimethylamino)propyl]-5-methyl-3-phenylhexanamide ("Compound 326")

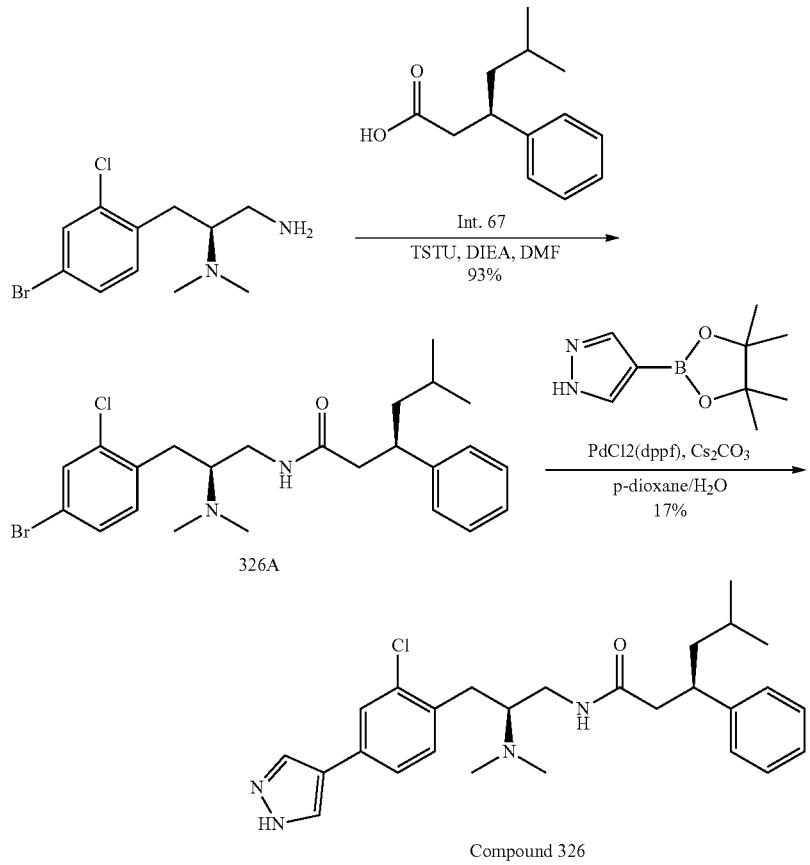

Compound 326

Step 1: Preparation of (3R)-N-[(2S)-3-(4-bromo-2-chlorophenyl)-2-(dimethylamino)propyl]-5-methyl-3-phenylhexanamide (326A). To a stirred solution of Int. 67 (159 mg, 772 mmol) in DMF (4 mL) was added N,N,N',N'-Tetramethyl-O-(N-succinimidyl)uronium tetrafluoroborate (232 mg, 772 mmol). After stirring for 30 minutes, DIEA (202 mL, 1.16 mmol), and [(2S)-1-amino-3-(4-bromo-2-chlorophenyl)propan-2-yl]dimethylamine (225 mg, 772 mmol) were added. After the addition was completed, the reaction mixture was stirred at RT for 1 h. $H_2O$ was added, extracted with EtOAc 93x). The combined extracts were dried over $MgSO_4$, filtered, concentrated, and purified by flash chromatography (0-15% MeOH/DCM) to give 326A (346 mg, 93%). MS (m/z): 479.3 (M+H).

Step 2: Preparation of (3R)-N-[(2S)-3-[2-chloro-4-(1H-pyrazol-4-yl)phenyl]-2-(dimethylamino)propyl]-5-methyl-3-phenylhexanamide (Compound 326). 326A (83 mg, 0.173 mmol),4-(4,4,5,5-tetramethyl-1,3,2-dioxaborolan-2-yl)-1H-pyrazole (53.7 mg, 0.277 mmol), $Cs_2CO_3$ (197 mg, 0.606 mmol), Pd(dppf)$Cl_2$ (6.33 mg, 0.00865 mmol), p-dioxane (2 mL)/water (0.2 mL), purged with nitrogen, heated at 100° C. for 4 hours. The reaction mixture was cooled down to room temperature. The reaction mixture was diluted with ethyl acetate, washed with water and brine. The organic layer was dried over $MgSO_4$, filtered, and concentrated. The crude material was purified on 24 g silica gel column, eluted with 0-10% MeOH in DCM with 1% $NH_4OH$ to provide Compound 326 (14 mg, 17%). MS (m/z): 467.3 (M+H).

Biological Assays

MOR cAMP Agonist and Antagonist Assays:

CHO Tag-lite human mOR stable cell line from Cisbio (NCBI accession number: NM_000914.3, Bedford, Mass.) were seeded and grown to approximately 80% confluence in Ham F-12 with 10% FBS, 50 U/ml penicillin, 50 µg/ml streptomycin, 2 mM Hepes, and 1 mg/ml geneticin (Invitrogen, Carlsbad, Calif.). Cells were then harvested using accutase (Corning. Corning, N.Y.), centrifuged at 1300 RPM for 5 min, and plated at 5000 cells per 5 µL per well in a 5× dilution of stimulation buffer consisting of the HTRF cAMP Gi kit, water and IBMX at 0.5 mM (Cisbio, Bedford, Mass.) in white HTRF low volume 384 well plates (Cisbio, Bedford, Mass.). Plates were then incubated at 37° C. in 5% $CO_2$ for 10 minutes. For the agonist assay, forskolin was added to a final concentration of 4 µM. For the antagonist assay, forskolin (4 µM) and DAMGO at $EC_{90}$ final concentration were added. Test compounds were dissolved in DMSO and water, and then serially diluted to working concentrations such that the concentration of DMSO was less than 0.1%. Diluted test compounds were added at 2.5 µL per well, and plates were incubated at 37° C., and 5% $CO_2$ for 15 minutes, and then at room temperature for 15 minutes. Next 5 μl/well of cAMP Eu-cryptate and 5 μl/well of anti-cAMP-d2 (both diluted 1:20 in lysis buffer) were added, and plates were incubated at room temperature for 1 hour. Following incubation, plates were read in a Synergy Neo2 multi-mode reader (Biotek, Winooski, Vt.). Plate reader settings were set to time resolved fluorescence with excitation at 330 nm and emissions of 620 nm and 665 nm. Emission fluorescence was normalized (665/620 nm signal×1000). For the agonist assay, data was normalized using the maximal DAMGO response. Measurements were performed in triplicate and the dose response was fit using nonlinear regression. The mOR antagonist activity of test compounds is recorded in Table 1, below. With respect to mOR antagonist activity, "+++" denotes an $IC_{50}$ less than or equal to 300 nM; "++" denotes an $IC_{50}$ greater than 300 nM but less than 3,000 nM; and "+" denotes an $IC_{50}$ greater than or equal to 3,000 nM.

DOR cAMP Agonist and Antagonist Assays.

The dOR cAMP agonist and antagonist assays were conducted in a manner similar as described above for the mOR assays using CHO Tag-lite human dOR stable cell line from Cisbio (NCBI accession number: NM_000911.3, Bedford, Mass.). The dOR agonist activity of test compounds is recorded in Table 1, below. With respect to dOR agonist activity, "+++" denotes an $EC_{50}$ less than or equal to 300 nM; "++" denotes an $EC_{50}$ greater than 300 nM but less than 3,000 nM; and "+" denotes an $EC_{50}$ greater than or equal to 3,000 nM.

KOR β-Arrestin Agonist and Antagonist Assays:

KOR β-Arrestin Agonist and Antagonist assays were preformed using the Tango™ OPRK1-bla U2OS cells from Invitrogen and purchased from ThermoFisher, catalog number K1576. The cells were used according to the manufacturer suggested instructions. The kOR antagonist activity of test compounds is recorded in Table 1, below. With respect to kOR antagonist activity, "+++" denotes an $IC_{50}$ less than or equal to 300 nM; "++" denotes an $IC_{50}$ greater than 300 nM but less than 3.000 nM; and "+" denotes an $IC_{50}$ greater than or equal to 3,000 nM.

TABLE 1

| Compound No. | mOR cAMP Antagonist Assay $IC_{50}$ | dOR cAMP Agonist Assay $EC_{50}$ | kOR β-Arrestin Antagonist Assay $IC_{50}$ |
| --- | --- | --- | --- |
| 1 | +++ | | |
| 2 | +++ | | |
| 3 | +++ | | |
| 4 | +++ | | |
| 5 | ++ | | |
| 6 | ++ | | ++ |
| 7 | + | +++ | +++ |
| 8 | + | + | +++ |
| 9 | +++ | + | |
| 10 | +++ | + | +++ |
| 11 | +++ | + | +++ |
| 12 | +++ | + | +++ |
| 13 | +++ | + | |
| 14 | +++ | +++ | ++ |
| 15 | +++ | +++ | +++ |
| 16 | +++ | | |
| 17 | + | | +++ |
| 18 | + | | +++ |
| 19 | +++ | | |
| 20 | +++ | ++ | +++ |
| 21 | +++ | ++ | +++ |
| 22 | +++ | | +++ |
| 23 | + | | +++ |
| 24 | +++ | | +++ |
| 25 | +++ | | ++ |
| 26 | +++ | | |
| 27 | +++ | | |
| 28 | +++ | | +++ |
| 29 | +++ | | |
| 30 | +++ | | |
| 31 | +++ | | |
| 32 | +++ | | +++ |
| 33 | +++ | | +++ |
| 34 | +++ | | +++ |
| 35 | +++ | | +++ |
| 36 | +++ | | +++ |
| 37 | +++ | | +++ |
| 38 | +++ | | +++ |
| 39 | +++ | + | +++ |
| 40 | + | +++ | |
| 41 | +++ | | +++ |
| 42 | + | | |
| 43 | +++ | | |
| 44 | +++ | | |
| 45 | +++ | | |
| 46 | +++ | | |
| 47 | +++ | | |
| 48 | + | | |
| 49 | + | | +++ |
| 50 | + | | |
| 51 | +++ | | |
| 52 | +++ | | |
| 53 | +++ | | |
| 54 | + | | |
| 55 | +++ | | |
| 56 | ++ | | |
| 57 | ++ | | |
| 58 | + | | |
| 59 | +++ | | |
| 60 | +++ | | |
| 61 | + | | |
| 62 | +++ | | |
| 63 | +++ | | |
| 64 | +++ | | |
| 65 | + | | ++ |
| 66 | +++ | | +++ |
| 67 | + | | |
| 68 | +++ | + | +++ |
| 69 | +++ | | |
| 70 | + | | |
| 71 | +++ | | |
| 72 | +++ | | +++ |
| 73 | +++ | | +++ |
| 74 | + | | +++ |
| 75 | +++ | | +++ |
| 76 | + | | +++ |
| 77 | +++ | + | +++ |
| 78 | + | | |
| 79 | +++ | | |
| 80 | +++ | +++ | +++ |
| 81 | +++ | | +++ |
| 82 | + | | |
| 83 | +++ | +++ | +++ |
| 84 | +++ | | +++ |
| 85 | +++ | | +++ |
| 86 | | | |
| 87 | | | |
| 88 | +++ | +++ | +++ |
| 89 | +++ | +++ | +++ |
| 90 | +++ | +++ | +++ |
| 91 | +++ | +++ | +++ |
| 92 | +++ | +++ | |
| 93 | +++ | +++ | |
| 94 | +++ | +++ | |
| 95 | +++ | + | |
| 96 | +++ | +++ | +++ |
| 97 | +++ | +++ | +++ |
| 98 | + | | |

TABLE 1-continued

| Compound No. | mOR cAMP Antagonist Assay IC$_{50}$ | dOR cAMP Agonist Assay EC$_{50}$ | kOR β-Arrestin Antagonist Assay IC$_{50}$ |
|---|---|---|---|
| 101 | +++ | ++ | |
| 102 | + | | |
| 103 | + | | |
| 104 | +++ | ++ | |
| 105 | ++ | | |
| 106 | + | | |
| 107 | +++ | | |
| 108 | + | | |
| 109 | +++ | | |
| 110 | + | | |
| 111 | +++ | | |
| 112 | + | | |
| 113 | +++ | | |
| 114 | +++ | | |
| 115 | ++ | | |
| 116 | +++ | | |
| 117 | + | | |
| 118 | + | | |
| 119 | +++ | | |
| 120 | +++ | | |
| 121 | +++ | | |
| 122 | +++ | | |
| 123 | +++ | | |
| 124 | + | | |
| 125 | +++ | | |
| 126 | + | | |
| 127 | +++ | | |
| 128 | +++ | | |
| 129 | +++ | | |
| 130 | +++ | | |
| 131 | +++ | | |
| 132 | +++ | | |
| 133 | + | | |
| 134 | +++ | | |
| 135 | + | | |
| 136 | +++ | ++ | +++ |
| 137 | +++ | | +++ |
| 138 | +++ | | +++ |
| 139 | + | | |
| 140 | + | | |
| 141 | +++ | | +++ |
| 142 | +++ | + | +++ |
| 143 | +++ | + | +++ |
| 144 | + | | |
| 145 | +++ | + | |
| 146 | +++ | + | |
| 147 | +++ | +++ | |
| 148 | ++ | ++ | |
| 149 | +++ | +++ | |
| 150 | +++ | + | |
| 151 | ++ | | |
| 152 | + | | |
| 153 | + | | |
| 154 | +++ | | |
| 155 | +++ | +++ | |
| 156 | +++ | ++ | |
| 157 | +++ | + | |
| 158 | +++ | + | |
| 159 | +++ | ++ | |
| 160 | +++ | +++ | |
| 161 | + | + | |
| 162 | +++ | ++ | |
| 163 | +++ | + | |
| 164 | + | ++ | |
| 165 | +++ | +++ | |
| 166 | +++ | | |
| 167 | + | +++ | |
| 168 | ++ | + | |
| 169 | + | | |
| 170 | +++ | | |
| 171 | +++ | + | |
| 172 | +++ | +++ | |
| 173 | +++ | +++ | |
| 174 | +++ | +++ | |
| 175 | +++ | | ++ |
| 176 | +++ | | |
| 177 | +++ | ++ | |
| 178 | +++ | ++ | |
| 179 | +++ | | |
| 180 | +++ | | |
| 181 | | + | |
| 182 | + | + | |
| 183 | +++ | + | |
| 186 | +++ | ++ | |
| 187 | +++ | +++ | |
| 188 | ++ | | |
| 189 | +++ | | |
| 190 | ++ | | |
| 191 | +++ | | |
| 192 | +++ | | |
| 193 | ++ | + | |
| 194 | +++ | + | |
| 195 | +++ | | |
| 196 | +++ | | |
| 197 | +++ | | |
| 198 | +++ | + | |
| 199 | +++ | | |
| 200 | ++ | | |
| 201 | + | | |
| 202 | +++ | | |
| 203 | ++ | | |
| 204 | +++ | | |
| 205 | +++ | | |
| 206 | ++ | | |
| 207 | + | | |
| 208 | +++ | | |
| 209 | +++ | | |
| 210 | +++ | | |
| 211 | +++ | | |
| 212 | + | | |
| 213 | +++ | | |
| 214 | +++ | +++ | |
| 215 | +++ | ++ | |
| 216 | +++ | ++ | |
| 217 | +++ | ++ | |
| 218 | +++ | + | |
| 219 | +++ | ++ | |
| 220 | +++ | + | |
| 221 | +++ | + | |
| 222 | +++ | + | |
| 223 | +++ | +++ | |
| 224 | + | +++ | |
| 225 | +++ | +++ | |
| 226 | +++ | ++ | +++ |
| 227 | +++ | ++ | ++ |
| 228 | +++ | | + |
| 229 | +++ | | |
| 230 | +++ | | |
| 231 | +++ | | |
| 232 | ++ | | |
| 233 | +++ | | |
| 234 | +++ | | |
| 235 | +++ | | |
| 236 | +++ | ++ | |
| 237 | +++ | | |
| 238 | +++ | | |
| 239 | +++ | | |
| 240 | +++ | | +++ |
| 241 | +++ | | |
| 242 | +++ | | |
| 243 | +++ | | |
| 244 | +++ | | |
| 245 | +++ | | |
| 246 | +++ | | |
| 247 | +++ | | |
| 248 | ++ | | |
| 249 | +++ | | |
| 250 | ++ | | |

TABLE 1-continued

| Compound No. | mOR cAMP Antagonist Assay IC$_{50}$ | dOR cAMP Agonist Assay EC$_{50}$ | kOR β-Arrestin Antagonist Assay IC$_{50}$ |
|---|---|---|---|
| 251 | +++ | + | +++ |
| 252 | +++ | | |
| 253 | +++ | | |
| 254 | +++ | | |
| 255 | +++ | | + |
| 256 | +++ | | |
| 257 | +++ | | |
| 258 | +++ | | |
| 259 | + | | |
| 260 | +++ | | |
| 261 | +++ | | |
| 262 | +++ | | |
| 263 | +++ | +++ | |
| 264 | +++ | | |
| 265 | +++ | | |
| 266 | +++ | | |
| 268 | +++ | | |
| 269 | +++ | | |
| 270 | +++ | | |
| 271 | +++ | | |
| 272 | +++ | | |
| 273 | +++ | | +++ |
| 274 | +++ | | |
| 275 | +++ | +++ | |
| 276 | +++ | | |
| 277 | +++ | | |
| 278 | +++ | | |
| 279 | +++ | | |
| 280 | ++ | | |
| 281 | +++ | | |
| 282 | +++ | | |
| 283 | +++ | | |
| 284 | +++ | | |
| 285 | +++ | | |
| 286 | +++ | | |
| 287 | +++ | | |
| 288 | +++ | +++ | ++ |
| 289 | +++ | | ++ |
| 290 | +++ | | |
| 291 | +++ | | |
| 292 | ++ | | |
| 293 | +++ | | |
| 294 | +++ | | |
| 295 | +++ | | |
| 296 | +++ | | |
| 297 | +++ | | |
| 298 | +++ | | |
| 299 | +++ | | |
| 300 | +++ | | |
| 302 | +++ | | |
| 303 | +++ | | |
| 304 | +++ | | |
| 306 | +++ | | |
| 307 | +++ | | |
| 308 | ++ | | |
| 309 | +++ | | |
| 310 | +++ | | |
| 311 | ++ | | |
| 312 | +++ | | |
| 313 | +++ | | |
| 314 | +++ | | |
| 315 | +++ | | |
| 316 | +++ | | +++ |
| 317 | +++ | | ++ |
| 318 | +++ | +++ | +++ |
| 319 | + | +++ | +++ |
| 320 | +++ | | +++ |
| 321 | +++ | | ++ |
| 322 | +++ | | |
| 323 | +++ | +++ | |
| 325 | ++ | | |
| 326 | ++ | + | |

What is claimed is:
1. A compound having the structure of Formula (I):
wherein:

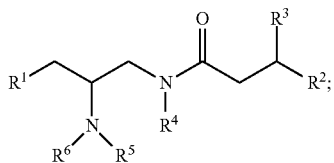

Formula (I)

R$^1$ is selected from C$_{6-10}$aryl and C$_{1-9}$heteroaryl, wherein C$_{6-10}$aryl and C$_{1-9}$heteroaryl are optionally substituted with one, two, three, four, or five R$^7$;
R$^2$ is selected from C$_{6-10}$aryl and C$_{1-9}$heteroaryl, wherein C$_{6-10}$aryl and C$_{1-9}$heteroaryl are optionally substituted with one, two, three, four, or five R$^8$;
R$^3$ is —X—R$^{3a}$;
X is a bond;
R$^{3a}$ is C$_{3-8}$cycloalkyl substituted with one, two, three, four, or five R$^9$;
R$^4$ is hydrogen, C$_1$-C$_6$alkyl, or C$_1$-C$_6$haloalkyl;
R$^5$ and R$^6$ are each independently selected from hydrogen, C$_1$-C$_6$alkyl, and C$_1$-C$_6$haloalkyl; or R$^5$ and R$^6$ are combined to form an azetidinyl, pyrrolidinyl, piperidinyl, or piperazinyl ring;
each R$^7$ is independently selected from halogen, —CN, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —C(O)OR$^{10}$, —OC(O)N(R$^{10}$(R$^{11}$), —N(R$^{12}$)C(O)N(R$^{10}$)(R$^{11}$), —N(R$^{12}$)C(O)R$^{13}$, —N(R$^{12}$)C(O)OR$^{13}$, N(R$^{12}$)S(O)$_2$R$^{13}$, —C(O)R$^{13}$, —OC(O)R$^{13}$, —C(O)N(R$^{10}$(R$^{11}$)-C(O)C(O)N(R$^{10}$)(R$^{11}$), —S(O)R$^{13}$, S(O)$_2$R$^{13}$ and —S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, C$_{2-9}$ heterocycloalkyl, C$_{6-10}$aryl, and C$_{1-9}$heteroaryl are optionally substituted with one, two, or three groups selected from halogen, —CN, C$_{1-6}$alkyl, C$_{1-6}$haloalkyl, C$_{2-6}$alkenyl, C$_{2-6}$alkynyl, C$_{3-6}$cycloalkyl, C$_{2-9}$ heterocycloalkyl, C$_{6-10}$aryl, C$_{1-9}$heteroaryl, —OR$^{14}$, —C(O)OR$^{14}$, —OC(O)N(R$^{14}$)(R$^{15}$), —N(R$^{16}$)C(O)N(R$^{14}$)(R$^{15}$), —N(R$^{16}$)C(O)R$^{17}$, —N(R$^{66}$)C(O)OR$^{17}$, —N(R$^{16}$)S(O)$_2$R$^{17}$, —C(O)R$^{17}$, —OC(O)R$^{17}$, —C(O)N(R$^{14}$)(R$^{15}$), —C(O)C(O)N(R$^{14}$)(R$^{15}$), —S(O)R$^{17}$, —S(O)$_2$R$^{17}$, and —S(O)$_2$N(R$^{14}$)(R$^{15}$); or two R$^7$ are combined to form a heterocycloalkyl ring optionally substituted with oxo; or R$^7$ and R$^6$ are combined to form a heterocycloalkyl ring;
each R$^8$ and each R$^9$ are each independently selected from halogen, —CN, C$_{1-6}$alkyl, C$_{1-6}$haloalkyl, C$_{2-6}$ alkenyl, C$_{2-6}$ alkynyl, C$_{3-6}$ cycloalkyl, C$_{2-9}$heterocycloalkyl, C$_{6-10}$aryl, C$_{1-9}$ heteroaryl, —OR$^{10}$, —C(O)OR$^{10}$, —OC(O)N(R$^{10}$)(R$^{11}$), —N(R$^{12}$)C(O)N(R$^{10}$)(R$^{11}$), —N(R$^{12}$)C(O)R$^{13}$, —N(R$^{12}$)C(O)OR$^{13}$, —N(R$^{12}$)S(O)$_2$R$^{13}$, —C(O)R$^{13}$, —OC(O)R$^{13}$, —C(O)N(R$^{10}$)(R$^{11}$), —C(O)C(O)N(R$^{10}$)(R$^{11}$), —S(O)R$^{13}$, —S(O)$_2$R$^{13}$, and —S(O)$_2$N(R$^{10}$)(R$^{11}$), wherein C$_{1-6}$alky, C$_{2-6}$ alkenyl, C$_{2-6}$ alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, C$_{1-6}$alkyl, C$_{2-6}$ haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$ heteroaryl, —OR$^{14}$, —SR$^{14}$, —C(O)OR$^{14}$, —OC(O)N(R$^{14}$)(R$^{16}$), —N(R$^{16}$)C(O)N(R$^{14}$)(R$^{15}$), —N(R$^{66}$)C(O)R$^{17}$, —N(R$^{16}$)C(O)OR$^{17}$, —N(R$^{16}$)S(O)$_2$R$^{17}$, —C(O)R$^{17}$, —OC(O)R$^{17}$, —OC(O)N(R$^{14}$)(R$^{15}$), —C(O)C(O)N(R$^{14}$)(R$^{15}$), —S(O)R$^{17}$, —S(O)$_2$R$^{17}$, and —S(O)$_2$N(R$^{14}$)(R$^{15}$);

each R$^{10}$ is independently selected from hydrogen, C$_{1-6}$alkyl, C$_{1-6}$haloalkyl, C$_{2-6}$alkenyl, C$_{2-6}$ alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, C$_{1-6}$alkyl C$_{1-6}$ haloalkyl, C$_{1-6}$alkoxy, C$_{3-6}$ cycloalkyl, C$_{2-9}$heterocycloalkyl, C$_{6-10}$aryl, and C$_{1-9}$heteroaryl;

each R$^{11}$ is independently selected from hydrogen, C$_{1-6}$alkyl, and C$_{1-6}$haloalkyl;

each R$^{12}$ is independently selected from hydrogen, C$_{1-6}$alkyl, and C$_{1-6}$haloalkyl;

each R$^{13}$ is independently selected C$_{1-6}$alkyl, C$_{2-6}$alkenyl, C$_{2-6}$alkynyl, C$_{3-6}$cycloalkyl, C$_{2-9}$ heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$ cycloalkyl, C$_{2-9}$heterocycloalkyl, C$_{6-100}$aryl, and C$_{1-9}$heteroaryl are optionally substituted with one, two, or three groups selected from halogen, C$_{1-6}$ alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{14}$ is independently selected from hydrogen, C$_{1-6}$alkyl, C$_{1-6}$haloalkyl, C$_{2-6}$alkenyl, C$_{2-6}$ alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$ alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, C$_{1-6}$alkyl, C$_{1-6}$ haloalkyl, C$_{1-6}$alkoxy, C$_{3-6}$cycloalkyl, C$_{2-9}$ heterocycloalkyl, C$_{6-10}$aryl, and C$_{1-9}$heteroaryl;

each R$^{15}$ is independently selected from hydrogen, C$_{1-6}$alkyl, and C$_{1-6}$haloalkyl;

each R$^{16}$ is independently selected from hydrogen, C$_{1-6}$alkyl, and C$_{1-6}$haloalkyl; and each R$^{17}$ is independently selected C$_{1-6}$alkyl, C$_{2-6}$alkenyl, C$_{2-6}$alkynyl, C$_{3-6}$cycloalkyl, C$_{2-9}$ heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$ cycloalkyl, C$_{2-9}$heterocycloalkyl, C$_{6-10}$aryl, and C$_{1-9}$heteroaryl are optionally substituted with one, two, or three groups selected from halogen, C$_{1-6}$alkyl, C$_{1-6}$haloalkyl, C$_{1-6}$alkoxy, C$_{3-6}$ cycloalkyl, C$_{2-9}$heterocycloalkyl, C$_{6-10}$aryl, and C$_{1-9}$heteroaryl;

or a pharmaceutically acceptable salt or solvate thereof.

2. The compound of claim 1, or a pharmaceutically acceptable salt or solvate thereof, having the structure of Formula (Ia):

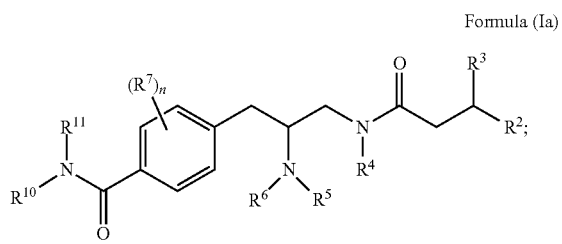

Formula (Ia)

wherein n is 0, 1, 2, 3, or 4.

3. The compound of claim 2, or a pharmaceutically acceptable salt or solvate thereof, wherein R$^{10}$ is independently selected from hydrogen and C$_{1-6}$alkyl.

4. The compound of claim 3, or a pharmaceutically acceptable salt or solvate thereof, wherein R$^4$ is hydrogen.

5. The compound of claim 4, or a pharmaceutically acceptable salt or solvate thereof, wherein R$^{11}$ is hydrogen.

6. The compound of claim 5, or a pharmaceutically acceptable salt or solvate thereof, wherein n is 0, 1, or 2.

7. The compound of claim 6, or a pharmaceutically acceptable salt or solvate thereof, wherein each R$^7$ is independently selected from halogen and C$_{1-6}$alkyl.

8. The compound of claim 7, or a pharmaceutically acceptable salt or solvate thereof, wherein R$^{3a}$ is cyclopropyl substituted with one, two, or three R$^9$.

9. The compound of claim 8, or a pharmaceutically acceptable salt or solvate thereof, wherein each R$^9$ is independently selected from halogen, —CN, C$_{1-6}$alkyl, and C$_{1-6}$haloalkyl.

10. The compound of claim 9, or a pharmaceutically acceptable salt or solvate thereof, wherein R$^{3a}$ is cyclopropyl substituted with one R$^9$.

11. The compound of claim 10, or a pharmaceutically acceptable salt or solvate thereof, wherein R$^{3a}$ is cyclopropyl substituted with —CF$_3$.

12. The compound of claim 7, or a pharmaceutically acceptable salt or solvate thereof, wherein R$^2$ is phenyl optionally substituted with one, two, or three R$^8$ or R$^2$ is pyridinyl, pyrimidinyl, or thiazolyl, wherein pyridinyl, pyrimidinyl, and thiazolyl are optionally substituted with one, two, or three R$^8$.

13. The compound of claim 12, or a pharmaceutically acceptable salt or solvate thereof, wherein each R$^8$ is independently selected from halogen C$_{1-6}$alkyl, C$_{1-6}$haloalkyl, and —OR$^{10}$.

14. The compound of claim 7, or a pharmaceutically acceptable salt or solvate thereof, wherein R$^5$ and R$^6$ are C$_1$-C$_6$alkyl.

15. A compound selected from:

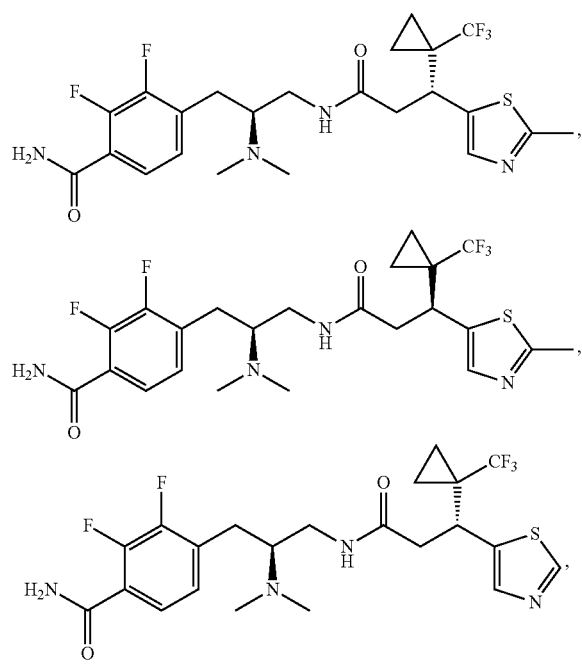

385
-continued
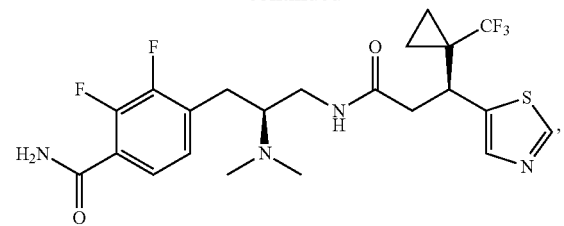
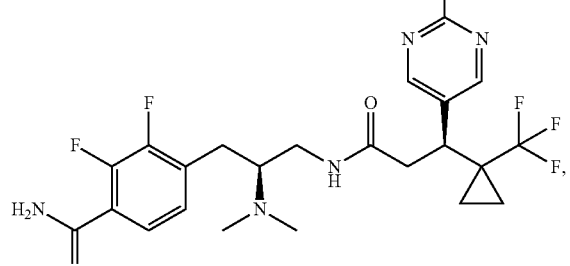
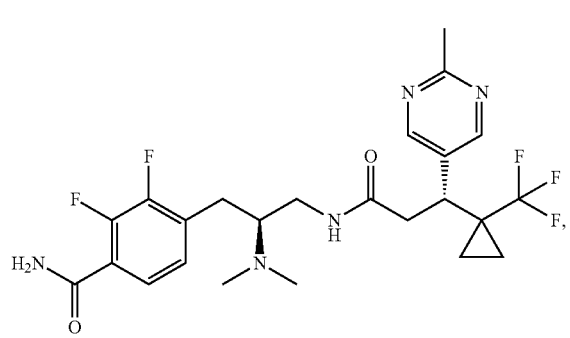
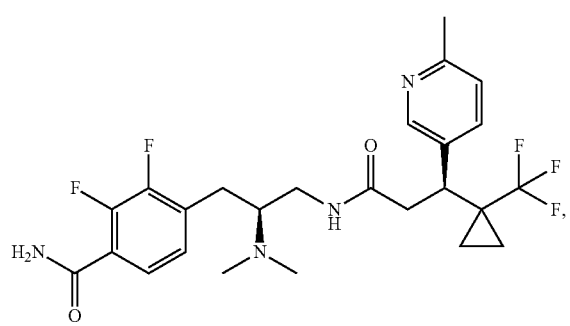
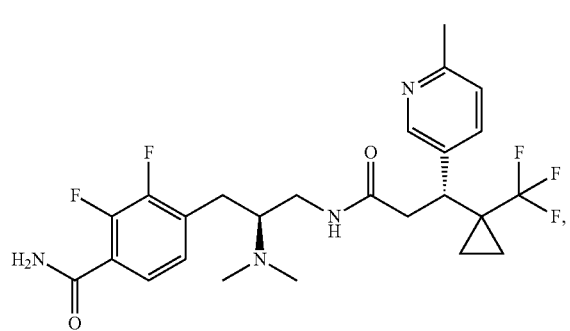
386
-continued
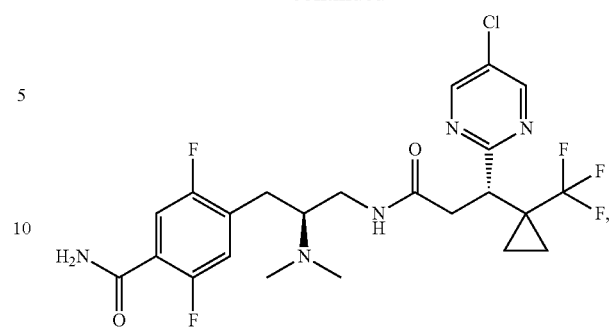
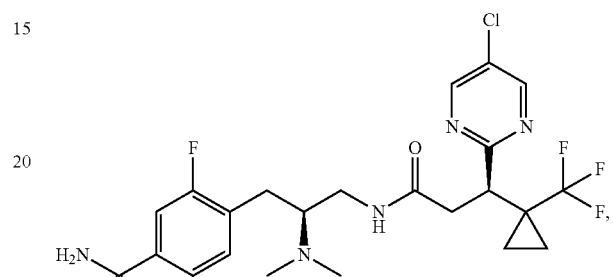
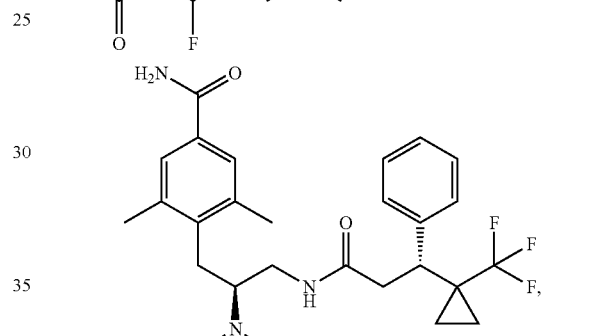
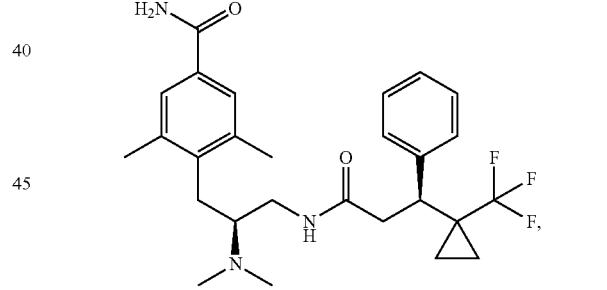
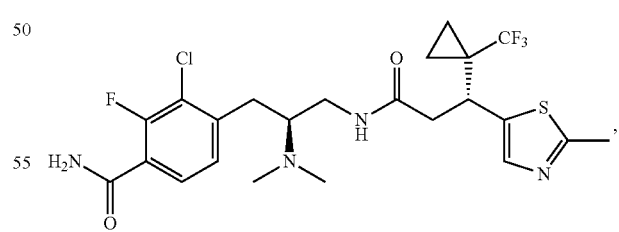
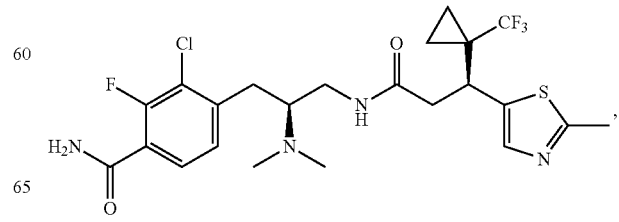

387
-continued
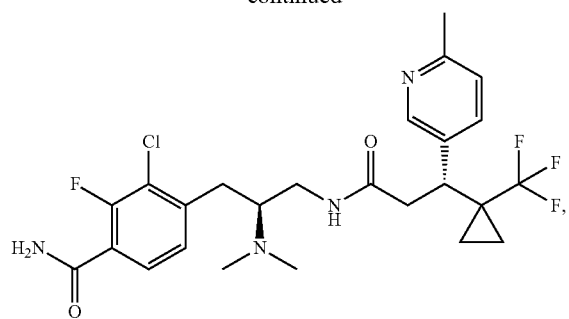
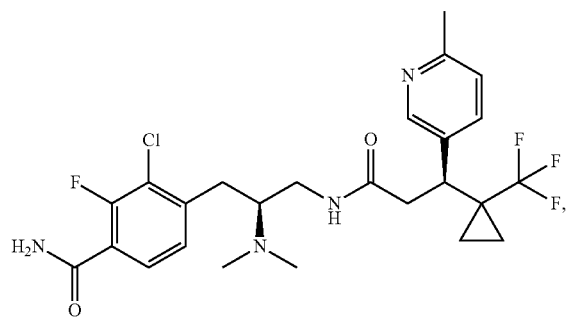
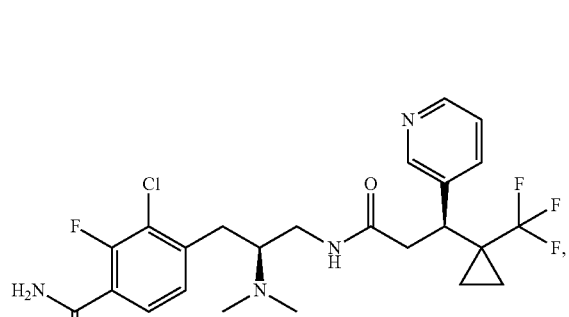
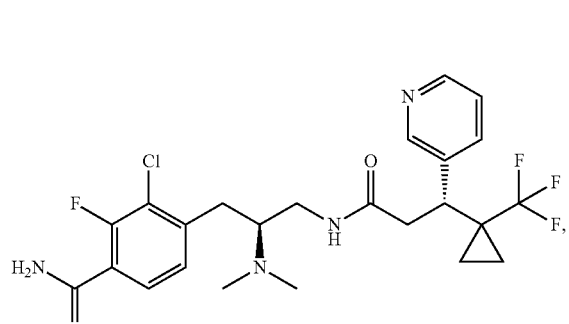
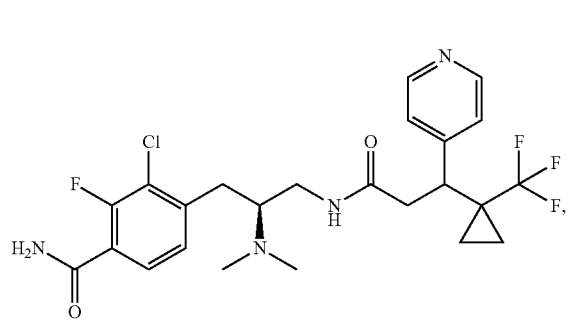
388
-continued
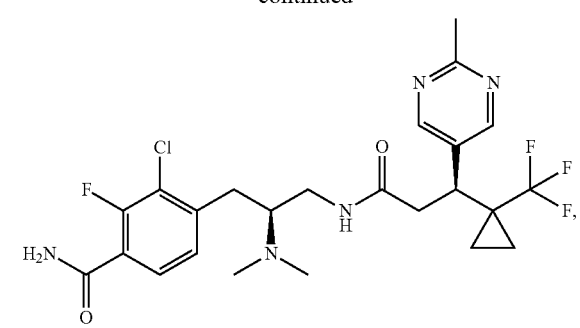
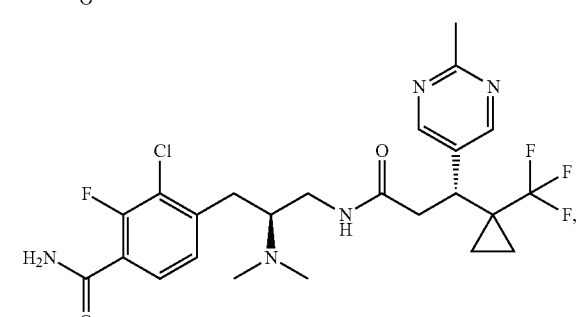
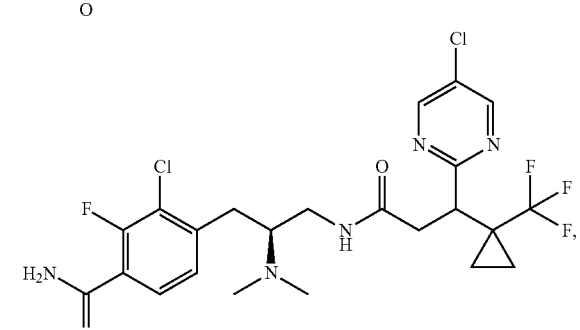
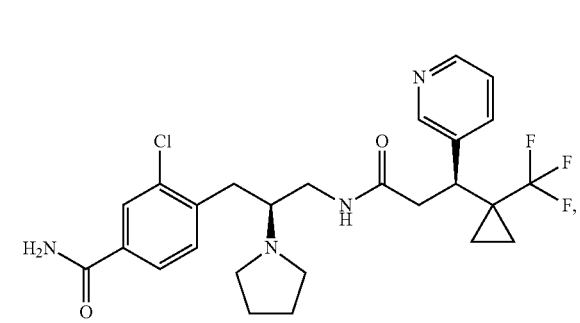
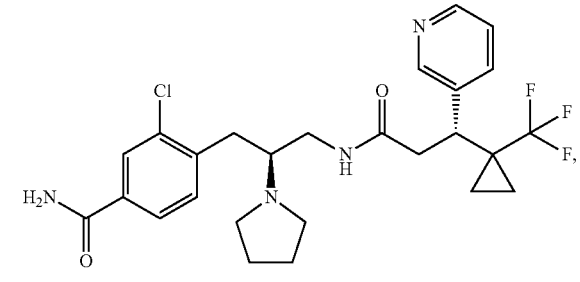

389
-continued
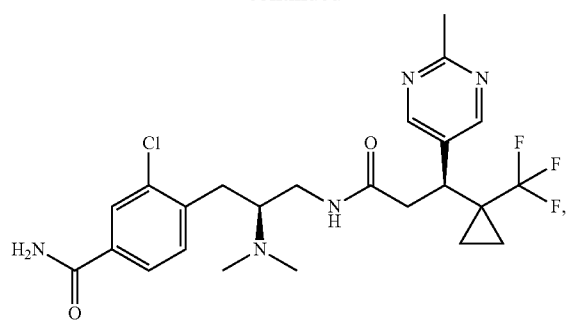
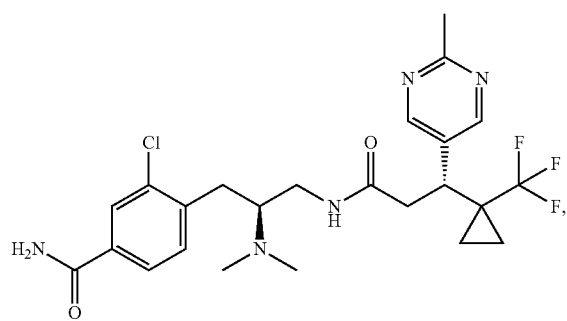
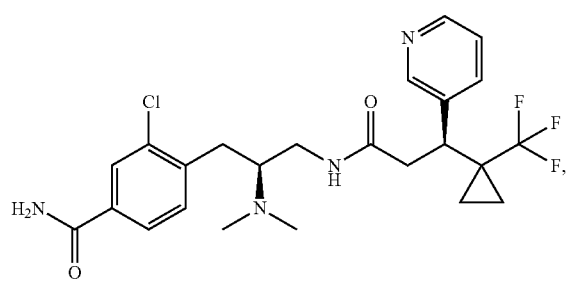
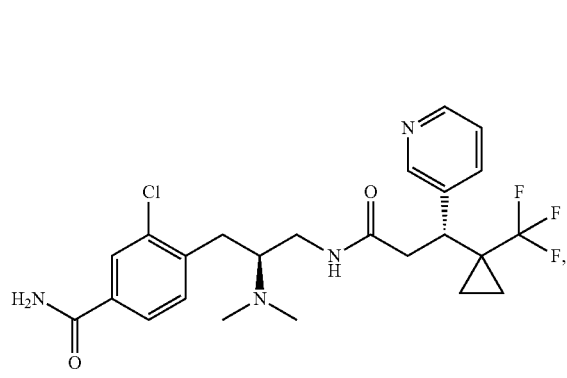
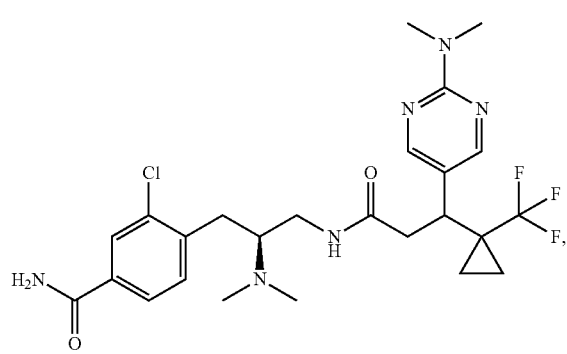
390
-continued
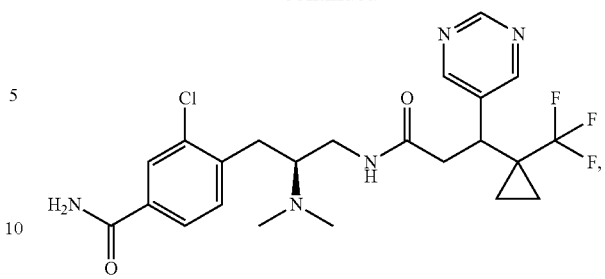
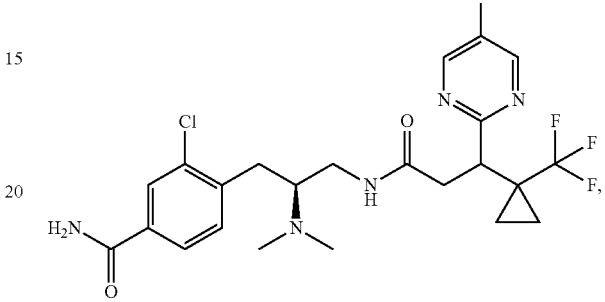
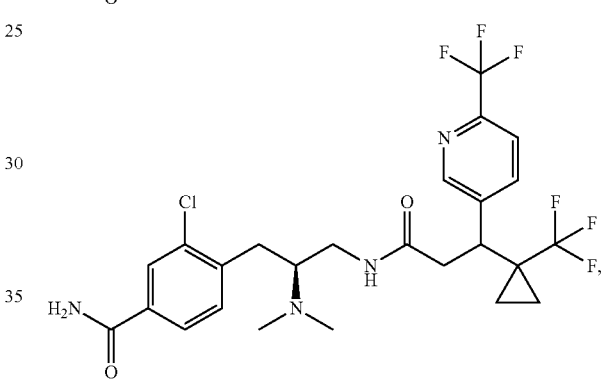
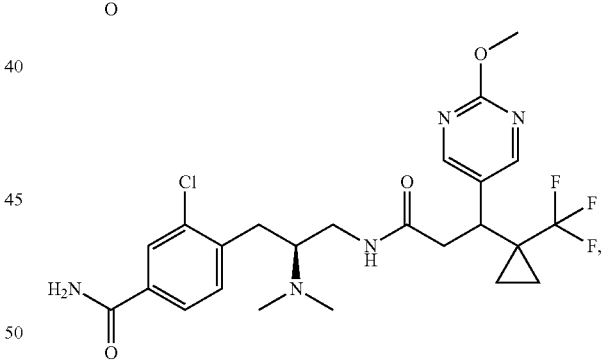
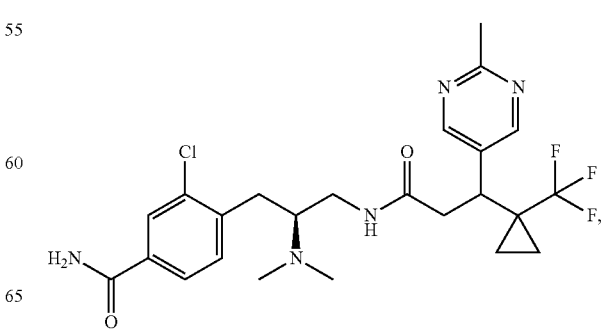

-continued
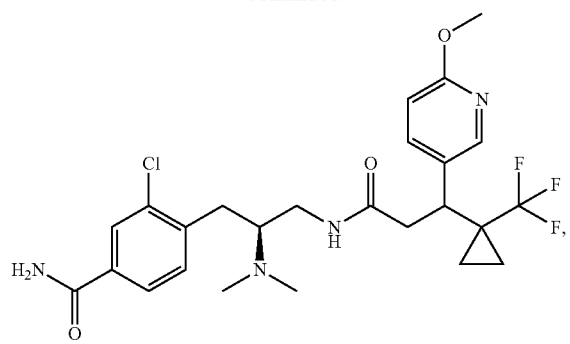
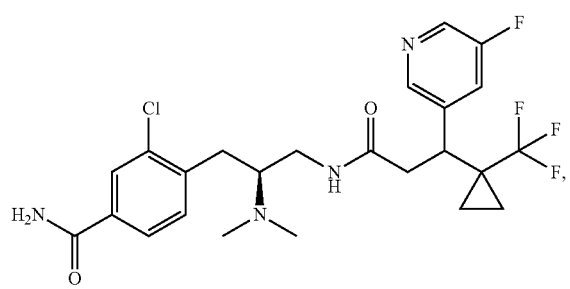
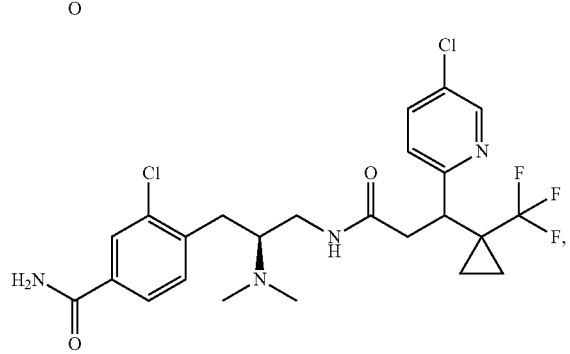
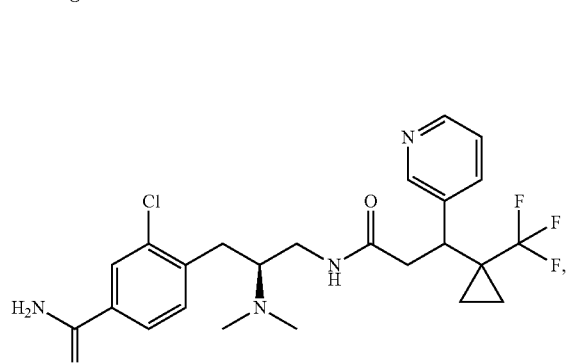
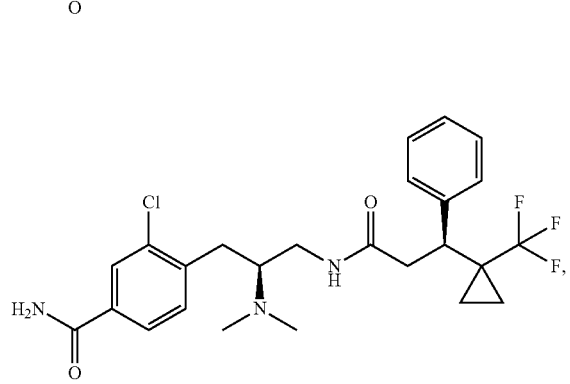
-continued
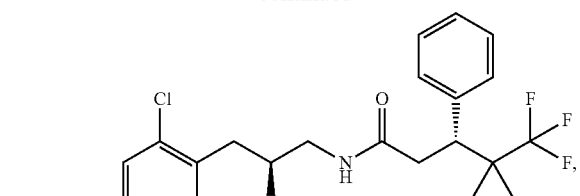
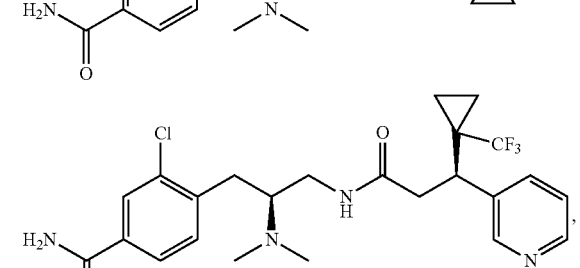
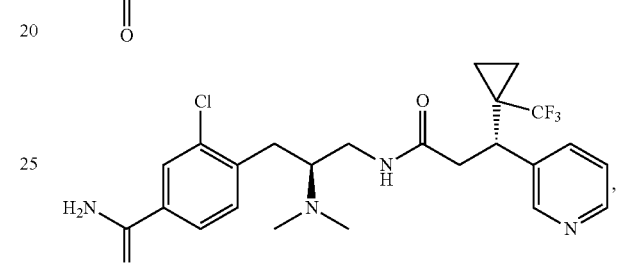
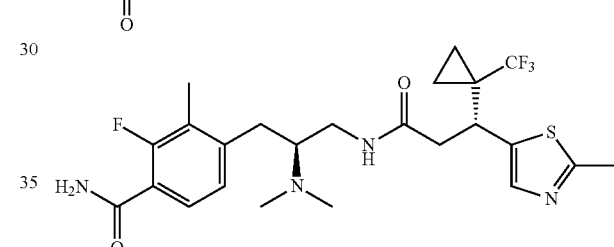
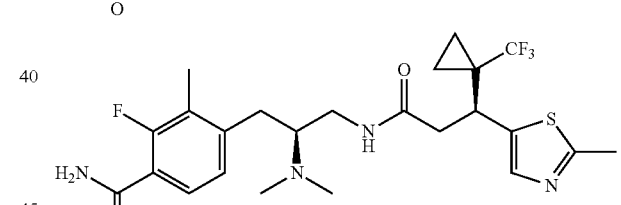
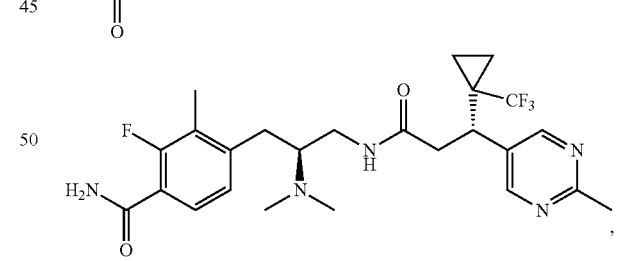
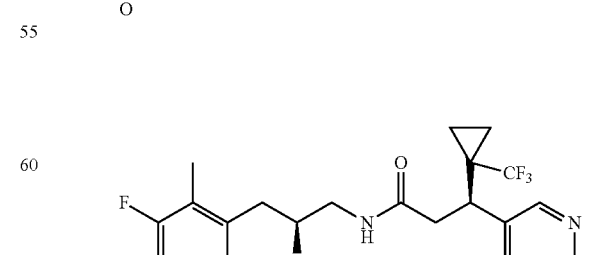
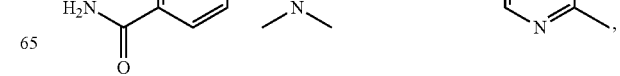

-continued
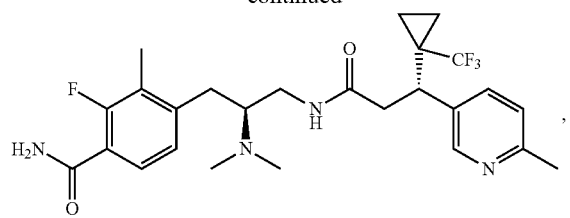,
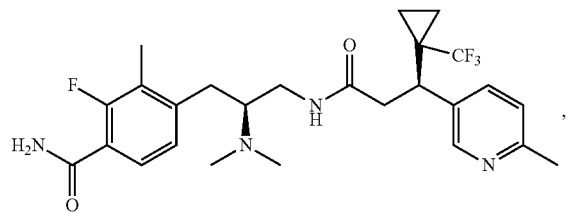,
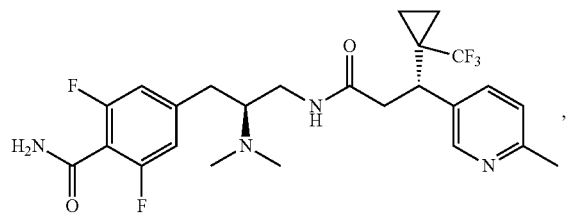,
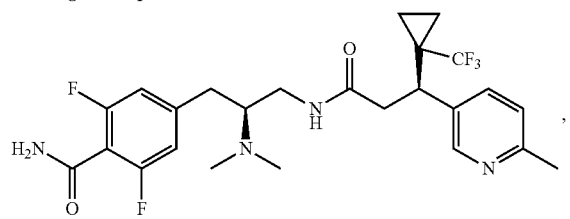,
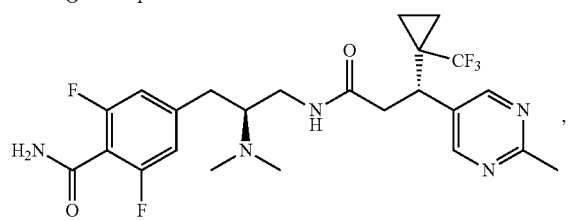,
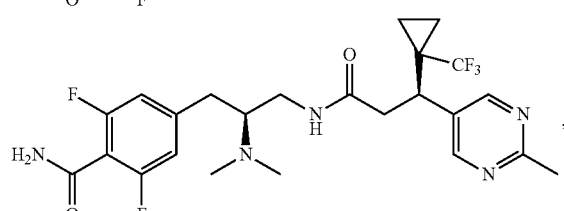,
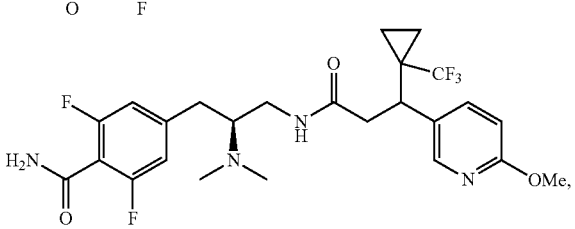,
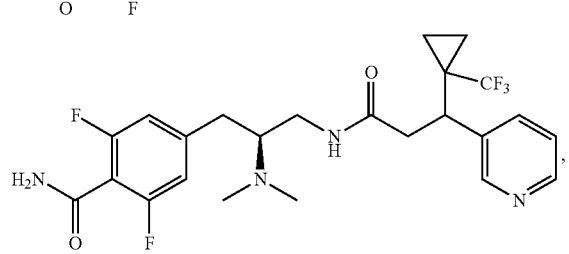,
-continued
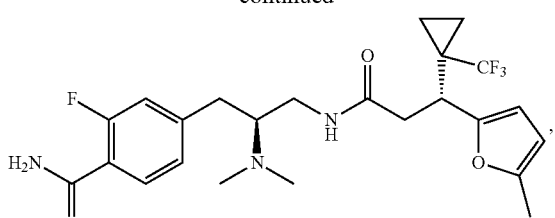,
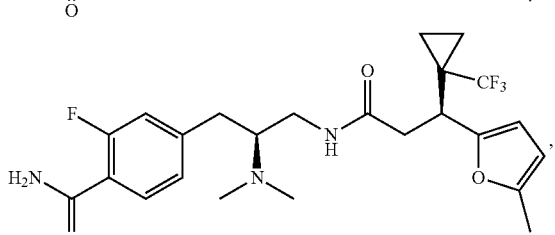,
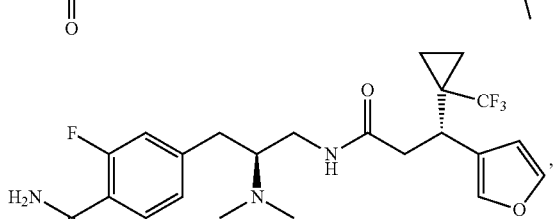,
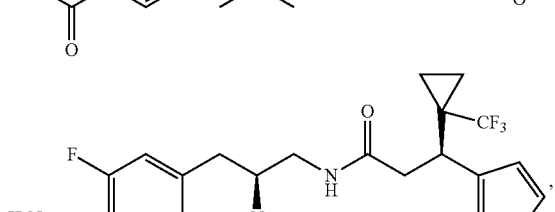,
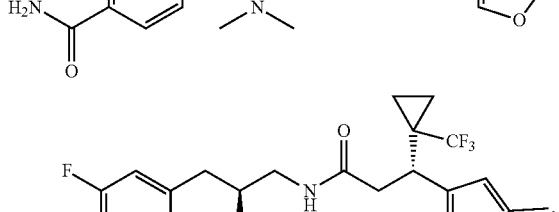,
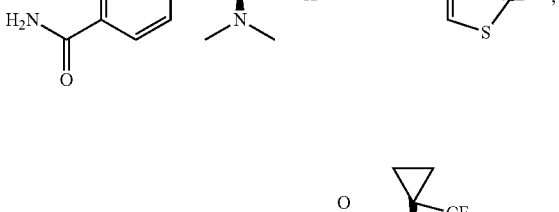,
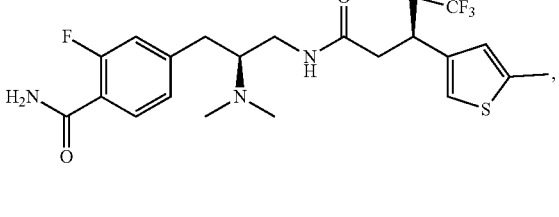,
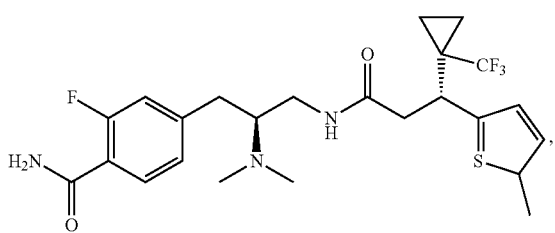, 395
-continued
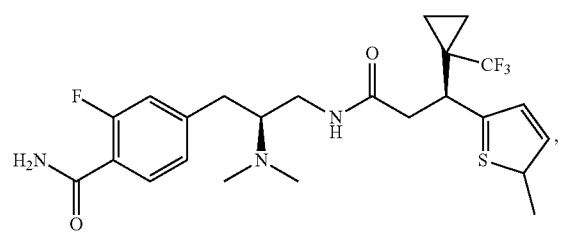
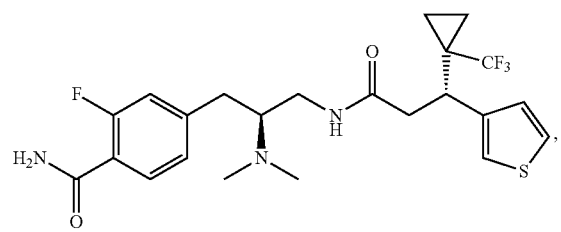
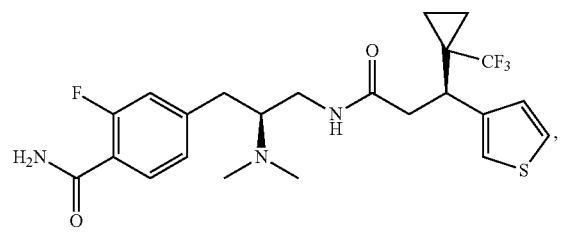
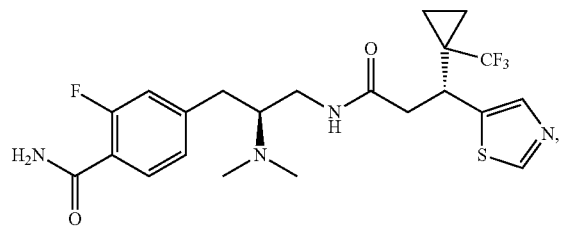
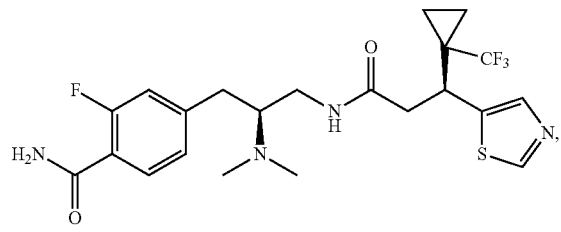
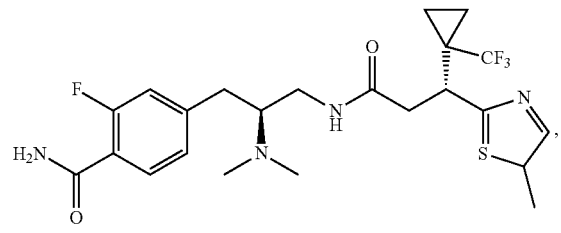
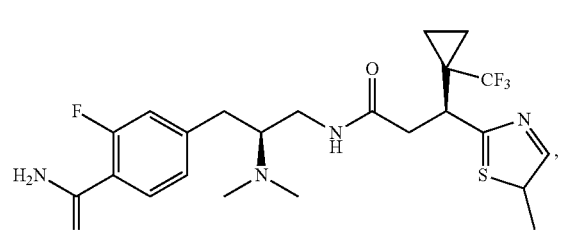
396
-continued
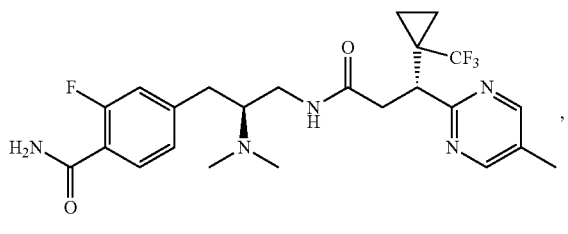
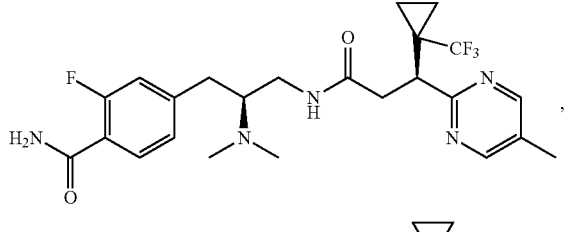
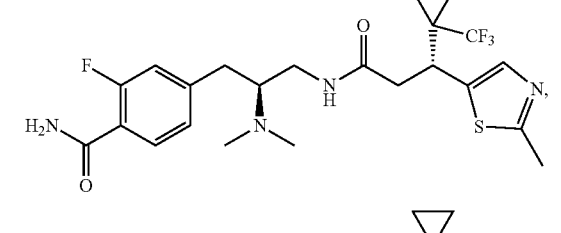
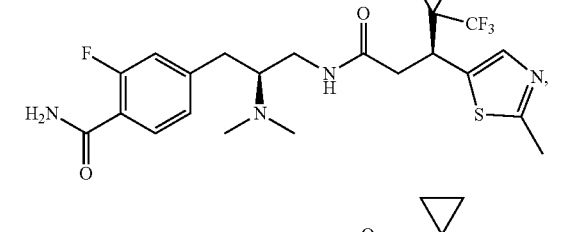
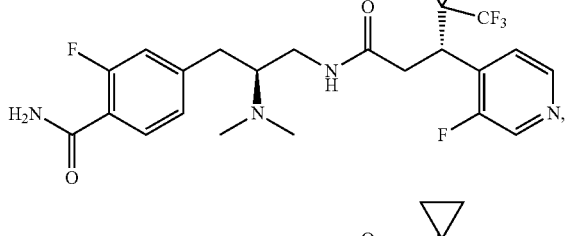
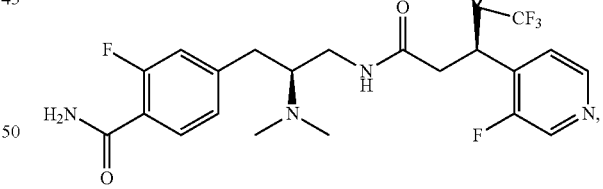
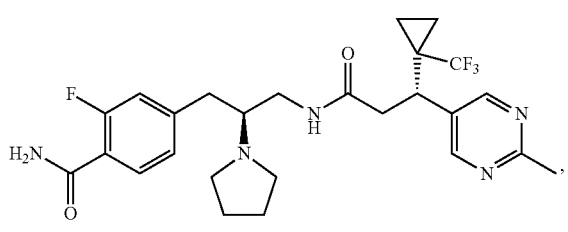

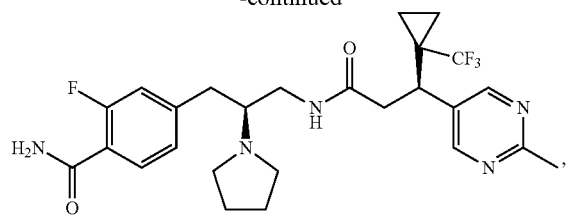
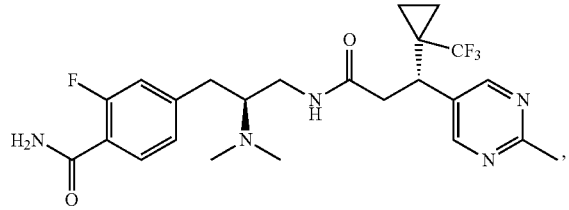
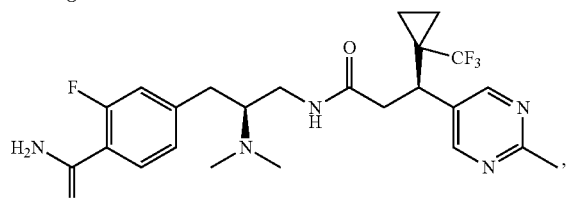
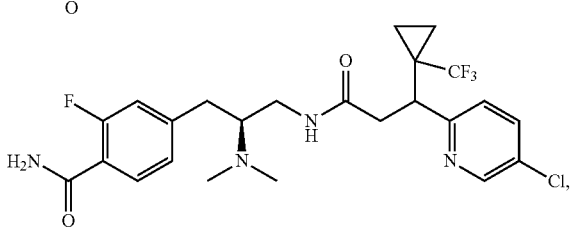
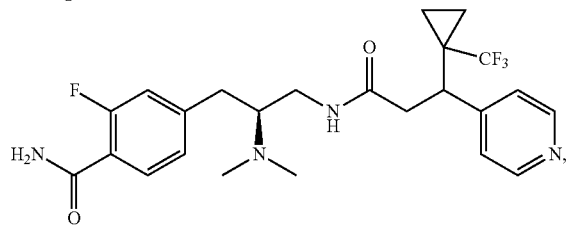
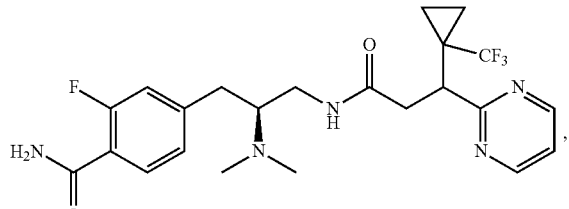
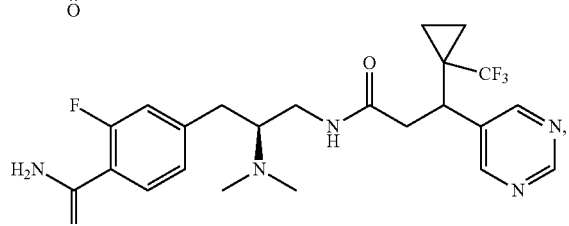
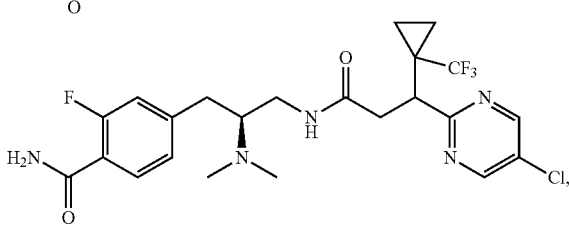
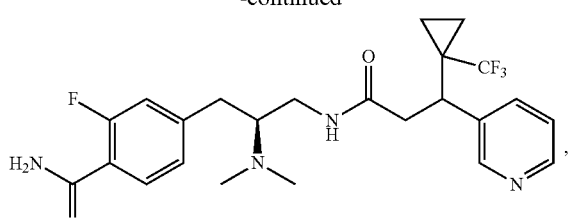
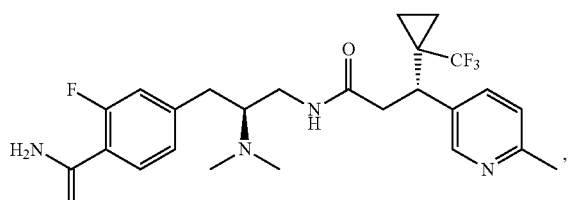
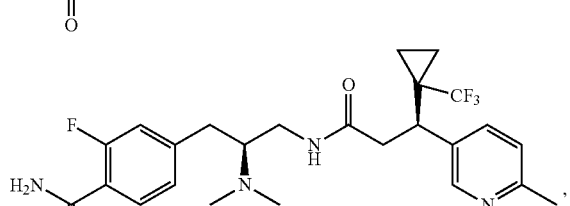
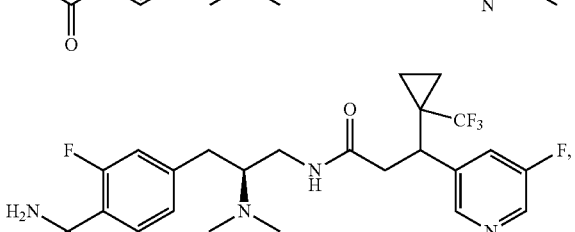
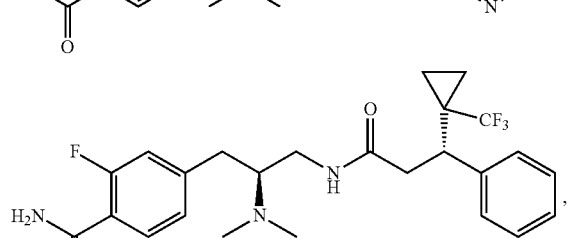
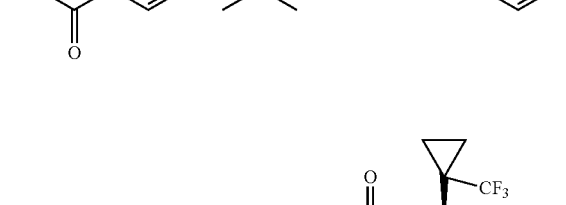
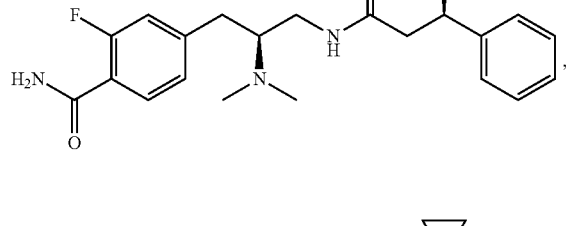
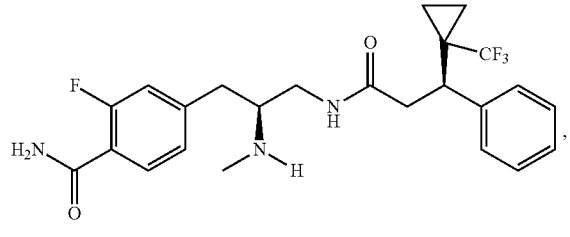

399
-continued
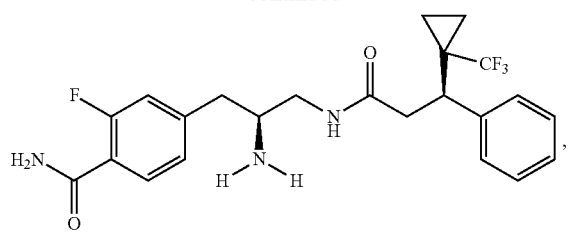,
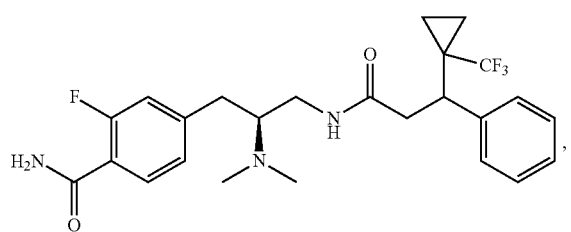,
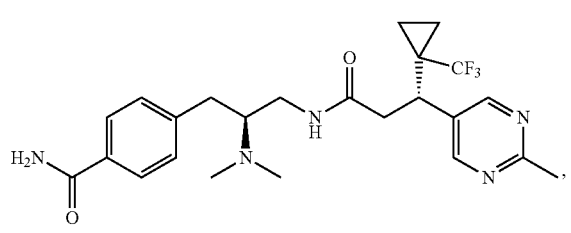,
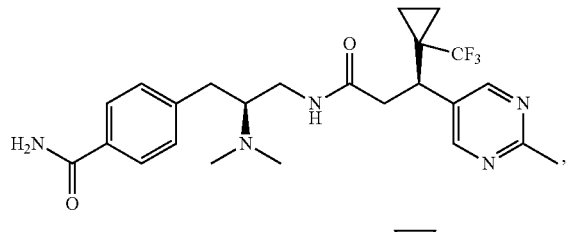,
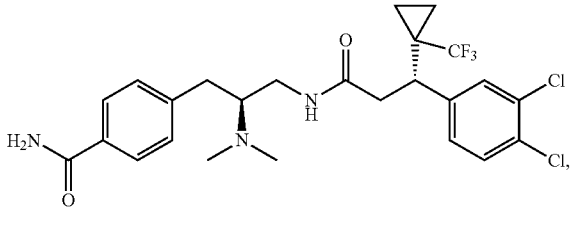,
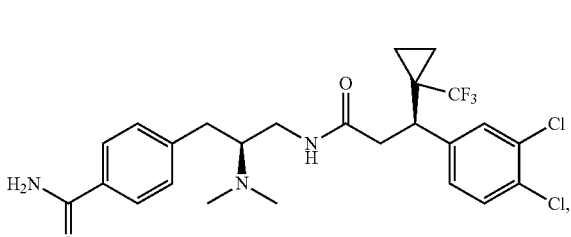,
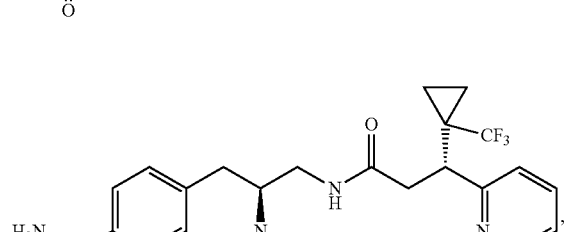,
400
-continued
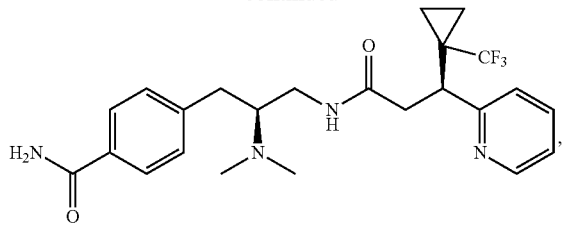,
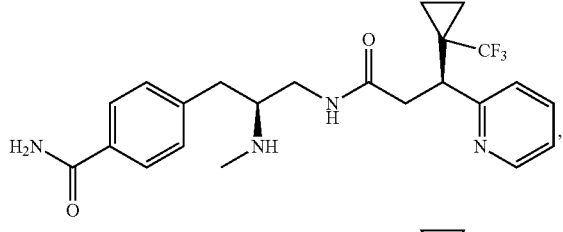,
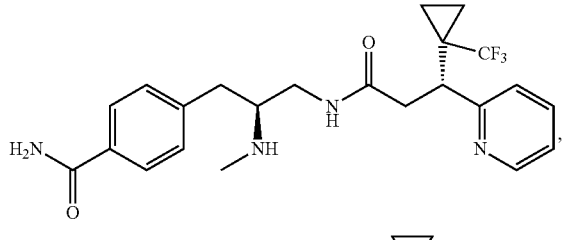,
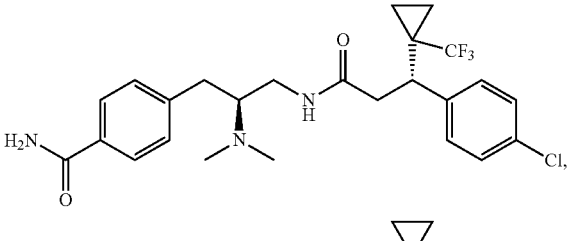,
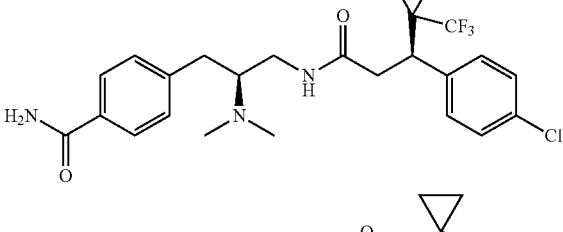,
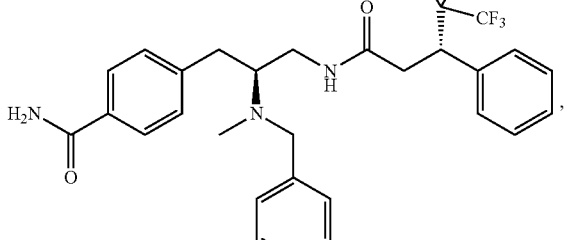,
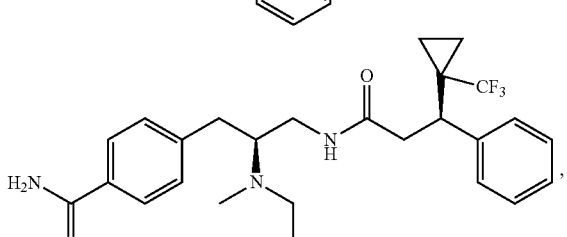,

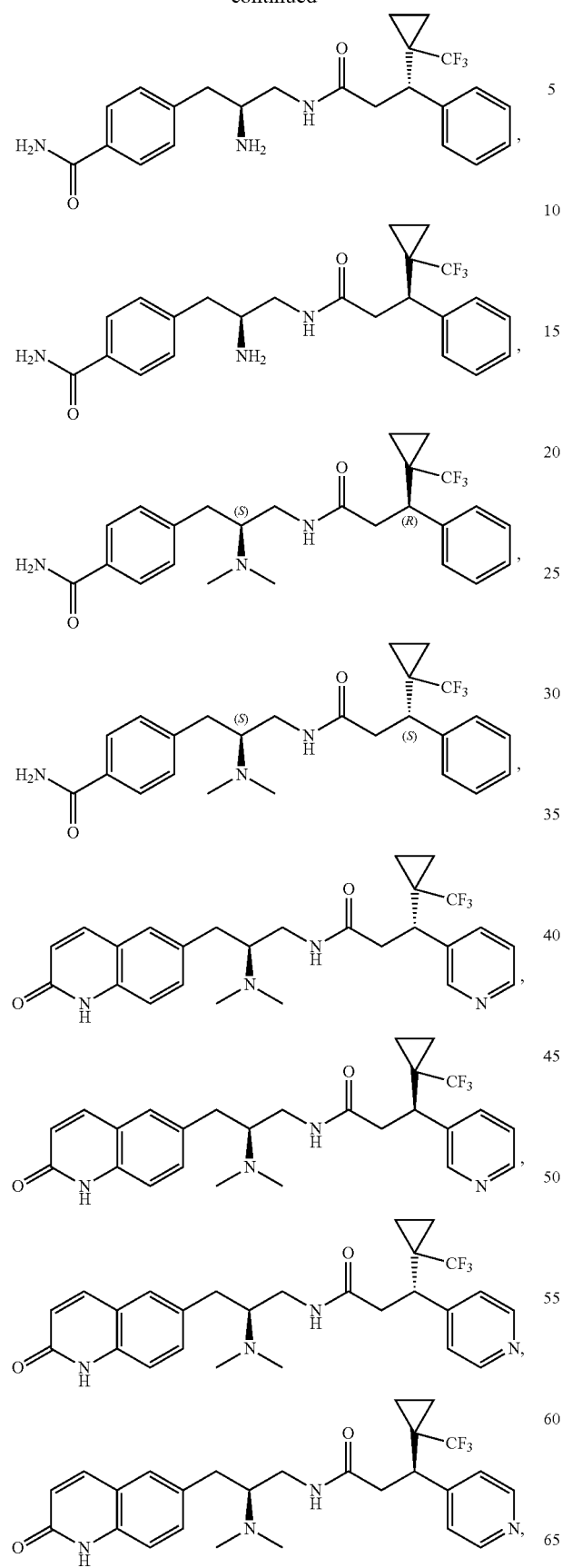
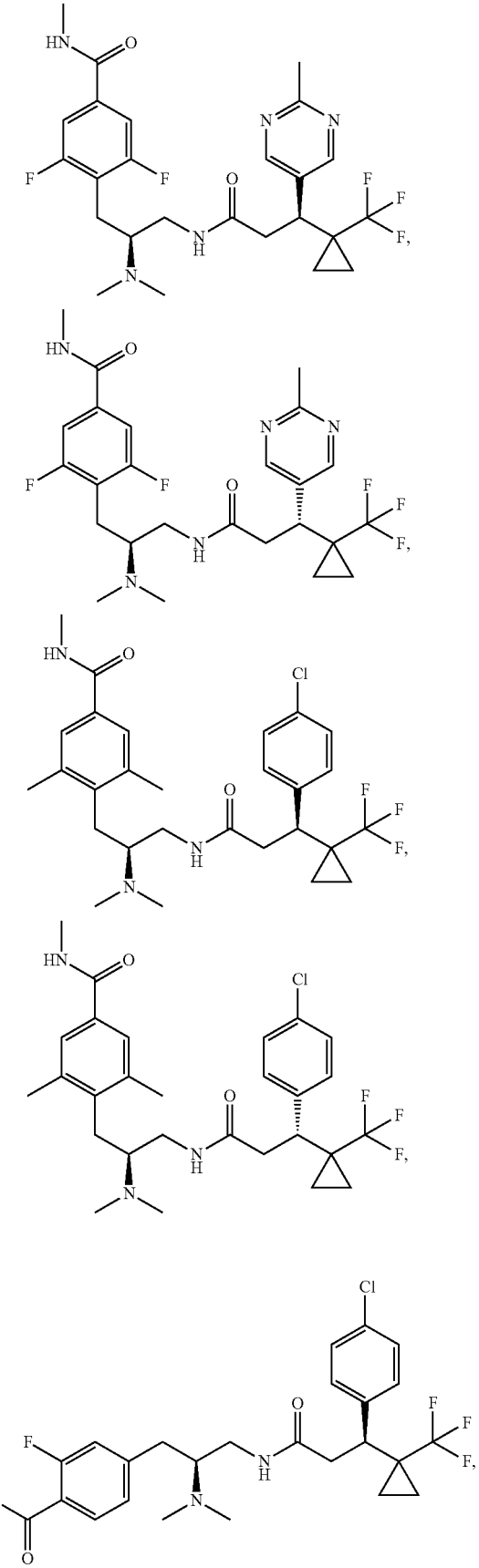

-continued
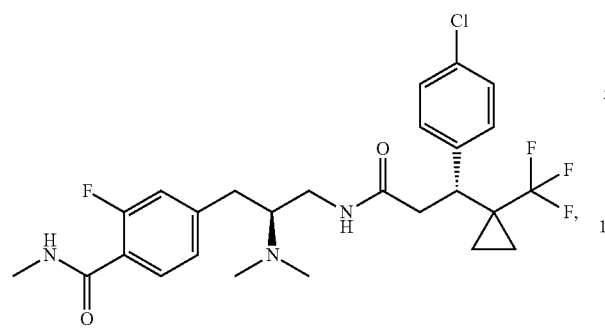
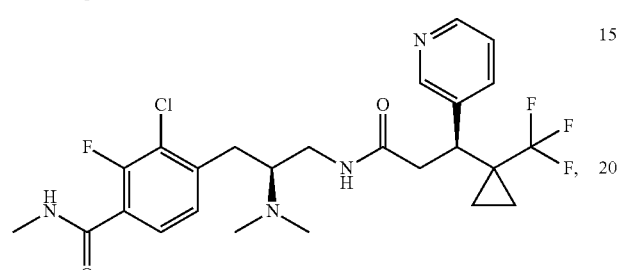
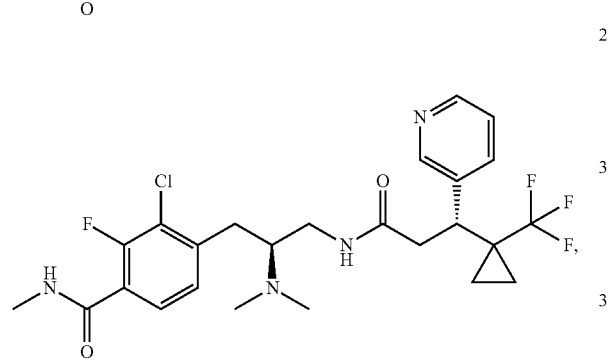
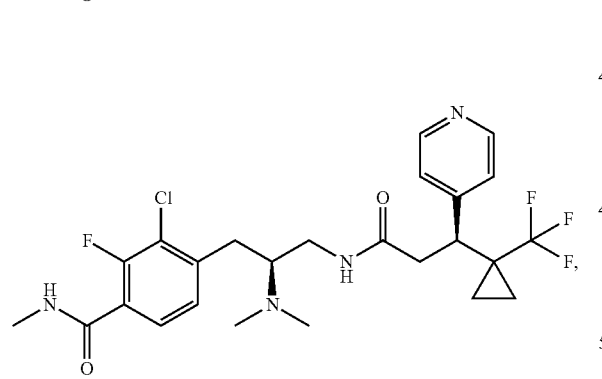
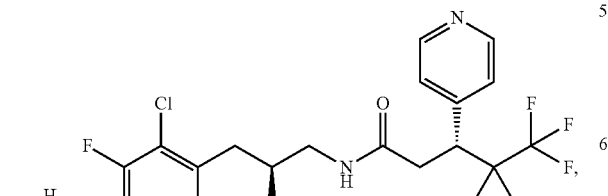
-continued
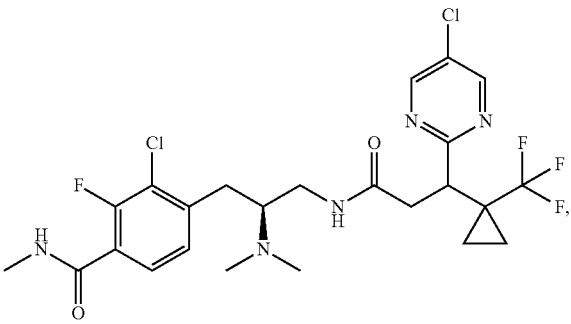
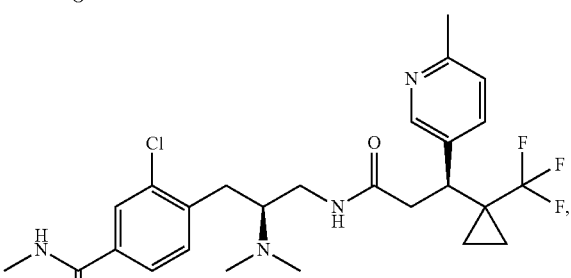
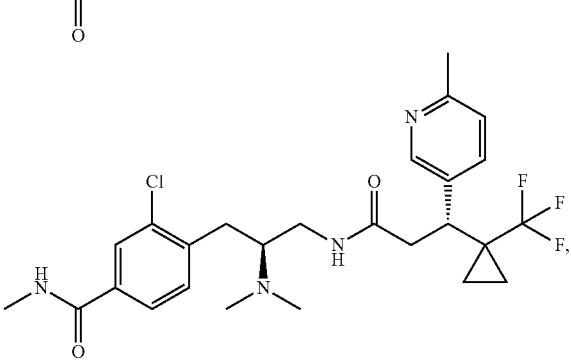
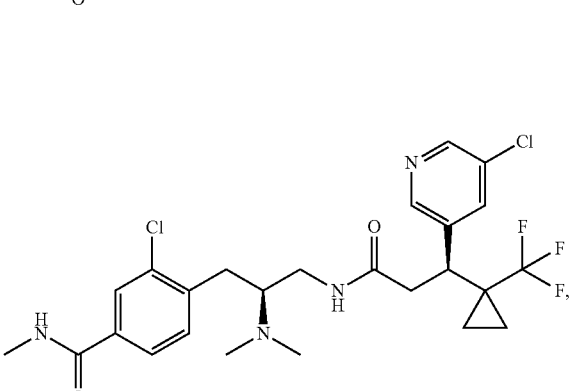
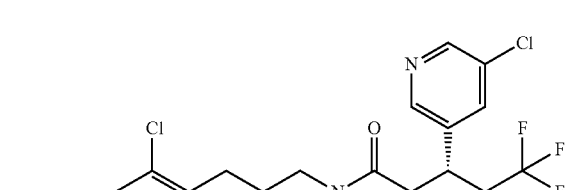

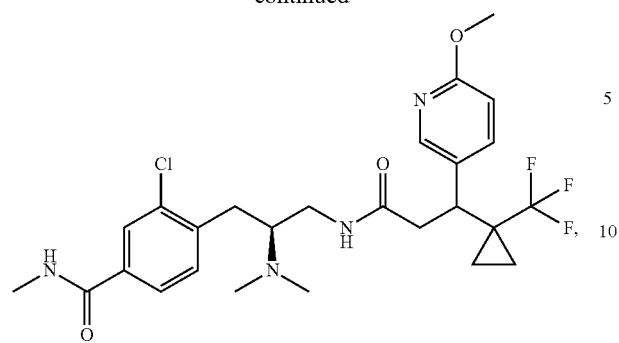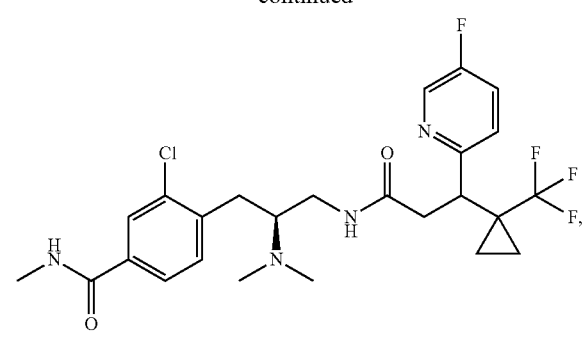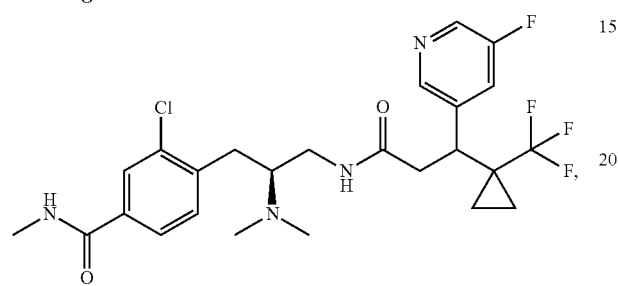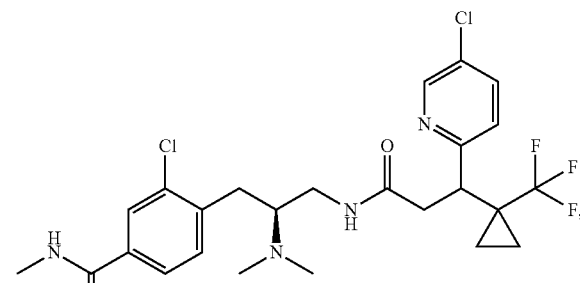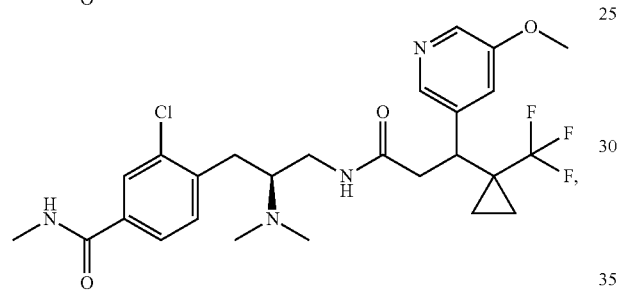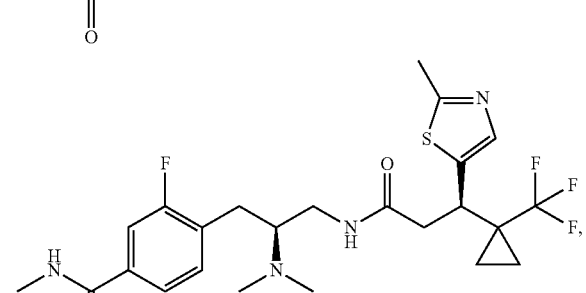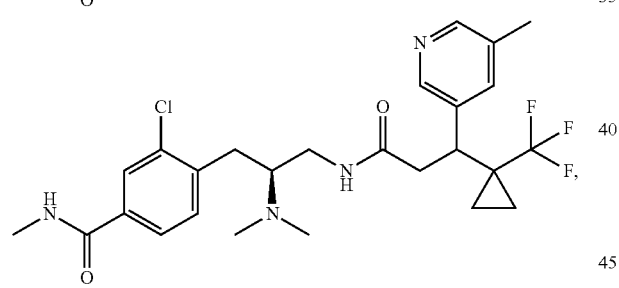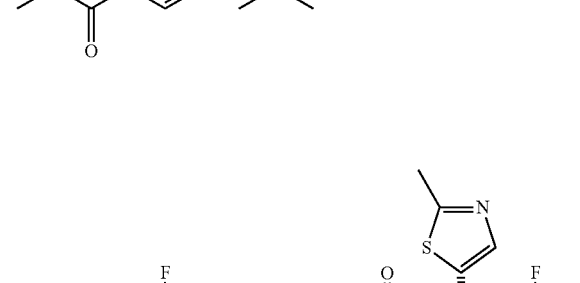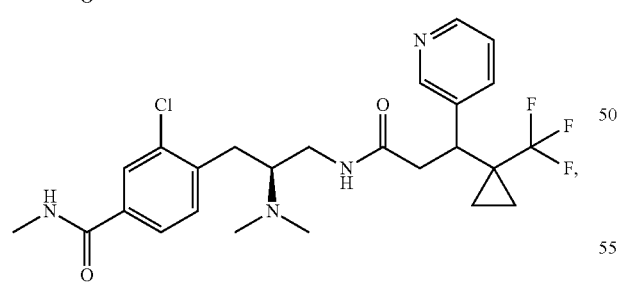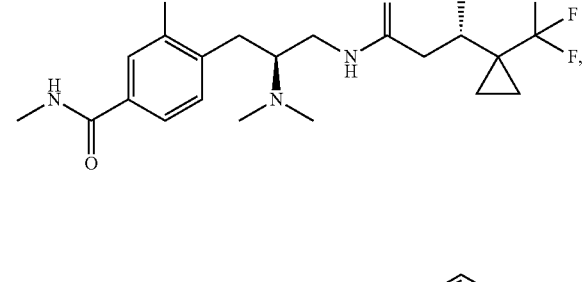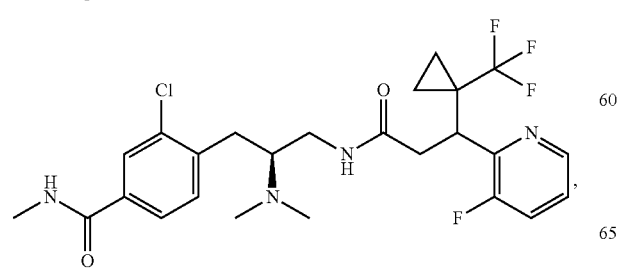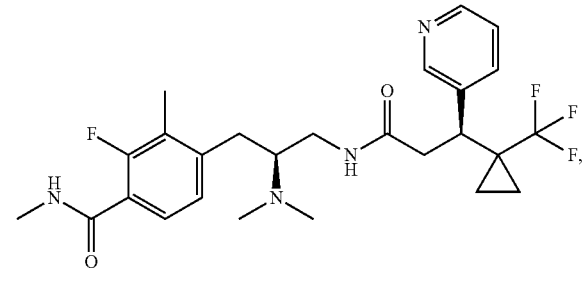

407
-continued
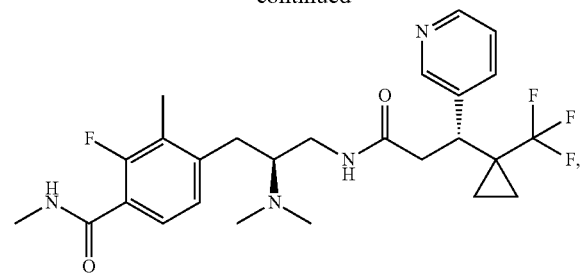
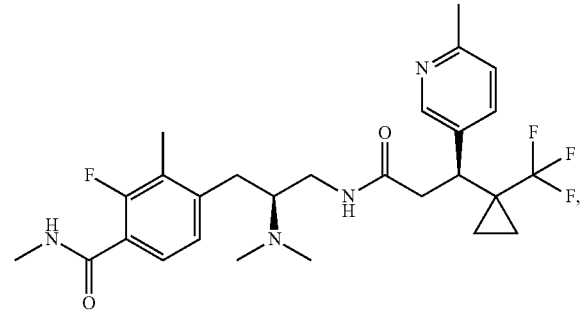
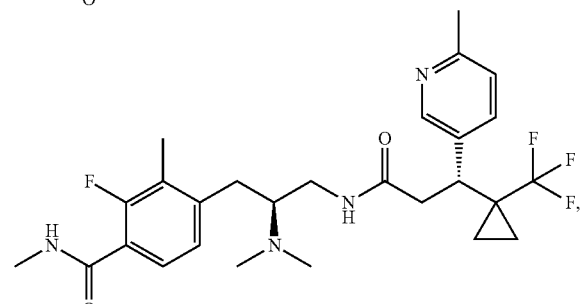
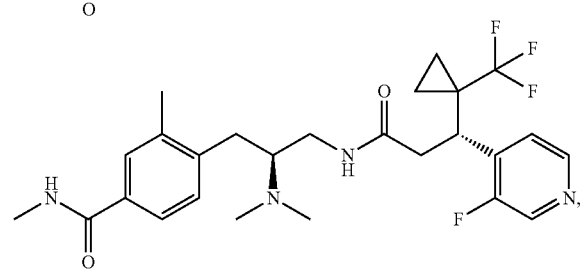
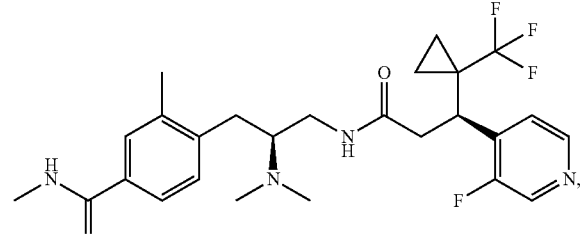
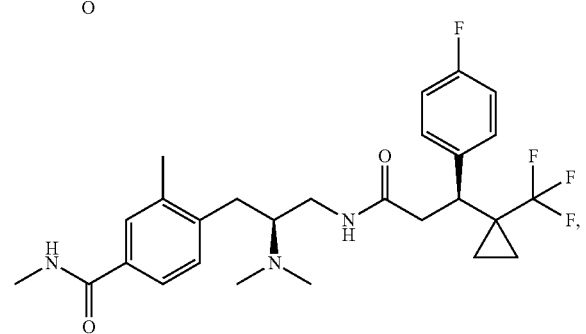
408
-continued
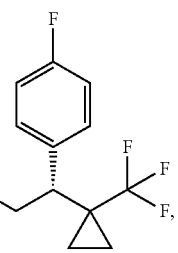
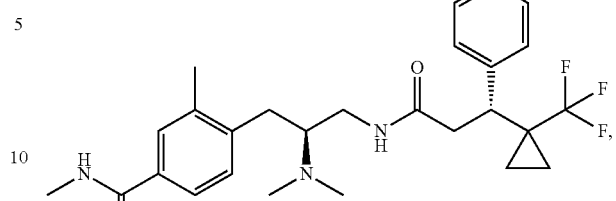
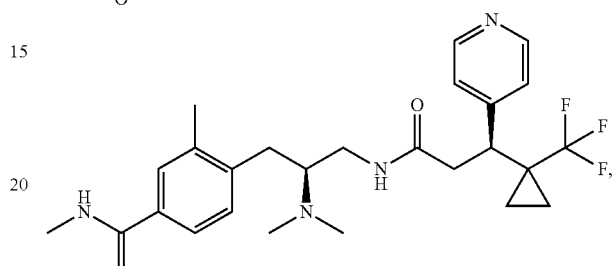
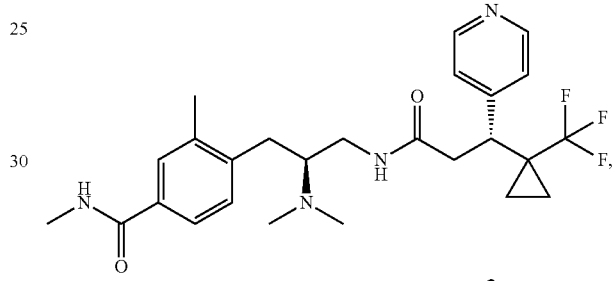
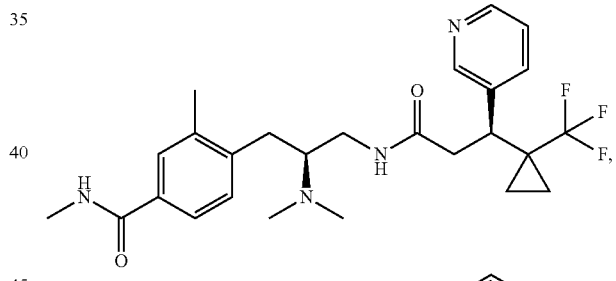
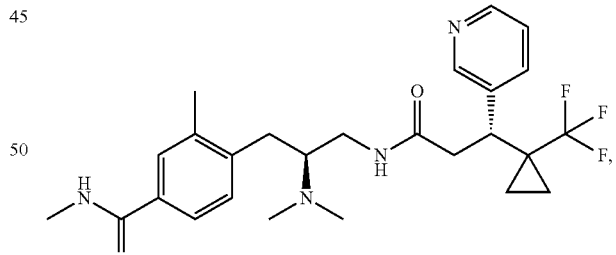
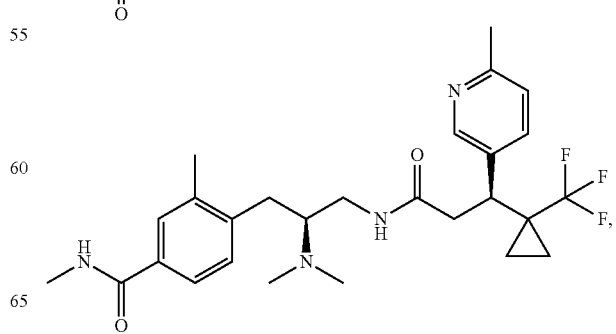

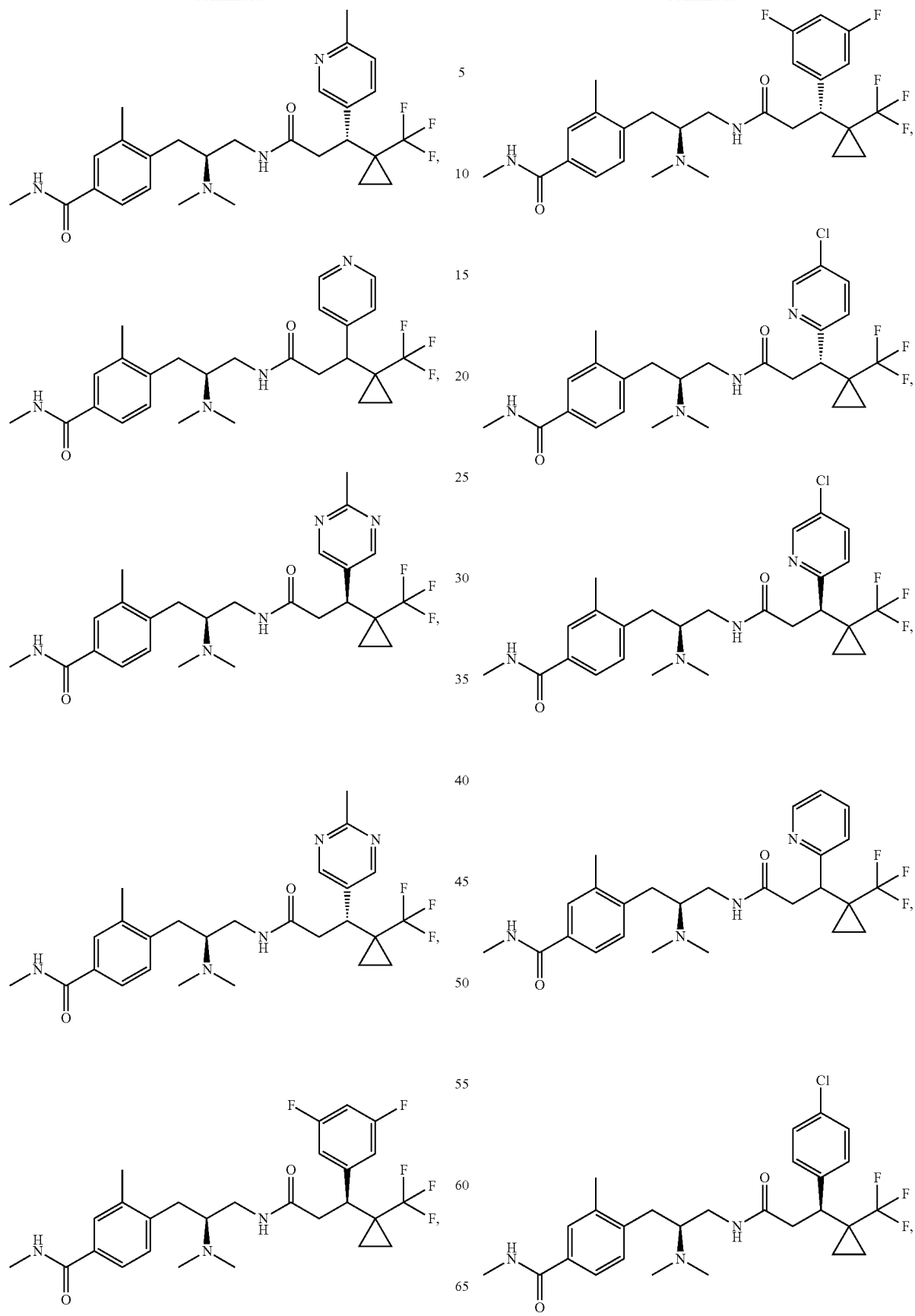

411
-continued
412
-continued
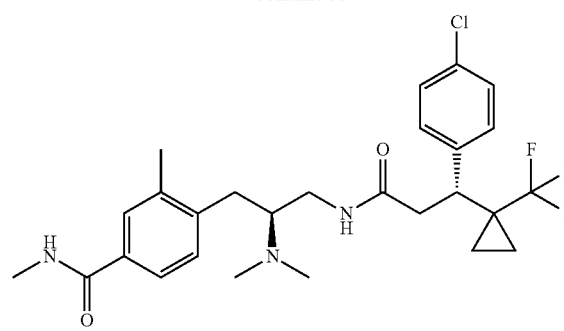
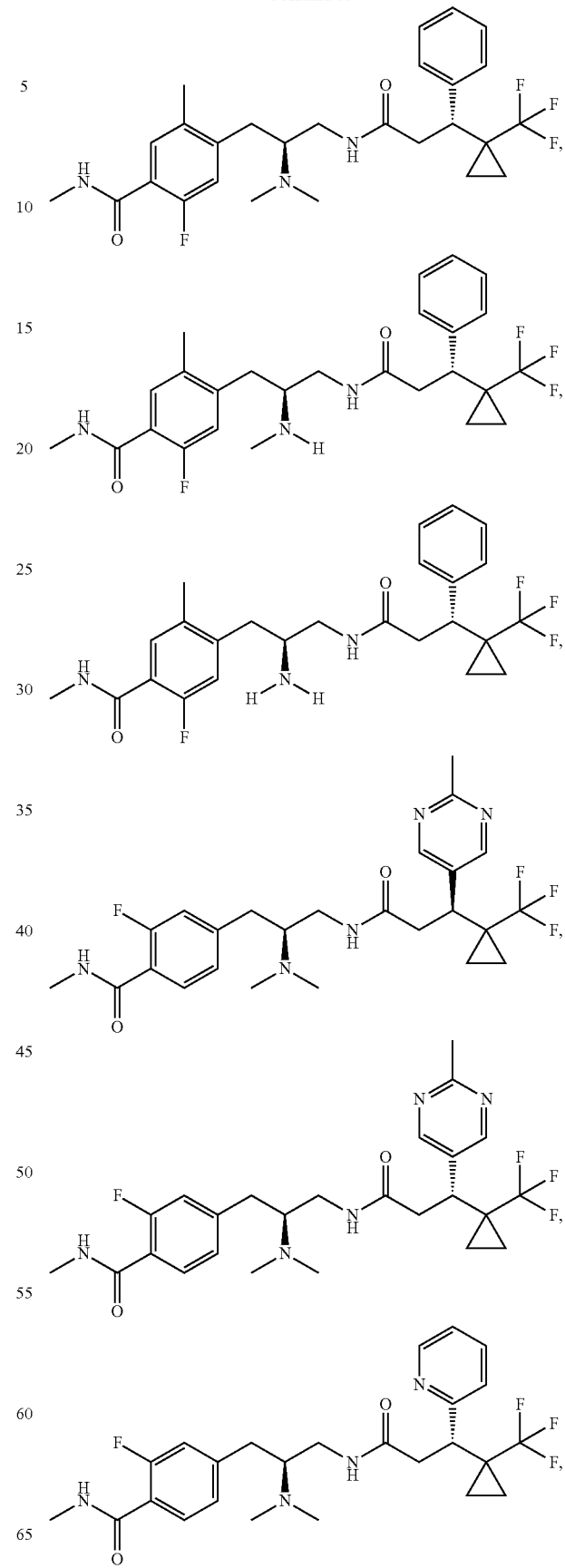

413
-continued
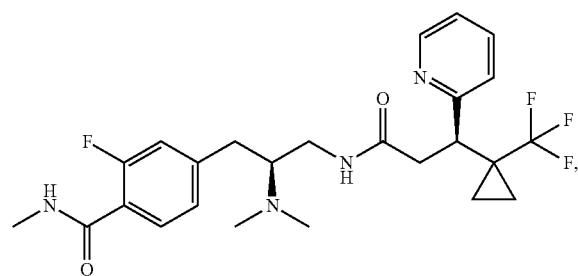 [SMILES: CNC(=O)c1ccc(C[C@@H](CNC(=O)C[C@@H](c2ccccc2)C2(C(F)(F)F)CC2)N(C)C)cc1F]
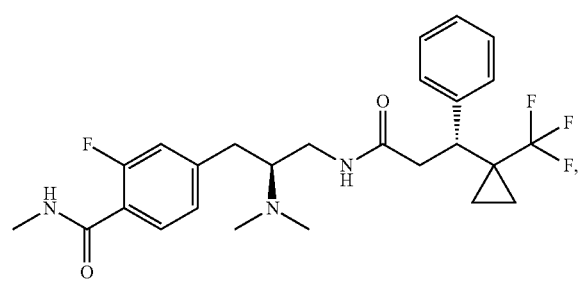
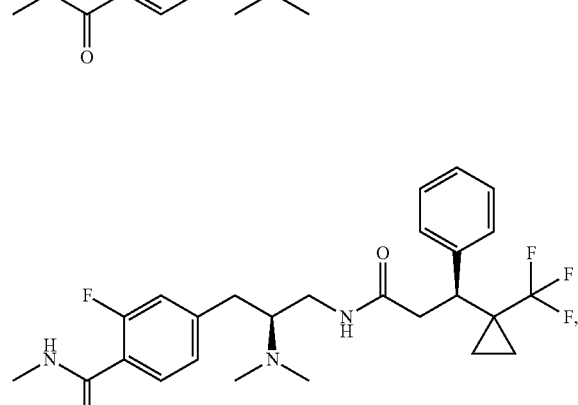
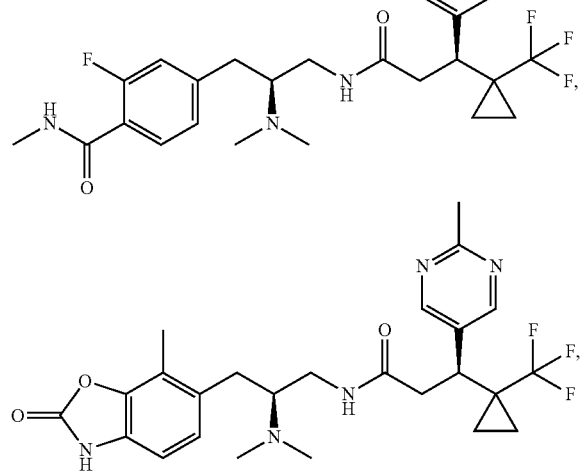
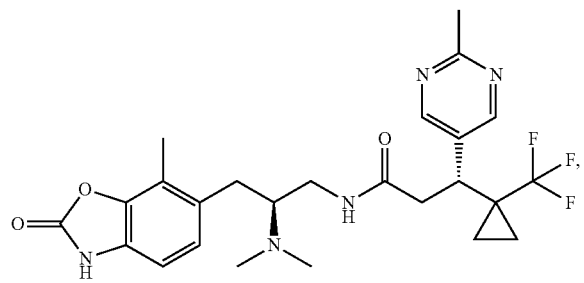
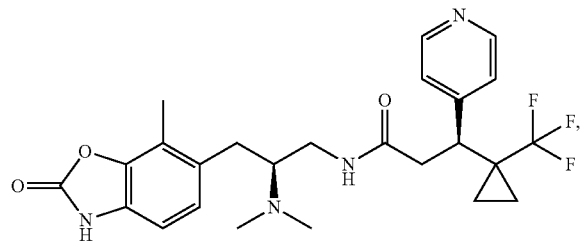
414
-continued
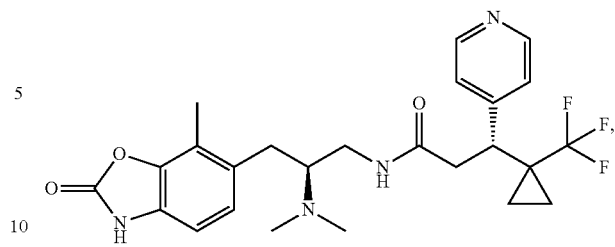
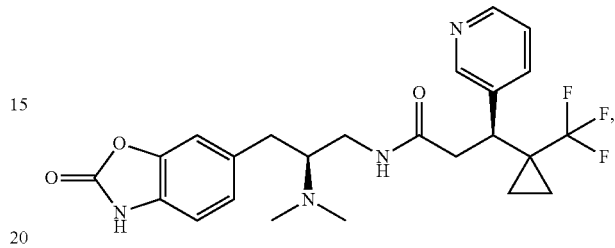
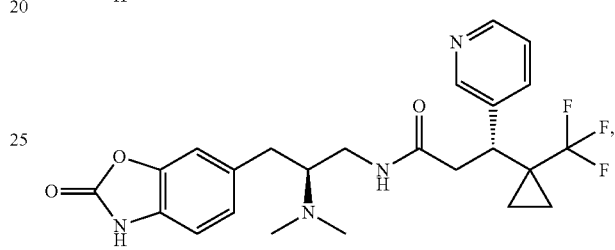
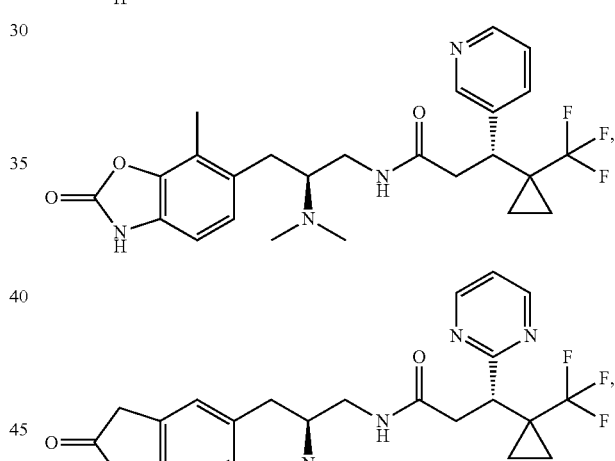
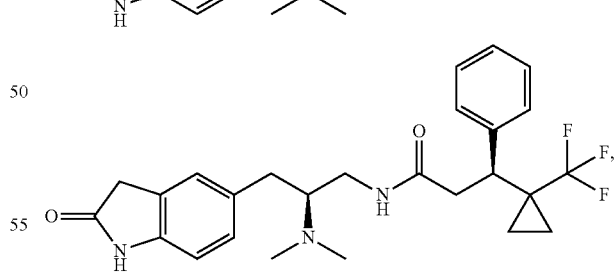
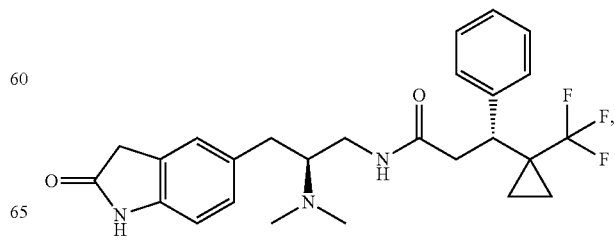

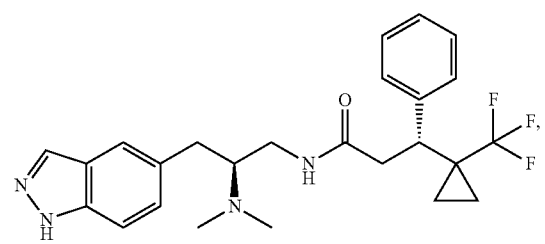
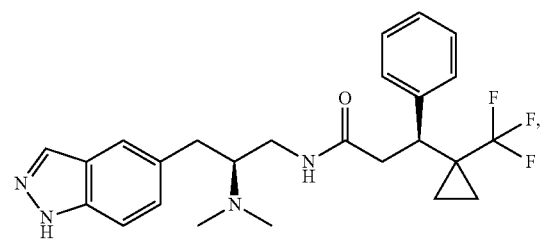
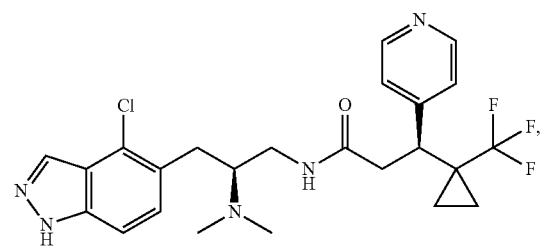
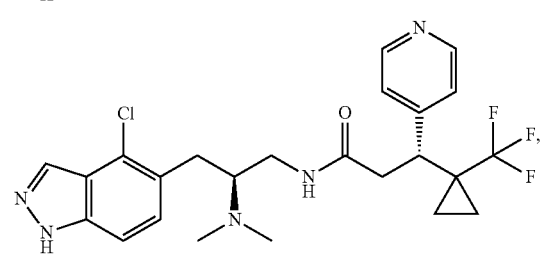
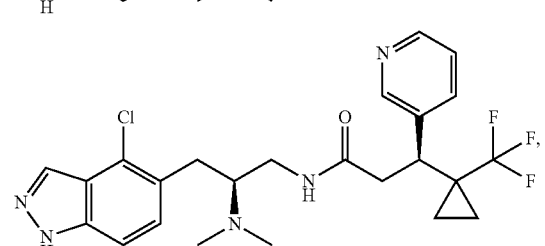
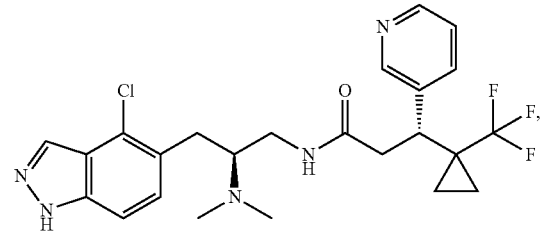
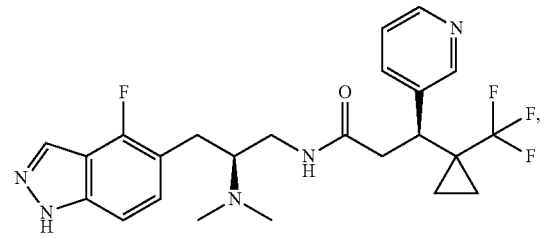
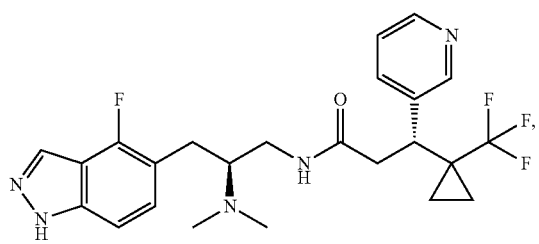
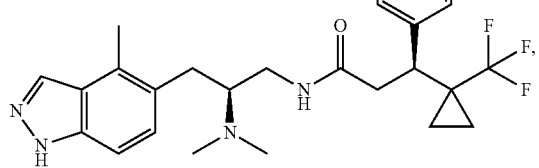
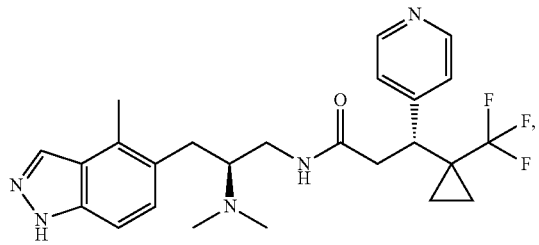
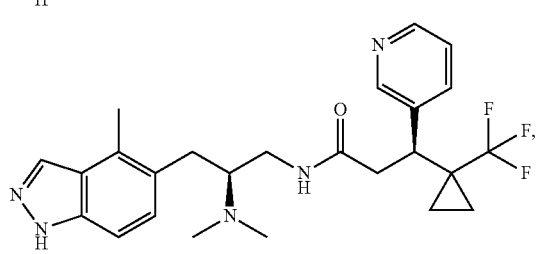
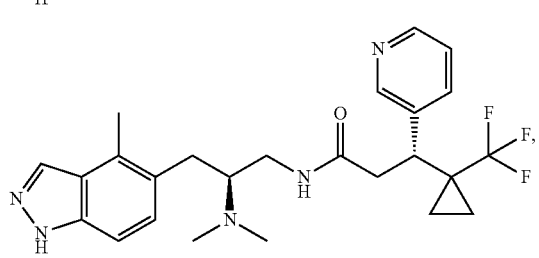
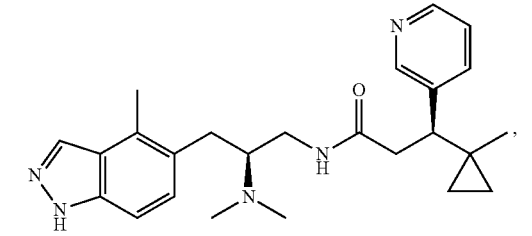
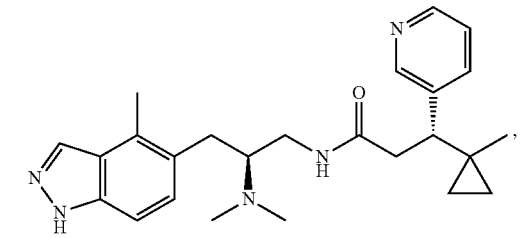

417
-continued
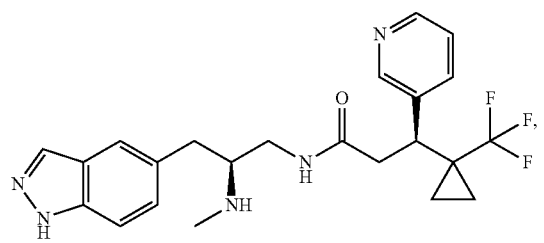
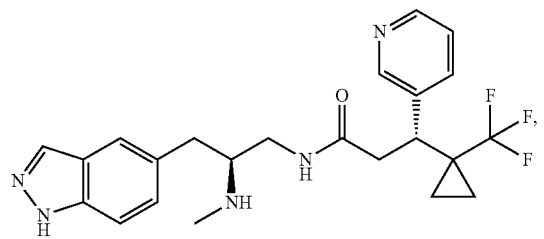
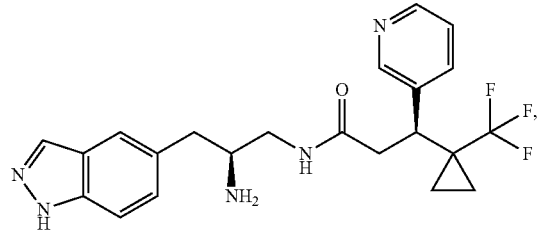
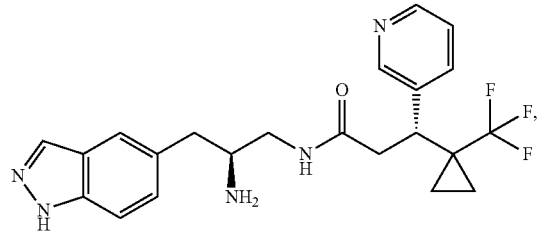
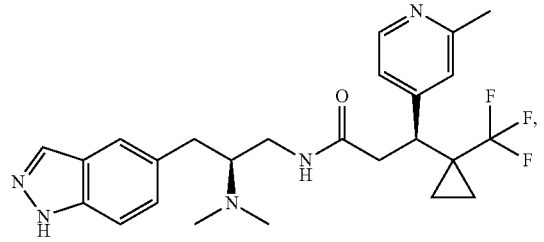
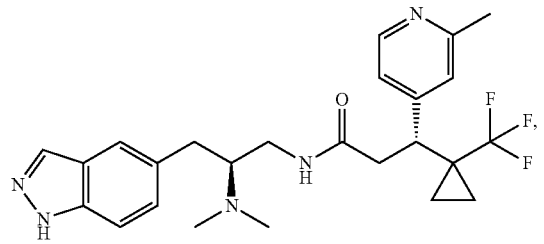
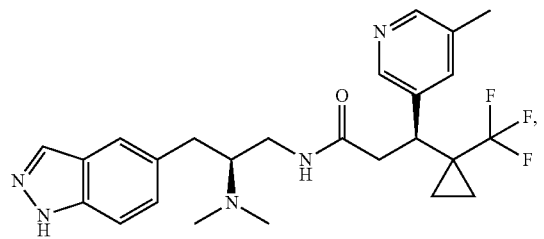
418
-continued
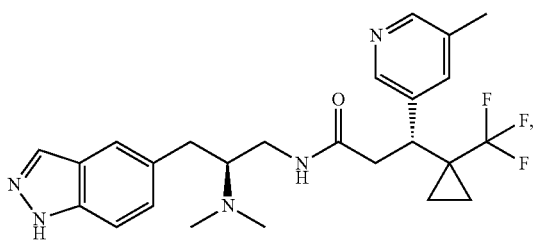
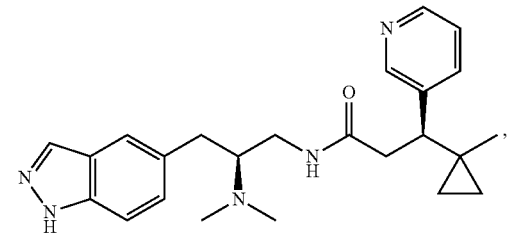
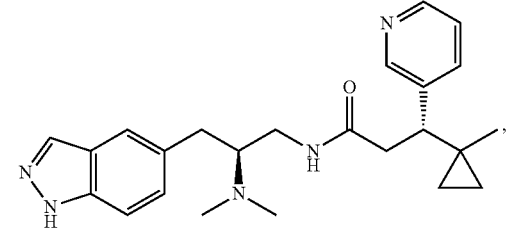
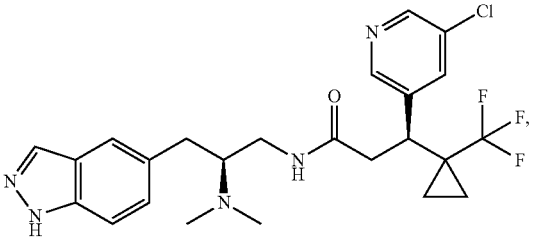
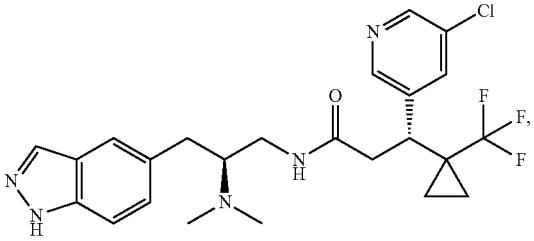
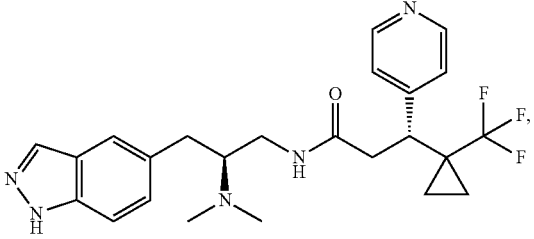
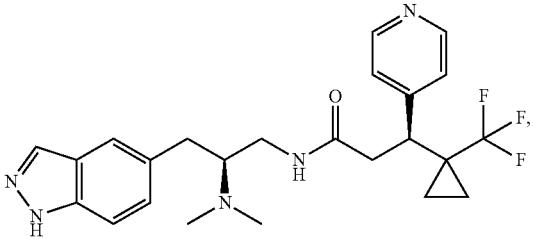

-continued
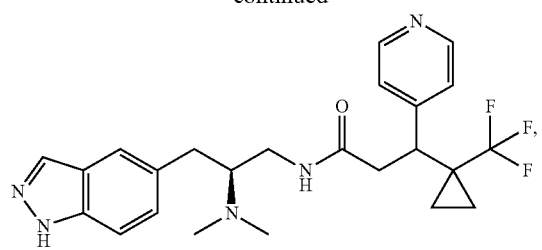
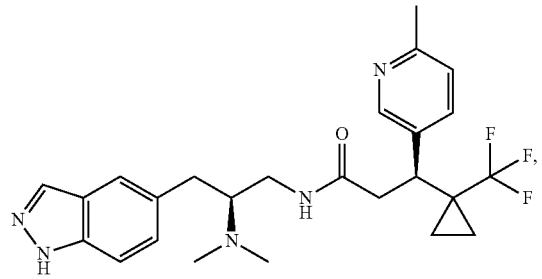
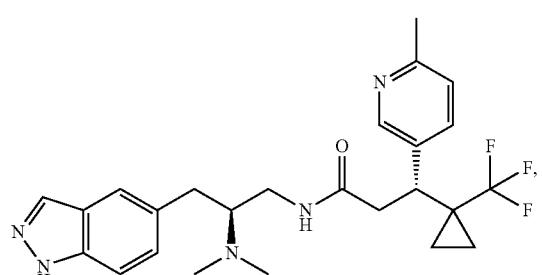
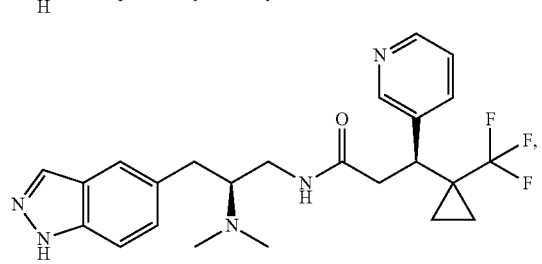
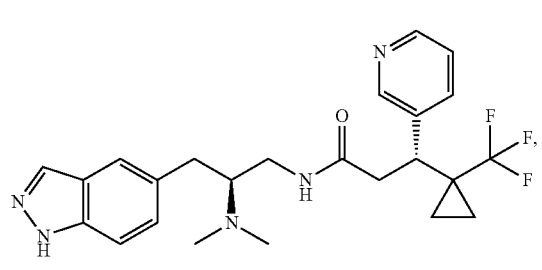
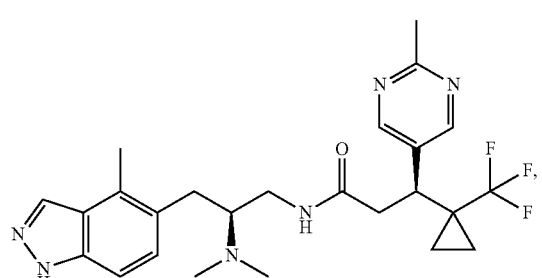
-continued
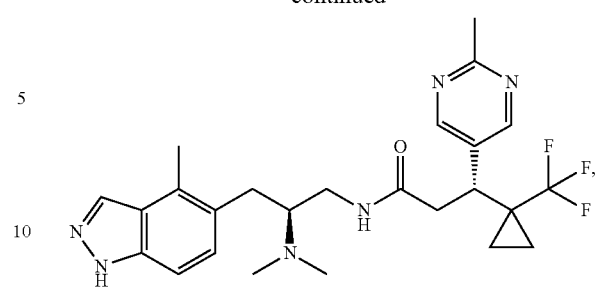
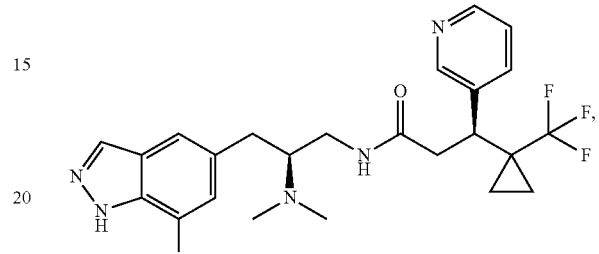
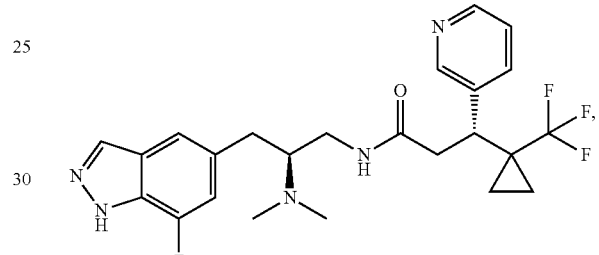
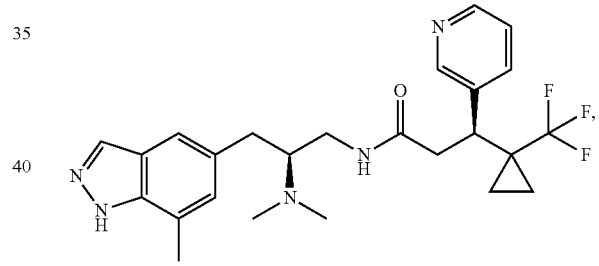
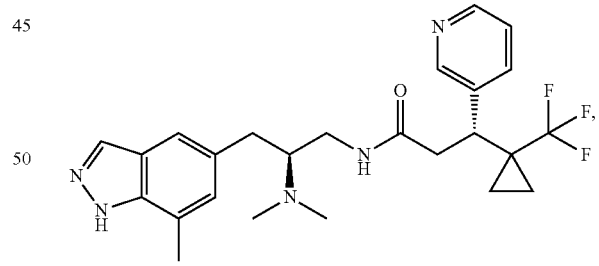
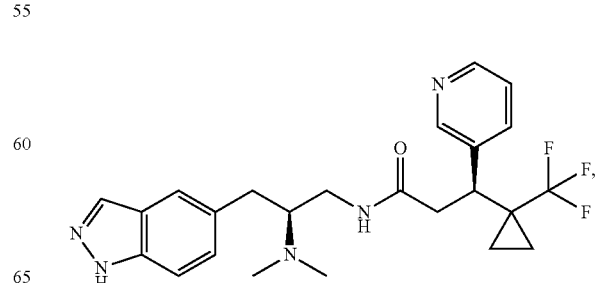

421
-continued
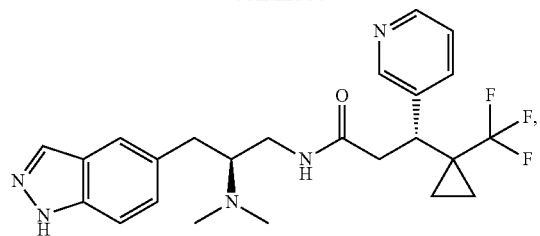
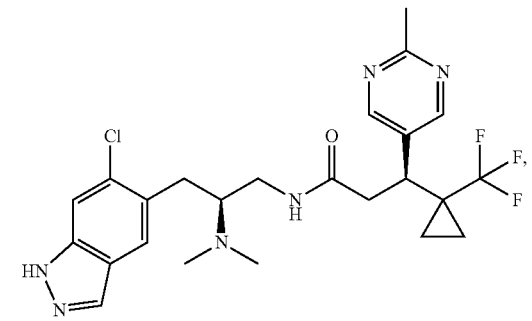
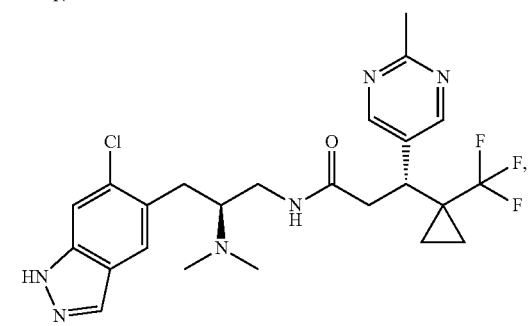
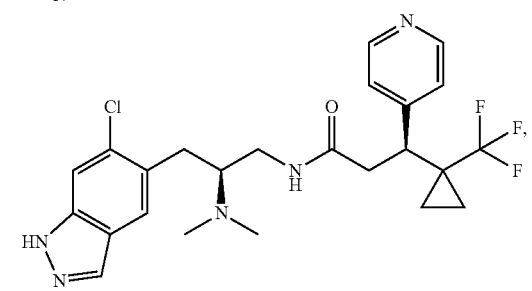
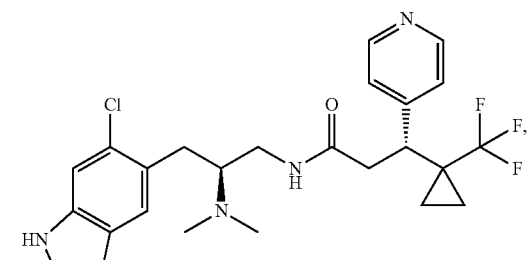
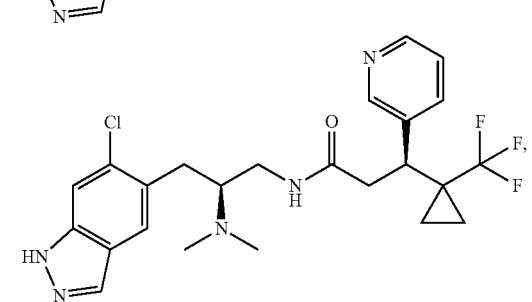
422
-continued
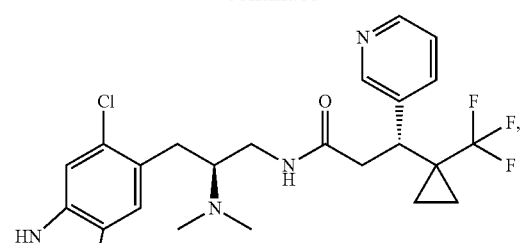
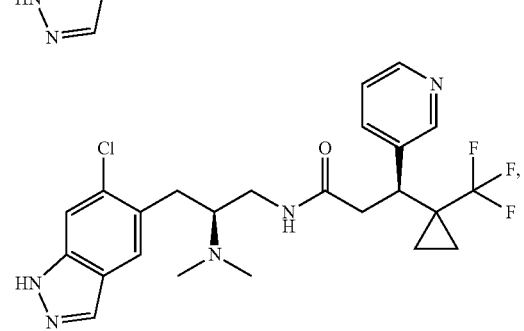
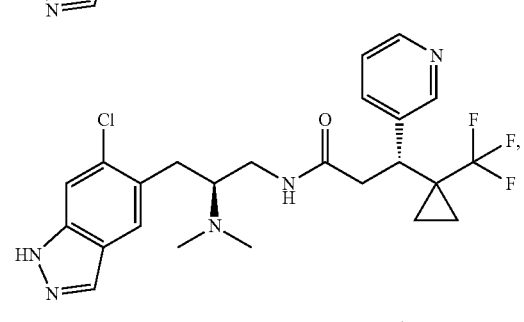
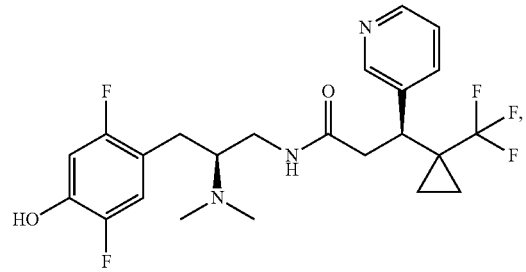
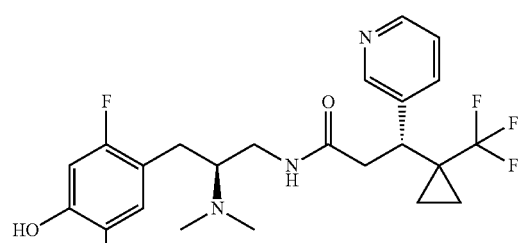
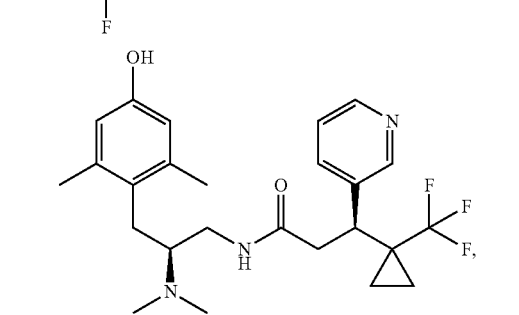

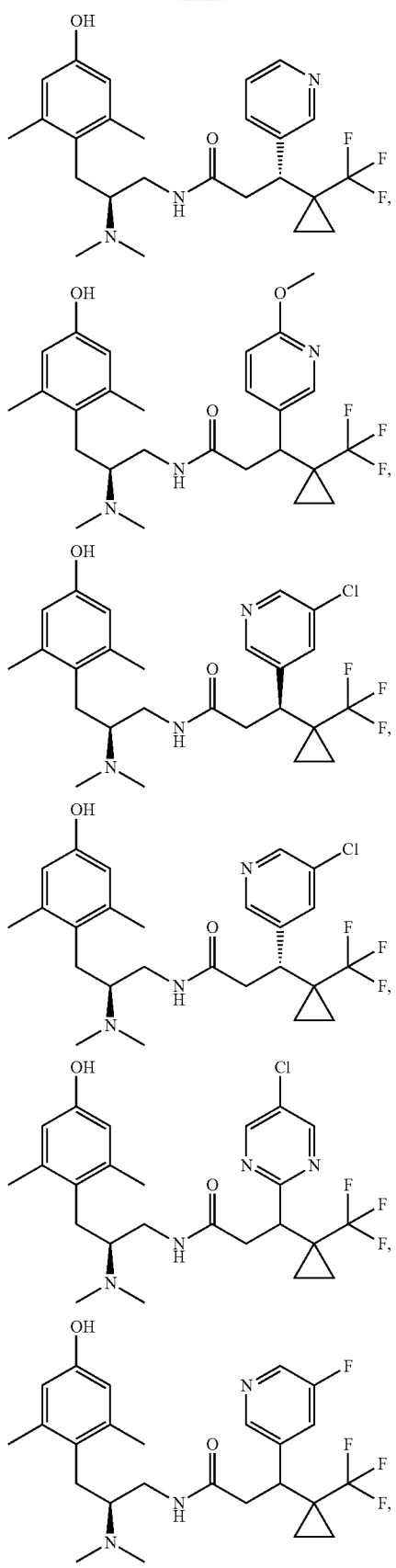
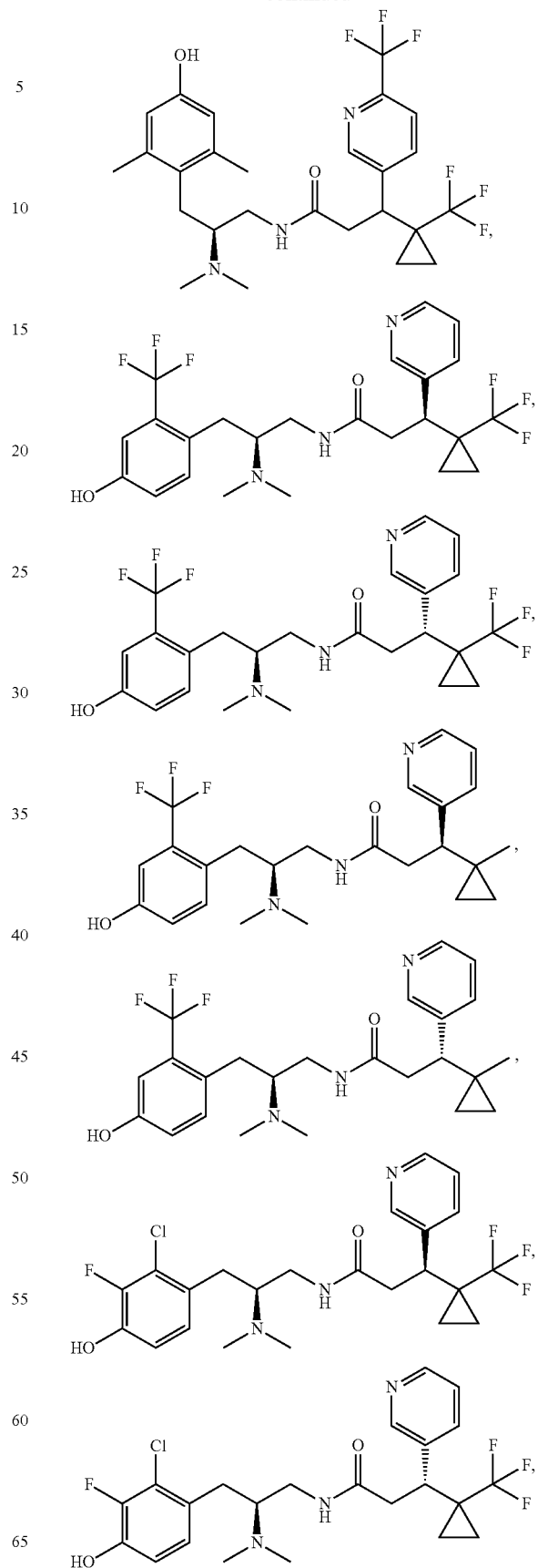

425
-continued
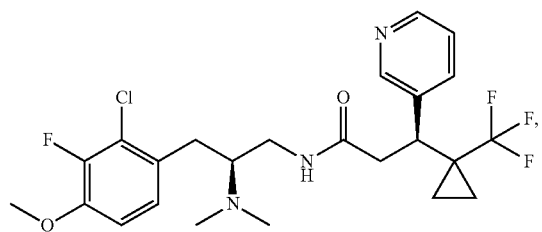
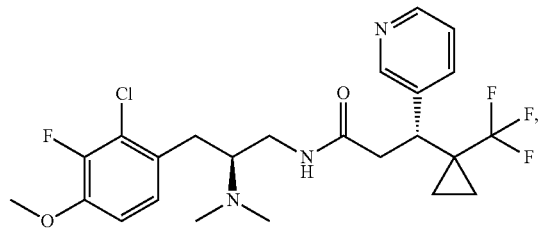
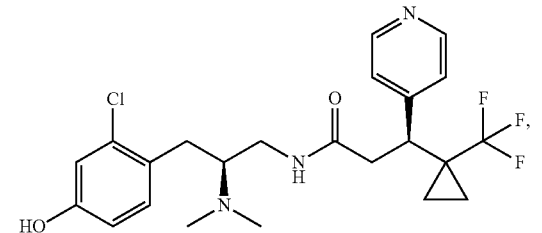
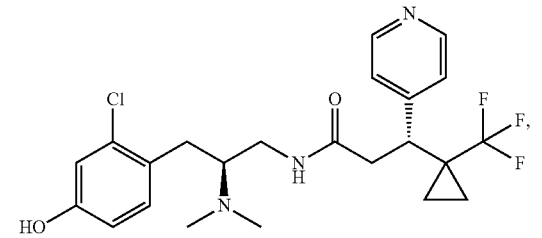
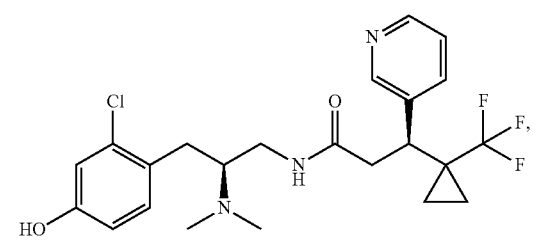
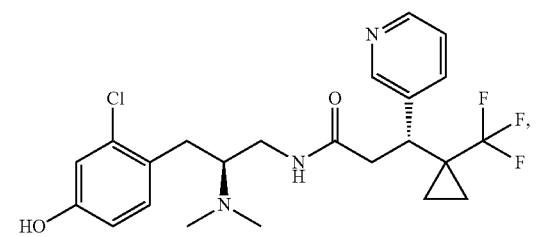
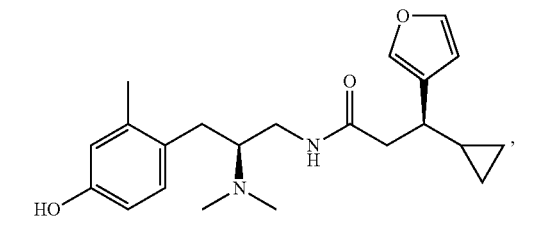
426
-continued
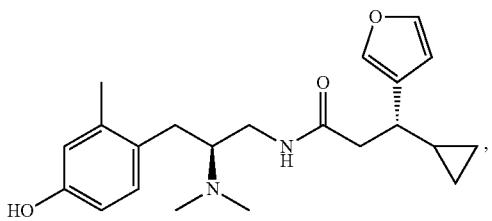
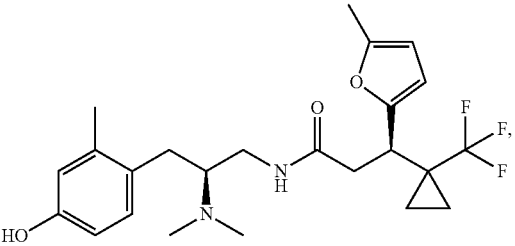 [SMILES: Cc1ccc([C@H](CC(=O)NC[C@H](Cc2ccc(O)cc2C)N(C)C)C2(C(F)(F)F)CC2)o1]
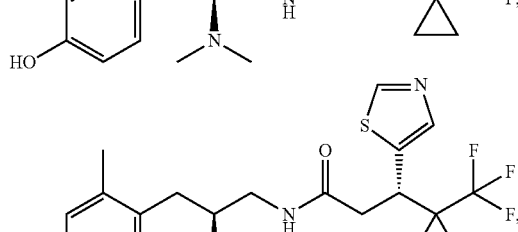
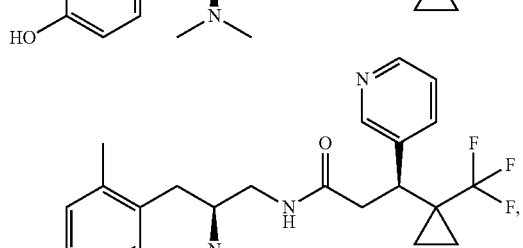
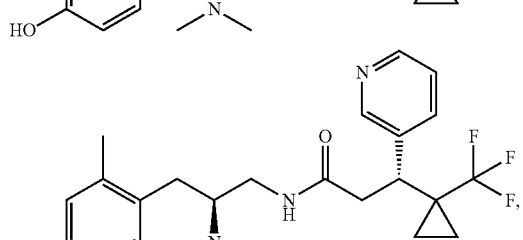

427
-continued
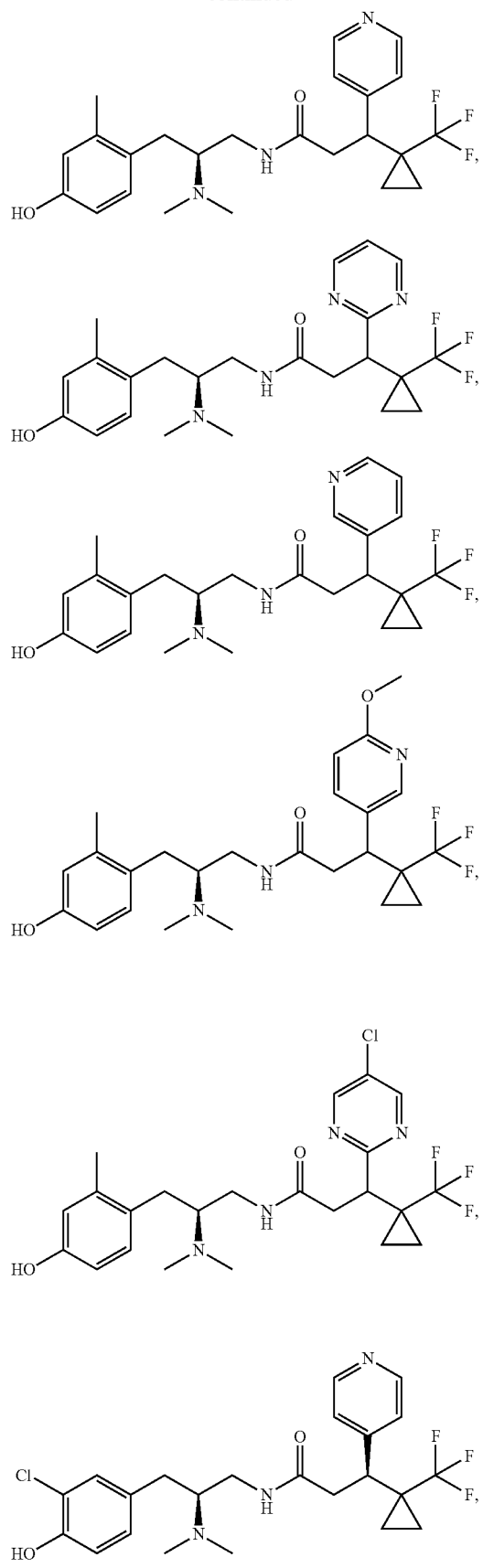
428
-continued
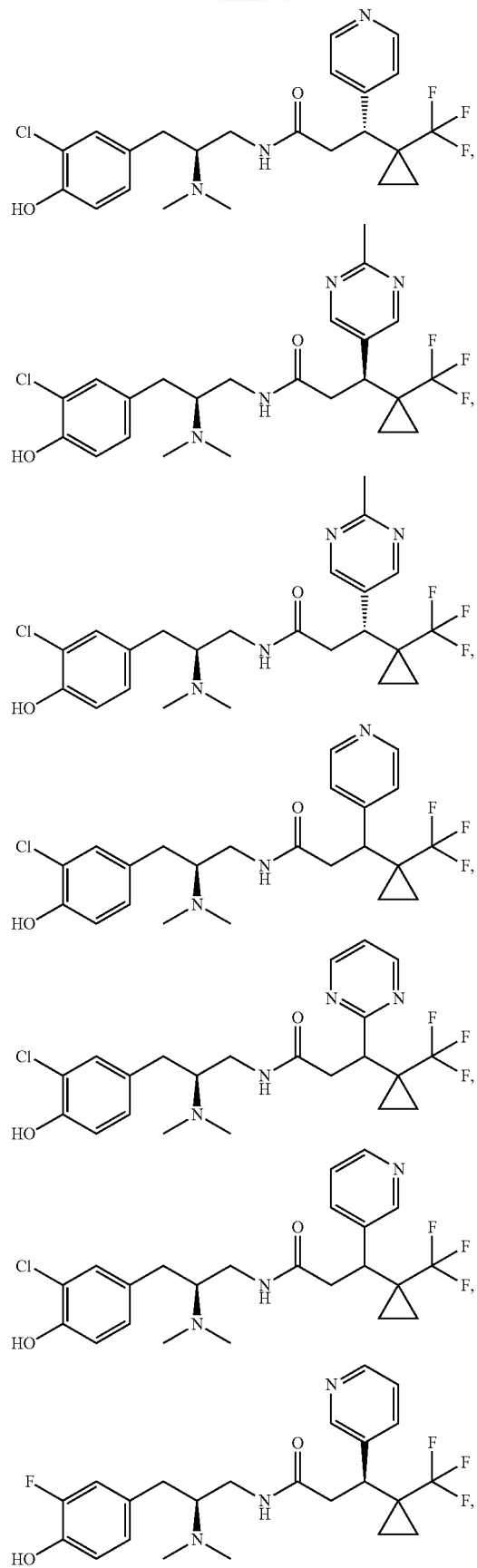

429
-continued
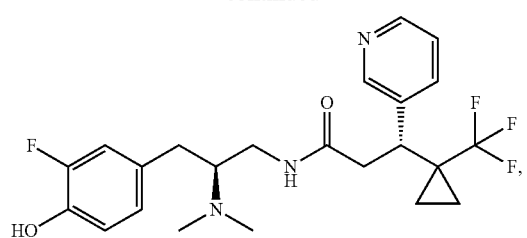
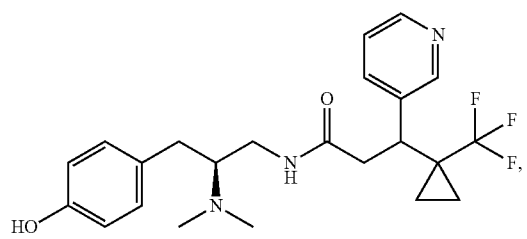
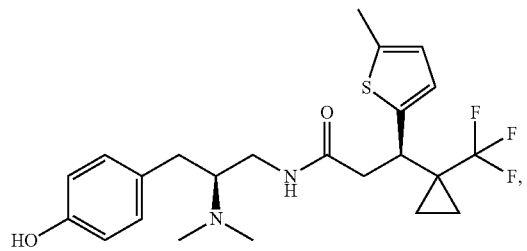
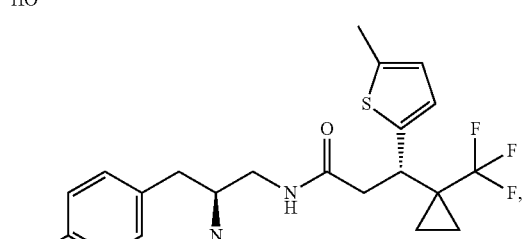
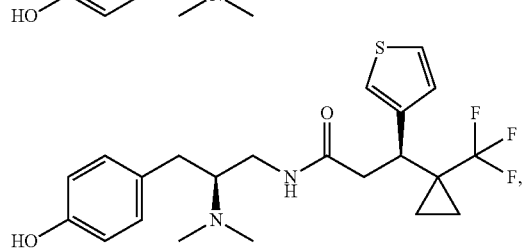
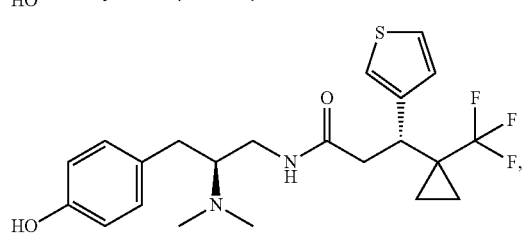
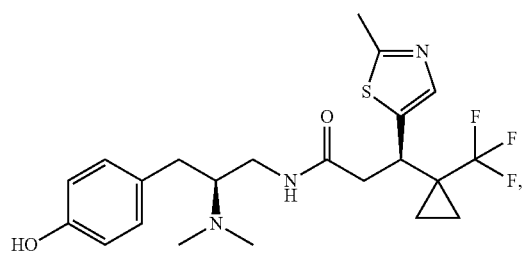
430
-continued
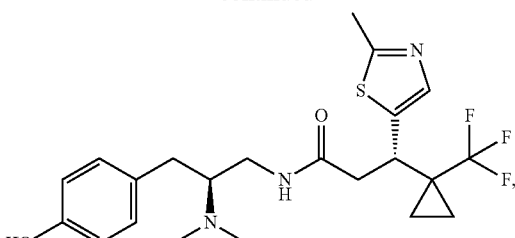
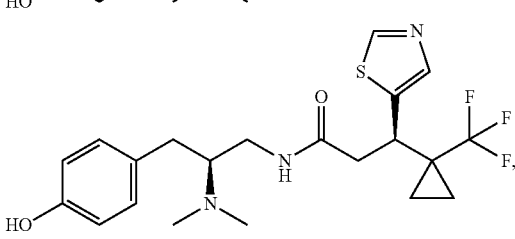
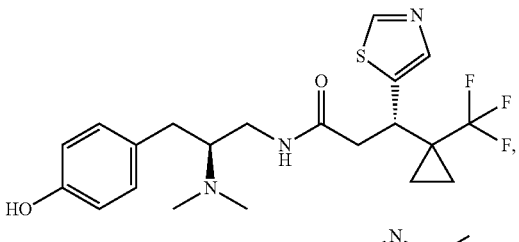
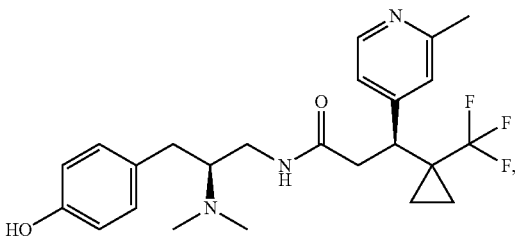
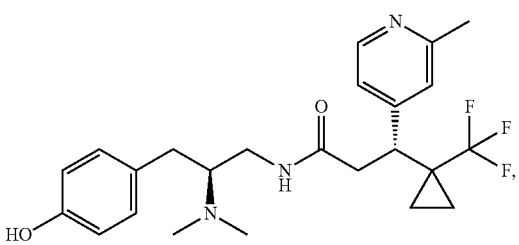 [SMILES: CN(C)[C@H](CNC(=O)CC(c1ccncc1)C1(C(F)(F)F)CC1)Cc1ccc(O)cc1]
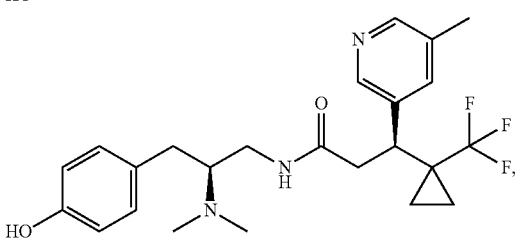
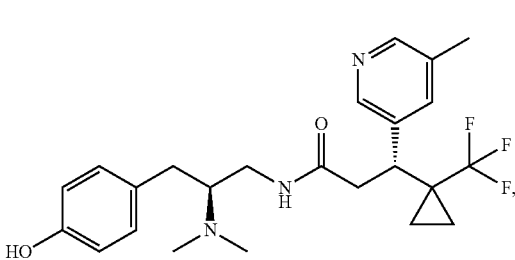

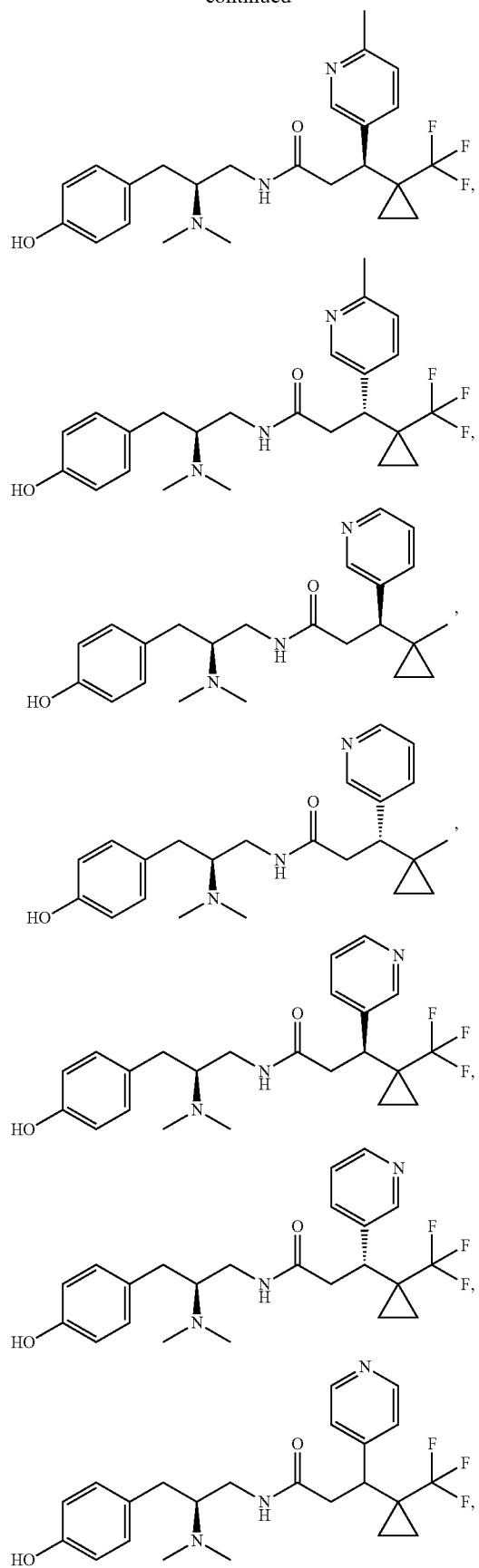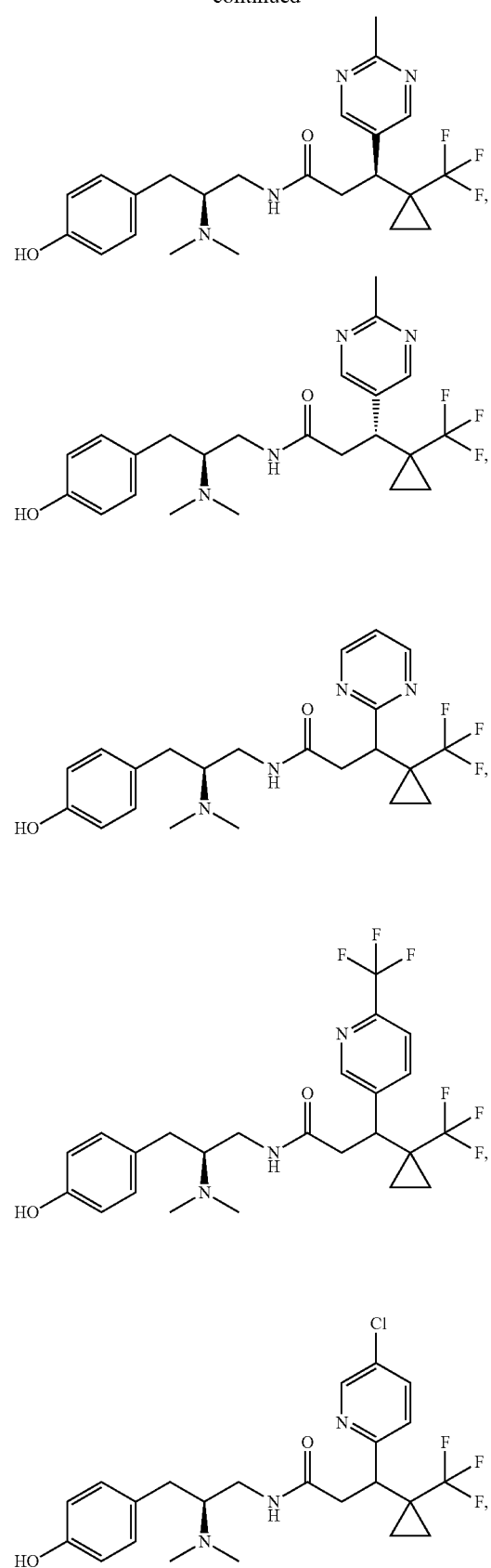

433
-continued
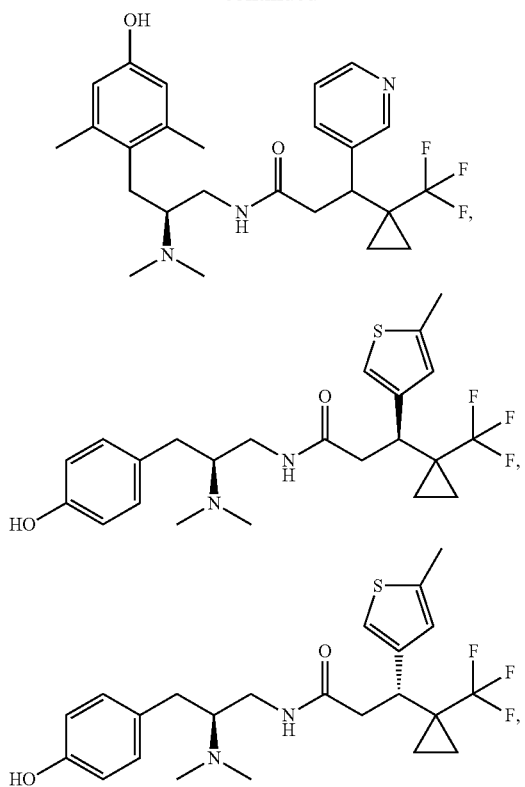
434
-continued
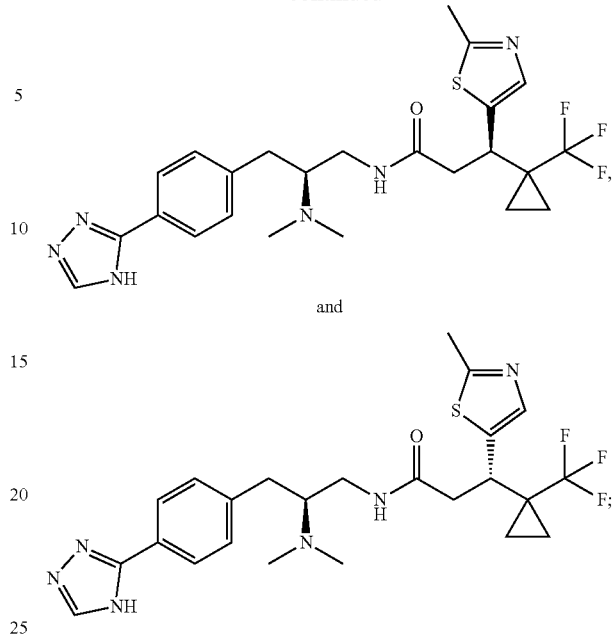
or a pharmaceutically acceptable salt or solvate thereof.
16. A pharmaceutical composition comprising a compound of claim 1, or a pharmaceutically acceptable salt or solvate thereof, and at least one pharmaceutically acceptable excipient.
* * * * *